United States Patent
Shapiro et al.

(10) Patent No.: US 9,732,337 B2
(45) Date of Patent: Aug. 15, 2017

(54) RNA NANOPARTICLES AND NANOTUBES

(75) Inventors: Bruce A. Shapiro, Gaithersburg, MD (US); Yaroslava G. Yingling, Cary, NC (US); Eckart Bindewald, Frederick, MD (US); Wojciech Kasprzak, Frederick, MD (US); Luc Jaeger, Goleta, CA (US); Isil Severcan, Niskayuna, NY (US); Cody Geary, Santa Barbara, CA (US); Kirill Afonin, Frederick, MD (US)

(73) Assignees: The United Stated of America, as represented by the Secretary, Department of Health & Human Services, Washington, DC (US); The Regents of the University of California, Oakland, CA (US)

( * ) Notice: Subject to any disclaimer, the term of this patent is extended or adjusted under 35 U.S.C. 154(b) by 340 days.

(21) Appl. No.: 13/378,935

(22) PCT Filed: Jun. 16, 2010

(86) PCT No.: PCT/US2010/038818
§ 371 (c)(1),
(2), (4) Date: Mar. 13, 2012

(87) PCT Pub. No.: WO2010/148085
PCT Pub. Date: Dec. 23, 2010

(65) Prior Publication Data
US 2012/0263648 A1    Oct. 18, 2012

Related U.S. Application Data

(60) Provisional application No. 61/187,495, filed on Jun. 16, 2009.

(51) Int. Cl.
| | | |
|---|---|---|
| *C07H 21/02* | (2006.01) | |
| *C12N 15/11* | (2006.01) | |
| *A61K 47/48* | (2006.01) | |
| *B82Y 5/00* | (2011.01) | |

(52) U.S. Cl.
CPC ........ *C12N 15/11* (2013.01); *A61K 47/48092* (2013.01); *B82Y 5/00* (2013.01); *C12N 2310/51* (2013.01)

(58) Field of Classification Search
None
See application file for complete search history.

(56) References Cited

U.S. PATENT DOCUMENTS 5,278,051 A * 1/1994 Seeman ................ C12N 15/10
                                                                 435/91.3

FOREIGN PATENT DOCUMENTS

WO    2008039254 A2    4/2008

OTHER PUBLICATIONS

Polyvalent. Oxford Dictionary Definition. Downloaded from www.oxforddictionaries.com/us/definition/american_english/polyvalent on Jan. 22, 2014.*
Rich et al. Transfer RNA: Molecular Structure, Sequence, and Properties. Annual Reviews in Biochemistry, 1976. 45:805-860.*
Pardridge, William M. shRNA and SiRNa Delivery to the Brain. Advanced Drug Delivery Rev., 2007. 59(2-3):141-152.*
Severcan et al., "Square-Shaped RNA Particles from Different RNA Folds", Nano Letters, vol. 9, No. 3, pp. 1270-1277 (2009).
Severcan et al., "Supporting Information: Square-Shaped RNA Particles From Different RNA Folds", Nano Letters, pp. 1-18 (2009).
Severcan et al., "Computational and Experimental RNA Nanoparticle Design", Automation in Proteomics and Genomics: An Engineering Case-Based Approach, pp. 193-220 (2009).
Peixuan Guo, "RNA Nanotechnology: Engineering, Assembly and Applications in Detection, Gene Delivery and Therapy", Journal of Nanoscience and Nanotechnology, vol. 5, pp. 1964-1982 (2005).
Jaeger et al., "The architectonics of programmable RNA and DNA nanostructures", Current Opinion in Structural Biology, vol. 16, No. 4, pp. 531-543 (2006).
Chworos et al., "Building Programmable Jigsaw Puzzles with RNA", Science, vol. 306, No. 5704, pp. 2068-2072 (2004).
Yingling et al., "Computational Design of an RNA Hexagonal Nanoring and an RNA Nanotube", Nano Letters, vol. 7, No. 8, pp. 2328-2334 (2007).
Khaled et al., "Controllable Self-Assembly of Nanoparticles for Specific Delivery of Multiple Therapeutic Molecules to Cancer Cells Using RNA Nanotechnology", Nano Letters, vol. 5, No. 9, pp. 1797-1808 (2005).
Nasalean et al., "Controlling RNA self-Assembly to for filaments", Nucleic Acids Research, vol. 34, No. 5, pp. 1381-1392 (2006).

* cited by examiner

*Primary Examiner* — Christopher M Babic
*Assistant Examiner* — Kimberly A Aron
(74) *Attorney, Agent, or Firm* — Locke Lord LLP; Gabriel J. McCool

(57) ABSTRACT

The instant invention provides polyvalent RNA nanoparticles comprising RNA motifs as building blocks that can form RNA nanotubes. The polyvalent RNA nanoparticles are suitable for therapeutic or diagnostic use in a number of diseases or disorders.

19 Claims, 162 Drawing Sheets

FIG. 1A
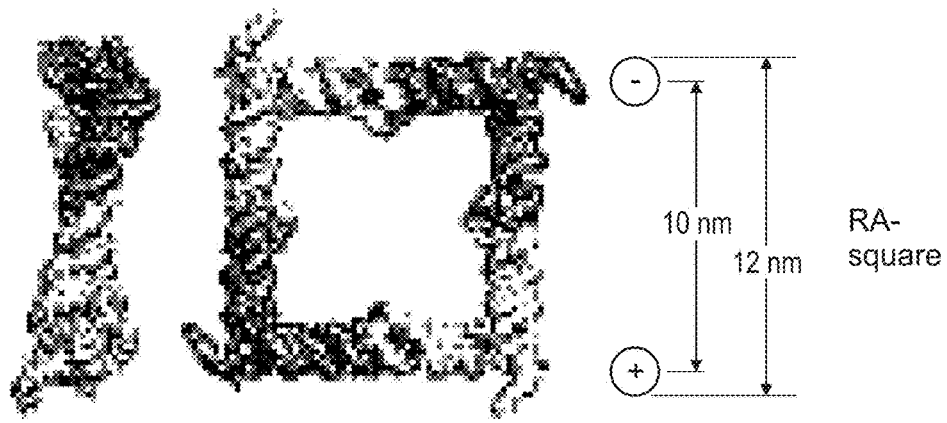
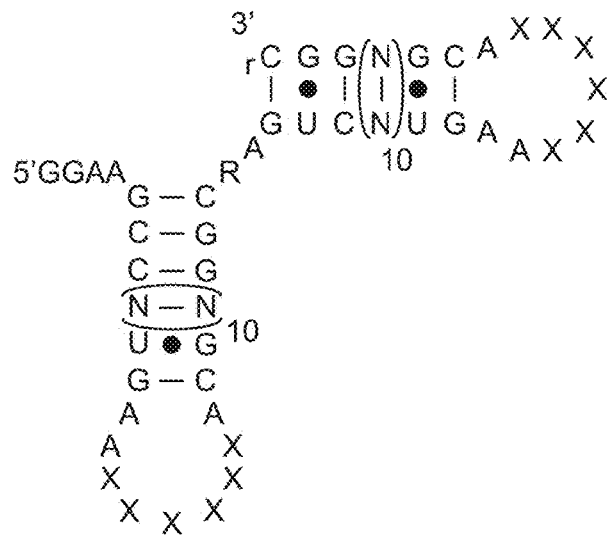
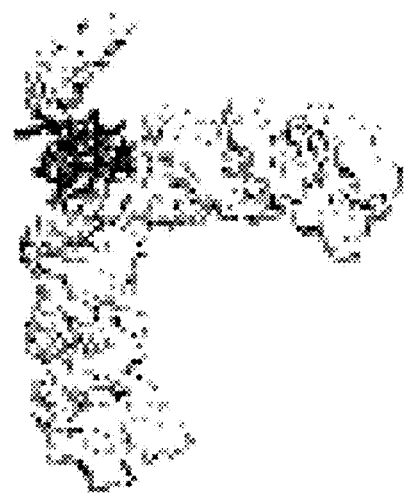

FIG. 1B
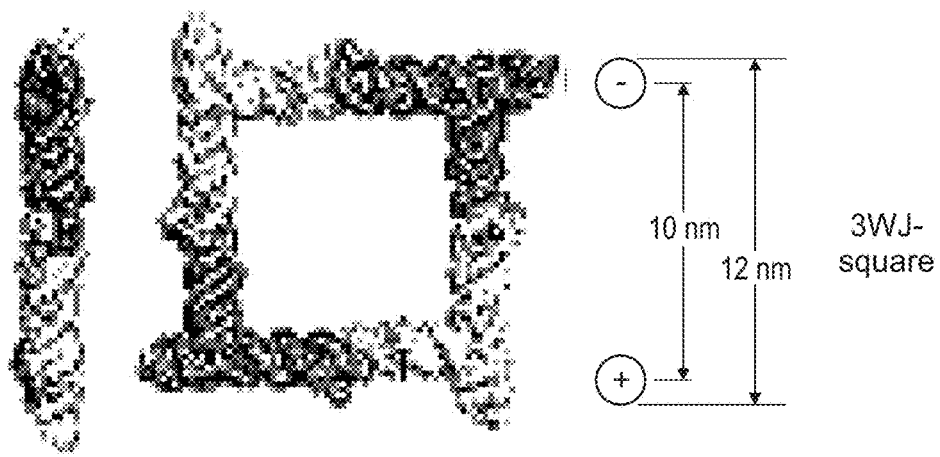
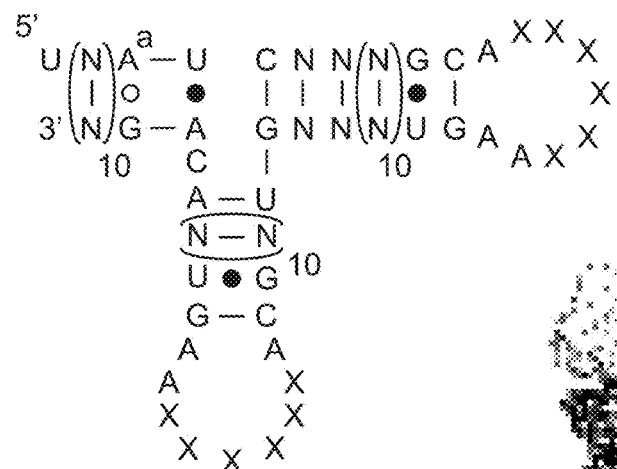
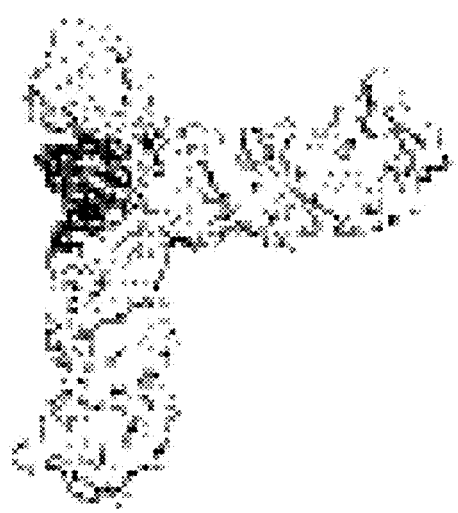

FIG. 1C
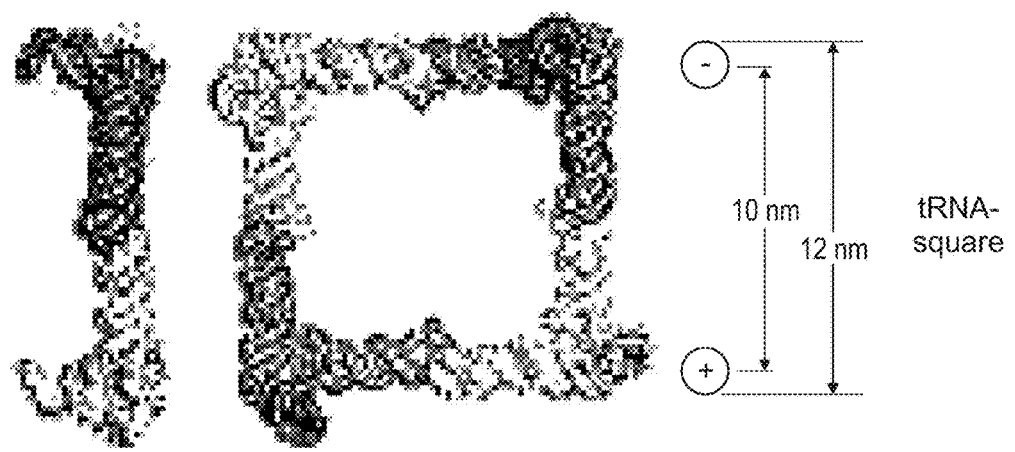
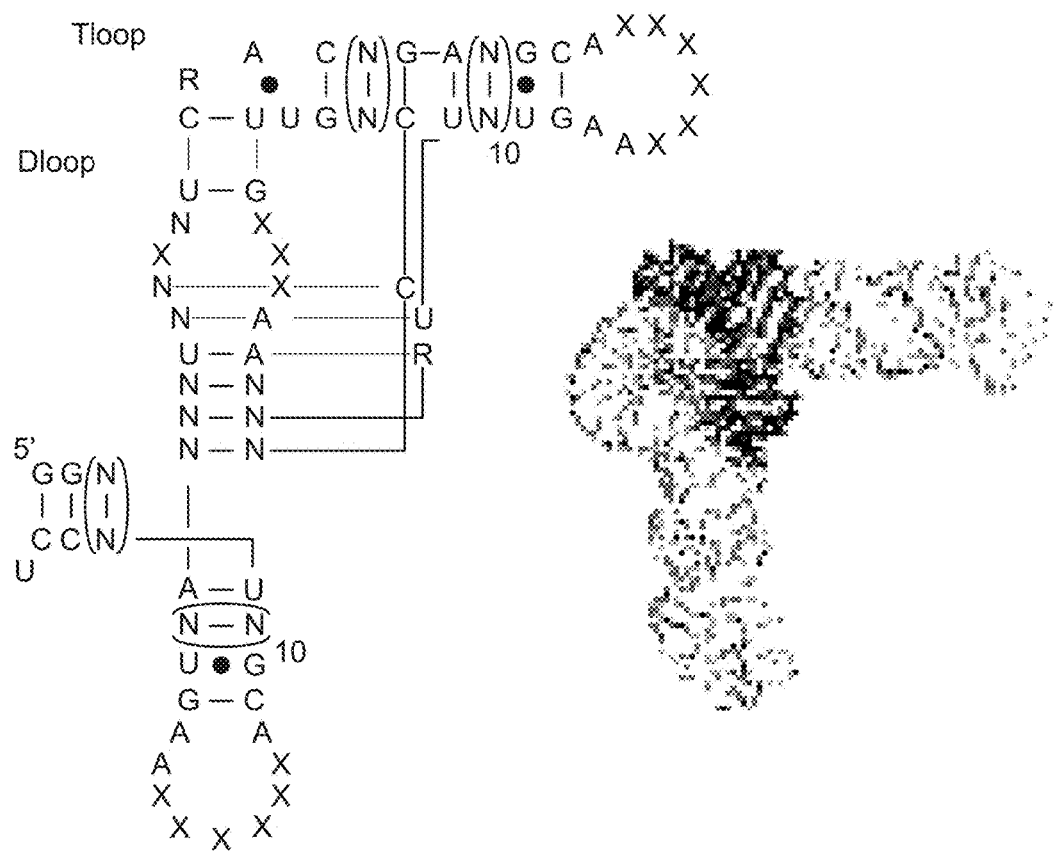

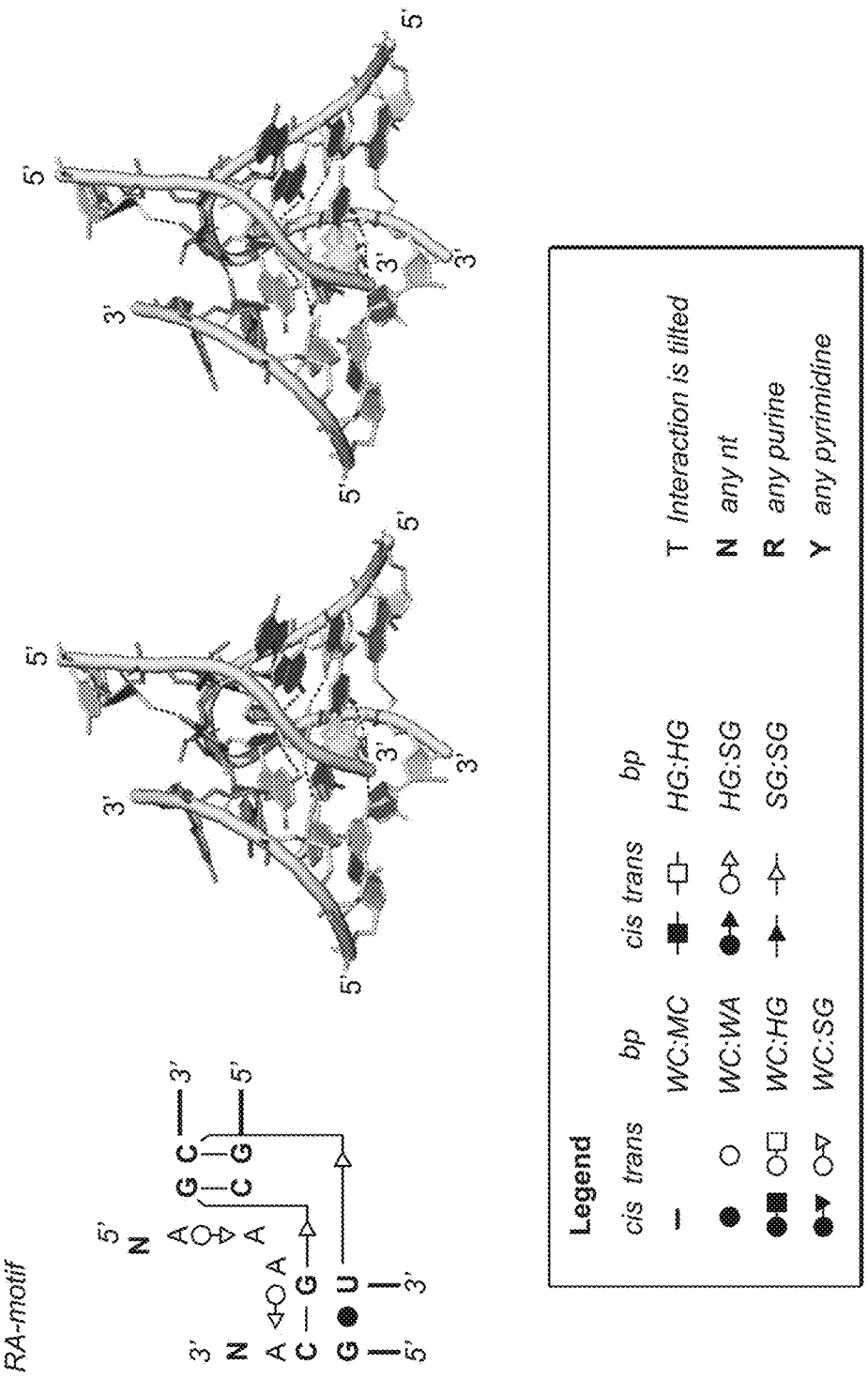

FIG. 2B
*3WJ-motif*
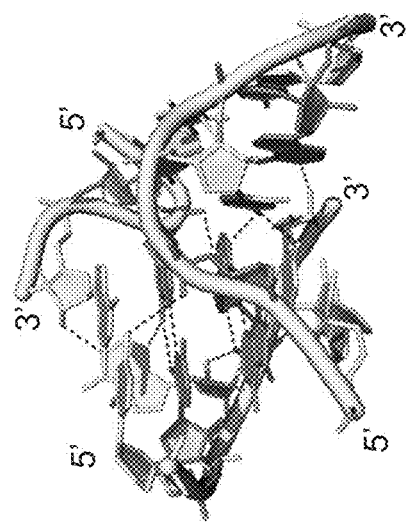
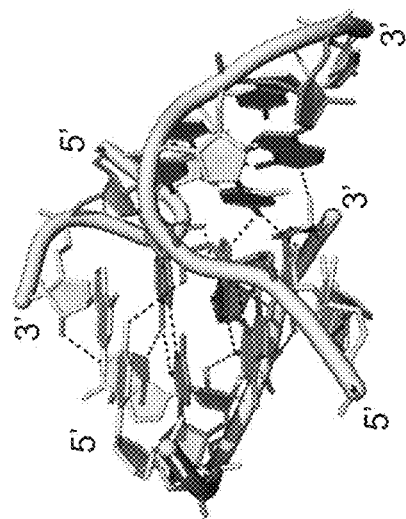
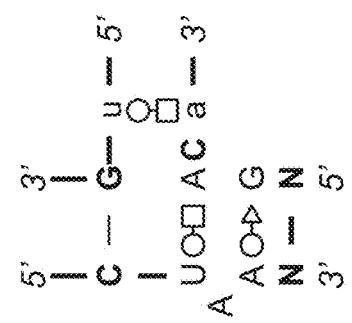

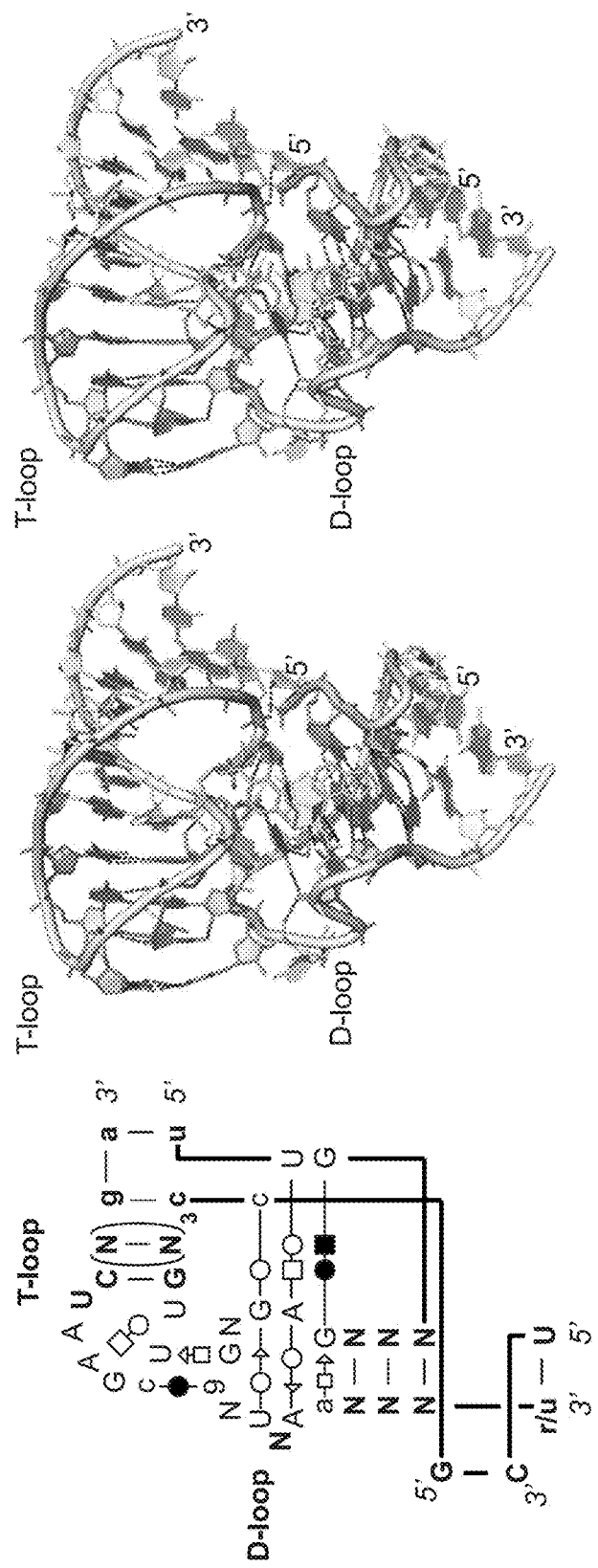

FIG. 5B
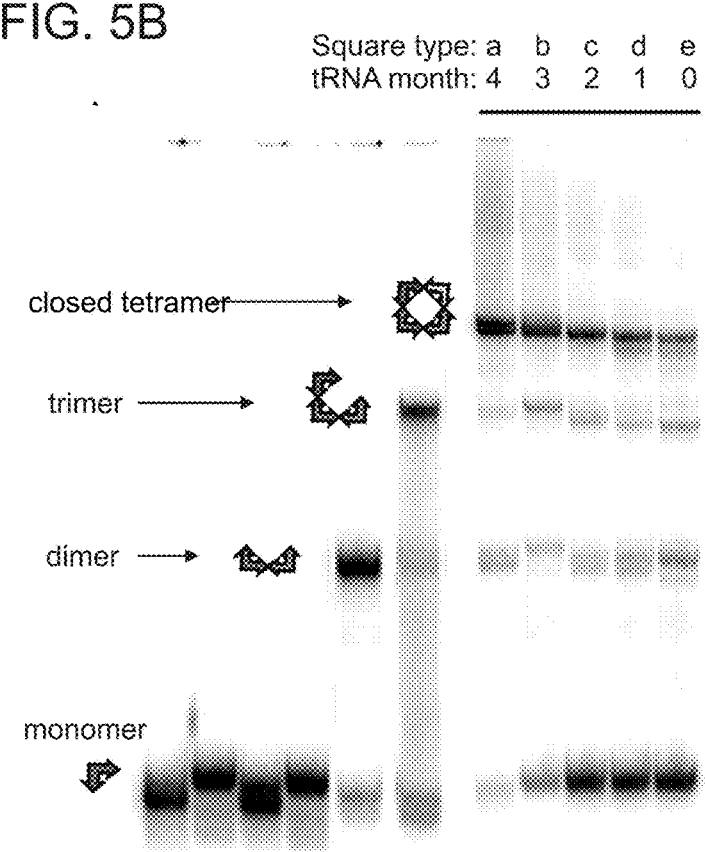
FIG. 5C T1 Structure Cleavage Profile
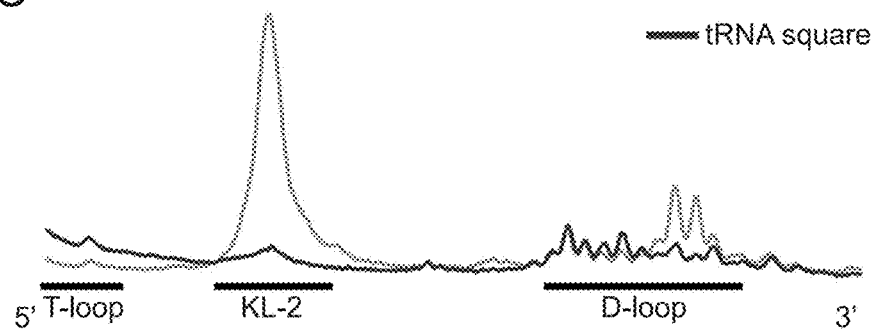
T1 Structure Cleavage Profile
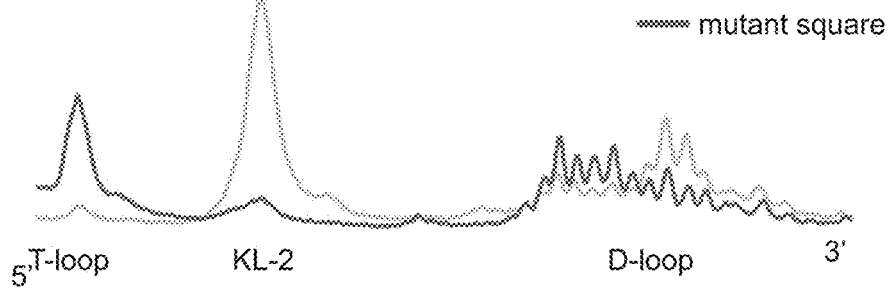

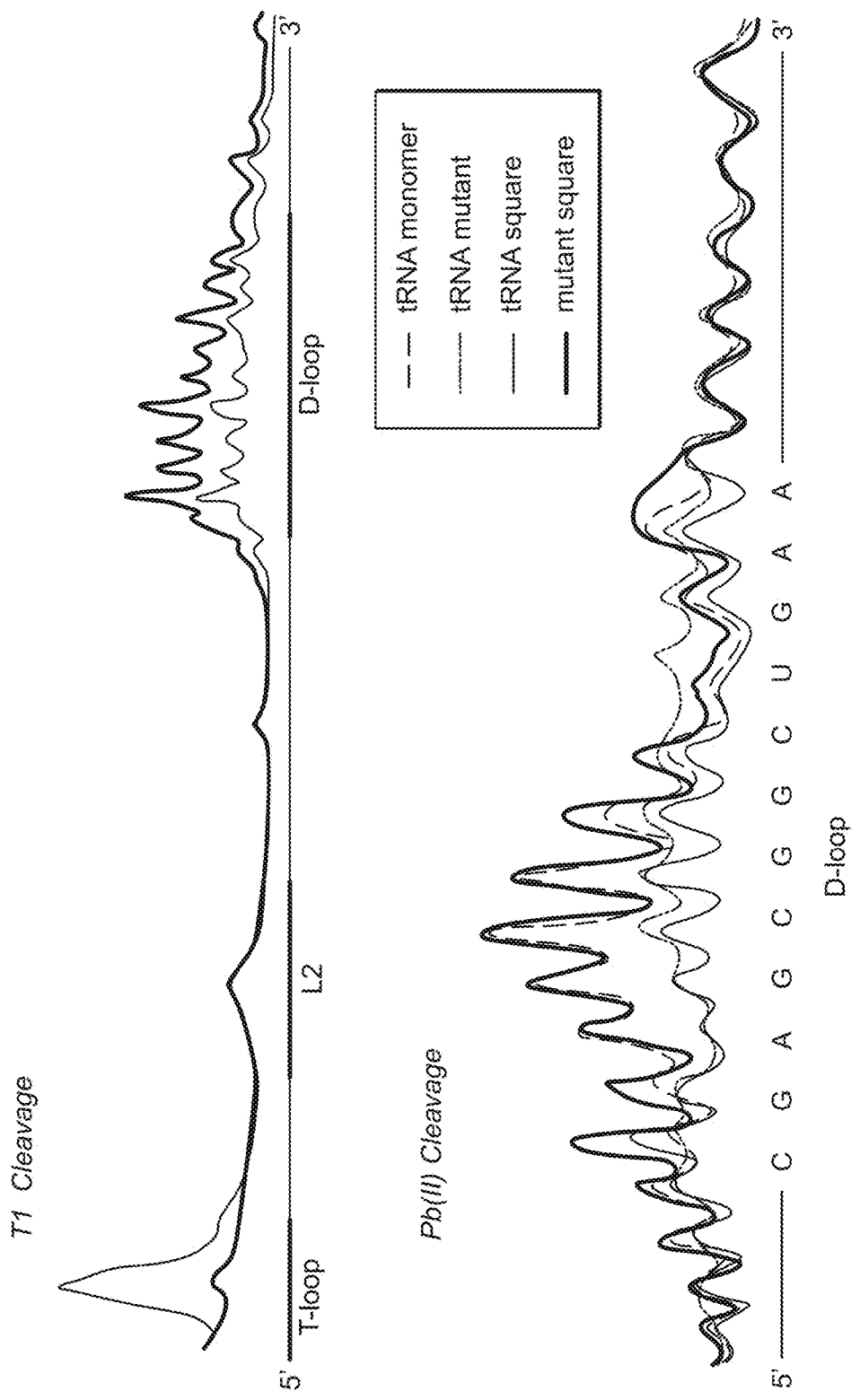

FIG. 8

| RA-square | | |
|---|---|---|
| | RA-A | GGGAAAGCCAUGGACAUGGUGAAGGAGCACGCCAUGUCCGUGGCAAGUCAGACCGAACGU GAAGUGGACACGCGUUCGGUCUGGCACUAGCGUGU |
| | RA-B | GGGAAAGCCAUGGACAUGGUGAAGGAGUCCACACGCCAUGUCCGUGGCAAGUCAGACCGAACGU GAAGCCUGCACGCGUUCGGUCUGGCACUAGCGUGU |
| | RA-C | GGGAAAGCCAUGGACAUGGUGAAGCAGGCACGCCAUGUCCGUGGCAAGUCAGACCGAACGU GAAGCGAGCACGCGUUCGGUCUGGCACUAGCGUGU |
| | RA-D | GGGAAAGCCAUGGACAUGGUGAAGGAGCUCGCCAUGUCCGUGGCAAGUCAGACCGAACGU GAAGCCUCCACGCGUUCGGUCUGGCACUAGCGUGU |
| | RA-sd_L1 | GGGAAAGCCAUGGACAUGGUGAAGGAGCACGCCAUGUCCGUGGCAAGUCAGACCGAACG UGAAGCCUCCACGCGUUCCACGCGUUCGGUCUGGCACGCGUGU |
| | RA-sd_L5 | GGGAAAGCCAUGGACAUGGUGAACGCGCCAUGUCCGUGGCAAGUCAGACCGAACG UGAAGCGAAGAGACGCGUUCGGUUCGGCACUAGCGUGU |

FIG. 8 (continued)

| | | |
|---|---|---|
| 3WJ-square | 3WJ-A | GGGACGGACAGCGUGCAUGGUGAAGGAGGCACGCCAUGCACGCUGCAGACCGAACGUGAAG UGGACACGCGUUCGGUCUGCUAACGUUCCU |
| | 3WJ-B | GGGACGGACAGCGUGCAUGGUGAAGUCCACGCCAUGCACGCUGCAGACCGAACGUGAAG CCUGCACGCGUUCGGUCUGCUAACGUUCCU |
| | 3WJ-C | GGGACGGACAGCGUGCAUGGUGAAGCAGGCACGCCAUGCACGCUGCAGACCGAACGUGAAG CGAGCACGCGUUCGGUCUGCUAACGUUCCU |
| | 3WJ-D | GGGACGGACAGCGUGCAUGGUGAAGCUCGCACGCCAUGCACGCUGCAGACCGAACGUGAAG CCUCCACGCGUUCGGUCUGCUAACGUUCCU |
| | 3WJ-sd_L1 | GGGACGGACAGCGUGCAUGGUGAAGGAGGCACGCCAUGCACGCUGCAGACCGAACGUGAAG CCUCCACGCGUUCGGUCUGCUAACGUUCCU |
| | 3WJ-sd_L5 | GGGACGGACAGCGUGCAUGGUGAACUUCGCACGCCAUGCACGCUGCAGACCGAACGUGAAG CGAAGACGCCGUUCGGUCUGCUAACGUUCCU |
| | 3WJ-P_L1 | GGGCUAACGCCAGACCGAUGAACUUCGCACGCCAUGCACGCUGCAUUGAAGCCU CCACGAUGCACGGCUGCCCGCAUCC |
| | 3WJ-P_L5 | GGGCUAACGCCAGACCGAUGAACUUCGCACGCCAUGCACGCUGCAUUGAAGCGA AGACGAUGCACGGCUGCCCGCAUCC |

FIG. 8 (continued)

| | | |
|---|---|---|
| w.t. tRNA-square | tRNA-A | GGGACCUCCGUGGUUCGAAUCCACGUAGGUCCGGAUGAAGUGGACAGCGUCCAGGCUGGU<br>AUGGCCGAGCGGUCUGAAGGCGCUGAAGGAGGCACUCGUAGUGAAGGCCUACGAGCCGUCCAGGUCCCU |
| | tRNA-B | GGGACCUCCGUGGUUCGAAUCCACGUAGGUCCGGAUGAAGUGGACACGCGUCCAGGCUGGU<br>AUGGCCGAGCGGUCUGAAGGCGCUGAAGUCCACGCUACGAGUAGGUCCCU |
| | tRNA-C | GGGACCUCCGUGGUUCGAAUCCACGUAGGUCCGGAUGAAGUGGAGAGCGUCCAGGCUGGU<br>AUGGCCGAGCGGUCUGAAGGCAGGCAGCCUACGAGUAGGUCCCU |
| | tRNA-D | GGGACCUCCGUGGUUCGAAUCCACGUAGGUCCGGAUGAAGCGAAGCCUCCAGGCUGGU<br>AUGGCCGAGCGGUCUGAAGGCUCGCCACGCUACGAGUAGGUCCCU |
| | tRNA-KL5a | GGGACCUCCGUGGUUCGAAUCCACGUAGGUCCGGAUGAAGUCCACGCUCCAGGCUGGU<br>AUGGCCGAGCGGUCUGAAGGCAACUUCGCACACGAGUAGGUCCCU |
| | tRNA-KL5b | GGGACCUCCGUGGUUCGAAUCCACGUAGGUCCGGAUGAAGUGGAGAGCCACGCUCCAGGCUGGU<br>AUGGCCGAGCGGUCUGAAGGCGAAGACGCUACGAGUAGGUCCCU |
| | tRNA sd_L1 | GGGACCUCCGUGGUUCGAAUCCACGUAGGUCCGGAUGAAGUGGAAGAGGCACGCUCCAGGCUGGU<br>AUGGCCGAGCGGUCUGAAGGCCUCCACGCUACGAGUAGGUCCCU |
| | tRNA sd_L5 | GGGACCUCCGUGGUUCGAAUCCACGUAGGUCCGGAUGAAGUGGAGAGACGCUUCGCACGCUCCAGGCUGGU<br>AUGGCCGAGCGGUCUGAAGGCGAAGACGCUACGAGUAGGUCCCU |

FIG. 8 (continued)

| Mutant tRNA-square | | |
|---|---|---|
| m-tRNA-A | GGGACCUUCCGUGUGG GAAUCCACGUACCAGCCUGGAUGAAGUGGACACGUCCAGGCUGGU AUGGCCGAGCGGUCUAAGGCGCUGCGUUCAGGUCUCGUAGCACGAGUAGGCUGGU | |
| m-tRNA-B | GGGACCUUCCGUGUGG GAAUCCACGUACCAGCCUGGAUGAAGUGGAGCACGUCCAGGUCCCU AUGGCCGAGCGGUCUAAGGCACUCGUAGUCCGCUACAGAUCCGUAGCACGAGUAGGUCCCU | |
| m-tRNA-C | GGGACCUUCCGUGUGG GAAUCCACGUACCAGCCUGGAUGAAGCGAGCACGUCCAGGCUGGU AUGGCCGAGCGGUCUAAGGCACUCGUAGUCCAGCUACGAGUAGGUCCCU | |
| m-tRNA-D | GGGACCUCCGUGUGG GAAUCCACGUACCAGCCUGGAUGAAGCCUCCACGUCCAGGCUGGU AUGGCCGAGCGGUCUAAGGCACUCGUAGUCUCCGCUACGAGUAGGUCCCU | |
| m-tRNA-sd_L1 | GGGACCUCCGUGUGG GAAUCCACGUACCAGCCUGGAUGAAGGAGGCACGUCCAGGCUGGU AUGGCCGAGCGGUCUAAGGCACUCGUAGUCUCCGCUACGAGUAGGUCCCU | |
| m-tRNA-sd_L5 | GGGACCUCCGUGUGG GAAUCCACGUACCAGCCUGGAUGAACUUCGACGUCCAGGCUGGU AUGGCCGAGCGGUCUAAGGCACUCGUAGAAGACGCUACGAGUAGGUCCCU | |

FIG. 9B
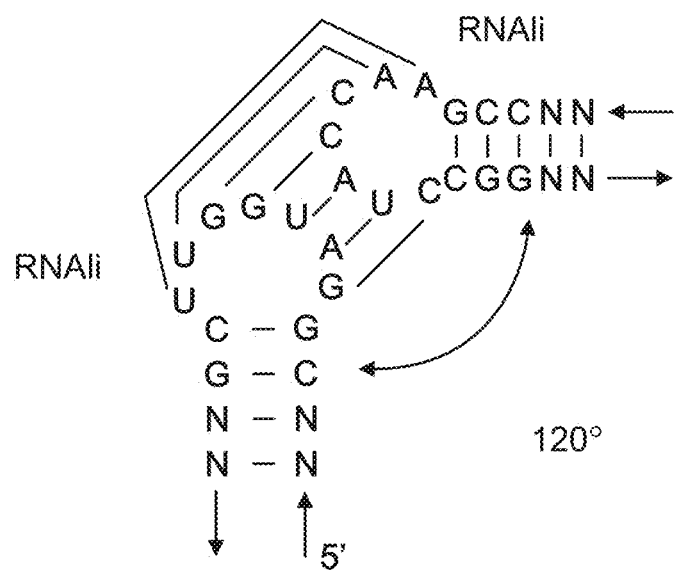
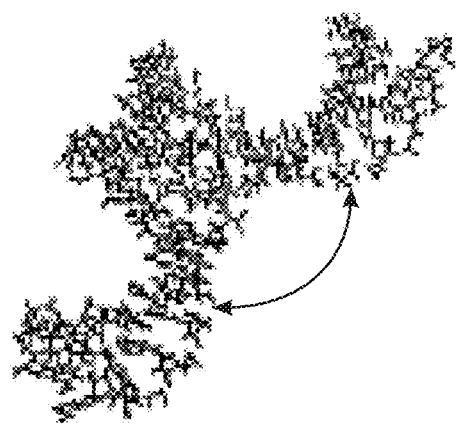

| # | Polygon | Circumference (nm) | AFM IMAGE Scale: 100nm | Circumference Measured |
|---|---------|--------------------|------------------------|------------------------|
| 3 | △ | 39.3 | | 39.0 |
| 4 | □ | 52.4 | | 45.0 |
| 5 | ⬠ | 65.5 | | 63.4 |
| 6 | ⬡ | 78.6 | | 73.1 |
| 7 | heptagon | 91.7 | | 87.8 |
| 8 | octagon | 104.8 | | 98.0 |
| 9 | nonagon | 117.9 | | 112.2 |
| 10 | decagon | 131 | | 126.6 |
| 11 | 11-gon | 144.1 | | 146.3 |
| 15 | 15-gon | 196.5 | | 195.1 |

FIG. 14

FIG. 15A
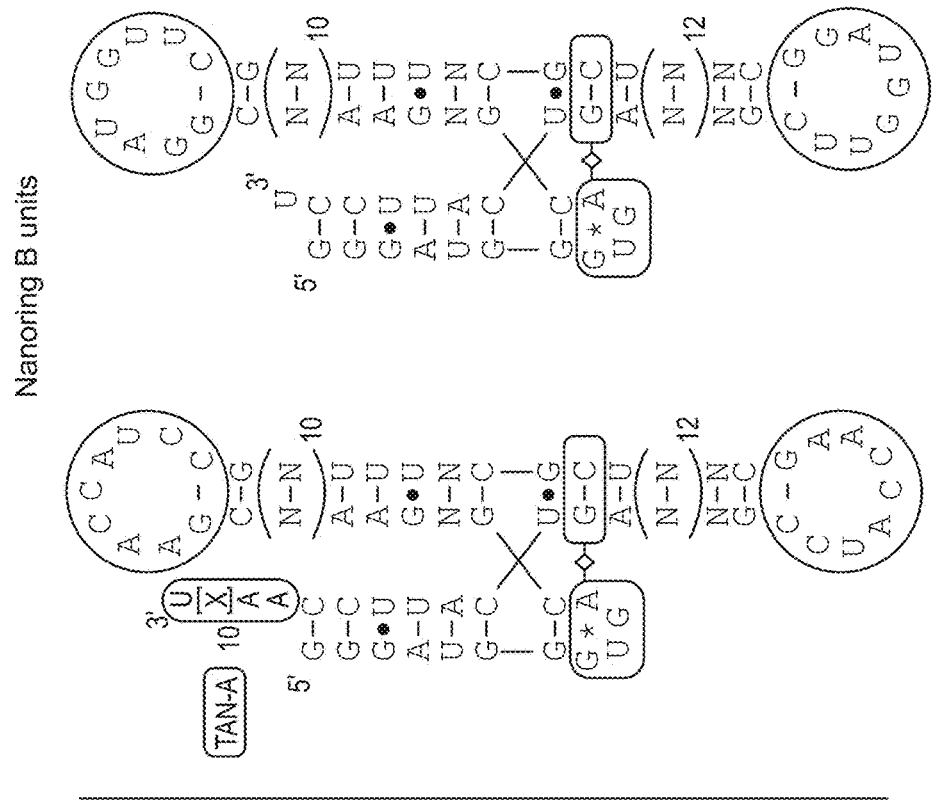
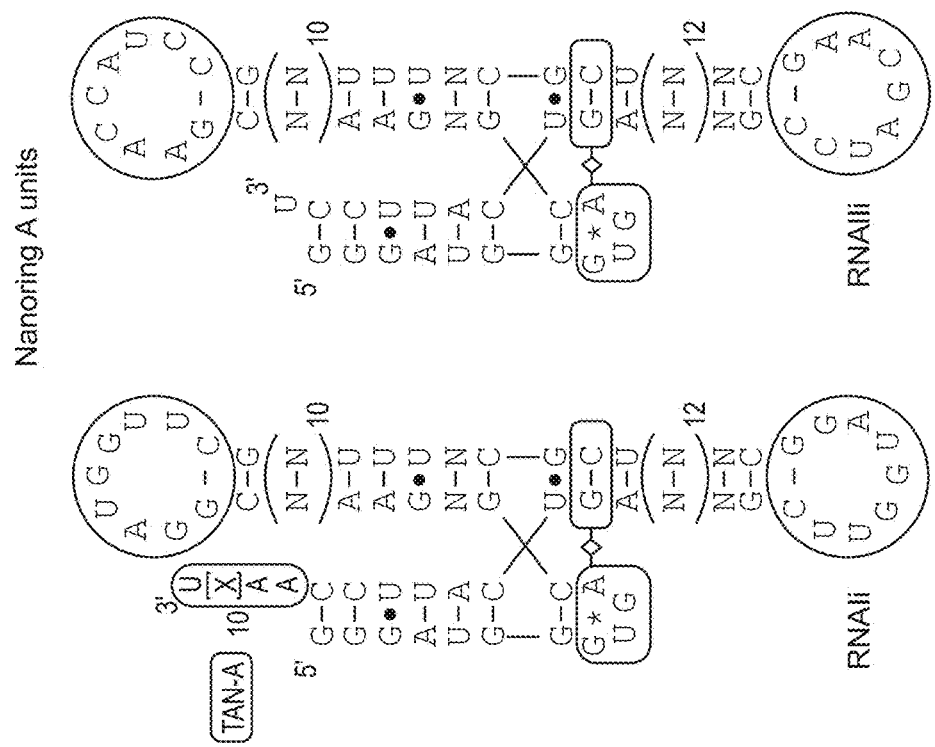

FIG. 16

| | Signature | |
|---|---|---|
| LARGE NANORING - REGULAR | A | GGGAAUCCAGGGGAACGGAUGGUUCGUUCCCCGUUCCCCGUUCUCAACCGCACCGGAUGGUUCGGUGCGGGUUGGGAACGGG |
| | B | GGGAAUCCAGGGGAACGAACCAUCCGUUCCCCGUUCCCCGUUCUCAACCGCACCGAACCAUCCGGUGCGGGUUGGGAACGGG |
| | SD | GGGAAUCCAGGGGAACGGAUGGUUCGUUCCCCGUUCCCCGUUCUCAACCGCACCGAACCAUCCGGUGCGGGUUGGGAACGGG |
| LARGE NANORING - STABILIZED | A<sub>S</sub> | GGGAUGGGUGACGUGGAAUCCAGGGAACGAUGGUUCGUUCCCUUGGGUUCCCUUGGGUUCUACGCUAAGCGCAACUGCACCGGAUGGUUCGGUGCGGGUUUAGUCAUUCCU |
| | B<sub>S</sub> | GGGAUGGGUGACGUGGAAUCCAGGGAACGAACCAUCCGUUCCCUUGGGUUCCCUUGGGUUCUACGCUAAGCGCAACUGCACCGAACCAUCCGGUGCGGGUUUAGUCAUUCCU |
| | SD<sub>S</sub> | GGGAUGGGUGACGUGGAAUCCAGGGAACGAUGGUUCGUUCCCUUGGGUUCCCUUGGGUUCUACGCUAAGCGCAACUGCACCGAACCAUCCGGUGCGGGUUUAGUCAUUCCU |
| | A<sub>C</sub> | GGGAUGGGUGACGUGGAAUCCAGGGAACGAGGAGGCACGGUUGCGGGUUGCCCUUGGUUCUACGCUAAGCCUGCGAAGCCUGCGAAGCAGGCUGCGUUUAGUCAUUCCU |
| | B<sub>C</sub> | GGGAUGGGUGACGUGGAAUCCAGGGAACGAGGAGGCACGAAGCAGGCUCCGAAGCCUCCGAAGCAGGCACGUUGCGGGUUCUACGCUAAGCGCAACUGCACCGAAGCAGGCUCCGAAGCCUCCGAAGCAGGCACGUUGCGGGUUUAGUCAUUCCU |

FIG. 16 (continued)

| | | Sequence |
|---|---|---|
| LARGE NANORING | K_D analysis | |
| | RNAII/L0 | GGGAUGGGUGACGUGGAAUCCAGGGGAACGGAUGGUUCGUCCCUUGGGUUCUAGCUAAGCGCAACUGCACCGAAAAAAACGGUGCCGGUUGCGUUUAGUCAUUCCU |
| | RNAIII/L0 | GGGAUGGGUGACGUGGAAUCCAGGGGAACGGAUGGUUCCUUGGGUUCUAGCUAAGCGCAACUGCACCGAAAAAAACGGUGCCGGUUGCGUUUAGUCAUUCCU |
| | L04/L0 | GGGAUGGGUGACGUGGAAUCCAGAAAAAAACGGAGGCACGUUCCCUUGGGUUCUACGCUAAGCCGCAACUGCAACCGAAAAAAACGGUGCCGGUUGCGUUUAGUCAUUCCU |
| | L04/L04' | GGGAUGGGUGACGUGGAAUCCAGAAAAAAACGGUGCCGGUUGCGUUUAGUCAUUCCUAGCCGCAACUGCAAGCCCUCCAAGCCUGCACCGAAAAAAACGGUGCCGGUUGCGUUUAGUCAUUCCU |
| | L0/L12 | GGGAUGGGUGACGUGGAAUCCAGGGGAACGAAAAAAACGUUCCCUUGGGUUCUACGCUAAGCCGCAACUGCAAGCCCUCCAAGCCUGCACCGAAAAAAACGGUGCCGGUUGCGUUUAGUCAUUCCU |
| | L12'/L0 | GGGAUGGGUGACGUGGAAUCCAGGGGAACGAGCAGGCACGUUCCCUUGGGUUCUACGCUAAGCCGCAACUGCACCGAAGCCUGCACCGAAAAAAACGGUGCCGGUUGCGUUUAGUCAUUCCU |
| | Array A1 | GGGAUGGGUGACGUGGAAUCCAGGGGAACGAAGACGGAUGGUUCGUUCCCUUGGGUUCUACGCUAACCGCAACUGCACCGGAUUCGGAACCAUCCGGUUGCGUUUAGUCAUUCCU |
| | Array B1' | GGGAUGGGUGACGUGGAAUCCAGGGGAACGGAUGGUUCUUCCCUUGGGUUCUACGCUAAGCGCAACUGCACCGAACCAUCCGGUUGCGUUUAGUCAUUCCAACGUAGCGCUCCU |

FIG. 16 (continued)

| SMALL NANORING | | | |
|---|---|---|---|
| REG. | Sm-A | | GGGAAUCGGAUGUUCGCUAACGGAUGGUUCGUUAGCU |
| | Sm-B | | GGGAAUCGGAUGUUCGCUAACGGAUGGUUCGUUAGCU |
| STAB | Sm-SD | | GGGAAUCGGAUGUUCGCUAACGAACCAUCCGUUAGCU |
| | Sm-A$_S$ | | GGGAUGGGACGGAUCGGAAUCGAAUCCCGCUAACGGAUGGUUCGUUAGUCAUCC CU |
| | Sm-B$_S$ | | GGGAUGGGACGGAAUCGGAAUCGAAUCCCGCUAACGAACCAUCCGUUAGUCAUCC CU |
| | Sm-SD$_S$ | | GGGAUGGGACGGAAUCGGAAUCGAAUCCCGCUAACGAACCAUCCGUUAGUCAUCC CU |
| K$_D$ | RNAII/L0 | | GGGAUGGGACGGAAUCGGAAUCCCGCUAAACGAAAAAACGUUAGUCAUCC CU |
| | RNAIII/L0 | | GGGAUGGGACGGAAUCGGAAUUCCCGCUAAACGAAAAAACGUUAGUCAUCC CU |

**Hybrid Junction Designs
(Specific Loop/Receptor Pairs)**

FIG. 23 (continued)

|  | H68 Motifs Ribosome | | | P12 Motifs RNase P | | |
|---|---|---|---|---|---|---|
|  | Ec | Tt | Sc | Ec | Tt | Sc |
|  | G–C | G–C | G–C | G–C | G–C | G–C |
|  | G–C | G–C | G–C | G–C | G–C | G–C |
|  | C C | C C | C C | A G | G A | A G |
|  | A G | A G | A A | C A | C G | A A |
|  | A G | A G | A G | A U | G C | C U |
|  | A U | G U | G U | C G | G G | U G |
|  | U•G | U•G | U•G | C G | U•G | A G |
|  | G–C | G–C | G–C | G–C | G–C | G–C |
|  | A–U | A–U | A–U | A–U | A–U | A–U |
|  | A–U | A–U | A–U | A–U | A–U | A–U |

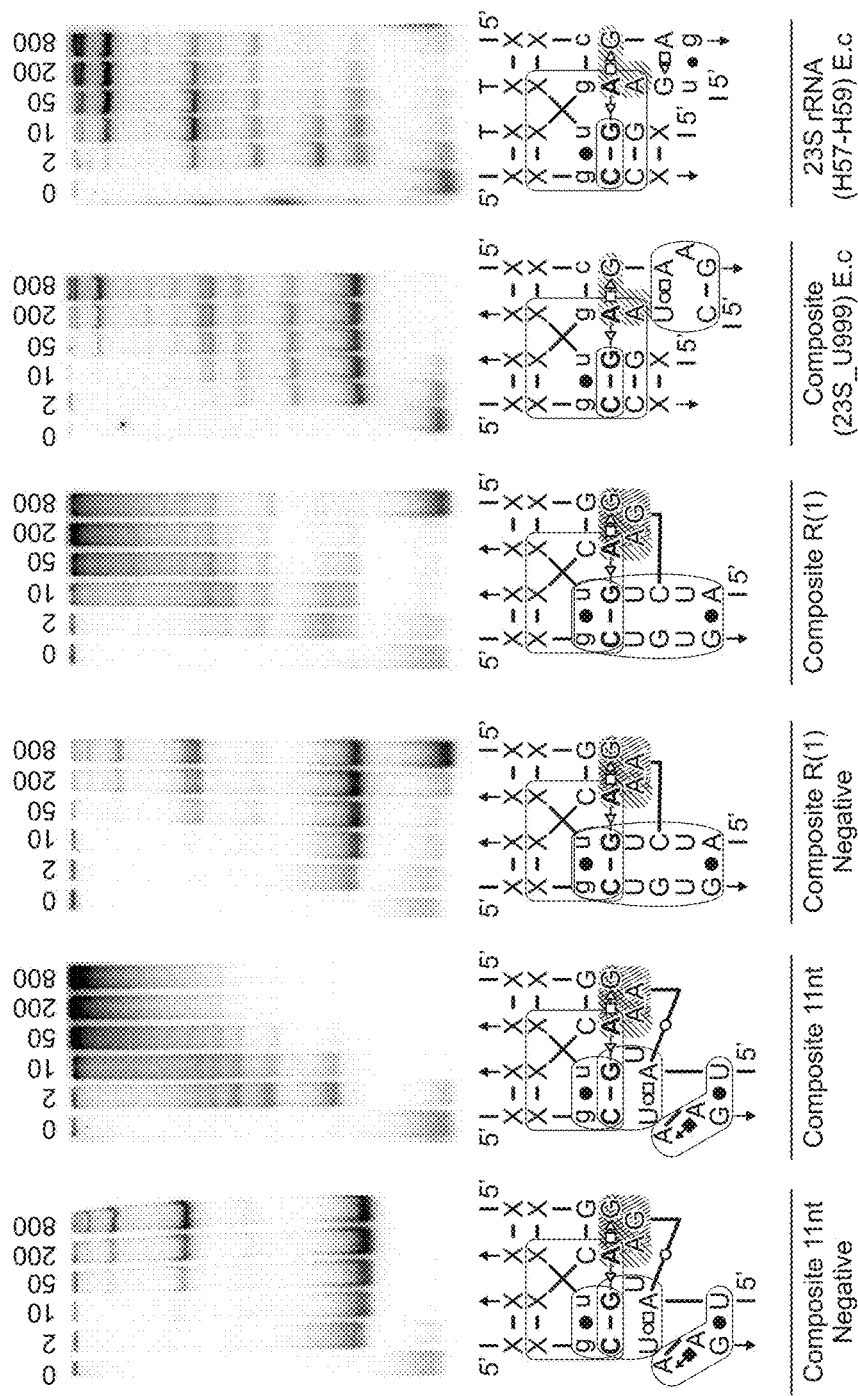

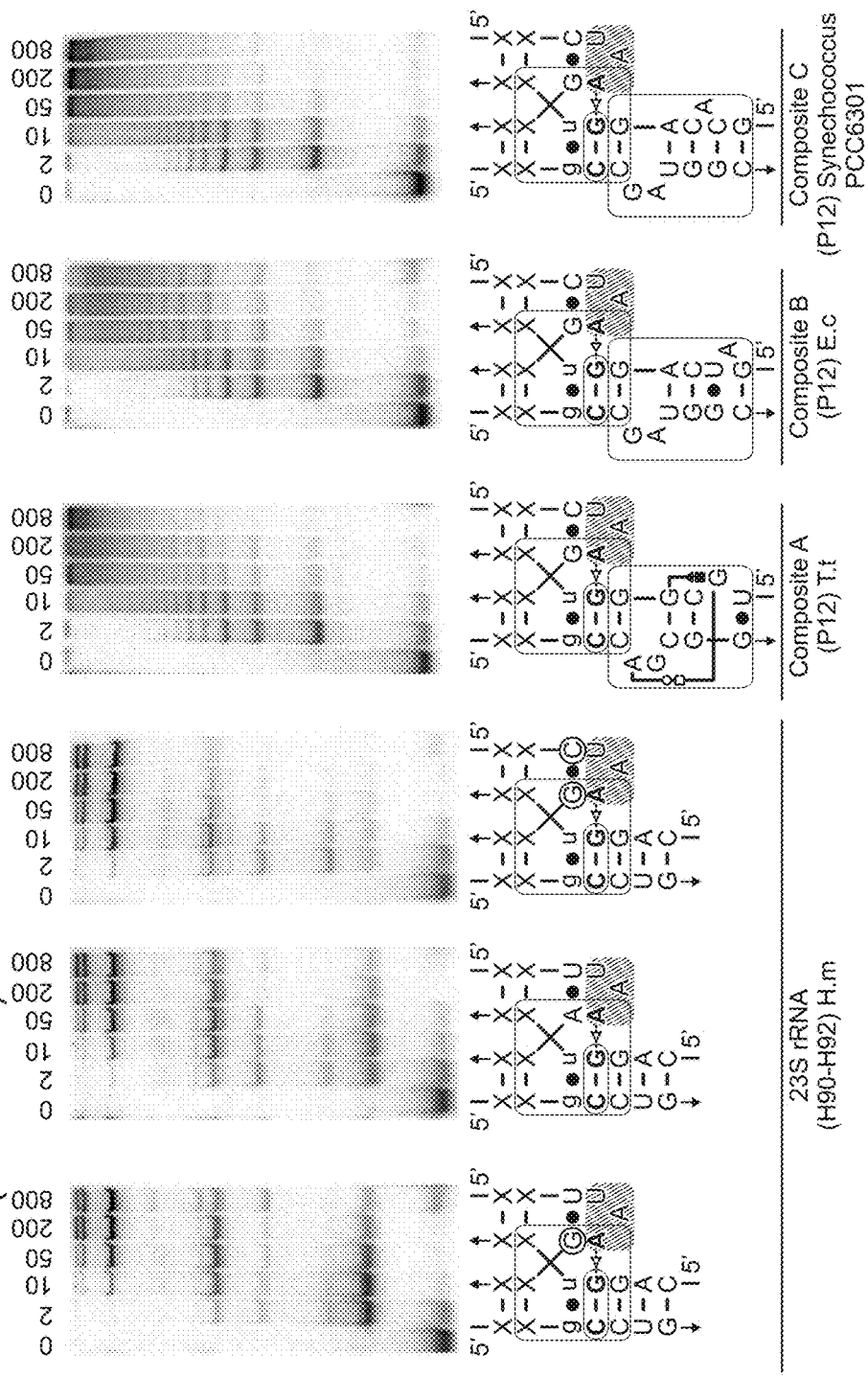

FIG. 26
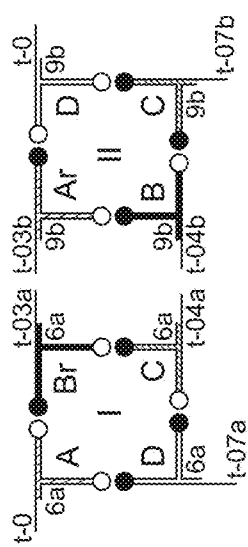
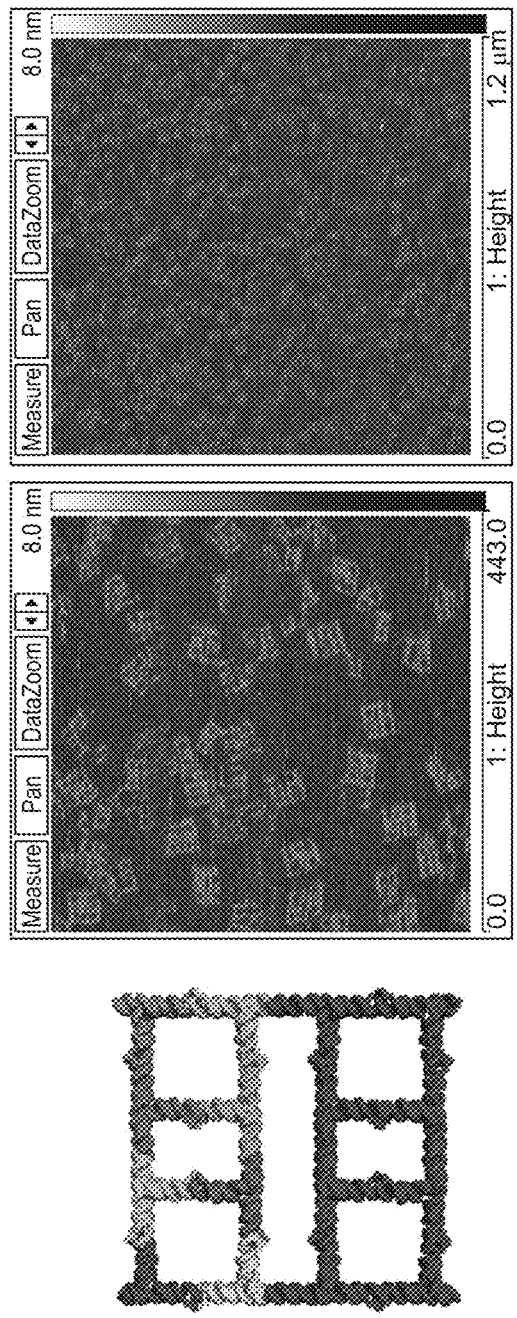

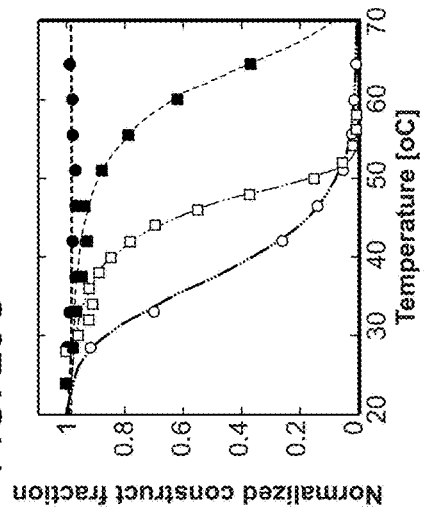
FIG. 29C
FIG. 29D
| Mg (OAc)$_2$ (mM) | 0.2 | 2 | 5 | 15 |
|---|---|---|---|---|
| Tm$^{TGGE}_{Square}$ (°C) | 46 | 60.6 | 60.1 | 65.3 |
| Tm$^{TGGE}_{Cuboid}$ (°C) | 32 | 61.7 | 64.5 | >65.0 |
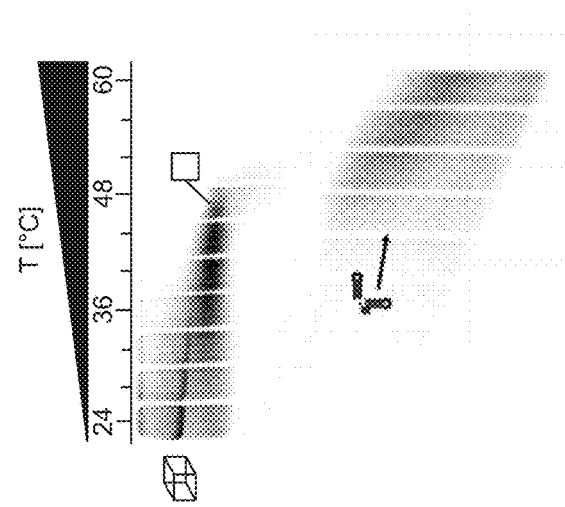
FIG. 29B

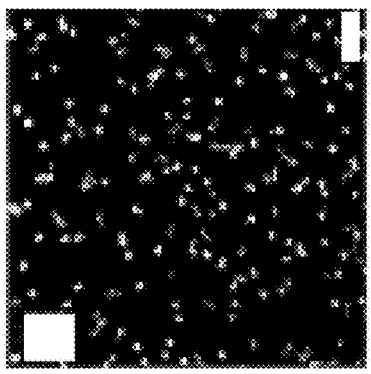 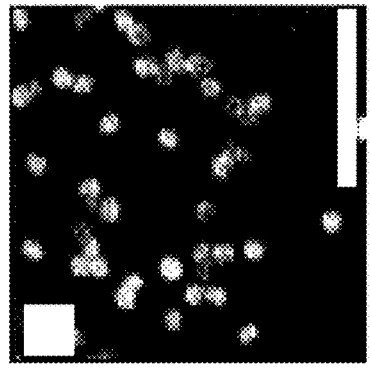 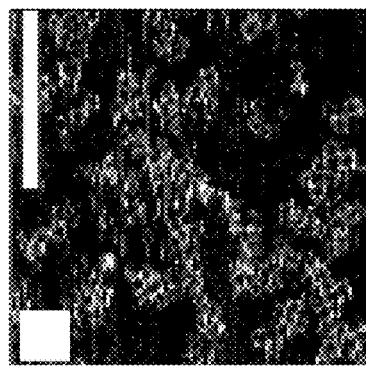 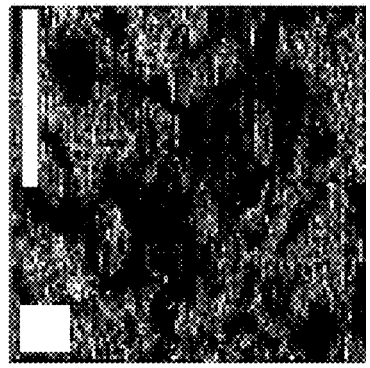
 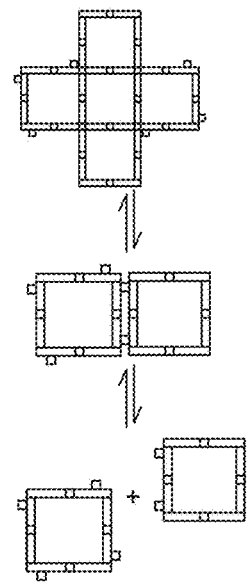 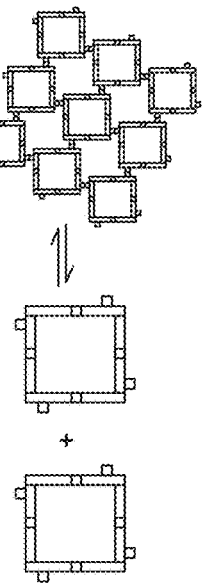
Scale bar = 200nm
FIG. 30a' FIG. 30b' FIG. 30c' FIG. 30d'
FIG. 30a,b FIG. 30c FIG. 30d Scale bar=50nm FIG. 31 (continued)
| Predicted dimensions (nm) | Observed dimensions (nm) |
|---|---|
| 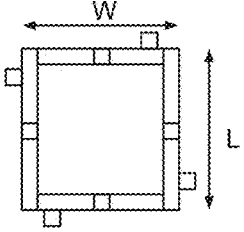<br>(WxLxH)<br>14x14x2.6 | 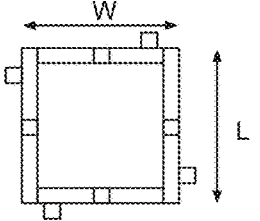<br>14x15x1.5 |
| 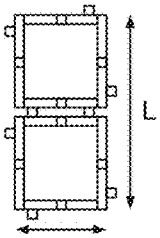<br>(WxLxH)<br>14x36x2.6 | 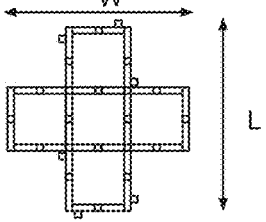<br>29x41x1.5 |
| 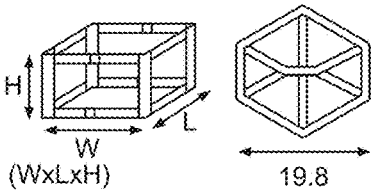<br>(WxLxH)<br>14x14x8 | 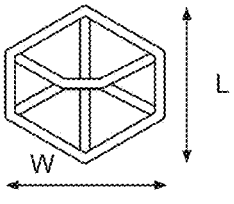<br>23x27x3.4 |
| 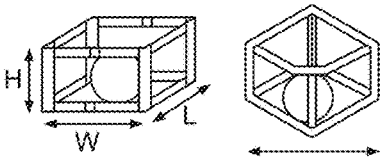<br>(WxLxH)<br>14x14x8 | 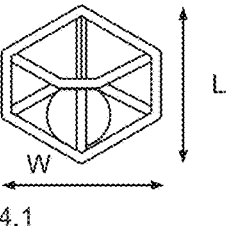<br>27x33x4.1 |

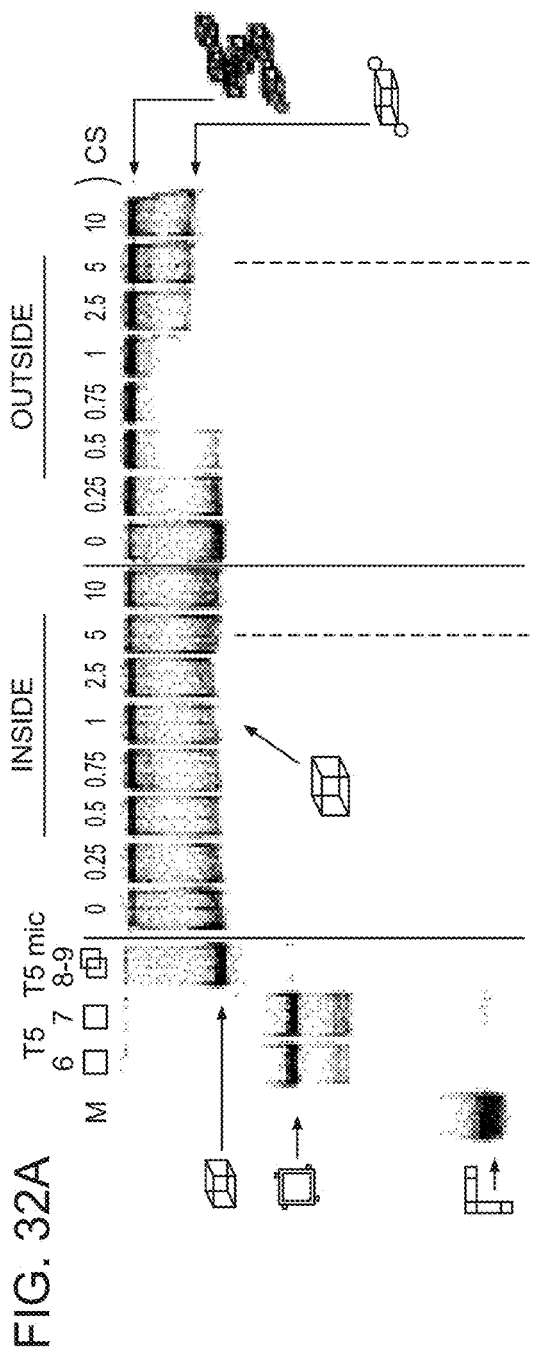
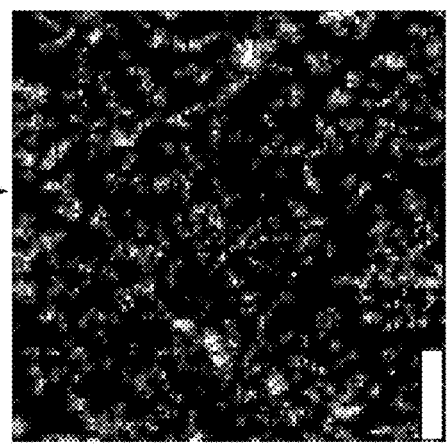
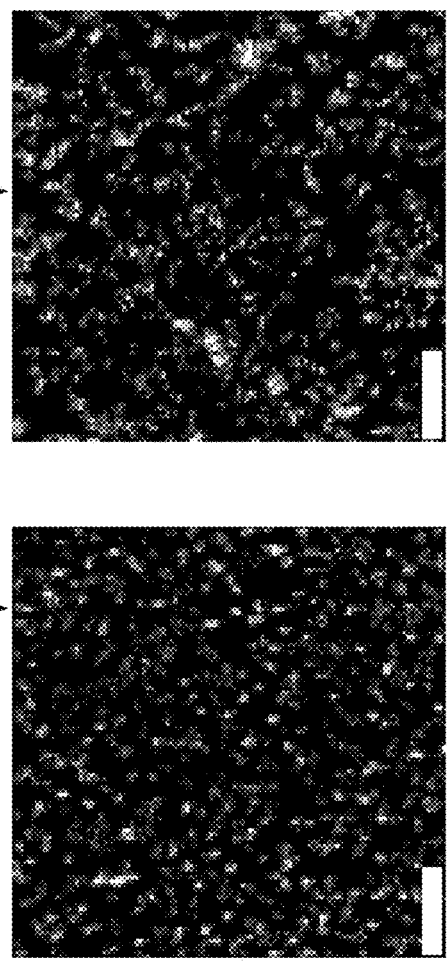
FIG. 32A
FIG. 32C
FIG. 32B

FIG. 33a, b
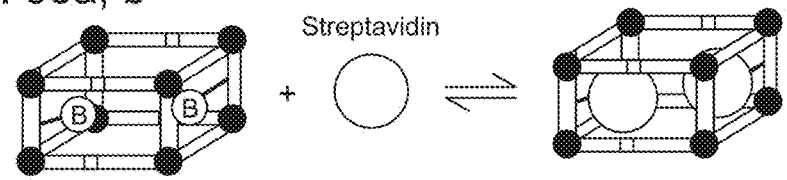
FIG. 33c, d
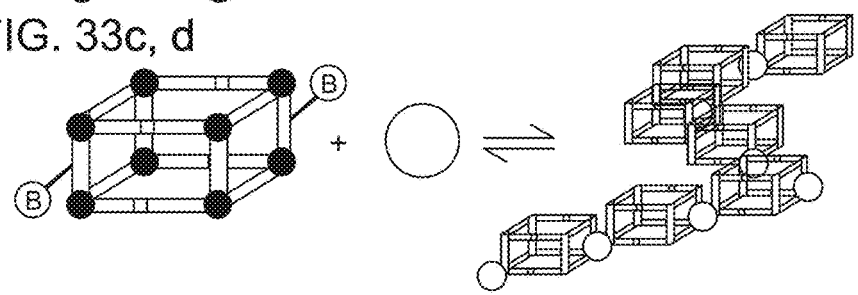
FIG. 33a'
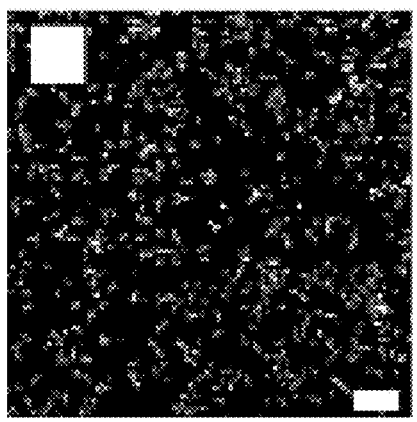
FIG. 33b'
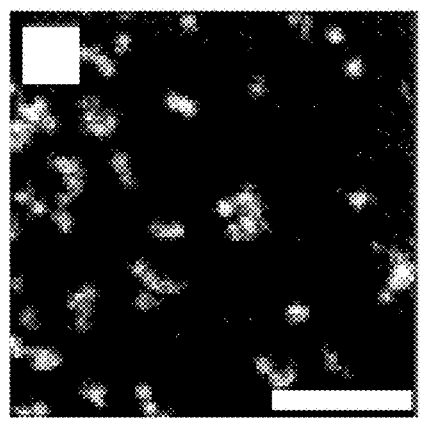
Scale bar=200nm
FIG. 33c'
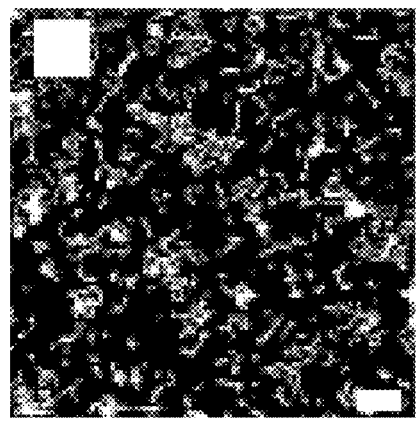
FIG. 33d'
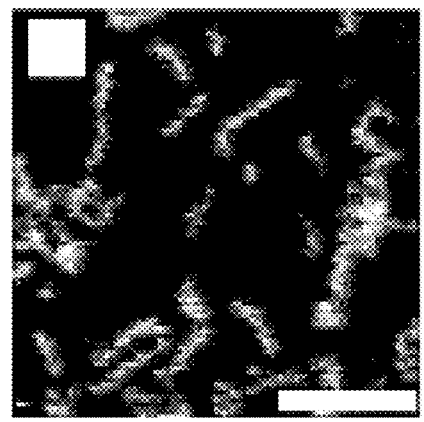

| Lanes | 1 | 2 | 3 | A | B |
|---|---|---|---|---|---|
| % Construct | 57 | 56 | 62 | 45 | 35 |
| Lanes | 4 | 5 | 6 | C | D |
| % Construct | 58 | 58 | 61 | 35 | 33 |

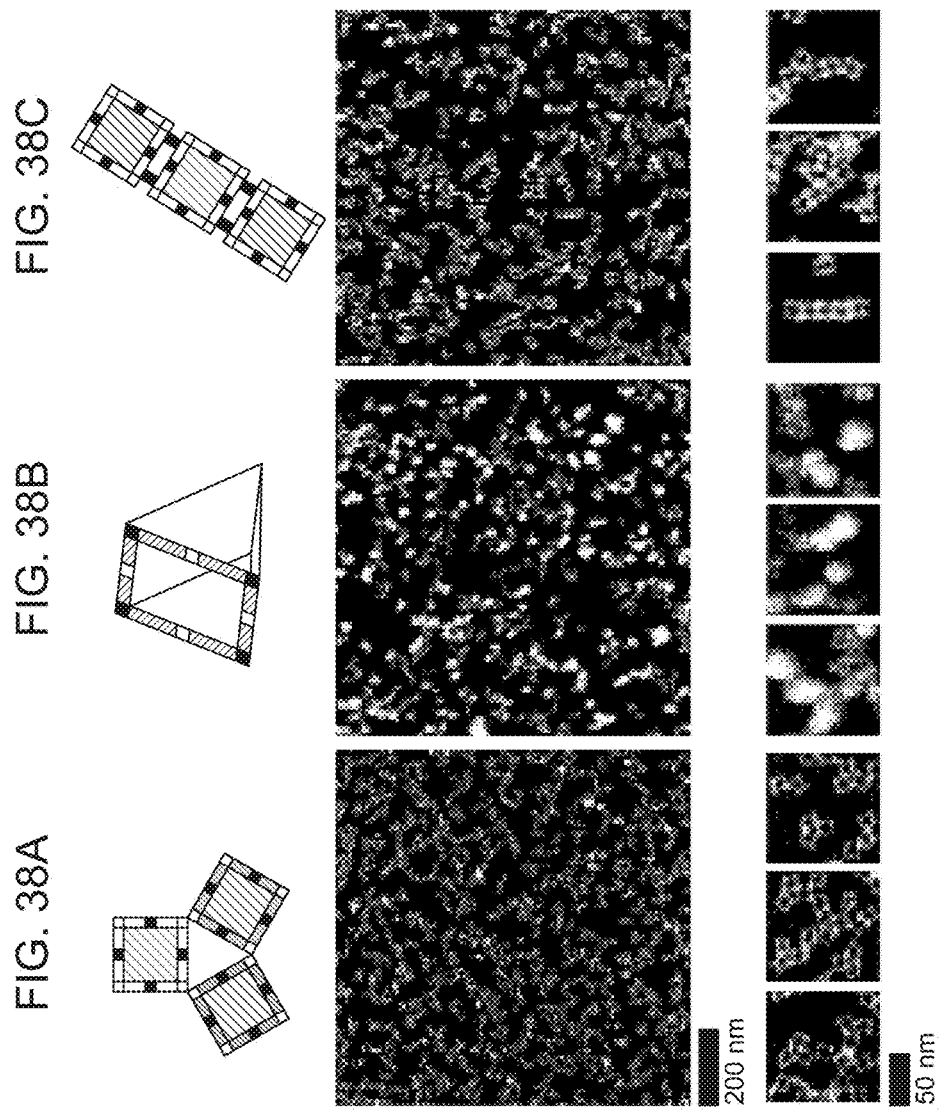

FIG. 39

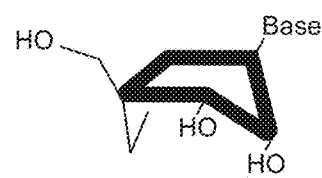
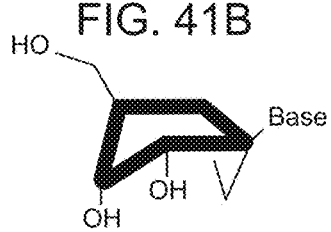
FIG. 41A North, 2'-exo
FIG. 41B South, 3'-exo
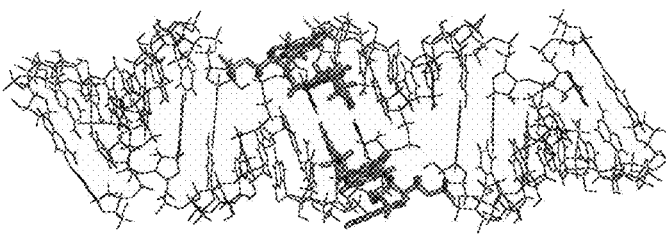
FIG. 41C
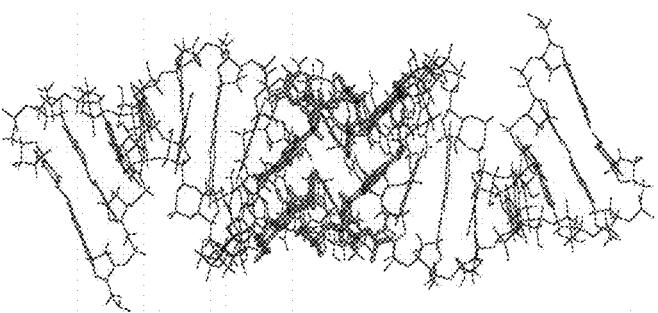
FIG. 41D
FIG. 41E
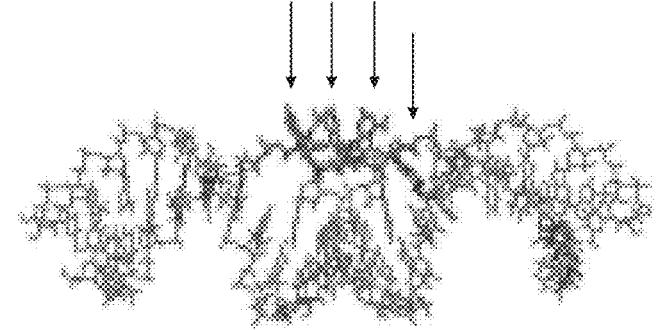

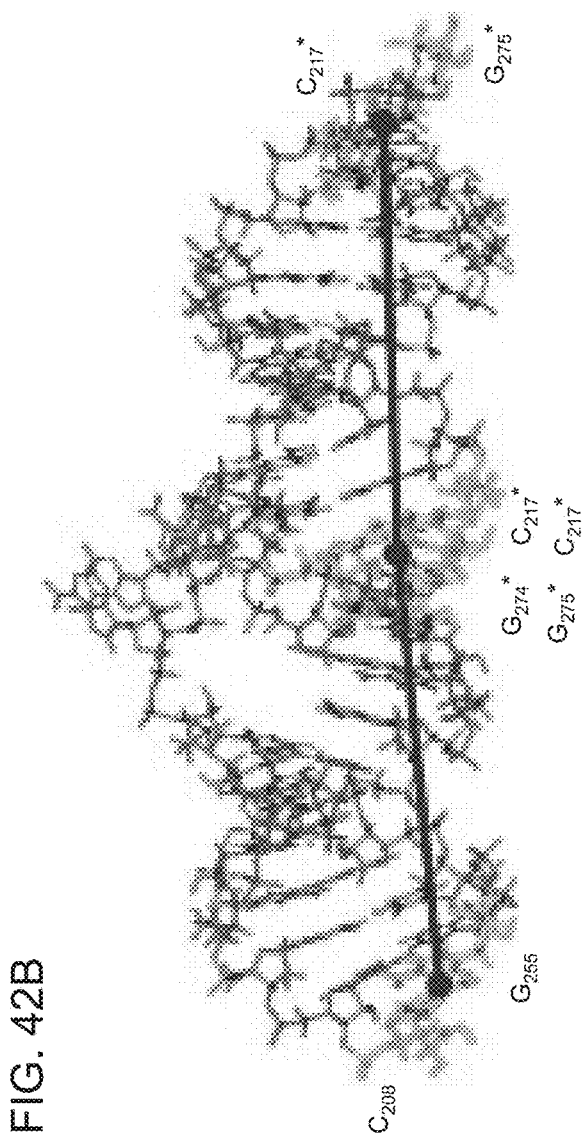

FIG. 48A

Search:

Enter at least one search value

Structure

Entry ID: [_____] (e.g. 11043)
Structure type: [Kissing Loop ▼]
NC-IUBMB Class.: [_____] (e.g. 2HS3)
Angle range: [_____] deg. (e.g. 85-95 85-95 100-180)

Sequence

Sequence: [AAGCGCGCA] (e.g. CGAAG)
Search only in loop region  ⦿
Search any part of sequence  ○

Source

Use non-redundant dataset:  ☐ Yes
Helix Fit Parameters:  ○ Most strict set
 ○ Medium strict set
 ⦿ Least strict set
PDB ID: [2B8R] (e.g. 1ffk)
Author(s) on original publication: [_____] (e.g. Tinoco)
Publication keywords: [_____] (e.g. trna)
Experimental method: [Select experimental method ▼]

[Begin Search] [Clear Fields]

FIG. 50A
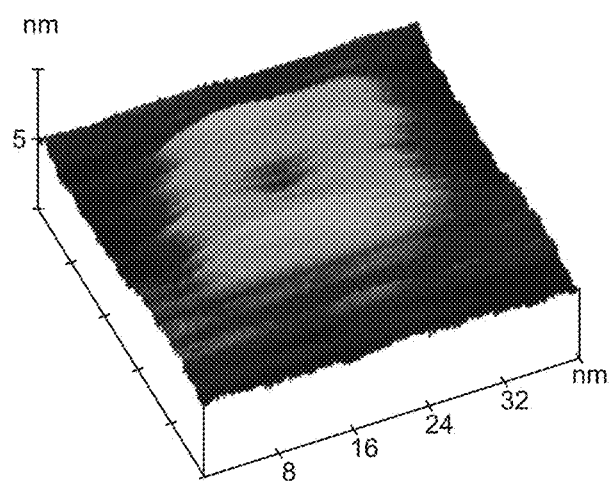
FIG. 50B
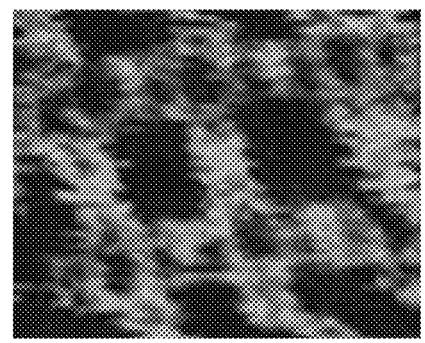
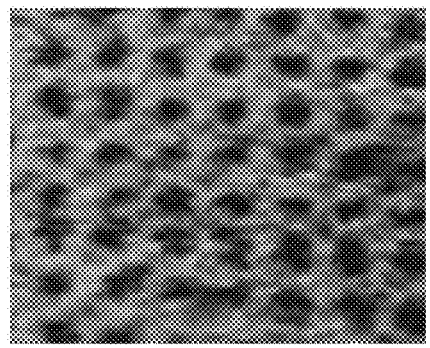

FIG. 57
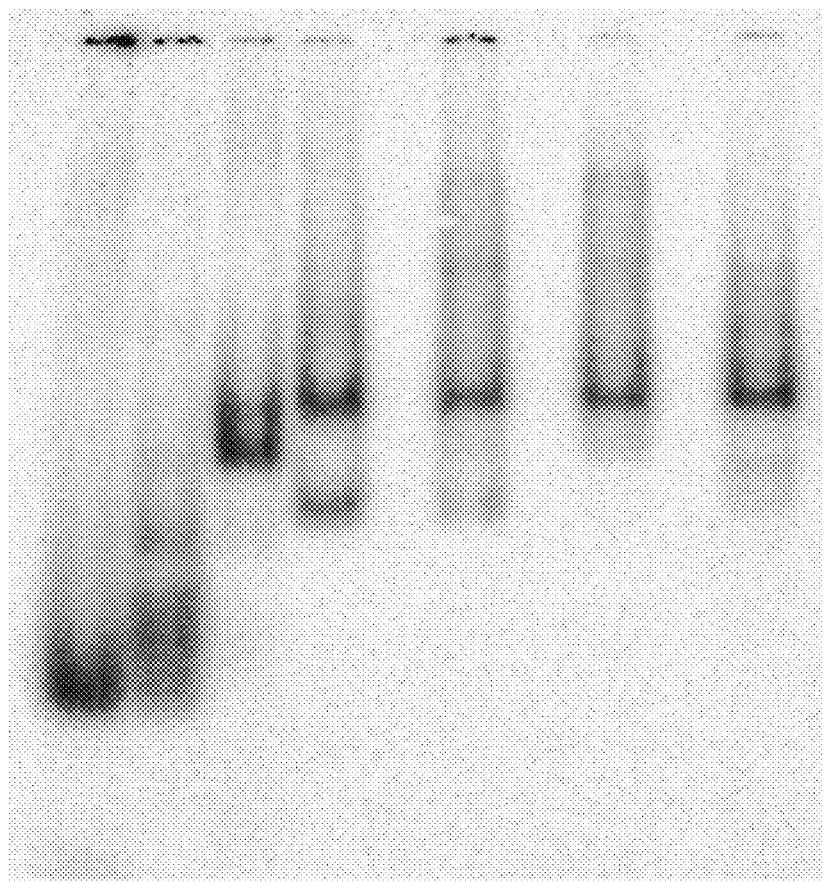
Triangle 4 strands, 1st TRY
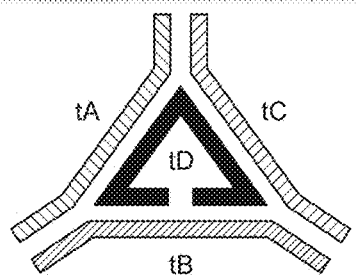

FIG. 60

6 stranded cube with starting sequences
incorporated into the helices:

A
ggcaacuugauccCUCGGuuagcgccGGCCuuucuccACACuuCACG
MMMMM..KKKKKLLLL..FFFFFGGGG..BBBBBCCCC..NNNN B
gggaaauuCGUGGUAGGUuugugcCCGUGuuCUACGAUUACuuGGUC
QQQQQ..PPPPPPPP..MMMMMNNNN..EEEEEEEEE..RRRR C
ggacauuuCGAGACAGCAuuuuuccCGACCuuGCGGAUUGUAuuUAGG
IIIIII..OOOOOOOOOO..QQQQQRRRR..DDDDDDDD..JJJJ D
ggcgcuuuGACCUUCUGCuuauguccCCUAuuCUUAAUGACUuuGGCC
FFFFFF..HHHHHHHHH..IIIIIJJJJ..AAAAAAAAA..GGGG E
gggagauuuAGUCAUUAAGuuACAAUCCGCuuGUAAUCGUAGuuGUGU
BBBBBB..AAAAAAAAA..DDDDDDDDD..EEEEEEEEE..CCCC

FIG. 60 (continued)

F
gggaucuuACCUACCGuuUGCUGUCUCGuuGCAGAAGGUCuuCCGA
KKKKK..PPPPPPPP..OOOOOOOOO..HHHHHHHHH..LLLL As
ggcaacuugaucccaaauucaacggaaaguaagaacacuucacg
MMMMM..KKKKK..............CCCC..NNNN

6 stranded cube with dangling starting
sequences:

A
gggaaaCCCGAGCuuCCUAGCCCCUuuUUAUACCCAAuuGUGUCGGCCUuuGCCGU
......MMMMM..KKKKKKLLLL..FFFFFGGGG..BBBBBCCCC..NNNN B
gggaaaCGCUCCuuCAUGCAGACGuuGCUCGGACGCuuAGGACAGUGCuuCGGG
.......QQQQQ..PPPPPPPPP..MMMMMNNNN..EEEEEEEEE..RRRR

FIG. 60 (continued)

C
gggaaaUGCGUGuuCAGCUAUAUCuuGGAGCGCCCGuuAUGAGAUUGUuGACC
......IIIIII..OOOOOOOOO..QQQQQQRRRR..DDDDDDDDD..JJJJ D
gggaaaGUAUAAuuCUGGAUAGUAuuCACGCAGGUCuuCCACGAUUAGuuUGG
......FFFFFF..HHHHHHHHH..IIIIIIJJJJ..AAAAAAAAA..GGGG E
gggaaaCGACACuuCUAAUCGUGGuuACAAUCUCAUuuGCACUGUCCUuuAGGC
......BBBBBB..AAAAAAAAA..DDDDDDDDD..EEEEEEEEE..CCCC F
gggaaaGCUAGGuuCGUCUGCAUGuuGAUAUAGCUGuuACUAUCCAGuuGAGG
......KKKKKK..PPPPPPPPP..OOOOOOOOO..HHHHHHHHH..LLLL 10 stranded cube with dangling starting sequences:

A
gggaaaGCUACGuuAUCACAUGGAuuGCCAUAGACCuuCUCAUACGACuuCAGC
......DDDDDD..AAAAAAAAA..BBBBBBBBB..CCCCCCCCC..EEEE FIG. 60 (continued)

B
gggaaaGCGAGGuuUACUCCGGCAuuAGAGGAUAGCuuGAUGGUGCGGuuAGGC
......FFFFFF..JJJJJJJJJ..IIIIIIII..HHHHHHHHH..GGGG C
gggaaauCCAUGUGAUuuGCAAGGAACC
......AAAAAAAAAA..KKKKKKKKK D
gggaaaCCUCGCGCCUuuCCUACCGAAG
......FFFFFFGGGG..LLLLLLLL E
gggaaaGGUCUAUGGCuuCUUCGGUAGG
......BBBBBBBB..LLLLLLLLL F
gggaaaCCCGCACCAUCuuGGCCGUGCUC
......HHHHHHHHHH..MMMMMMMM G
gggaaaGUCGUAUGAGuuGAGCACGGCC
......CCCCCCCC..MMMMMMMMM H
gggaaaGCUAUCCUCUuuACCAAACUGC
......IIIIIIII..NNNNNNNNN

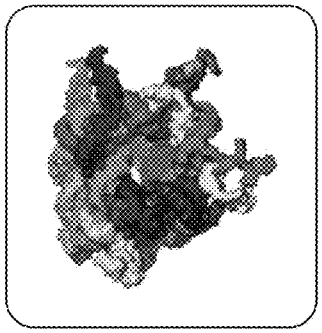

```
I
gggaaaCGUAGCGCUGuuGCAGUUUGGU
......DDDDDEEEE..NNNNNNNNNN
J
gggaaaUGCCGGAGUAuuGGUUCCUUGC
......JJJJJJJJJ..KKKKKKKKKK
```

MC aptamer containing sequences:

```
Cmg
gggaaaUCCAUGUGAUuuGCAAGGAACCcAUgguaacgaauggcgcc
......AAAAAAAAAA..KKKKKKKKK..................ZZZZZ
Dmg
GGCGCccgacAUgCCUCGCGCCUuuCCUACCGAAG
ZZZZZ.........FFFFFFGGGG..LLLLLLLLLL
```

FIG. 60 (continued)

```
Jmg
gggaaaUGCCCGGAGUAuuGGUUCCUUGCcAUgguaaacgaauggcgcc
.....JJJJJJJJJ..KKKKKKKK.................YYYYY
Img
GGCGCccgacAUgCGUAGCGCUGuuGCAGUUGGU
YYYY........DDDDDEEEE..NNNNNNNNN control MG Aptamer
gggaaccgacuggcgagagccagguaaacgaauguuccccu
```

FIG. 61 Computational Sequence Optimization Technique

FIG. 64B
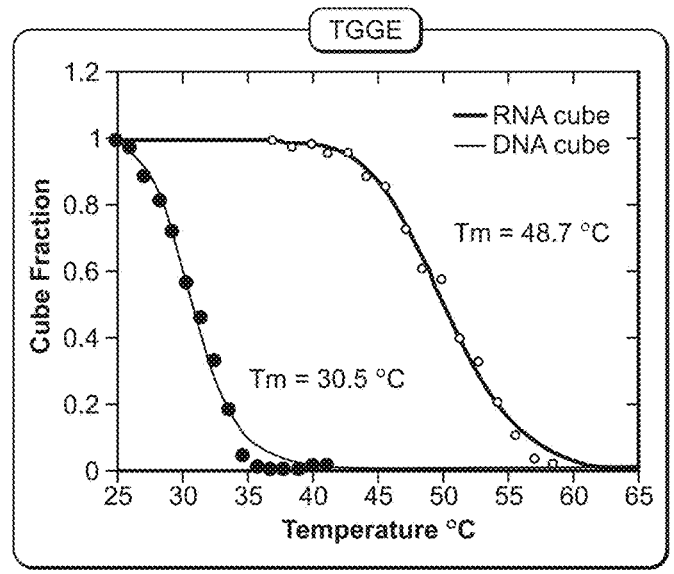
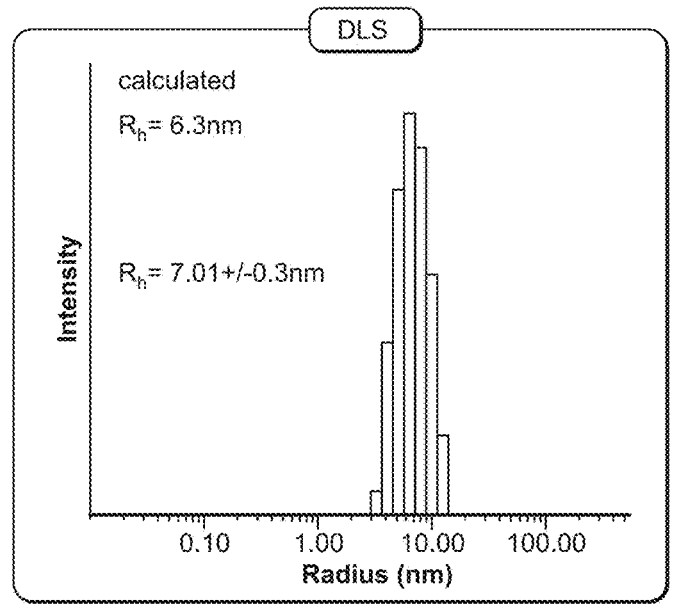
FIG. 64C

FIG. 65B
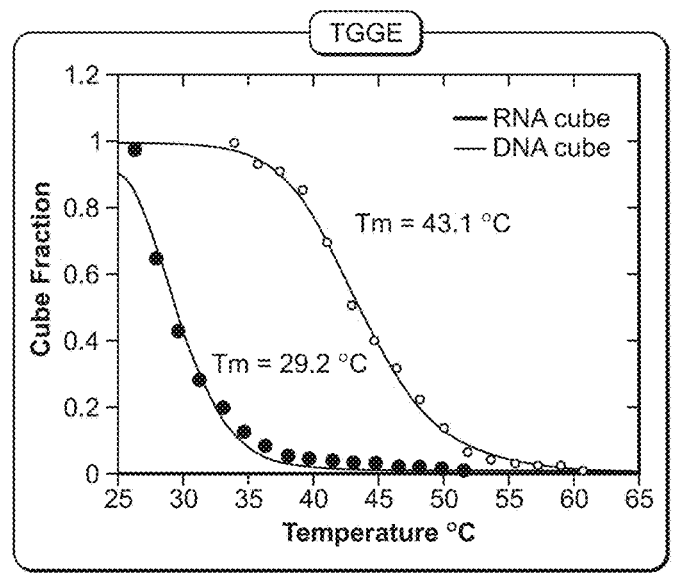
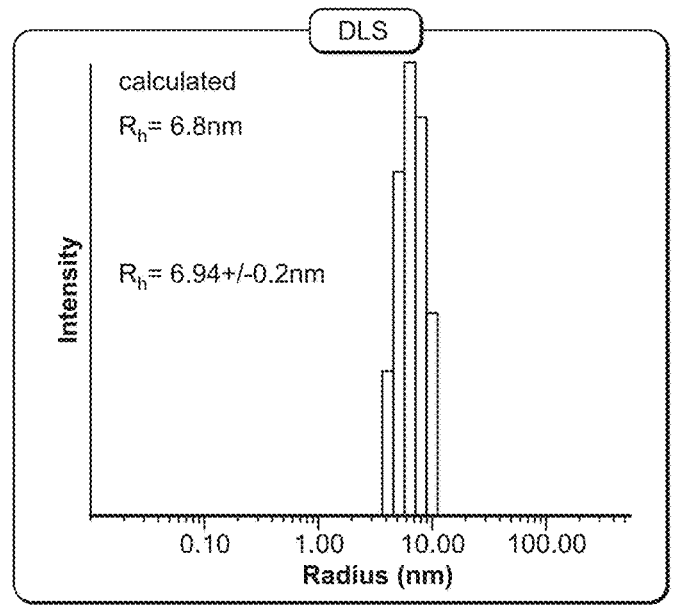
FIG. 65C

Radial distribution functions g(r) and running coordination numbers N(r) for P-OH2 pairs at two temperatures for the "no salt" Mg system.

SEQUENCE LISTING

<160> NUMBER OF SEQ ID NOS: 204

<210> SEQ ID NO 1
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggaaagcca uggacauggu gaaggaggca cgccaugucc guggcaaguc agaccgaacg      60
ugaaguggac acgcguucgg ucuggcacua gcgugu                               96

<210> SEQ ID NO 2

```
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gggaaagcca uggacauggu gaaguccaca cgccaugucc guggcaaguc agaccgaacg        60
ugaagccugc acgcguucgg ucuggcacua gcgugu                                  96

<210> SEQ ID NO 3
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggaaagcca uggacauggu gaagcaggca cgccaugucc guggcaaguc agaccgaacg        60
ugaagcgagc acgcguucgg ucuggcacua gcgugu                                  96

<210> SEQ ID NO 4
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gggaaagcca uggacauggu gaagcucgca cgccaugucc guggcaaguc agaccgaacg        60
ugaagccucc acgcguucgg ucuggcacua gcgugu                                  96

<210> SEQ ID NO 5
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggacggaca gcgugcaugg ugaaggaggc acgccaugca cgcugcagac cgaacgugaa        60
guggacacgc guucggucug cuaacguucc u                                       91

<210> SEQ ID NO 6
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggacggaca gcgugcaugg ugaaguccac acgccaugca cgcugcagac cgaacgugaa        60
gccugcacgc guucggucug cuaacguucc u                                       91

<210> SEQ ID NO 7
<211> LENGTH: 91
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 7
gggacggaca gcgugcaugg ugaagcaggc acgccaugca cgcugcagac cgaacgugaa    60
gcgagcacgc guucggucug cuaacguucc u                                  91

<210> SEQ ID NO 8
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggacggaca gcgugcaugg ugaagcucgc acgccaugca cgcugcagac cgaacgugaa    60
gccuccacgc guucggucug cuaacguucc u                                  91

<210> SEQ ID NO 9
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9 gggaccuccgugguucgaau ccacguacca gccuggauga aguggacacg uccaggcugg    60
uauggccgag cggcugaagg cacucguagu gaaggaggca cgcuacgagu agguccccu   118

<210> SEQ ID NO 10
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10
gggaccuccg ugguucgaau ccacguacca gccuggauga agccugcacg uccaggcugg    60
uauggccgag cggcugaagg cacucguagu gaaguccaca cgcuacgagu agguccccu   118

<210> SEQ ID NO 11
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
gggaccuccg ugguucgaau ccacguacca gccuggauga agcgagcacg uccaggcugg    60
uauggccgag cggcugaagg cacucguagu gaagcaggca cgcuacgagu agguccccu   118

<210> SEQ ID NO 12
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 12
gggaccuccg ugguucgaau ccacguacca gccuggauga agccuccacg uccaggcugg    60
uauggccgag cggcugaagg cacucguagu gaagcucgca cgcuacgagu aggucccu     118

<210> SEQ ID NO 13
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13
gggaccuccg ugugggaau ccacguacca gccuggauga aguggacacg uccaggcugg    60
uauggccgag cggcugaagg cacucguagu gaaggaggca cgcuacgagu aggucccu     118

<210> SEQ ID NO 14
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 14
gggaccuccg ugugggaau ccacguacca gccuggauga agccugcacg uccaggcugg    60
uauggccgag cggcugaagg cacucguagu gaaguccaca cgcuacgagu aggucccu     118

<210> SEQ ID NO 15
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 15
gggaccuccg ugugggaau ccacguacca gccuggauga agcgagcacg uccaggcugg    60
uauggccgag cggcugaagg cacucguagu gaagcaggca cgcuacgagu aggucccu     118

<210> SEQ ID NO 16
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16
gggaccuccg ugugggaau ccacguacca gccuggauga agccuccacg uccaggcugg    60
uauggccgag cggcugaagg cacucguagu gaagcucgca cgcuacgagu aggucccu     118

<210> SEQ ID NO 17
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17 aaggaggca                                                             9

```
<210> SEQ ID NO 18
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18 aaguccaca                                                                  9

<210> SEQ ID NO 19
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19 aagcaggca                                                                  9

<210> SEQ ID NO 20
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20 aagcucgca                                                                  9

<210> SEQ ID NO 21
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aacuuucgca                                                                10

<210> SEQ ID NO 22
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22 aagucacca                                                                  9

<210> SEQ ID NO 23
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23 aacguggua                                                                  9

<210> SEQ ID NO 24
```

```
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24 aagagccua                                                                  9

<210> SEQ ID NO 25
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gggaaagcca uggacauggu gaaggaggca cgccaugucc guggcaaguc agaccgaacg          60
ugaagccucc acgcguucgg ucuggcacua gcgugu                                    96

<210> SEQ ID NO 26
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gggaaagcca uggacauggu gaacuucgca cgccaugucc guggcaaguc agaccgaacg          60
ugaagcgaag acgcguucgg ucuggcacua gcgugu                                    96

<210> SEQ ID NO 27
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gggacggaca gcgugcaugg ugaaggaggc acgccaugca cgcugcagac cgaacgugaa          60
gccuccacgc guucggucug cuaacguucc u                                         91

<210> SEQ ID NO 28
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gggacggaca gcgugcaugg ugaacuucgc acgccaugca cgcugcagac cgaacgugaa          60
gcgaagacgc guucggucug cuaacguucc u                                         91

<210> SEQ ID NO 29
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 29
gggcuaacgc agaccgauga aggaggcacg ucggucugcg dacagccgug cauugaagcc      60
uccacgaugc acggcugccc gcaucc                                          86

<210> SEQ ID NO 30
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gggcuaacgc agaccgauga acuucgcacg ucggucugcg dacagccgug cauugaagcg      60
aagacgaugc acggcugccc gcaucc                                          86

<210> SEQ ID NO 31
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 31
gggaccuccg ugguucgaau ccacguacca gccuggauga acuucgcacg uccaggcugg      60
uauggccgag cggcugaagg cacucguagu gaaguccaca cgcuacgagu aggcccu       118

<210> SEQ ID NO 32
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 32
gggaccuccg ugguucgaau ccacguacca gccuggauga agcgagcacg uccaggcugg      60
uauggccgag cggcugaagg cacucguagu gaagcgaaga cgcuacgagu aggcccu       118

<210> SEQ ID NO 33
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 33
gggaccuccg ugguucgaau ccacguacca gccuggauga aggaggcacg uccaggcugg      60
uauggccgag cggcugaagg cacucguagu gaagccucca cgcuacgagu aggcccu       118

<210> SEQ ID NO 34
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 34
gggaccuccg ugguucgaau ccacguacca gccuggauga acuucgcacg uccaggcugg      60
```

```
uauggccgag cggcugaagg cacucguagu gaagcgaaga cgcuacgagu aggucccu        118

<210> SEQ ID NO 35
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 35
gggaccuccg ugugggaau ccacguacca gccuggauga aggaggcacg uccaggcugg        60
uauggccgag cggcugaagg cacucguagu gaagccucca cgcuacgagu aggucccu        118

<210> SEQ ID NO 36
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 36
gggaccuccg ugugggaau ccacguacca gccuggauga acuucgcacg uccaggcugg        60
uauggccgag cggcugaagg cacucguagu gaagcgaaga cgcuacgagu aggucccu        118

<210> SEQ ID NO 37
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaugggaaa cgugguccga ucugaaggag gcacggauug gacuacgcca agucgaugaa       60
guggacacgu cgauuuggu auucuu                                             86

<210> SEQ ID NO 38
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ggaugggaaa cgugguccga ucugaagucc acacggauug gacuacgcca agucgaugaa       60
gccuccacgu cgauuuggu auucuu                                             86

<210> SEQ ID NO 39
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
gggaaaucca ggggaacgga ugguucguuc ccuuggguuu cccccguuc ucaaccgcac        60 cggaugguuc ggugcgguug ggaacggg                                          88
```

```
<210> SEQ ID NO 40
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gggaaaucca ggggaacgaa ccauccguuc ccuuggguuu cccccguuc ucaaccgcac      60 cgaaccaucc ggugcgguug ggaacggg                                       88

<210> SEQ ID NO 41
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gggaaaucca ggggaacgga ugguucguuc ccuuggguag cgccccguuc ucaaccgcac     60
cgaaccaucc ggugcgguug ggaacggg                                       88

<210> SEQ ID NO 42
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 42
gggaugggug acguggaauc caggggaacg gaugguucgu ucccuugggu ucuacgcuaa     60
gcgcaacugc accggauggu ucggugcggu ugcguuuagu cauuccu                 107

<210> SEQ ID NO 43
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 43
gggaugggug acguggaauc caggggaacg aaccauccgu ucccuugggu ucuacgcuaa     60
gcgcaacugc accgaaccau ccggugcggu ugcguuuagu cauuccu                 107

<210> SEQ ID NO 44
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 44
gggaugggug acguggaauc caggggaacg gaugguucgu ucccuugggu ucuacgcuaa     60
gcgcaacugc accgaaccau ccggugcggu ugcguuuagu cauuccu                 107

<210> SEQ ID NO 45
<211> LENGTH: 111
<212> TYPE: RNA
<213> ORGANISM: Artificial Sequence
```

<220> FEATURE:
<223> OTHER INFORMATION: Description of Artificial Sequence: Synthetic
      polynucleotide

<400> SEQUENCE: 45
gggaugggug acguggaauc caggggaacg aaggaggcac guucccuugg guucuacgcu      60
aagcgcaacu gcaccgaagc cugcacggug cgguugcguu uagucauucc u              111

<210> SEQ ID NO 46
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 46
gggaugggug acguggaauc caggggaacg aagcaggcac guucccuugg guucuacgcu      60
aagcgcaacu gcaccgaagc cuccacggug cgguugcguu uagucauucc u              111

<210> SEQ ID NO 47
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 47
gggaugggug acguggaauc caggggaacg gaugguucgu ucccuugggu ucuacgcuaa      60
gcgcaacugc accgaaaaaa acggugcggu ugcguuuagu cauuccu                   107

<210> SEQ ID NO 48
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 48
gggaugggug acguggaauc caggggaacg aaccauccgu ucccuugggu ucuacgcuaa      60
gcgcaacugc accgaaaaaa acggugcggu ugcguuuagu cauuccu                   107

<210> SEQ ID NO 49
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 49
gggaugggug acguggaauc caggggaacg aaggaggcac guucccuugg guucuacgcu      60
aagcgcaacu gcaccgaaaa aaaaacggug cgguugcguu uagucauucc u              111

<210> SEQ ID NO 50
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide

```
<400> SEQUENCE: 50
gggaugggug acguggaauc caggggaacg aaaaaaaaac guucccuugg guucuacgcu      60
aagcgcaacu gcaccgaagc cuccacggug cgguugcguu uagucauucc u             111

<210> SEQ ID NO 51
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 51
gggaugggug acguggaauc caggggaacg aaaaaaaaac guucccuugg guucuacgcu      60
aagcgcaacu gcaccgaagc cugcacggug cgguugcguu uagucauucc u             111

<210> SEQ ID NO 52
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 52
gggaugggug acguggaauc caggggaacg aagcaggcac guucccuugg guucuacgcu      60
aagcgcaacu gcaccgaaaa aaaaacggug cgguugcguu uagucauucc u             111

<210> SEQ ID NO 53
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 53
gggaugggug acguggaauc caggggaacg gauggUUcgu ucccuugggu ucuacgcuaa      60
ccgcaacugc accggauggu ucggugcggu ugcguuuagu cauccaagg agcgcuacgu     120

<210> SEQ ID NO 54
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 54
gggaugggug acguggaauc caggggaacg aaccauccgu ucccuugggu ucuacgcuaa      60
gcgcaacugc accgaaccau ccggugcggu ugcguuuagu cauccaacg uagcgcuccu     120

<210> SEQ ID NO 55
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gggaaucgga ugguucgauu uccgcuaacg gaugguucgu uagcu                     45
```

<210> SEQ ID NO 56
<211> LENGTH: 45
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 56
gggaaucgaa ccauccgauu uccgcuaacg aaccauccgu uagcu        45

<210> SEQ ID NO 57
<211> LENGTH: 45
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 57
gggaaucgga ugguucgauu uccgcuaacg aaccauccgu uagcu        45

<210> SEQ ID NO 58
<211> LENGTH: 63
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 58
gggaugggug acgggaaucg gaugguucga uucccgcuaa cggaugguuc guuagucauc        60
ccu        63

<210> SEQ ID NO 59
<211> LENGTH: 63
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 59
gggaugggug acgggaaucg aaccauccga uucccgcuaa cgaaccaucc guuagucauc        60
ccu        63

<210> SEQ ID NO 60
<211> LENGTH: 63
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 60
gggaugggug acgggaaucg gaugguucga uucccgcuaa cgaaccaucc guuagucauc        60
ccu        63

<210> SEQ ID NO 61
<211> LENGTH: 63
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 61
gggaugggug acgggaaucg gaugguucga uucccgcuaa cgaaaaaaac guuagucauc    60
ccu    63

<210> SEQ ID NO 62
<211> LENGTH: 63
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gggaugggug acgggaaucg aaccauccga uucccgcuaa cgaaaaaaac guuagucauc    60
ccu    63

<210> SEQ ID NO 63
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 63
ggcagccucc gugguucgaa uccacguacc agccuggaug aaguggacac guccaggcug    60
guauggccga gcggcugaag gcacucguag ugaaggaggc acgcuacgag uagguugccc   120
cagaguc   127

<210> SEQ ID NO 64
<211> LENGTH: 125
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 64
ggcaccuccg ugguucgaau ccacguacca gccuggauga agccugcacg uccaggcugg    60
uauggccgag cggcugaagg cacucguagu gaaguccaca cgcuacgagu aggugcccgg   120
ugauc   125

<210> SEQ ID NO 65
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 65
ggcagccucc gugguucgaa uccacguacc agccuggaug aagcgagcac guccaggcug    60
guauggccga gcggcugaag gcacucguag ugaagcaggc acgcuacgag uagguugccg   120
cauccuc   127

<210> SEQ ID NO 66
<211> LENGTH: 125
<212> TYPE: RNA
<213> ORGANISM: Artificial Sequence
<220> FEATURE:

<223> OTHER INFORMATION: Description of Artificial Sequence: Synthetic
      polynucleotide

<400> SEQUENCE: 66
ggcaccuccg ugguucgaau ccacguacca gccuggauga agccuccacc uccaggcugg    60
uauggccgag cggcugaagg cacucguagu gaagcucgca cgcuacgagu aggugccccu   120
gucuc                                                              125

<210> SEQ ID NO 67
<211> LENGTH: 125
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 67
ggcaccuccg ugguucgaau ccacguacca gccuggauga agcguucacg uccaggcugg    60
uauggccgag cggcugaagg cacucguagu gaaaggcuca cgcuacgagu aggugcccuc   120
ugguc                                                              125

<210> SEQ ID NO 68
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 68
ggcagccucc gugguucgaa uccacguacc agccuggaug aagucaccac guccaggcug    60
guauggccga gcggcugaag ccacucguac ugaagaacgc acgcuacgag uagguugccg   120
acagguc                                                            127

<210> SEQ ID NO 69
<211> LENGTH: 125
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 69
ggcaccuccg ugguucgaau ccacguacca gccuggauga acguguacg uccaggcugg    60 uauggccgag cggcugaagg cacucguagu gaaggugaca cgcuacgagu aggugccgga   120
ugcuc                                                              125

<210> SEQ ID NO 70
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 70
ggcagccucc gugguucgaa uccacguacc agccuggaug aagagccuac guccaggcug    60
guauggccga gcggcugaag gcacucguag ugagaccacg acgcuacgag uagguugccu   120
caccguc                                                            127

<210> SEQ ID NO 71
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ggaugggaaa cgugguccga ucugaaggag gcacggauug gacuacgcca agucgaugaa    60
guggacacgu cgauuugguc auucuu                                         86

<210> SEQ ID NO 72
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ggaugggaaa cgugguccga ucugaagucc acacggauug gacuacgcca agucgaugaa    60
gccuccacgu cgauuugguc auucuu                                         86

<210> SEQ ID NO 73
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ggaugggaaa cguggcggcg caugaaggag gcacgugcgg gaagaaacug cgccacgcca    60
agucgaugaa guggacacgu cgauuugguc auucuu                              96

<210> SEQ ID NO 74
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ggaugggaaa cguggcggcg caugaagucc acacgugcgg gaagaaacug cgccacgcca    60
agucgaugaa gccuccacgu cgauuugguc auucuu                              96

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cgcgaattcg cgcgcgaatt cgcg                                           24

<210> SEQ ID NO 76
<211> LENGTH: 12
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 76
cgcgaauucg cg                                                              12

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Locked nucleic acid
<220> FEATURE:
<221> NAME/KEY: modified_base
<222> LOCATION: (5)..(6)
<223> OTHER INFORMATION: Locked nucleic acid
<220> FEATURE:
<221> NAME/KEY: modified_base
<222> LOCATION: (8)..(8)
<223> OTHER INFORMATION: Locked nucleic acid

<400> SEQUENCE: 77
ctgcttctgc gcagaagcag                                                      20

<210> SEQ ID NO 78
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
cgagcggcug aa                                                              12

<210> SEQ ID NO 79
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (14)..(15)
<223> OTHER INFORMATION: a, c, u, g, unknown or other

<400> SEQUENCE: 79
nncggauggu ucgnn                                                           15

<210> SEQ ID NO 80
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other
<220> FEATURE:
```

<221> NAME/KEY: modified_base
<222> LOCATION: (16)..(17)
<223> OTHER INFORMATION: a, c, u, g, unknown or other

<400> SEQUENCE: 80
nnccgaacca uccggnn    17

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (17)..(19)
<223> OTHER INFORMATION: a, c, u, g, unknown or other

<400> SEQUENCE: 81
nnngggaaga aacugcnnn    19

<210> SEQ ID NO 82
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ggaugggaaa cgugguccga ucugaaggag gcacggauug gacuacgcca agucgaugaa    60
guggacacgu cgauuugguc auuc    84

<210> SEQ ID NO 83
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ggaugggaaa cgugguccga ucugaagucc acacggauug gacuacgcca agucgaugaa    60
gccuccacgu cgauuugguc auuc    84

<210> SEQ ID NO 84
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ggaugggaaa cguggcggca ucugaaggag gcacggaugg saagaaacug cgccacgcca    60
agucgaugaa guggacacgu cgauuugguc auuc    94

<210> SEQ ID NO 85
<211> LENGTH: 94
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 85
ggaugggaaa cguggcggca ucugaagucc acacggaugg saagaaacug cgccacgcca    60
agucgaugaa gccuccacgu cgauuugguc auuc                                94

<210> SEQ ID NO 86
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ggaugggaaa cgugguc                                                   17

<210> SEQ ID NO 87
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uaugucauuc                                                           10

<210> SEQ ID NO 88
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
gacuacgcua ag                                                        12

<210> SEQ ID NO 89
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ggaugggaaa cgugguccga ucugaaggag gcacggauug gacuacgcua agucgaugaa    60
guggacacgu cgauauguca uuc                                            83

<210> SEQ ID NO 90
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ggaugggaaa cgugguccga ucugaaggag gcacggauug gacuacgcug ugucgaugaa    60
guggacacgu cgaaucuguc auuc                                           84
```

<210> SEQ ID NO 91
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
ggaugcuaag gugguccgau cugaaggagg cacggauugg acuacgccca gugcgaugaa    60
guggacacgu cgucaacggu cauuc                                          85

<210> SEQ ID NO 92
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ggcaaaugaa                                                           10

<210> SEQ ID NO 93
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
uucguggccc                                                           10

<210> SEQ ID NO 94
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ggcaagugaa                                                           10

<210> SEQ ID NO 95
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
uucgugaccc                                                           10

<210> SEQ ID NO 96
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
uucgguagcc                                                           10

<210> SEQ ID NO 97
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uucggcgacc                                                           10

<210> SEQ ID NO 98
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ggaugcgaag cuucggcuaa ggugguccga ucugaaggag gcacggauug gacuacgcca    60
agucgaugaa guggacacgu cgauuugguc auuc                                94

<210> SEQ ID NO 99
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ggauacgagc uucggugaag cagguccgau cugaaggagg cacggauugg acuuggccaa    60
gucgaugaag uggacacguc gauuugguua uuc                                 93

<210> SEQ ID NO 100
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other; positions
      involved in kissing loop
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (3)..(3)
<223> OTHER INFORMATION: a, c, u, g, unknown or other; positions
      involved in kissing loop
<220> FEATURE:
<221> NAME/KEY: modified_base
<222> LOCATION: (8)..(8)
<223> OTHER INFORMATION: a, c, u, g, unknown or other; positions
      involved in kissing loop
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (10)..(10)
<223> OTHER INFORMATION: a, c, u, g, unknown or other; positions involved in kissing loop

<400> SEQUENCE: 100 nnngugannn                                                                10

<210> SEQ ID NO 101
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other; positions
      involved in kissing loop
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (3)..(3)
<223> OTHER INFORMATION: a, c, u, g, unknown or other; positions
      involved in kissing loop
<220> FEATURE:
<221> NAME/KEY: modified_base
<222> LOCATION: (8)..(8)
<223> OTHER INFORMATION: a, c, u, g, unknown or other; positions
      involved in kissing loop
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (10)..(10)
<223> OTHER INFORMATION: a, c, u, g, unknown or other; positions
      involved in kissing loop

<400> SEQUENCE: 101 nnnuucgnnn                                                                10

<210> SEQ ID NO 102
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other; positions
      involved in kissing loop
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (3)..(3)
<223> OTHER INFORMATION: a, c, u, g, unknown or other; positions
      involved in kissing loop
<220> FEATURE:
<221> NAME/KEY: modified_base
<222> LOCATION: (8)..(8)
<223> OTHER INFORMATION: a, c, u, g, unknown or other; positions
      involved in kissing loop
<220> FEATURE:
<221> NAME/KEY: modified_base
<222> LOCATION: (9)..(9)
<223> OTHER INFORMATION: a, c, u, g, unknown or other
<220> FEATURE:

```
<221> NAME/KEY: modified_base
<222> LOCATION: (10)..(10)
<223> OTHER INFORMATION: a, c, u, g, unknown or other; positions
      involved in kissing loop

<400> SEQUENCE: 102 nnngaaannn                                                              10

<210> SEQ ID NO 103
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other; positions
      involved in kissing loop
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (3)..(3)
<223> OTHER INFORMATION: a, c, u, g, unknown or other; positions
      involved in kissing loop
<220> FEATURE:
<221> NAME/KEY: modified_base
<222> LOCATION: (8)..(8)
<223> OTHER INFORMATION: a, c, u, g, unknown or other; positions
      involved in kissing loop
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (10)..(10)
<223> OTHER INFORMATION: a, c, u, g, unknown or other; positions
      involved in kissing loop

<400> SEQUENCE: 103 nnnguaannn                                                              10

<210> SEQ ID NO 104
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other; positions
      involved in kissing loop

<400> SEQUENCE: 104 nngcccagug                                                              10

<210> SEQ ID NO 105
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(10)
```

<223> OTHER INFORMATION: a, c, u, g, unknown or other; positions
      involved in kissing loop

<400> SEQUENCE: 105 ucaacggunn                                                              10

<210> SEQ ID NO 106
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other; positions
      involved in kissing loop

<400> SEQUENCE: 106 nngcccggug                                                              10

<210> SEQ ID NO 107
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(10)
<223> OTHER INFORMATION: a, c, u, g, unknown or other; positions
      involved in kissing loop

<400> SEQUENCE: 107 uaaacggunn                                                              10

<210> SEQ ID NO 108
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(10)
<223> OTHER INFORMATION: a, c, u, g, unknown or other; positions
      involved in kissing loop

<400> SEQUENCE: 108 ugaacggunn                                                              10

<210> SEQ ID NO 109
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other; positions
      involved in kissing loop
<220> FEATURE:
<221> NAME/KEY: modified_base
<222> LOCATION: (9)..(10)
<223> OTHER INFORMATION: a, c, u, g, unknown or other; positions
      involved in kissing loop

<400> SEQUENCE: 109 nngggaacnn                                                              10

<210> SEQ ID NO 110
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other; positions
      involved in kissing loop
<220> FEATURE:
<221> NAME/KEY: modified_base
<222> LOCATION: (9)..(10)
<223> OTHER INFORMATION: a, c, u, g, unknown or other; positions
      involved in kissing loop

<400> SEQUENCE: 110 nnggaaacnn                                                              10

<210> SEQ ID NO 111
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other; positions
      involved in kissing loop

<400> SEQUENCE: 111 nngccagcgg                                                              10

<210> SEQ ID NO 112
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other; positions
      involved in kissing loop

<400> SEQUENCE: 112
nngccgaugg c                                                            11

<210> SEQ ID NO 113
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(10)
<223> OTHER INFORMATION: a, c, u, g, unknown or other; positions
      involved in kissing loop

<400> SEQUENCE: 113 gaucaggunn                                                                                      10

<210> SEQ ID NO 114
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(10)
<223> OTHER INFORMATION: a, c, u, g, unknown or other; positions
      involved in kissing loop

<400> SEQUENCE: 114 gcacaggunn                                                                                      10

<210> SEQ ID NO 115
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (5)..(10)
<223> OTHER INFORMATION: a, c, u, g, unknown or other; positions
      involved in kissing loop
<220> FEATURE:
<221> NAME/KEY: modified_base
<222> LOCATION: (15)..(15)
<223> OTHER INFORMATION: a, c, u, g, unknown or other

<400> SEQUENCE: 115
nucannnnnn aacun                                                                                15

<210> SEQ ID NO 116
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (5)..(10)
<223> OTHER INFORMATION: a, c, u, g, unknown or other; positions
      involved in kissing loop
<220> FEATURE:
<221> NAME/KEY: modified_base
<222> LOCATION: (15)..(15)
<223> OTHER INFORMATION: a, c, u, g, unknown or other

<400> SEQUENCE: 116
ngcannnnnn aacun                                                                                15

<210> SEQ ID NO 117
<211> LENGTH: 14
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (4)..(11)
<223> OTHER INFORMATION: a, c, u, g, unknown or other; positions
      involved in kissing loop
<220> FEATURE:
<221> NAME/KEY: modified_base
<222> LOCATION: (14)..(14)
<223> OTHER INFORMATION: a, c, u, g, unknown or other

<400> SEQUENCE: 117
ngcnnnnnnn nggn                                                         14

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
auguugcccc agauggcacc u                                                 21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
aggugcccuc ugggcaccc u                                                  21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
auguugcccg guuaggcacc u                                                 21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
aggugccuca ccgggcaccc u                                                 21

<210> SEQ ID NO 122
<211> LENGTH: 15
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 122
cugaagcgcg cacgg                                                    15

<210> SEQ ID NO 123
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
agaacaccga acgg                                                     14

<210> SEQ ID NO 124
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
aaguggacag g                                                        11

<210> SEQ ID NO 125
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ggcaccccau gucc                                                     14

<210> SEQ ID NO 126
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
agaccgaacc ugaagu                                                   16

<210> SEQ ID NO 127
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ucuggcaccc agag                                                     14

<210> SEQ ID NO 128
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
cauggugaag gaggca                                                    16

<210> SEQ ID NO 129
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gcgauguccg                                                           10

<210> SEQ ID NO 130
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ggcaacuuga ucccucgguu agcgccggcc uuucucccac acuucacg                 48

<210> SEQ ID NO 131
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gggaaauucg ugguagguuu guugcccgug uucuacgauu acugguc                  48

<210> SEQ ID NO 132
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ggacauuucg agacagcauu uucccgacc uugcggauug uauuuagg                  48

<210> SEQ ID NO 133
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ggcgcuuuga ccuucugcuu auguccccua uucuuaauga cuuuggcc                 48

<210> SEQ ID NO 134
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 134
gggagauuag ucauuaaguu uacaauccgc uuguaaucgu aguugugu                         48

<210> SEQ ID NO 135
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gggaucuuac cuaccacguu ugcugucucg uugcagaagg ucuuccga                        48

<210> SEQ ID NO 136
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ggcaacuuga uccccaaauu caacggaaag uaaguagaac acuucacg                         48

<210> SEQ ID NO 137
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gggaaaccga gcuuccuagc ccucuuuuau acccaauugu gucggccuuu gcgu                 54

<210> SEQ ID NO 138
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gggaaacgcu ccuucaugca gacguugcuc ggacgcuuag gacagugcuu cggg                 54

<210> SEQ ID NO 139
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gggaaaugcg uguucagcua uaucuuggag cgcccguuau gagauuguuu gacc                 54

<210> SEQ ID NO 140
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
```
gggaaaguau aauucuggau aguauucacg caggucuucc acgauuaguu uugg    54

<210> SEQ ID NO 141
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gggaaacgac acuucuaauc gugguuacaa ucucauuugc acguccuuu aggc    54

<210> SEQ ID NO 142
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
gggaaagcua gguucgucug cauguugaua uagcuguuua cuauccaguu gagg    54

<210> SEQ ID NO 143
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
gggaaagcua cguuaucaca uggauugcca uagaccuucu cauacgacuu cagc    54

<210> SEQ ID NO 144
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
gggaaagcga gguuuacucc ggcauuagag gauagcuuga uggugcgguu aggc    54

<210> SEQ ID NO 145
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
gggaaaucca ugugauuugc aaggaacc    28

<210> SEQ ID NO 146
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gggaaaccuc gcgccuuucc uaccgaag 28

<210> SEQ ID NO 147
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gggaaagguc uauggcuucu ucgguagg 28

<210> SEQ ID NO 148
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gggaaaccgc accaucuugg ccgugcuc 28

<210> SEQ ID NO 149
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
gggaaagucg uaugaguuga gcacggcc 28

<210> SEQ ID NO 150
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gggaaagcua uccucuuuac caaacugc 28

<210> SEQ ID NO 151
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gggaaacgua gcgcuguugc aguuuggu 28

<210> SEQ ID NO 152
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gggaaaugcc ggaguauugg uuccuugc 28

<210> SEQ ID NO 153
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gggaaaucca ugugauuugc aaggaaccca ugguaacgaa uggcgcc          47

<210> SEQ ID NO 154
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
ggcgcccgac augccucgcg ccuuuccuac cgaag          35

<210> SEQ ID NO 155
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
gggaaaugcc ggaguauugg uuccuugcca ugguaacgaa uggcgcc          47

<210> SEQ ID NO 156
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ggcgcccgac augcguagcg cuguugcagu uuggu          35

<210> SEQ ID NO 157
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
gggaaccgac uggcgagagc cagguaacga auguuccu          39

<210> SEQ ID NO 158
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
augguaacga auga          14

<210> SEQ ID NO 159
<211> LENGTH: 107
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (5)..(7)
<223> OTHER INFORMATION: a, c, u, g, unknown or other
<220> FEATURE:
<221> NAME/KEY: modified_base
<222> LOCATION: (12)..(12)
<223> OTHER INFORMATION: a, c, u, g, unknown or other
<220> FEATURE:
<221> NAME/KEY: modified_base
<222> LOCATION: (14)..(30)
<223> OTHER INFORMATION: a, c, u, g, unknown or other
<220> FEATURE:
<221> NAME/KEY: modified_base
<222> LOCATION: (31)..(37)
<223> OTHER INFORMATION: a, c, u, g, unknown or other; positions involved in kissing loop
<220> FEATURE:
<221> NAME/KEY: modified_base
<222> LOCATION: (38)..(54)
<223> OTHER INFORMATION: a, c, u, g, unknown or other
<220> FEATURE:
<221> NAME/KEY: modified_base
<222> LOCATION: (58)..(74)
<223> OTHER INFORMATION: a, c, u, g, unknown or other
<220> FEATURE:
<221> NAME/KEY: modified_base
<222> LOCATION: (75)..(81)
<223> OTHER INFORMATION: a, c, u, g, unknown or other; positions involved in kissing loop
<220> FEATURE:
<221> NAME/KEY: modified_base
<222> LOCATION: (82)..(98)
<223> OTHER INFORMATION: a, c, u, g, unknown or other
<220> FEATURE:
<221> NAME/KEY: modified_base
<222> LOCATION: (101)..(104)
<223> OTHER INFORMATION: a, c, u, g, unknown or other

<400> SEQUENCE: 159
gggannngug angnnnnnnn nnnnnnnnnn yyyyyyynnn nnnnnnnnnn nnnncgcnnn    60
nnnnnnnnnn nnnyyyyyy ynnnnnnnnn nnnnnnnngu nnnnccu                 107

<210> SEQ ID NO 160
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (8)..(17)
<223> OTHER INFORMATION: a, c, u, g, unknown or other
<220> FEATURE:
<221> NAME/KEY: modified_base
<222> LOCATION: (22)..(27)
<223> OTHER INFORMATION: a, c, u, g, unknown or other; positions involved in kissing loop
<220> FEATURE:
<221> NAME/KEY: modified_base
<222> LOCATION: (31)..(40)
<223> OTHER INFORMATION: a, c, u, g, unknown or other
<220> FEATURE:
<221> NAME/KEY: modified_base
<222> LOCATION: (44)..(44)
<223> OTHER INFORMATION: Purine nucleotide
<220> FEATURE:

```
<221> NAME/KEY: modified_base
<222> LOCATION: (49)..(58)
<223> OTHER INFORMATION: a, c, u, g, unknown or other
<220> FEATURE:
<221> NAME/KEY: modified_base
<222> LOCATION: (63)..(68)
<223> OTHER INFORMATION: a, c, u, g, unknown or other; positions
      involved in kissing loop
<220> FEATURE:
<221> NAME/KEY: modified_base
<222> LOCATION: (72)..(81)
<223> OTHER INFORMATION: a, c, u, g, unknown or other
<220> FEATURE:
<221> NAME/KEY: modified_base
<222> LOCATION: (85)..(85)
<223> OTHER INFORMATION: Purine nucleotide

<400> SEQUENCE: 160
ggaagccnnn nnnnnnnuga annnnnnacg nnnnnnnnnn ggcnagucnn nnnnnnnnug    60
aannnnnnac gnnnnnnnnn nggcn                                         85

<210> SEQ ID NO 161
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2)..(11)
<223> OTHER INFORMATION: a, c, u, g, unknown or other
<220> FEATURE:
<221> NAME/KEY: modified_base
<222> LOCATION: (15)..(26)
<223> OTHER INFORMATION: a, c, u, g, unknown or other
<220> FEATURE:
<221> NAME/KEY: modified_base
<222> LOCATION: (30)..(35)
<223> OTHER INFORMATION: a, c, u, g, unknown or other; positions
      involved in kissing loop
<220> FEATURE:
<221> NAME/KEY: modified_base
<222> LOCATION: (40)..(51)
<223> OTHER INFORMATION: a, c, u, g, unknown or other
<220> FEATURE:
<221> NAME/KEY: modified_base
<222> LOCATION: (54)..(63)
<223> OTHER INFORMATION: a, c, u, g, unknown or other
<220> FEATURE:
<221> NAME/KEY: modified_base
<222> LOCATION: (67)..(72)
<223> OTHER INFORMATION: a, c, u, g, unknown or other; positions
      involved in kissing loop
<220> FEATURE:
<221> NAME/KEY: modified_base
<222> LOCATION: (77)..(86)
<223> OTHER INFORMATION: a, c, u, g, unknown or other
<220> FEATURE:
<221> NAME/KEY: modified_base
<222> LOCATION: (91)..(100)
<223> OTHER INFORMATION: a, c, u, g, unknown or other

<400> SEQUENCE: 161
unnnnnnnnn naucnnnnnn nnnnnngcan nnnnaagun nnnnnnnnnn ngunnnnnnn    60
nnngcannnn nnaagunnnn nnnnnnacag nnnnnnnnnn                        100

<210> SEQ ID NO 162
<211> LENGTH: 118
<212> TYPE: RNA
<213> ORGANISM: Artificial Sequence
<220> FEATURE:
<223> OTHER INFORMATION: Description of Artificial Sequence: Synthetic
```

```
                polynucleotide
<220> FEATURE:
<221> NAME/KEY: modified_base
<222> LOCATION: (3)..(7)
<223> OTHER INFORMATION: a, c, u, g, unknown or other
<220> FEATURE:
<221> NAME/KEY: modified_base
<222> LOCATION: (12)..(22)
<223> OTHER INFORMATION: a, c, u, g, unknown or other
<220> FEATURE:
<221> NAME/KEY: modified_base
<222> LOCATION: (36)..(46)
<223> OTHER INFORMATION: a, c, u, g, unknown or other
<220> FEATURE:
<221> NAME/KEY: modified_base
<222> LOCATION: (61)..(66)
<223> OTHER INFORMATION: a, c, u, g, unknown or other
<220> FEATURE:
<221> NAME/KEY: modified_base
<222> LOCATION: (83)..(89)
<223> OTHER INFORMATION: a, c, u, g, unknown or other
<220> FEATURE:
<221> NAME/KEY: modified_base
<222> LOCATION: (103)..(109)
<223> OTHER INFORMATION: a, c, u, g, unknown or other
<220> FEATURE:
<221> NAME/KEY: modified_base
<222> LOCATION: (111)..(115)
<223> OTHER INFORMATION: a, c, u, g, unknown or other

<400> SEQUENCE: 162
ggnnnnnccg annnnnnnnn nnugaagugg acacgnnnnn nnnnnnuugg ccgagcggug      60
nnnnnncuaa gggcugaagg cannnnnnnu gaaggaggca cgnnnnnnnu nnnnnccu       118

<210> SEQ ID NO 163
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (27)..(36)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (44)..(44)
<223> OTHER INFORMATION: a, c, u, g, unknown or other
<220> FEATURE:
<221> NAME/KEY: modified_base
<222> LOCATION: (45)..(56)
<223> OTHER INFORMATION: a, c, u, g, unknown or other and this region
      may encompass 1 to 12 nucleotides, wherein some positions may be
      absent
<220> FEATURE:
<221> NAME/KEY: modified_base
<222> LOCATION: (57)..(57)
<223> OTHER INFORMATION: a, c, u, g, unknown or other
<220> FEATURE:
<221> NAME/KEY: modified_base
<222> LOCATION: (69)..(69)
<223> OTHER INFORMATION: a, c, u, g, unknown or other
<220> FEATURE:
<221> NAME/KEY: modified_base
<222> LOCATION: (70)..(81)
<223> OTHER INFORMATION: a, c, u, g, unknown or other and this region
      may encompass 1 to 12 nucleotides, wherein some positions may be
```

```
              absent
<220> FEATURE:
<221> NAME/KEY: modified_base
<222> LOCATION: (82)..(82)
<223> OTHER INFORMATION: a, c, u, g, unknown or other

<400> SEQUENCE: 163
gggaannnnn nnnnncggau gguucgnnnn nnnnnnuucc cgcnnnnnnn nnnnnnncgg     60
augguucgnn nnnnnnnnnn nngcu                                          85

<210> SEQ ID NO 164
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (27)..(36)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (44)..(44)
<223> OTHER INFORMATION: a, c, u, g, unknown or other
<220> FEATURE:
<221> NAME/KEY: modified_base
<222> LOCATION: (45)..(56)
<223> OTHER INFORMATION: a, c, u, g, unknown or other and this region
      may encompass 1 to 12 nucleotides, wherein some positions may be
      absent
<220> FEATURE:
<221> NAME/KEY: modified_base
<222> LOCATION: (57)..(57)
<223> OTHER INFORMATION: a, c, u, g, unknown or other
<220> FEATURE:
<221> NAME/KEY: modified_base
<222> LOCATION: (69)..(69)
<223> OTHER INFORMATION: a, c, u, g, unknown or other
<220> FEATURE:
<221> NAME/KEY: modified_base
<222> LOCATION: (70)..(81)
<223> OTHER INFORMATION: a, c, u, g, unknown or other and this region
      may encompass 1 to 12 nucleotides, wherein some positions may be
      absent
<220> FEATURE:
<221> NAME/KEY: modified_base
<222> LOCATION: (82)..(82)
<223> OTHER INFORMATION: a, c, u, g, unknown or other

<400> SEQUENCE: 164
gggaannnnn nnnnncgaac cauccgnnnn nnnnnnuucc cgcnnnnnnn nnnnnnncga     60
accauccgnn nnnnnnnnnn nngcu                                          85

<210> SEQ ID NO 165
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, c, u, g, unknown or other and this region
```

```
      may encompass 1 to 10 nucleotides, wherein some positions may be
      absent
<220> FEATURE:
<221> NAME/KEY: modified_base
<222> LOCATION: (27)..(36)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (44)..(44)
<223> OTHER INFORMATION: a, c, u, g, unknown or other
<220> FEATURE:
<221> NAME/KEY: modified_base
<222> LOCATION: (45)..(56)
<223> OTHER INFORMATION: a, c, u, g, unknown or other and this region
      may encompass 1 to 12 nucleotides, wherein some positions may be
      absent
<220> FEATURE:
<221> NAME/KEY: modified_base
<222> LOCATION: (57)..(57)
<223> OTHER INFORMATION: a, c, u, g, unknown or other
<220> FEATURE:
<221> NAME/KEY: modified_base
<222> LOCATION: (69)..(69)
<223> OTHER INFORMATION: a, c, u, g, unknown or other
<220> FEATURE:
<221> NAME/KEY: modified_base
<222> LOCATION: (70)..(81)
<223> OTHER INFORMATION: a, c, u, g, unknown or other and this region
      may encompass 1 to 12 nucleotides, wherein some positions may be
      absent
<220> FEATURE:
<221> NAME/KEY: modified_base
<222> LOCATION: (82)..(82)
<223> OTHER INFORMATION: a, c, u, g, unknown or other

<400> SEQUENCE: 165
gggaannnnn nnnnncggau gguucgnnnn nnnnnnuucc cgcnnnnnnn nnnnnnncga    60
accauccgnn nnnnnnnnnn nngcu                                         85

<210> SEQ ID NO 166
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (39)..(48)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (52)..(52)
<223> OTHER INFORMATION: a, c, u, g, unknown or other
<220> FEATURE:
<221> NAME/KEY: modified_base
<222> LOCATION: (57)..(68)
<223> OTHER INFORMATION: a, c, u, g, unknown or other and this region
      may encompass 1 to 12 nucleotides, wherein some positions may be
      absent
<220> FEATURE:
<221> NAME/KEY: modified_base
```

```
<222> LOCATION: (69)..(69)
<223> OTHER INFORMATION: a, c, u, g, unknown or other
<220> FEATURE:
<221> NAME/KEY: modified_base
<222> LOCATION: (81)..(81)
<223> OTHER INFORMATION: a, c, u, g, unknown or other
<220> FEATURE:
<221> NAME/KEY: modified_base
<222> LOCATION: (82)..(93)
<223> OTHER INFORMATION: a, c, u, g, unknown or other and this region
      may encompass 1 to 12 nucleotides, wherein some positions may be
      absent

<400> SEQUENCE: 166
gggaugggug acgngaannn nnnnnnncgg augguucgnn nnnnnnnnuu cncgcunnnn     60
nnnnnnnnnc ggaugguucg nnnnnnnnnn nnnagucauc ccu                      103

<210> SEQ ID NO 167
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (39)..(48)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (52)..(52)
<223> OTHER INFORMATION: a, c, u, g, unknown or other
<220> FEATURE:
<221> NAME/KEY: modified_base
<222> LOCATION: (57)..(68)
<223> OTHER INFORMATION: a, c, u, g, unknown or other and this region
      may encompass 1 to 12 nucleotides, wherein some positions may be
      absent
<220> FEATURE:
<221> NAME/KEY: modified_base
<222> LOCATION: (69)..(69)
<223> OTHER INFORMATION: a, c, u, g, unknown or other
<220> FEATURE:
<221> NAME/KEY: modified_base
<222> LOCATION: (81)..(81)
<223> OTHER INFORMATION: a, c, u, g, unknown or other
<220> FEATURE:
<221> NAME/KEY: modified_base
<222> LOCATION: (82)..(93)
<223> OTHER INFORMATION: a, c, u, g, unknown or other and this region
      may encompass 1 to 12 nucleotides, wherein some positions may be
      absent

<400> SEQUENCE: 167
gggaugggug acgngaannn nnnnnnncga accauucgnn nnnnnnnnuu cncgcunnnn     60
nnnnnnnnnc gaaccguccg nnnnnnnnnn nnnagucauc ccu                      103

<210> SEQ ID NO 168
<211> LENGTH: 103
<212> TYPE: RNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (39)..(48)
<223> OTHER INFORMATION: a, c, u, g, unknown or other and this region
      may encompass 1 to 10 nucleotides, wherein some positions may be
      absent
<220> FEATURE:
<221> NAME/KEY: modified_base
<222> LOCATION: (52)..(52)
<223> OTHER INFORMATION: a, c, u, g, unknown or other
<220> FEATURE:
<221> NAME/KEY: modified_base
<222> LOCATION: (57)..(68)
<223> OTHER INFORMATION: a, c, u, g, unknown or other and this region
      may encompass 1 to 12 nucleotides, wherein some positions may be
      absent
<220> FEATURE:
<221> NAME/KEY: modified_base
<222> LOCATION: (69)..(69)
<223> OTHER INFORMATION: a, c, u, g, unknown or other
<220> FEATURE:
<221> NAME/KEY: modified_base
<222> LOCATION: (81)..(81)
<223> OTHER INFORMATION: a, c, u, g, unknown or other
<220> FEATURE:
<221> NAME/KEY: modified_base
<222> LOCATION: (82)..(93)
<223> OTHER INFORMATION: a, c, u, g, unknown or other and this region
      may encompass 1 to 12 nucleotides, wherein some positions may be
      absent

<400> SEQUENCE: 168
gggaugggug acgngaannn nnnnnnncgg augguucgnn nnnnnnnnuu cncgcunnnn       60
nnnnnnnnnc gaaccauccg nnnnnnnnnn nnnagucauc ccu                        103

<210> SEQ ID NO 169
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other
<220> FEATURE:
<221> NAME/KEY: modified_base
<222> LOCATION: (41)..(50)
<223> OTHER INFORMATION: a, c, u, g, unknown or other
<220> FEATURE:
<221> NAME/KEY: modified_base
<222> LOCATION: (54)..(54)
<223> OTHER INFORMATION: a, c, u, g, unknown or other
<220> FEATURE:
<221> NAME/KEY: modified_base
<222> LOCATION: (59)..(71)
<223> OTHER INFORMATION: a, c, u, g, unknown or other
<220> FEATURE:
```

<221> NAME/KEY: modified_base
<222> LOCATION: (85)..(97)
<223> OTHER INFORMATION: a, c, u, g, unknown or other

<400> SEQUENCE: 169
gggaugggug acgngaannn nnnnnnncga aggaggcacg nnnnnnnnnn uuuncgcunn    60
nnnnnnnnnn ncgaacggac gacgnnnnnn nnnnnnnagu cauuccu                107

<210> SEQ ID NO 170
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other
<220> FEATURE:
<221> NAME/KEY: modified_base
<222> LOCATION: (41)..(50)
<223> OTHER INFORMATION: a, c, u, g, unknown or other
<220> FEATURE:
<221> NAME/KEY: modified_base
<222> LOCATION: (54)..(54)
<223> OTHER INFORMATION: a, c, u, g, unknown or other
<220> FEATURE:
<221> NAME/KEY: modified_base
<222> LOCATION: (59)..(71)
<223> OTHER INFORMATION: a, c, u, g, unknown or other
<220> FEATURE:
<221> NAME/KEY: modified_base
<222> LOCATION: (85)..(97)
<223> OTHER INFORMATION: a, c, u, g, unknown or other

<400> SEQUENCE: 170
gggaugggug acgngaannn nnnnnnncga agcaggcacg nnnnnnnnnn uuuncgcunn    60
nnnnnnnnnn ncgaagccuc cacgnnnnnn nnnnnnnagu cauuccu                107

<210> SEQ ID NO 171
<211> LENGTH: 115
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other
<220> FEATURE:
<221> NAME/KEY: modified_base
<222> LOCATION: (39)..(48)
<223> OTHER INFORMATION: a, c, u, g, unknown or other
<220> FEATURE:
<221> NAME/KEY: modified_base
<222> LOCATION: (52)..(52)
<223> OTHER INFORMATION: a, c, u, g, unknown or other
<220> FEATURE:
<221> NAME/KEY: modified_base
<222> LOCATION: (57)..(69)
<223> OTHER INFORMATION: a, c, u, g, unknown or other
<220> FEATURE:
<221> NAME/KEY: modified_base

```
<222> LOCATION: (81)..(93)
<223> OTHER INFORMATION: a, c, u, g, unknown or other
<220> FEATURE:
<221> NAME/KEY: modified_base
<222> LOCATION: (105)..(114)
<223> OTHER INFORMATION: a, c, u, g, unknown or other; positions
      involved in kissing loop

<400> SEQUENCE: 171
gggaugggug acgngaannn nnnnnnncgg augguucgnn nnnnnnnnuu uncgcunnnn    60
nnnnnnnnnc ggaugguucg nnnnnnnnnn nnnagucauu ccaannnnnn nnnnu        115

<210> SEQ ID NO 172
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other
<220> FEATURE:
<221> NAME/KEY: modified_base
<222> LOCATION: (39)..(48)
<223> OTHER INFORMATION: a, c, u, g, unknown or other
<220> FEATURE:
<221> NAME/KEY: modified_base
<222> LOCATION: (52)..(52)
<223> OTHER INFORMATION: a, c, u, g, unknown or other
<220> FEATURE:
<221> NAME/KEY: modified_base
<222> LOCATION: (57)..(69)
<223> OTHER INFORMATION: a, c, u, g, unknown or other
<220> FEATURE:
<221> NAME/KEY: modified_base
<222> LOCATION: (81)..(93)
<223> OTHER INFORMATION: a, c, u, g, unknown or other

<400> SEQUENCE: 172
gggaugggug acgngaannn nnnnnnncga accauccgnn nnnnnnnnuu uncgcunnnn    60
nnnnnnnnnc gaacgauccg nnnnnnnnnn nnnagucauu ccu                     103

<210> SEQ ID NO 173
<211> LENGTH: 115
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other
<220> FEATURE:
<221> NAME/KEY: modified_base
<222> LOCATION: (39)..(48)
<223> OTHER INFORMATION: a, c, u, g, unknown or other
<220> FEATURE:
<221> NAME/KEY: modified_base
<222> LOCATION: (52)..(52)
<223> OTHER INFORMATION: a, c, u, g, unknown or other
<220> FEATURE:
<221> NAME/KEY: modified_base
```

```
<222> LOCATION: (57)..(69)
<223> OTHER INFORMATION: a, c, u, g, unknown or other
<220> FEATURE:
<221> NAME/KEY: modified_base
<222> LOCATION: (81)..(93)
<223> OTHER INFORMATION: a, c, u, g, unknown or other
<220> FEATURE:
<221> NAME/KEY: modified_base
<222> LOCATION: (105)..(114)
<223> OTHER INFORMATION: a, c, u, g, unknown or other; positions
      involved in kissing loop

<400> SEQUENCE: 173
gggaugggug acgngaannn nnnnnnncga accauccgnn nnnnnnnnuu uncgcunnnn      60
nnnnnnnnnc gaaccauccg nnnnnnnnnn nnnagucauu ccaannnnnn nnnnu          115

<210> SEQ ID NO 174
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (18)..(27)
<223> OTHER INFORMATION: a, c, u, g, unknown or other
<220> FEATURE:
<221> NAME/KEY: modified_base
<222> LOCATION: (39)..(48)
<223> OTHER INFORMATION: a, c, u, g, unknown or other
<220> FEATURE:
<221> NAME/KEY: modified_base
<222> LOCATION: (52)..(52)
<223> OTHER INFORMATION: a, c, u, g, unknown or other
<220> FEATURE:
<221> NAME/KEY: modified_base
<222> LOCATION: (57)..(69)
<223> OTHER INFORMATION: a, c, u, g, unknown or other
<220> FEATURE:
<221> NAME/KEY: modified_base
<222> LOCATION: (81)..(93)
<223> OTHER INFORMATION: a, c, u, g, unknown or other

<400> SEQUENCE: 174
gggaugggug acgngaannn nnnnnnncgg augguucgnn nnnnnnnnuu uncgcunnnn      60
nnnnnnnnnc ggauguucg nnnnnnnnnn nnnagucauu ccu                       103

<210> SEQ ID NO 175
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (25)..(30)
<223> OTHER INFORMATION: a, c, u, g, unknown or other; positions
      involved in loop portion of sequence
<220> FEATURE:
<221> NAME/KEY: modified_base
<222> LOCATION: (61)..(66)
<223> OTHER INFORMATION: a, c, u, g, unknown or other; positions
      involved in loop portion of sequence
```

-continued

<400> SEQUENCE: 175
gggacggaca gcgugcaugg ugaannnnnn acgccaugca cgcugcagac cgaacgugaa    60
nnnnnnacgc guucggucug cuaacguucc tttttt                             96

<210> SEQ ID NO 176
<211> LENGTH: 131
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(10)
<223> OTHER INFORMATION: a, c, u, g, unknown or other and this region
      may encompass 0 to 7 nucleotides, wherein some or all positions
      may be absent
<220> FEATURE:
<221> NAME/KEY: modified_base
<222> LOCATION: (16)..(25)
<223> OTHER INFORMATION: a, c, u, g, unknown or other
<220> FEATURE:
<221> NAME/KEY: modified_base
<222> LOCATION: (30)..(35)
<223> OTHER INFORMATION: a, c, u, g, unknown or other; positions
      involved in kissing loop
<220> FEATURE:
<221> NAME/KEY: modified_base
<222> LOCATION: (39)..(48)
<223> OTHER INFORMATION: a, c, u, g, unknown or other
<220> FEATURE:
<221> NAME/KEY: modified_base
<222> LOCATION: (53)..(55)
<223> OTHER INFORMATION: a, c, u, g, unknown or other
<220> FEATURE:
<221> NAME/KEY: modified_base
<222> LOCATION: (64)..(69)
<223> OTHER INFORMATION: a, c, u, g, unknown or other
<220> FEATURE:
<221> NAME/KEY: modified_base
<222> LOCATION: (82)..(84)
<223> OTHER INFORMATION: a, c, u, g, unknown or other
<220> FEATURE:
<221> NAME/KEY: modified_base
<222> LOCATION: (86)..(92)
<223> OTHER INFORMATION: a, c, u, g, unknown or other
<220> FEATURE:
<221> NAME/KEY: modified_base
<222> LOCATION: (97)..(102)
<223> OTHER INFORMATION: a, c, u, g, unknown or other; positions
      involved in kissing loop
<220> FEATURE:
<221> NAME/KEY: modified_base
<222> LOCATION: (106)..(112)
<223> OTHER INFORMATION: a, c, u, g, unknown or other
<220> FEATURE:
<221> NAME/KEY: modified_base
<222> LOCATION: (114)..(120)
<223> OTHER INFORMATION: a, c, u, g, unknown or other and this region
      may encompass 0 to 7 nucleotides, wherein some or all positions
      may be absent
<220> FEATURE:
<221> NAME/KEY: modified_base
<222> LOCATION: (124)..(129)
<223> OTHER INFORMATION: a, c, u, g, unknown or other; positions
      involved in kissing loop

<400> SEQUENCE: 176
ggcnnnnnnn ccguannnnn nnnnnugaan nnnnnacgnn nnnnnnnnua ugnnngagcg    60
uugnnnnnnc uaagcgcuga annnannnnn nnugaannnn nnacgnnnnn nnunnnnnnn   120
gccnnnnnnu c                                                       131

```
<210> SEQ ID NO 177
<211> LENGTH: 131
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(10)
<223> OTHER INFORMATION: a, c, u, g, unknown or other
<220> FEATURE:
<221> NAME/KEY: modified_base
<222> LOCATION: (13)..(15)
<223> OTHER INFORMATION: a, c, u, g, unknown or other
<220> FEATURE:
<221> NAME/KEY: modified_base
<222> LOCATION: (22)..(22)
<223> OTHER INFORMATION: a, c, u, g, unknown or other
<220> FEATURE:
<221> NAME/KEY: modified_base
<222> LOCATION: (25)..(27)
<223> OTHER INFORMATION: a, c, u, g, unknown or other
<220> FEATURE:
<221> NAME/KEY: modified_base
<222> LOCATION: (29)..(40)
<223> OTHER INFORMATION: a, c, u, g, unknown or other
<220> FEATURE:
<221> NAME/KEY: modified_base
<222> LOCATION: (45)..(50)
<223> OTHER INFORMATION: a, c, u, g, unknown or other
<220> FEATURE:
<221> NAME/KEY: modified_base
<222> LOCATION: (54)..(65)
<223> OTHER INFORMATION: a, c, u, g, unknown or other
<220> FEATURE:
<221> NAME/KEY: modified_base
<222> LOCATION: (68)..(70)
<223> OTHER INFORMATION: a, c, u, g, unknown or other
<220> FEATURE:
<221> NAME/KEY: modified_base
<222> LOCATION: (73)..(74)
<223> OTHER INFORMATION: a, c, u, g, unknown or other
<220> FEATURE:
<221> NAME/KEY: modified_base
<222> LOCATION: (77)..(79)
<223> OTHER INFORMATION: a, c, u, g, unknown or other
<220> FEATURE:
<221> NAME/KEY: modified_base
<222> LOCATION: (82)..(84)
<223> OTHER INFORMATION: a, c, u, g, unknown or other
<220> FEATURE:
<221> NAME/KEY: modified_base
<222> LOCATION: (86)..(92)
<223> OTHER INFORMATION: a, c, u, g, unknown or other
<220> FEATURE:
<221> NAME/KEY: modified_base
<222> LOCATION: (97)..(102)
<223> OTHER INFORMATION: a, c, u, g, unknown or other
<220> FEATURE:
<221> NAME/KEY: modified_base
<222> LOCATION: (106)..(112)
<223> OTHER INFORMATION: a, c, u, g, unknown or other
<220> FEATURE:
<221> NAME/KEY: modified_base
<222> LOCATION: (114)..(121)
<223> OTHER INFORMATION: a, c, u, g, unknown or other
<220> FEATURE:
<221> NAME/KEY: modified_base
<222> LOCATION: (124)..(129)
<223> OTHER INFORMATION: a, c, u, g, unknown or other; positions
      involved in kissing loop

<400> SEQUENCE: 177
ggnnnnnnnn ccnnnguucr anycnnngnn nnnnnnnnnn ugaannnnnn acgnnnnnnn      60
nnnnnurnnn ranngggnnnr annnrnnnnn nnugaannnn nnacgnnnnn nnunnnnnnn    120
```
nccnnnnnnu c                                                         131

<210> SEQ ID NO 178
<211> LENGTH: 118
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 178
gggaccuccg ugguucgaau ccacguacca gccuggauga agccugcacg uccaggcugg    60
uauggccgag cggcugaagg cacucguagu gaaguccaga cgcuacgagu aggucccu    118

<210> SEQ ID NO 179
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 179
ggcagccucc gugguucgaa uccacguacc agccuggaug aagccugcac guccaggcug    60
guauggccga gcggcugaag gcacucguag ugaaguccag acgcuacgag uagguugccc   120
cagaguc                                                             127

<210> SEQ ID NO 180
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 180
ggcagccucc gugguucgaa uccacguacc agccuggaug aagcgagcac guccaggcug    60
guauggccga gcggcugaag gcacucguag ugaagcaggc acgcuacgag uagguugccc   120
cagaguc                                                             127

<210> SEQ ID NO 181
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 181
ggcagccucc gugguucgaa uccacguacc agccuggaug aagccuccac guccaggcug    60
guauggccga gcggcugaag gcacucguag ugaagcucgc acgcuacgag uagguugccc   120
cagaguc                                                             127

<210> SEQ ID NO 182
<211> LENGTH: 126
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 182

```
ggcaccuccg igguucgaau ccacguacca gccuggauga aguggacacg uccaggcugg    60
uauggccgag cggcugaagg cacucguagu gaaggaggca cgcuacgagu aggugcccu    120 cugguc                                                              126

<210> SEQ ID NO 183
<211> LENGTH: 125
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 183 ggcaccuccg igguucgaau ccacguacca gccuggauga agccugcacg uccaggcugg    60
uauggccgag cggcugaagg cacucguagu gaaguccaga cgcuacgagu aggugcccuc   120
ugguc                                                              125

<210> SEQ ID NO 184
<211> LENGTH: 125
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 184 ggcaccuccg igguucgaau ccacguacca gccuggauga agcgagcacg uccaggcugg    60
uauggccgag cggcugaagg cacucguagu gaagcaggca cgcuacgagu aggugcccuc   120
ugguc                                                              125

<210> SEQ ID NO 185
<211> LENGTH: 125
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 185 ggcaccuccg igguucgaau ccacguacca gccuggauga agccuccacg uccaggcugg    60
uauggccgag cggcugaagg cacucguagu gaagcucgca cgcuacgagu aggugcccuc   120
ugguc                                                              125

<210> SEQ ID NO 186
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 186
gggaaggaua ccgugguucg aauccacgua ccagccugga ugaaguggac acguccaggc    60
ugguauggcc gagcggcuga aggcacucgu agugaaggag gcacgcuacg aguuauccuu   120
ccucucugg                                                          129

<210> SEQ ID NO 187
<211> LENGTH: 129
<212> TYPE: RNA
<213> ORGANISM: Artificial Sequence
```

-continued

```
<220> FEATURE:
<223> OTHER INFORMATION: Description of Artificial Sequence: Synthetic
      polynucleotide

<400> SEQUENCE: 187
gggaaggaua ccgugguucg aauccacgua ccagccugga ugaagccugc acguccaggc    60
ugguauggcc gagcggcuga aggcacucgu agugaagucc acacgcuacg aguuauccuu   120
ccuucaccg                                                           129

<210> SEQ ID NO 188
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 188
gggaaggaua ccgugguucg aauccacgua ccagccugga ugaagcgagc acguccaggc    60
ugguauggcc gagcggcuga aggcacucgu agugaagcag gcacgcuacg aguuauccuu   120
ccuggaugc                                                           129

<210> SEQ ID NO 189
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 189
gggaaggaua ccgugguucg aauccacgua ccagccugga ugaagccucc acguccaggc    60
ugguauggcc gagcggcuga aggcacucgu agugaagcuc gcacgcuacg aguuauccuu   120
ccugacagg                                                           129

<210> SEQ ID NO 190
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 190
ggauaccgug guucgaaucc acguaccagc cuggaugaag uggacacguc caggcuggua    60
uggccgagcg gcugaaggca cucguaguga aggaggcacg cuacgaguua uccccagag   119

<210> SEQ ID NO 191
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 191
ggauaccgug guucgaaucc acguaccagc cuggaugaag ccugcacguc caggcuggua    60
uggccgagcg gcugaaggca cucguaguga aguccacacg cuacgaguua uccccuguc   119

<210> SEQ ID NO 192
<211> LENGTH: 119
```

```
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 192
ggauaccgug guucgaaucc acguaccagc cuggaugaag cgagcacguc caggcuggua    60
uggccgagcg gcugaaggca cucguaguga agcaggcacg cuacgaguua uccgcaucc   119

<210> SEQ ID NO 193
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 193
ggauaccgug guucgaaucc acguaccagc cuggaugaag ccuccacguc caggcuggua    60
uggccgagcg gcugaaggca cucguaguga agcucgcacg cuacgaguua ucccgguga   119

<210> SEQ ID NO 194
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 194
ggagggaccu ccgugguucg aauccacgua ccagccugga ugaaguggac acguccaggc    60
ugguauggcc gagcggcuga aggcacucgu agugaaggag gcacgcuacg aguaagcccc   120
uccgcaucc                                                          129

<210> SEQ ID NO 195
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 195
ggagggaccu ccgugguucg aauccacgua ccagccugga ugaagccugc acguccaggc    60
ugguauggcc gagcggcuga aggcacucgu agugaagucc acacgcuacg aguaggcccc   120
uccucaccg                                                          129

<210> SEQ ID NO 196
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 196
ggagggaccu ccgugguucg aauccacgua ccagccugga ugaagcgagc acguccaggc    60
ugguauggcc gagcggcuga aggcacucgu agugaagcag gcacgcuacg aguaggcccc   120
uccccagag                                                          129
```

```
<210> SEQ ID NO 197
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 197
ggagggaccu ccgugguucg aauccacgua ccagccugga ugaagccucc acguccaggc    60
ugguauggcc gagcggcuga aggcacucgu agugaagcuc gcacgcuacg aguagguccc   120
uccgacagg                                                          129

<210> SEQ ID NO 198
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 198
ggagggaccu ccgugguucg aauccacgua ccagccugga ugaaguggac acguccaggc    60
ugguauggcc gagcggcuga aggcacucgu agugaaggag gcacgcuacg aguagguccc   120
uccccuguc                                                          129

<210> SEQ ID NO 199
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 199
ggagggaccu ccgugguucg aauccacgua ccagccugga ugaagccugc acguccaggc    60
ugguauggcc gagcggcuga aggcacucgu agugaagucc acacgcuacg aguagguccc   120
ucccucugg                                                          129

<210> SEQ ID NO 200
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 200
ggagggaccu ccgugguucg aauccacgua ccagccugga ugaagcgagc acguccaggc    60
ugguauggcc gagcggcuga aggcacucgu agugaagcag gcacgcuacg aguagguccc   120
ucccgguga                                                          129

<210> SEQ ID NO 201
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 201
ggagggaccu ccgugguucg aauccacgua ccagccugga ugaagccucc acguccaggc    60
```

```
ugguauggcc gagcggcuga aggcacucgu agugaagcuc gcacgcuacg aguagguccc    120
uccggaugc                                                            129

<210> SEQ ID NO 202
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
cuugcugaag cgcgcacagc aag                                             23

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uaagcuaugg cuaugcuau                                                  19

<210> SEQ ID NO 204
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
cguaccaacg c                                                          11
```

RNA NANOPARTICLES AND NANOTUBES

RELATED APPLICATIONS

This application is a 35 U.S.C. §371 U.S. national entry of International Application PCT/US2010/038818 (WO 2010/148085) having an International filing date of Jun. 16, 2010, which claims the benefit of U.S. Provisional application No. 61/187,495, filed on Jun. 16, 2009. The entire contents of the aforementioned application are hereby incorporated herein by reference.

GOVERNMENT FUNDING

Research supporting this application was carried out by the United States of America as represented by the Secretary, Department of Health and Human Services.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 30, 2014, is named 84230(47992)_SL.txt and is 81,372 bytes in size.

BACKGROUND OF THE INVENTION

The folding of RNA into compact 3D structures is a hierarchical process in which the formation of RNA helices is followed by the formation of tertiary RNA motifs that specify the positioning of the helices within the structure. Due to the folding process of RNA, modular tertiary motifs have likely emerged for the purpose of adopting specific topological arrangements of helices. RNA motifs are defined by sequence signatures that correspond to a limited set of conserved and semi-conserved nucleotides specifying well-defined 3D conformers. Recent developments in RNA architectonics, an approach for rationally designing 3D RNA architectures, have established that RNA structure information can be implemented into an RNA sequence to direct its tertiary folding and supramolecular assembly with a high degree of control and predictability. Nevertheless, knowledge about the kinetics, thermodynamics and autonomous folding properties of most RNA tertiary motifs remains scarce, presently limiting their use as building blocks for nano-construction.

DNA has been extensively used as a medium for constructing nanoarchitectures. To build a DNA polyhedra two different design approaches have been used, which involves the use of single stranded DNA or identical tiles that are generated from single stranded DNA. Using the former strategy a DNA polyhedra with the connectivity of a cube, a truncated octahedron, a regular octahedron, a DNA cage in the shape of a tetrahedron and a bipyramid have been reported; however many of the DNA structures that have been reported suffer from poor assembly yields due to unspecific assembly of the building blocks, which increases the instability of the constructed nanoparticles.

While being more chemically labile than DNA, RNA molecules exhibit complex tertiary structures and provide a large repertoire of novel RNA-RNA interaction motifs that can be used as a medium, to construct a variety of highly complex architectures. Also, while RNA architectures are programmable like DNA, they can be more readily expressed in vivo. Moreover, natural RNA molecules display interesting functionalities that can be encoded within the RNA assemblies such as aptamers, or ribozymes. Compared to protein cages, nanocages made of RNA might induce a lower immune response, thus reducing the antibody production that leads to the clearance of the foreign nanoparticle. The organization of RNA duplexes in the shape of specific symmetrical 3D architectures is an alternative way of RNA packaging in living organisms. The 3.0 A resolution crystal structure of dodecahedral cage of duplex RNA, which is located inside the viral capsid of Pariacoto virus, is the only reported natural RNA polyhedral structure. However, this RNA cage is not thought to be stable in the absence of proteins. Previous studies have demonstrated that RNA can be designed as rigid modular units to construct filaments, and a variety of self-assembling programmable 2D arrays. Recently, the Φ29 packaging RNA complex was engineered to form functionalized 2D trimeric nanoparticles that deliver siRNA to induce apoptosis in cancer cells.

The rapidly expanding field of nanobiology opens up the possibilities for the development of new methods and compositions that can be used for the diagnosis, prognosis, and treatment of various diseases such as cancer. However, while an increasing number of novel drugs and therapeutic agents are being discovered, the problem of delivering them specifically to the desired site or cell has not been solved. RNA nanoparticles have been shown to be able to carry multiple components, including molecules for specific cell recognition, image detection, and therapeutic treatment. The use of such protein-free nanoparticles holds the promise for the repeated long-term treatment of chronic diseases with low immune response and should avoid the problems of short retention time of small molecules and the difficulty of delivery of particles larger than 100 nanometers.

Nanoparticles are ideal drug delivery devices due to their novel properties and functions and ability to operate at the same scale as biological entities. Nanoparticles, because of their small size, can penetrate through smaller capillaries and are taken up by cells, which allow efficient drug accumulation at the target sites (Panyam J et al., Fluorescence and electron microscopy probes for cellular and tissue uptake of poly (D, L-lactide-co-glycolide) nanoparticles, Int J Pharm. 262:1-11, 2003). There are several issues that are important for efficient design and drug delivery by nanoparticles, including the efficient attachment of drugs and vectors, controlled drug release, size, toxicity, biodegradability, and activity of the nanoparticle. Moreover, for successful design one needs to understand and control the intermolecular associations, based on natural favorability of interactions and various physical components.

Targeted delivery of nanoparticles can be achieved by either passive or active targeting. Active targeting of a therapeutic agent is achieved by conjugating the therapeutic agent or the carrier system to a tissue or cell-specific ligand (Lamprecht et al., Biodegradable nanoparticles for targeted drug delivery in treatment of inflammatory bowel disease, J Pharmacol Exp Ther. 299:775-81, 2002). Passive targeting is achieved by coupling the therapeutic agent to a macromolecule that passively reaches the target organ (Monsky W L et al., Augmentation of transvascular transport of macromolecules and nanoparticles in tumors using vascular endothelial growth factor, Cancer Res. 59:4129-35, 1999). Drugs encapsulated in nanoparticles or drugs coupled to macromolecules such as high molecular weight polymers passively target tumor tissue through the enhanced permeation and retention effect (Maeda H, The enhanced permeability and retention (EPR) effect in tumor vasculature: the key role of tumor-selective macromolecular drug targeting, Adv Enzyme Regul. 41:189-207, 2001; Sahoo S K et al., Pegylated zinc protoporphyrin: a water-soluble heme oxygenase inhibitor with tumor-targeting capacity, Bioconjugate Chem. 13:1031-8, 2002).

It would be desirable to possess multifunctional engineered nanoparticles and complexes that are capable of bypassing biological barriers and have low immune response to deliver multiple therapeutic agents into specific cells and tissues. Accordingly, a safe and efficient nanoparticle needs to be designed for the delivery of effective therapeutic and diagnostic RNAs.

SUMMARY OF THE INVENTION

The present invention describes the design and synthesis of various RNA nanoparticles. In preferred embodiments, the nanoparticles of the invention can utilize various unique positions to carry molecules for cell recognition (e.g. cancer cells), therapy and detection.

The RNA nanoparticles of the present invention can be designed to self-assemble into predefined size and geometric shapes, in particular a three dimensional RNA polyhedral cage that can carry multiple components including molecules for specific cell recognition, image detection, and therapeutic treatment, and to encapsulate small therapeutic molecules inside their cages and release them upon being triggered by small ligands. In particular, the RNA nanoparticles of the present invention can be further designed to be spatially addressable by optimizing the location of 3'-tail connectors in the variable stem and thus controlling the positioning of the biotin within the cage. This allows either the encapsulation of proteins inside the cage or their attachment to the outside forming aggregates of cages. Like proteins and DNA, RNA can potentially lead to stable polyhedral RNA architectures for use as carriers in nanomedicine and synthetic biology.

Accordingly, in a first aspect, the invention provides a polyvalent RNA nanoparticle comprising RNA motifs as building blocks.

In one embodiment, the building blocks comprise a motif that allows for non-covalent assembly between 2 or more building blocks.

In another embodiment of the invention, the RNA motifs are RNA I or RNA II motifs. In a related embodiment, the RNA motif is a 90 degree angle bend motif or a 120 degree angle bend motif. In a further embodiment, the RNAII motif is selected from the group consisting of: right angle (RA) motifs, three way junction (3WJ) motifs, four way junction motifs and class II tRNA motifs.

In one embodiment, the RA motif is selected from the group consisting of: SEQ ID NO: 1, SEQ ID NO: 2, SEQ ID NO: 3 and SEQ ID NO: 4 as shown in the Table in FIG. 8.

In a related embodiment, the polyvalent RNA nanoparticle comprises SEQ ID NO: 1, 2, 3 and 4.

In another embodiment, the 3WJ motif is selected from the group consisting of: SEQ ID NO: 5, SEQ ID NO: 6, SEQ ID NO: 7 and SEQ ID NO: 8 as shown in the Table in FIG. 8. In a related embodiment, the polyvalent RNA nanoparticle comprises SEQ ID NO: 5, 6, 7 and 8.

In another embodiment, the class II tRNA motif is selected from the group consisting of: SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16 as shown in the Table in FIG. 8. In a related embodiment, the polyvalent RNA nanoparticle comprises SEQ ID NO: 9, 10, 11 and 12. In another related embodiment, the polyvalent RNA nanoparticle comprises SEQ ID NO: 12, 13, 14 and 15.

In another embodiment, the RNAII motif is a class II tRNA motif.

In one embodiment of the invention, four RNAII motifs comprise a tectosquare.

In another embodiment, each 90 degree angle bend motif comprises a corner of a tectosquare.

In another embodiment, the RNA nanoparticle of the aspects described herein further comprises one or more kissing loops (KL). In a related embodiment, the KL are selected from the group consisting of KL1 (AA-ggAggC-A SEQ ID NO: 17), KL2 (AA-gUCCAC-A SEQ ID NO: 18), KL3 (AA-gCAggC-A SEQ ID NO: 19), KL4 (AA-gCUCgC-A SEQ ID NO: 20), and KL5 (AA-CUUUCgC-A SEQ ID NO: 21), L6 (AAGUCACCA SEQ ID NO: 22), L7 (AACGUGGUA SEQ ID NO: 23), L8 (AAGAGCCUA SEQ ID NO: 24).

In another embodiment, the polyvalent nanoparticle comprises SEQ ID NO: 25 (RA-sd_L1) or 26 (RA-sd_L5) as shown in the Table in FIG. 8.

In another embodiment, the polyvalent nanoparticle comprises SEQ ID NO: 27 (3WJ-sd_L1), 28 (3WJ-sd_L5), 29 (3WJ-P_L1) or 30 (3WJ-sd_L5) as shown in the Table in FIG. 8.

In another embodiment, the polyvalent nanoparticle comprises SEQ ID NO: 31 (tRNAKL5a), 32 (tRNAKL5b), 33 (tRNA-sd_L1) or 34 (tRNA-sd_L5) as shown in the Table in FIG. 8.

In another embodiment, the polyvalent nanoparticle comprises SEQ ID NO: 35 (mtRNA-sd_L1) or 36 (mtRNA-sd_L5) as shown in the Table in FIG. 8.

In a further embodiment, the kissing loops of the RNA nanoparticle are covalently joined by helical stems. In another further embodiment, the tectosquare further comprises four kissing loops.

In one embodiment, one side of the tectosquare measures 12-14 nm.

In another embodiment, the RNA motifs are RNA I inverse (RNA Ii) or RNA II inverse (RNA IIi) motifs.

In another embodiment of the present invention, the polyvalent RNA nanoparticle is in the shape of a circular nanoparticle. In a further embodiment, the circular nanoparticle comprises one or more building blocks.

In a related embodiment, the building blocks contain helical stems between 10-15 base pairs in length. In another related embodiment, the building blocks contain helical stems between 35-45 base pairs in length.

In still another embodiment, the circular nanoparticle comprises 6-15 building blocks that form a ring.

In another embodiment, the circular nanoparticle has a diagonal dimension of between 15 nm-25 nm.

In still another embodiment, the circular nanoparticle has a diagonal dimension of between 25 nm-35 nm. In one embodiment, the circular nanoparticle has a diagonal dimension of 26.2 nm.

In a further embodiment, the polyvalent nanoparticle further comprises kissing loops (KL).

In another further embodiment, the polyvalent nanoparticle further comprises a stabilizing motif. In a related embodiment, the stabilizing motif is a four way junction (4WJ) motif. In a further related embodiment, the 4WJ motif further comprises an 11 nucleotide receptor. In still another related embodiment, the 4WJ motif comprises SEQ ID NO: 37. (GGAUGGGAAACGUGGUCCGAUCUGAAGGAG-GCACGGAUUGGACUACGCCAAG UCGAUGAA GUGGACACGUCGAUUUGGUCAUUCUU) or SEQ ID NO: 38 (GGAUGGGAAACGUGGUCCGAUCUGAAGU-CCACACGGAUUGGACUACGCCAAG UCGAUGAA GCCUCCACGUCGAUUUGGUCAUUCUU).

In another embodiment, the circular nanoparticle comprises a sequence selected from the group consisting of SEQ ID NO: 39-62 as shown on the Table in FIG. 16.

In one embodiment of the present invention, the class II tRNA motif comprises an aminoacyl stem, a variable stem, and an anticodon stem.

In another embodiment of the present invention, the class II tRNA motif is modified.

In still another embodiment, the modification comprises relocation of the 5'/3' termini from the aminoacyl stem to the variable stem.

In a related embodiment, the modification further comprises insertion of one or more KLs in the class II tRNA motif.

In another further embodiment, the variable stem comprises a 3' tail connector. In a related embodiment, the 3' tail connector is between 7-10 base pairs in length. In another related embodiment, the 3' tail connector further comprises a one-half or more triple helical turn. In a further embodiment, the triple helical turn is in the major groove side.

In another embodiment, eight class II tRNA motifs self assemble into a three dimensional shape. In a further embodiment, eight class II tRNA motifs that assemble into a three dimensional shape are selected from the group consisting of: SEQ ID NO 63-70 as shown in Table 6. In another embodiment, assembly of the class II tRNA motifs comprises KL interactions.

In another embodiment, assembly of the class II tRNA motifs further comprises interactions between 3' tail connectors.

In certain aspects, the nanoparticles are cubic nanoparticles. In another embodiment, the cubic nanoparticles comprise RNA strands assembled in the shape of a cube. In a related embodiment, the cubic nanoparticles comprise RNA/DNA strands assembled in the shape of a cube.

In another further embodiment, the number of RNA or RNA/DNA strands is between 6-10. In a further related embodiment, the RNA or RNA/DNA strands comprise 10 base pairs.

In another embodiment, the RNA strands comprise 5' dangling ends.

In a related embodiment, the 5' dangling ends are modified with an agent. In certain embodiments, the agent is selected from a therapeutic agent, an imaging agent and a diagnostic agent. In another embodiment, the agent is an aptamer.

In still another embodiment, the three dimensional shape is a nanocage.

In another embodiment of the present invention, the nanoparticle comprises one or more agents. In a related embodiment, the agent is selected from the group consisting of: a therapeutic agent, an imaging agent and a diagnostic agent. In still another embodiment, the agent is a small inhibitory nucleic acid. In another further embodiment, the agent is conjugated to the nanoparticle. In still another embodiment, the agent is biotin. In another further embodiment, the agent is conjugated to the nanoparticle by a covalent bond.

In another embodiment of the present invention, the RNA motifs further comprise nucleic acid modifications. In a related embodiment, the nucleic acid modifications comprise nucleic acid analogues.

In another aspect, the present invention features a drug delivery composition comprising the polyvalent RNA nanoparticle as described in the aspects herein, wherein the drug delivery composition can gain entry into a cell or tissue.

In one embodiment, the drug delivery composition further comprises a second agent. In a further embodiment, the second agent is biotin. In another further embodiment, the second agent is selected from the group consisting of: a therapeutic agent, an imaging agent and a diagnostic agent.

In still another embodiment, the second agent is selected from the group consisting of: chemotherapeutic agents, cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, anti-anxiety agents, immunosuppressive agents, immunomodulatory agents, antimigraine agents, sedatives/hypnotics, anti-anginal agents, antipsychotics, antimanic agents, antiarrhythmics, antiarthritic agents, antigout agents, anti-coagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodialators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

In another related embodiment, the chemotherapeutic agent is selected from the group consisting of: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

In another aspect, the invention features a method of treating or preventing a disease or disorder, the method comprising administering to a subject in need thereof an effective amount of a polyvalent RNA nanoparticle of the invention as described herein.

In one embodiment, the disease or disorder is selected from the group consisting of: Adenoma, Ageing, AIDS, Alopecia, Alzheimer's disease, Anemia, Arthritis, Asthma, Atherosclerosis, Cancer, Cardiac conditions or disease, Diabetes mellitus, Foodborne illness, Hemophilia A-E, Herpes, Huntington's disease, Hypertension, Headache, Influenza, Multiple Sclerosis, Myasthenia gravis, Neoplasm, Obesity, Osteoarthritis, Pancreatitis, Parkinson's disease, Pelvic inflammatory disease, Peritonitis, Periodontal disease, Rheumatoid arthritis, Sepsis, Sickle-cell disease, Teratoma, Ulcerative colitis, Uveitis.

In another embodiment, the method comprises targeting the polyvalent nanoparticle to a delivery site.

In another aspect, the present invention features a method of treating a tumor in a subject comprising administering an anticancer agent to the subject, wherein a polyvalent nanoparticle comprises an anticancer agent; and thereby treating the tumor in a subject.

In one embodiment, the method further comprises the step of targeting the polyvalent nanoparticle to the tumor site.

In another aspect, the invention features a method for making the polyvalent nanoparticle of any one of the aspects described herein, the method comprising overexpressing an RNA sequence comprising an RNA motif in a cell; and allowing the RNA sequences to assemble into a polyvalent nanoparticle, thereby making a polyvalent nanoparticle.

In another aspect, the invention features a method for making the polyvalent nanoparticle of any one of the aspects described herein comprising mixing a sample comprising RNA sequences comprising an RNA motif, heating the sample, cooling the sample; and allowing the RNA sequences to assemble into a polyvalent nanoparticle; thereby making a polyvalent nanoparticle.

In another embodiment of the method, the RNA sequences comprising an RNA motif are mixed in an equimolar ratio. In still another embodiment of the method, the method further comprises the step of incubating the samples after the cooling step. In another embodiment of the method, the method further comprises the step of raising the magnesium concentration after the incubation step. In another embodiment, the RNA motifs allow for non-covalent assembly between 2 or more building blocks.

In another aspect, the invention features a kit comprising the polyvalent nanoparticle according to any one of the aspects described herein, and instructions for use.

Other aspects of the invention are described in, or are obvious from, the following disclosure, and are within the ambit of the invention.

BRIEF DESCRIPTION OF THE DRAWINGS

FIG. 1 (A-C) shows 90° motifs and corresponding tectoRNA and tectosquare structures. (Top) Front and side views of tectosquare models built from the RA- (A), 3WJ- (B) and tRNA- (C) motifs. (Middle and Bottom) Secondary and tertiary structures corresponding to L-shaped tectoRNAs. Each motif sequence signature is in blue. N, any nucleotide (nt); R, purine; Y, pyrimidine; X, nt positions involved in kissing loops (KL); Plain black bars, classic Watson crick (WC) bps; Black circles or dashed lines, non-classic WC bps; Capital letters, conserved positions (>95%); lower case letters, semi-conserved positions (>75%). For tRNA-tectoRNAs, aa, ac and var stand for amino-acyl, anticodon and variable stems, respectively. For 3WJ-P tectoRNAs, the 3WJ sequence signature (nt in blue) is rotated by 90° anticlockwise. Images were rendered in PyMol (11). FIG. 1A discloses SEQ ID NO: 160 and FIG. 1B discloses SEQ ID NO: 161.

FIG. 8 is a table that shows a list of sequences (SEQ ID NOS 1-4, 25-26, 5-8, 27-30, 9-12, 31-34, 13-16, and 35-36, respectively, in order of appearance) for the tectoRNA constructs used in the experiments described herein. TectoRNA nomenclature: A, B, C, and D indicate the type of the unit with respect of their kissing loop (KL) motifs in a clock-wise fashion within the context of the tectosquare; sd—stands for self-dimer; m stands for mutant; nucleotides underlined in yellow indicate the kissing loops; nucleotides underlined in blue indicates point mutations. Constructs tRNA-KL5a/b were used to measure the Kd of KL5.

FIG. 14 shows structure prediction of closed nanorings (class 8) by circumference measurements. According to the 3D model, the estimated length of the large hexagon is approximately 13 nm from side to side. The circumference values of various polygons that can potentially assemble has been calculated and the nanorings have been classified by comparison with their measured circumference values accordingly.

FIG. 16 is a table showing a list of sequences (SEQ ID NOS 159 and 39-62, respectively, in order of appearance) used to construct circular nanoparticles. The characters in bold letters represent the loop regions. The unit letter is followed by s in the case of a stabilized building block. The unit letter is followed by c (control) when the unit is designed to include KL loops instead of RNAIi/RNAIii complex.

FIG. 22 discloses SEQ ID NOS 86-88, respectively, in order of appearance.

FIG. 23 discloses SEQ ID NOS 82, 89-94, 93-97, 96 and 98-99, respectively, in order of appearance.

FIG. 23 discloses SEQ ID NOS 100-102, 102, 100, 103-105, 104-105, 104-107, 104, 107, 106, 108-110, 110, 109, 111-113, 112 and 114, respectively, in order of appearance.

FIG. 25 discloses SEQ ID NO: 175.

FIG. 26 shows an example of a finite sized nanogrid composed of four tetrameric nanorings.

FIG. 29 (A-E) shows that cuboids are stable supra-molecular assemblies. FIG. 29(B) shows TGGE gels with horizontal temperature gradient for cuboids (20 nM) at 0.2 mM Mg(OAc)2. FIG. 29(C) Comparison of melting curves for tectosquares (TS 1) and cuboids (TS 1 and TS5 mix) obtained from TGGE gels at 0.2 and 15 mM Mg(OAc)2. Legend: (---o---) square at 0.2 mM Mg2+, –) square at 15 mM Mg2+, (---o---) cuboid at 0.2 mM Mg2+, cuboid at 15 mM Mg2+.

FIG. 29(D) Tm values for tectosquare (TS1) and cuboids (TS 1 and TS5 mix) at various Mg2+ concentrations are tabulated.

FIG. 32 (A-C) shows programming the cuboid to control the positioning of a protein with respect to the cage. FIG. (A) 5% native-PAGE showing the difference in gel shifts when a protein is encapsulated inside the cage or attached outside the cage. The numbers indicate the molar ratio of cuboid to streptavidin. First 4 lanes are control lanes showing the migration of monomer, squares and an empty cuboid. FIG. (B) and FIG. (C) 200 rim scale AFM images of 1:5 cuboid to streptavidin molar ratio for both cases (inside (B) and outside (C)) obtained in air.

FIG. 33 shows engineering spatially addressable cuboids (TS6 and TS7 mix). Monomers functionalized with biotin with inward (Bc2 and Dc4) or outward (Bc4' and Dc2') orientation can be used to control the positioning of streptavidin inside the cuboid (a,b) or outside the cuboid (c,d), respectively. In the later case, cuboids were connected in a beads on a string type supramolecular architectures as expected by the programming of the functionalized units within the cuboid. Streptavidin to cuboid molar ratio is 1:1.

FIG. 39 is a table that shows a list of tectoRNAs (SEQ ID NOS 177, 9, 178, 11-12, 63 and 179-201, respectively, in order of appearance) used in the described experiments.

FIG. 41 shows the modified nucleosides which contain an embedded cyclopentane ring constrained in (a) the north and (b) south conformation. The conformation of flanking bases, (c) open, (d) closed, (e) 3R bulged-out and (f) secondary structure of subtype-B (pdb ID: 1JJM and 1XPE).

FIGS. 48 (A and B) shows an example of the RNAJunction Web server query and results pages.

FIGS. 50 (A and B), A) shows AFM images of an individual tectosquare and self-assembling nanoarrays of multiple tectosquares. B) shows Type V tectosquare and MD simulation domains.

Figure 56:
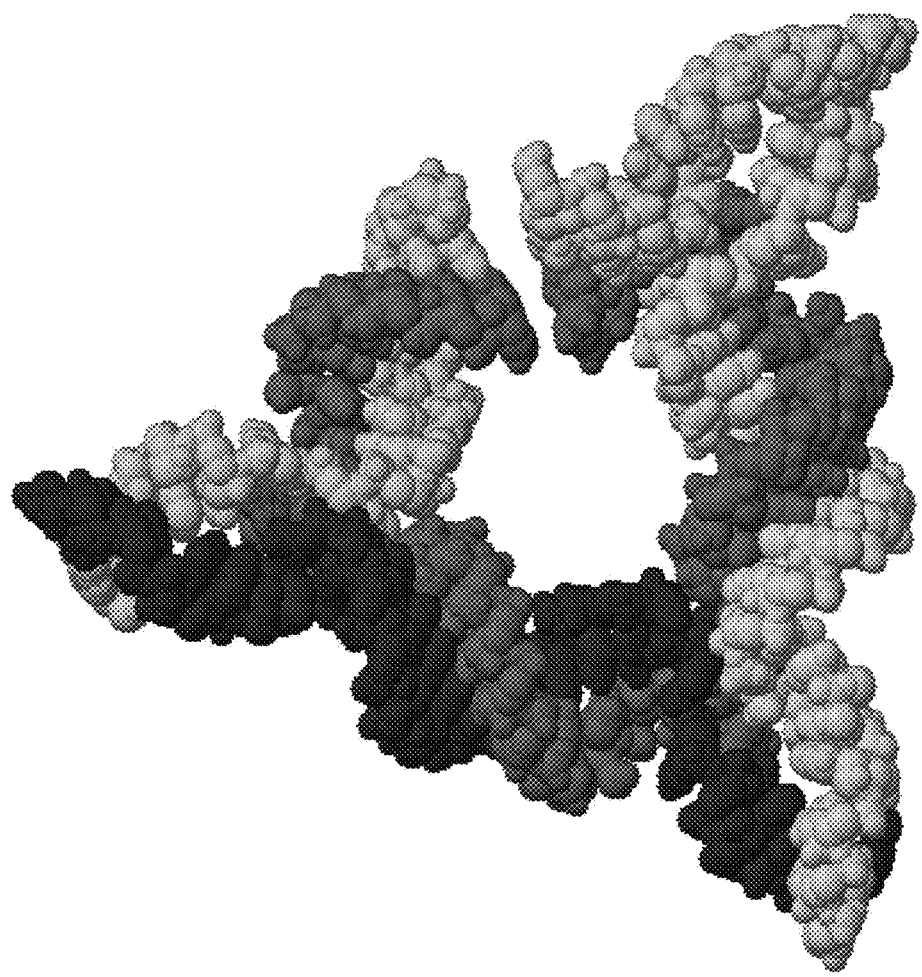

FIG. 56 shows design of a junction-based triangle.

FIG. 57 shows a native PAGE experiment for the four designed sequences of an RNA triangle shows that the sequences interact as expected.

Figure 58:
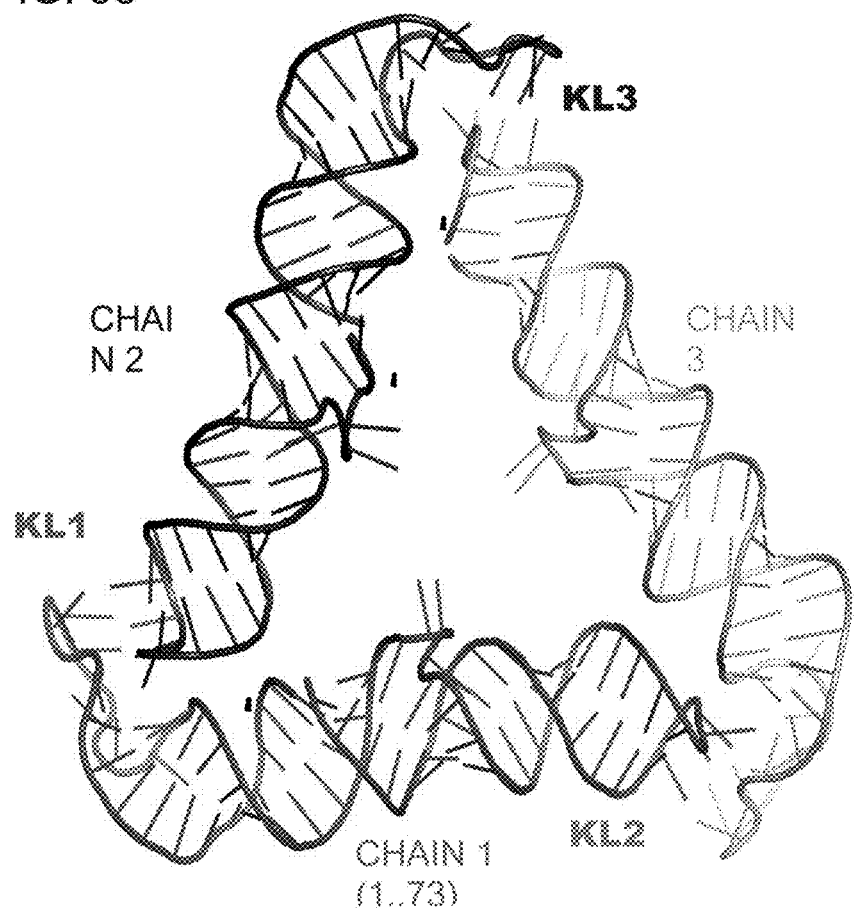
Figure 58:
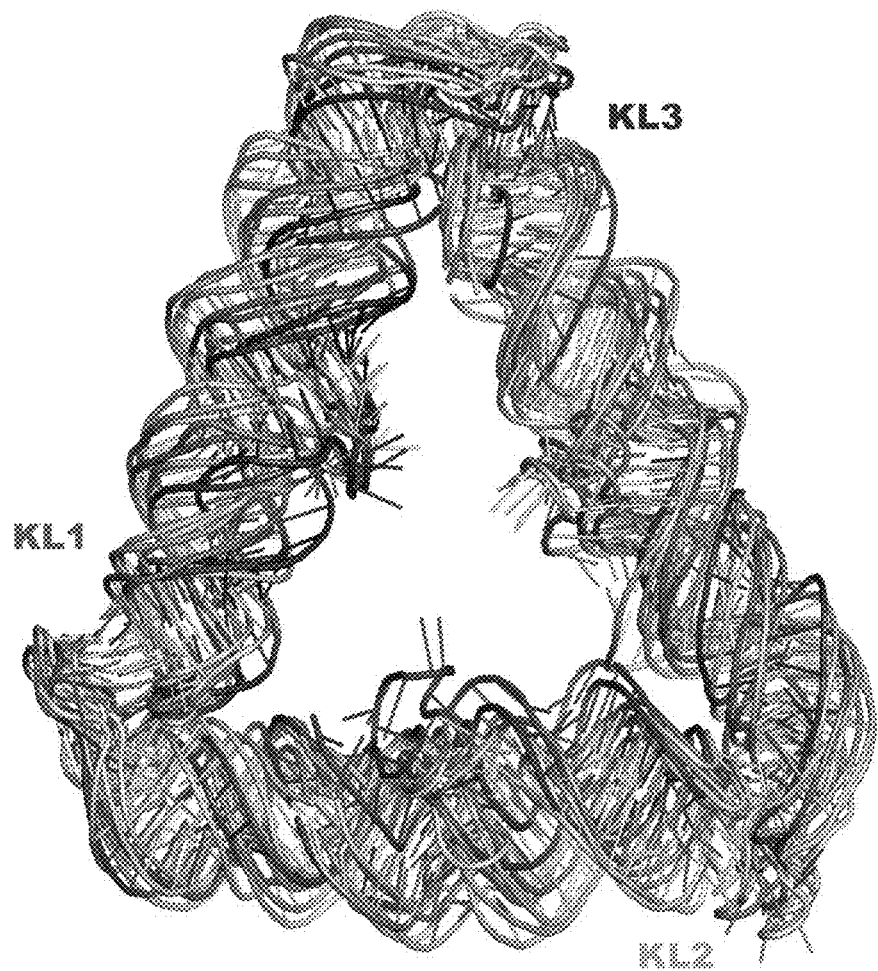
Figure 58:
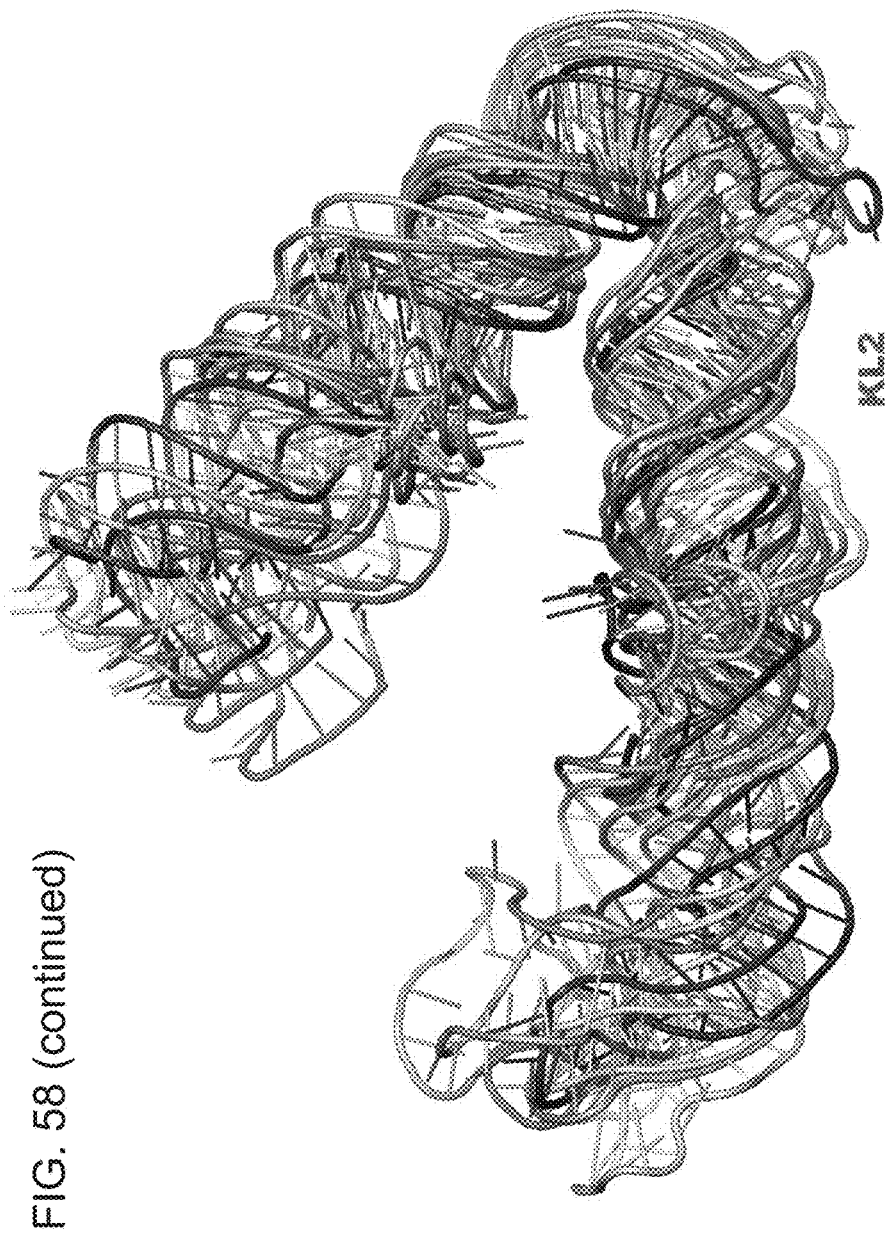

FIG. 58 shows design of a KL-based Triangle. A triangle was designed with the help of NanoTiler. The design combines a KL complex (RNAJunction DB entry 12948), a two-way junction and fragments of A-form helices fitted to form a closed ring structure.

Figure 59:
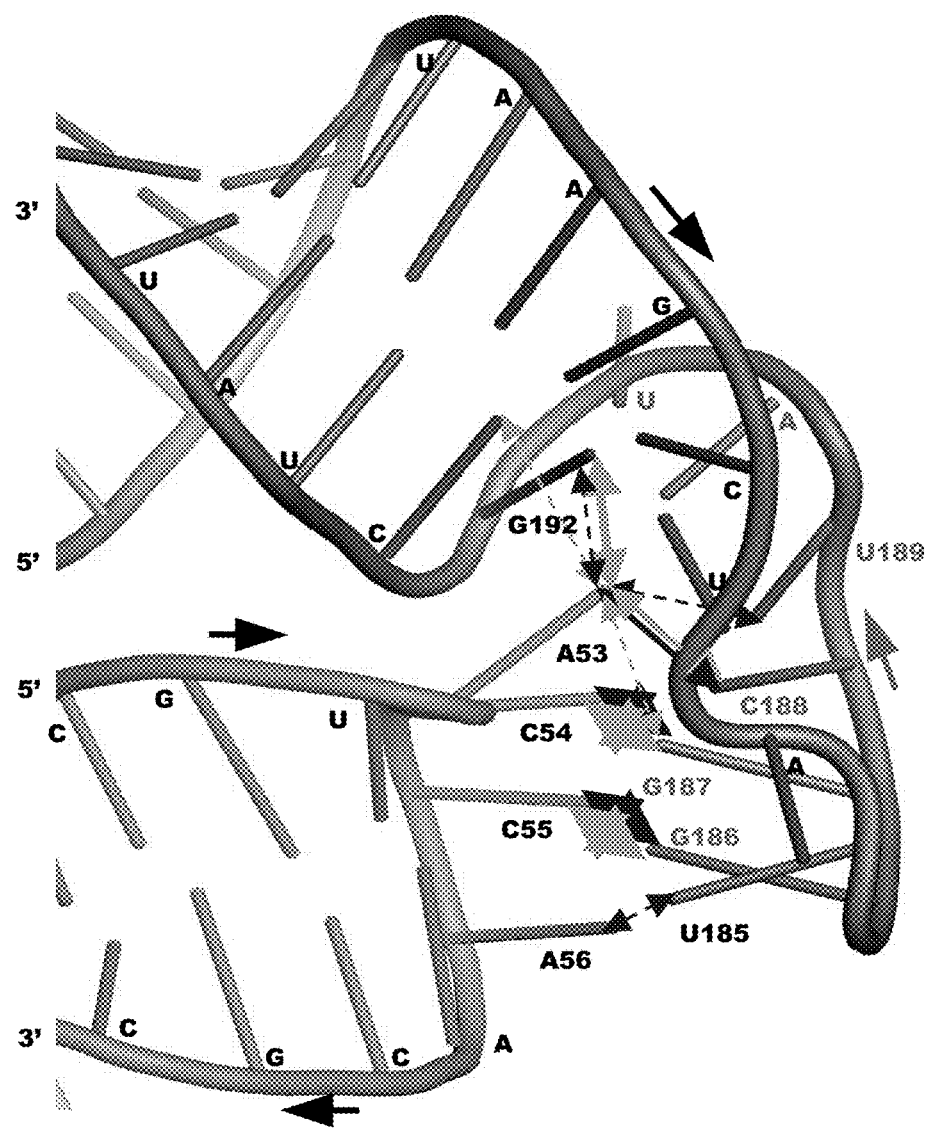

FIG. 59 shows hydrogen bonds formed by A53 aid in stabilizing the KL complex and show variability in the three triangle KLs. There are differences in the partners of A53 and hydrogen bond occupancy rates for the KL2 in the triangle (blue arrows) and the dimer (red arrows). In the Figure A53-C188: two bonds; 54% and 59% occupancy. A53-G192: single bond; 80% occupancy. A53-C193 & A53-G187 intermittent, low occupancy. 53-AC188: two bonds after ~2.0 ns; 44% and 71% occupancy. A53 bonds with U189 and G192 break after the first 1.5 ns. FIG. 59 discloses SEQ ID NOS 203 and 204, respectively, in order of appearance.

Figure 60:
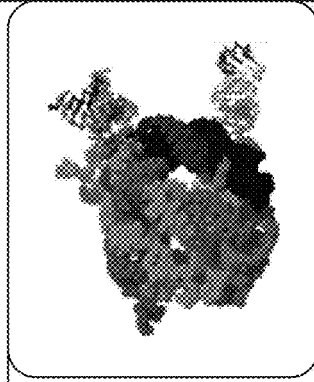

FIG. 60 is a Table that shows cube sequences and control MG aptamer sequences used in the experiments. FIG. 60 discloses SEQ ID NOS 130-157, respectively, in order of appearance.

Figure 61:
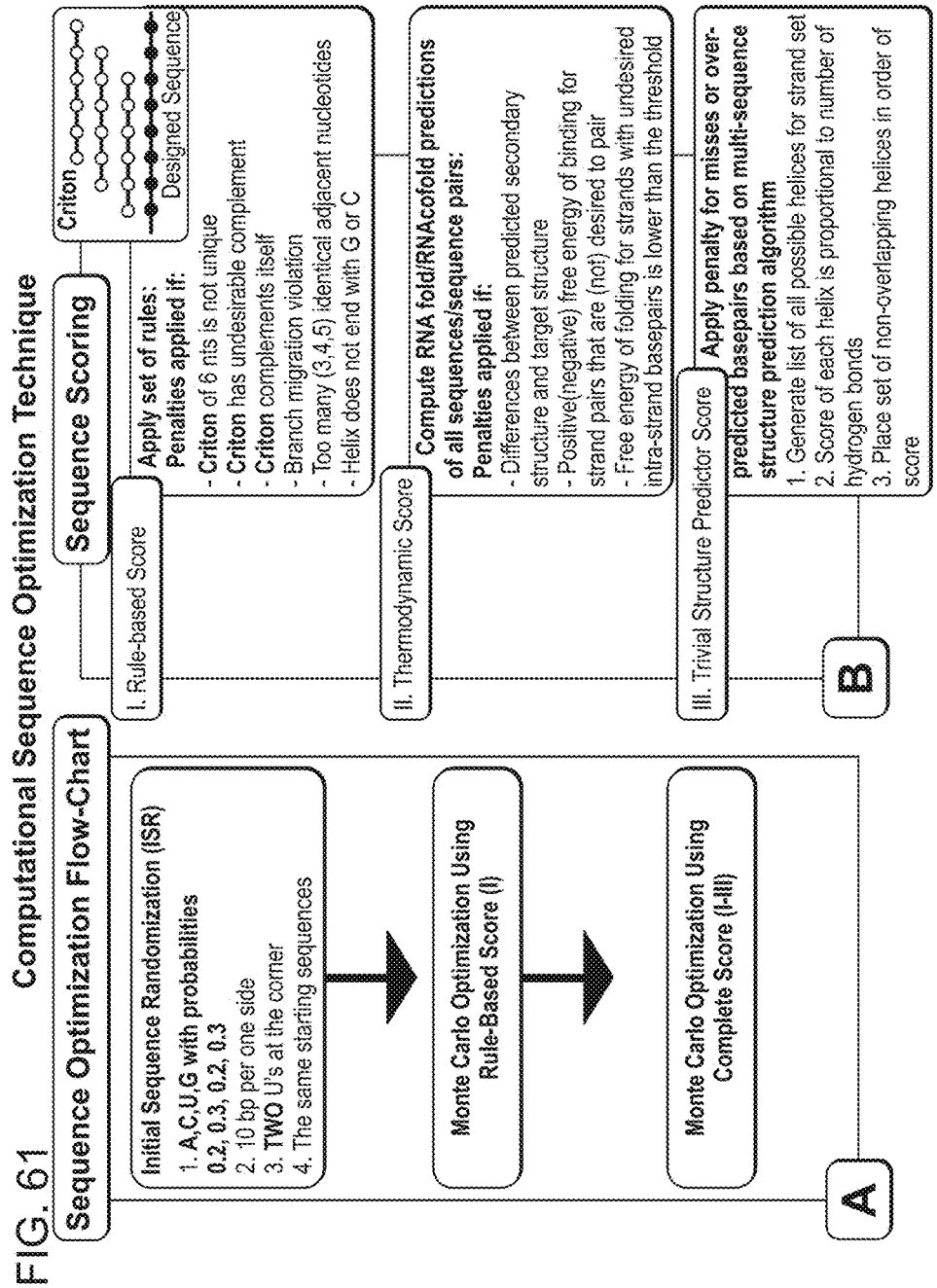

FIGS. 61 (a and b) shows a flow chart of sequence optimization steps. The initial sequence randomization is performed by choosing the nucleotides A, C, G, U with probabilities 0.2, 0.3, 0.3, 0.2 respectively (corresponding to a target G+C content of about 60%). Nucleotides that are designed to form a basepair (bp), are chosen to be complementary. Two stages of Monte-Carlo optimization are performed. The first optimization stage is based on the fast-to-compute rule-based scoring function. When a specified score threshold has been reached, the complete scoring function (consisting of the three components outlined in part B) is applied in a second stage of Monte Carlo optimization. B. All three components of the sequence design scoring function. (I) A scoring function that applies empirical rules that can be quickly determined based on the character string composition without folding predictions; (II) A thermodynamic scoring function that scores if both RNAcofold and RNAfold predictions are compatible with the desired folding characteristics of all designed sequences and sequence pairs; (III) A score comparing a multisequence structure prediction (based on placing predicted helices in order of a simple helix score) with the target secondary structure.

Figure 62:
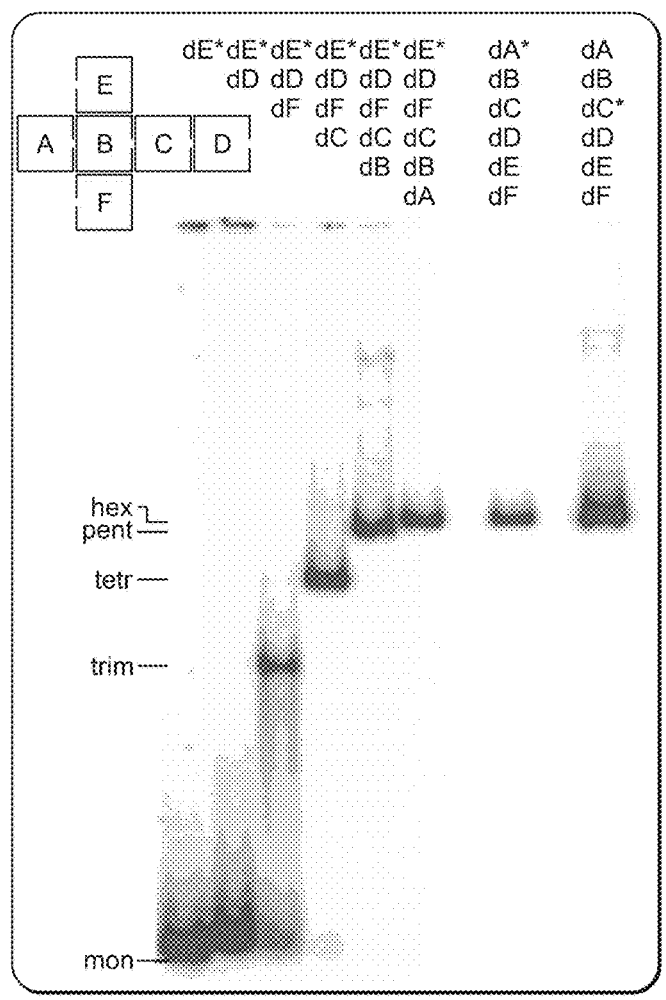

FIG. 62 shows native gel assembly experiments for the six stranded DNA cube without 5' dangling end. The 5' end γ[32P]ATP radiolabeled molecules are marked with asterisks. The variations in monomer through pentamer assembly patterns between RNA and DNA (i.e. dimer migration rate) can be explained by the differences in stabilities between A-form and B-form helices.

Figure 63:
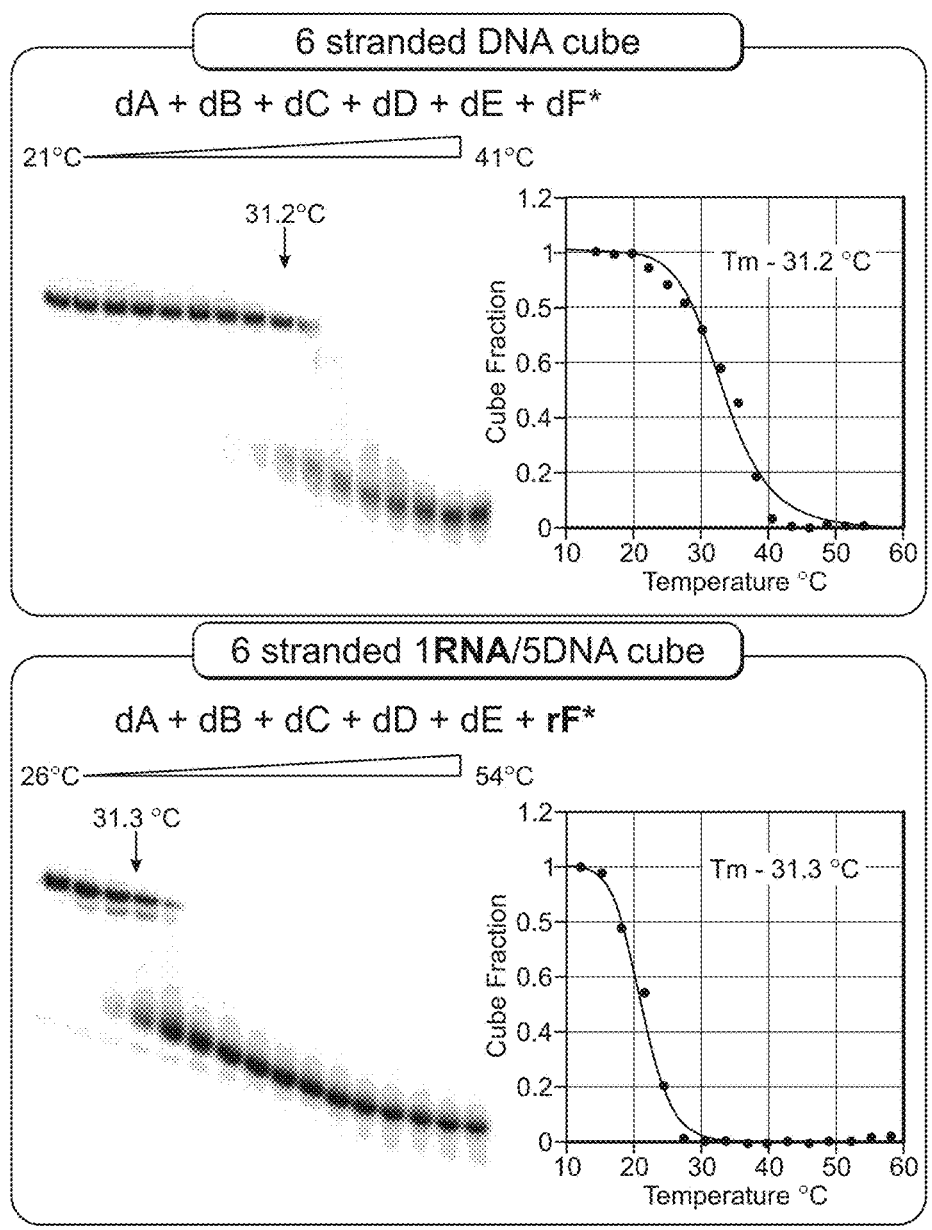
Figure 63:
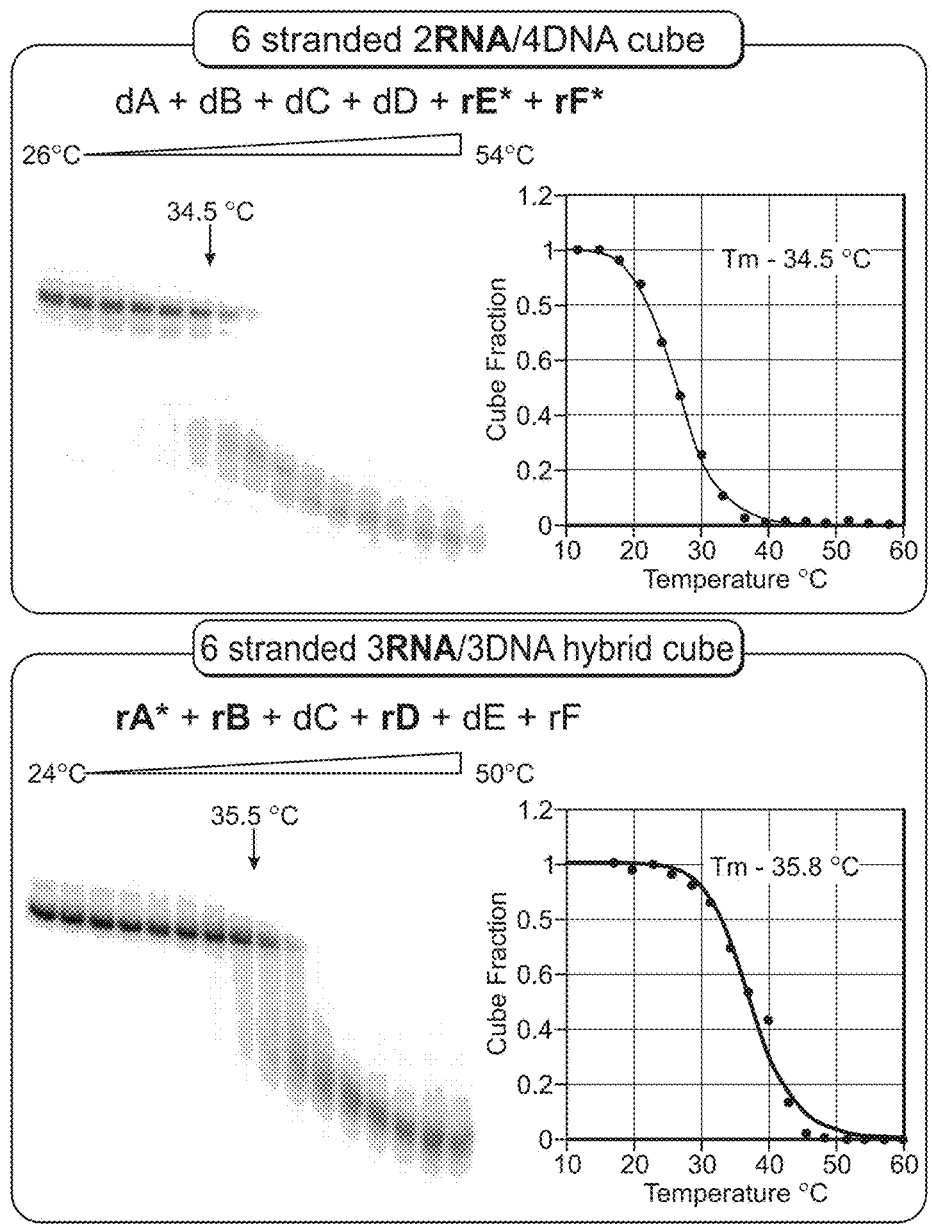
Figure 63:
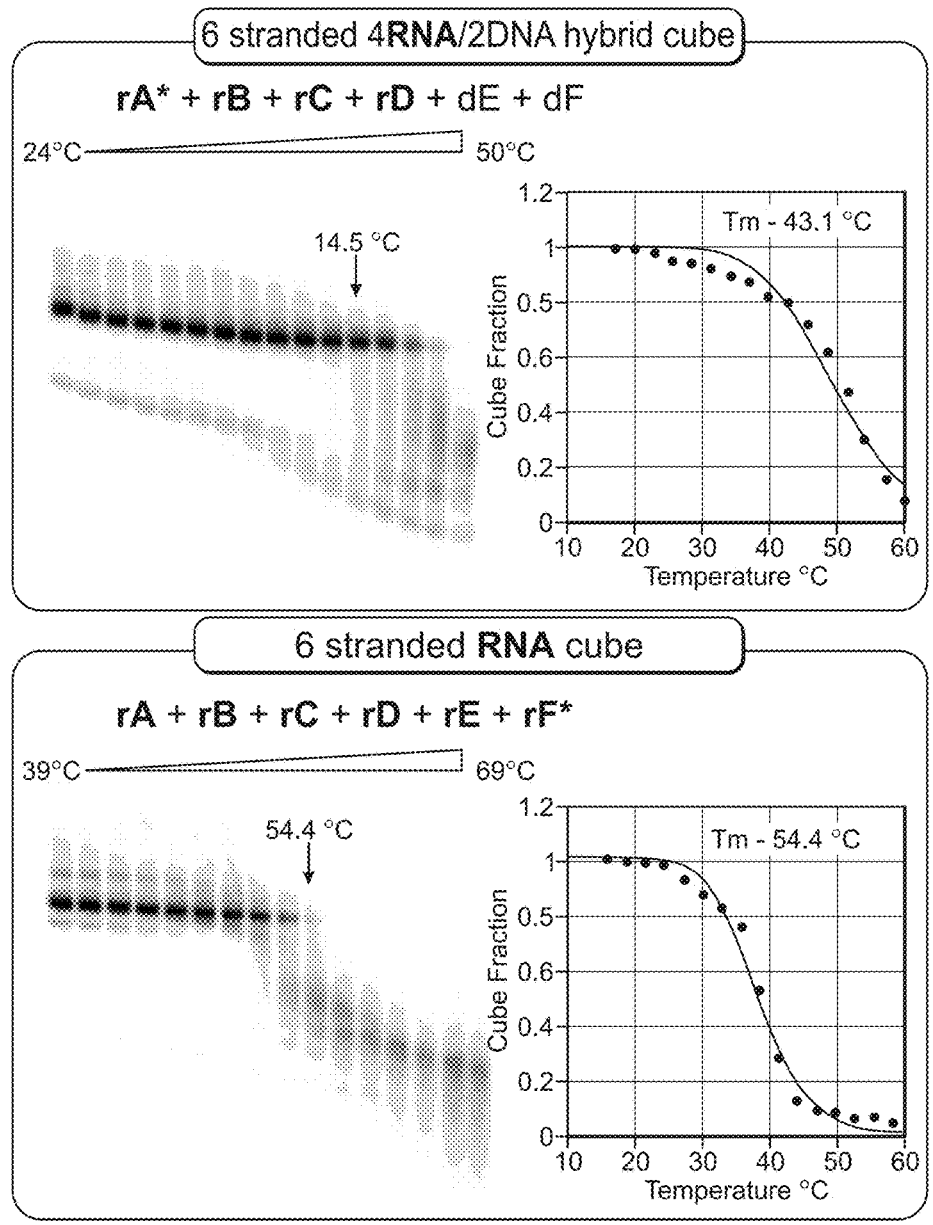

FIG. 63 shows TGGE experiments at 2 mM Mg(OAc)2 with horizontal temperature gradient and corresponding thermal melting curves for RNA (r), DNA (d), and RNA/DNA hybrid 6 stranded cubes without 5' dangling end.

Figure 64A:
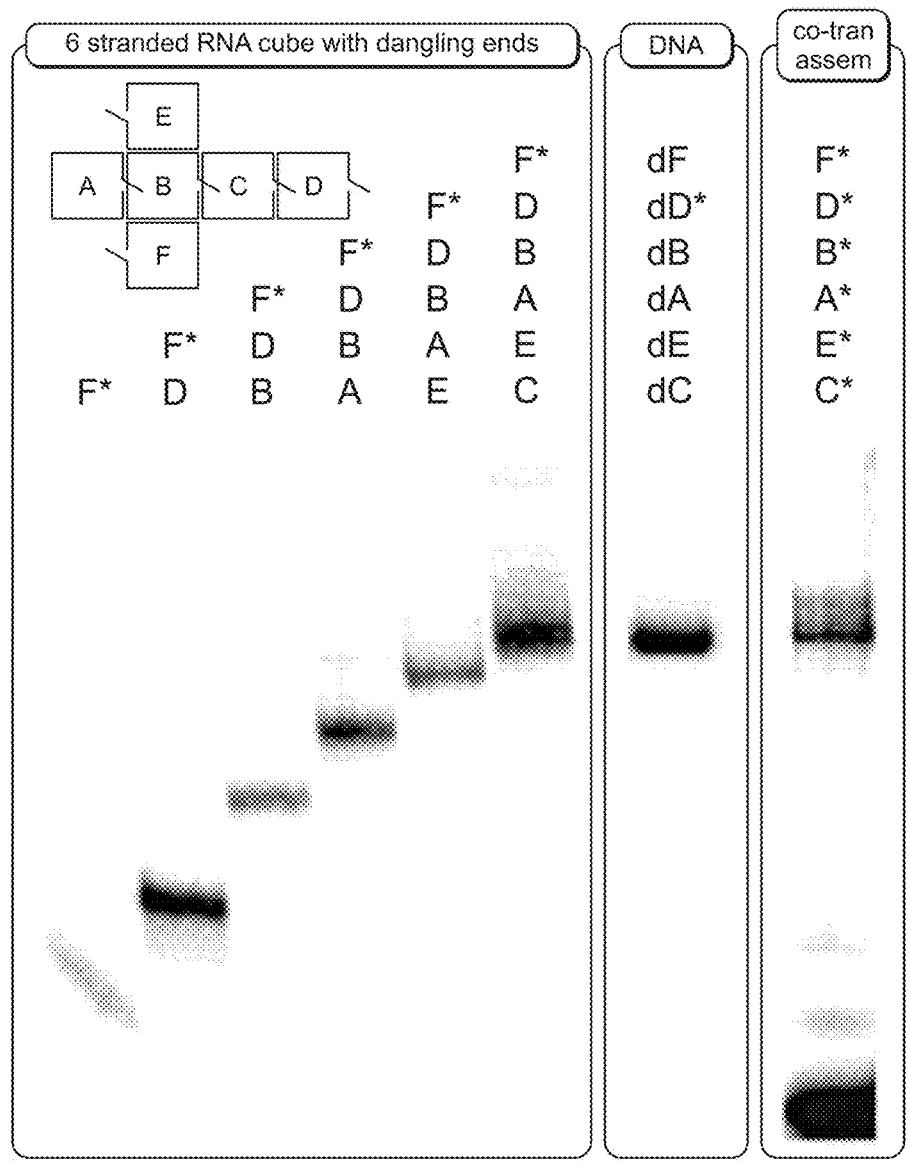

FIG. 64 (a-c) shows native PAGE and DLS characterizations of the 6 stranded RNA nanocube with 5' dangling ends. (a) Native gel assembly experiments for the 6 stranded RNA (left panel) and DNA (middle panel) cubes. (right panel) Co-transcriptional self assembly of α[32P]ATP body labeled RNA molecules. [32P] radiolabeled molecules are marked with asterisks. (b) TGGE experiments at 2 mM Mg(OAc)2 with horizontal temperature gradient for RNA and DNA cubes. (c) A size histogram of the RNA cube measured by DLS.

Figure 65A:
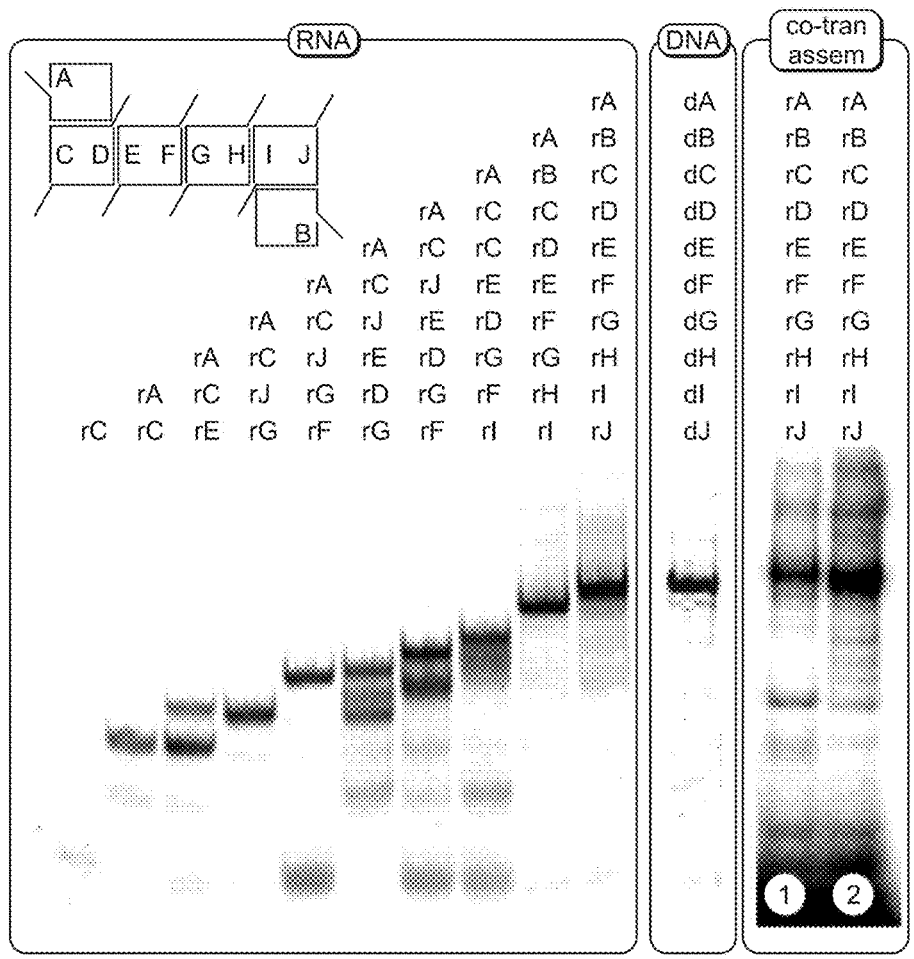

FIG. 65 (a-c) shows nNative PAGE and DLS characterizations of the 10 stranded RNA nanocube with 5' dangling ends. (a) Total staining native gel assembly experiments for the 10 stranded RNA cube (left panel) and DNA cube (middle panel). Co-transcriptional self assembly (right panel) of α[32P]ATP body labeled RNA molecules: for (1), DNA templates for all ten molecules were mixed at equimolar concentrations; for (2), DNA templates of molecules A and B were added in 2× excess with respect of the templates of C to J. (b) Thermal melting curves obtained from TGGE experiments for the RNA (red) and DNA (blue) ten stranded nano-cubes. TGGE experiments were performed at 2 mM Mg(OAc)2 with an horizontal grandient of temperature. (c) A size histogram of the RNA cube measured by DLS.

Figure 66:
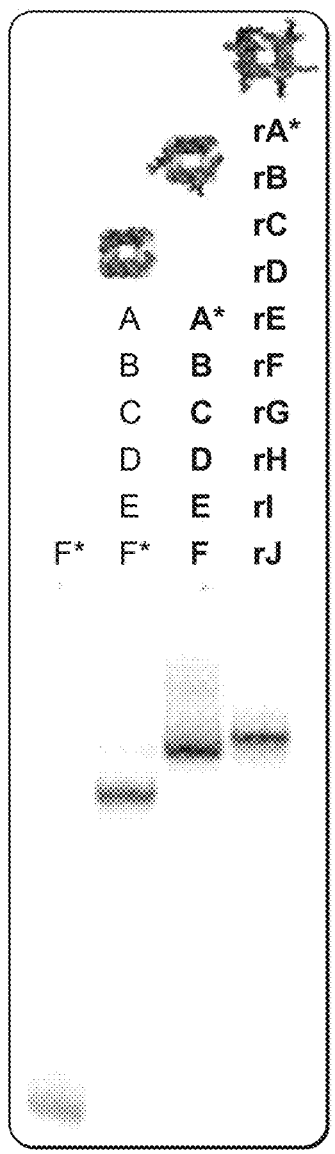

FIG. 66 shows Comparative native gel assembly experiments of the three different types of RNA cube shown FIG. 1. Radiolabeled molecules are marked with asterisks.

Figure 67A:
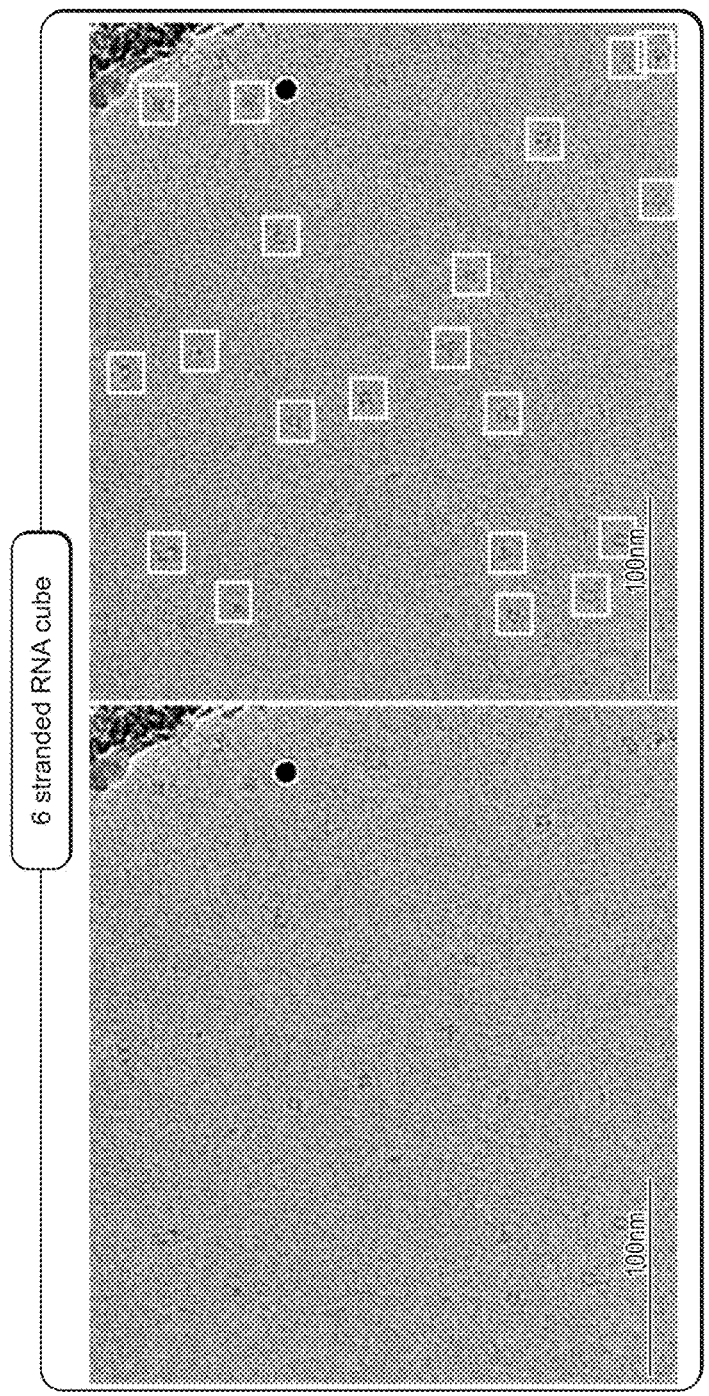
Figure 67B:
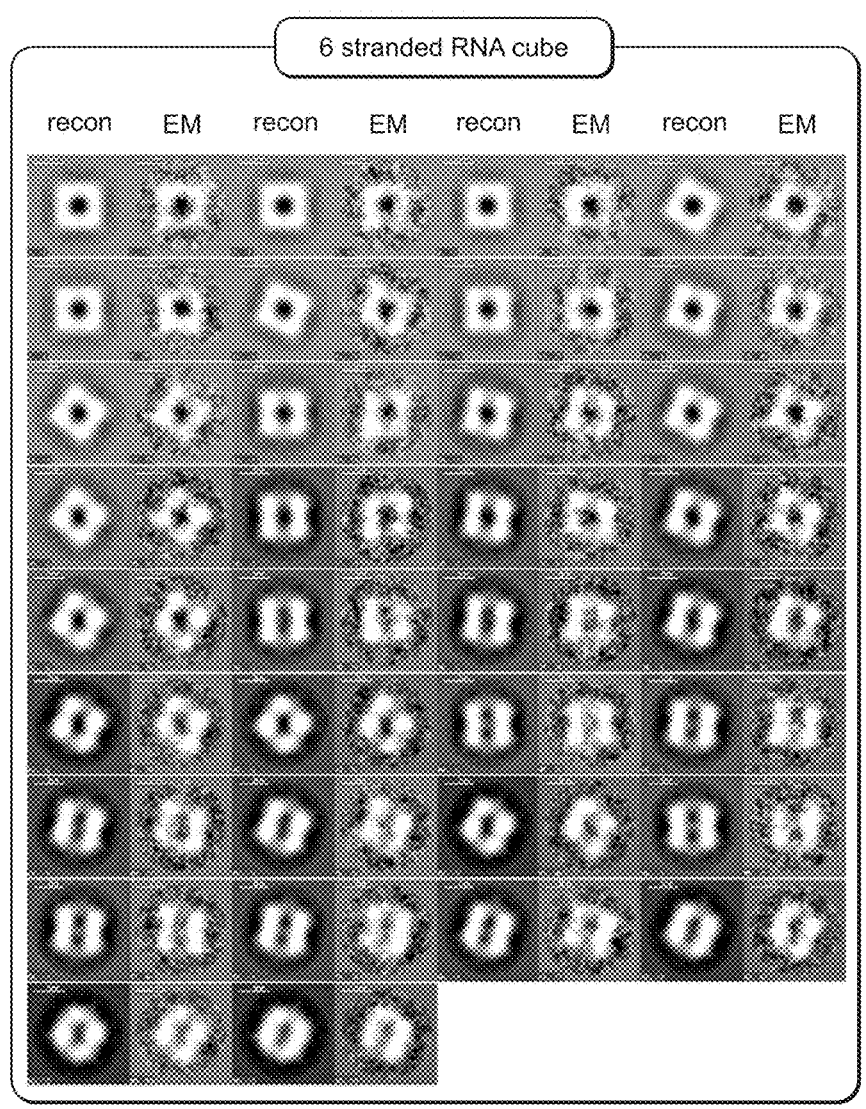
Figure 67C:
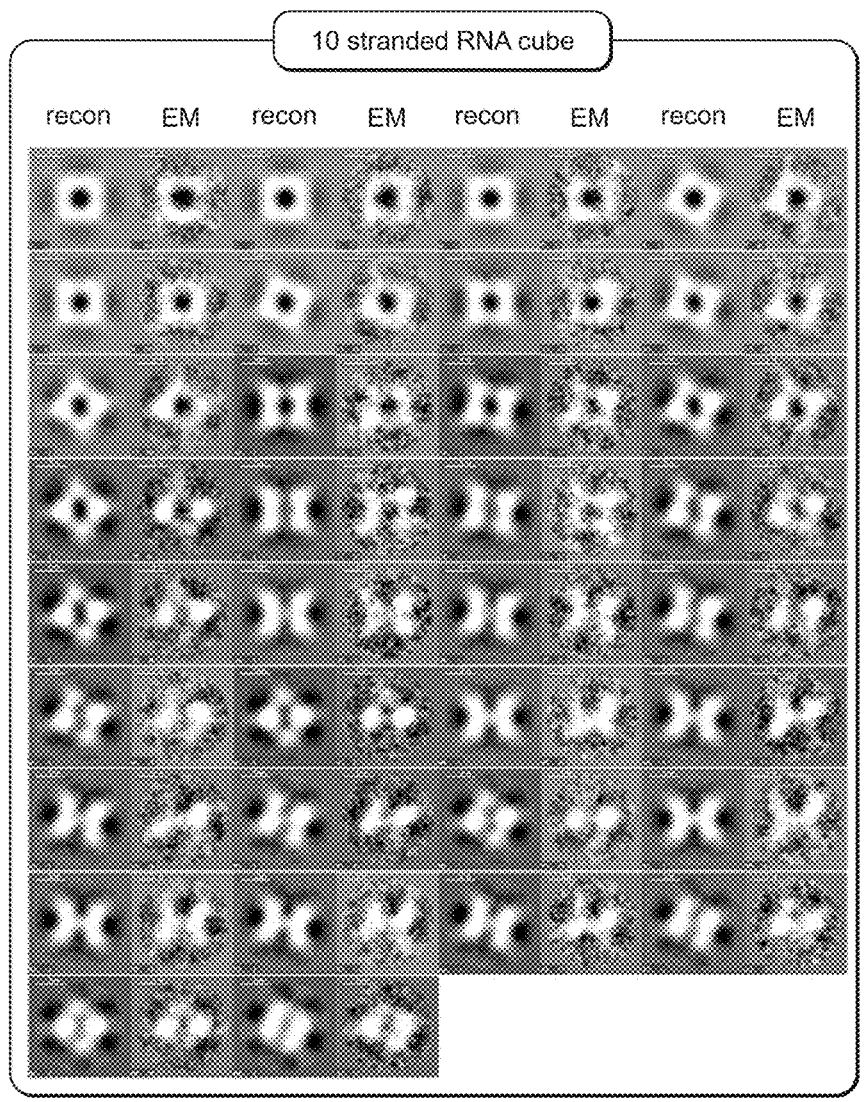

FIG. 67 (a-c) shows Additional Cryo-EM data. (a) Typical example of a cryo-EM image of six stranded cube. The squared particles correspond to well-formed nano-cubes. Full set of EM class averages used for the 6 stranded (b) and 10 stranded (c) cubes reconstruction. EM indicates class averages of nano-particles with similar views observed by cryo-EM. Recon indicates the corresponding projections of the RNA cubes in 3D structure reconstructed from the cryo-EM images.

Figure 68:
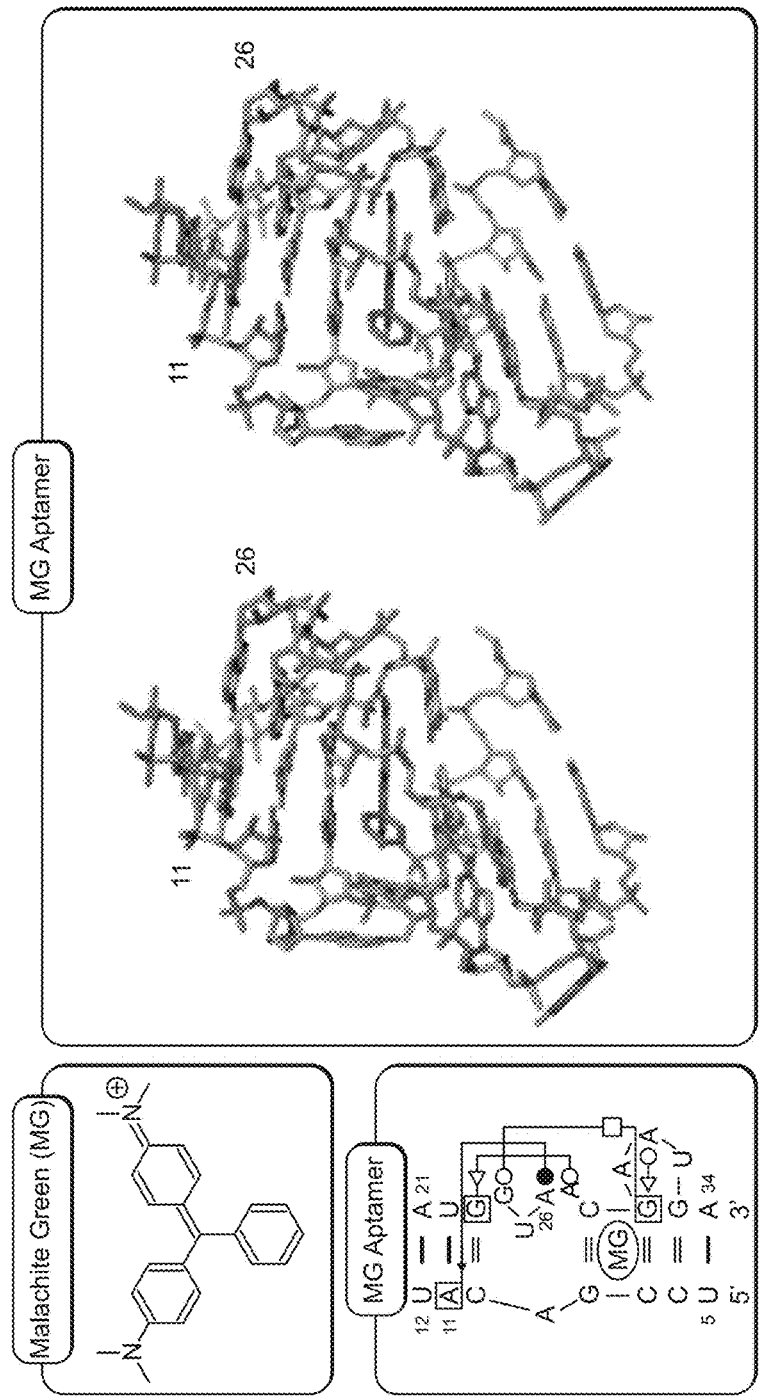
Figure 68:
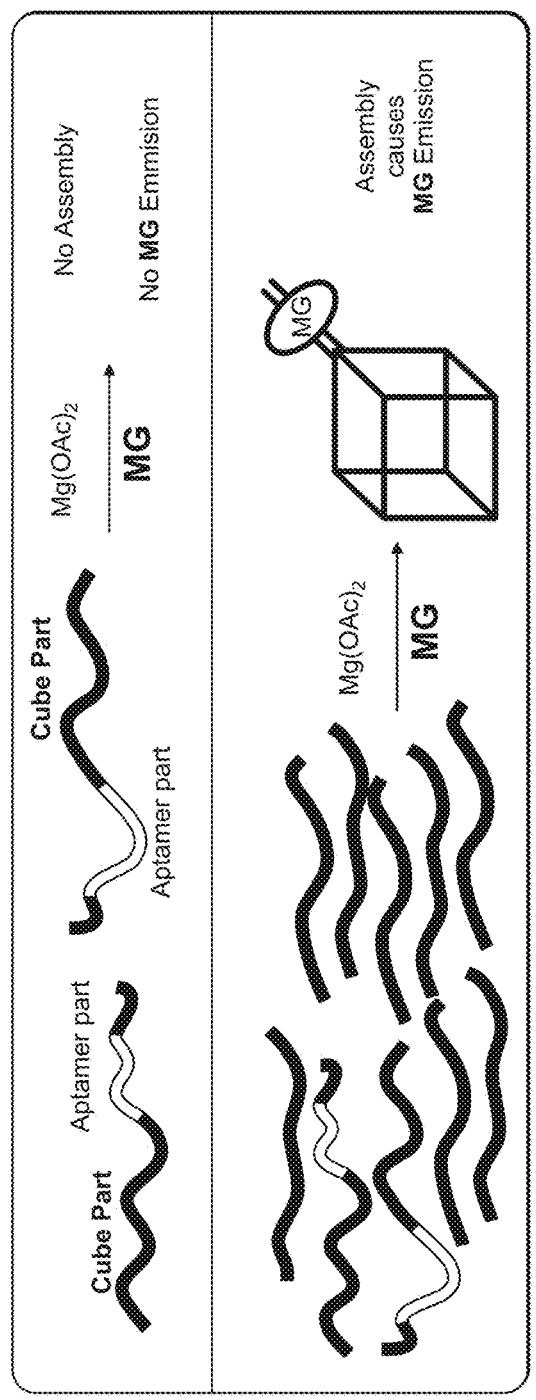

FIG. 68 illustrates the concept of functional activation through nano-scaffold assembly. The triphenylmethane dye, Malachite Green (referred to further as MG and colored in red) was chosen as a signaling agent due to its fluorescent properties. Free aqueous MG displays no fluorescence while binding to the aptamer increases its fluorescence tremendously. MG aptamer (in green) is integrated into the cube sequences (in blue). These modified sequences are designed to prevent dimerization leading to aptamer formation and should not affect MG fluorescence. Cube assembly brings MG aptamer sequences into close proximity allowing folding of the active MG aptamer. This results in the increase in MG fluorescence. Annotation of the MG aptamer 3D structure using the Leontis-Westhof basepair nomenclature (Leontis et al, 2001). FIG. 68 discloses SEQ ID NO: 158.

Figure 69:
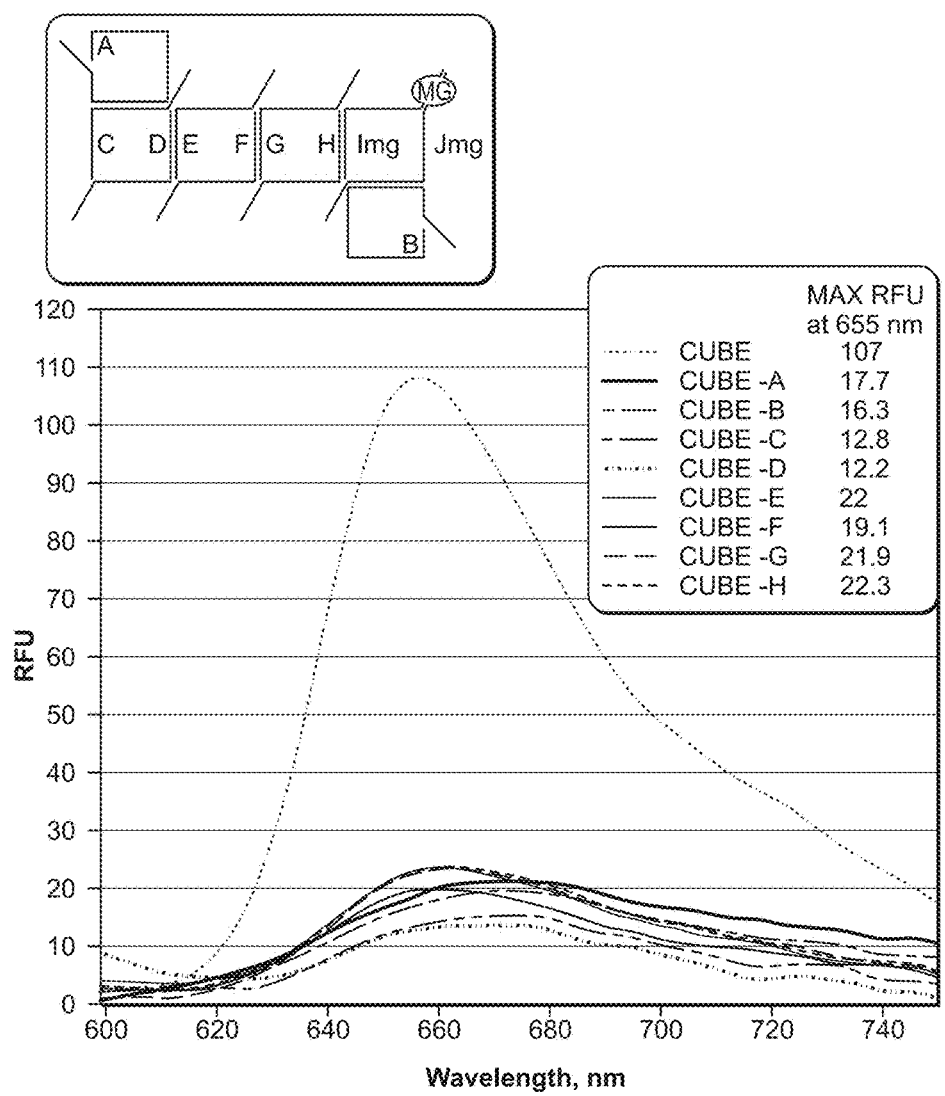

FIG. 69 shows emission spectra representing the concept of functional activation through nanoscaffold assembly. Functionalized 10 stranded cube (cyan curve) shows an increase in fluorescence demonstrating correct formation of the MG binding pocket while nonamers demonstrate a fluorescence drop due to disruption of the MG aptamer.

FIG. 70 shows co-transcriptional self-assembly of (a) 10 stranded RNA nano-cube functionalized with MG aptamer and (b and c) two nonamers. Emission spectra represent binding of MG to RNA aptamer formed only upon the assembly of 10 stranded RNA cube. Aliquots of the transcription mixture were taken after 2, 3, 4, 5, and 7 hours. The reaction was stopped by addition of DNAse to the transcription mix and fluorescence measurements were immediately performed after MG addition. Note that at 5.5 h, more T7RNAPolymerase was added to the transcription mix.

Figure 71B:
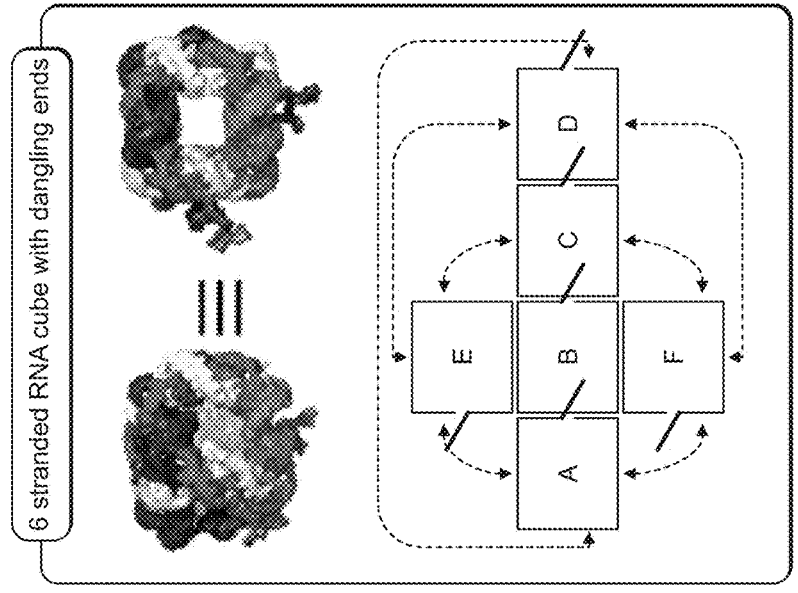
Figure 71A:
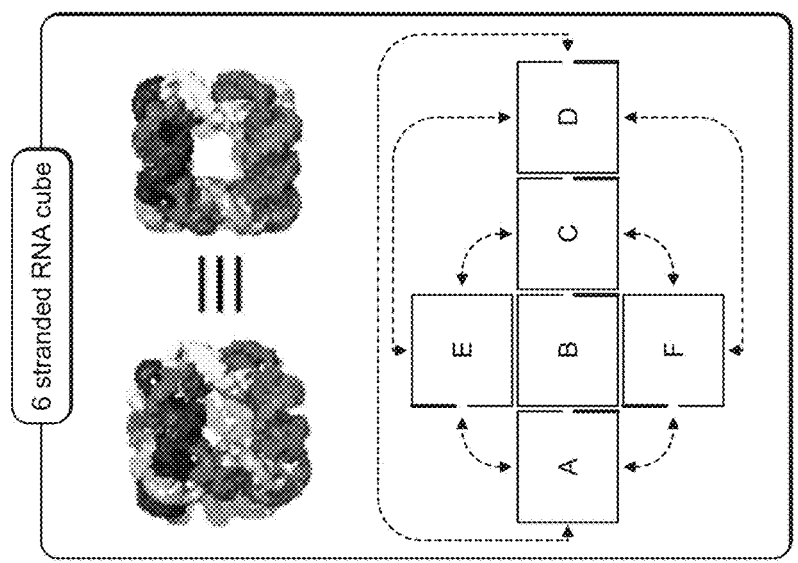
Figure 71C:
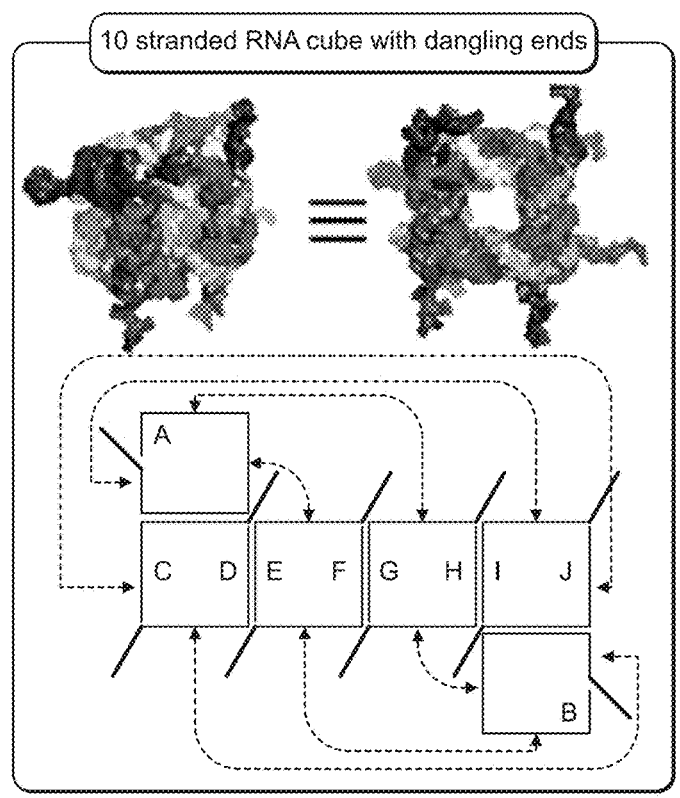

FIG. 71 (a-c) is three panels that show 3D models for ten and six stranded cubes with corresponding 2D schematics of sequence interactions. Note that 5' start sequences (in black) are base paired in (a) and singlestranded in (b) and (c). The diagrams are drawn to emphasize the symmetry of 3' and 5' positions.

FIG. 72 (a-d) shows is four panels that shows the characterization of 6 stranded cube assemblies (without dangling ends). (a) shows native PAGE assembly experiments: (left) radioactive assemblies with 32P radiolabeled RNA molecules indicated with asterisks. Am was designed to assemble with B-F to form an open hexamer. (middle) Co-transcriptional self-assembly of body-labeled RNA cube strands. (right) Native PAGE assembly experiments with RNA visualization by total SYBR Green II staining. Estimated yields of the hexamers (in %) are shown at the bottom of corresponding lanes. All lanes are numbered to distinguish between twelve different compositions of RNA, RNA/DNA and DNA complexes. (b) shows titration curve fitting data collected from three independent experiments of RNA cube assembly. (c) shows thermal melting curves of RNA, DNA, and RNA/DNA hybrid cubes. Corresponding Tm's are shown FIG. 63 in SI. (d) shows size histograms of six stranded cubes measured by DLS. Compositions are specified for each measurement. Color code is consistent with b and c. Relative assembly yields are calculated from each histogram. All RNA complexes used in a, c, and d experiments were assembled as described in Materials and Methods at 1 µM concentrations.

Figures 73A, 73B:
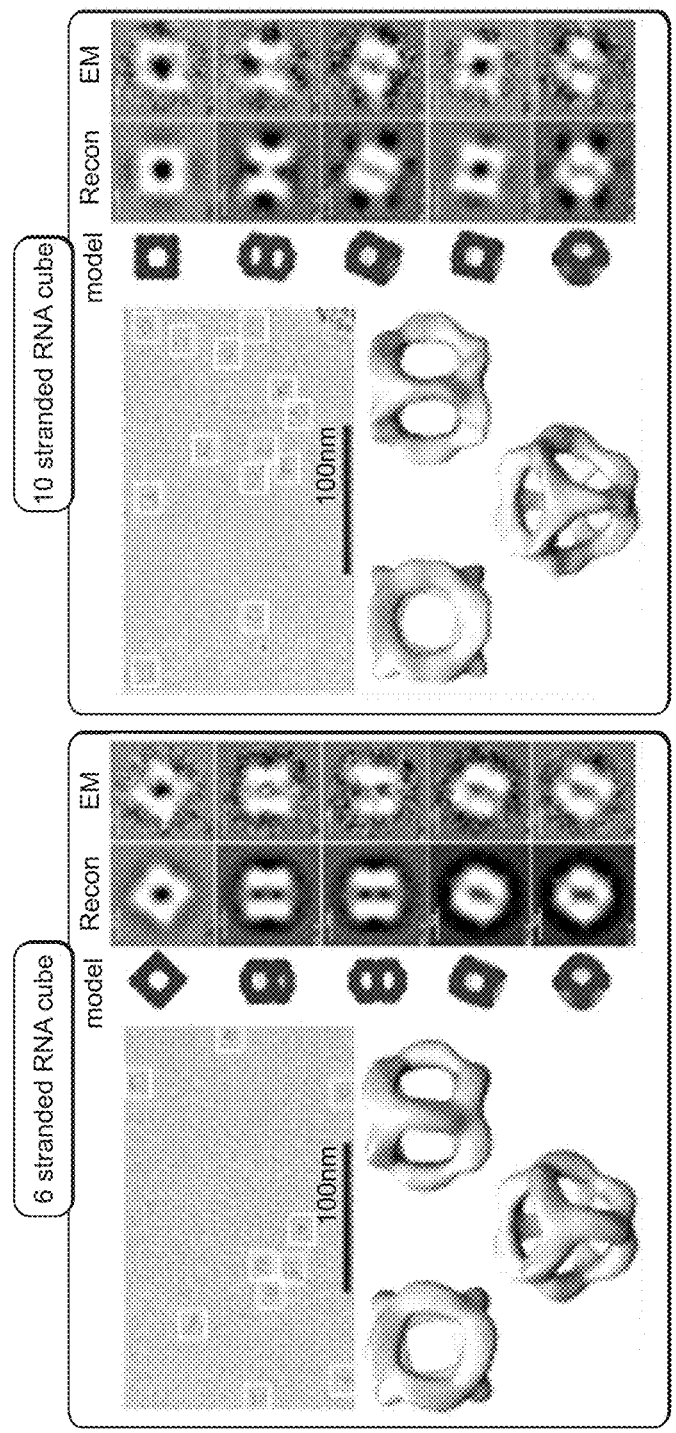

FIGS. 73 (a and b) shows structural characterization of 6 stranded (panel a) and 10 stranded (panel b) RNA cubes by cryo-EM with single particle image reconstruction. Each panel on the top left represents typical cryo-EM images of the RNA particles. On the right side, class averages for each RNA cube as observed by cryo-EM (EM) with corresponding projections of the reconstructed 3D structure and theoretical RNA cube model. Reconstructed 3D models of the six and ten stranded RNA cubes have been obtained at 8.9 Å and 11.7 Å resolution, respectively. All RNA complexes used in cryo-EM experiments were assembled at 1 µM of each RNA strand as described in the Materials and Methods.

Figure 74A:
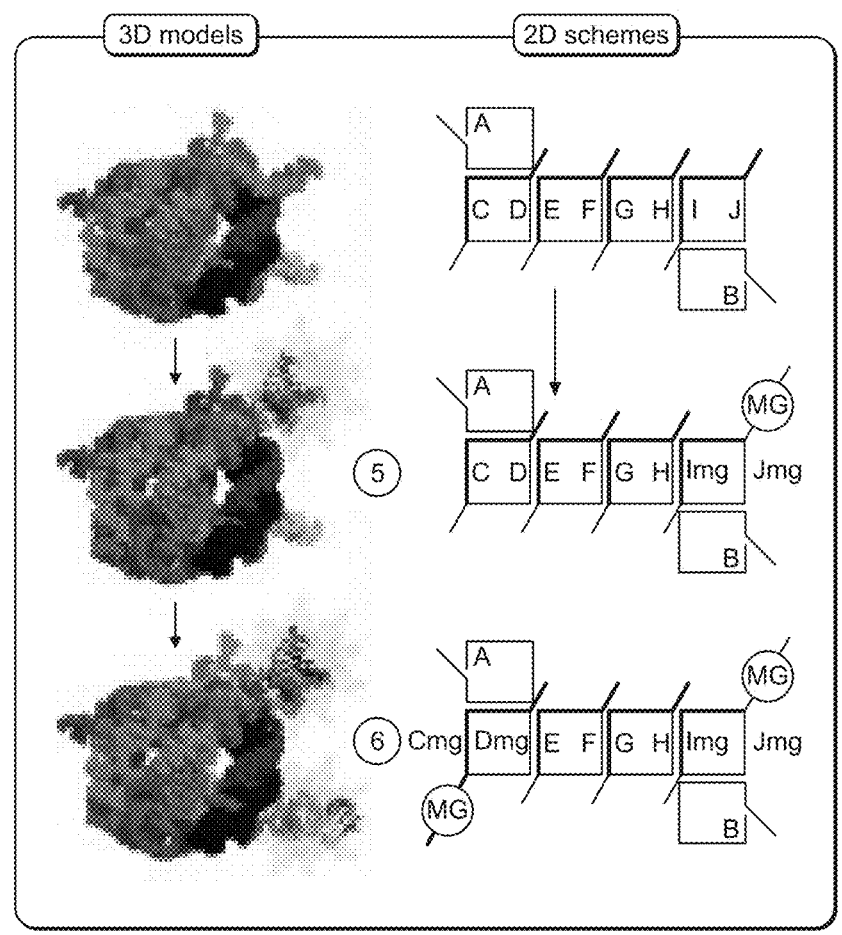
Figure 74B:
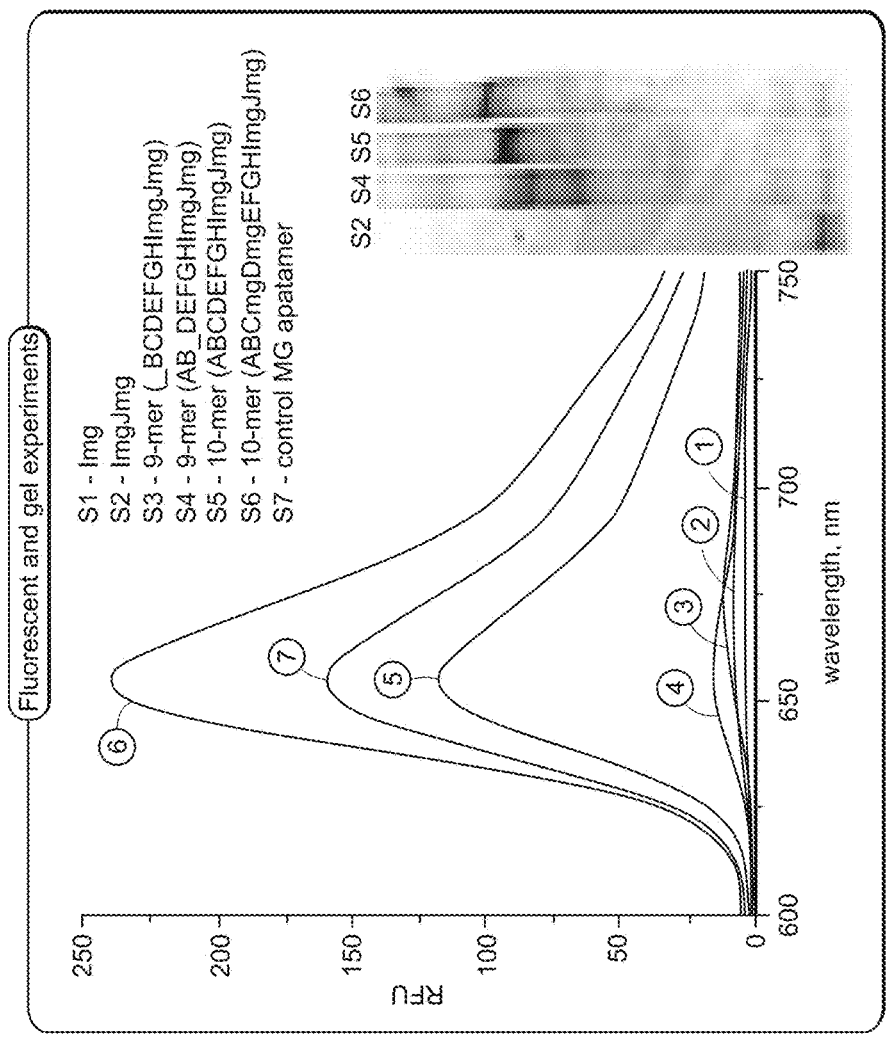

FIG. 74 (a-c) shows functionalization of RNA nano-cube scaffold with Malachite Green (MG) aptamer. (a) is a scheme showing the functionalization. (b) shows emission spectra representing binding of MG to RNA aptamer and native PAGE demonstrating the formation of the constructs. Monomer, dimer and nonamer samples (S1, S2, S3, S4) are unable to bring the aptamers into close enough proximity necessary for fluorescent emission in presence of MG. The functionalized cube sample (S5) shows an increase in fluorescence demonstrating correct formation of the MG binding pocket. The cube sample (S6) shows two-fold increase in fluorescence demonstrating simultaneous correct formation of its two MG binding pockets. All RNA complexes used in the fluorescent experiments were assembled at RNA strand concentration of 1 µM as described in Materials and Methods. Based on the emission signal of the control molecule, the yield of the functionally active cube (S5) was estimated to be 77.3%. (c) shows comparison of co-transcriptional self-assembly of nonamers S3 and S4 with 10 stranded RNA nano-cube (S5) functionalized with one MG aptamer at 37° C. Aliquots of the transcription mixture were taken after 2, 3, 4, 5, and 7 hours, followed by the addition of DNAse to stop the reaction. MG was added just prior to fluorescent data acquisition. Note that after 5 h, more T7 RNA polymerase was added to each transcription mix. Control S7 corresponds to a MG aptamer molecule.

Figure 75A:
Figure 75B:
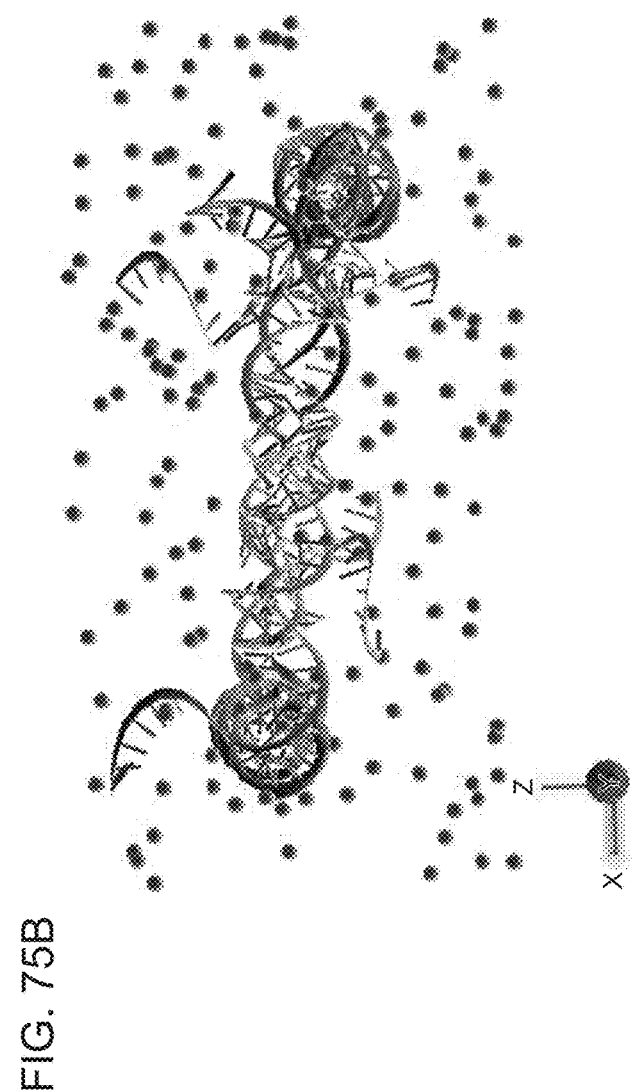

FIGS. 75 (A and B) shows top (A) and side (B) views of the simulation box with a sample initial configuration for our MD simulations: RNA nanoring together with 165 Mg2+ ions (green spheres) and 88 664 H2O molecules (not shown).

Figure 76:
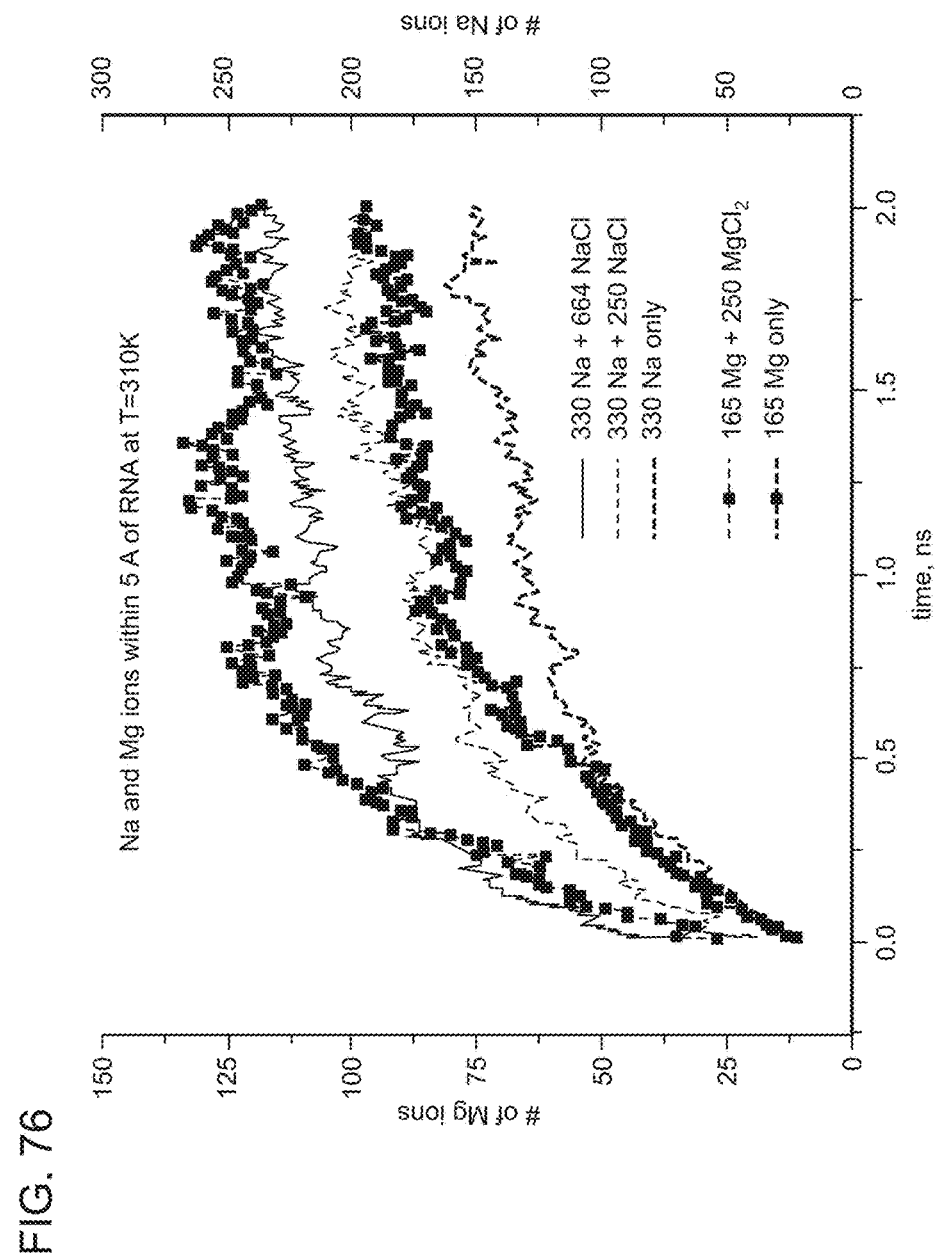
Figure 76:
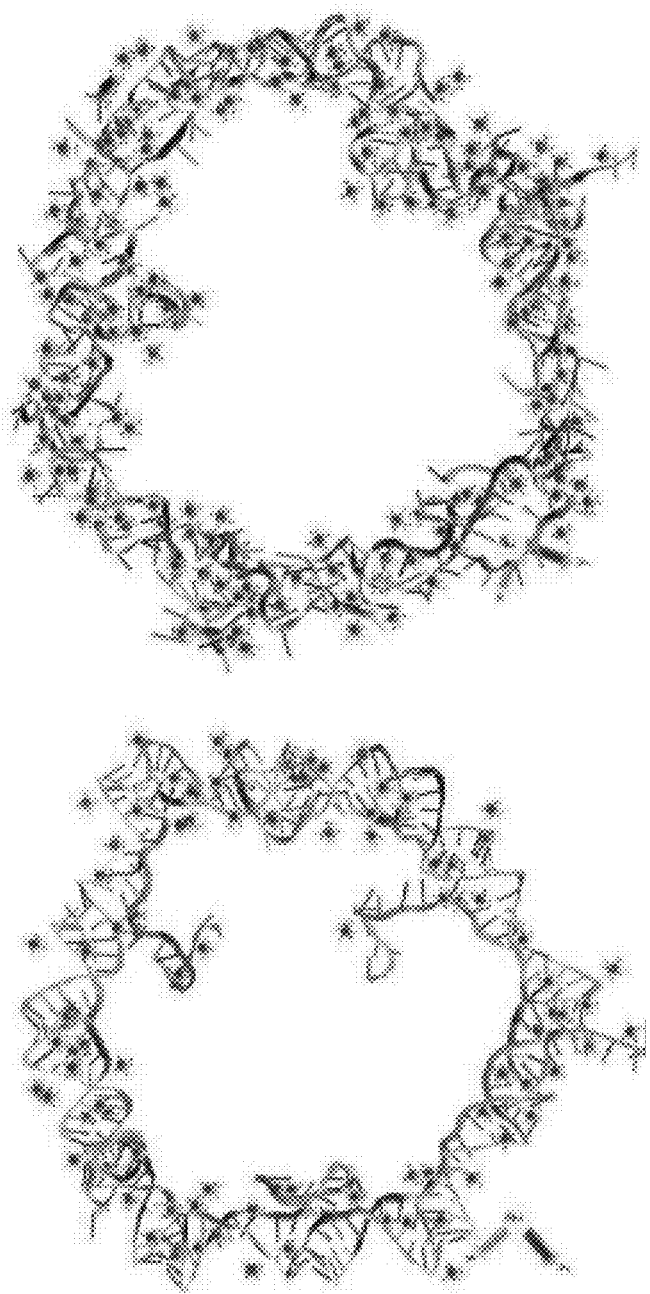

FIG. 76 is three panels. The top shows the number of ions within 5° A of RNA versus time for different concentrations of Na and Mg ions at 310 K. The color coding is explained in the body of the figure. The scale of the y-axis for Mg2+ ions is made two times smaller than that for Na+ ions to allow better visual comparison. The adsorption of the Cl ions (not shown) on the nanoring is much lower. Bottom: sample snapshots of the RNA nanoring after 2 ns equilibration, in the 'no salt' system (165 Mg) at T=310 K (left), in the 'physiological solution' (415 Mg) at T=510 K (right). Mg ions situated only within 5° A of the RNA ring are shown in green, together with six bound water molecules (red and white), Cl ions are not shown.

Figure 77:
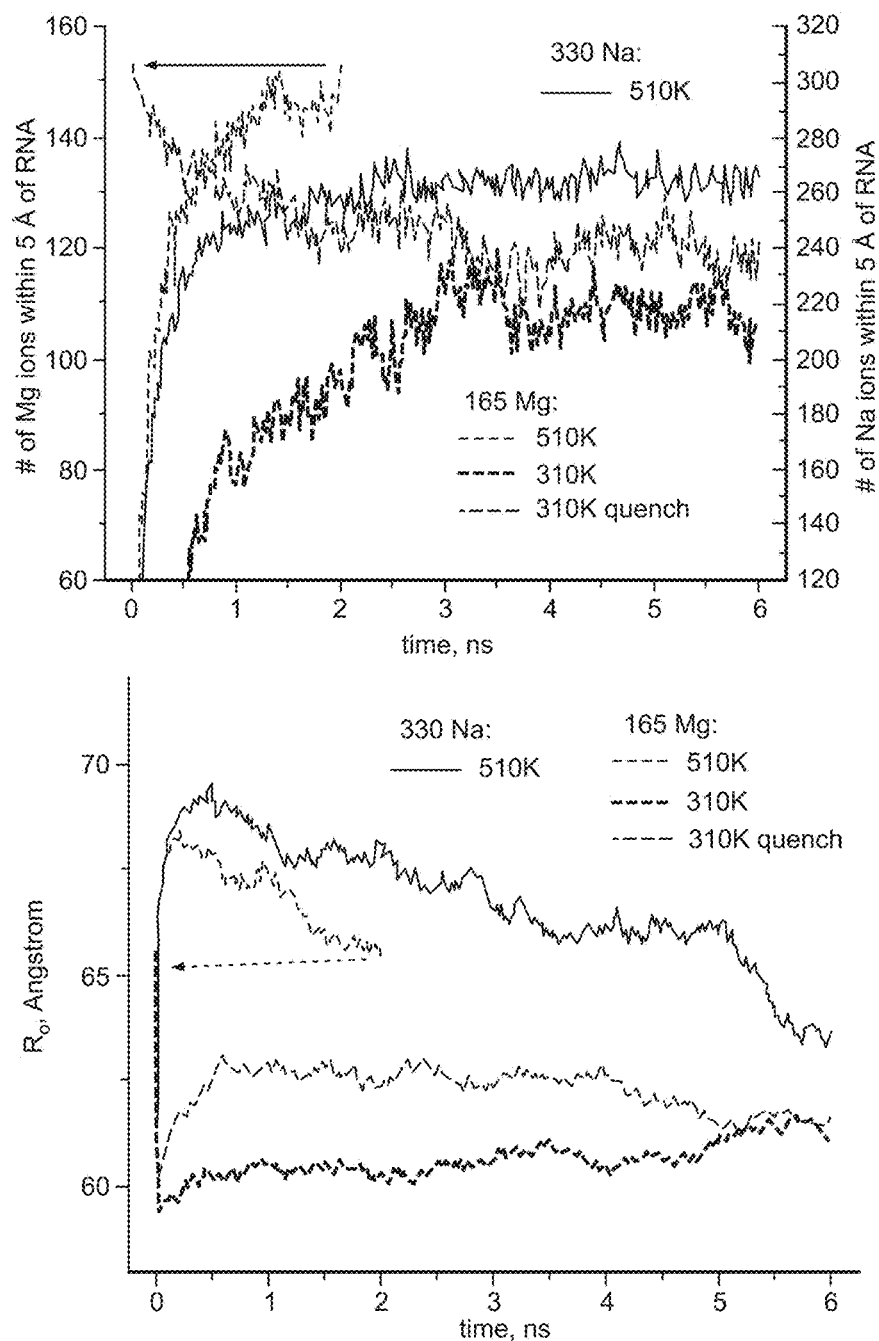

FIG. 77 is two graphs that show the number of ions found within 5° A of RNA (top) and the radius of gyration Rg of the RNA nanoring (bottom) versus time in the selected 6 ns runs for the 'no salt' systems (165 Mg or 330 Na) at 510 K and 310 K. The arrows indicate the 510 K run serving as a starting point for 310 K quenched run.

Figure 78:
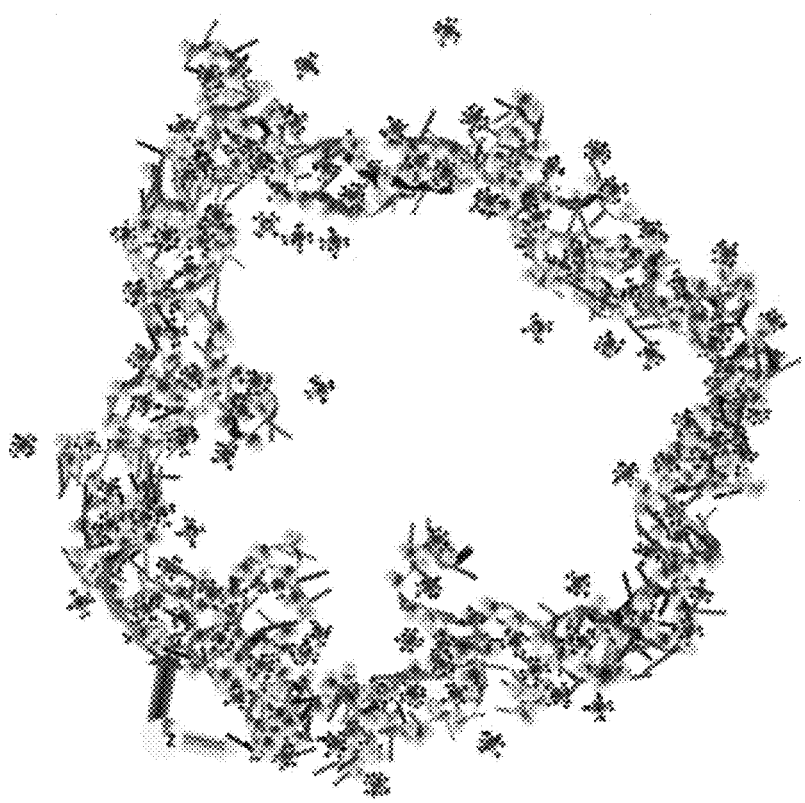
Figure 78:
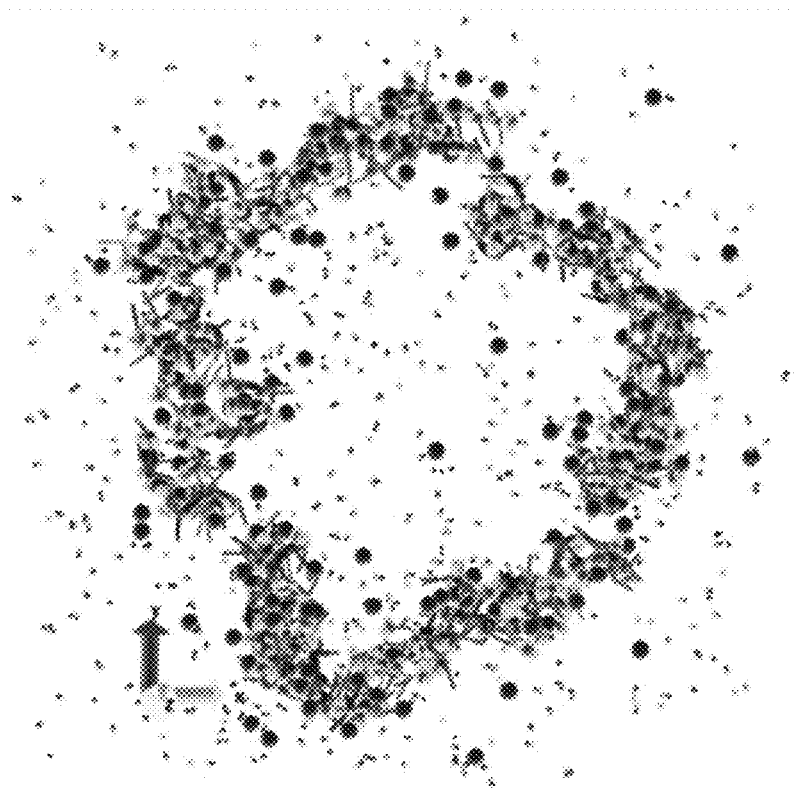

FIG. 78 is two panels that show top views of the RNA nanoring in the 'no salt' systems (165 Mg or 330 Na) after 1 ns 'quenched' equilibration at T=310 K. Only those Mg and Na atoms that have been located within 5° A of RNA nanoring in the beginning of the runs are shown (such representations allow one to visualize the process of evaporation of the ions from the nanoring). Mg atoms are shown in green, Na atoms are shown in yellow. Water molecules that have been located in the first solvation spheres for Mg and Na in the beginning of the runs are shown in red and white. The phosphorus and two non-bridging oxygens atoms in each phosphate group are shown as brown and red spheres.

Figure 3A:
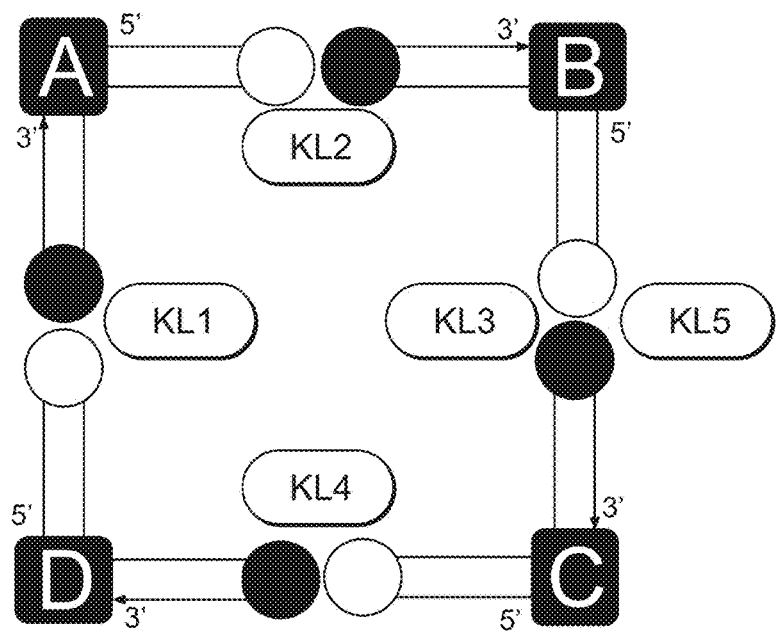
FIG. 3 (A-C) shows examples of gels measuring the apparent KD of KL interactions. (A) shows the general assembly scheme of a tRNA tectosquare composed of four units. The location of each KL complex within the square is indicated on the diagram. (B) Kd were measured at 0.2 mM Mg(OAc)2 by quantitating bands from the native PAGE shown in (C) as described in the materials and methods. $K_D$ values are determined by measuring the concentration at which half of the RNA molecules are dimerized.
FIG. 3C discloses SEQ ID NOS 17-20, respectively, in order of appearance.
Figure 3B:
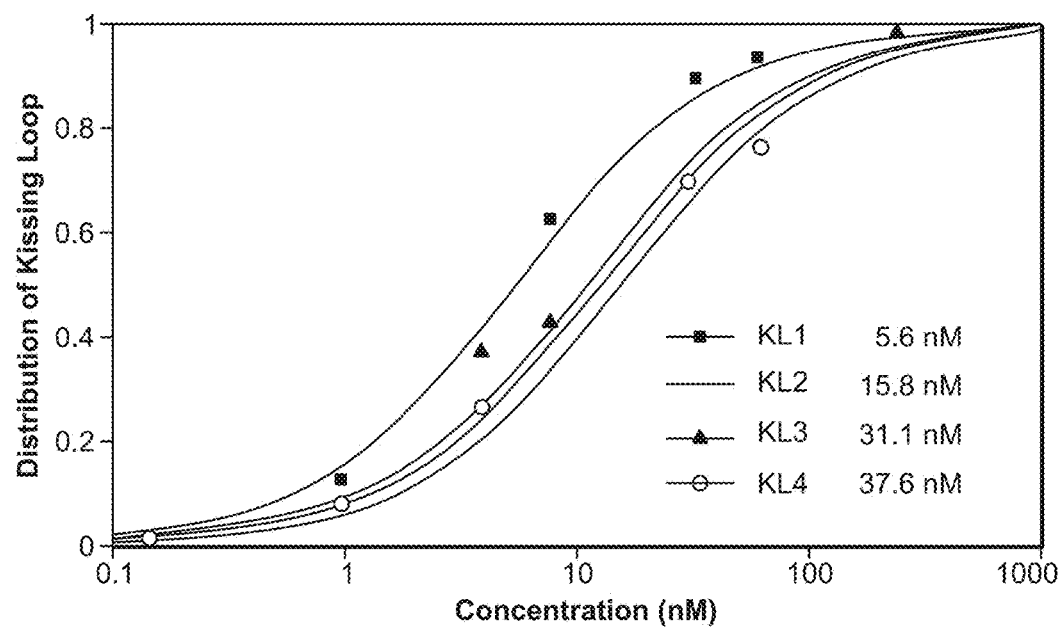
Figure 3C:
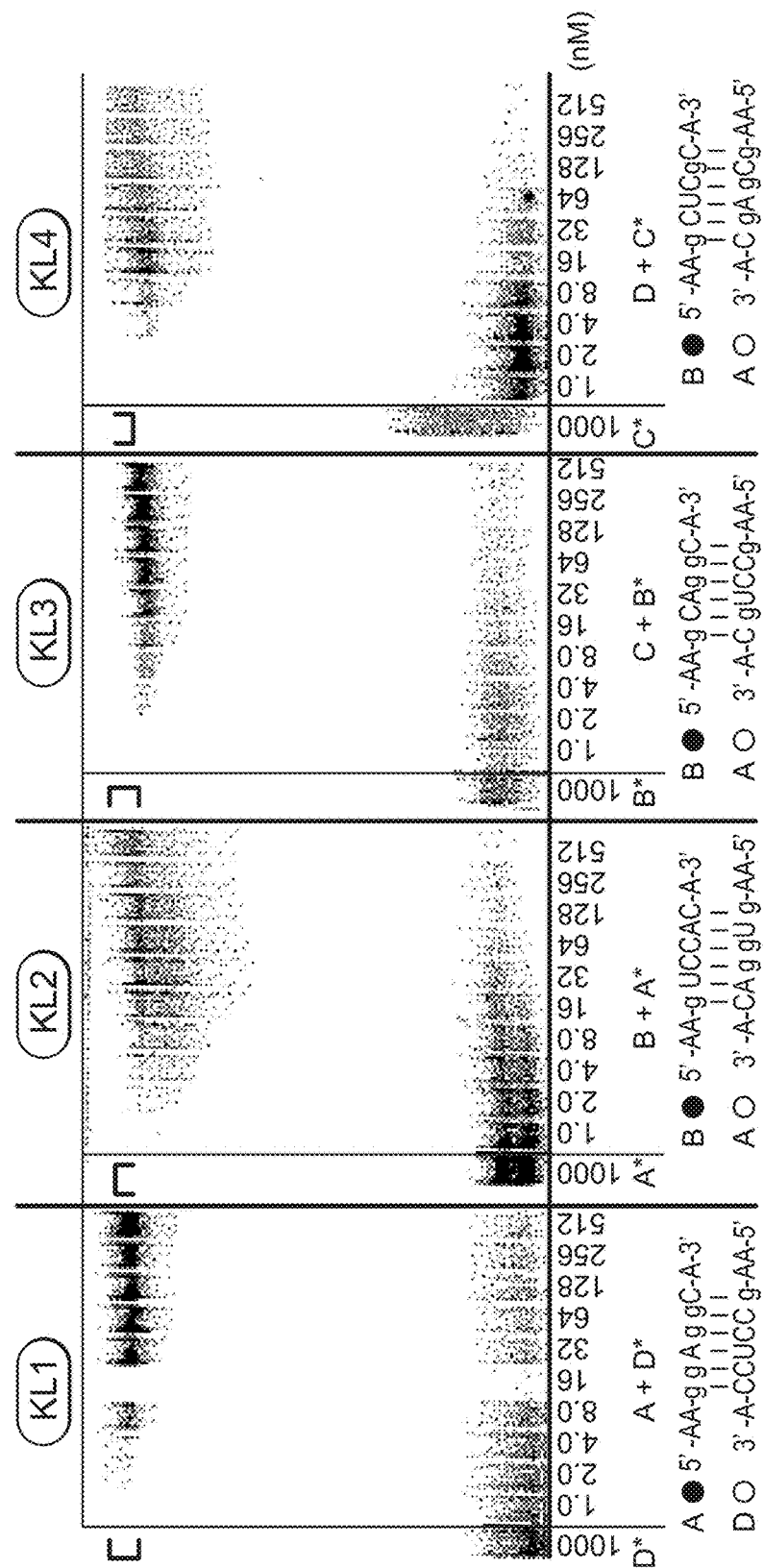
Figure 79:
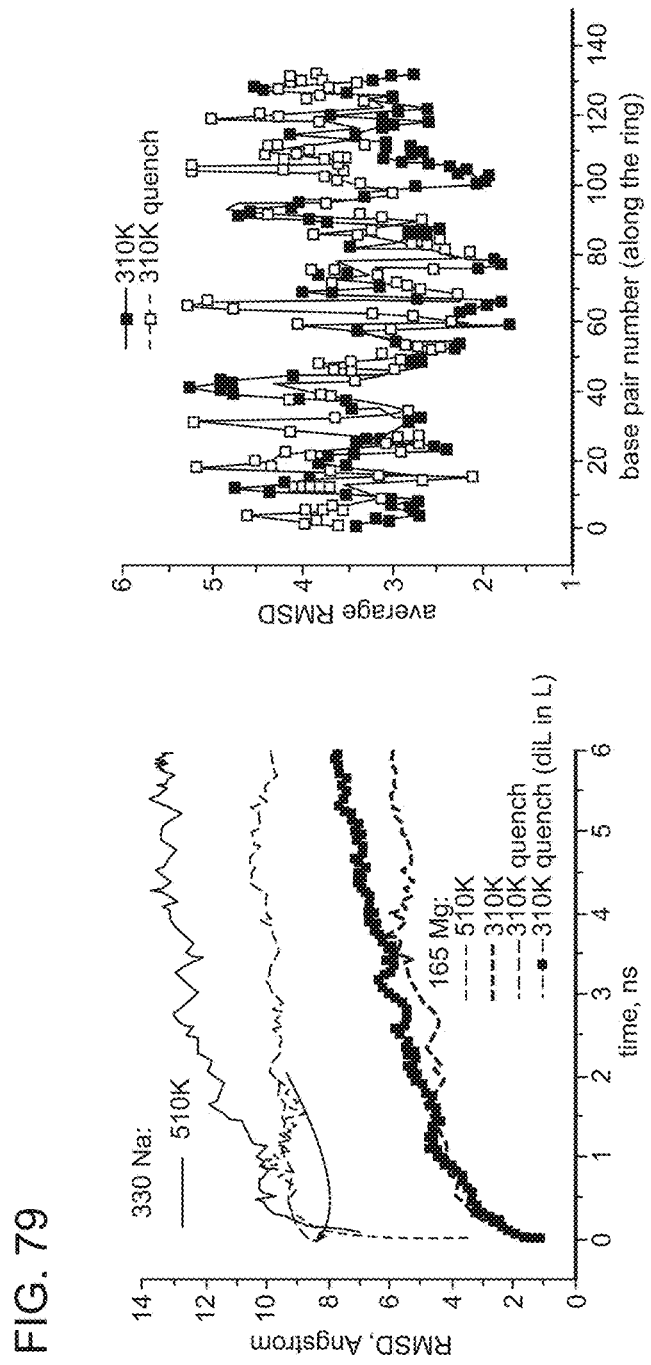
Figure 79:
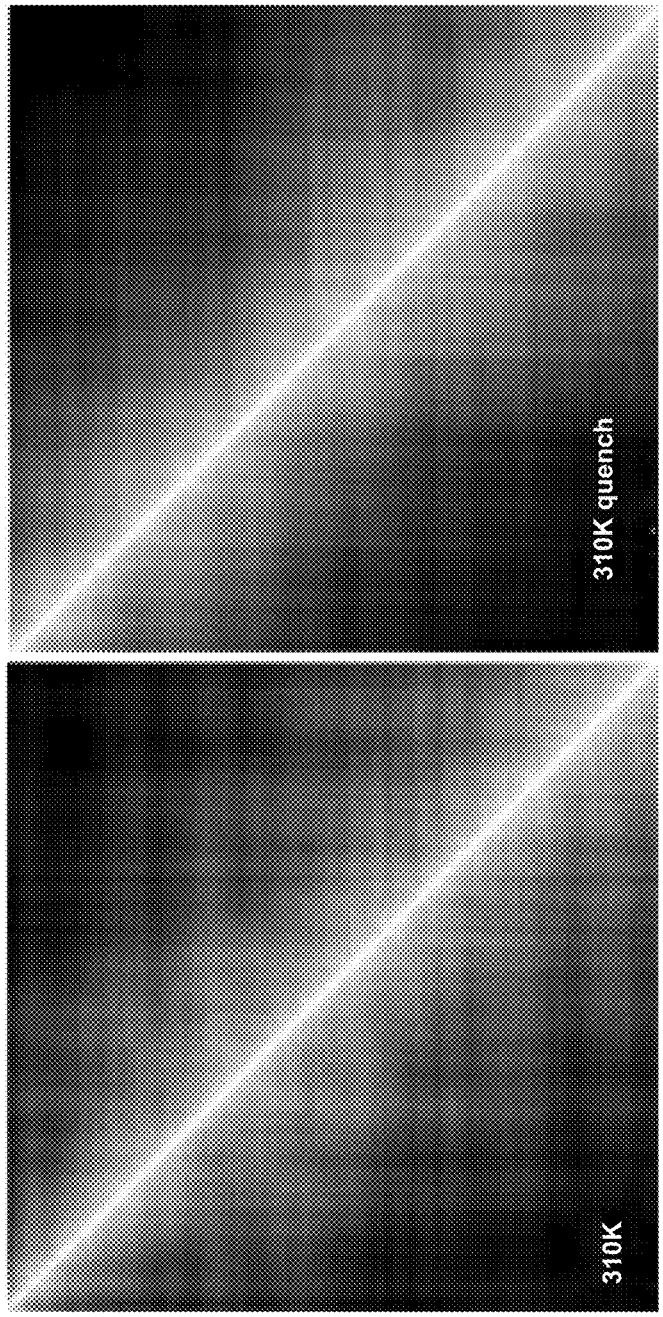

FIG. 79 Top part: (left) overall RMSD of the nanoring calculated from the reference structure in FIG. 1 versus time for the same quenched and non-quenched runs that are shown in FIG. 3; the RMSD for the quenched 310 K run is also replotted taking the last configuration of the preceding 510 K run as the reference (green symbols), the arrow indicates the 510 K run serving as a starting point for 310 K quenched run; (right) RMSD for separate base pairs versus the base pair number, averaged over the last 2 ns chunks of runs depicted on the left. Bottom part: 2D RMSD maps for 310 K run (left) and 310 K quenched run (right) depicted above. The span of both directions is 6 ns, the coordinate origin is at the top-left corner. The grayscale (white to black) is drawn from 1° A to 6° A for 310 K run and to 7 A° for 310 K quenched run.

Figure 80:
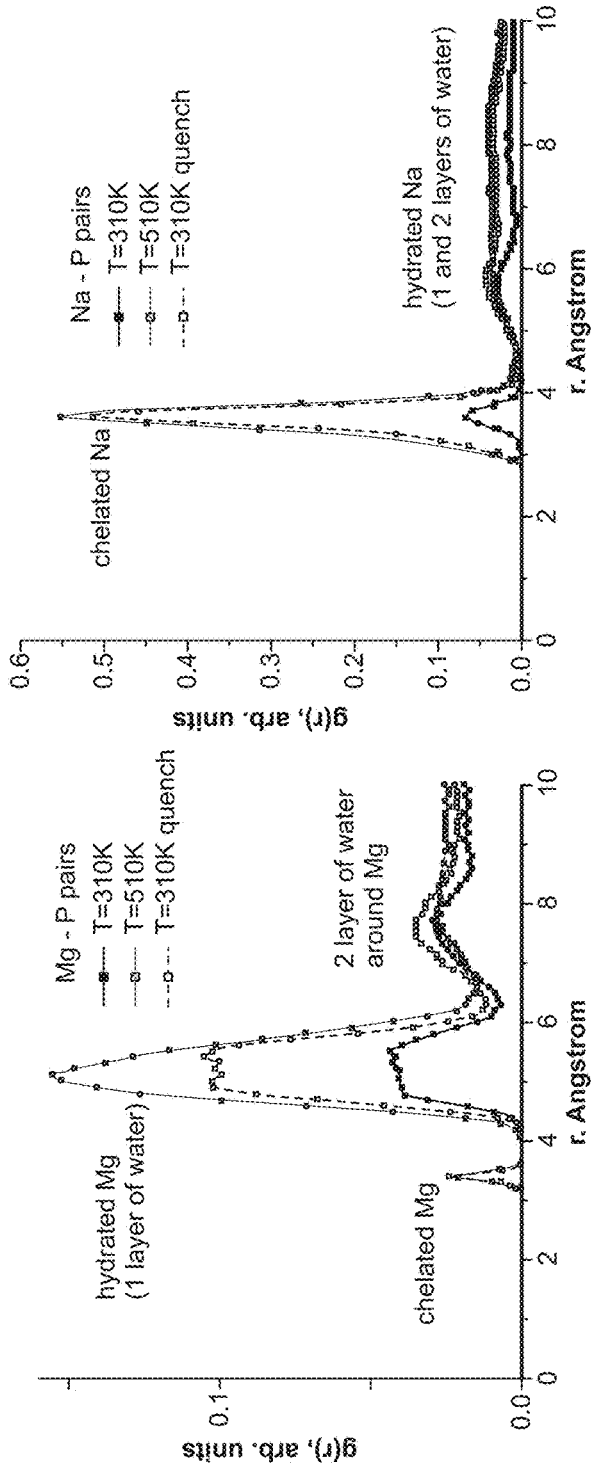
Figure 80:
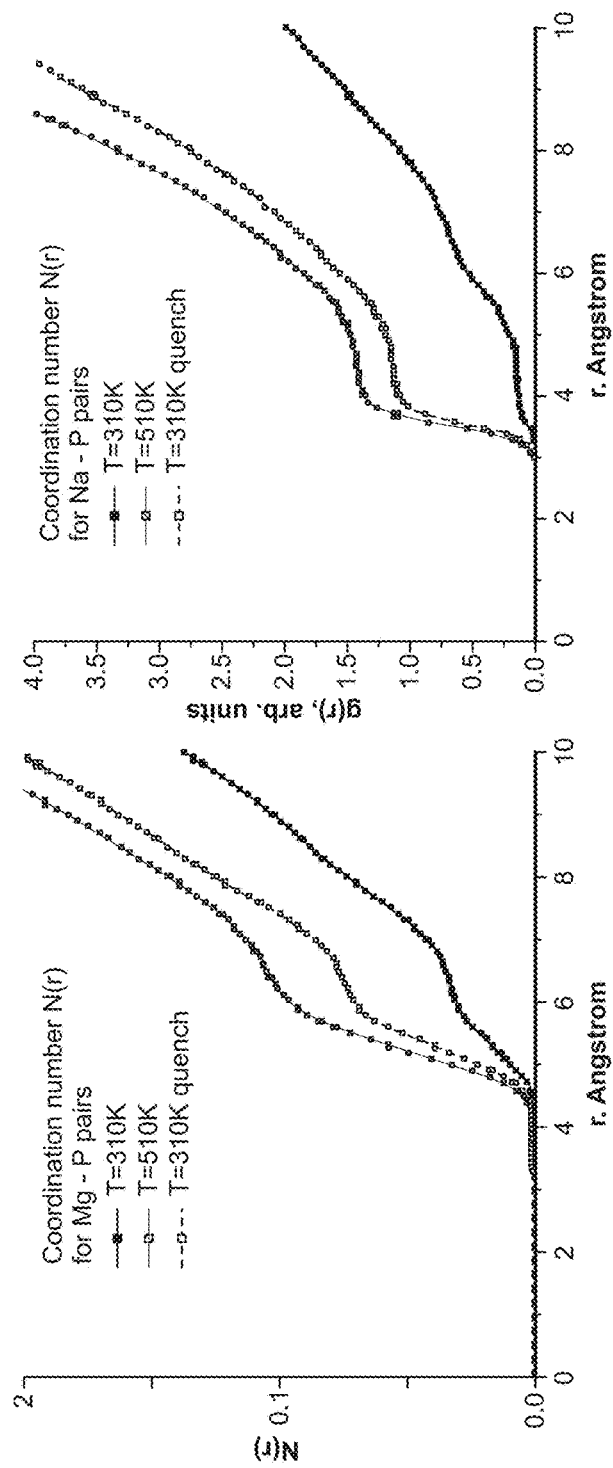

FIG. 80 is four graphs that show radial distribution functions g(r) and running coordination numbers N(r) for Mg—P and Na—P pairs at two temperatures for the 'no salt' systems with Mg and Na, respectively.

Figure 81:
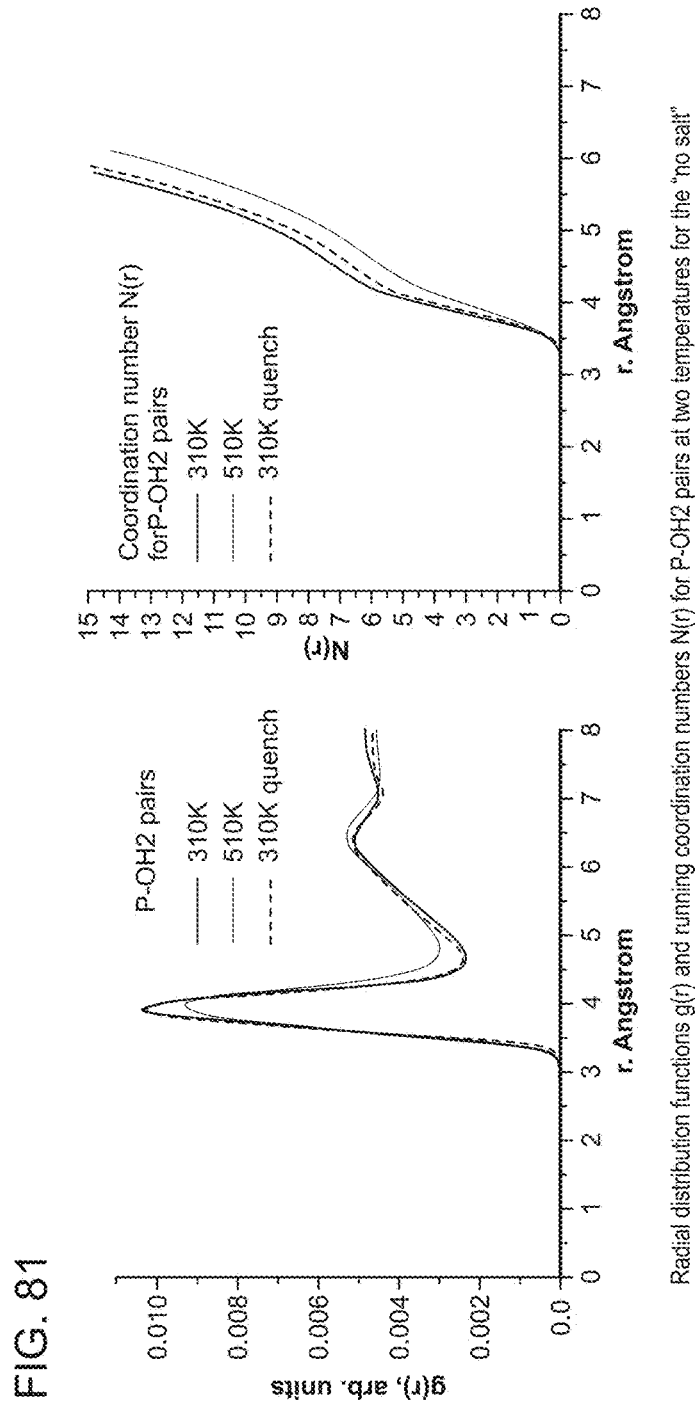
Figure 81:
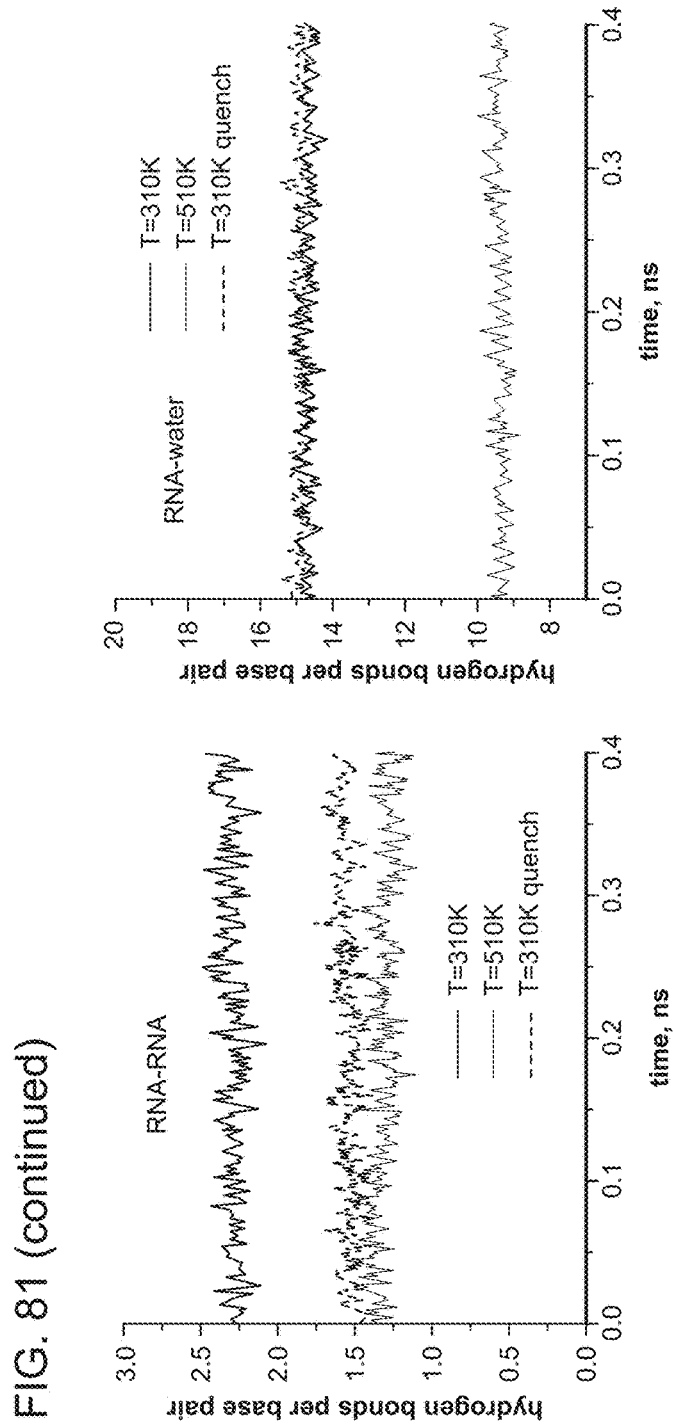
Figure 81:
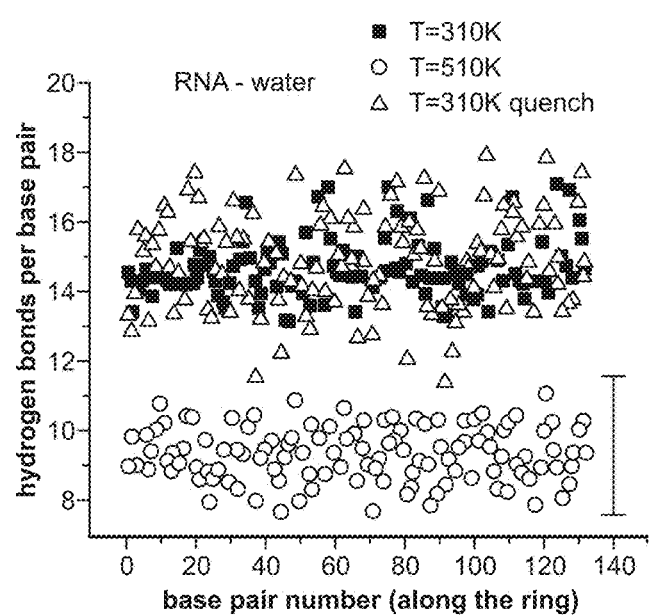

FIG. 81 shows hydrogen bonds in the RNA nanoring system. Top: typical time dependences of total number of hydrogen bonds for RNA-RNA and RNA-water interactions (data are given per base pair) during the last 400 ps long chunks of the simulated trajectories. Bottom: time-averaged number of hydrogen bonds (RNA-water) for every base pair versus base pair number (along the ring). The vertical black bar shows typical dispersion for this number in a trajectory.

Figure 82:
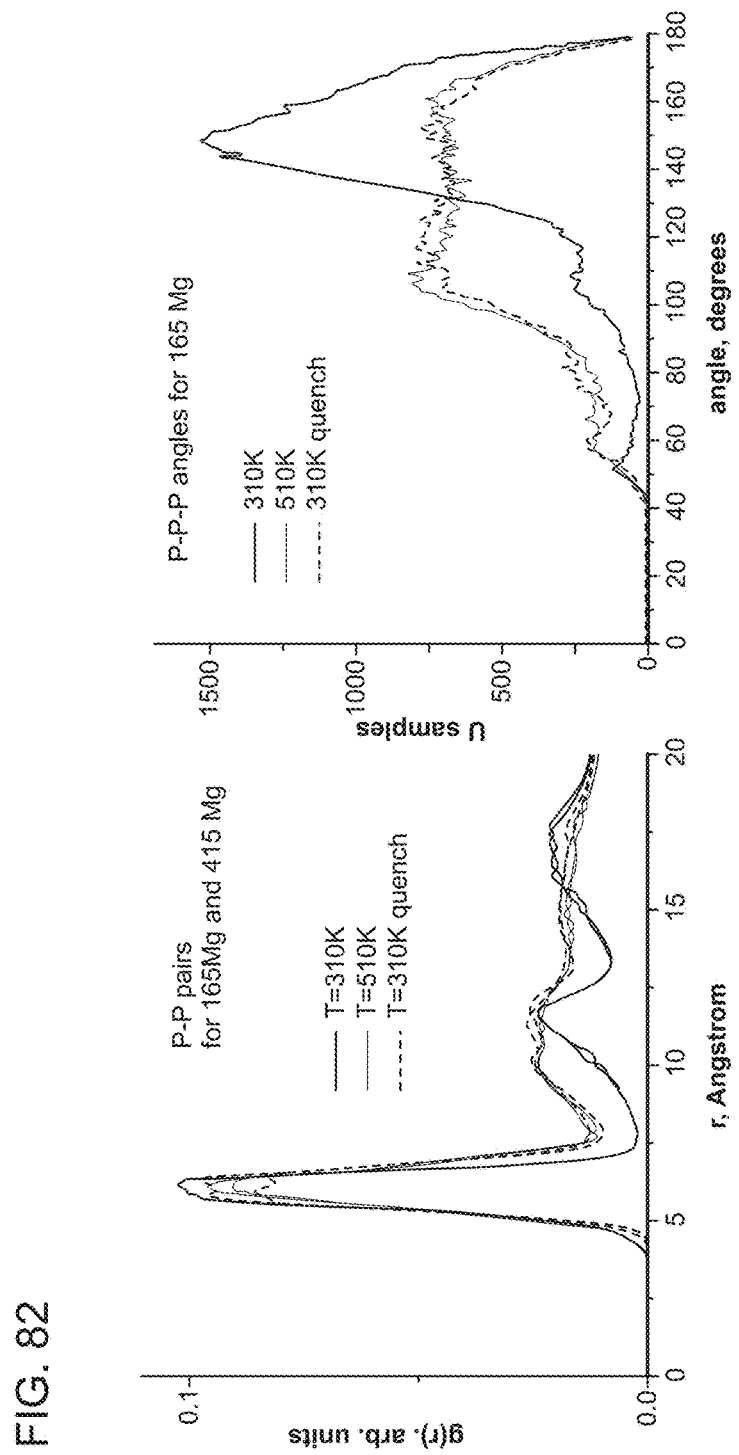

FIG. 82 is two graphs that show the radial distribution functions for P-P pairs (left) and the distribution of the P-P-P angles (right) at two studied temperatures for the systems with Mg ions. The multiple lines of the same color in the plots of RDFs are for different concentrations of Mg.

Figure 83:
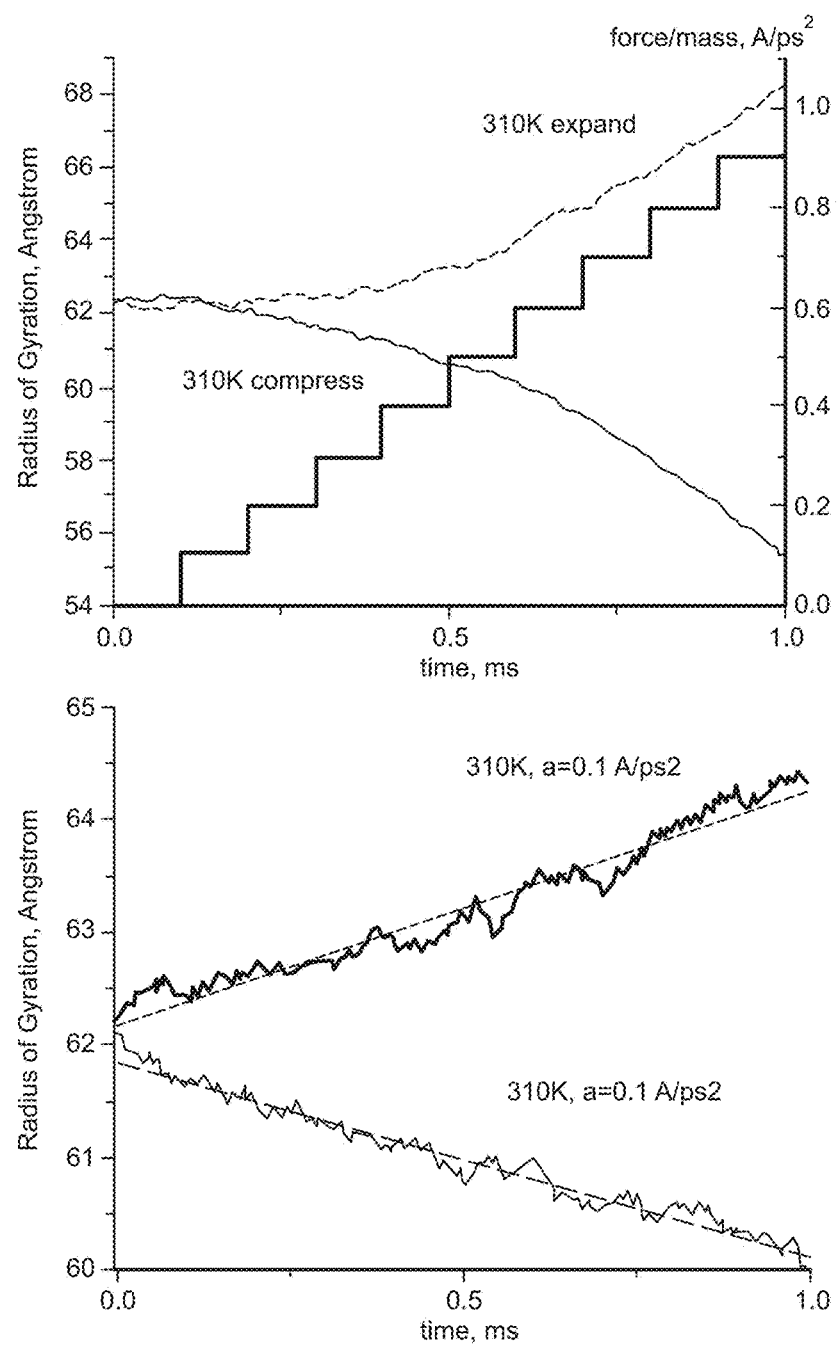
Figure 83:
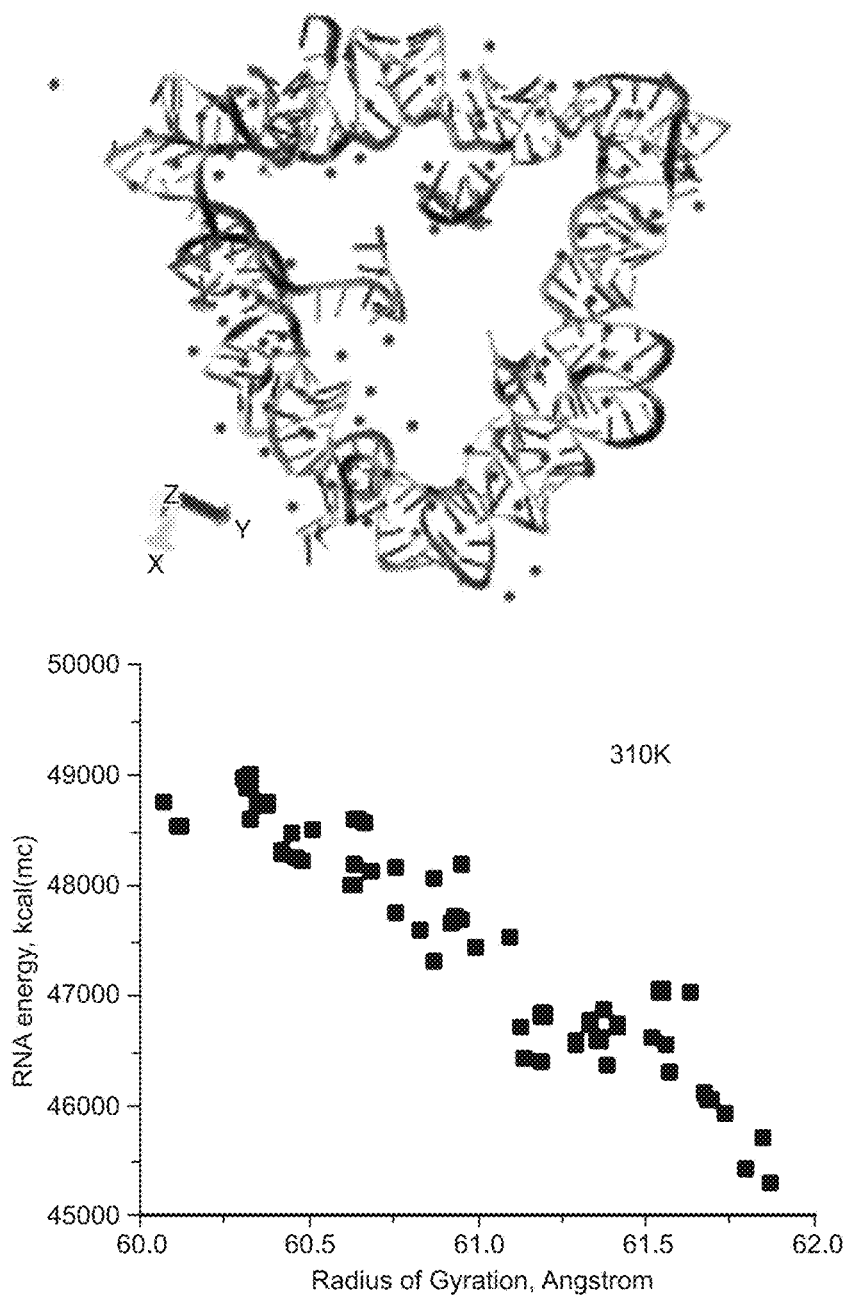

FIG. 83 Top part: (left) radius of gyration of the RNA nanoring (left y-axis) versus time upon the application of quasi-linearly increasing (staircase-like) radial external force (right y-axis); (right) snapshot of the RNA ring subjected to further extreme compression at 310 K, when the force reaches a value a=1.7 Å° ps$^{-2}$. Bottom part: (left) radius of gyration of the RNA nanoring versus time under the application of the constant compressive/expansive force of intermediate magnitude a=0.1 Å° ps$^{-2}$, as described in section 4; (right) the dependence of the total energy of the RNA ring versus its radius of gyration for the set of the compressed configurations generated under the application of the force of a=0.1 Å° ps$^{-2}$.

Figure 84:
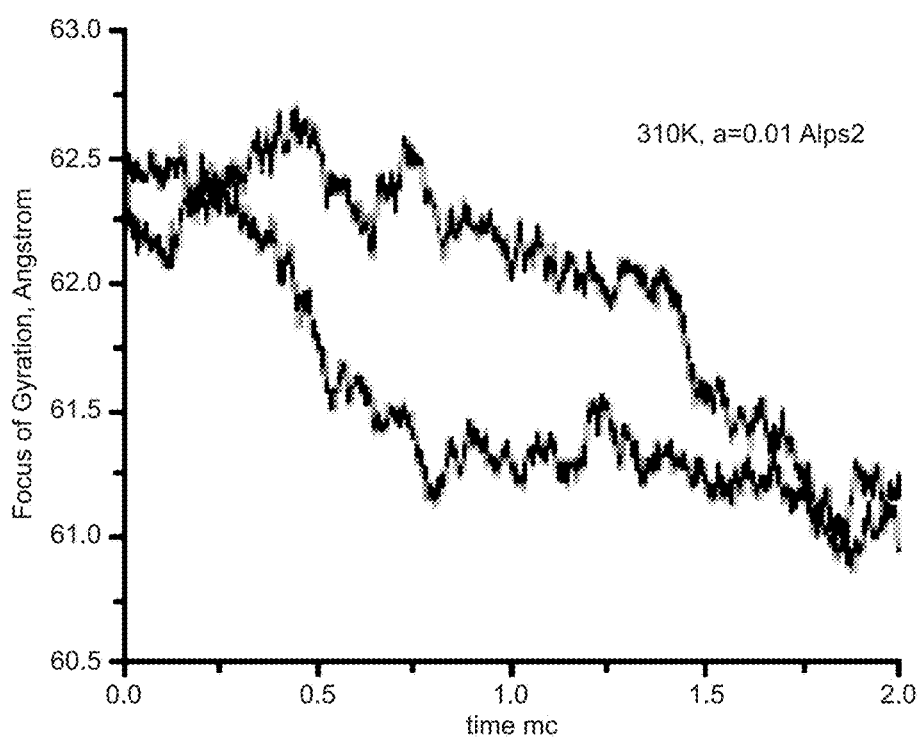

FIG. 84 is a graph where gyration radius of the RNA nanoring versus time under the application of the smallest constant compressive force of a=0.01 Å° ps$^{-2}$, as described in section 4. Two independent Langevin runs are shown.

DETAILED DESCRIPTION OF THE INVENTION

The instant invention is based on the discovery of multifunctional-engineered nanoparticles. The instant invention provides polyvalent RNA nanoparticles comprising RNA motifs as building blocks. The polyvalent RNA nanoparticles are suitable for therapeutic or diagnostic use in a number of diseases or disorders.

The RNA nanoparticles described herein have the ability to assemble, e.g., self-assemble, in to higher order structures, e.g., a ring, a cage, or a nanotube. For example, the RNA nanoparticles can be designed to self-assemble into predefined size and geometrical shapes and can be designed to carry multiple components including molecules for specific cell recognition, image detection, and therapeutic treatment. The present invention describes circular RNA nanoparticles or filaments that are assembled to form nanorings or filaments of various size by the assembly of non-covalent loop-loop interaction based on kissing loop interaction derived from RNAI/RNAII inverse complex of the ColE1 plasmid of *E. Coli* and variants of the DIS region of the HIV genome.

Advantageously, the nanorings can be further designed to assemble into nanoarrays, nanocages and nanotubes via their dangling sticky tails. The nanoparticles described herein can be designed to encapsulate small therapeutic molecules. The use of such nanoparticles holds great promise in areas such as nanomedicine due to their low immunogenicity, low toxicity, and biodegradability. They should also avoid the problems of short retention time of small molecules and the difficulty of delivery of particles larger than 100 nanometers. The nanoparticled described herein can serve as scaffolds for the generation of complex molecular architectures. They can also be generated as polyvalent, multifunctional nanoparticles that can respond to environmental cues for biological and biomedical applications.

Advantageously, the nanoparticles of the instant invention provide a number of improvements over nanoparticles currently available. For example, the RNA nanoparticles of the invention may not induce a significant immune response like the protein nanoparticles currently used. Moreover, the nanoparticles of the invention are smaller than many currently available nanoparticles and therefore allow for increased efficiency of administration. The nanoparticles described herein comprise multiple RNA subunits each of which has the ability to bind, for example, a therapeutic or diagnostic agent. Moreover, multiple different agents can be present within a single nanoparticle. In an exemplary embodiment, the RNA nanoparticle comprises one or more agents that will specifically target the nanoparticle to a particular type of cell and one or more therapeutic agents. In other exemplary embodiments, the present invention provides that the RNA polyhedral cage can be further functionalized using biotin-streptavidin interaction to immobilize molecules inside or outside the polyhedral cage. A specific example of this type of nanoparticle would have an agent that specifically targets a particular type of cancer cell one or more cancer therapeutic agents. Previous studies have shown that RNA nanostructures are effective drug delivery vehicles (see, for example, Khaled et al. (2005) Nano Letters 5:1797-1808).

Definitions

The instant invention provides polyvalent RNA nanoparticles comprising RNA motifs as building blocks. The polyvalent RNA nanoparticles described herein can further comprise therapeutic, diagnostic and/or delivery agents. Further, the polyvalent RNA nanoparticles described herein can be used as drug delivery compositions to treat various diseases or conditions.

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "administering" is meant to refer to a means of providing the composition to the subject in a manner that results in the composition being inside the subject's body. Such an administration can be by any route including, without limitation, subcutaneous, intradermal, intravenous, intra-arterial, intraperitoneal, and intramuscular.

As used herein, the term "agent" refers to substances which are capable of being contained in, or attached, to the nanoparticle. In exemplary embodiments, such an agent will be a "therapeutic agent" capable of exerting an effect on a target, in vitro or in vivo. Exemplary agents include, for example, prodrugs, diagnostic agents, imaging agents, therapeutic agents, chemotherapeutic agents, pharmaceutical agents, drugs, synthetic organic molecules, proteins, peptides, vitamins, and steroids.

As used herein, the term "chemotherapeutic agent" is meant to include a compound or molecule that can be used to treat or prevent a cancer. A "chemotherapeutic agent" is meant to include acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

As used herein, the term "effective amount" refers to that amount of a therapeutic agent alone that produces the desired effect (such as treatment of a medical condition such as a disease or the like, or alleviation of a symptom such as pain) in a patient. In some aspects, the phrase refers to an amount of therapeutic agent that, when incorporated into a composition of the invention, provides a preventative effect sufficient to prevent or protect an individual from future medical risk associated with a particular disease or disorder. A physician or veterinarian of ordinary skill can readily determine and prescribe the effective amount of the bioactive agent required to treat and/or prevent the progress of the condition.

As used herein, the term "cancer" is used to mean a condition in which a cell in a subject's body undergoes abnormal, uncontrolled proliferation. Thus, "cancer" is a cell-proliferative disorder. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases. The terms "cancer," "neoplasm," and "tumor," are used interchangeably and in either the singular or plural form, refer to cells that have undergone a malignant transformation that makes them pathological to the host organism.

As used herein, a "composition" refers to the combination of an active agent (e.g., a polyvalent RNA nanoparticle). The composition additionally can comprise a pharmaceutically acceptable carrier or excipient and/or one or more therapeutic agents for use in vitro or in vivo.

As used herein, the term "conjugated" is understood as attached, linked, or otherwise present on a nanoparticle.

As used herein, the term "kissing loop" (KL) is meant to refer to the base-pairing formed by complementary sequences in the apical loops of two hairpins which is a basic type of RNA tertiary contact. The simplest kissing interaction is formed between a pair of hairpins each with a GACG tetraloop. In exemplary embodiments, kissing loops are selected from, but not limited to KL1 (AA-ggAggC-A SEQ ID NO: 17), KL2 (AA-gUCCAC-A SEQ ID NO: 18), KL3 (AA-gCAggC-A SEQ ID NO: 19), KL4 (AA-gCUCgC-A SEQ ID NO: 20), and KL5 (AA-CUUUCgC-A SEQ ID NO: 21), L6 (AAGUCACCA SEQ ID NO: 22), L7 (AACGUGGUA SEQ ID NO: 23), L8 (AAGAGCCUA SEQ ID NO: 24).

As used herein, "kits" are understood to contain at least the non-standard laboratory reagents of the invention and one or more non-standard laboratory reagents for use in the methods of the invention.

As used herein, the term "nanoparticle" is meant to refer to a particle between 10 nm and 200 nm in size. A nanoparticle according to the invention comprises a ribonucleic acid (RNA). The RNA can be obtained from any source, for example bacteriophages phi 29, HIV, *Drosophila*, the ribosome, or be a synthetic RNA.

As used herein, the term "nanotube" is meant to refer to the assembly of nanoparticles from RNA into a two or three dimensional structure.

As used herein, the term "motif" in reference to a nanoparticle is meant to refer to a double-stranded or single-stranded ribonucleic acid or analog thereof. Individual motifs are joined together into larger particles by attachment to each other. Attachment can occur by non-covalent linking.

The term "obtaining" is understood herein as manufacturing, purchasing, or otherwise coming into possession of.

The term "oligonucleotide" as used herein includes linear oligomers of nucleotides or analogs thereof, including deoxyribonucleosides, ribonucleosides, and the like. Typically, oligonucleotides range in size from a few monomeric units, e.g., 3-4, to several hundreds of monomeric units. Olgionucleotides can have inhibitory activity or stimulatory activity.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.*, 15th Ed. (Mack Publ. Co., Easton (1975)).

By "self-assembly" is meant to refer to the formation of nanoparticles into two dimensional or three dimensional structures. In certain embodiments, self-assembly can occur by ligation, chemical conjugation, covalent linkage, and non-covalent interactions of RNA, especially in the formation of RNA multimeric complexes.

The term "subject" is intended to include organisms needing treatment. Examples of subjects include mammals, e.g., humans, dogs, cows, horses, pigs, sheep, goats, cats, mice, rabbits, rats, and transgenic non-human animals. In certain embodiments, the subject is a human.

By "class II tRNA motif" is meant to refer to a 90 degree motif. In preferred embodiments, the class II tRNA motif comprises a tRNA unit. In further preferred embodiments, the tRNA unit comprises a variable (var) arm, anticodon arm and amino acid arms. In other further embodiments, the tRNA unit is designed so that the 5' and 3' ends are localized at the tip of the var arm. In other further embodiments, kissing loops (KL) are inserted at the extremities of the anticodon and amino-acid (aa) arms.

The term "tectosquares" as used herein is meant to refer to a nanoparticle comprised of four different tectoRNA units. A tectosquare can refer to a square shaped tetramer. In preferred embodiments, the RNA units self-assemble to form a square-shaped nanoparticle, where the interactions are preferably through four non-covalent loop-loop interactions. In further embodiments, the non-covalent interactions are distinct and are kissing loop (KL) complexes.

As used herein, the term "therapeutic agent" includes a drug and means a molecule, group of molecules, complex or substance administered to an organism for diagnostic, therapeutic, preventative medical, or veterinary purposes. This term includes externally and internally administered topical, localized and systemic human and animal pharmaceuticals, treatments, remedies, nutraceuticals, cosmeceuticals, biologicals, devices, diagnostics and contraceptives, including preparations useful in clinical screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA), ribonucleic acid (RNA), or mixtures or combinations thereof, including, for example, DNA nanoplexes. Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a growth factor, e.g., NGF or GNDF, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an anti-arrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

As used herein, the term "treated," "treating" or "treatment" includes the diminishment or alleviation of at least one symptom associated or caused by the state, disorder or disease being treated. A subject that has been treated can exhibit a partial or total alleviation of symptoms (for example, tumor load), or symptoms can remain static following treatment according to the invention. The term "treatment" is intended to encompass prophylaxis, therapy and cure.

As used here, the phrase "5' or 3' sticky ends" is meant to refer to the 3' and/or 5' protruding ends of DNA or RNA that will bond with complementary sequences of bases. In certain embodiments, the RNA motifs have 5' or 3' sticky ends. In certain embodiments, the 5' or 3' sticky ends are located in the middle of a helix. According to the invention, the 5' and 3' sticky ends can be engineered to be used for self-assembly of the nanorings into an RNA nanotube.

Other definitions appear in context throughout the disclosure.

RNA and Nanostructure Design

RNA has a number of advantages for nanostructure design. Nanoparticle structures provide a size range that is large enough to avoid the problem of expulsion from the cell, but are small enough to avoid the problems of cell delivery often encountered with larger particles. RNA is the only biopolymer that can carry genetic information and has catalytic properties. RNA can naturally fold into complex motifs, and RNA motifs are capable of self-assembly. RNA has a natural functionality, for instance RNA can function as ribozymes or riboswitches. Further, RNA is advantageous in eliciting a very low immune response. Moreover, the construction of RNA into ordered, patterned superstuctures has a number of desirable characteristics, including the ability to self-assemble in precisely defined ways, the ability to undergo editing and replication, the ability to undergo controlled disassembly. RNA has versatility in function and structure. Functionally, RNA is the only biopolymer that can carry genetic information and that possesses catalytic properties. Structurally, RNA has predictable intra and intermolecular interactions with well-known structural geometry. The RNA strands that consist of adenine (A), guanine (G), cytosine (C), and uridine (U) can naturally, or can be programmed, to self-assemble via complementary base pairing. The helical region of RNA has a well-known nanometer scale structural geometry of 2.86 nm per helical turn with 11 base pairs and a 2.3 nm diameter. The self-assembly of RNA into complex structures can be facilitated via complementary base pairing or inter- and intra-molecular interactions of the different single stranded regions in the RNA, including internal bulges and loop motifs, and single-stranded overhangs or "sticky-ends".

RNA Synthesis

RNA molecules used to make the nanoparticles of the invention can be produced recombinantly or synthetically by methods that are routine for one of skill in the art. For example, synthetic RNA molecules can be made as described in US Patent Application Publication No.: 20020161219, or U.S. Pat. Nos. 6,469,158, 5,466,586, 5,281,781, or 6,787,305.

RNA Self-Assembly

Small RNA structural motifs can code the precise topology of large molecular architectures. It has been shown that RNA structural motifs participate in a predictable manner to stabilize, position and pack RNA helices without the need of proteins (Chworos A et al., Science 306:2068-2072.2004). RNAI and RNAII are loop structures that interact in what is called a 'kiss' or 'kissing' complex (Lee et al., Structure 6:993-1005.1998). This contact facilitates the pairing of the RNAI and RNAII loops, until the two RNAs form a duplex. As such, the "kissing" interaction between RNAI and RNAII is one means of self-assembly between the RNA building blocks. The interaction between the RNAIi/RNAIIi complex involves all the bases in the base pairing, and dissociates nearly 7000 times more slowly than the wild-type complex.

The self-assembly of nanoparticles from RNA involves cooperative interaction of individual RNA molecules that spontaneously assemble in a predefined manner to form a larger two- or three-dimensional structure. Within the realm of self-assembly two main categories have been described: template and non-template (Lee et al. J Nanosci Nanotechnol. 2005 December; 5(12):1964-82). Template assembly involves interaction of RNA molecules under the influence of specific external sequence, forces, or spatial constraints such as RNA transcription, hybridization, replication, annealing, molding, or replicas. In contrast, non-template assembly involves formation of a larger structure by individual components without the influence of external forces. Examples of non-template assembly are ligation, chemical conjugation, covalent linkage, and loop/loop interaction of RNA, especially the formation of RNA multimeric complexes (Lee et al. 2005, as above).

Previously, RNA has been demonstrated to assemble into nanoparticles of various shapes and sizes. The first RNA nanoparticles were generated using loop-receptor interfaces to form dimeric nanoparticles. The assembly of this H-shaped nanoparticle was mediated by GAAA/Hnt receptor interaction, which is a highly recurrent motif found in group I and group II introns and other ribozymes and riboswitches. This interaction was further used to generate oriented filaments by combining multiple loop-receptor interactions with a four-way junction motif. One of the first examples of RNA nanoparticles that incorporate multiple RNA motifs within its context is the tectosquare, which is composed of four artificial RNA building blocks called tectoRNAs that self-assemble through specific, non-covalent loop-loop interactions called kissing loops (KL) found at the end of each stem. These tectoRNAs were further programmed to self-assemble into complex arrays via 3' sticky tails with controllable topology, directionality and geometry. The first example of a therapeutic RNA nanoparticle was designed from phi-29-encoded packaging motor (pRNA), a natural RNA motif found in bacteriophages. The pRNA dimers were reengineered for targeted delivery of ribozymes to attack the hepatitis B virus by specifically cleaving the virus's poly-A signal. In a subsequent study, the pRNA trimers were functionalized with cell receptor-binding RNA aptamers and were used to deliver siRNAs that target a specific gene for silencing and thus enabling apoptosis in cancer cells.

In certain embodiments the RNA building blocks of the invention can self-assemble in buffer conditions suitable for RNA, and that can be determined by one of skill in the art. In other certain embodiments, the nanostructures of the invention can be formed in a cell. In certain examples, the RNA sequence will be expressed in the cell and formation of the nanoparticle will be observed via electron microscope tomography (EMT). To satisfy the EMT resolution requirements the minimal size of the nanoparticle will be between 15 nm, 20 nm, 25 nm, 30, nm, 35 nm, 40 nm, 45 nm or more. In preferred embodiments, the minimal size of the nanoparticle will be 25 nm. Moreover, in preferred embodiments, the nanoparticle can further assemble into bundles, such as nanotubes, sheets, or clusters.

RNA Nanoparticles

RNA has been demonstrated to be an efficient nanoparticle. A bacteriophage phi29-encoded RNA (pRNA) has been reengineered to form dimmers, trimers, rods, hexamers, and 3D arrays several microns in size through interactions of interlocking loops (Shu, D.; Moll, W.-D.; Deng, Z.; Mao, C.; Guo, P. Nano Letters 2004, 4, (9), 1717-1723; Guo, P. J Nanosci Nanotechnol 2005, 5, (12), 1964-82). A nanoparticle, containing a pRNA trimer as a delivery vehicle was used to deliver siRNAs and receptor-binding aptamers, and has been demonstrated to block cancer development both in vitro in cell culture, and in vivo in mice (Khaled, A.; Guo, S.; Li, F.; Guo, P. Nano Lett 2005, 5, (9), 1797-808; Guo, S.; Huang, F.; Guo, P. Gene Ther 2006, 13, (10), 814-20). An H-shaped RNA molecular unit built from a portion of group I intron domain has been shown to form oriented filaments (Hansma, H. G.; Oroudjev, E.; Baudrey, S.; Jaeger, L. J Microsc 2003, 212, (Pt 3), 273-9; Nasalean, L.; Baudrey, S.; Leontis, N. B.; Jaeger, L. Nucleic Acids Res 2006, 34, (5), 1381-92). Further, specific RNA nano-arrangements based on HIV dimerization initiation site stem-loops were shown to be capable of thermal isomerization to alternative structures (Horiya, S.; Li, X.; Kawai, G.; Saito, R.; Katoh, A.; Kobayashi, K.; Harada, K. Nucleic Acids Res Suppl 2002, (2), 41-2; Horiya, S.; Li, X.; Kawai, G.; Saito, R.; Katoh, A.; Kobayashi, K.; Harada, K. Chem Biol 2003, 10, (7), 645-54; Li, X.; Horiya, S.; Harada, K. J Am Chem Soc 2006, 128, (12), 4035-40). Small structural fragments found in the ribosome and HIV have been used in the design of artificial RNA building blocks, called tectoRNAs (Chworos, A.; Severcan, I.; Koyfman, A. Y.; Weinkam, P.; Oroudjev, E.; Hansma, H. G.; Jaeger, L. Science 2004, 306, (5704), 2068-72). Each tectoRNA contains a right angle motif that forms a 90-degree angle between adjacent helices, two interacting hairpin loops at the end of each stem, and a 3' "sticky stem". The hairpin loops direct the formation of the tetramer via formation of specific noncovalent loop-loop interactions, called "kissing loops", and the "sticky stems" further assemble tetramers into complex nanoarrays. In bionanotechnology, RNA-RNA interactions can guide precise deposition of gold nanoparticles (Bates, A. D.; Callen, B. P.; Cooper, J. M.; Cosstick, R.; Geary, C.; Glidle, A.; Jaeger, L.; Pearson, J. L.; Proupin-Perez, M.; Xu, C.; Cumming, D. R. Nano Lett 2006, 6, (3), 445-8). For example, self-assembling tectoRNA-ladders have been shown to induce a precise linear arrangement of cationic gold nanoparticles, demonstrating that RNA can control regular spacing of gold nanoparticles and can act as a nanocrown scaffold (Koyfman, A. Y.; Braun, G.; Magonov, S.; Chworos, A.; Reich, N. O.; Jaeger, L. J Am Chem Soc 2005, 127, (34), 11886-7).

Design

The general approach used to create RNA nano-particles and nano-materials is to take known RNA structures, cut them into the building blocks, and reengineer single-stranded loops and regions to facilitate the desired self-assembly. The self-assembly of all the above discussed RNA building blocks into nanostructures is mediated by the complementarity of hairpin loops and loop receptors that form non-covalent RNA-RNA interactions. For precise assembly of the RNA building blocks, each of the corresponding complementary loop-loop interactions are uniquely reengineered.

Two main experimental approaches are used for programmable self-assembly of nucleic acids nanostructures (Jaeger, L.; Chworos, A. Curr Opin Struct Biol 2006, 16, (4), 531-43). The first is a single-step assembly, which is commonly used for DNA nanostructures (Chelyapov, N.; Brun, Y.; Gopalkrishnan, M.; Reishus, D.; Shaw, B.; Adleman, L. J Am Chem Soc 2004, 126, (43), 13924-5; Mathieu, F.; Liao, S.; Kopatsch, J.; Wang, T.; Mao, C.; Seeman, N. C. Nano Lett 2005, 5, (4), 661-5.). The second is a stepwise assembly, which has been commonly described for RNA nanostructures (Chworos, A.; Severcan, I.; Koyfman, A. Y.; Weinkam, P.; Oroudjev, E.; Hansma, H. G.; Jaeger, L. Science 2004, 306, (5704), 2068-72). In the single-step assembly approach, all molecules are mixed together followed by the slow cool annealing procedure. This is only possible if the target building block structure is the one that has the highest number of Watson-Crick base pairs and is therefore the most stable. This approach is, thus, based on the preferential folding of the building blocks at higher temperatures followed by the self-assembly of these building blocks through weaker interactions into final nanostructures at lower temperatures. However, usually there are many other possible structures that are only slightly less stable. In this case, the stepwise approach can be used where the building blocks are separately formed in the first step are then mixed together in the presence of high magnesium (Mg++) concentration to form a final nanostructure. This approach is more time consuming and the melting temperatures of the building blocks and the final nanostructure should be well separated.

The instant invention describes polyvalent RNA nanoparticles that comprise RNA motifs as building blocks, where the RNA motifs direct the formation of supramolecular assemblies. In certain embodiments, the building blocks comprise a motif that allows for non-covalent assembly between 2, 3, 4, 5, 6, 7, 8, 9, 10 or more building blocks.

A number of RNA motifs are available as building blocks, including but not limited to RNA I and/or RNA II motifs, kissing loops, RNA I inverse (RNA Ii) and/or RNA II inverse (RNA IIi) motifs. Numerous high-resolution RNA structures determined by NMR or X-ray crystallography can be separated into building blocks for design of new RNA nanoparticles and nanomaterials.

In certain embodiments of the invention, the RNAII motif is a 90 degree angle bend motif. In certain preferred embodiments, these motifs, embedded within rationally designed RNAs (tectoRNA), are chosen in order to generate square-shaped tetrameric RNA nanoparticles (NPs).

In further preferred embodiments, the RNAII motif is selected from the group consisting of right angle (RA) motifs, three way junction (3WJ) motifs, four way junction motifs and class II tRNA motifs.

In further preferred embodiments, the RA-motif can form at least 10 tertiary H-bonds and 4 stacking interactions, the 3WJ-niotif at least 14H-bonds and 9 stacks, while the tRNA motif can form approximately 33H-bonds and 15 stacking interactions.

Preferably, the three different 90° motifs can be used as structural cores for designing L-shaped tectoRNAs able to assemble into tectosquares.

The polyvalent RNA nanoparticle of according to the invention can be in the shape of a ring, in the shape of a square or in the shape of a triangle; however it is to be understood that other geometries are possible. Accordingly, the ring, square, triangle or other shape comprises 1, 2, 3, 4, 5, 6, 7, 8, 9, 10, or more building blocks as described by the invention. In certain preferred embodiments of the invention, the ring comprises 6 building blocks that form a hexameric ring. In the hexameric ring, there is a 120-degree angle at the loop-loop interactions at the corners of the hexameric ring.

In the tectosquares, there in a 90-degree angle at the loop-loop interactions at the corners of the squares.

In certain embodiments, there is a positive relationship between the stability of RNA assemblies and the complexity of the tertiary structures that define the assembly.

The RNA building blocks can contain hairpin loops. In certain specific example, each building block contains two or more hairpin loops. The hairpin loops are connected by a helix. The RNA building blocks can be held together by non-covalent loop-loop contacts. Further, the building blocks have 5' or 3' sticky ends, and in certain preferred embodiments of the invention, the 5' or 3' sticky ends are located in the middle of a helix.

As described, the polyvalent RNA nanoparticles consist of building blocks, which have 5' or 3' sticky ends. These 5' or 3' sticky ends can be engineered as sticky ends for self-assembly into polyhedral architecture. Advantageously, in certain embodiments, the RNA nanoparticles can be connected via complementary ends. This polyvalent RNA nanoparticle is capable of self-assembly. As discussed herein, in certain preferred embodiments, self-assembly may occur as a single-step process.

Conjugation to Nanoparticles

The polyvalent RNA nanoparticles can be used to deliver therapeutics, as diagnostic tools, or as delivery agents.

The compositions of the present invention have therapeutic uses. Any number of diseases or disorders can be treated by the compositions of the present invention and may be limited, in fact, only by the agent or agents that can be loaded in the inside of the nanoparticle or conjugated to the outside.

For example, one obstacle that arises in chemotherapy is the dose-limiting systemic toxicity of conventional drugs. It would be advantageous to develop methodology to allow for a chemotherapeutic agent to be delivered selectively to tumor tissue without significant systemic toxicity following intravenous infusion.

Advantageously, the 5' and 3' sticky ends are positions for conjugation of one or more therapeutic, diagnostic, or delivery agents.

Exemplary potential applications of multi-functional nanoparticles of the invention in which 2, 3, 4, or more agents are coupled to a nanoparticle include using one or more agents to target a macromolecular structure or a cell and using the second one to alter the function/properties of the macromolecule or cell, e.g., using a protein to target a cell and using a toxin or cell death protein to kill the targeted cell, using an siRNA to silence genes, or using a fluorescent particle for visualization, or using a chemical or protein to target a protein within a complex and another one to alter the function of a different component of the complex.

In certain embodiments, the nanoparticle comprises one or more agents. In further preferred embodiments, the agent can be conjugated to the nanoparticle. Conjugated can be understood as attached, linked, mixed, or otherwise present on or in a magnetoliposome. For example, an agent can be conjugated by covalent or ionic linkage, by use of a chelate or other linker moiety. As used herein, conjugation of an agent to a nanoparticle does not disrupt the desired activity of the agent.

The agent can comprise any material or compound or composition or agent for in vivo or in vitro use for imaging, diagnostic or therapeutic treatment that can be enclosed in the inside the nanoparticle or can be conjugated with the nanoparticle without appreciably disturbing the physical integrity of the nanoparticle. A nanoparticle can comprise one or more agents of one or more types. For example, a nanoparticle can comprise a therapeutic agent, and the targeting of the agent can be followed by further conjugation with an imaging agent. Similarly, cocktails of therapeutic agents are typically used in the treatment of cancer. A nanoparticle can comprise more than one type of therapeutic agent.

Examples of agents include imagining agents (for example gadolinium, manganese, chromium, or iron) and therapeutic agents, in particular chemotherapeutic agents.

The agent may also be a targeting agent that directs the nanoparticle to a delivery site. For example, the targeting agent may be a ligand, e.g. a peptide ligand that has specific cell surface binding partners, e.g., ligand receptors, that are preferentially exhibited on the surface of a target cell. As used herein, "receptor" and "ligand" refer to two members of a specific binding pair that are binding partners. A receptor is that member of the pair that is found localized on the surface of the target; the ligand is the member of the pair that is found on the surface of the nanoparticle. Accordingly, the in certain embodiments, the invention features a nanoparticle comprising a member of a binding pair, or a fragment thereof that retains the capacity to specifically bind the other member of the binding pair, on its surface and the other member of that binding pair, or a fragment thereof that retains the capacity to specifically bind its partner, is present on the surface of a target. In certain embodiments, the targeting agent may be an antibody, for example a single-chain antibody, for which a binding partner would include an antigen thereof, or a fragment, derivative or variant thereof that retains the capacity to bind to the single-chain antibody.

A therapeutic agent may be a molecule, atom, ion, receptor and/or other entity which is capable of detecting, identifying, inhibiting, treating, catalyzing, controlling, killing, enhancing or modifying a target such as a protein, glyco protein, lipoprotein, lipid, a targeted cell, a targeted organ, or a targeted tissue.

In certain cases, the therapeutic agent is a radiotherapeutic agent, and can be selected from, but is not limited to radioactive gadolinium, radioactive boron, and radioactive iodine.

In certain examples, the agent can be, but is not limited to: drugs, such as antibiotics, analgesics, hypertensives, cardiotonics, and the like, such as acetaminaphen, acyclovir, alkeran, amikacin, ampicillin, aspirin, bisantrene, bleomycin, neocardiostatin, carboplatin, chloroambucil, chloramphenicol, cytarabine, daunomycin, doxorubicin, fluorouracil, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, temozolamide, trimethoprim, cisplatin, oxaliplatin, mechlorethamine, cyclophosphamide, chlorambucil, azathioprine, mercaptopurine, vinca alkaloids, taxanes, vincristine, vinblastine vinorelbine, vindesine, etoposide, teniposide, paclitaxel, irinotecan, topotecan, amsacrine, etoposide, etoposide phosphate, teniposide, and dactinomycinand valban; diphtheria toxin, gelonin, exotoxin A, abrin, modeccin, ricin, radioactive gadolinium, radioactive boron, and radioactive iodine; or toxic fragments thereof; metal ions, such as the alkali and alkaline-earth metals; radionuclides, such as those generated from actinides or lanthanides or other similar transition elements or from other elements, such as 51Cr, 47 Sc, 67 Cu, 67 Ga, 82 Rb, 89 Sr, 88 Y, 90 Y, 99m Tc, 105 Rh, 109 Pd, 111 In, 115m In, 125 I, 131 I, 140 Ba, 140 La, 149 Pm, 153 Sm, 159 Gd, 166 Ho, 175 Yb, 177 Lu, 186 Re, 188 Re, 194 Ir, and 199 Au; signal generators, which includes anything that results in a detectable and measurable perturbation of the system due to its presence, such as fluorescing entities, phosphorescence entities and radiation; signal reflectors, such as paramagnetic entities, for example, Fe, Gd, Cr, or Mn; chelated metal, such as any of the metals given above, whether or not they are radioactive, when associated with a chelant; signal absorbers, such as contrast agents and electron beam opacifiers, for example, Fe, Gd, Cr, or Mn; antibodies, including monoclonal antibodies and anti-idiotype antibodies; antibody fragments; hormones; biological response modifiers such as interleukins, interferons, viruses and viral fragments; diagnostic opacifiers; and fluorescent moieties. Other pharmaceutical materials include scavenging agents such as chelants, antigens, antibodies or any moieties capable of selectively scavenging therapeutic or diagnostic agents.

Other examples of therapeutic agents include antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic moieties include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Nanoparticles may be directed to target sites. Preferred target sites comprise cancer cells, solid tumors, sites of inflammation and damaged bone or tissue.

For example, nanoparticle may further comprise an antibody or a peptide that acts as a targeting moiety to enable specific binding to a target cell bearing a target molecule, e.g., a cell surface marker to which the antibody or peptide is directed or a disease-specific marker to which the antibody or peptide is directed. The nanoparticle may further comprise a nucleotide, e.g. an oligonucleotide, that acts as a targeting moiety to enable specic binding to a target cell bearing a target molecule. For example, the oligonucleotide may be an aptamer that binds a specific target molecule.

Further exemplary potential applications of the multifunctional nanoparticles of the invention include use of the nanoparticles as riboswitch aptamers, ribozymes, or beacons.

Riboswitches are a type of control element that use untranslated sequence in an mRNA to form a binding pocket for a metabolite that regulates expression of that gene. Riboswitches are dual function molecules that undergo conformational changes and that communicate metabolite binding typically as either increased transcription termination or reduced translation efficiency via an expression platform.

Ribozymes catalyze fundamental biological processes, such as RNA cleavage by transesterification. The polyvalent RNA nanoparticles of the invention can be incorporated in to ribozymes using methods described in, for example, U.S. Pat. No. 6,916,653, incorporated by reference in its entirety herein.

A number of "molecular beacons" (often fluorescence compounds) can be attached to RNA nanoparticles of the invention to provide a means for signaling the presence of, and quantifying, a target analyte. Molecular beacons, for example, employ fluorescence resonance energy transfer-based methods to provide fluorescence signals in the presence of a particular analyte/biomarker of interest. In preferred embodiments, the term "molecular beacon" refers to a molecule or group of molecules (i.e., a nucleic acid molecule hybridized to an energy transfer complex or chromophore(s)) that can become detectable and can be attached to a nanoparticle under preselected conditions. Similarly, amplifying fluorescent polymers (AFPs) can be utilized in the present invention. An AFP is a polymer containing several chromophores that are linked together. As opposed to isolated chromophores that require 1:1 interaction with an analyte in conventional fluorescence detection, the fluorescence of many chromophores in an AFP can be influenced by a single molecule. For example, a single binding event to an AFP can quench the fluorescence of many polymer repeat units, resulting in an amplification of the quenching. Quenching is a process which decreases the intensity of the fluorescence emission. Molecular beacons and AFPs, including their methods for preparation, that can be used in the present invention are described in numerous patents and publications, including U.S. Pat. No. 6,261,783.

Any protein can be coupled to nanoparticles. For instance, glycoproteins are most easily coupled, as they can be oxidized to generate an active aldehyde group. Other proteins can be coupled via their —COOH group(s) but with lower efficiency. However, other means known in the art, such as di-imide reagents, e.g. carbodiimide can be used to couple proteins lacking sugars to the nanoparticles.

Polyethylene Glyocol (PEG) chains can be conjugated to the nanoparticles. PEG chains render the nanotubes highly water-soluble. PEG-phospholipids (PEG-PL) have been used in the formation of micelles and liposomes for drug delivery (Adlakha-Hutcheon, G.; Bally, M. B.; Shew, C. R.; Madden, T. D. Nature Biotech. 1999, 17, 775-779; Meyer, O.; Kirpotin, D.; Hong, K.; Sternberg, B.; Park, J. W.; Woodle, M. C.; Papahadjopoulos, D. J. Biol. Chem. 1998, 273, 15621-15627; Papahadjopoulos, D.; Allen, T. M.; Gabizon, A.; Mayhew, E.; Matthay, K.; Huang, S. K.; Lee, K. D.; Woodle, M. C.; Lasic, D. D.; Redemann, C.; Martin, F. J. Proc. Nat. Acad. Sci. USA. 1991, 88, 11460-11464).

Functional groups can be coupled to the nanoparticle, for instance the functional group can be a reactive functional group. Suitable functional groups include, but are not limited to, a haloacetyl group, an amine, a thiol, a phosphate, a carboxylate, a hydrazine, a hydrazide an aldehyde or a combination thereof. Other functional groups include groups such as a reactive functionality or a complementary group. In addition, RNA functional groups can be attached, as for example ribozymes or riboswitch aptamers.

The nanoparticle can be used for attachment of small molecules for specific interactions with nucleic acids, carbohydrates, lipids, proteins, antibodies, or other ligands.

The nanoparticle can have dyes attached. The dye is can be a fluorescent dye, or a plurality of fluorescent dyes. Suitable dyes include, but are not limited to, YOYO-1, JOJO-1, LOLO-1, YOYO-3, TOTO, BOBO-3, SYBR, SYTO, SYTOX, PicoGreen, OliGreen, and combinations thereof. Other dyes include, thiazole orange, oxazole yellow, or non-intercalating dyes such as fluorescein, rhodamine, cyanine or coumarin based dyes, and combinations thereof. Other suitable dyes include, but are not limited to, 4-acetamido-4'-isothiocyanatostilbene-2,2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,-2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalocyanine; and naphthalo cyanine. Suitable dyes for use in the nanoparticles of the present invention include, without limitation, a family of homodimeric cyanine DNA intercalating dyes from Molecular Probes that cover the visible spectrum, such as YOYO-1 (488/509), JOJO-1 (532/545), LOLO-1 (565/579), and YOYO-3 (612/631), SYBR-101 (488/505) and SYTO-62 (652/676). Given sufficient detection SN, dyes are mixed in various ratios in a single particle such that, for example, different fluorescence spectra are obtained from mixtures of just 2 dyes. According to the invention, one or more therapeutic, diagnostic, or delivery agents are directly included in the building block sequences. In certain embodiments, the delivery agent can be a targeting agent. Targeting agents are used to direct the nanoparticle to a tissue or cell target. An exemplary embodiment of a targeting agent is an antibody. For example, antibodies suitable for use as targeting agents in the present invention include antibodies directed to cell surface antigens which cause the antibody-nanoparticle complex to be internalized, either directly or indirectly. For example, in the treatment of cancer, suitable antibodies include antibodies to CD33 and CD22. CD33 and CD22 that are over-expressed and dimerized on lymphomas.

In certain preferred embodiments of the invention biotin is conjugated to the nanoparticle. For example, the nanoparticles of the invention can be further functionalized using biotin-streptavidin interactions to immobilize molecules inside or outside the polyhedra, e.g. polyhedral cages. For example, streptavidin can be conjugated to guanosine monophosphothioate (GMPS)-modified tectoRNAs by means of a biotin linker. In certain preferred embodiments, the biotin linker is incorporated to a mono-phosphothioate at the 5' position of tectoRNAs.

A wide variety of particle sizes are suitable for the present invention. In certain aspects, the particle has a diameter of about 10 nanometers to about 10 microns. Preferably the particle diameter is about 10 to 700 nanometers, and more preferably, the diameter of about 10 nanometers to about 100 nanometers.

The polyvalent RNA nanoparticle or the polyvalent RNA nanotube as described herein has a number of uses. For example, the polyvalent RNA nanoparticle or the polyvalent RNA nanotube can be used in drug delivery, imaging, nanocircuits, cell growth surfaces, medical implants, medical testing, or gene therapy.

In one particular embodiment, the polyvalent RNA nanoparticle or the polyvalent RNA polyhedra, e.g. cages, as described can be used in biological meshes. In one exemplary embodiment, the invention as described herein may find use as a biosensor in, for example, pathogen detection. In one particular embodiment, self-assembling nano-meshes are used to attach biosensors for pathogen detection or for x-ray crystallography by placing multiple copies of a protein or functional RNAs, for example, on the mesh. Biosensors for pathogen detection are advantageously employed in bioterrorism capacities.

In another exemplary embodiment, the polyvalent nanoparticles of the invention, as described herein, are employed as skeletons or scaffolds for tissue growth.

These uses are exemplary, and not considered to be limiting.

Compositions

The invention, in part, pertains to a drug delivery composition comprising the polyvalent RNA nanoparticle as described herein. The drug delivery composition of the invention can gain entry into a cell or tissue.

Advantageously, the drug delivery composition of the invention provides for a more controlled delivery of an active agent, especially a therapeutic agent, to a site of action at an optimum rate and therapeutic dose. Thus, improvements in therapeutic index may be obtained by modulating the distribution of the active ingredient in the body. Association of the active ingredient with a delivery system enables, in particular, its specific delivery to the site of action or its controlled release after targeting the action site. By reducing the amount of active ingredient in the compartments in which its presence is not desired, it is possible to increase the efficacy of the active ingredient, to reduce its toxic side effects and even modify or restore its activity.

It is understood by one of skill in the art that changing the base composition of RNA changes the half-life of RNA and thus the release of RNA from the composition. For instance, the composition can be modified to consist of fast release, slow release or a staged release of polyvalent RNA nanoparticle.

In certain preferred embodiments, the drug delivery composition can comprise a second therapeutic agent. In some embodiments, the composition comprising nanoparticles and the second therapeutic agent are administered simultaneously, either in the same composition or in separate compositions. In some embodiments, the nanoparticle composition and the second therapeutic agent are administered sequentially, i.e., the nanoparticle composition is administered either prior to or after the administration of the second therapeutic agent. The term "sequential administration" as used herein means that the drug in the nanoparticle composition and the second agent are administered with a time separation of more than about 15 minutes, such as more than about any of 20, 30, 40, 50, 60 or more minutes. Either the nanoparticle composition or the chemotherapeutic agent may be administered first. The nanoparticle composition and the chemotherapeutic agent are contained in separate compositions, which may be contained in the same or different packages. In some embodiments, the administration of the nanoparticle composition and the second therapeutic agent are concurrent, i.e., the administration period of the nanoparticle composition and that of the second therapeutic agent overlap with each other. In some embodiments, the administration of the nanoparticle composition and the second therapeutic agent are non-concurrent. For example, in some embodiments, the administration of the nanoparticle composition is terminated before the second therapeutic agent is administered. In some embodiments, the administration of the second therapeutic agent is terminated before the nanoparticle composition is administered. Administration may also be controlled by designing the RNA nanoparticle or nano-tube to have different half lives. Thus, particle dissolution would be controlled by a timed release based upon variations in designed RNA stability.

The second therapeutic agent is selected from, but not limited to chemotherapeutic agents, cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodialators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

When the second therapeutic agent is a chemotherapeutic agent, the chemotherapeutic agent is selected from, but not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol;

mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

Reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

The invention also relates to pharmaceutical or diagnostic compositions comprising the nanoparticles of the invention and a pharmaceutically acceptable carrier. The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in Remington's Pharmaceutical Sciences, Mack Publishing Company, a standard reference text in this field.

Methods of Treatment

The methods of the invention encompass method of treating or preventing diseases or disorders by administering to subjects in need thereof an effective amount of a polyvalent RNA nanoparticle or nanotube as described herein. Accordingly, a number of diseases or disorders are suitable for treatment according to the methods of the invention. Examples include, but are not limited to, Adenoma, Ageing, AIDS, Alopecia, Alzheimer's disease, Anemia, Arthritis, Asthma, Atherosclerosis, Cancer, Cardiac conditions or disease, Diabetes mellitus, Foodborne illness, Hemophilia A-E, Herpes, Huntington's disease, Hypertension, Headache, Influenza, Multiple Sclerosis, Myasthenia gravis, Neoplasm, Obesity, Osteoarthritis, Pancreatitis, Parkinson's disease, Pelvic inflammatory disease, Peritonitis, Periodontal disease, Rheumatoid arthritis, Sepsis, Sickle-cell disease, Teratoma, Ulcerative colitis, and Uveitis.

The methods of the invention further encompass diagnostics.

The methods may be practiced in an adjuvant setting. "Adjuvant setting" refers to a clinical setting in which, for example, an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated. The methods provided herein may also be practiced in a neoadjuvant setting, i.e., the method may be carried out before the primary/definitive therapy. Thus, in some embodiments, the individual has previously been treated. In other embodiments, the individual has not previously been treated. In some embodiments, the treatment is a first line therapy.

Methods of Delivery

The nanoparticle compositions described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the nanoparticle composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administrated intravenously. In some embodiments, the nanoparticle composition is administered orally.

The dosing frequency of the administration of the nanoparticle composition depends on the nature of the therapy and the particular disease being treated. For example, dosing frequency may include, but is not limited to, once daily, twice daily, weekly without break; weekly, three out of four weeks; once every three weeks; once every two weeks; weekly, two out of three weeks.

The administration of nanoparticles may be carried out at a single dose or at a dose repeated once or several times after a certain time interval. The appropriate dosage varies according to various parameters, for example the individual treated or the mode of administration.

The dosing frequency of the nanoparticle composition or the nanoparticle composition and the second therapeutic agent may be adjusted over the course of the treatment, based on the judgment of the administering physician.

When administered separately, the nanoparticle composition and the second therapeutic agent can be administered at different dosing frequency or intervals. For example, the nanoparticle composition can be administered weekly, while a second agent can be administered more or less frequently. In some embodiments, sustained continuous release formulation of the nanoparticle and/or second agent may be used. Various formulations and devices for achieving sustained release are known in the art. The doses required for the nanoparticle composition and/or the second agent may (but not necessarily) be lower than what is normally required when each agent is administered alone. Thus, in some embodiments, a subtherapeutic amount of the drug in the nanoparticle composition and/or the second agent are administered. "Subtherapeutic amount" or "subtherapeutic level" refer to an amount that is less than the therapeutic amount, that is, less than the amount normally used when the drug in the nanoparticle composition and/or the second agent are administered alone. The reduction may be reflected in terms of the amount administered at a given administration and/or the amount administered over a given period of time (reduced frequency).

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the disease to be treated may receive treatments to inhibit or and/or delay the development of the disease. The dose of nanoparticle composition will vary with the nature of the therapy and the particular disease being treated. The dose should be sufficient to effect a desirable response, such as a therapeutic or prophylactic response against a particular disease. Appropriate doses will be established by persons skilled in the art of pharmaceutical dosing such as physicians.

EXAMPLES

It should be appreciated that the invention should not be construed to be limited to the examples that are now described; rather, the invention should be construed to include any and all applications provided herein and all equivalent variations within the skill of the ordinary artisan.

Example 1. Square-Shaped RNA Nanoparticles from Different RNA Folds

The structural information encoding specific conformations of natural RNAs can be implemented within artificial RNA sequences to control both three-dimensional (3D) shape and self-assembling interfaces. Described herein are three natural RNA motifs with different degrees of structural complexity known to direct helical topology into approximately 90° bends: the tRNA, a three-way junction and a two-helix bend. These three motifs, embedded within rationally designed RNAs (tectoRNA), were chosen for generating square-shaped tetrameric RNA nanoparticles (NPs). The ability of each motif to direct the formation of supramolecular assemblies was compared by both native gel assays and atomic force microscopy (AFM). The experiments described herein show that there is a positive relationship between the stability of RNA assemblies and the complexity of the tertiary structures that define the assembly. Moreover, while there are multiple structural solutions for building square-shaped RNA particles, differences in the thermodynamics and molecular dynamics of the 90° motif can lead to different biophysical behaviors for the resulting supramolecular complexes.

The folding of RNA into compact 3D structures is a hierarchical process in which the formation of RNA helices is followed by the formation of tertiary RNA motifs that specify the positioning of the helices within the structure. Due to the folding process of RNA, modular tertiary motifs have likely emerged for the purpose of adopting specific topological arrangements of helices. RNA motifs are defined by sequence signatures that correspond to a limited set of conserved and semi-conserved nucleotides (nt) specifying well-defined 3D conformers. Recent developments in RNA architectonics, an approach for rationally designing 3D RNA architectures, have established that RNA structure information can be implemented into an RNA sequence to direct its tertiary folding and supramolecular assembly with a high degree of control and predictability. Nevertheless, knowledge about the kinetics, thermodynamics and autonomous folding properties of most RNA tertiary motifs remain scarce, presently limiting their use as building blocks for nano-construction. This prompted the present comparison of various 90°-angle bend (90°) motifs identified within RNAs from the translational apparatus for their ability to promote the assembly of square-shaped RNA nanoparticles (NPs). For example, the right-angle motif (RA-motif), three-way junction motif (3W5-motif) and tRNA-motif, which all have different local folds, contribute to forming 90° bend structures that could be seen as topologically equivalent (FIG. 1).

The RA-motif is a prevalent conserved structural motif found in ribosomal RNAs. It arranges adjacent helices in a cabin-log stacked configuration by promoting packing of two helical stems along their shallow-grooves through ribose-zipper interactions. It has been demonstrated that this motif is able to guide the assembly of L-shaped tectoRNAs into tetramers. Within its natural ribosomal context, the 3WJ-motif forms T-shaped arrangements of three helices (e.g. H75-H76-H79 in Haloarcula rnarismortui), where the coaxial stacking of two helices is enforced and the third stem protrudes at a roughly 90° angle. Lastly, the well-studied tRNA-motif consists of a four to five helical junction that folds into an L-shape tertiary structure stabilized by highly conserved T-D loop and triple helix interactions.

The primary difference between the three 90° motifs is their degree of structural complexity, assessed by measuring the number of tertiary hydrogen bonds (H-bond) and tertiary base stacking interactions. The RA-motif can form at least 10 tertiary H-bonds and 4 stacking interactions, the 3WJ-niotif at least 14H-bonds and 9 stacks, while the tRNA motif can form approximately 33H-bonds and 15 stacking interactions (FIG. 2). Therefore, in terms of structural complexity, the 3WJ-motif is slightly more complex than the RA-motif while the tRNA-motif is considerably more complex than both.

While these motifs are topologically equivalent, differences in their thermodynamics, kinetics and overall complexity are likely to result from their different functions within their natural context. However, if these structural motifs are truly topologically equivalent they should be interchangeable irrespective of their functional differences. The result presented herein report, in part, on the design and characterization of square-shaped RNA NPs using these three different 90° motifs as a means to compare the effect of RNA folds of different structural complexity within a similar structural context (FIG. 1). One of these RNA NPs is significantly more stable than the previously described tectosquare particle 32. This work suggests a direct correlation between the structural complexity of RNA motifs and their stability, dynamic and self-assembly properties within the NP context. It also provides means to generate rationally designed RNA NPs with tunable thermodynamic and self-assembly properties. Therefore, modular RNA NPs could have potential as scaffoldings for the delivery of RNA-based therapeutic molecules.

Example 2. Rational Design of Square-Shaped Particles

The three different 90° motifs were used as structural cores for designing L-shaped tectoRNAs able to assemble into square-shaped tetramers (tectosquares) (FIG. 1). The design strategy was similar to the one previously used to construct RA-squares. Each 90°-angle motif specifies for the tectoRNA corner. Further supramolecular assembly is promoted by two kissing loops (KL) that are covalently joined to this corner by two helical stems. A set of four different selective KL interactions (FIG. 3A) leads to highly specific and addressable tectoRNA assembly into three different tectosquares (FIG. 1) of similar dimension, ranging from 12 to 14 rim on a side: the minor size variation results from ring-closure constraints imposed by the 3D structure of the different 90° motifs. The comparatively simple RA and 3WJ sequence signatures (indicated as blue nts in FIG. 2A,B) facilitated the design of the corresponding tectoRNAs (FIG. 1). To test the effect on the orientation of the 3WJ motif, the 3WJ-P-tectoRNA was designed with the 3WJ motif rotated 90° anticlockwise. By contrast, additional factors needed to be addressed for constructing the tRNA-square. A class II tRNA fold was chosen in order to circularly permutate the sequence of the molecule (FIG. 2C). This allowed relocation of the 5'/3' termini from the aminoacyl stem to the variable stem, and insertion of KL motifs at the ends of extended aminoacyl and anticodon stems (FIG. 1). The tRNA-motif sequence was derived from the engineered tRNAq$^{ser}$, a hybrid class 1/class II tRNA known to fold into the correct tRNA tertiary structure without post-transcriptional modifications. As the proper folding of the class I tRNA$^{Phe}$ has been shown to be independent of the location of the 5'/3' termini, this suggests that the permutated tRNAq$^{ser}$ should likewise fold properly.

Example 3. Tectosquare Assembly

Figure 4A:
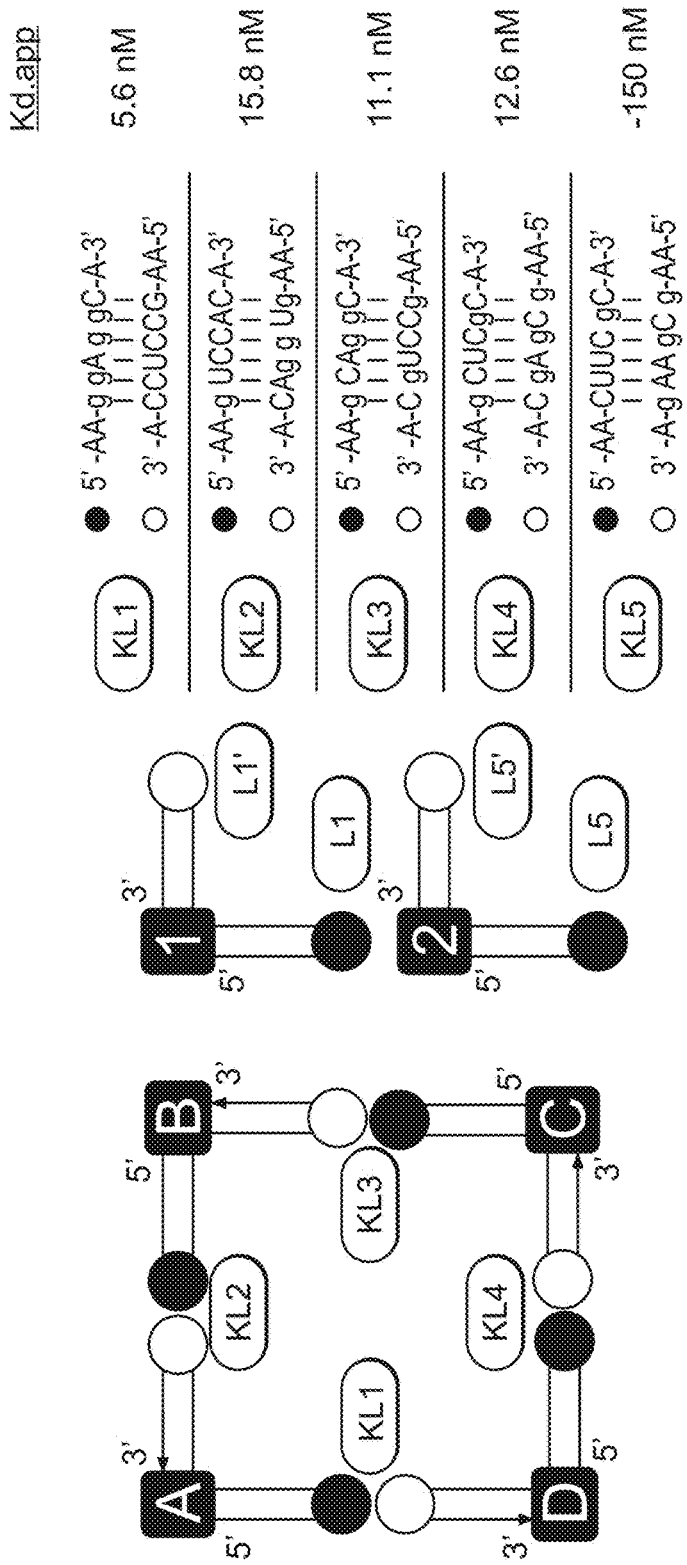
FIG. 4 (A-D) shows an assembly scheme and native gel shift characterization of tectosquares incorporating different 90° motifs. (A) Each tectosquare is formed of 4 tectoRNAs (A,B,C and D) assembled through the same set of kissing loops (KL1-4). ("KL1-4" disclosed as SEQ ID NOS 17-20, respectively, in order of appearance). Self-complementary tectoRNAs (1 and 2) assemble through KL1 or KL5. (B) Native PAGE of various tectosquares (100 nM) assembled at 15 mM Mg(OAc)2. I, monomer A; II, dimer AD; III, trimer ABC; IV, tetramer ABCD. The hybrid square is composed of RA-tectoRNAs (A, C units) and tRNA-tectoRNAs (B, D units). (C) Thermal melting curves of tectosquares (100 nM) are measured from native TGGE at 0.2 Mg(OAc)2. (D) Assembly of self-complementary tectoRNAs (100 nM) into closed-NPs of various sizes at 15 mM Mg(OAc)2.
Figure 4B:
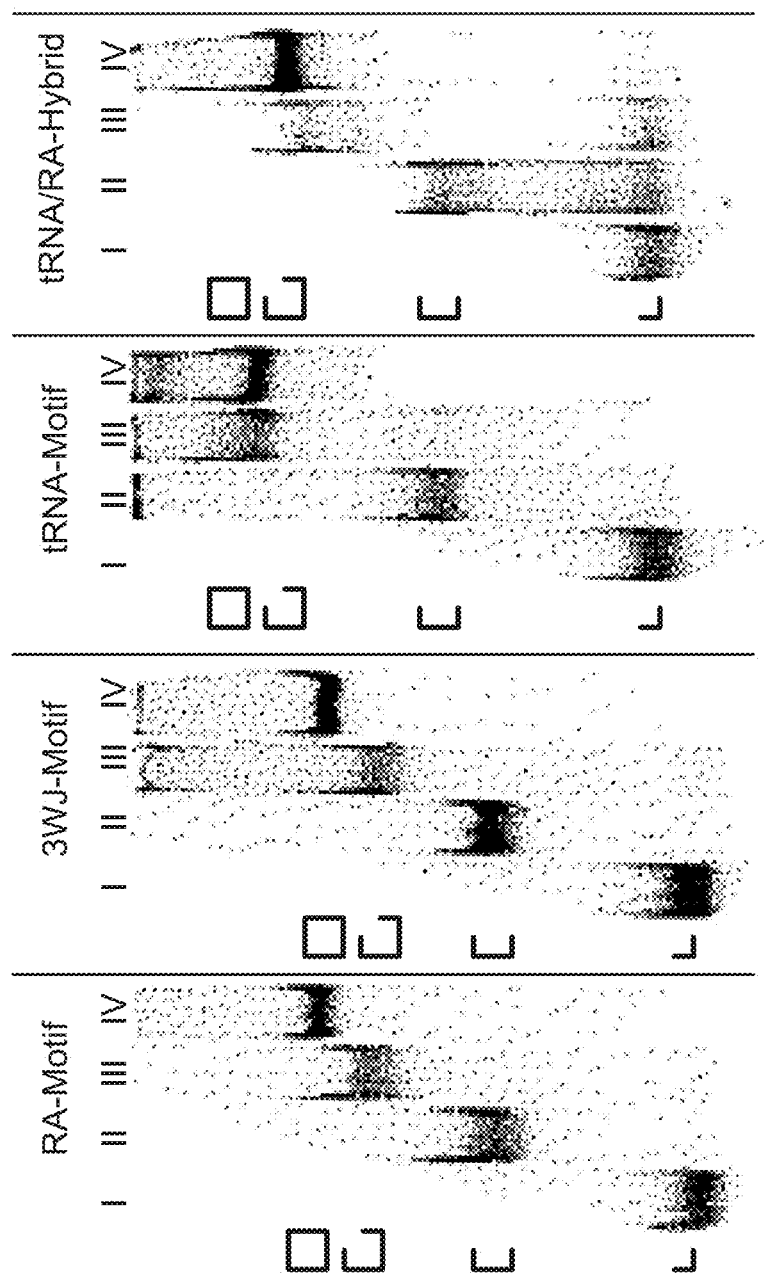

Each tectosquare was assembled in a single annealing step by subjecting an equimolar mixture of four tectoRNAs to a denaturation-renaturation folding process (see Methods). At 0.2 mM Mg2+ and 4° C., most kissing loop (KL) interactions used in this study (KL1-4) promote assembly with apparent equilibrium constants of dissociation (KD) in the 10 nM range (FIG. 3). These KL interactions are therefore similar in stability and assemble at concentrations well below the usual working RNA concentration of 100 nM. Selective formation of tectosquares mediated by four different KL interactions (KL1-4) was confirmed by native PAGE analysis (FIG. 4B). The yield of correctly assembled tectosquares was estimated to be ~80% by PAGE. Two primary factors contribute to tectosquare assembly: a well-folded and rigid 90° motif that stabilizes the square corners, and stable KL interactions that form the square sides. Therefore, depending on the structure, stability and rigidity of the 90° motif and the stability of the KL interactions, tectoRNAs can potentially assemble into NPs of different sizes. Previous studies of similar tectoRNAs lacking a 90° motif yield octameric and dodecameric closed-structures. By contrast, the three 90° tectoRNAs in this study essentially assemble into tetramers (FIG. 3B), indicating that the bend motif considerably contributes to the formation of specific-sized NPs.

Example 4. Self-Complementary tectoRNA Assembly

Figure 4C:
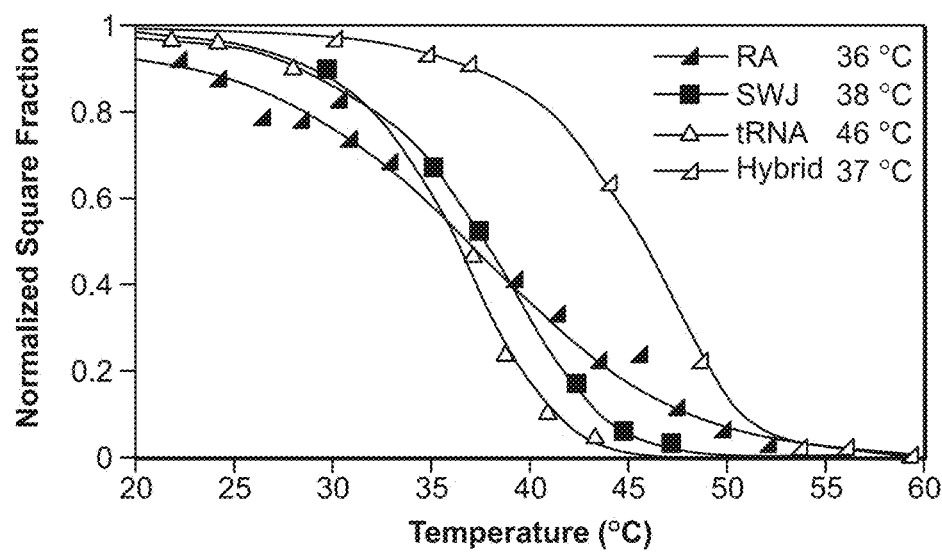
Figure 4D:
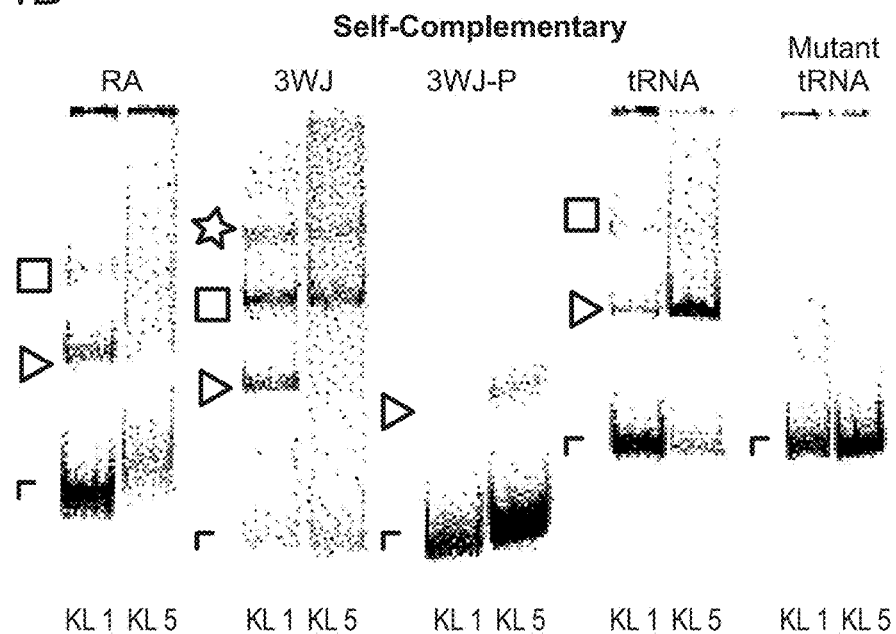

The contribution of each 90° motif to the formation of closed NP multimers was examined using two different self-complementary tectoRNAs (FIG. 4D). These tectoRNAs assemble end-to-end, either through KL1 or KL5 interactions, with KL1 being thermodynamically five times stronger than KL5 (data not shown). Self-complementary tectoRNAs without a 90° motif (but with secondary structure similar to RA-tectoRNAs) were previously observed to assemble into a mixture of linear and circular multimers ranging from dimers to dodecamers and even larger assemblies. By contrast, self-complementary 90° tectoRNAs assemble under similar experimental conditions into small closed structures, mostly dimers, trimers or tetramers (FIG. 4D). The three 90° motifs apparently facilitate NP closure by pre-disposing formation of KL interactions.

Figure 2D:
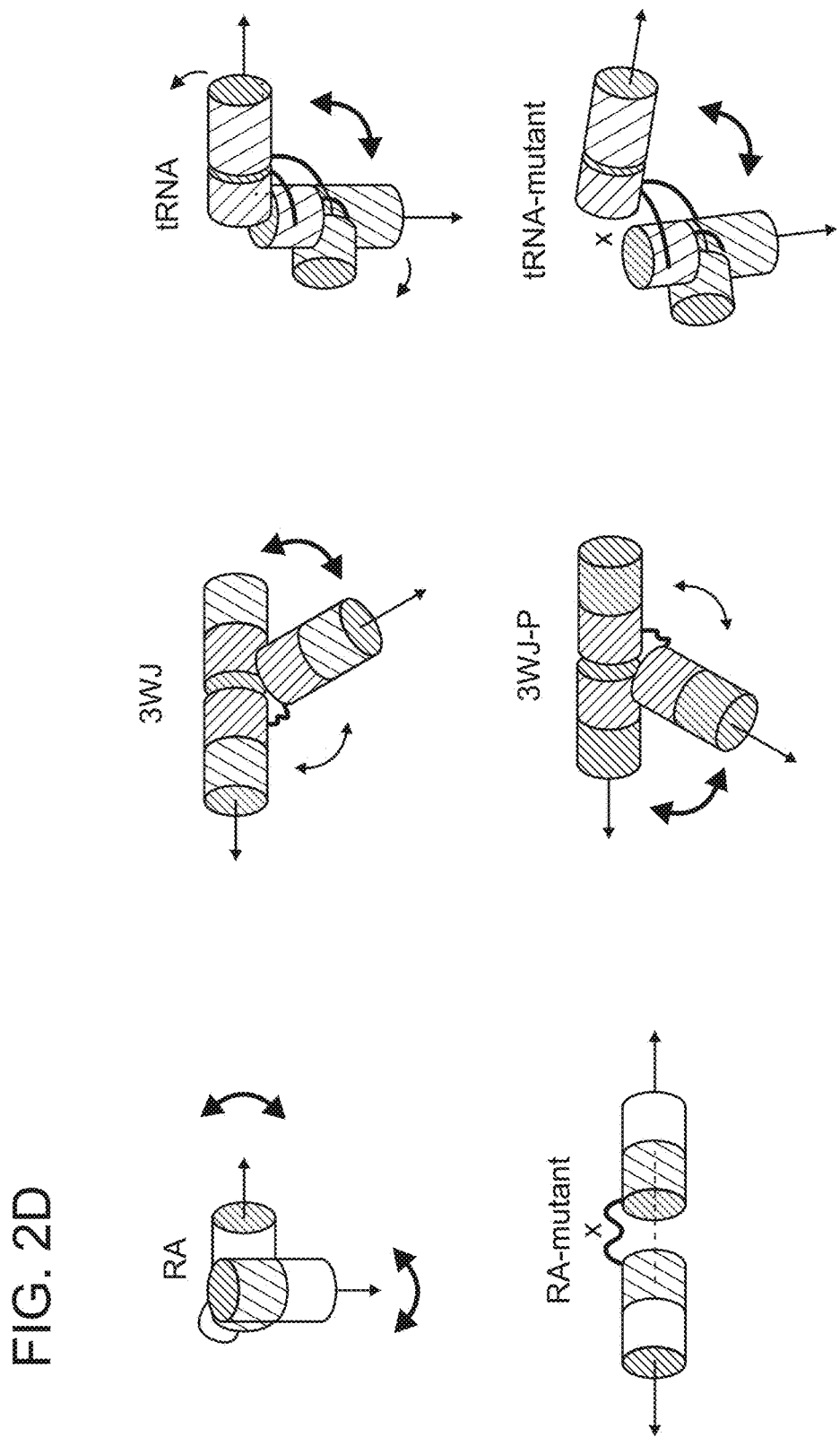
FIG. 2 (A-D) shows diagrams of 90°-angle motifs. (A,B, C) Base pairings are represented according to Leontis-Westhof notation (7). Orange nucleotides (nts) represent nts involved in tertiary contacts that are also involved in base stacking. (A) The RA-motif consists of ribose zipper interactions between the ribose 2'OH and phosphate backbones of the two adjacent helices, it forms 10H-bonds and 4 nt stacking interactions. (B) The 3WJ-motif is characterized by its central U-A WC:HG trans bp, the motif contains 14 tertiary H-bonds and 9 nt stacking interactions. (C) The tRNA-motif is made of two separate tertiary regions: the T/D loop interaction and base triples in the D-stem. The T/D loop is the region that forms the 90°-angle bend. The overall tRNA motif contains about 33 tertiary H-bonds and 15 tertiary stacking interactions. (D) The apparent dynamics (based on self-complementary experiments) of different 90°-angle motifs are summarized. Straight arrows indicate the direction of KL-assembly. Curved arrows show the relative dynamics in a direction, larger arrows indicate greater dynamics. X indicates the position of knockout mutations. WC stands for Watson-Crick edge, HG stands for Hoogsteen edge, SG stands for Shallow-Groove edge.

In the presence of 15 mM $Mg^{2+}$, RA, 3WJ-P and tRNA tectoRNAs with KL1 form mostly dimers (FIG. 4D), indicating that KL1 interactions can considerably distort the structure of the three types of 90° motifs. In comparison, the thermodynamically weaker KL5 interaction shifts most tectoRNAs towards formation of trimers and tetramers (FIG. 4D). The observed differences in assembly patterns are clearly dependent on the energy of the KL interactions, but are also related to the structural, dynamical and stability properties of their constitutive 90° motif. For instance, the orientation of the 3WJ motif within the tectoRNA dramatically affects its assembly. The 3WJ-tectoRNA yields a fraction of tetramers for both KL1 and KL5, while the permutated 3WJ-P tectoRNA essentially forms dimers in both cases (FIG. 4D). This suggests that the topological constraints of the 3WJ motif dictate a preferential modality of motion for bending the stems with respect of one another (FIG. 2D). Self-assembly into particular NPs is therefore dependent on the ability of tectoRNAs to adopt alternate topologies. This effect is further exemplified by the behavior of the tRNA-tectoRNAs. Their topological constraints favor only formation of small closed-structures (FIG. 2D). In assemblies with the weaker KL5 interaction, a tRNA-tectoRNA with mutations in key nucleotide positions (C56→G, U55→G) known to destabilize the T/D loop interaction of the tRNA motif (FIG. 4D) remains trapped into dimers, while the regular tRNA-tectoRNA forms mostly trimers (FIG. 4D). The T/D loop interaction in the tRNA-motif could behave as a topological energy barrier to slow the formation of kinetically trapped dimers, such that KL1 is energetic enough to overcome the barrier but KL5 is not.

Example 5. Tectosquare Thermal Stability

Figure 5A:
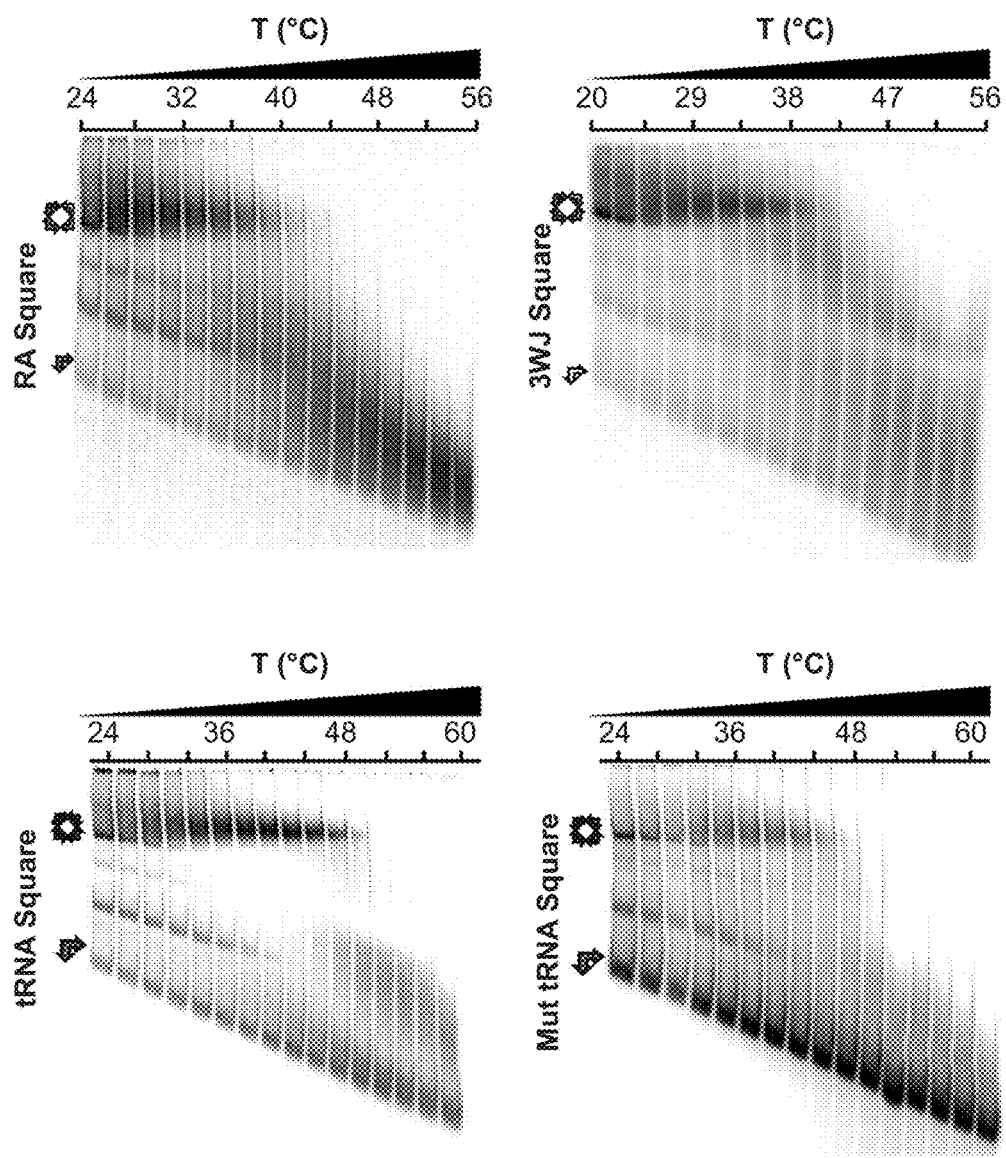
FIG. 5 (A-D) shows examples of TGGE and chemical probing experiments. (A) shows TGGE gels (8% nondenaturing PAGE) with a horizontal temperature gradient at 0.2 mM Mg(OAc)2 of various types of tectoRNA squares at a final concentration of 40 nM. (B) shows nondenaturing PAGE at 0.2 mM Mg(OAc)2 showing the assembly of tRNA square at a final concentration of 200 nM. Lanes a, b, c, d, and e show different yields of tRNA squares with respect to the number of mutated right angle motif within the square (see also FIG. 3A). (a=A-B-C-D, b=mA-B-C-D, c—mA-mB-C-D, d=mA-mB-mC-D, e=mA-mB-mC-inD). As the number of properly folded right angle motifs decrease within a nanoparticle, the yield of square assembly also decreases by 80%. (C) shows superposition of RNase T1 digestion profiles corresponding to tRNA monomer vs tRNA square (upper profile) and tRNA monomer vs square with mutated right angle motifs (lower profile). KL complexes that are cleaved in monomers are mostly protected in squares. Moreover, mutant squares are not protected against RNase T1 cleavage in T and D-loops. (D) is a 15% denaturing gel showing Pb2+ induced cleavage along with RNase Ti digestion pattern for tRNA monomers (400 nM) and squares (100 nM). Monomer lanes are indicated by M and square lanes are indicated by S. M1: regular tRNA monomer, M2: mutated tRNA monomer, Si: regular tRNA square and S2: mutated tRNA square respectively. To achieve comparable cleavage pattern RNA concentration for the mutant monomer and square was adjusted by gel purification. Blue arrows indicate the positions that are cleaved in the monomer but mostly protected in the square.
Figure 6A:
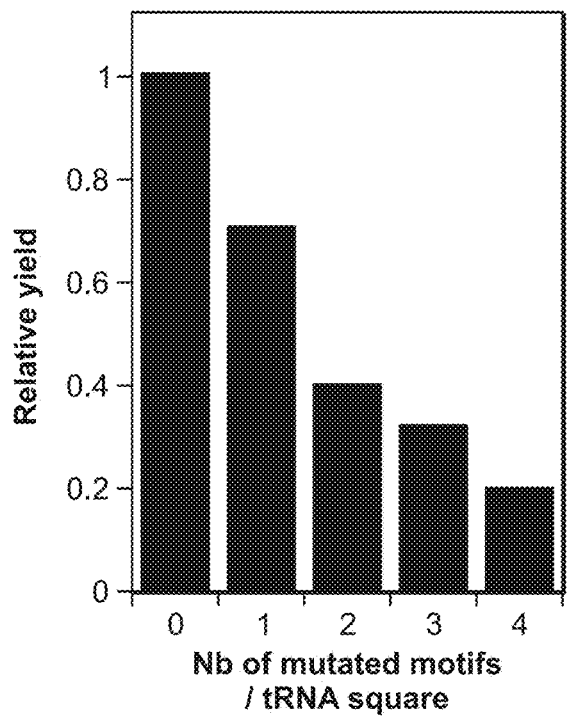
FIG. 6 (A-D) shows the tRNA-square requires a folded tRNA motif for optimal assembly and stability. (A) is a graph that shows comparative yields of tRNA-square in relation to the number of mutated T/D loop motifs per square. Yields were determined by native PAGE in presence of 0.2 mM Mg(OAc)2. (B) is a graph showing the thermal melting curve of the tRNA-square with all four units mutated compared to the w.t. (C) shows examples of RNase T1 and Pb2+ cleavage profiles of various tRNA constructs at 15 mM Mg(OAc)2.
FIG. 6C discloses SEQ ID NO: 78. (D) shows differential Pb2+ and RNase T1 cleavage patterns mapped on the secondary structure diagram of the mutated tRNA-square: Nt positions in red show enhanced T1 cleavage with respect of the w.t. (cleavage occurs 3' of the nt). Phosphate positions that show enhanced or reduced Pb2+ cleavage with respect to the w.t. are indicated by red or blue arrows, respectively.
FIG. 6D discloses SEQ ID NO: 162.
Figure 6B:
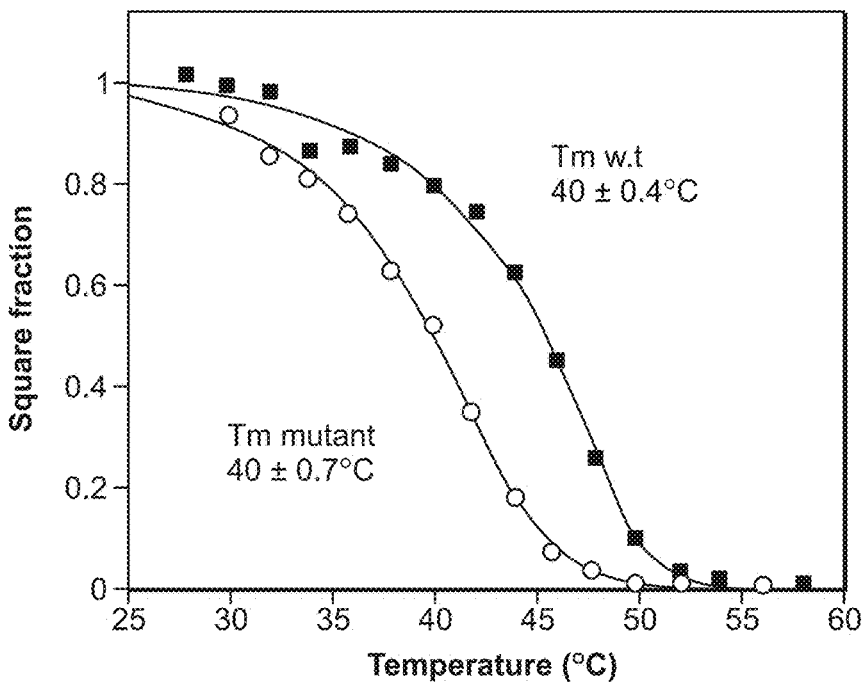
Figure 6D:
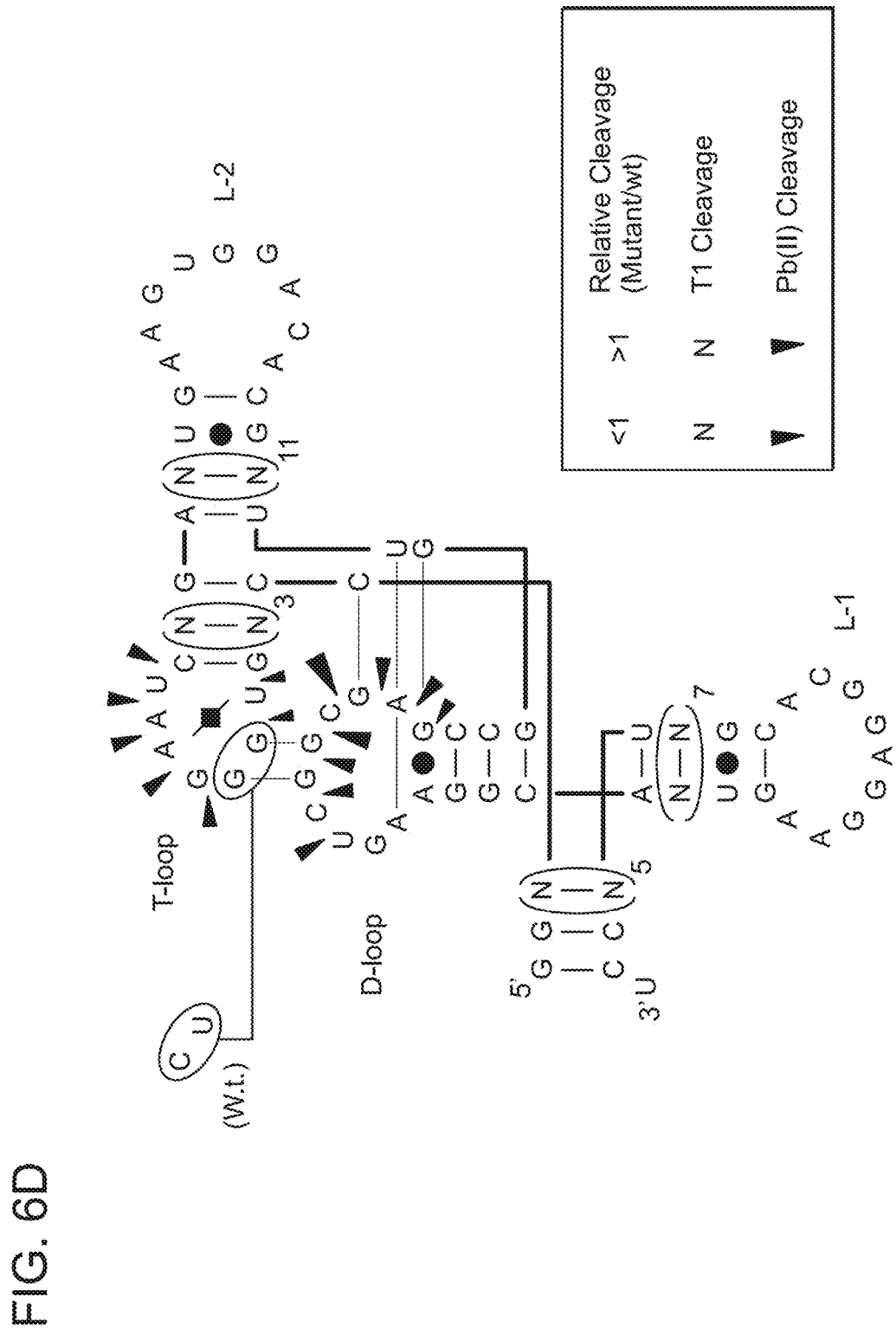

The contribution of 90° motifs to the thermal stability of assembled tectosquares was investigated by thermal gradient gel electrophoresis (TGGE), a method for separating different species based on a temperature-dependent conformational change Apparent melting temperatures were determined for each tectosquare by measuring the decrease in the yield of squares versus temperature (FIG. 4C). At 15 mM $Mg^{2+}$, none of the three tectosquares disassemble within the range of temperature tested (Data not shown). By contrast at 0.2 mM $Mg^{2+}$, all TGGE profiles are typically characterized by two-phase transitions (FIG. 5A). The first transition corresponds to a decrease in the mobility of the tectosquares around 25°-33° C., and is probably due to transient opening of the tetramers at one of the KL interactions (Data not shown). The second transition corresponds to the dissociation of the tectosquares into monomers. The tRNA-square has an apparent Tm of 46° C., about 8-10° C. higher than the Tm of the RA- and 3WJ-squares (FIGS. 4C and 5A). Because all tectosquares have the same assembly interfaces, these results indicate that the tRNA motif contributes more to the overall tectosquare thermal stability than the 3WJ and RA motifs, in agreement with the idea that increasing structural complexity in motifs can increase thermostability. The melting process is highly cooperative as it occurs over 15° C. A hybrid tectosquare with two RA tectoRNAs and two tRNA-tectoRNAs shows a wider dissociation profile, suggesting that, despite an apparent Tm of 37° C. comparable to the RA-square, its melting process is somewhat less cooperative than the RA and tRNA-squares (FIG. 4B,C). It was previously demonstrated that tectosquares with RA-motifs were more stable than those without any. Accordingly, the thermal stability of the RA square was shown to increase with an increasing number of RA-motifs present within its assembly. The same trend is also observed for the new tectosquares, strongly supporting the notion that the proper tertiary conformation of the 90° motif cooperatively contributes to the overall tectosquare stability and assembly. For instance, various mutated tRNA-squares were generated from tectoRNAs with mutations knocking out the T/D loop interaction of the tRNA motif (FIG. 6D). Decrease in square formation is directly correlated with an increasing number of mutated motifs incorporated per tRNA-square (FIGS. 6A and 5B). The yield of assembly of the tRNA-square with four mutated tRNA motifs is five times lower than the one for the regular tRNA-square. Additionally, thermal stability of the fully mutated tRNA-square was shown by TGGE to be 6° C. lower than the regular tRNA-square in presence of 0.2 mM $Mg^{2+}$ (FIG. 6B). Interestingly, this is still 3 to 4° C. above the stability of the RA and 3WJ-squares, suggesting that the structure of the mutated tRNA motif is only partially disrupted and still contributes significantly to the overall stability of the mutated tRNA-square.

Example 6. Structural Probing of tRNA-Squares

To investigate the 3D structure of our most stable tectosquare, chemical and enzymatic probing were performed on purified regular and mutated tRNA squares in presence of 15 mM $Mg^{2+}$ and 50 mM K+ (FIGS. 6C,D and 5C,D). $Pb^{2+}$ is known to induce specific cleavages at the level of a magnesium-binding pocket within the D-loop of tRNA native folds. Comparison of the $Pb^{2+}$-cleavage patterns of regular and mutated tRNA-squares showed a significant reduction of specific $Pb^{2+}$ induced cleavages within the D-loop of the mutated tRNA-motif, evidence that the mutated tRNA-square does not form stable T/D-loop interactions (FIG. 6C,D).

Figure 5D:
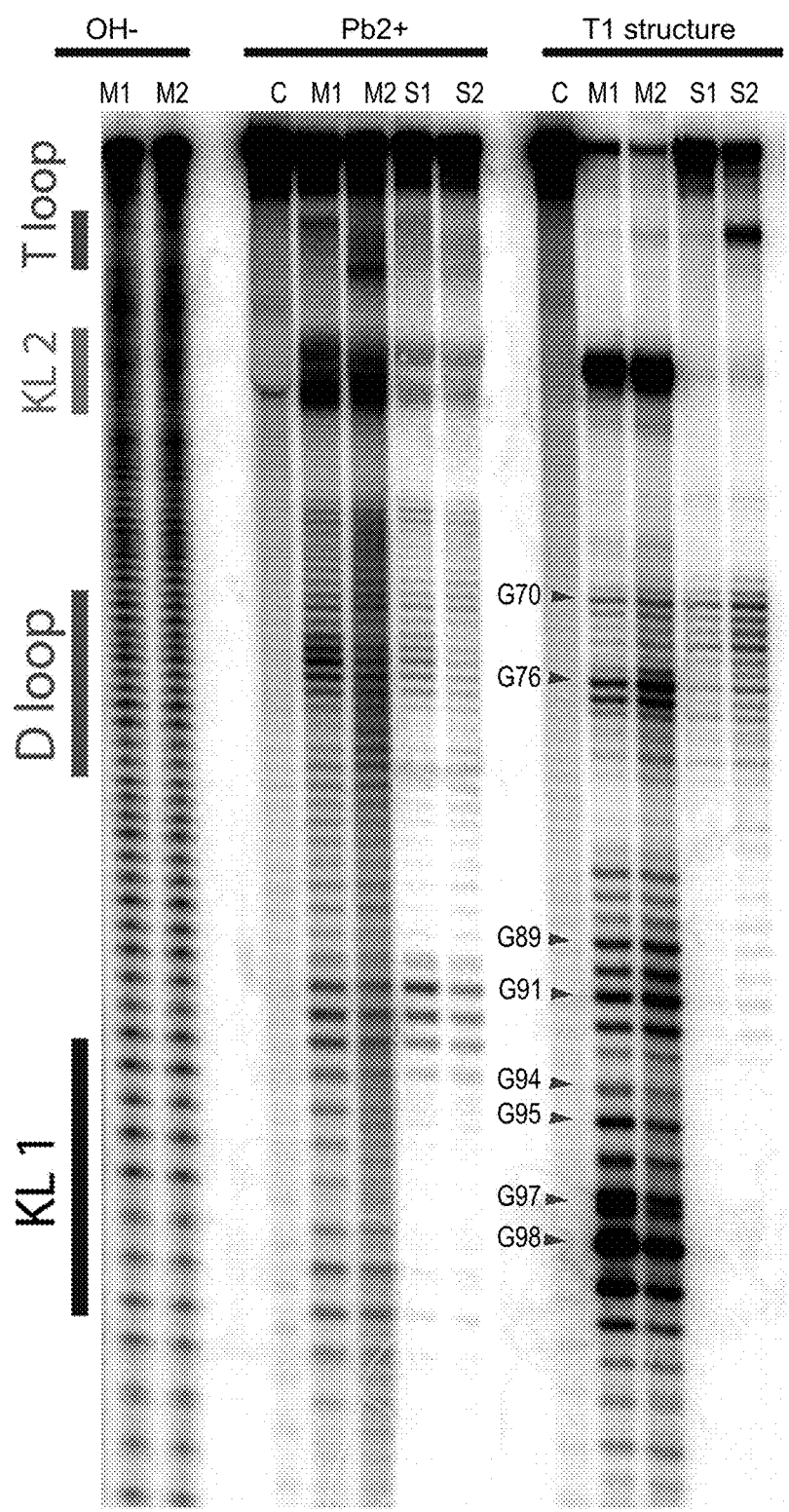

Moreover, an increase in the accessibility of the T and D loops of the mutated tRNA-square was observed by cleavage with RNase T1, a ribonuclease that specifically cleaves in 3' of single stranded Gs and As. These data corroborate the direct involvement of the tRNA motif on square stability. At the exception of the KL regions, there is no observed difference between $Pb^{2+}$-cleavage patterns of the motif as a monomer alone or within the tetramer, suggesting that the assembly of tectoRNAs into tRNA-squares does not alter the native fold of the tRNA motif (FIGS. 6C and 5C,D). However, T1 cleavage patterns reveal an increased protection from digestion for the tRNA-square versus the tectoRNA alone. This demonstrates that NP assembly can contribute to protecting RNA from ribonuclease degradation (FIG. 5)

Example 7. AFM Structural Analysis

Figure 7A:
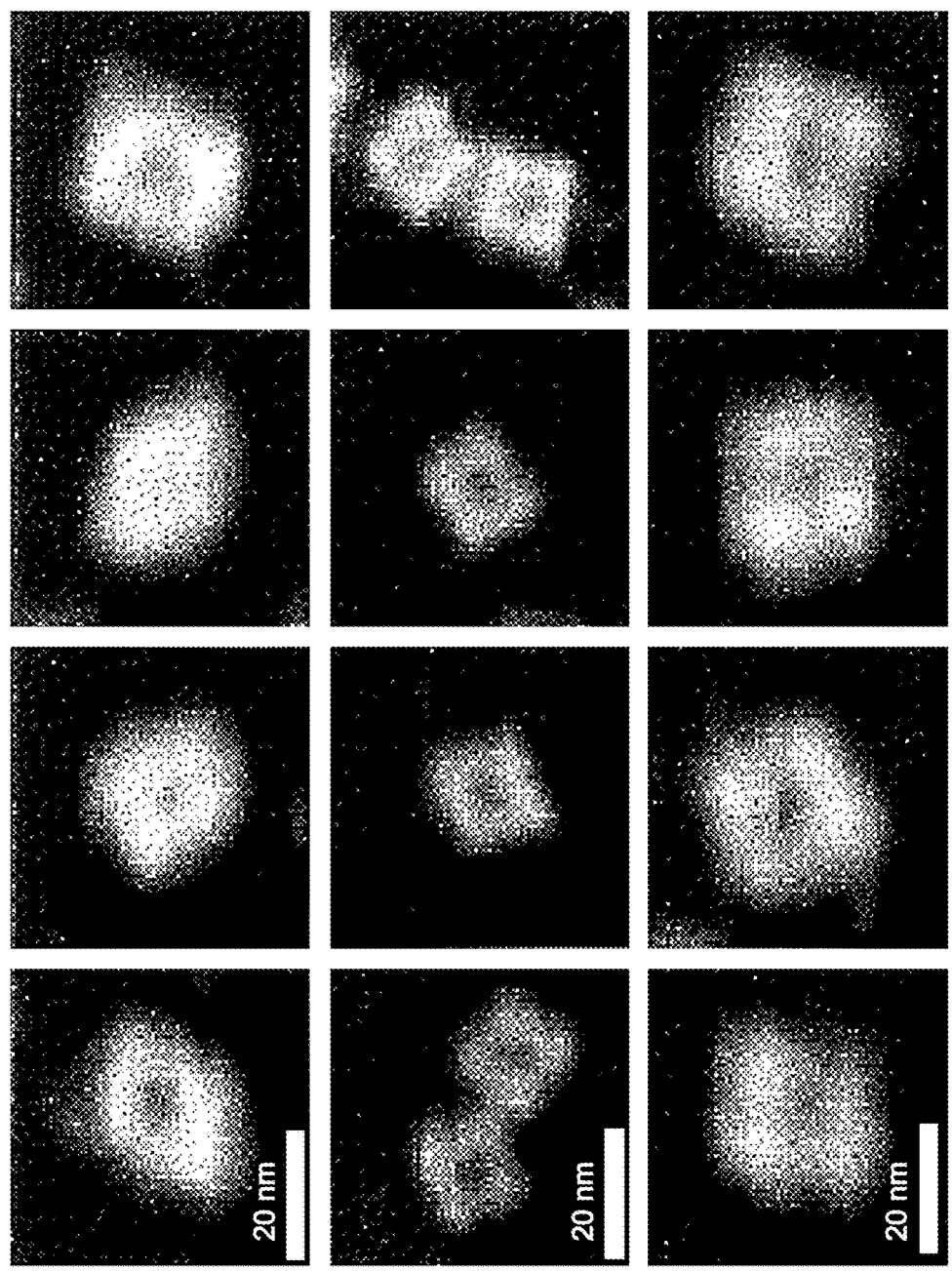
FIG. 7(A-C) shows AFM characterization of the RA-, 3WJ- and tRNA-squares. (A) Magnification of AFM images (scale bar 20 nm) for the RA-square (top), 3WJ-square (middle) and tRNA-square (bottom). (B) AFM images of the respective tectosquares (scale bar, 100 nm). Each image obtained in air corresponds to 100 nM solution of tectosquare deposited on freshly cleaved mica surface and dried. (C) shows histograms showing the population distribution of NPs with respect to particle size.
Figure 7B:
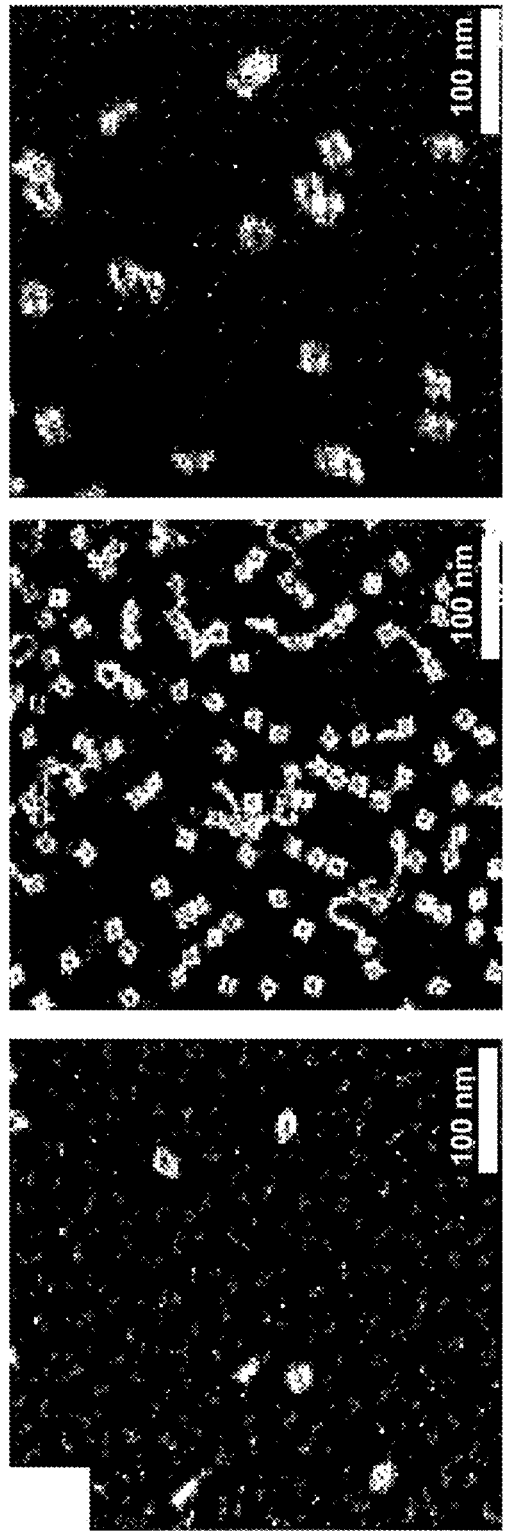
Figure 7C:
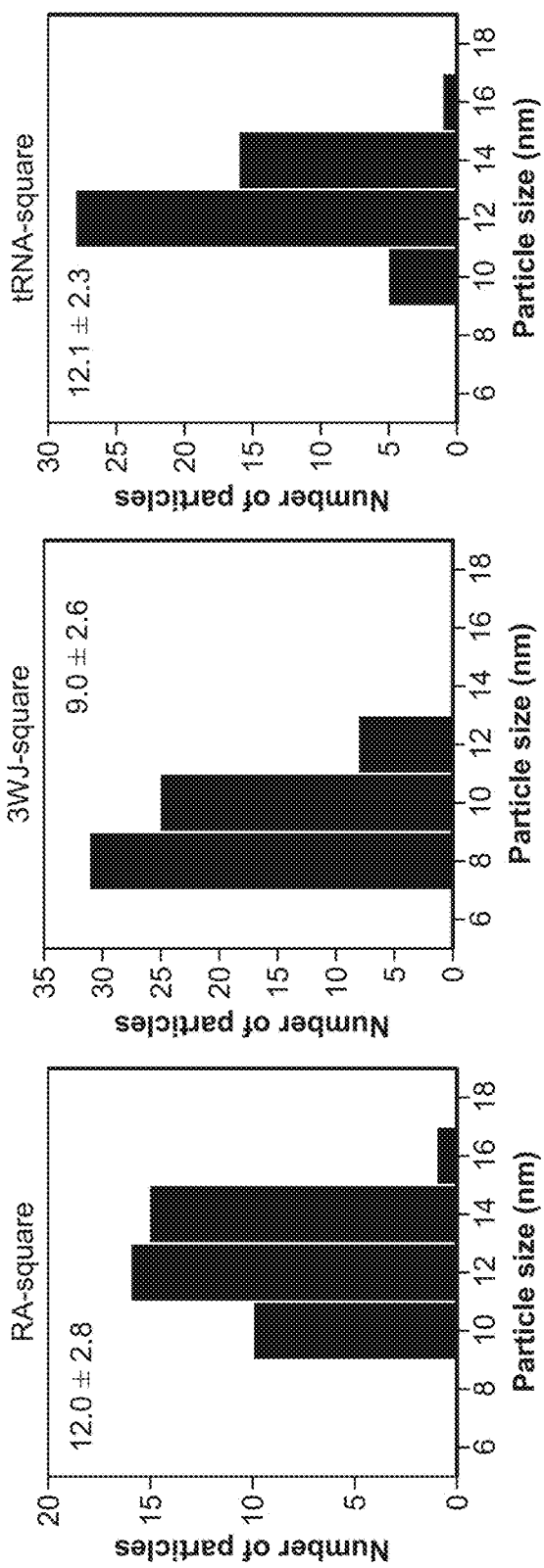

Further structural characterizations were performed by AFM to demonstrate that the RA, 3WJ and tRNA-squares are square-shaped assemblies. Tectosquares were assembled in solution and then deposited on a mica surface in 15 mM Mg2+ buffer, as reported previously. For all three tectosquares, AFM revealed uniform mono-dispersed particles with size and shape similar to the theoretical 3D models (FIG. 7A,B). A central cavity is visible for each tectosquare. The theoretical estimated size of the RA, 3WJ and tRNA-square models are 10 nm, 10 nm and 12 nm, (helix-center to center) respectively. Their average sizes were measured by AFM to be 12.0±2.8, 9.0±2.6 and 12.1±2.3 nm respectively (FIG. 7C). Tectosquare heights were all measured to be ~1.5 nm, consistent with the previously observed height for a double helix of nucleic acid on a mica surface 32. However, the corners of the tRNA-square appear to be bulkier in the images (FIG. 7A), which is consistent with the 3D model predicting the variable leap stem to be oriented out of the plane of the square (FIG. 1, side view).

A difference between the three tectosquares is their apparent yield on the surface. The adsorption ratios estimated from the number of NPs observed in a 1 µm² window, were calculated to be 12, 595 and 125 NP/µm² for RA, 3WJ and tRNA-squares, respectively (FIG. 7B). Since the yield of squares determined by PAGE is roughly equivalent between the three varieties, the difference in adsorption ratio of NPs on the mica surface is likely due to differences in the overall 3D shape of the NPs that result from their different constitutive 90° motifs. The high yield of adsorption of 3WJ squares onto the mica surface is most likely due to the flatness of the square, as predicted from 3D computer models (FIG. 1, side view). In the case of the tRNA-squares, the variable stems, which protrude approximately perpendicular to one side of tRNA-squares, likely decrease the ability of these tectosquares to bind mica on that side. The RA-square, being non-planar on both sides (FIG. 1, side view) has the lowest yield of the three squares as well as the greatest tip convolution, which also explains the slight discrepancy in the measured size of the square (FIG. 7C) compared to its predicted size (FIG. 1A). Therefore, efficiency of NP adsorption onto a mica surface is strongly related to the structural characteristics of the 90° motifs used to construct the NPs (FIG. 7B).

Artificial self-assembling RNAs can contribute to our understanding of the topological properties and structural dynamics of RNA motifs outside their natural context. Topologically equivalent 90° motifs characterized by different local tertiary folds can lead to similar square-shaped RNA NPs. Even so, the usage of different types of structural motifs can affect the overall biophysical properties of the resulting NPs. A direct correlation between the degree of structural complexity of a 90° motif and the higher thermodynamic stability of NPs built from the motif has been observed. However, the propensity to form a particular NP assembly is not only dependent on the thermodynamic stability of its constitutive motif but also on its molecular flexibility and dynamics. Furthermore, small local structural variations associated to the 90° motifs used to assemble NPs can dramatically impact the flatness of the resulting particles, and consequently their property of adhesion on mineral surfaces. Therefore, an assortment of different RNA modules might be required for different technological applications.

The contribution of RNA tertiary motifs to precisely controlling structural flexibility and dynamics may play a critical role in RNA folding and assembly of complex architectures. The choice of 90° motif has an effect on both the size and distribution of multimers formed via self-complementary KL interactions (FIG. 4D). In cases where the choice of motif yields mostly circular dimers, the tertiary structure of the 90° motif in the dimeric NPs must be significantly deformed to allow ring closure. Similar RNA constructs without 90° motif tend to preferentially assemble into an assortment of multimers, presumably because the two helices tend to coaxially stack in absence of a defined-bend motif (FIG. 2D). This is evidence that folding of a tertiary motif can contribute kinetically to the final architecture of an RNA, even though the motif is likely to adopt an alternative partially-unfolded or non-native conformation in the final state of the particle. Therefore, structural motifs may be used as transient folds to kinetically direct an RNA assembly, a strategy that might also be used by natural RNA molecules during their folding process for allowing a particular final conformation to be reached.

Molecular competition experiments suggest that the energy needed to overcome the folding of the RA-motif is only on the order of few kcal/mol, in agreement with the notion that the RA-motif is a rather dynamic bending motif. Therefore, once the RA-tectoRNA forms a dimer bridged by a single KL interaction, there is a propensity for the structure to entropically close via the other KL-ends into a circular dimer, at a tradeoff of deforming the RA-motif (FIG. 2D). Because the motifs are likely unfolded by the formation of circular dimers, the final structure is unlikely to be the most energetically stable, suggesting that the formation of this particle is under kinetic control rather than thermodynamic control.

The interplay between structural stability and dynamics is particularly apparent in the cases of the 3WJ- and the tRNA-motifs. Their behaviors within our tectoRNA system can be compared to similar motif studied within their natural contexts. The dramatic difference in the behavior of the 3WJ and 3WJ-P motifs in the self-complementary experiment (FIG. 4D) demonstrates that the 3WJ-motif has a propensity to bend in a specifically oriented direction (FIG. 2D). This highlights that flexibility is not equally distributed between the three stems of the motif. The 3WJ-motif is closely related to the S15-RNA binding motif from the 30S ribosomal subunit that is known to have similar dynamic behavior. The S15-RNA undergoes an induced-fit conformational change upon binding S15 protein, thereby triggering a cascade of additional protein binding events during the folding of the 30S ribosomal central domain. The conformational dynamics of a tertiary motif does not preclude it from being a thermostable and rigid building block in a suitable context. The tRNA-motif can be easily distorted from 90°-angle to 60° and smaller (FIGS. 2, 4B,D), even tRNA-squares were highly thermostable and rigid compared to the other tectosquares (FIG. 4C). The tRNA has evolved to be structurally dynamic as well as thermostable, two properties that are useful in a molecule required to interact with multiple other molecular components. tRNAs are found to undergo significant conformational changes during translocation in the ribosome. Biophysical characterizations reveal that the tRNA folds into an approximately 70°-angle bend at low Mg2+ (0.2 mM) and expands to a 900 bend structure at higher salt concentration (above 4 mM), in agreement with our observations of the bending capacity of the tRNA-tectoRNA (FIG. 2D). By contrast to tectoRNA lacking 90° motifs, self-complementary mutated tRNA-tectoRNAs preferentially lead to formation of closed dimers, indicating that despite partial destabilization of the tertiary motif it is still possible to constrain closure. As predicted by early molecular dynamic simulations, the loss of the T/D loop interaction allows the tRNA to easily bend into a U-shape (FIG. 2D).

The experiments described herein show that supramolecular assembly can be used to explore and compare the biophysical properties of RNA tertiary motifs that would otherwise be more difficult to investigate in isolation or within their natural context Additionally, this strategy offers great potential in nanobiology and nanomedicine. Structural RNA NPs can be used to combine multiple functionalities in one delivery particle for various therapeutic purposes. For example, the natural pRNA molecule from the phi29 DNA-packing motor[163] was engineered to create multifunctional particles for delivery of siRNAs to cancer cells via specific targeting of CD4 receptors or for targeted delivery of ribozymes against the hepatitis B virus. The tectosquares presented herein are stable scaffoldings that offer an alternative to the pRNA scaffolding. Their thermodynamic properties can be finely tuned based on the complexity of their constitutive 90° motifs. Moreover, the ability to kinetically control NP assembly with tertiary motifs can further expand their range of applications. An additional potential benefit of RNA NPs is their apparent increased protection towards RNase degradation. RNA NPs have the potential to will contribute positively to the development of new biomedical applications in the future.

Example 8. Factors Affecting the Assembly of Nanoparticles

Developments in the field of nanobiology have demonstrated that nanoparticles can be ideal drug delivery particles due to their novel designs and functions. There are several factors that are important for efficient design and drug delivery by nanoparticles, including the controlled attachment and release of drugs, low immunogenicity, biodegradability, stability and sufficient retention time in vivo. Preferably, the minimum size requirement of such nanoparticles is less than 100 nm in diameter in order to enter cells and larger than 20 nm in order to have a longer retention time in the body (Khaled, A. et al. Nano Lett 5, 1797-808 (2005)).

RNA is an attractive candidate for nanoparticle design as it offers vast number of structural motifs that can be used to generate complex nanoarchitectures via complementary base pairing using inter or intra molecular interactions such as loop-loop, loop-receptor, or single stranded overhangs (Jaeger, L. et al. Nucleic Acids Res 29, 455-63 (2001); Chworos, A. et al. Science 306, 2068-72 (2004); Nasalean, L. et al. Nucleic Acids Res 34, 1381-92 (2006)). Also, an important aspect of RNA is that it induces a minimal immune response and, thereby, reduces the antibody production that leads to the clearance of the nanoparticle from the body (Khaled et al. (2005); Famulok, M. et al. Chemical Reviews 107, 3715-3743 (2007)). Furthermore, therapeutic agents such as small interfering siRNAs, ribozymes, nucleic acid aptamers and antisense RNAs show significant potential in new therapies to down regulate specific gene expression in cancerous or virus-infected cells (Lee, J. F., et al. Curr Opin Chem Biol 10, 282-9 (2006); Hoeprich, S. et al. Gene Ther 10, 1258-67 (2003)). The development of efficient, non-toxic, and specific nanoparticles that are capable of combining multiple functionalities in one delivery agent is thus highly desirable.

The experiments herein describe circular RNA nanoparticles that are assembled to form hexameric nanorings by the assembly of non-covalent loop-loop interactions based on RNAI/RNAII inverse complex. The design of hexameric nanoparticles was based on the computational model proposed by Yingling and Shapiro (Yingling, Y. G. et al. Nano Lett 7, 2328-34 (2007)) and described in PCT/US2007/013027, incorporated by reference in its entirety herein. The present study investigates the generation of hexameric nanoparticles in vitro that were designed by the computational approach, and how to improve their design using the RNA architectonics methodology. The present study also investigates how flexibility of a building block would affect its ability to form unique closed assemblies.

The circular RNA nanoparticles that are presented in this study offer an alternative to phi29 (Φ) pRNA scaffolding. For example, the nanoparticles described herein meet the size requirements for the delivery vehicles. Furthermore, in preferred embodiments of the present invention, the helical sequences can be designed to include siRNAs for drug delivery. Additionally, the self-assembly can be kinetically controlled by modifying stem length, or including a stabilizing motif in the design.

Figure 9A:
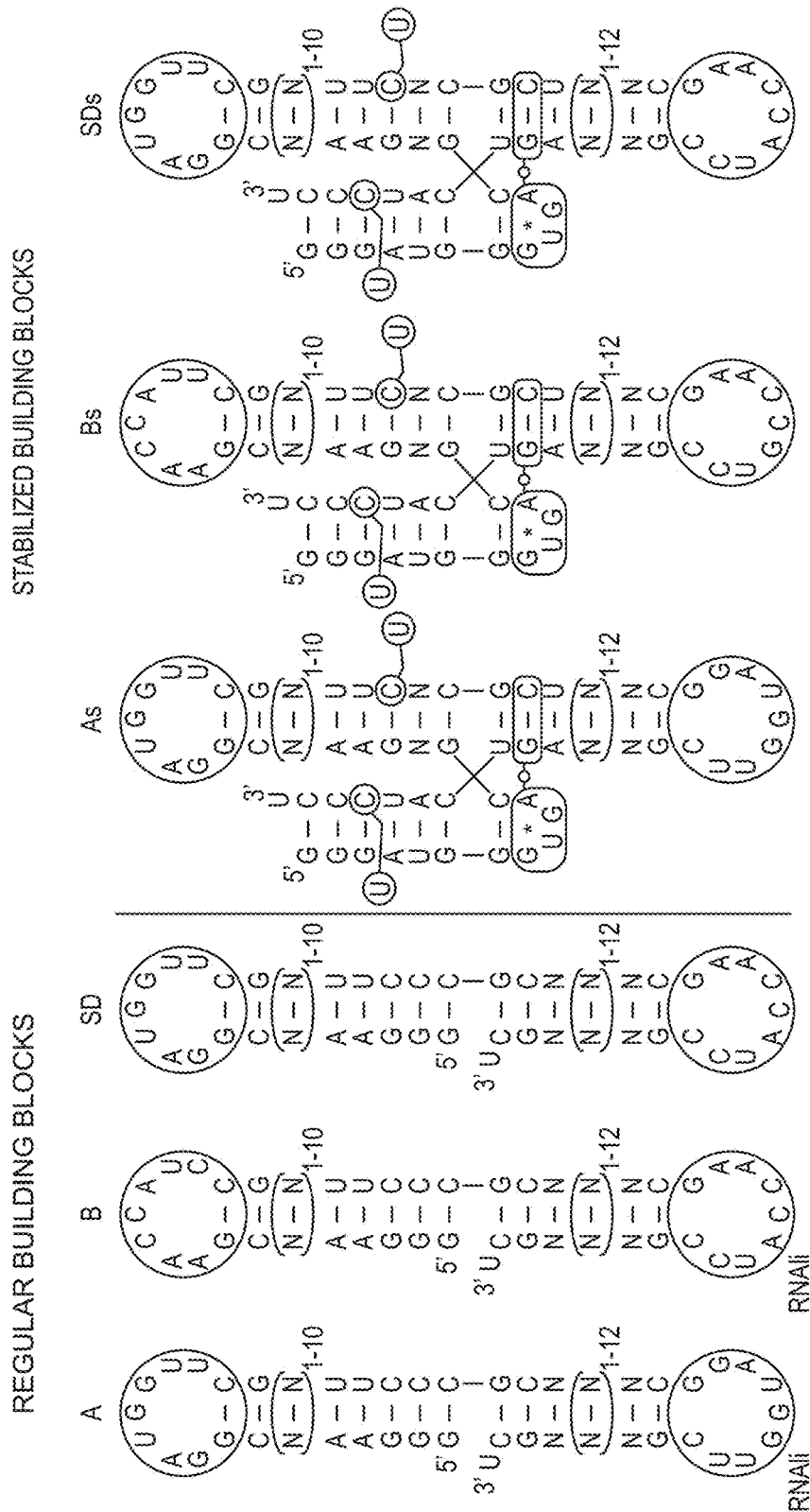
FIG. 9A discloses SEQ ID NOS 163-168, respectively, in order of appearance. B) shows secondary (up) and tertiary structure (down) of RNAI/RNAIIi loops forming a 1200 between the adjacent stems.

Understanding the kinetic and thermodynamic factors influencing the assembly of nanoparticles is preferably an important consideration for rational design and to have a better control of size and shape. It is reasoned that during the self-assembly process at least three factors play a major role in the formation of closed nanoparticles: (i) the length of the stems, (ii) the nature of the kissing loops, and (iii) the presence of stabilizing RNA motifs. In order to investigate the effect of stem size, the present experiments describe the design of building blocks that contain short (15 bp) and long (37 bp) helical stems. By doing so, small and large nanorings were generated with diagonal dimensions of 15 nm and 26.2 nm respectively (FIG. 9 A,C). The helices were capped with two loops whose sequences were based on the RNAIi and RNAIIi complex (FIG. 9 A).

There are two design approaches to form a closed nanoring. In the first approach one can use two building blocks, with each building block containing a single loop sequence on both ends (FIG. 9 building blocks A and B). In the second approach a single building block called selfdimer (SD) can be designed, where one loop has the RNAIi and the other has the RNAIii sequence (FIG. 9 building block SD). Using the first assembly approach it is possible to form even numbered polygons such as dimers, tetramers, hexamers etc. On the other hand, second approach leads to both odd and even numbered polygons. A second set of building blocks containing the RNAI/RNAIIi loop complex were designed containing a four-way junction (4WJ)-A-minor motif (colored blue and pink in FIG. 9) at the junction between the stems. An A-minor motif is the tertiary interaction of adenine (blue box, FIG. 9) interacting in the shallow groove with the Watson-crick G-C base pair (pink box, FIG. 9) in the adjacent helix. Having extra hydrogen-bonding interactions, the 4WJ motif stabilizes the building blocks by decreasing the amount of bending compared to that of regular helices at the junction of 5' and 3' ends. A-minor interactions are abundant in ribosomal RNAs and ribozymes, constituting one of the most common tertiary RNA-RNA recognition motifs (Lescoute, A. & Westhof, E. Biochimie 88, 993-9 (2006).

Figure 9C:
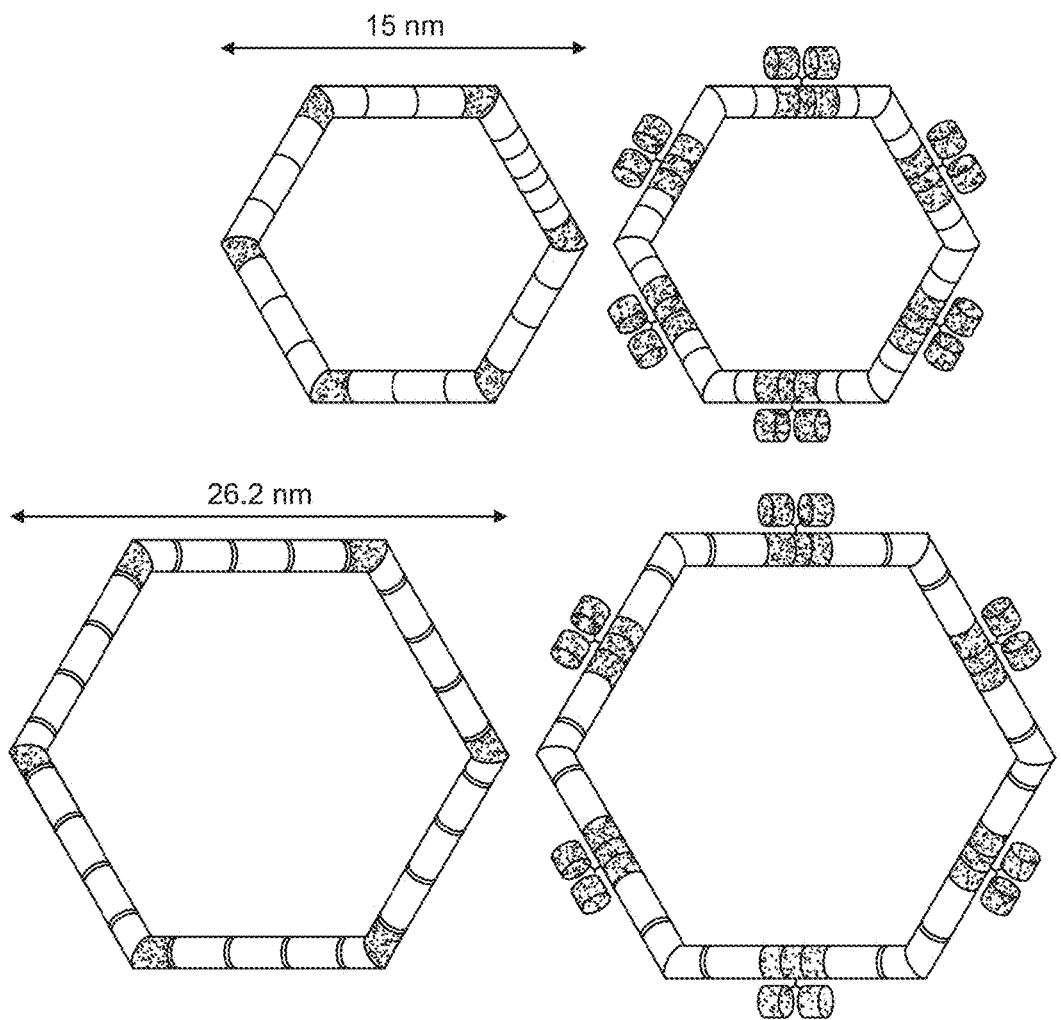
FIG. 9 (A-C) shows self-assembly of small and large hexagonal nanorings. A) shows secondary structures of building blocks with different stem size that contain the RNAI/RNAIIi loop complex. The circled nucleotides in large stabilized building blocks were replaced with U during sequence optimization with mFOLD.
FIG. 9B discloses SEQ ID NOS 79-80, respectively, in order of appearance. C) is a schematic diagram showing the assembly of regular and stabilized hexagonal nanorings.

RNAI and RNAII are sense and antisense plasmid-encoded transcripts that control the replication of the ColE1 plasmid of *E. Coli* (Lee, A. et al. Structure 6, 993-1005 (1998)). Also, inversion of the RNAI/RNAII sequences has been found to decrease the KD of the complex 7000 times relative to the wild type sequences (Eguchi, Y. & Tomizawa, J. J Mol Biol 220, 831-42 (1991)). NMR studies has determined that RNAI/RNAII inverse (i) loop complex forms a bend of 120° between the adjacent helices, which makes it suitable for the corners of the hexagonal ring. Another important structural feature is that all the bases in the loop participate in base pairing (FIG. 9 B). Molecular dynamics simulations indicate that the loop complex is stable and fluctuates around a 120° bend at the loop-loop interface, with the majority of the movement coming from the RNAIi part of the complex. Thus, by using six copies of this complex it is possible to design hexagonal nanoparticles of various sizes (FIG. 9C).

Figure 10A:
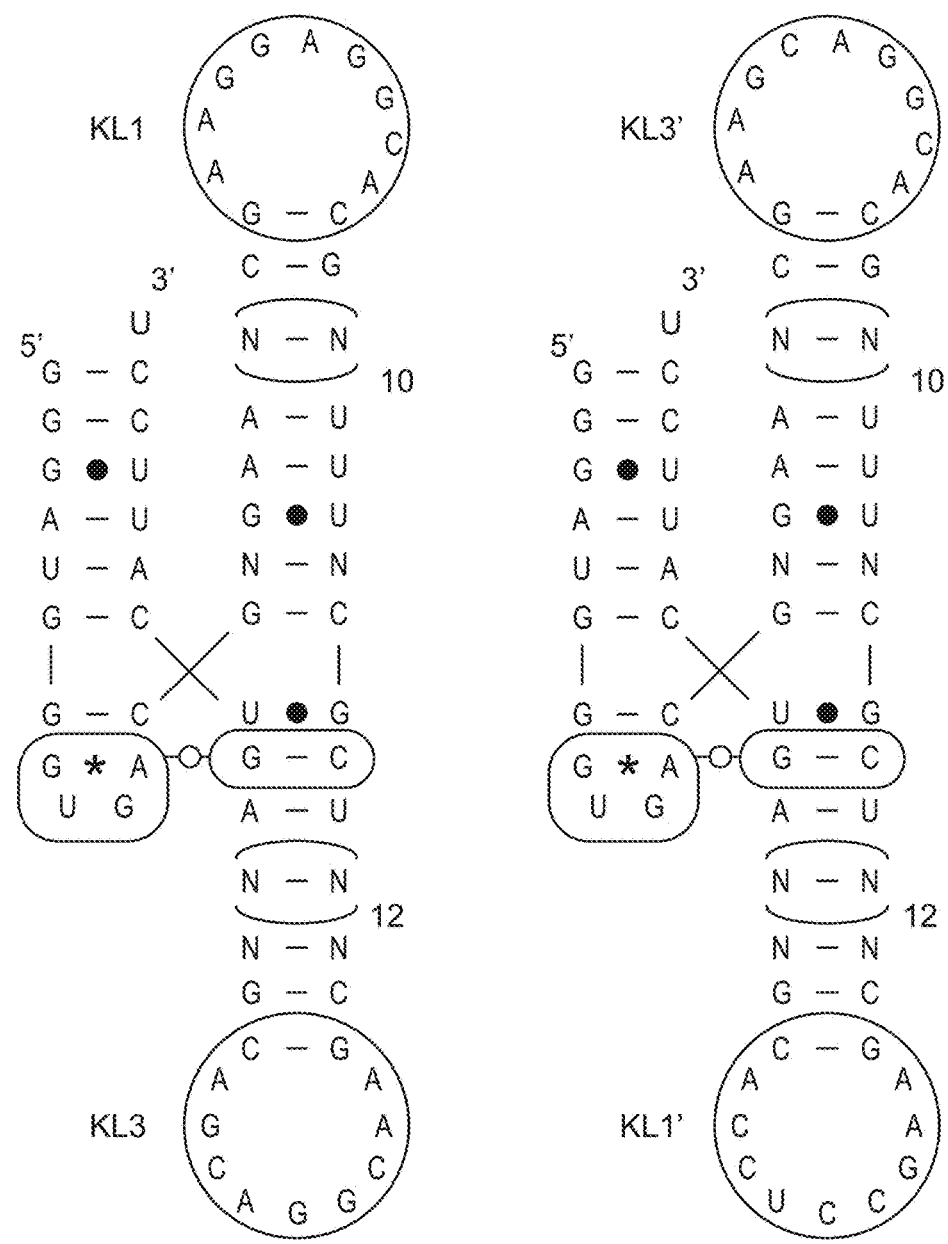
FIG. 10A discloses SEQ ID NOS 169-170, respectively, in order of appearance. B) Secondary structure (left) and three dimensional model (right) of a kissing loop interaction adopting a collinear helical structure.
Figure 10B:
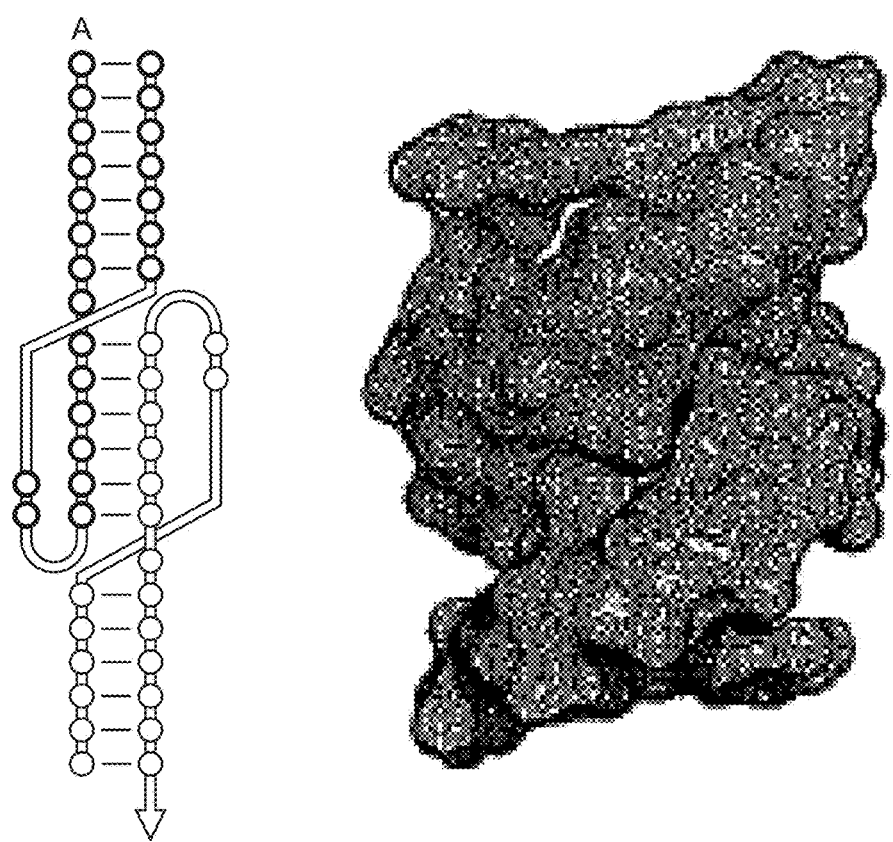
FIGS. 10 (A and B) shows the design of control building blocks. A) Secondary structure of building blocks containing 4WJ motif at the junction with KL complexes.

To be able to compare the degree of flexibility that comes from the RNAI/RNAIIi loop complex, two control building blocks that have two specific non-covalent loop-loop interactions, called the kissing loop (KL) complexes have been designed (Horiya, S. et al. Chem Biol 10, 645-54 (2003)). (FIG. 10A). According to the crystallographic studies the KL complexes adopt a collinear helical structure (FIG. 10B) and are abundant among RNA molecules such as the 23S rRNA, large ribozymes and the dimerization initiation site (DIS) of the human immunodeficiency virus (Ennifar, E. et al. Nature Structural Biology 8, 1064-1068 (2001)). These control building blocks were designed to include the 4WJ stabilization motif. Thus, the effect of the flexibility of the loops on the closure of nanorings with a lesser degree of interference from the flexibility exerted by the helical stem were investigated. Taking all the different possible combinations into account, nine different classes of nanorings were generated (Table 2, below). For example, nanoring class 7 is comparable to class 9, with the only difference being the type of kissing loops used.

TABLE 2

| Nanoring Class | Size | # of building blocks | Loop type | Stabilizing motif |
| --- | --- | --- | --- | --- |
| 1 | small | 2 | RNAI/RNAIIi | none |
| 2 | small | 1 | RNAI/RNAIIi | none |
| 3 | small | 2 | RNAI/RNAIIi | 4WJ |
| 4 | small | 1 | RNAI/RNAIIi | 4WJ |
| 5 | large | 2 | RNAI/RNAIIi | none |
| 6 | large | 1 | RNAI/RNAIIi | none |
| 7 | large | 2 | RNAI/RNAIIi | 4WJ |
| 8 | large | 1 | RNAI/RNAIIi | 4WJ |
| 9 (control) | large | 2 | KL1/KL3 | 4WJ |

Example 9. Characterization of Circular Nanoparticles by PAGE and AFM

Figure 11A:
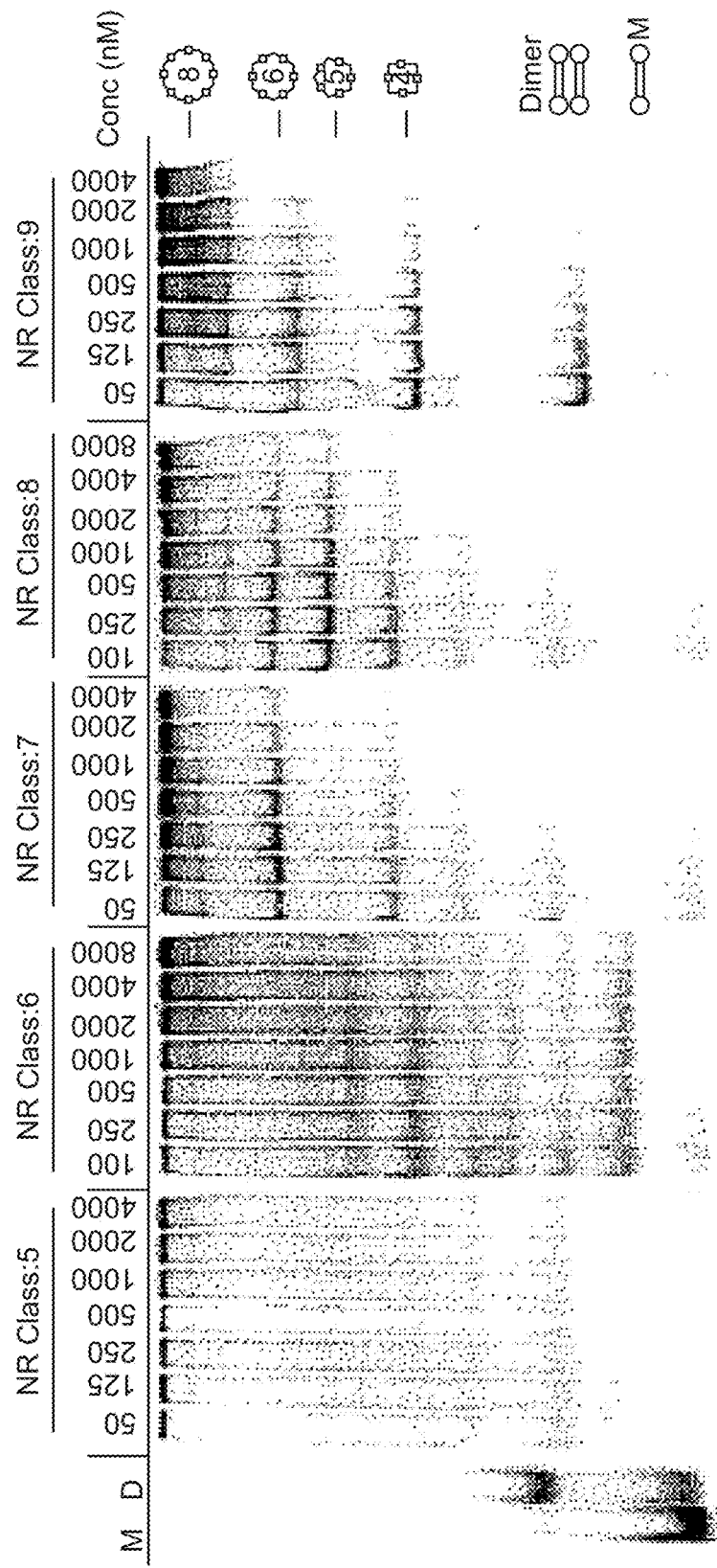
FIG. 11 (A-C) shows the characterization of large nanorings using native-PAGE A) Large nanorings without the stabilizing 4WJ motif (classes 5 and 6) and with the stabilizing motif (classes 7 to 9) were assembled in solution in the presence of 2 mM Mg(OAc)2 to a final concentration ranging from 50 nM to 4 μM for nanoring with two building blocks (Unit A and B) and from 100 nM to 8 μM for nanorings with a single building blocks (self-dinners SD). Not having the stabilizing motif lead to smeary gels (classes 5 and 6). However, nanorings with the 4WJ motif were able to assemble into closed multimers. Nanorings composed of two different building blocks (class 7) were able to form mainly hexamers as expected from the 3D model in low RNA concentrations. However, at high RNA concentrations the formation larger nanorings are observed, which stuck in the wells due to their low mobility. B and C) The yield of assemblies of various multimers estimated from native-PAGE analysis for large nanorings with 4WJ motif composed of two building blocks (class 7) in B and self-dimers (class 8) in C.

First, large nanorings with and without the 4WJ stabilizing motif (classes 5 to 9) were studied. Nanorings were assembled at various final concentrations varying from 50 nM to 8 uM in the presence of 2 mM Mg(Ac)$_2$ and slowly cooled from 50° C. to 10° C. (FIG. 11A). Non-denaturing PAGE of the resultant association shows that for RNA concentrations of <1 µM, the dominant closed structure is a hexagon in the presence of the 4WJ motif. By comparing the regular and stabilized nanorings it can be concluded that not having the 4WJ stabilizing motif leads to smeary assembly gels and poor assembly yields (class 5 and 6). On the other hand, in the presence of a stabilizing motif much more discreet closed assemblies were obtained with a product yield of ~18% for hexamers composed of two building blocks (class 7) and ~13% for hexamers composed of self-dimers (class 8). The smearing bands observed in PAGE gels was thought to be due the absence of the stabilizing motif at the junction which increased the flexibility of the building blocks, thus leading to the dissociation of the loop-loop interaction.

Figure 11B:
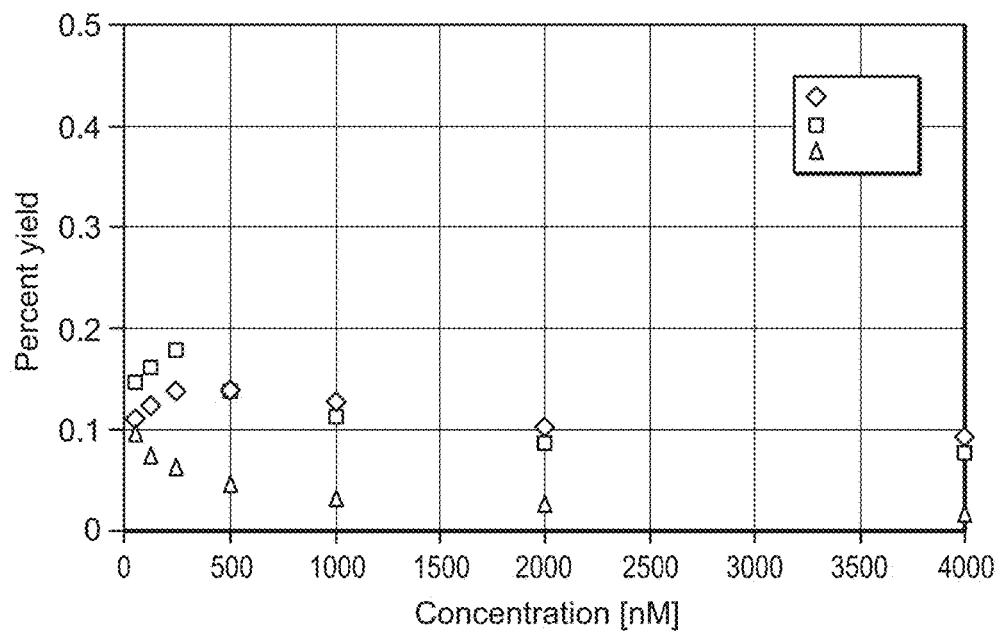
Figure 11C:
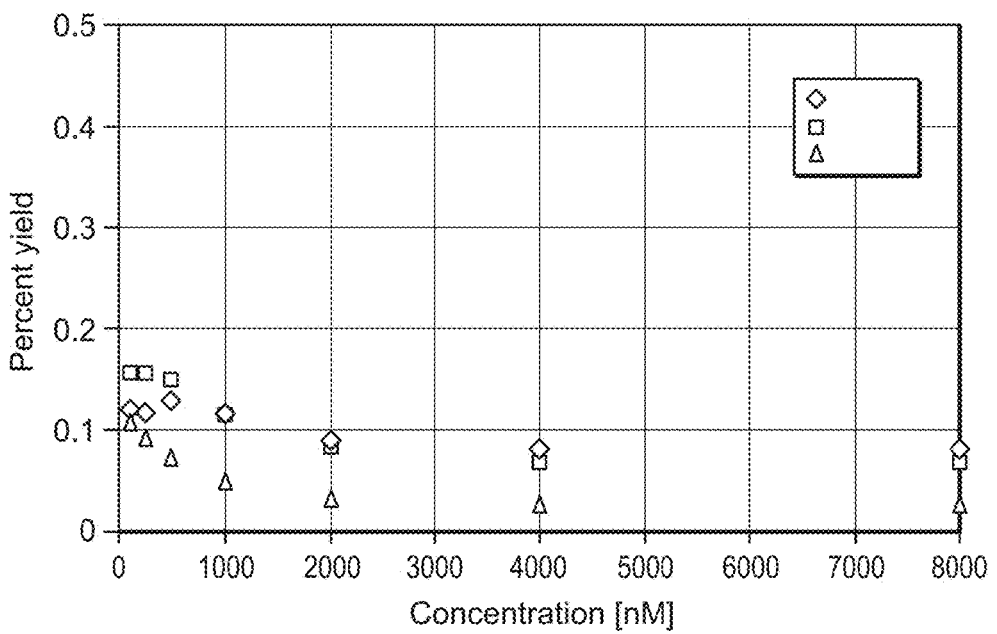

It has been observed that the size of the closed assemblies is concentration dependent (FIG. 11). High RNA concentrations (>2 pM) favored large assemblies, where low mobility products appeared to be accumulating in the wells. On the contrary, at sufficiently low RNA concentrations (<250 nM) tetramers and pentamers formed. These might be the smallest closed architectures that can be assembled without deformation of the RNA helices due to the flexibility of the 4WJ motif at the junctions and disruption of the loop-loop interaction.

In order to provide direct evidence that the nature of the loop-loop interaction is the major driving force in the formation of kinetically trapped assemblies nanorings have been assembled using building blocks that have KL complexes (FIG. 10 A, FIG. 11 A). The programming of the loops changes the flexibility of the building blocks, thus affecting the final size of the closed assemblies. Using RNAI/RNAIIi loop complex the formation of larger assemblies such as hexamers and octarners was favored, whereas KL complex lead to the kinetic trapping into dimers and tetramers. The two classes of kissing loops were compared in terms of their dissociation constants. To do this, building blocks were designed that contain non-self complementary loop sequences at one end (Table 2). By knocking out the loop-loop interaction the KD of dimerization could be measured at 0.2 mM Mg$^{2+}$. The results indicate that KD for RNAI/RNAIE complex is ~170-250 nM, whereas for KI, complex ~7 nM. The RNAI/RNAIIi complex appeared to be thermodynamically weaker compared to KL complex, which may explain the kinetically trapped assemblies in dimers in the case of nanorings with the KL complex.

Figure 12A:
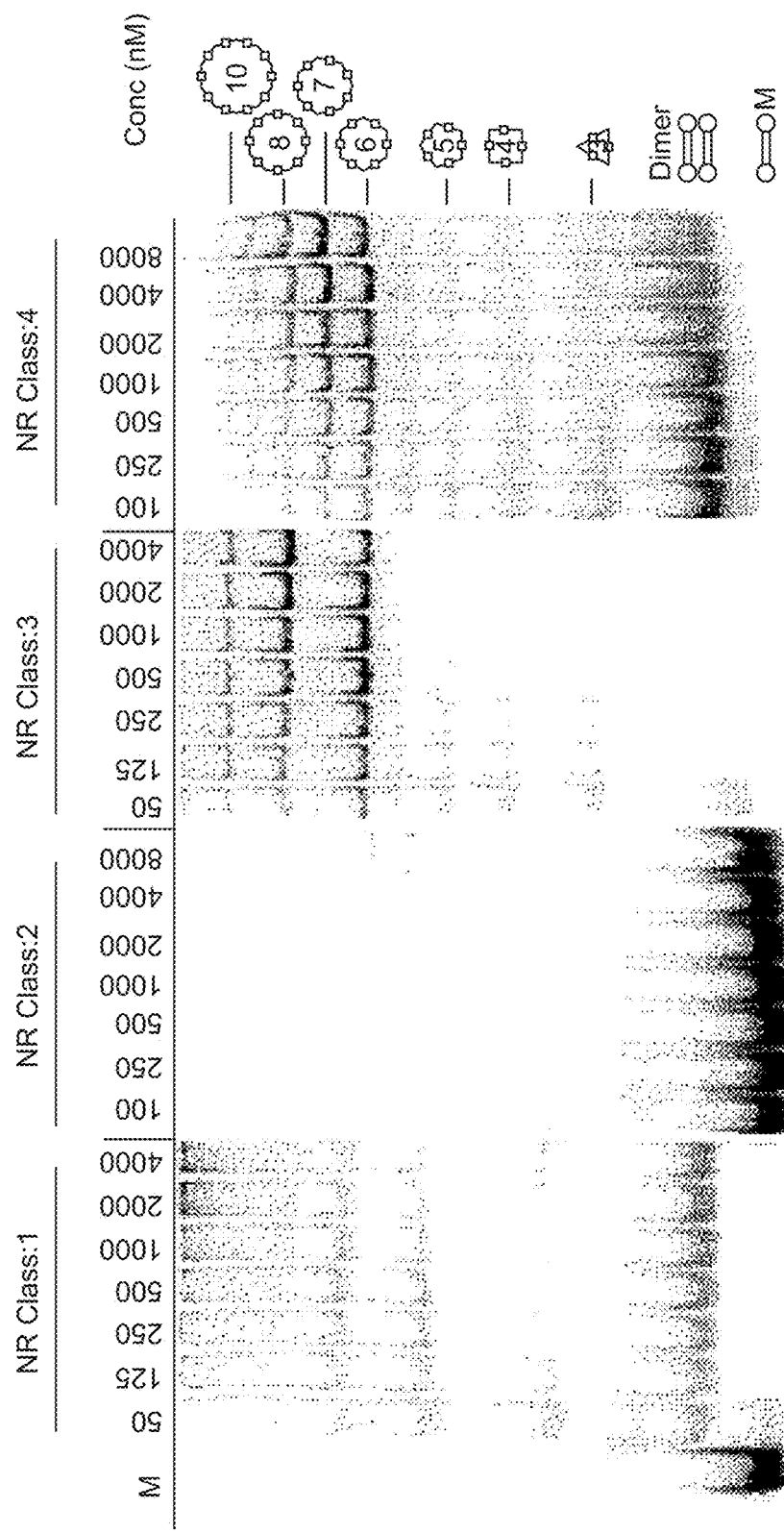
FIG. 12 (A-C) shows the characterization of small nanorings using native-PAGE. A) Small nanorings without the stabilizing 4WJ motif (classes 1 and 2) and with the stabilizing motif (classes 3 to 4) were assembled in solution in the presence of 2 mM Mg(OAc)2 to a final concentration ranging from 50 nM to 4 µM for nanoring with two building blocks (Unit A and B) and from 100 nM to 8 µM for nanorings with a single building blocks (self-dimers SD). Not having the stabilizing motif lead lower yield of formation in class 1 and no successful formation was observed in class 2. However, nanorings with the 4WJ motif were able to assemble into closed multimers with higher yields compared to large nanorings. Nanorings composed of two different building blocks (class 3) were able to form mainly hexamers at low RNA concentrations and octamers at high RNA concentrations. B and C) The yield of assemblies of various multimers estimated from native-PAGE analysis for small nanorings with 4WJ motif composed of two building blocks (class 3) in B and self-dimers (class 4) in C.
Figure 12B:
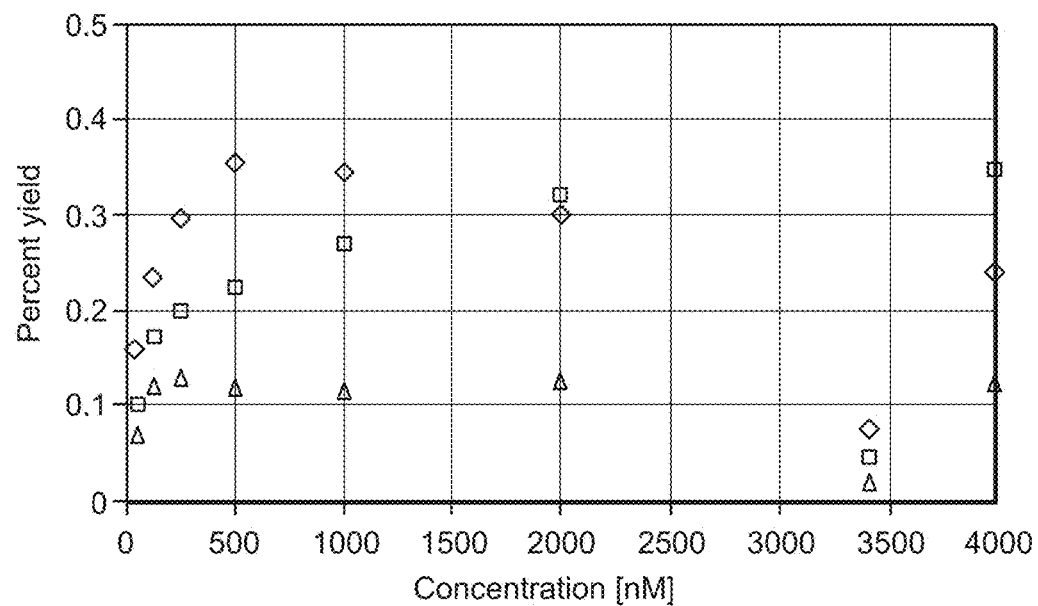
Figure 12C:
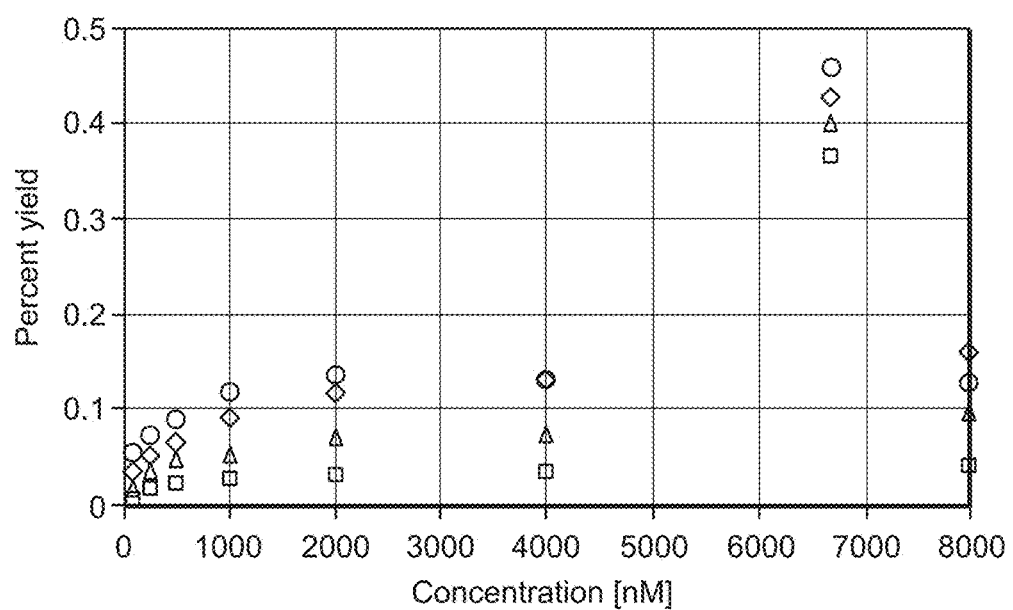

Next, the size of the helical stems was shortened by two full helical turns and the effect of stem length on the formation of closed assemblies was investigated (classes 1 to 4). Shortening of the stem length leads to an increase in the yield of hexamer formation up to ~36% in case of small nanorings composed of two building blocks (class 3) (FIG. 12 B). Non-denaturing PAGE gels of the resultant assemblies showed that shorter stems favor ring closure of smaller multimers, mainly hexamers and octamers in the presence of the 4WJ motif (FIG. 12 A). The results also indicate the absence of the low mobility products in the wells as seen in the case of large nanorings. The quantification of the gels indicates that at a final RNA concentration of 500 nM the dominant closed assembly is a hexamer. At higher RNA concentrations (>4 µM) octamer formation is favored (FIG. 12 B), suggesting that the concentration dependency may provide control over the final product size in kinetically controlled self-assemblies. It has also been observed that not having the stabilizing motif at the junction leads to poor assembly yields regardless of the stem length.

Figure 13A:
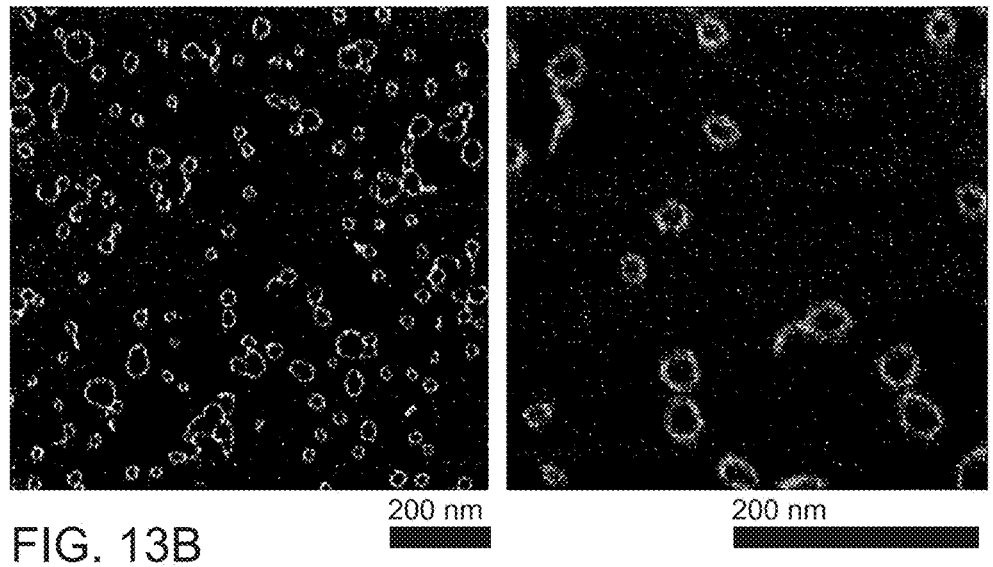
FIG. 13 shows 200 nm scale AFM images of nanorings obtained in air. A) Large nanorings assembled from single building block containing the 4WJ motif (nanoring class 8) at a final concentration of 2 µM. B) Large nanorings assembled from two building blocks containing the 4WJ motif (nanoring class 7) at a final concentration of 1 µM.
Figure 13B:
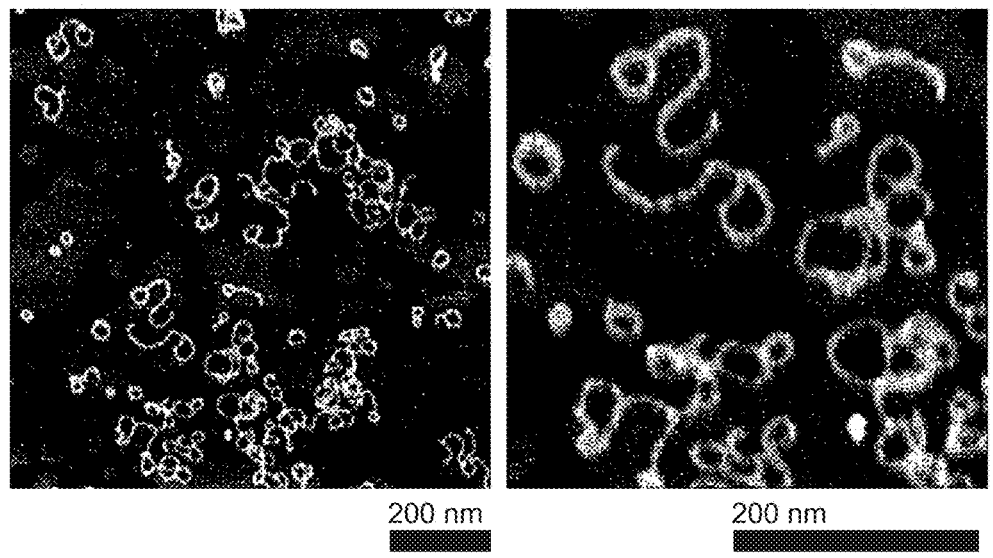

To provide direct evidence for the self-assembly of large circular nanoparticles with the stabilizing motif, the samples were imaged using atomic force microscopy. The nanoparticles were assembled in solution at a final concentration of 1 uM for A/B nanorings (class 7) and 2 µM for SD nanorings (class 8) in the presence of 2 mM Mg(OAc)$_2$ prior to deposition on mica surface. 200 nm scale AFM images of the resultant assemblies obtained in air is shown in FIG. 12. The results indicate the successfully assembly of closed circular nanoparticles using SD nanorings compared to A/B nanorings. However, the size of the final product could not be controlled and closed multimers of various sizes were produced (FIG. 13 A and FIG. 14), which is in agreement with the PAGE results. From AFM images the formation of much bigger nanorings with diagonal dimensions varying between 30 nm to 100 nm for both type of nanorings has been observed. The yield of correctly assembled hexamers made of SD nanorings (class 8) is ~18%, as estimated from the number of closed nanorings observed by AFM, which is in agreement with the quantification of the PAGE gels. Alternatively, prediction of the structure of SD nanorings by measuring their circumference in AFM images has been attempted. According to the 3D model, the estimated length of the large hexagon is ~13 nm from side to side, thus its circumference is 78.6 nm. From these values the circumference values of various polygons that can potentially assemble was calculated. The nanorings were classified by comparing them with respect of their measured circumference values accordingly (FIG. 14).

Figure 15B:
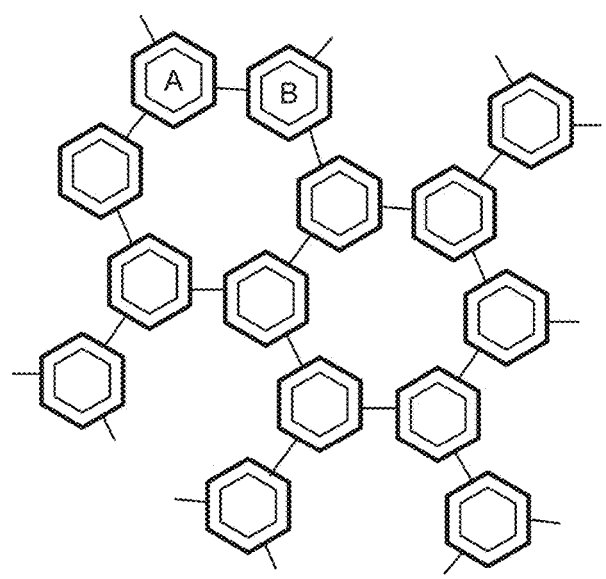
FIG. 15 (A-C) shows supra-molecular assembly of nanorings into two dimensional grids. A) Secondary structure of building blocks that are designed to assemble into 2D arrays through tail-tail interaction. Nanoring A has a dangling 3' tail that is complementary to the 3' tail of nanoring B.
FIG. 15A discloses SEQ ID NOS 171-174, respectively, in order of appearance. B) The schematic diagram showing the assembly of nanoring A and B into 2D arrays. Each nanoring was composed of 3 subunits with no tails and 3 subunits that have a 3' tail complementary to that of other nanoring. C) 200 nm scale AFM images obtained in air showing the formation of array by mixing nanoring A and B in stoichiometric amounts.
Figure 15C:
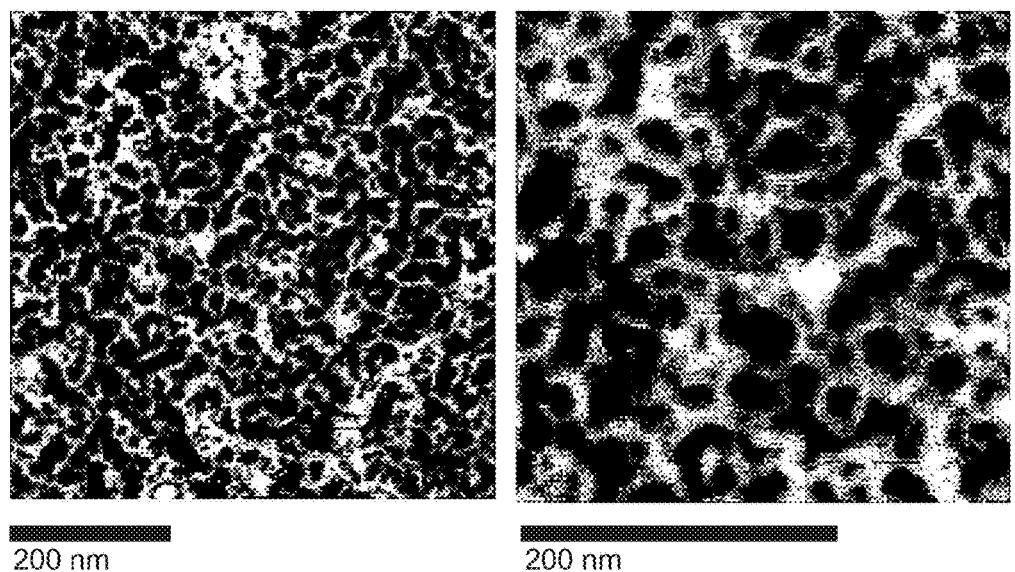

The dangling sticky tails at the 3' ends offer different design possibilities. The positioning of the 3' tail with respect to the nanoring can either lead to a 2D supramolecular assembly if it is positioned parallel to the plane or to a 3D nanotube if it is positioned out of the plane. In the first step RNA building blocks that contain complementary 10 by tails were first assembled into nanorings. Each nanoring was composed of two building blocks, one with the 3' tail and the other one without the tail (FIG. 15 A).

By doing so, each hexamer contained three tails facing opposite sides. Nanorings were further assembled into 2D arrays though sticky tail interaction by mixing two complementary nanorings in stoichiometric amounts (FIG. 15 B). AFM images of the resultant solution showed an array formation; however, it was disordered due to the poor control over the final size of the resulting closed nanorings. On the other hand, the surface coverage was good. Better control over the final shape of the nanoring and much more ordered arrays can be obtained through improvements of the design. Moreover, by modifying the current design it is also possible to generate nanotubes that will assemble from complementary nanorings.

The results described herein demonstrate a RNAI/RNAIIi kissing complex of the ColE1 plasmid of *E. Coli* is an alternative kissing loop motif which is suitable to be used in designing circular nanoparticles. The experiments described herein confirm that the nanoring self-assembly is kinetically controlled and that the nanoring closure is affected by various factors including the length of the stems, the nature of the kissing loops and the presence of stabilizing motifs. For example, the choice of thermodynamically weaker or stronger kissing loop interaction leads to kinetic trapping of nanorings of different sizes. For the moment, our results indicate that it is not possible to generate circular nanoparticles of unique size by using only one type of kissing loop sequence. However, by manipulating the structural parameters described above and the experimental conditions such as concentrations of RNA or $Mg^{2+}$, it is possible to favor the formation of one closed species over the other. Eventually, a good control might be to generate fully circular building blocks that have their 5' and 3' ends ligated after transcription. These building blocks might form very stable RNA duplexes and their ability to font' closed structures will then be tested. The computational design of nanorings proposed by Yingling and Shapiro did not lead to fixed size hexameric nanoparticles as evidenced by these results, however, such computational design can significantly aide in speeding up and focusing attention on potential specific nano-constructs made of nucleic acids.

Example 10. RNA Self-Assembly with Responsive and Stabilizing RNA Motifs

Figure 17:
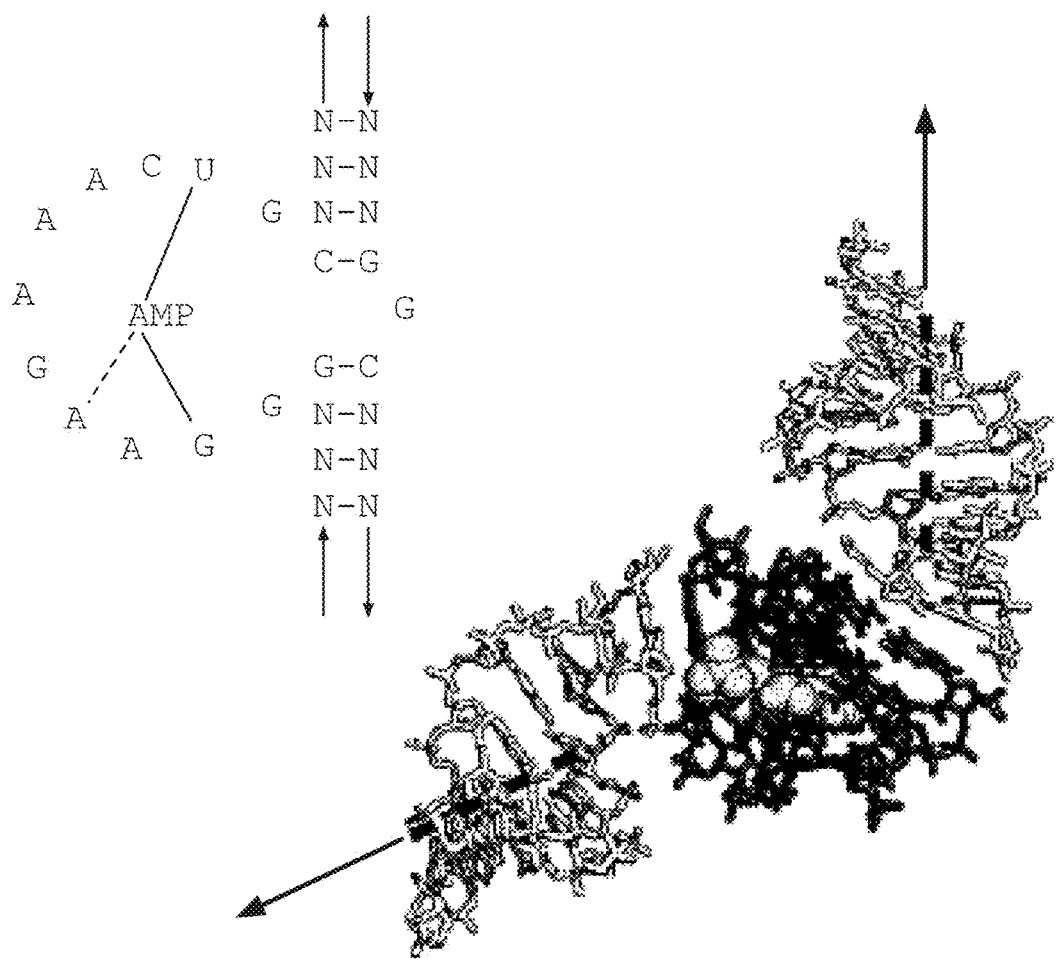
FIG. 17 is a diagram showing the binding of an ATP aptamer (SEQ ID NO: 81) to create an approximately 108 degree bend in an RNA.

The experiments described herein demonstrate that the binding of a ligand to an artificially designed RNA scaffolding can direct the macromolecular self-assembly of that RNA. The three-dimensional structure of an NMR (Dieckmann et al 1997 JMB) characterized in vitro selected ATP aptamer suggests that the ATP aptamer motif can be used to create an approximately 108° bend in an RNA, as illustrated in FIG. 17. Furthermore, in absence of its cognate ligand, this sequence was found to be unstructured. This characteristic has been applied to rationally designed tectoRNAs.

The ATP aptamer was experimentally determined to bind Adenosine, AMP and AMP, but not dAMP or other NTPs/dNTPS. To eliminate the problem of ATP altering the free Mg2+ concentration in buffers, all experiments were performed using AMP as the ligand.

Figure 18:
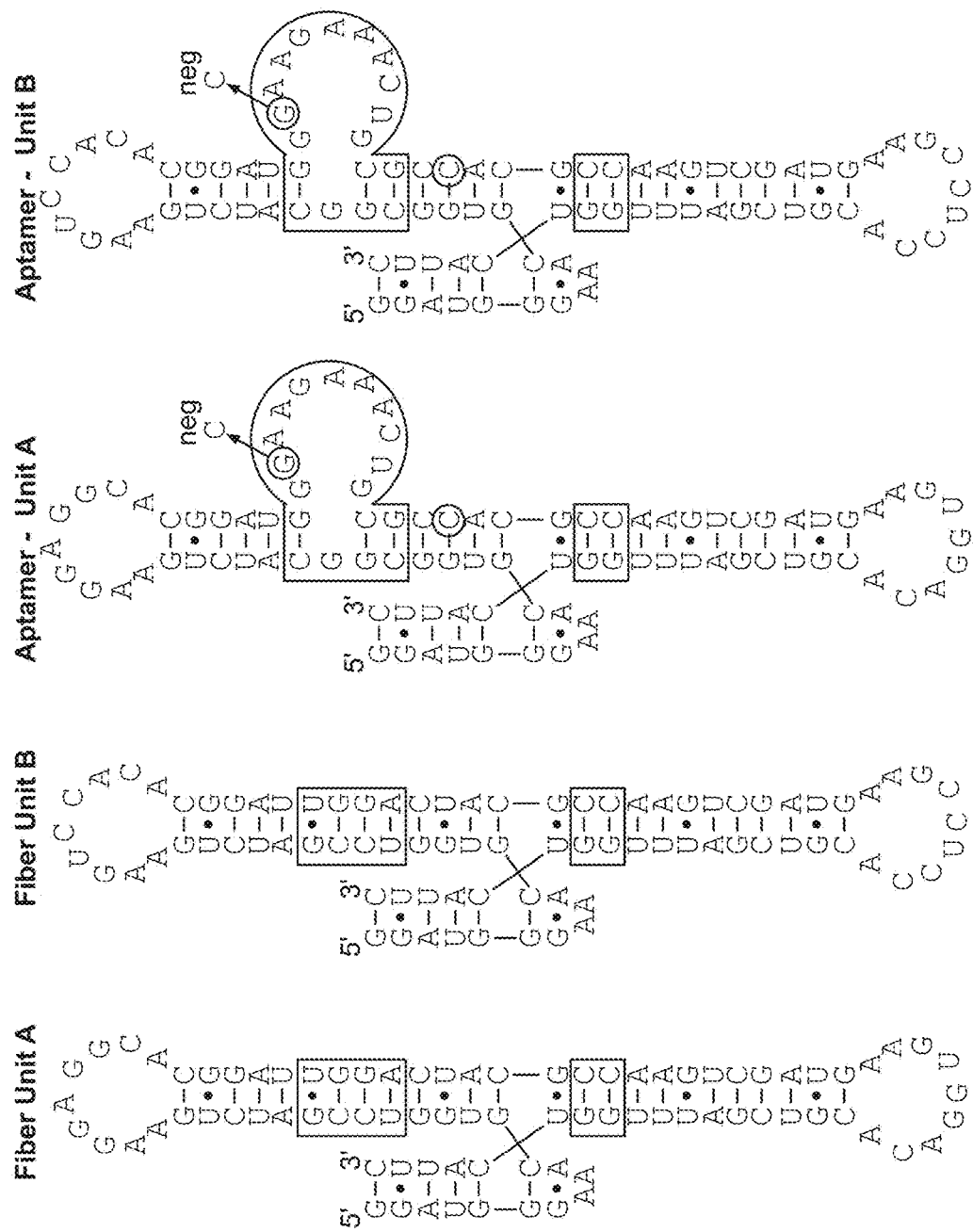
FIG. 18 shows experimental constructs (SEQ ID NOS 82-85, respectively, in order of appearance) designed by inserting the sequence of the ATP aptamer into a previously engineered RNA.

The experimental construct was designed by inserting the sequence of the ATP aptamer into a previously engineered RNA. The initial construct consists of a coaxial stack of two helices that is rigidified by the 4WJ interaction stabilized through a GAAA/GG:CC tetraloop-helix interaction—the construct assembles through HIV-based KL interactions that allow end-to-end assembly into multimeric fibers as shown in FIG. 18.

The sequence of the 4WJ multimeric fiber used is as follows:

SEQ ID NO: 71
Fiber Unit A
GGAUGGGAAACGUGGUCCGAUCUGAAGGAGGCACGGAUUGGACUACGCCA

AGUCGAUGAA GUGGACACGUCGAUUUGGUCAUUCUU

SEQ ID NO: 72
Fiber Unit B
GGAUGGGAAACGUGGUCCGAUCUGAAGUCCACACGGAUUGGACUACGCCA

AGUCGAUGAA GCCUCCACGUCGAUUUGGUCAUUCUU

The sequences of the ATP-sensitive construct is:

SEQ ID NO: 73
Aptamer-Unit A
GGAUGGGAAACGUGGCGGCGCAUGAAGGAGGCACGUGCGGGAAGAAACUG

CGCCACGCCA AGUCGAUGAAGUGGACACGUCGAUUUGGUCAUUCUU

SEQ ID NO: 74
Aptamer Unit B
GGAUGGGAAACGUGGCGGCGCAUGAAGUCCACACGUGCGGGAAGAAACUG

CGCCACGCCAA GUCGAUGAAGCCUCCACGUCGAUUUGGUCAUUCUU

Figure 19:
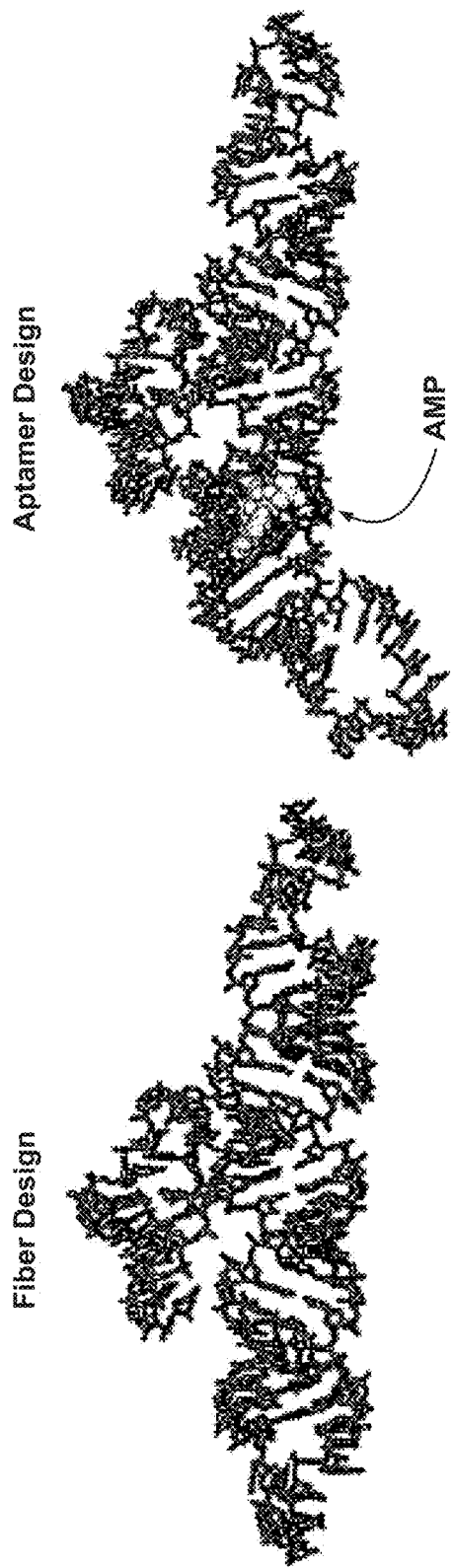
FIG. 19 is a schematic showing fiber and aptamer design.

The mutation G>C in the aptamer sequence is known to prevent AMP binding to the aptamer. A schematic illustrating this is shown in FIG. 19. This mutation was chosen as the negative control for comparing the effect of the aptamer on multimeric assembly. RNA assemblies were prepared by denaturing/renaturing protocol (90° C., 4°, 30° for 3 mins each) prior to incubation 30° C. 30 mins in buffer 1 mM Mg(OAc)$_2$, 50 mM KCl, TB 1× with either 1 mM or no AMP. RNA assemblies were separated by native PAGE in 1 mM Mg(OAc)$_2$, TB 1× in 7% 29:1 (acrylamide:bisacrylamide) at 10° C. RNAs were monitored via a 3' $^{32}$pCp label.

Figure 20A:
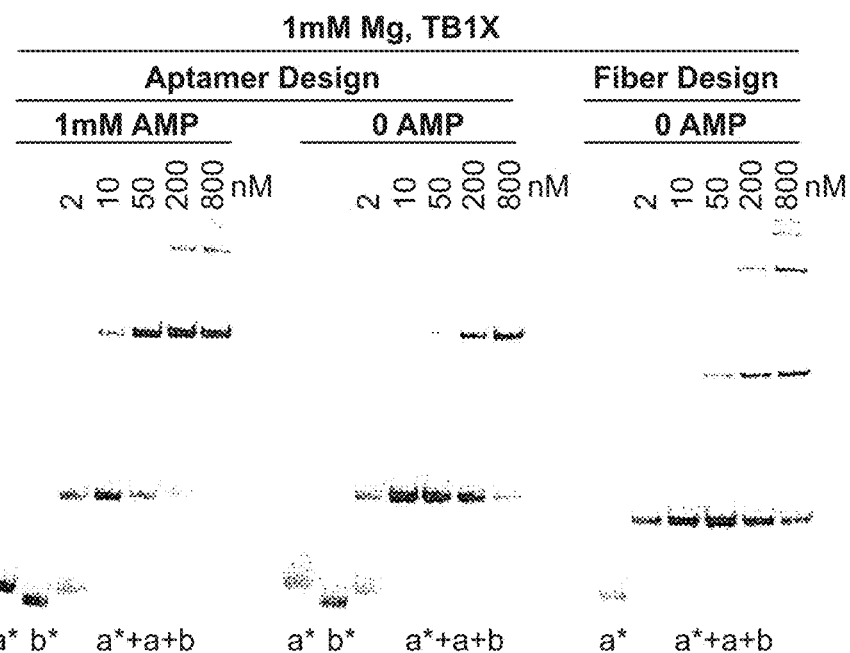
FIGS. 20 (A and B) shows the results of an experiment comparing the aptamer and negative controls in the presence of AMP at various salt concentrations. In A) the experiment was performed at 1 mM Mg concentration and in B) the experiment was performed at 5 mM Mg concentration.
Figure 20B:
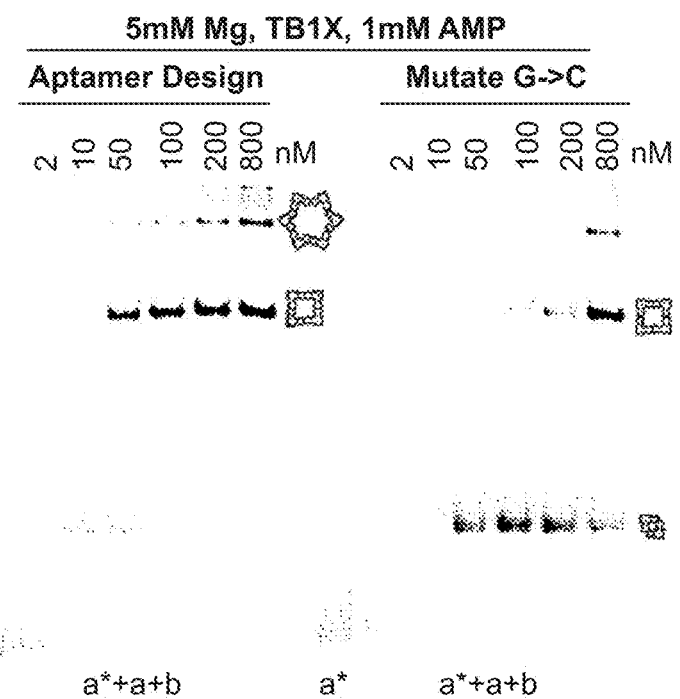

In one experiment, the presence of 1 mM AMP increases the average size of multimers formed in the aptamer design. The results are shown in FIG. 20 A. A similar experiment at higher salt (5 mM Mg), comparing the aptamer and negative controls in presence of 1 mM AMP. The difference in final assembly between the two constructs is more apparent, likely because of the salt requirement of the aptamer structure. This demonstrates that the sensitivity of the aptamer assemblies can be modulated both by the concentration of ligand, as well as the concentration of Mg salt, as shown in FIG. 20B.

Figure 21:
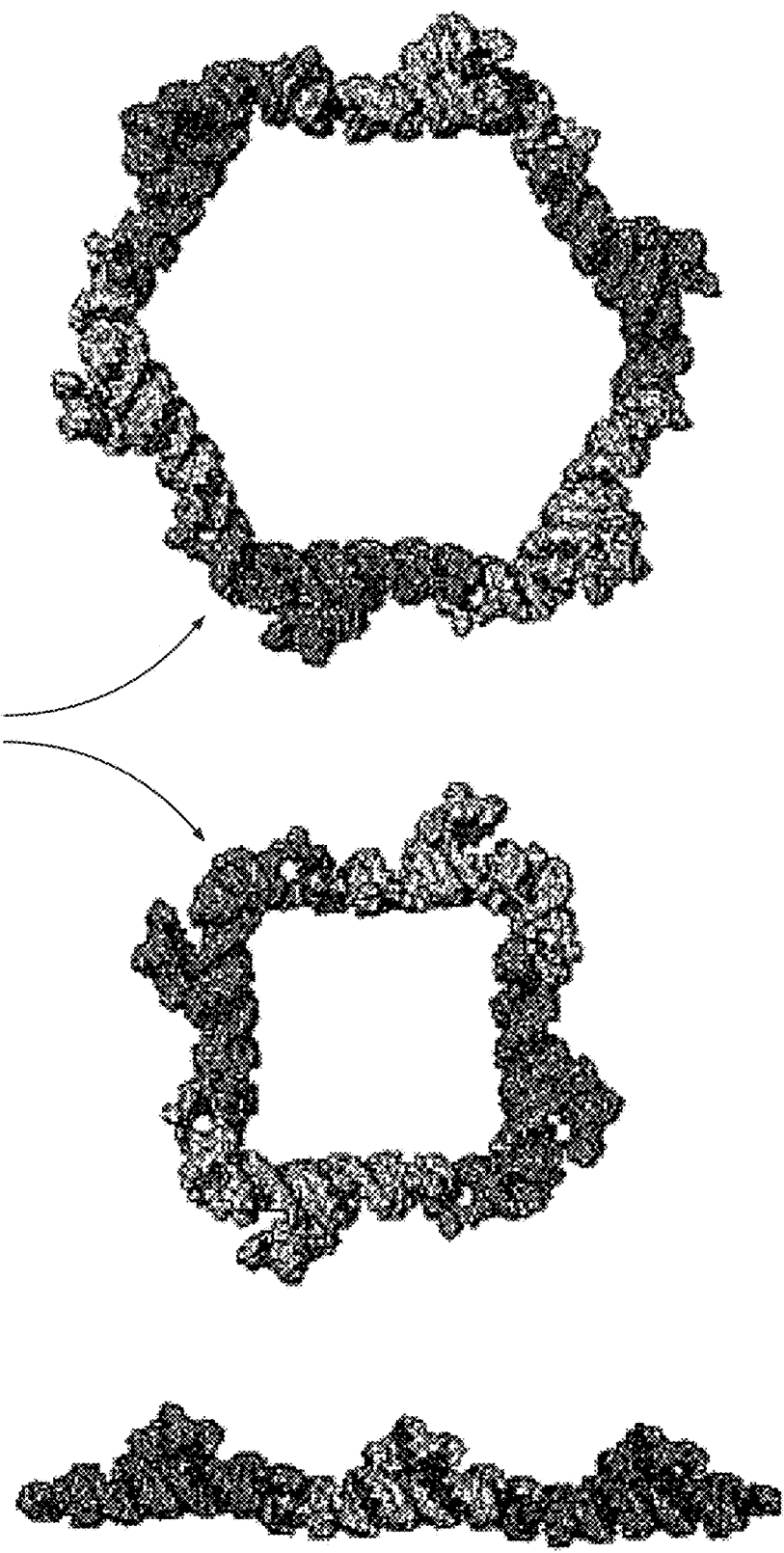
FIG. 21 is a schematic showing the insertion of the aptamer sequence into the 4WJ construct.
Figure 22:
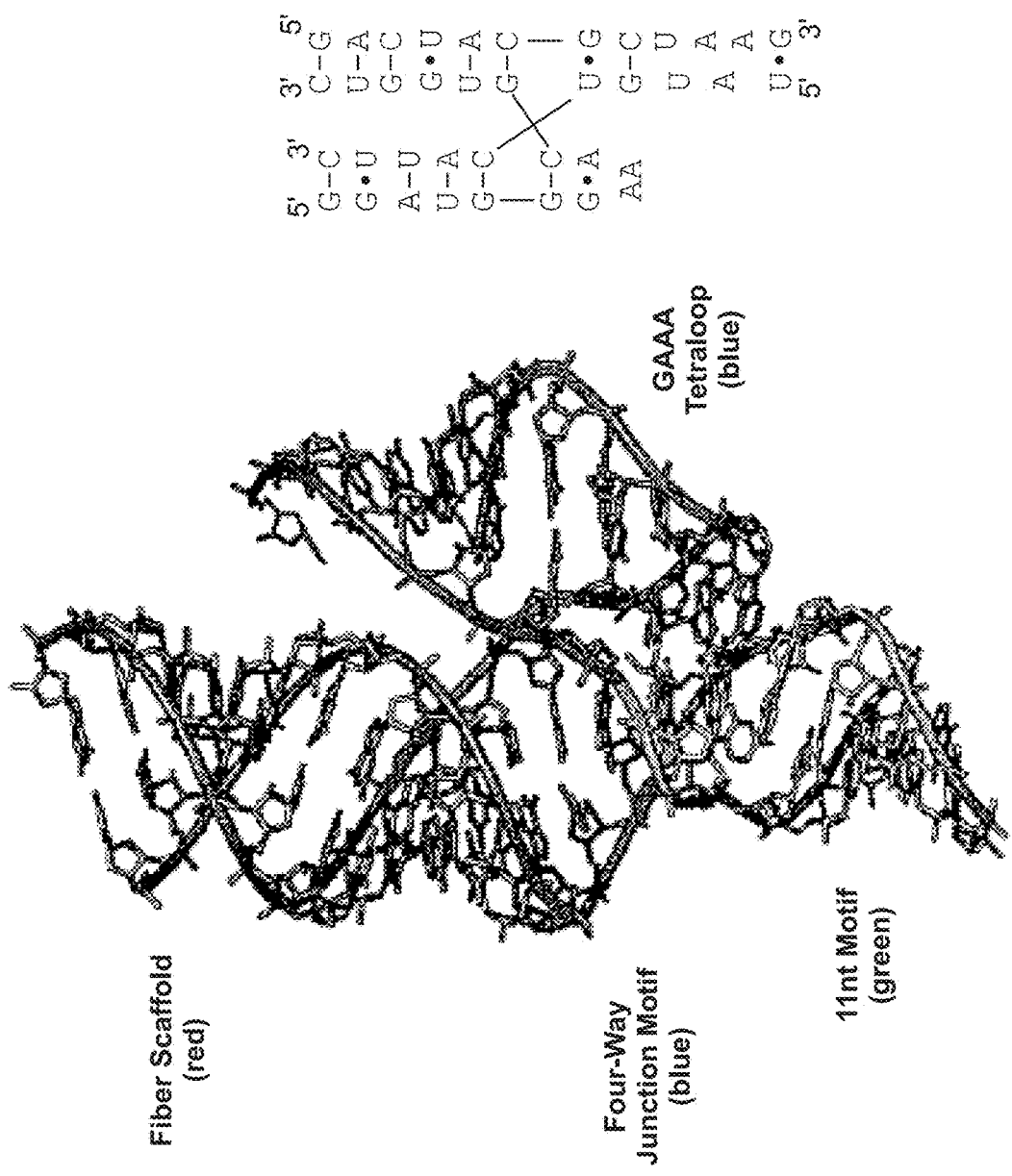
FIG. 22 is a schematic showing that they typical sequence of the 4WJ domain can be augmented by the addition of the 11 nt receptor.

The insertion of the aptamer sequence in the 4WJ construct is intended to increase the yield of tetrameric and hexameric closed-ring species. In absence of AMP the aptamer is known to be unstructured, consequently favoring entropic closure of dimers in our design. A schematic is shown in FIG. 21. In addition, 4WJ motifs can be further rigidified by rational design. Shown in FIG. 22, the typical sequence of the 4WJ (indicated as blue) from the 23S ribosomal RNA can be augmented by the addition of the 11 nt receptor. The U-G interaction of the 4WJ motif overlaps the 11 nt motif, deviating from the natural consensus sequence of the 11 nt motif. However, this modification is necessary to satisfy steric constrains of the 4WJ.

Figure 23:
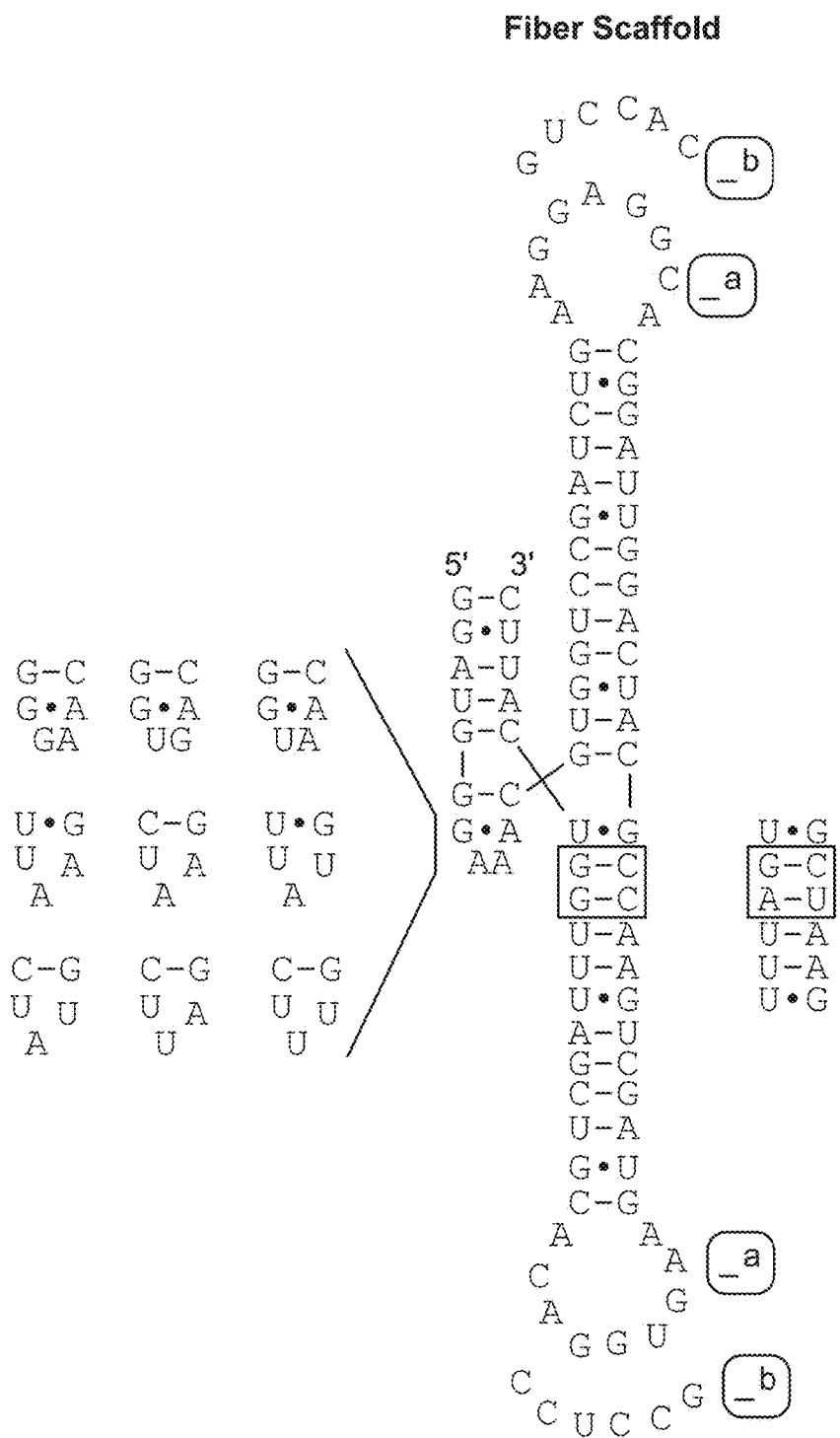
FIG. 23 shows examples of different loop/receptor combinations that can stabilize coaxial stacking.
Figure 23:
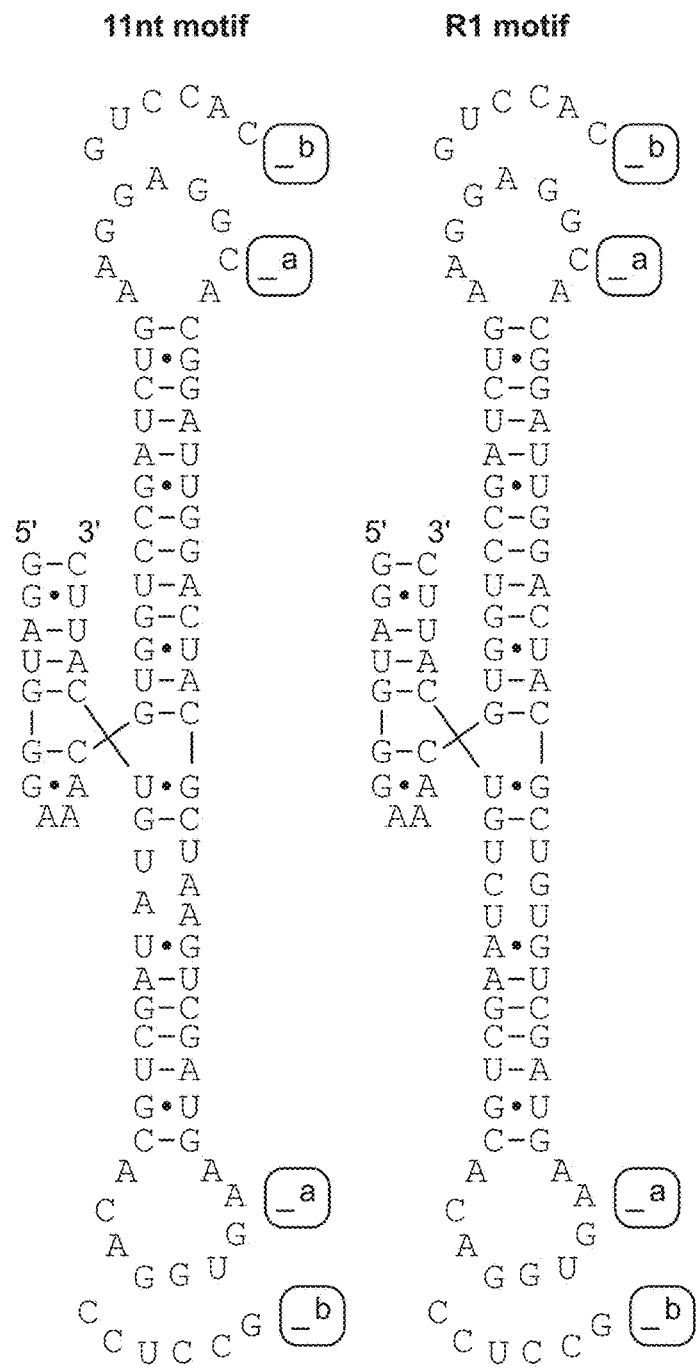
Figure 23:
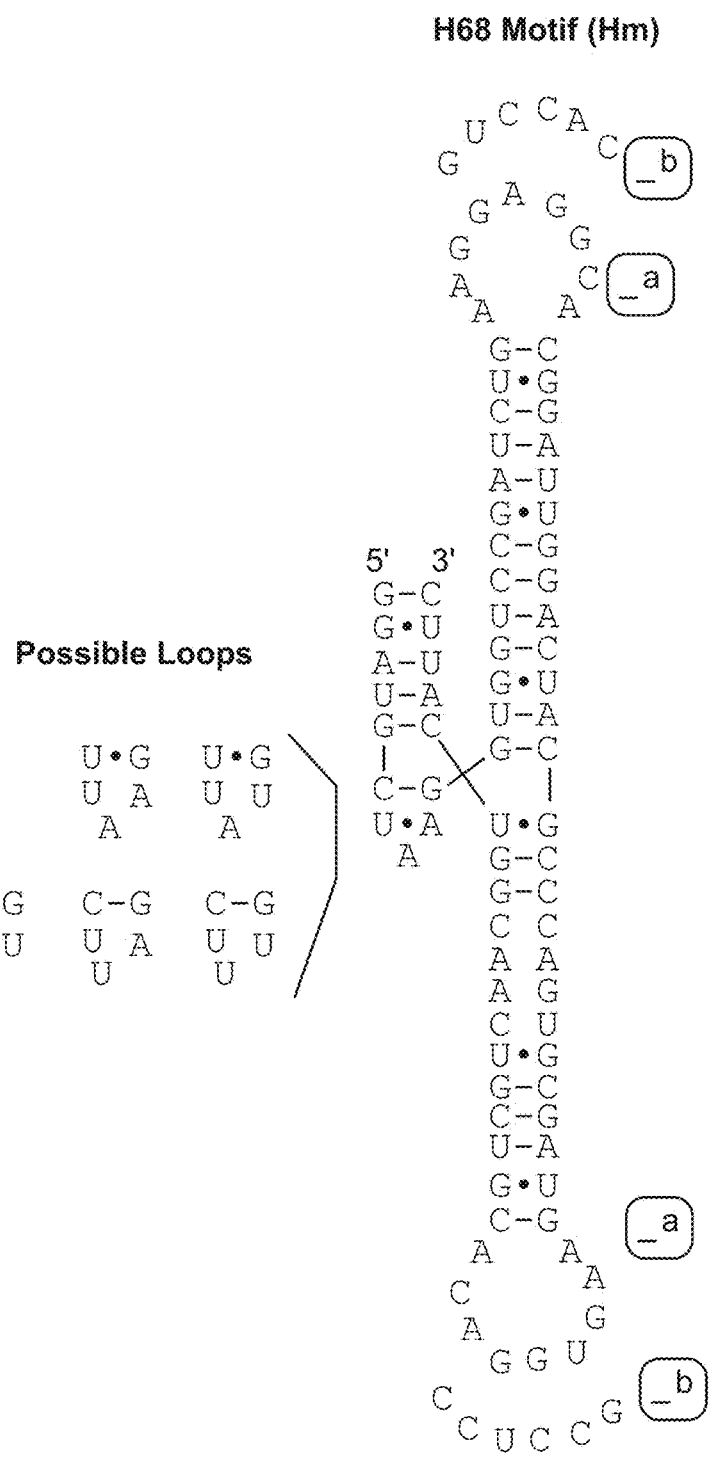
Figure 23:
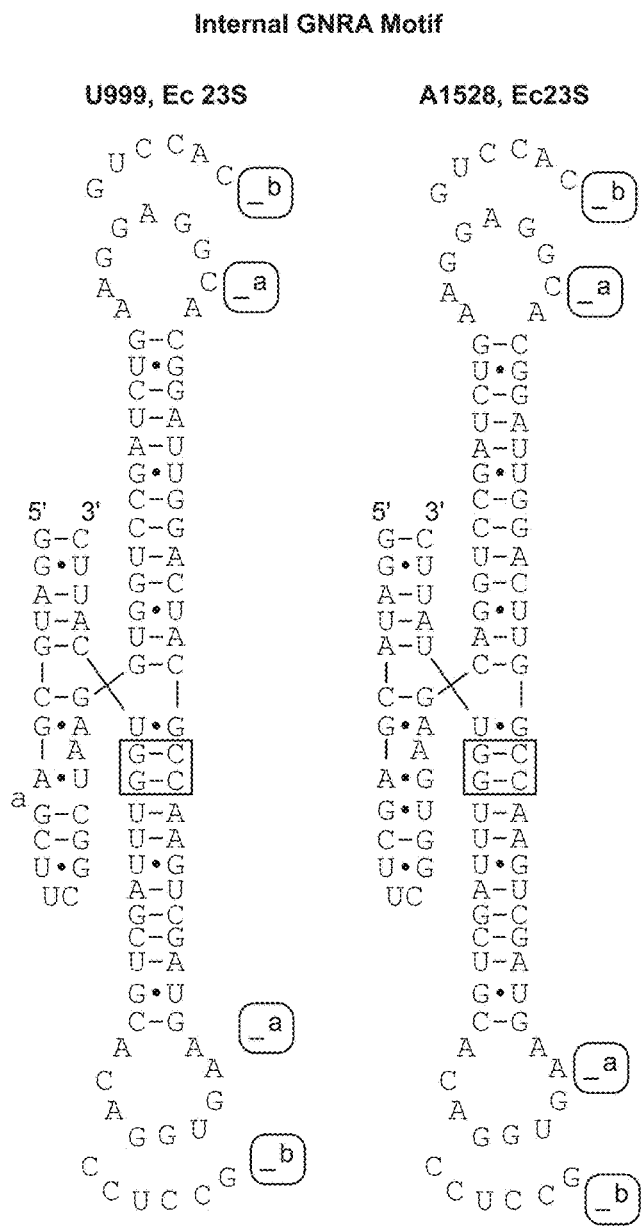

FIG. 23 shows examples of different loop/receptor combinations that can stabilize coaxial stacking. Four-way junctions in RNA have multiple possible coaxial stacking configurations, these motifs (but not limited to) shift the equilibrium between these conformors towards a single structure. The different loop/receptor combinations have been compared by native PAGE (see, e.g. FIG. 24). Depending on the sequence of loop/receptor chosen the relative amount of coaxial stacking in the can be tuned.

Figure 24:
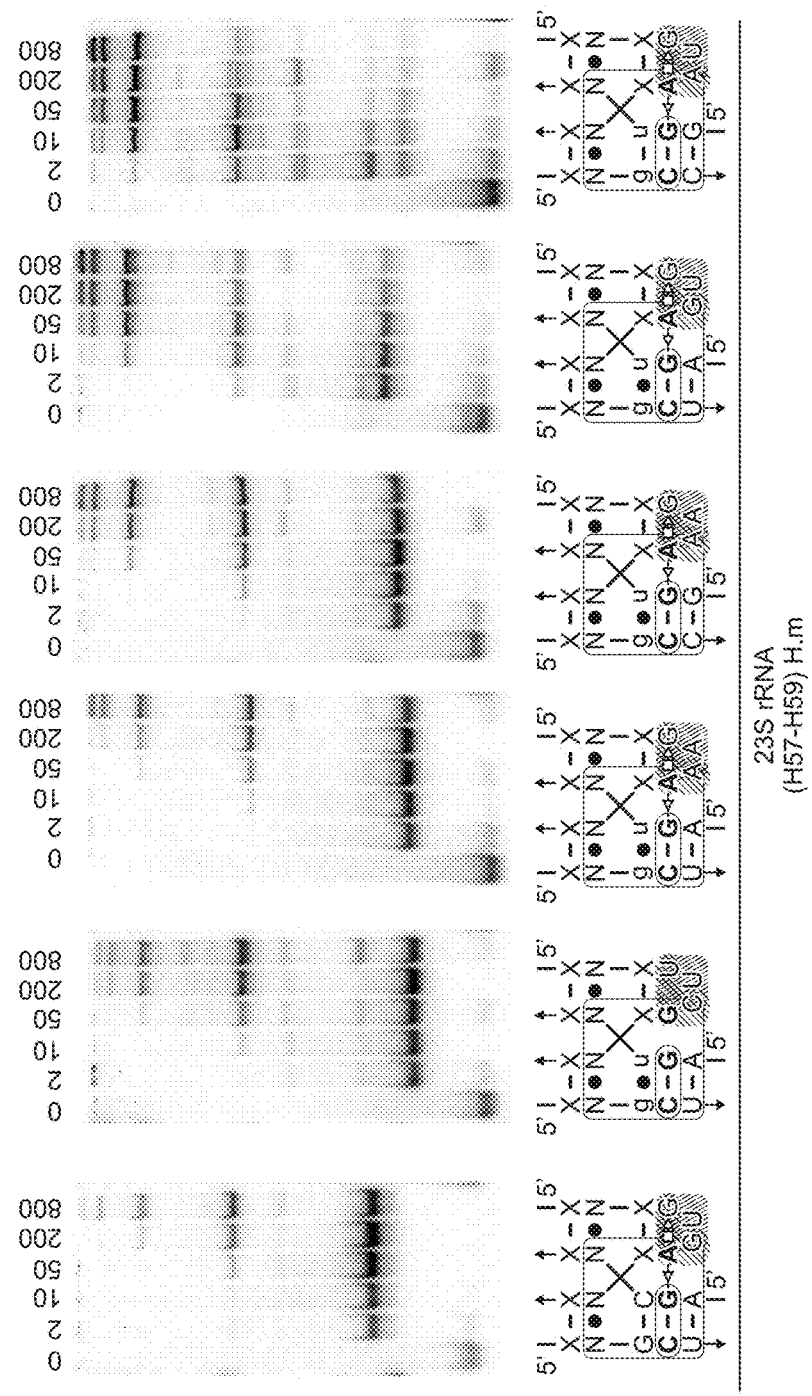
FIG. 24 is a panel of gels.
Figure 24:
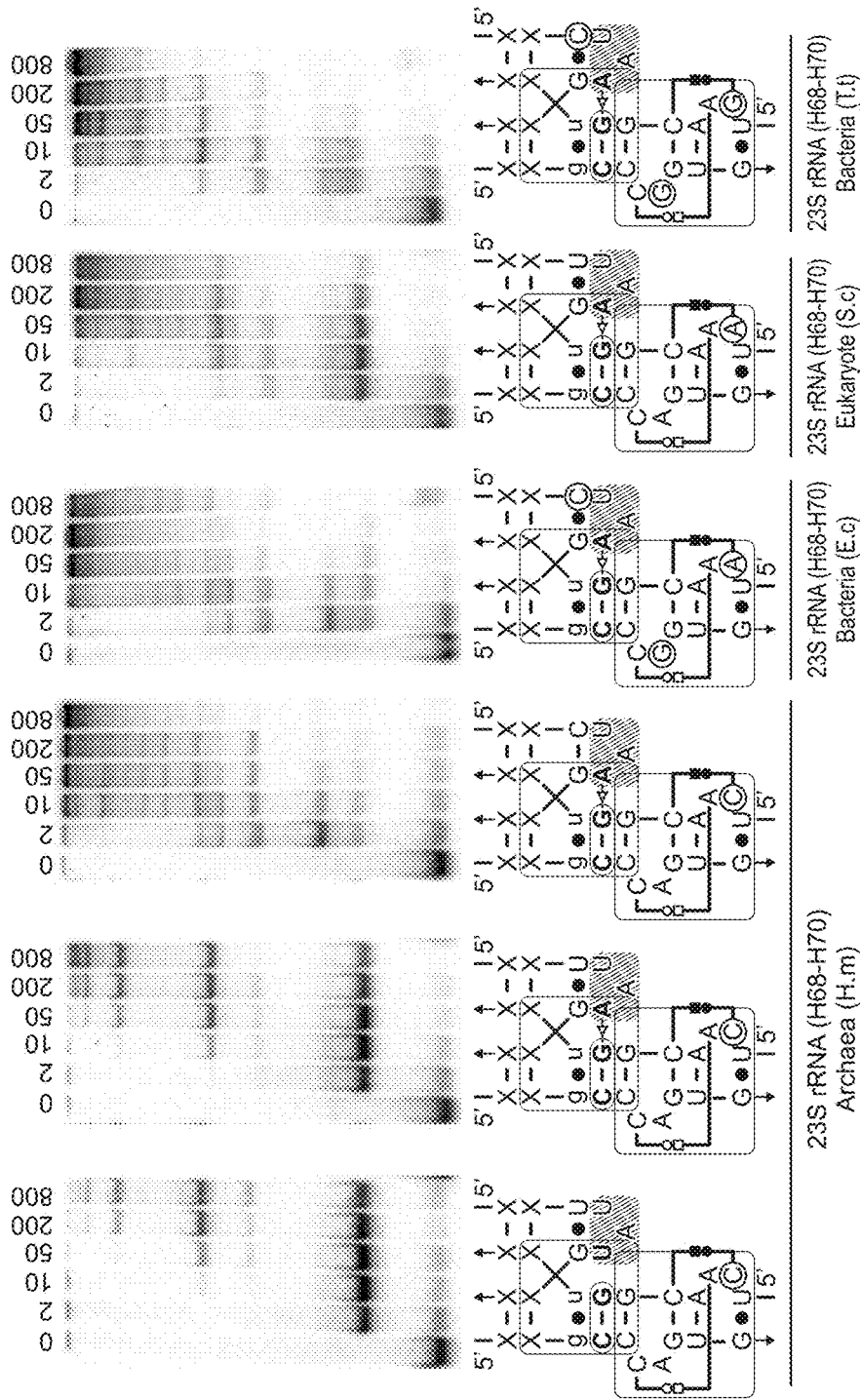
Figure 25:
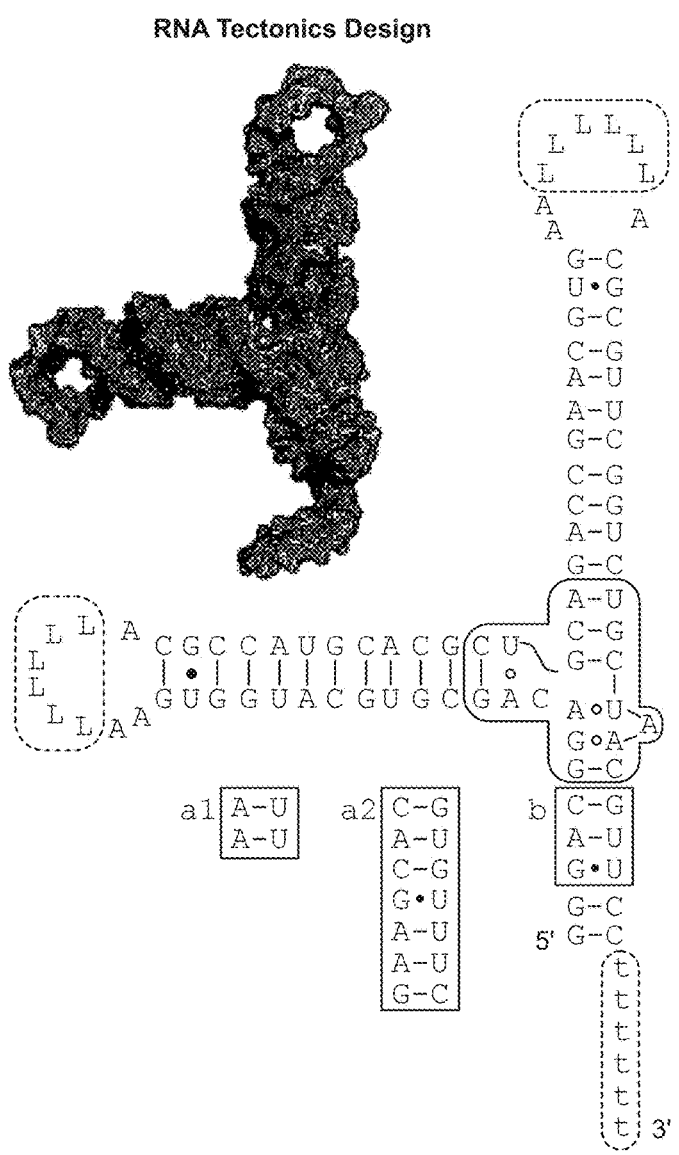
FIG. 25 shows an example of a tetrameric nanoparticle design leading to the formation of a finite nanogrid.
Figure 25:
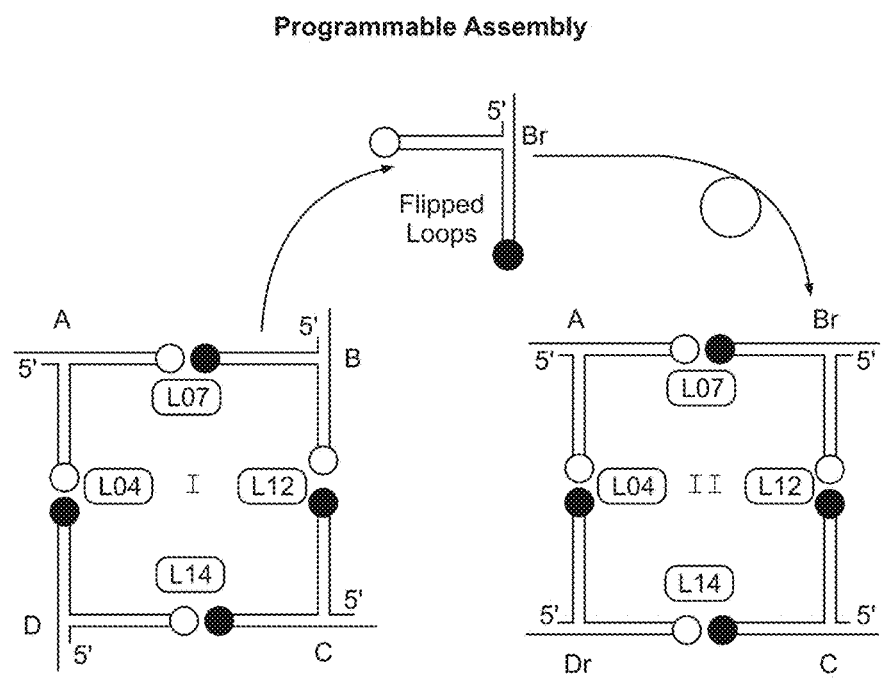
Figure 27A:
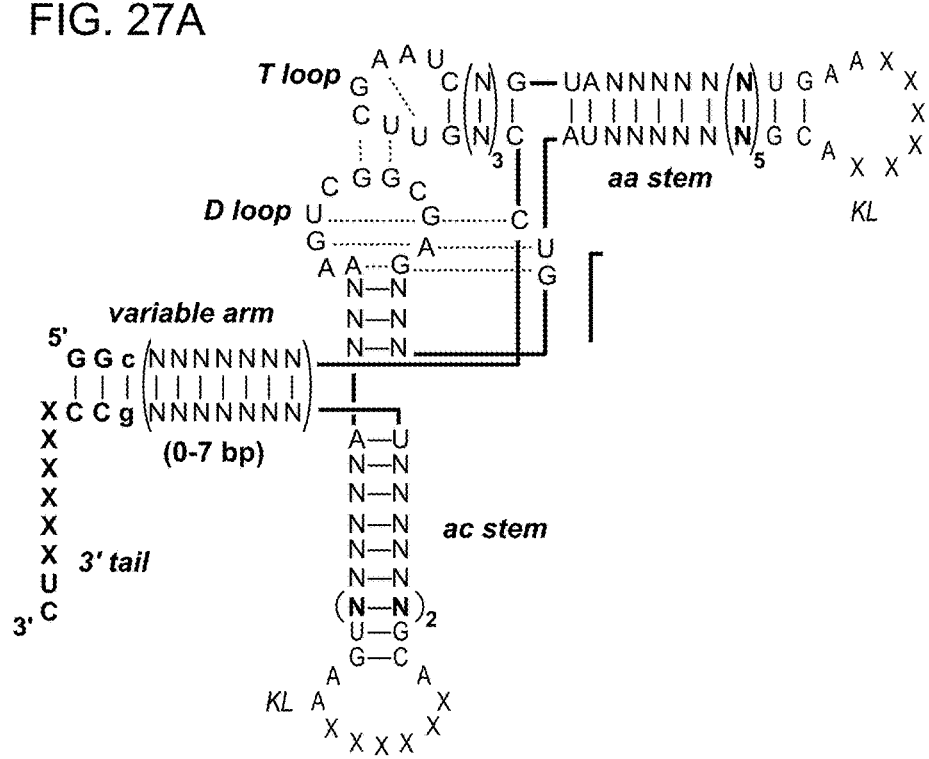
FIG. 27a discloses SEQ ID NO: 176. b) shows the 2D structure of the tectosquare showing the arrangement of four tectoRNAs that self-assemble to form a closed square shaped architecture through KL motif. c) shows the three-dimensional model of the tRNA unit: the var arm points out of the plane defined by the AC and aa arms that are perpendicular to each other. According to crystallographic data, the variable arm makes a 30° angle with respect of the plane. However, three-dimensional modeling indicates that it can faun a 90° angle degree. d) shows that the variation of the length of the variable stem and tail-connectors allows cis and trans configuration of tectosquares with respect to each other. e) shows assembly of tectoRNAs into tectosquares and in the second step into a cuboid-shaped three-dimensional architecture (8 units) through tail-tail connectors localized at the level of the var arms.
Figure 27B:
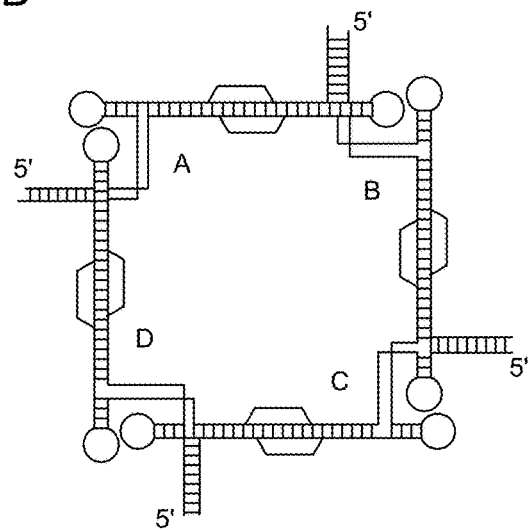
FIG. 27 (a-e) shows structure and design principles of tRNA-based architectures. a) shows the secondary structure diagram of the tRNA unit. The unit is derived from the structure of class II tRNA. The strand topology of the tRNA unit is designed so that the 5' and 3' ends are localized at the tip of the variable (var) arm (in color black). Kissing loops (KL) are inserted at the extremities of the anti-codon (AC) and amino-acid (aa) aims. 18 nucleotide (nt) position involved in aa stem and 11 nt position in ac stem; 6 nt from the 3' end tail (red) and KL loops (green and blue) involved in Watson-Crick base pairs (bp) for tail-connectors or KL motif formation.
Figure 27C:
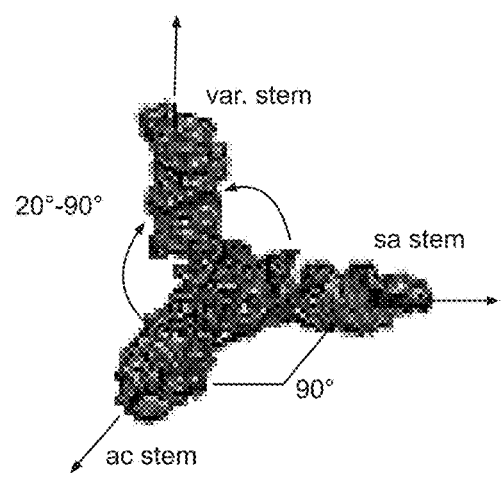
Figure 27D:
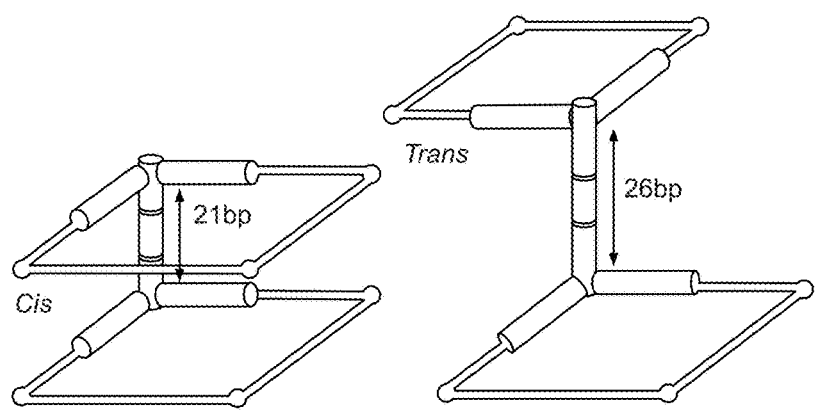
Figure 27E:
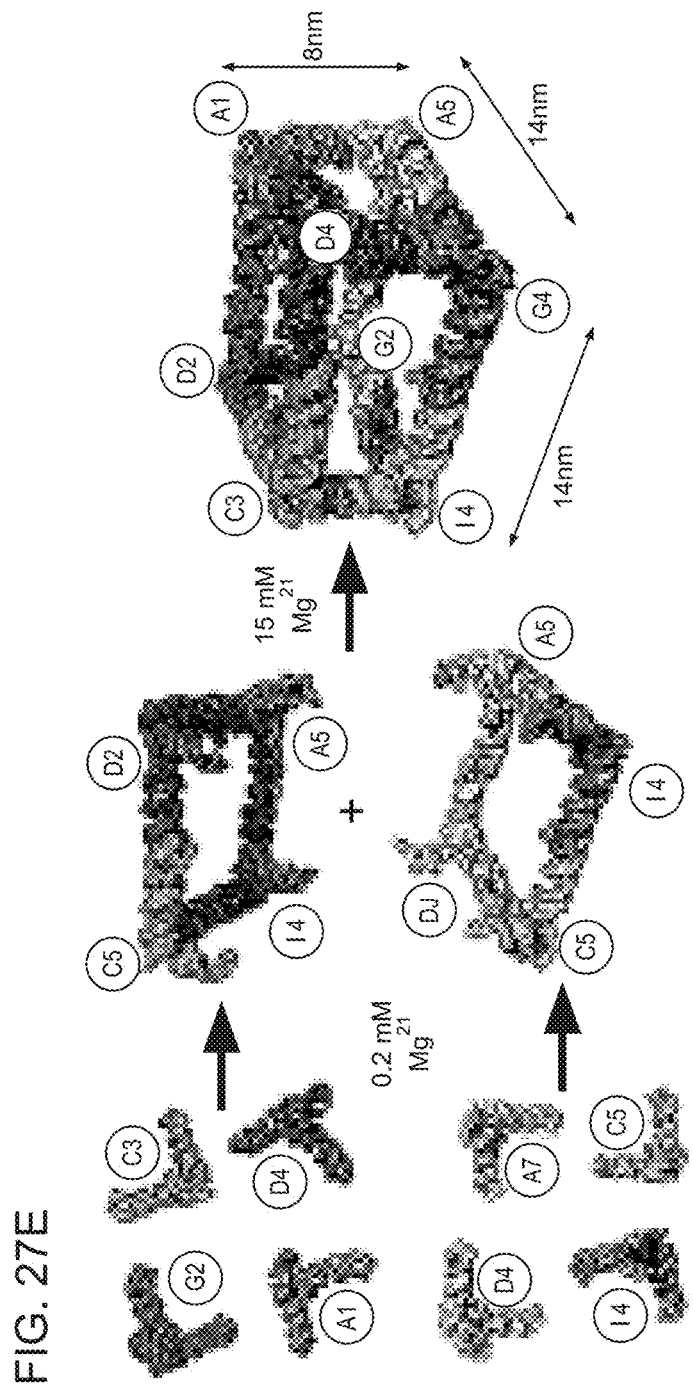
Figure 28A:
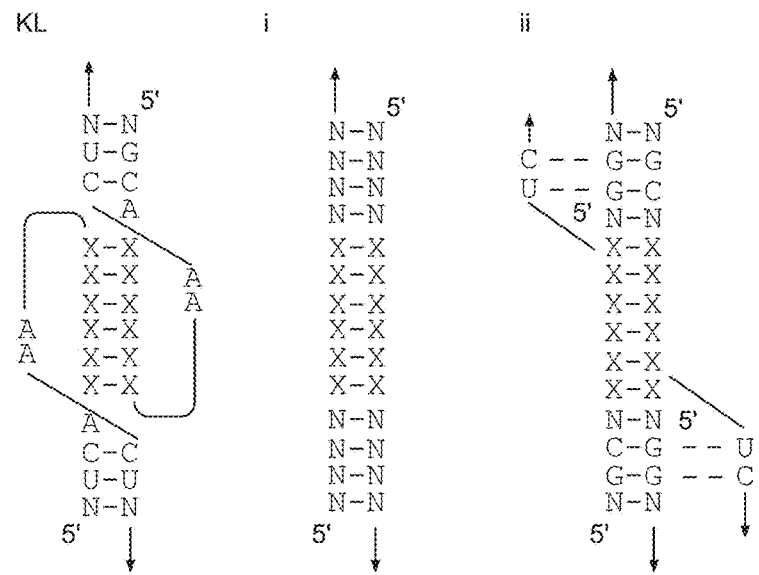
FIG. 28A discloses SEQ ID NOS 115-117 and 117, respectively, in order of appearance.
Figure 28B:
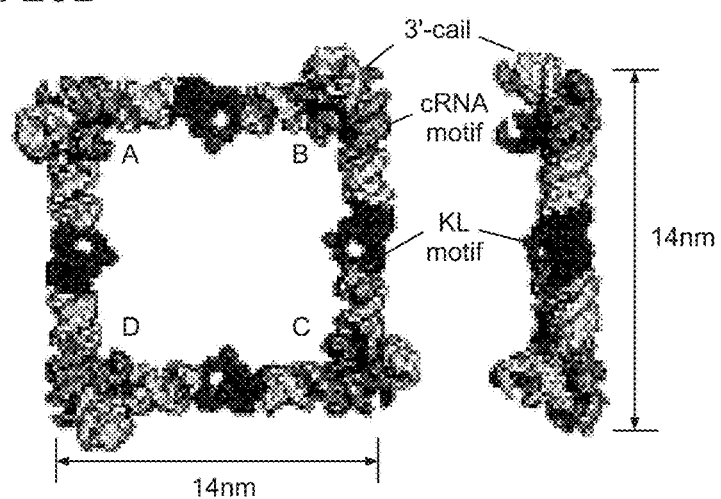
FIG. 28 (a-d) shows a 3D model of the addressable cuboid in detail. a) shows 2D diagrams loop-loop (KL) and tail-tail (type i and ii) interaction. Tail-connectors can also be designed to form local triple helical (Ill) interactions (type ii). Type (i) tail connectors were used in the design of spatially addressable cuboids, whereas type (ii) tail connectors have extra triple helix interaction to increase the stability. b) shows tectosquare 3D model. Front and side views are shown. c) shows programmation of the variable stem that controls the positioning of the protein with respect to the cuboid. Functionalization of the tectoRNAs with 10 by stem (yellow) leads to encapsulation of streptavidin inside the cage. Whereas, functionalization of the tectoRNAs with 5 by stem (blue) leads to attachment of streptavidin outside the cage. d) shows a 3D model of cuboids with streptavidin attached outside or encapsulated inside.
Figure 28C:
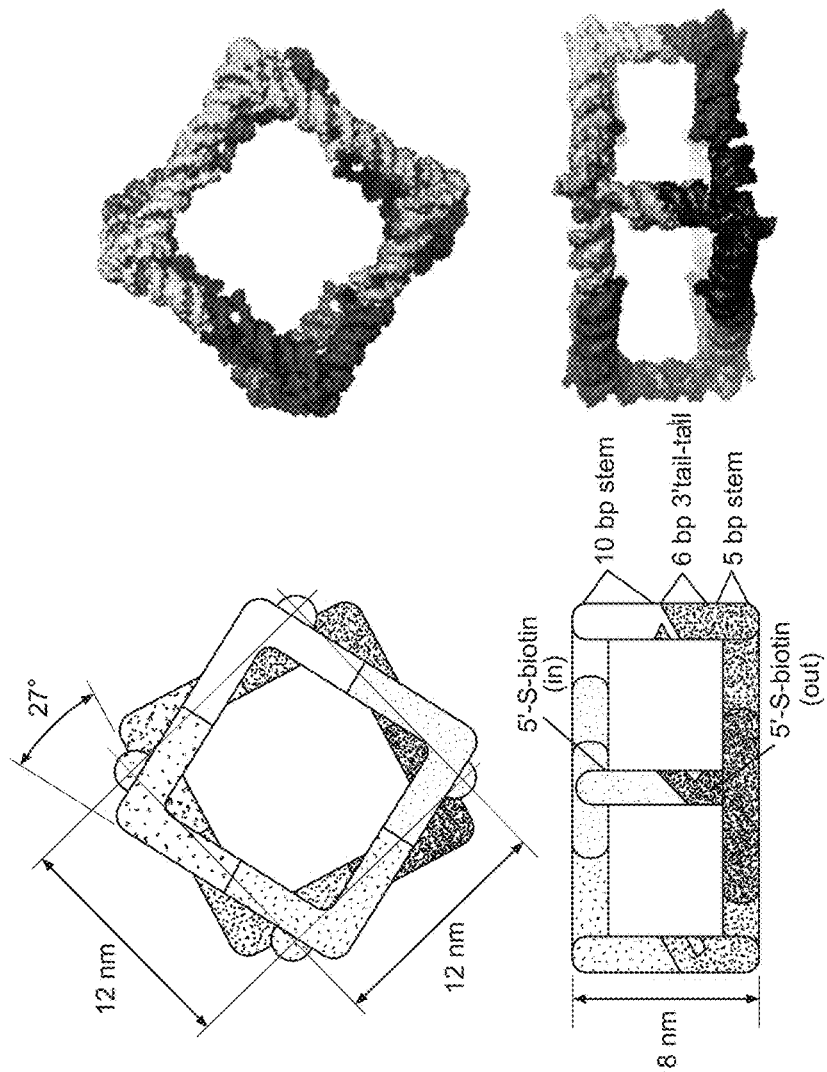
Figure 28D:
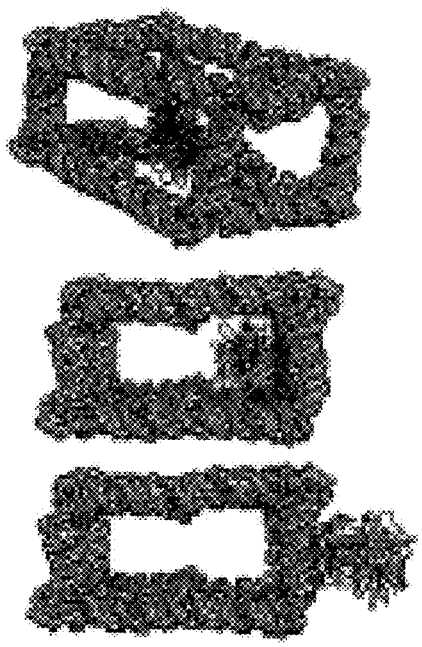

Assembly conditions for the gels shown in FIG. 24 are detailed here. RNA assemblies were prepared by denaturing/renaturing protocol (90° C., 4°, 30° for 3 mins each) prior to incubation 30° C. 30 mins in buffer 1 mM $Mg(OAc)_2$, 50 mM KCl, TB 1× with either 1 mM or no AMP. RNA assemblies were separated by native PAGE in 15 mM $Mg(OAc)_2$, mix in 7% 29:1 (acrylamide:bisacrylamide) at 10° C. RNAs were monitored via a 3' 32pCp label FIGS. 25 and 26 show an example of a tetrameric nanoparticle design leading to the formation of a finite RNA nano-grid. FIG. 26 shows a schematic of possible planar tetramerci nanoring variants (determined by computer modeling). Variations include different tail-tail and kissing loop programming as shown on the right. The design of the kissing-loop programming and stem length (a1, a2 or b) can result in a wide variety of assembly of nanorings. Depending on the choice of stems, tails and kissing loops the tetrameric nanorings can assemble into ladders, nano-arrays of different patterns, finite-sized nanogrids or even potentially three-dimensional structures (3D structure not yet characterized). One example of a finite-sized nanogrid composed of four tetrameric nanorings. The two nanorings (I and II) multimerize into the final structure when mixed together in presence of 15 mM Magnesium. The precisely-defined connectivity of this nanogrid is revealed by AFM imaging under buffered solution Example 11. Spatially Addressable Three Dimensional Cages Made of tRNA In this set of experiments, the main aim was to design spatially addressable and programmable RNA cages using the tRNA motif as the main architectural element. Compared to RA and 3WJ motifs described herein, the class II tRNA motif offers various advantages in terms of 3D polyhedra design. It has more tertiary interactions that stabilize its folding, a higher thermal stability, and the possibility of circular permutation that allows the relocation of nacent termini. The square-shaped nanoparticles with RA and 3WJ motifs, having the 5' and 3' tails mostly planar, offer the possibility of 2D self-assembly formation. However, class II tRNA motif has a long variable stem-loop region that is positioned out of the plane. Therefore, it can be used to build 3D nanocages. The RNA cages can be further designed to be spatially addressable by optimizing the location of 3'-tail connectors in the variable stem and thus controlling the positioning of the biotin within the cage. This allows either the encapsulation of proteins inside the cage or their attachment to the outside forming aggregates of cages.

Bottom up self-assembly of nucleic acids and proteins is a powerful strategy used by nature for building nano-scale polyhedral architectures with predefined size and shapes. Numerous challenges remain however to be solved in order to demonstrate precise control over the folding and assembly of rationally designed nano-objects for potential bionanotechnology applications. Here we show that RNA architectonics, the concept behind the construction of RNA nanostructures from folding principles uncovered from natural RNAs, can be applied to the design, engineering and hierarchical assembly of modular cuboid nano-cages of predictable size and shape with reasonable yields. The spatial position of each constitutive unit is known and therefore addressable within the final architecture, allowing precise positioning and encapsulation of a protein. The experiments described herein demonstrate that like proteins and DNA, RNA can potentially lead to stable polyhedral RNA architectures for use as carriers in nano-medicine and synthetic biology.

One strategy to construct polyhedral cages is to use molecules that are already found in nature such as viral capsids (He, Y. et al. Nature 452, 198-201 (2008)), clathrin (Edeling, M. A. et al. Nat Rev Mal Cell Biol 7, 32-44 (2006)) and ferritin cages (Padilla, J. E. et al. Proc Natl Acad Sci USA 98, 2217-21 (2001)). These are highly efficient cargo vehicles. Recent studies indicate that these 3D architectures can be reconstructed in vitro in the absence of their natural contents and further functionalized as targeted delivery vehicle[s] (Chen, C. et al. Nano Lett 6, 611-5 (2006)). Compared to proteins, nucleic acids are better candidates as building blocks due to their predictable folding and assembly, and the ease of rational design. When designing a polyhedral cage, several considerations must be kept in mind. These include the control of size and shape, addressability of building blocks for the efficient functionalization of the nanoparticle and a good yield of synthesis.

DNA has been extensively used as a medium for constructing nanoarchitectures. To build a DNA polyhedra two different design approaches have been used, which involves the use of single stranded DNA or identical tiles that are generated from ssDNA. Using the former strategy a DNA polyhedra with the connectivity of a cube6, a truncated octahedron (Zhang, Y. et al. Journal of American Chemical Society 116, 1661-1669 (1994), a regular octahedron (Shih, W. M. et al. Nature 427, 618-21 (2004)), a DNA cage in the shape of a tetrahedron (Goodman, R. P. et al. Chem Commun (Camb), 1372-3 (2004) and a bipyramid (Erben, C. M. et al. J. Am Chem Sac 129, 6992-3 (2007)) have been constructed. In a subsequent study, the tetrahedron was engineered to encapsulate a small protein inside the cage. Encapsulation was achieved by controlling the position of 3' and 5' ends relative to the cage, which also determined the positioning of the protein linker (Erben, C. M. et al. Angew Chem Int Ed Engl 45, 7414-7 (2006)). 3D DNA structures that are mentioned above with the exception of tetrahedron (Goodman, R. P. et al. Chem Commun (Camb), 1372-3 (2004)) suffer from poor assembly yields ranging from 1% in cube, 30% in octahedron, to 40% in bipyramid due to unspecific assembly of the building blocks, which increase the instability of the constructed nanoparticles. On the other hand, using the tile-based self-assembly approach higher yields can be achieved and the final shape of the 3D architecture can be controlled by fine-tuning the flexibility and the concentration of the tiles (12. He, Y. et al. Nature 452, 198-201 (2008).

While being more chemically labile than DNA, RNA molecules exhibit complex tertiary structures and provide a large repertoire of novel RNA-RNA interaction motifs that can be used as a medium, to construct a variety of highly complex architectures. Also, while RNA architectures are programmable like DNA, they can be more readily expressed in vivo. Moreover, natural RNA molecules display interesting functionalities that can be encoded within the RNA assemblies such as aptamers, or ribozymes. Compared to protein cages (Padilla, J. E. et al. Proc Natl Acad Sci USA 98, 2217-21 (2001); Matsuura, K. et al. J Am Chem Soc 127, 10148-9 (2005)), nanocages made of RNA might induce a lower immune response, thus reducing the antibody production that leads to the clearance of the foreign nanoparticle (Khaled et al. (2005)).

The organization of RNA duplexes in the shape of specific symmetrical 3D architectures is an alternative way of RNA packaging in living organisms. The 3.0 A resolution crystal structure of dodecahedral cage of duplex RNA, which is located inside the viral capsid of Pariacoto virus, is the only reported natural RNA polyhedral structure (Tang, L. et al. Nat Struct Biol 8, 77-83 (2001)). However, this RNA cage is not thought to be stable in absence of proteins. Previous studies have demonstrated that RNA can be designed as rigid modular units to construct filaments (Geary, C. et al. Nucleic Acids Res 36, 1138-52 (2008); Jaeger, L. & Leontis (2000)) and a variety of self-assembling programmable 2D arrays20. Recently, the Φ29 packaging RNA complex was engineered to form functionalized 2D trimeric nanoparticles that deliver siRNA to induce apoptosis in cancer cells (Khaled et al. (2005)). Described herein is a versatile strategy to generate thermally stable, self-assembling 3D RNA nanoparticles of predetermined size and cuboid polyhedral shape. The approach is based on self-folded RNAs that are similar in shape but of different sequences to generate an addressable 3D structure that can be further functionalized to immobilize molecules inside or outside the cage. The cuboid design is essentially based on a tRNA motif used as vertices. These studies are the first to incorporate RNA and spatial addressability to generate 3D polyhedral nanoparticles.

Example 12. Design and Engineering of Cuboids

To design the tectoRNA an inverse folding and design strategy has been used (see Methods section). A class II tRNA fold was chosen and relocated the nascent 573' termini from the aminoacyl stem (aa arm) to the variable stem (var arm), and inserted KL motifs at the ends of extended aminoacyl and anticodon stems (ac arm) (FIG. 27 a). Folding into a well known L-shape tertiary structure, tRNAs have been previously implemented as a 90° motif in generating square-shaped nanoparticles. The tRNA motif is proven to be more stable compared to the previously used 90° motifs. An important advantage of using tRNAs as a building block is that the variable stem of tRNAs is positioned out of the plane by almost 90° angle (FIG. 27 c), which offers the possibility to be used as a three dimensional vertice in designing 3D architectures. Furthermore, tRNAs can be circularly permuted without the disruption of the native fold.

Figure 35A:
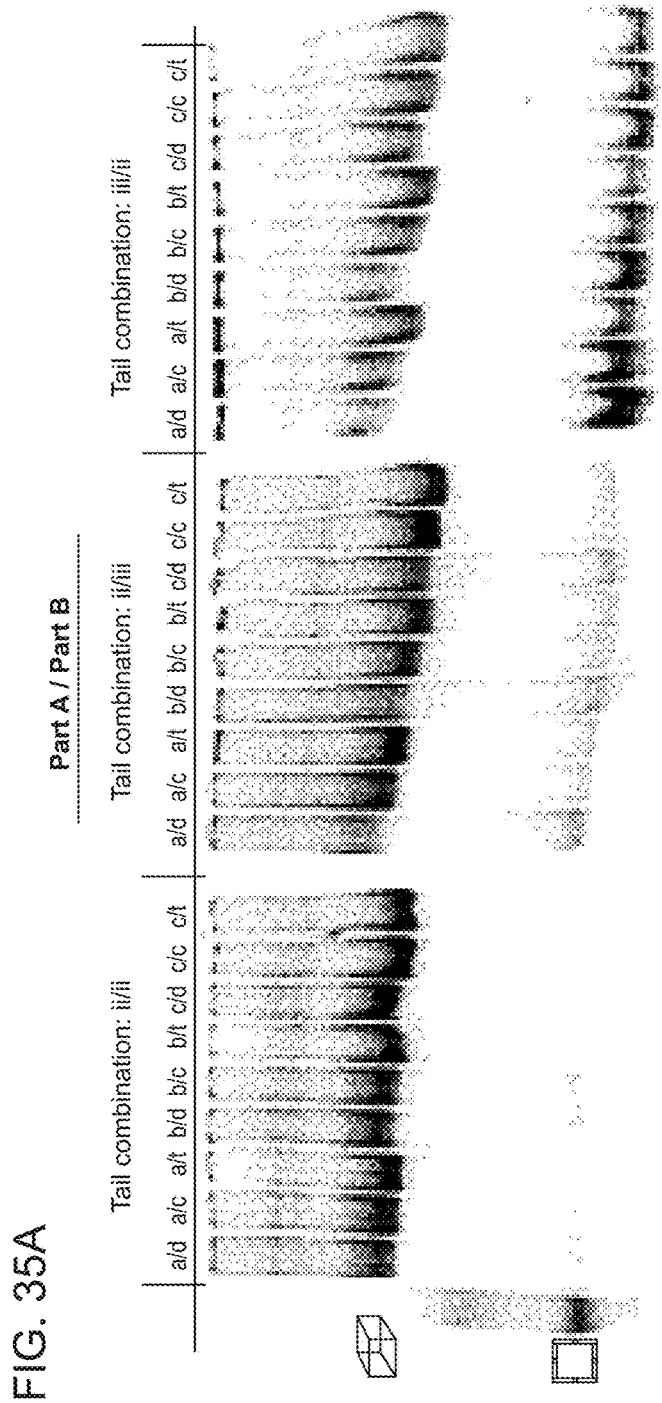
FIG. 35 shows optimization of variable stem length and tail connectors. A Using the tectosquare combinations listed in Table 5.1 27 different types of cuboids can be generated by varying the variable stem length and the type of tail connectors. These cuboids (50 nM) were associated at 60° C. (protocol 60S in FIG. 36 C) and were characterized by a native PAGE at 2 mM Mg(OAc)2. Comparison of gel shifts indicate that tail combination (ii/ii) has the highest yield among the different tail combinations irrespective of the different variable stem lengths. B) Quantification of the gel shows that yield of cuboid assembly can be increased up to 60% (cuboid type a/f with tail combination ii/ii) by optimizing the number of base pairs in the variable stem and stabilizing the tail connectors.
Figure 35B:
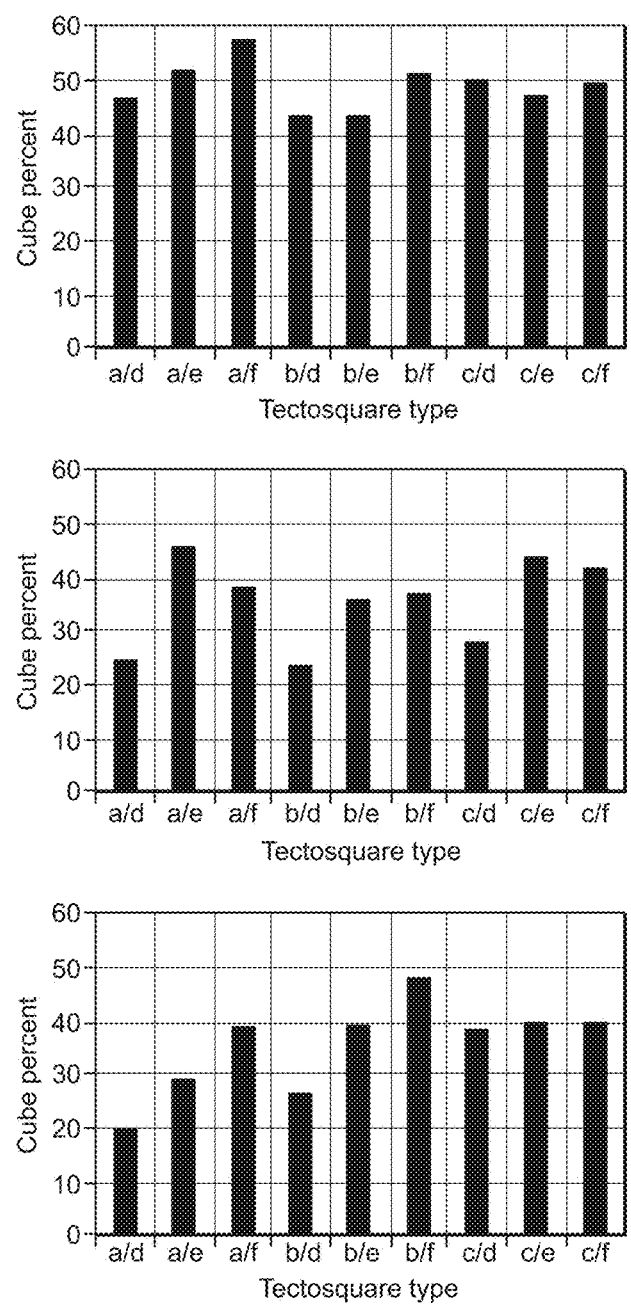

Each tectosquare is composed of four different tectoRNA units (FIG. 27 b) that self-assemble to form a square-shaped nanoparticle through four distinct, non-covalent loop-loop interactions, called the kissing loop (KL) complexes (FIG. 28 a). The size of the tectosquare is estimated from the computer model to be 14 nm by 14 nm from side to side with a central cavity ~10 nm (FIG. 28 a). The cuboid consists of eight different building blocks (tectoRNAs) based on the class II tRNA motif that can assemble in a stepwise fashion, first by utilizing KL complexes than through sticky tail-tail interaction (FIG. 27 e). The 3D model of the cuboid obtained by positioning two tectosquares (eighth tectoRNAs) in silico has the dimensions of 14×14 nm side lengths with a height of 8 nm (FIG. 27 e). Cuboid assembly is controlled through the 3' tail connectors of tectosquares in the variable stem. The sticky tails were designed to be 6 base pair long single stranded overhangs that protrude from the 3' end of each subunit positioned in the variable stem (FIG. 27 a). The variable stem length has been optimized by generating cuboids with variable connector sizes ranging from 7 to 10 bp. The results showed that the highest yield in cube assembly was achieved with a cuboid that has variable stem lengths 8 bp and 7 bp (FIG. 35). The yield of the cuboid was increased by incorporating a triple helix interaction to the 3'tails in the major groove side (FIG. 28 a). By changing the number of base pairs at the level of the variable stem it is also possible to have control over the final supramolecular architecture. When half a helical turn (5 bp) is added to the var stem it allows the tectosquare (TS1) to rotate clockwise with respect to the TS5. Similarly, when 5 by is subtracted from the var stem the rotation is counter clockwise. This allowed the positioning of the tectosquares in cis or tran confirmation with respect to each other (FIG. 27 d). Cis confirmation of two tectosquares formed a closed cuboid, whereas, the trans confirmation lead to the formation of 2D assemblies such as flat arrays.

Figure 29A:
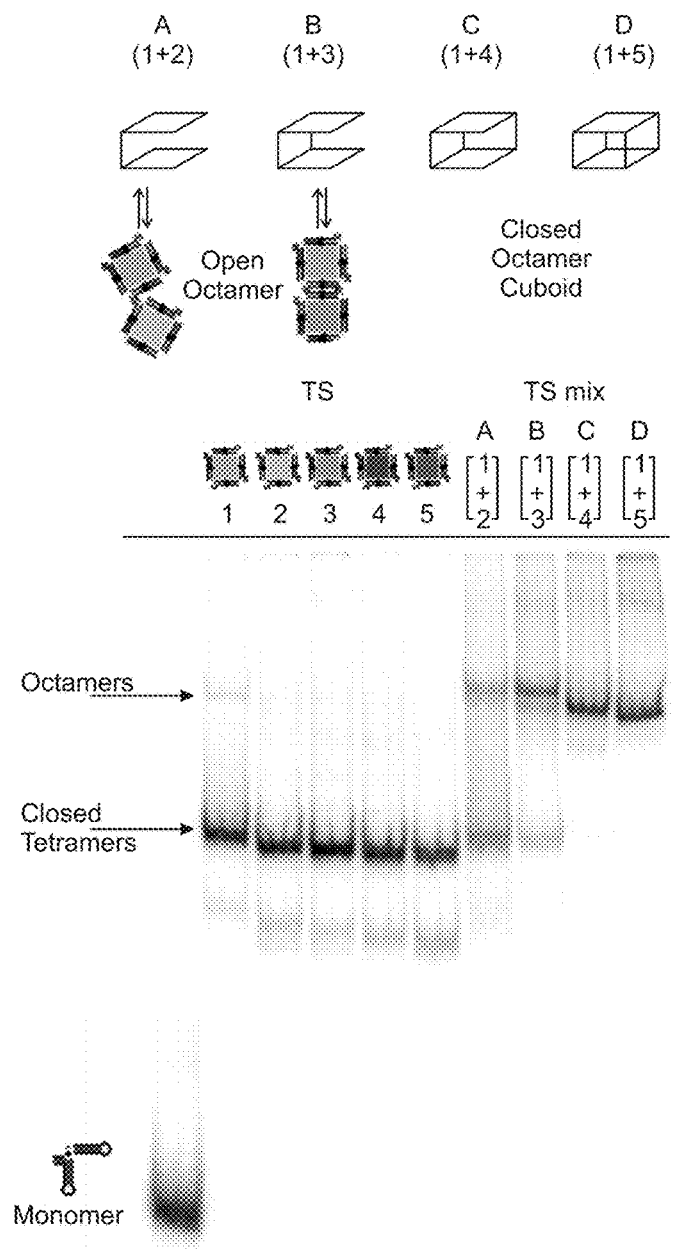
FIG. 29(A) Characterization of tRNA supramolecular assemblies by a non-denaturing PAGE at 2 μM Mg(OAc)2 of tRNA units assembling into various tectosquares and octameric architectures. Lanes 1 to 5 are tectosquares at a final concentration of 100 nM. Lanes A to D are cuboids at a final concentration of 50 nM. The gel shifts of squares and octamers were compared by designing cuboids with a varying number of complementary connectors. Constructs A and B form open octamers whereas constructs C and D form closed octamers (cuboids). Quantification of the gels shows a 50 to 60% yield of cuboids.
Figure 29E:
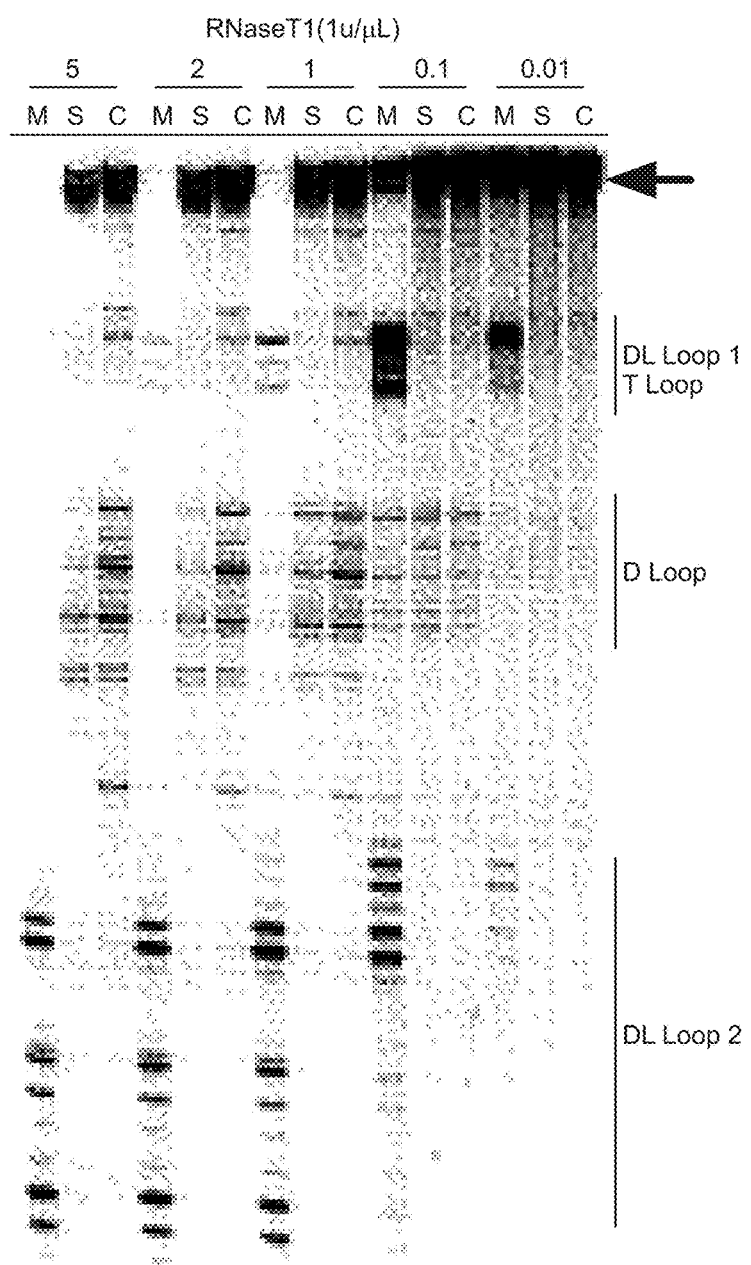
FIG. 29(E) tRNA monomers (A1) (800 nM), tectosquares (TS1) (200 nM) and cuboids (TS1 and TS5 mix) (100 nM) in presence of 15 mM Mg(OAc)2 were digested with RNase T1 for 1 hr at 25° C. and loaded on a 15% denaturing gel. The result indicates that cuboids are more protected towards RNase T1 degradation compared to squares and monomers.

Example 13. Assembly and Characterization of Cuboids by Polyacrylamide Gel Electrophoresis Cuboids were generated using a stepwise assembly approach, which is a useful technique in generating programmable architectures of finite size in which the location of each unit is known and therefore addressable within the final construct. First, to assemble the tectosquare all four tectoRNAs were mixed in stoichiometric amounts in a low-salt containing (0.2 mM Mg2) buffer and subjected to a denaturation/renaturation process, followed by incubating at 30° C. Second, to assemble the cuboid the two tectosquares were mixed in stoichiometric amounts on ice in a high-salt containing (15 mM Mg2+) buffer, heated at 60° C., and allowed to cool to 10° C. Native polyacrylamide gel electrophoresis (PAGE) was used to demonstrate the formation of cuboid by comparing the appropriate gel shifts between monomers, tetramers and octamers (FIG. 29 a). Quantification of the gels indicated that squares formation was achieved with an 80% yield and the cuboid formation with a 55% yield. To investigate the cooperative effect of tail connectors 4 different tectosquares were generated with varying the number of tail connectors between the two tectosquares (FIG. 29 a, constructs A to D in increasing order of number of tail connectors). According to predictions when 2 tail-tail interactions were knocked out it would lead to an open octamer with a slower gel shift. From native-PAGE analysis (FIG. 29 a) a transition in gel shifts was observed as more compact octamers formed. Having the most compact conformation (all 4 tail connectors present), cuboid D had the highest gel mobility.

Example 14. Thermal and Enzymatic Stability of Cuboids Vs. Tectosquares

The thermal stability of cuboid and squares was investigated at various Mg(OAc)2 concentrations by thermal gradient gel electrophoresis (TGGE), which is an efficient method to separate different species based on their temperature dependent conformational change. In TGGE gels two phase transitions were observed, which resulted from the fact that different motifs that make up the 3D architecture contribute differently to the overall thermal stability (FIG. 29 b). These motifs include the T-D loop motif which provides the extra tertiary interactions that stabilizes the 90° motif in the vertices of the cuboid, the KL interaction that holds the square intact, and the tail-tail interaction that holds two squares assembled in a closed cuboid state. The phase transitions that have been observed in the melting plots indicate the cooperativity of these motifs in the assembly/disassembly process. At 15 mM Mg(OAc)2 Tm of a square was measured to be around 65° C., interestingly, cuboids were still intact at 65° C., indicating that cuboids are thermally more stable than squares (FIG. 29 c). At 0.2 mM Mg(OAc)2 on the other hand, cuboids were observed to disassociate first into two separate tectosquares at ~32° C. The second transition occurred around 46° C., where squares disassembled into its monomers (FIG. 29 b). However, as Mg2+ concentrations were increased the melting temperatures of the cuboid were higher than that of square respectively (FIG. 29 d). Starting from 2 mM Mg2+ cuboids disassembled into monomers directly, which proves the importance of cooperativity in the overall thermostability of the polyhedral constructs. The melting behavior of a cuboid has also been investigated when its tails are knocked out (constructs A to D in FIG. 29 a). Of these constructs, construct D (4 tails, closed cuboid) had the highest melting temperature of 62° C. at 2 mM Mg(OAc)2, and construct C (3 tails) disassembled to monomers directly at ~55° C. On the contrary, construct B (2 tails, open octamer) had the first phase transition to squares at ~43° C. and the second transition from squares to monomers at ~55° C., whereas construct A (one tail, open octamer) had the a melting profile that is similar to that of a square. These results indicate the difference of the open and closed states of the cuboid in the thermal stability.

Next, it was examined whether a cuboid is more resilient toward enzymatic degradation compared to squares. We have labeled the same monomer (unit A) of square and cuboid, in order to compare the degradation rate of monomer in the presence of RNase Ti within the context of square and cuboid. The results indicated that after 1 hr of incubation with RNase T1 at room temperature in the presence of 15 mM Mg(OAc)2 more than 60% of the radiolabeled units stayed intact within the cuboid, whereas square and monomer degraded completely (FIG. 29 e).

Example 15. Characterization of tRNA Architectures by AFM

Figure 30E:
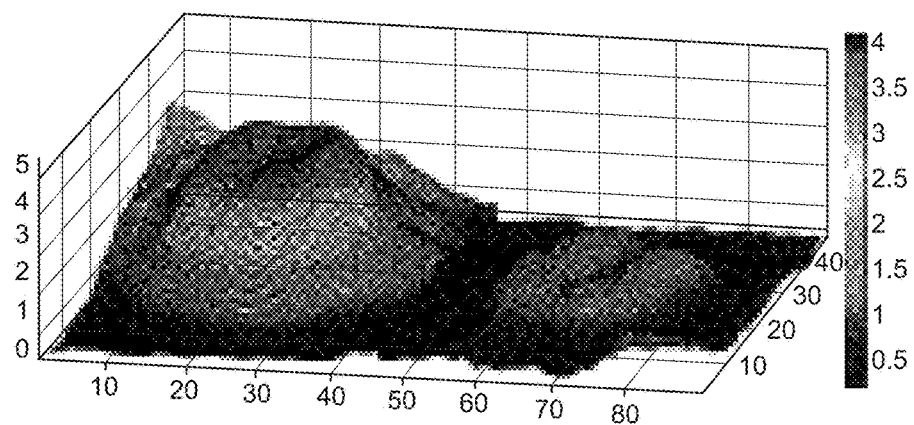
FIG. 30 (a-g) shows diagrams and AFM images of supra-molecular assemblies that are generated using tRNA motif. Hierarchical stepwise assembly schemes of tRNA tectosquares designed by varying the length of the variable stem and tail connectors that form cis and trans configuration. 200 manometer scale AFM images were obtained in air for a,b) cuboids (closed octamers) (TS 1 and TS5 mix), c) open octamer (TS1 and TS3 mix) formed by knocking off two tail connectors, d) nano-grid formation (trans configuration of 2 tectosquares) (TS8 and TS9). e) Three-dimensional rendering of AFM images to compare the relative height of cuboid versus square f,g) Size and height distribution of cuboids obtained from AFM analysis indicate that more than 60% of supra-molecular assemblies have the expected height and size profile. (A list of square configurations is shown in Table 3)
Figure 30F:
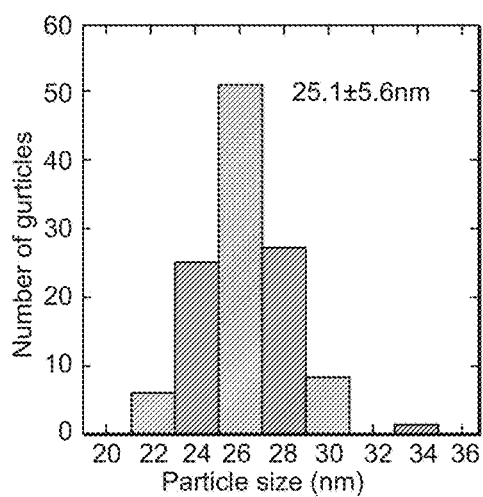
Figure 30G:
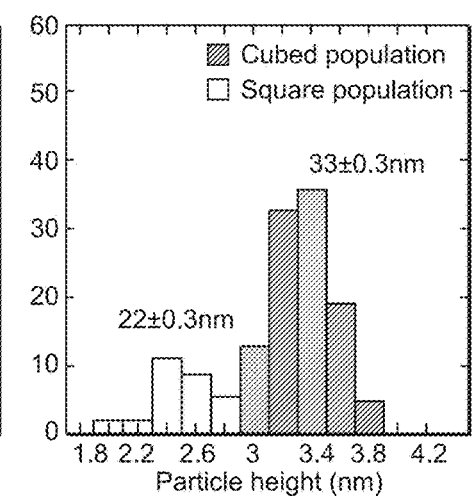
Figure 31:
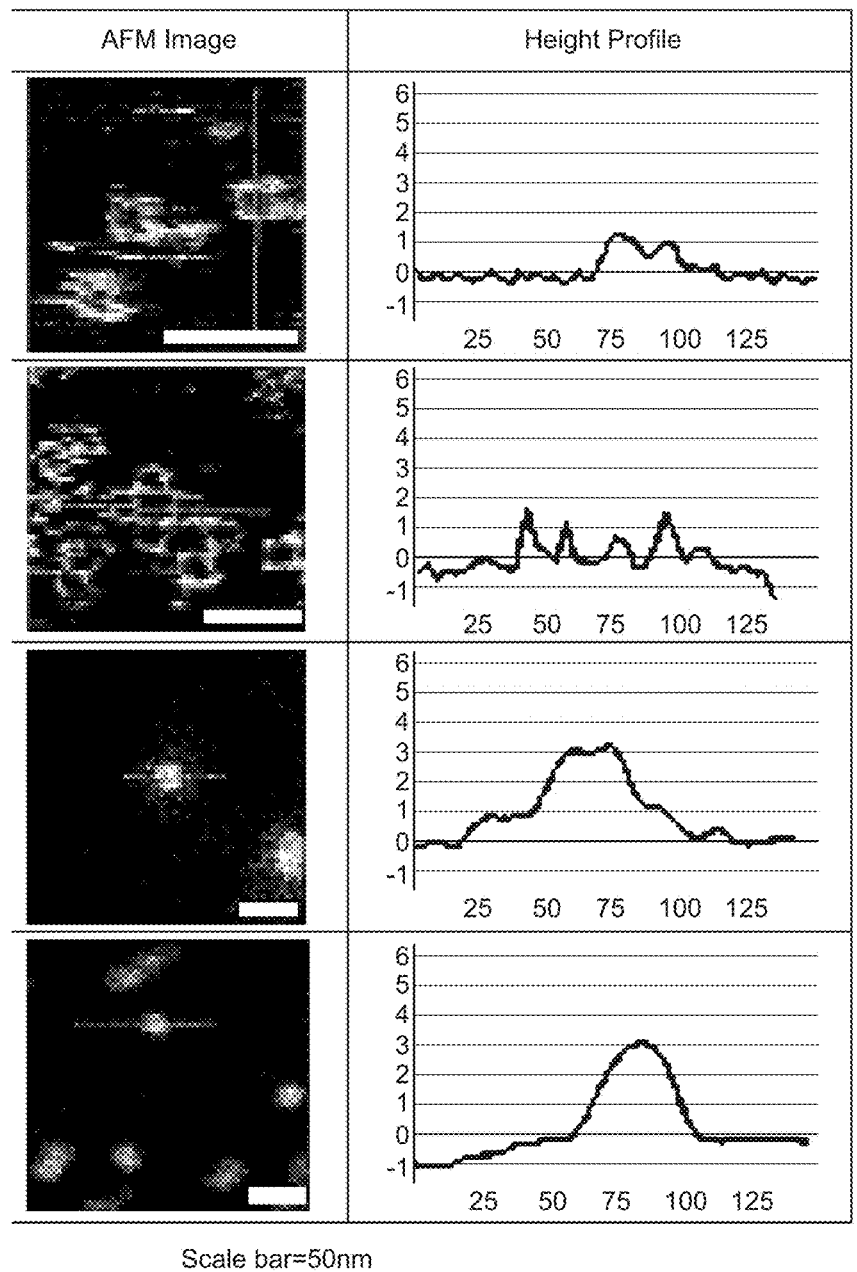
FIG. 31 shows a comparison of expected and observed dimensions of tectosquare, open and closed octameric assemblies using 50 nanometer scale size magnifications of patterns in FIGS. 30 and 33 with their respective height profiles. Measured size dimensions are bigger compared to the predicted dimensions due to tip deconvolution in AFM. On the contrary, observed height dimensions are smaller than predicted heights due to the flattening caused by the force exerted by the AFM tip. Statistical analysis of architectures indicate that the average height of a tectosquare is 1.5 nm, on the other hand average height of a cuboids is 3.4 nm, which is equal to the height of two squares placed on top of each other. The height of cuboids that contain an encapsulated streptavidin was measured to be 4.1 nm, indicating that proteins inside the cuboid prevent the flattening of the three-dimensional structure.

To provide direct evidence on the self-assembly of cuboid, we have used atomic force microscopy. A previously reported strategy was used, where cuboids and squares are first self-assembled in solution in the presence of 15 mM Mg(OAc)2 and then directly deposited on mica surface. AFM images of tectosquares obtained in air supported the predicted shape and theoretical 3D model (FIG. 31) with an average measured width of 14 nm and height of 1.5 nm, which is less than the predicted height of 2.6 nm due to the force exerted by the AFM tip23. We were able to get successful AFM images that showed the cuboid on the mica surface with a high homogeneity in size and shape (FIG. 30 a,b) that supported the predicted theoretical values (FIG. 31). The measured height of the cuboid is 3.4 urn, which corresponds to the diameter of two double helices placed on top of each other. The average width and length of a cuboid was measured to be 23 and 27 nm, which is close to the estimated value of 19.8 and 27.8 nm, when two squares slide on top of each other due to the force exerted by the AFM tip (FIG. 31).

These dimensions correspond to the value of the diagonals. The distribution of cuboid population that falls into the estimated height and size range is more than 60% (FIG. 30 f,g), which indicates the homogeneity in size and shape and is consistent with the yield estimated from native-PAGE gels.

The topology of open octamers was also investigated by AFM. This architecture was generated by knocking out two tails from one of the tectosquares that makes up the cuboid (tectosquare mix Ts1 and Ts3 in Table 3). Interestingly, destabilization of the closed octamers (cuboid) by the absence of two tail connectors lead to and open octamer that rearranges from cis to trans confirmation into nanogrids (FIG. 30 c). The three-way junction characteristic of tRNAs that control the final geometry of the supra-molecular architecture is particularly interesting. To provide direct evidence that it is possible to switch from cis to trans confirmation, tRNA monomers were designed to assemble into a 2D grid by the addition of half a helical turn (5 bp) to the tail-tail connector between the tectosquares. For the purpose of planar assembly, two types of squares have been designed (tectosquare mix Ts8 and Ts9 in Table 3). Each square has 4 single stranded tails complementary to the four specific tails in the second square. The overall topology of grid was investigated by AFM and the results were in agreement with the predicted model (FIG. 30 d). However, we were not able to get a good yield of array compared to architectures generated by the previous 90° motif, proving that tRNA is better suited for constructing polyhedral architectures rather than 2D arrays.

Example 16. Engineering Spatially Addressable Cuboids

To demonstrate the spatial addressability, an RNA cage has been designed with a defined inside and outside by optimizing the location of the tail-tail within the connector stem. This enabled the precise positioning of the 5' end of the variable stem either outside or inside of the cube. In order to do this, 2 bp have been added to previously 8 bp long variable stem and 2 bp have been deleted from the previously 7 bp long var stem. Addition and deletion of bp did not change the total number of bp in the variable stem/tail connector (21 by total) however lead to the rotation of 5' ends about the axis of the helical stem, thus enabling to position each 5'end in opposite directions (FIG. 28 c). Also, we were able make the cuboid addressable by using four different set of tail connectors. It is estimated that the central cavity of the cuboid can accommodate two proteins about 5 nm in diameter (FIG. 28 d). Conjugation of streptavidin to addressable cuboids was performed by incorporating two tectoRNAs functionalized with biotin at opposite corners of cuboid. The choice of tectoRNAs to be functionalized (long or short variable stem) determines whether the protein is encapsulated or held outside the cage. Native-PAGE was used to compare the gel shifts for both cases with various cuboid to streptavidin molar ratios (FIG. 32 a). The difference in mobility of cuboids with proteins attached outside is maximal compared to empty cages or cages with encapsulated proteins at cuboid to streptavidin molar ratios 1:1 and higher. As there is excess streptavidin in the medium, the cuboid is coupled with proteins on both sides and therefore string formation has not been observed. AFM results indicate that when 5'-linker is positioned inward streptavidin was successfully encapsulated within the RNA cage (FIG. 33 a,b). The observed width was 27 nm, which is in agreement with the measured value of an empty cuboid. Also, streptavidin encapsulated cuboids appeared to be taller than the empty cubes, with a height of 4.1 nm (FIG. 31, height profiles). These results show that the empty cube is squished upon drying and under the force applied by the AFM tip, however, when streptavidin is encapsulated inside the cube, it prevents the deformation of the cube under the applied force. On the contrary, when 5'-linker is positioned outward cuboids were found to form beads on a string type supramolecular architectures through streptavidin biotin interaction (FIG. 33 c,d) which is consistent with the design.

The results described herein strongly support the 3D model that we have designed. This study also provides a practical approach in designing closed finite shape cages using RNA motifs that could be used in therapeutic applications. First, a programmable and addressable RNA cage offers a way to have control over the positioning of the encapsulated molecule within the cage. Second, an RNA cage offers a closed environment and protects the encapsulated molecule against the surrounding environment. Third, the modular units can be modified and functionalized to have novel properties or exhibit specific targeting against different molecules. It is also possible to design a dynamic cuboid that is capable of cycling between a closed state and an open state by making it responsive to specific molecular signals, which is an important aspect in the design of delivery vehicles with controlled release of cargo. These experiments confirm that RNA cuboid cages are thermostable. They also confirm that there is partial protection towards RNase degradation. However, in the future, the use of RNA as delivery vehicles may require some kind of chemical modification by taking advantage of nucleic acid analogs or additional protective envelops. This strategy offers interesting prospects in synthetic biology for generating self-assembling devices able to be produced and assembled within a cell. This RNA molecular system may be used to build more stable and complex RNA polyhedra. Finally, cuboids made of tRNAs could also be valuable tools for studying multifunctional responsive systems that can be used as delivery vehicles for therapeutic RNAs.

Example 17. Increasing the Cuboid Yield by Tuning the Design and Experimental Parameters One of the motivations in this research has been to achieve a high assembly yield for the 3D objects. Assembly yield can be increased by tuning the experimental parameters such as concentrations of monovalent and divalent cations, temperature of association, as well as by optimizing the design parameters including connector lengths and the choice of interface connectors such as loops or sticky tails.

Figure 34A:
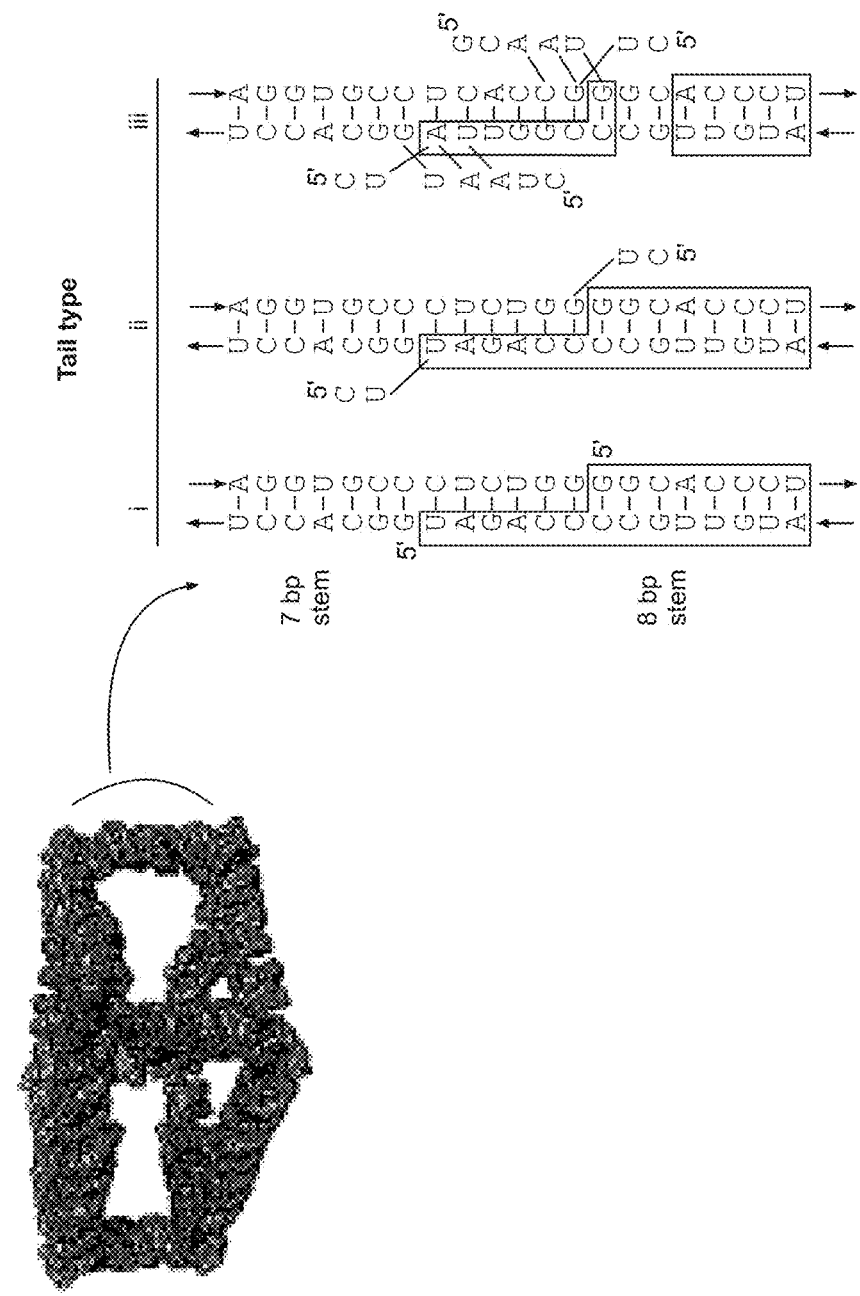
FIG. 34A discloses SEQ ID NOS 118-119 and 118-121, respectively, in order of appearance.
Figures 34B, 34C:
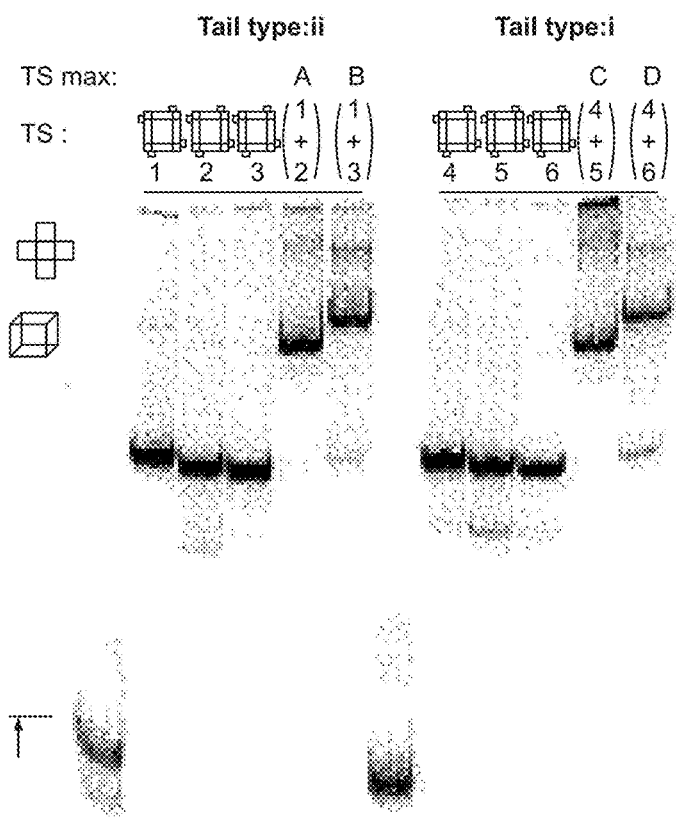
FIG. 34 (A-C) illustrates designing a cuboid with different types of tail connectors. A) shows secondary structure diagrams corresponding to different type of tail connectors. Type (i) is the regular 6 bp single stranded tail, type (ii) connector has an additional triple helix interaction coming from the 2 by overhangs at the 3' end, type (iii) connector has triple helix interactions on both 5' and 3' ends. B) shows characterization of tRNA supramolecular assemblies by a non-denaturing PAGE at 2 mM Mg(OAc)2 of tRNA units assembling into tectosquares and cuboids. Lanes 1 to 3 are tectosquares (100 nM) with tail connector type (ii) that assemble to form a cuboid (50 nM) (TS mix 1 and 2) and an open octamers (50 nM) (TS mix 1 and 3). Lanes 4 to 6 are tectosquares with tail connector type (i) that assemble to from a cuboid and an open octamers. C) shows quantification of the gel shows a 10% increase in the cuboid yield when the cuboid has triple helix tail connectors instead of regular tails (Lanes A vs. C).

Three types of 3'-tail connectors have been designed and tested (FIG. 34 A). Tail connector type (i) is a 6 by long single stranded RNA that protrudes from the 3' end of the variable stem of tRNA-tectoRNAs. To uncouple the tectosquare association from the cuboid association the tail connectors were chosen to be less stable by—2 orders of magnitude than those of KL complexes that are used as interface connectors within the tectosquare. Thus, by simply tuning the association temperatures it is possible to hierarchically control the cuboid assembly process. However, in order to rigidify the sides of the cuboids a more stable tail-tail connector is needed. Therefore, we rationalized that the usage of triple helix motif, whose sequence was based on a conserved motif identified within the structure of Tetrahymena group I ribozyme192, could potentially stabilize tail connectors.

There are two possibilities in designing tail-connectors that are stabilized with triple helix interactions. In connector type (ii) (single triple helix) a two by overhang that protrudes from the 3'end of the 6 by tail region formed a triple helix interaction with the variable stem. In connector type (iii) (double triple helix), in addition to the interaction mentioned in the connector type (ii) a 3 by overhang that protrudes from the 5'-end formed a triple helix interaction with the 6 by tail region with low yields (data not shown). Cuboids were successfully assembled using the connectors (i) and (ii) (FIG. 34 B), however. The assembly yields estimated from native-PAGE indicated that using a single triple helix motif in the tail-tail connectors increased the assembly yield by 10% (FIG. 34 C).

Having verified that cuboids with the tail connector type (ii) had the highest yield of formation, further design optimizations were performed on this cuboid. Next, the number of base pairs in the variable stem was optimized. According to the 3D computer model of the cuboid, variable stem length of 7 by on one side and 8 by on the other was the best conformation. However, due to the flexibility of the variable stem of tRNAs the number of by on each side still needed to be optimized. For this purpose, nine different cuboids were generated (with tail connector type ii) from six different tectosquares with variable stem lengths varying from 7 to 9 by (Table 4, below). Moreover, 18 additional cuboids were generated by using tail type (iii) in part A (TS1) or part B (TS5). The cuboids were assembled in presence of 15 mM Mg2+ at 60° C. and characterized using native-PAGE (FIG. 35 A). The assembly yields estimated from the native-PAGE indicated that the yield of formation could be increased up to 60% with the tail combination (ii/ii). On the other hand, using double A variety of cuboids were generated in the presence of 15 mM Mg2+ by using varying combinations of three different tail connectors. Native-PAGE characterization of cuboid assemblies indicated that the cuboids with tail-connector (iii) on both sides assembled with low yields (data not shown). Cuboids were successfully assembled using the connectors (i) and (ii) (FIG. 34 B), however. The assembly yields estimated from native-PAGE indicated that using a single triple helix motif in the tail-tail connectors increased the assembly yield by 10% (FIG. 34 C).

Having verified that cuboids with the tail connector type (ii) had the highest yield of formation, further design optimizations were performed on this cuboid. Next, the number of base pairs in the variable stem was optimized. According to the 3D computer model of the cuboid, variable stem length of 7 by on one side and 8 by on the other was the best conformation. However, due to the flexibility of the variable stem of tRNAs the number of by on each side still needed to be optimized. For this purpose, nine different cuboids were generated (with tail connector type ii) from six different tectosquares with variable stem lengths varying from 7 to 9 by (Table 4). Moreover, 18 additional cuboids were generated by using tail type (iii) in part A (TS1) or part B (TS5). The cuboids were assembled in presence of 15 mM Mg2+ at 60° C. and characterized using native-PAGE (FIG. 35 A). The assembly yields estimated from the native-PAGE indicated that the yield of formation could be increased up to 60% with the tail combination (ii/ii). On the other hand, using double triple helix interaction (cuboids with tail combinations ii/iii and iii/ii) decreased the yield of assembly in both cases (FIG. 35 B). Optimizing the folding protocol along with the concentrations of monovalent and divalent ions has been the next step of this research. Preliminary results showed that in the second step of the assembly protocol (appendix C materials and methods) high Mg2+ concentrations (15 mM) were necessary in order to avoid smeary products in gels. However once the cuboid is stabilized, the Mg2+ concentration in the gel and the buffer could be reduced without disrupting the tail-tail interaction. For this reason, native-PAGE gels were run in presence of 2 mM Mg2+.

Figure 36A:
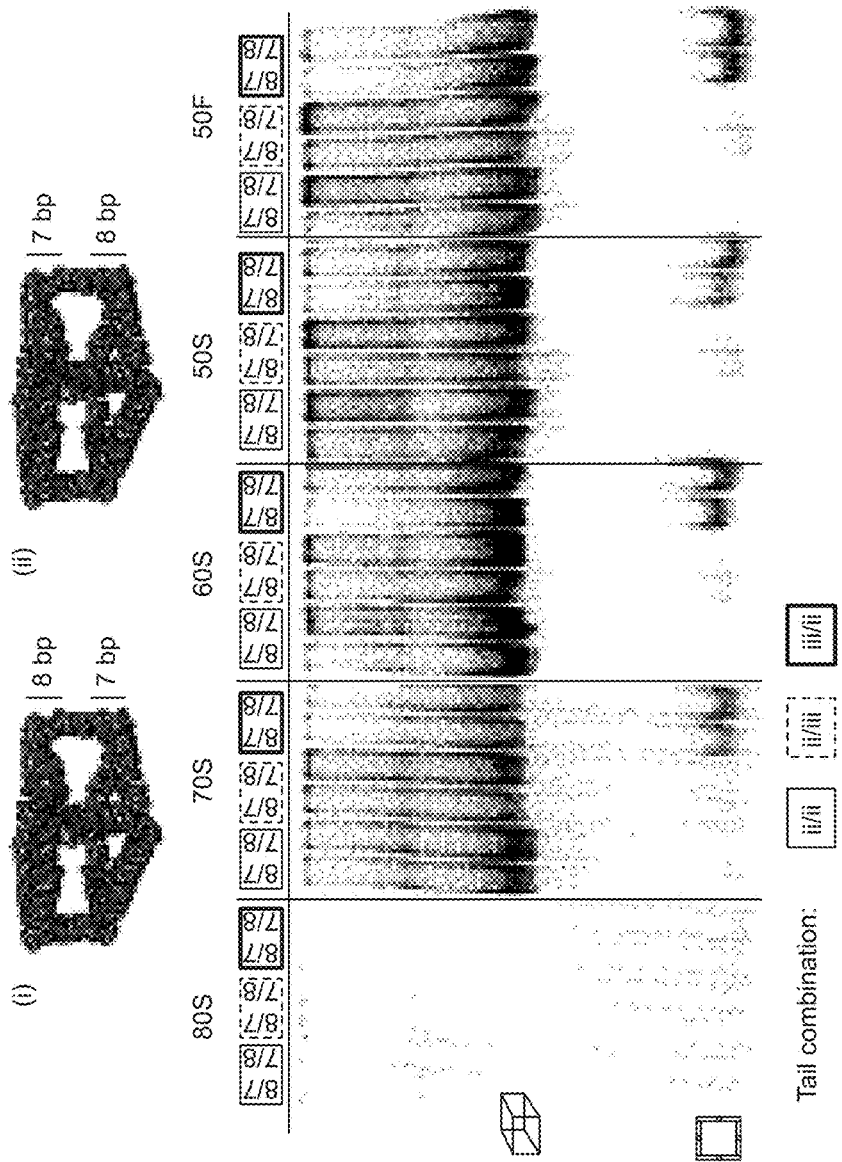
FIG. 36 shows optimization of cube association protocols. A 100 nM tectosquares were mixed and incubated at various association temperatures ranging from 50 to 80° C. in presence of 15 mM Mg(OAc)2. The resultant cuboid assemblies were characterized by a non-denaturing PAGE at 2 mM Mg(OAc)2. Six different cuboids were generated with variable stem length of 8 bp/7 bp (b/0 and 7 bp/8 bp (c/e) or varying the type of tail connectors on each side (ii/ii green), (ii/iii yellow) and (iii/ii blue). B) shows quantification of the gel shows that the highest cube yield is obtained when the tectosquares are incubated at 60° C. and slow cooled (S) to 10° C. irrespective of the variable stem length (except combination ciii/fii). Tail combination (ii/ii) and (ii/iii) also had the highest cuboid yield. C) is a schematic diagram corresponding to different cuboid association protocols. Following the tectosquare association (step 1), the tectosquares are mixed in presence of 15 mM Mg(OAc)2 and incubated at different temperatures for various incubation times and either slow (S) (cooling rate 1° C./min) or fast (F) cooled to 10° C.
Figure 36B:
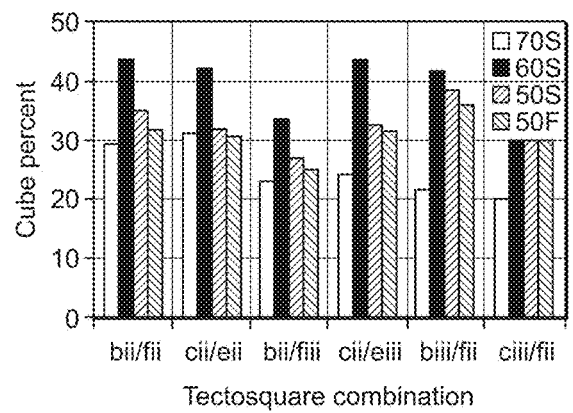
Figure 36C:
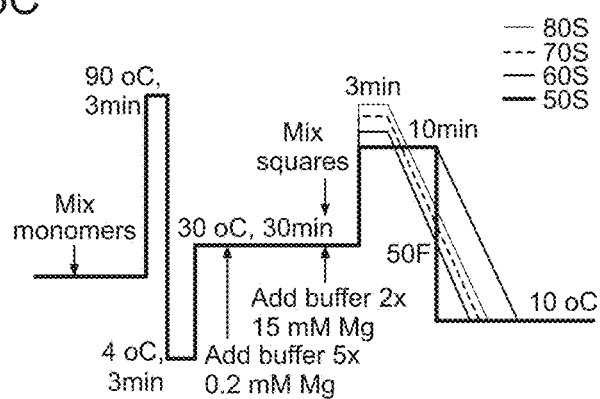

The annealing temperature and the incubation time during the second step of assembly protocol were also optimized (FIG. 36). The cuboids with variable stem size of 8 and 7 base pairs were selected (b/f and c/e) due to their high assembly yields. Five different association protocols were tested on six different cuboids with stem size combinations 7/8, 8/7 and tail combinations (ii/ii), (ii/iii) and (iii/ii). A schematic of various assembly protocols that have been tested is presented in FIG. 36 C. Following the square association step at 0.2 mM Mg2+, the tectosquares were annealed at various temperatures ranging from 50 to 80° C. in presence of 15 mM Mg2+. In addition to various incubation temperatures, the effect of slow (S) and fast (F) cooling has also been investigated. The yields of various cuboid assemblies were compared as estimated from the native-PAGE essays (FIG. 36 B). Of these association protocols, protocol 60S produced the highest cuboid yield.

TABLE 4

| Cuboid-part A Tectosquare TS1 | | Cuboid-part B Tectosquare TS5 | |
|---|---|---|---|
| Tectosquare | Var. stem (bp) | Tectosquare | Var. stem (bp) |
| a | 9 | d | 9 |
| a | 9 | e | 8 |
| a | 9 | f | 7 |
| b | 8 | d | 9 |
| b | 8 | e | 8 |
| b | 8 | f | 7 |
| c | 7 | d | 9 |
| c | 7 | e | 8 |
| c | 7 | f | 7 |

Example 18. Building Complex Supra-Molecular Assemblies Using tRNA Tectosquares

Figure 37A:
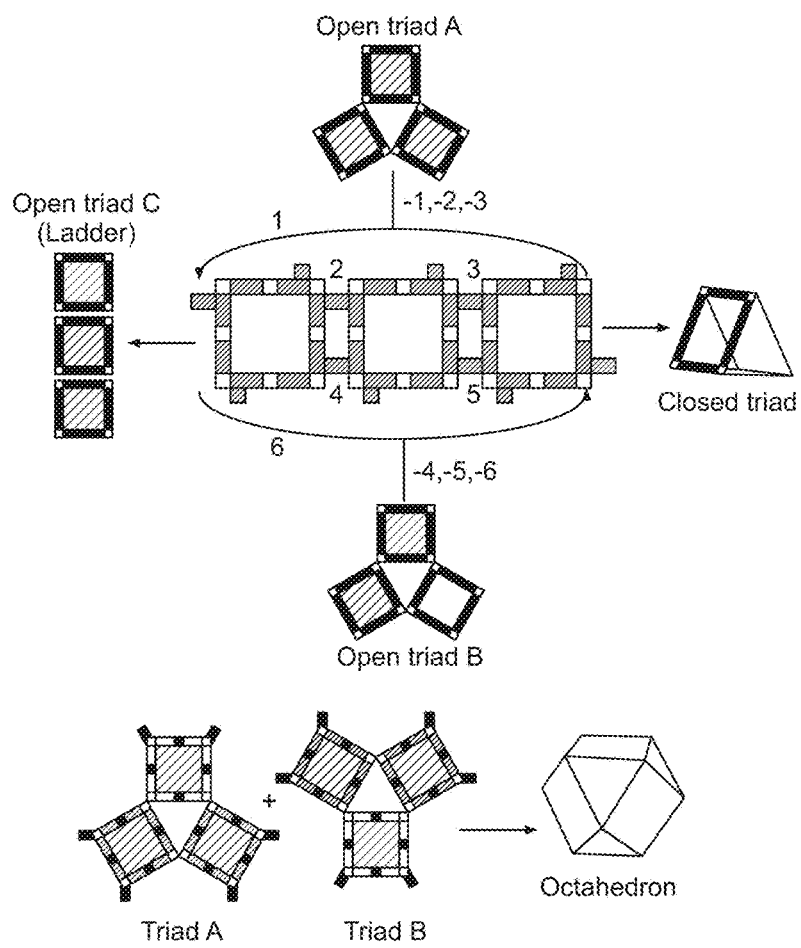
FIG. 37 shows building complex supra-molecular assemblies using three tectosquares. A Schematic diagrams that show the assembly of complex architectures to from closed triad (prism) open triad and ladder. Open triads A and B can be further designed to assemble into an octahedron by complementary 3'-tails. Tail programmations of tectosquares Si to S I are listed in the Tables. B Supra-molecular architectures closed triads (130 nM), and open triads A and C (130 nM) were assembled in presence of 15 mM Mg(OAc)2 and characterized by a non-denaturing PAGE at 2 mM Mg(OAc)2. For comparison tectosquares (400 nM), cuboid (200 nM) and open octamers (200 nM) were also loaded onto the gel. The association conditions for closed triads were optimized (inset). Open triads were associated using protocol 40S (inset). Comparison of gel shifts of prism (closed triad) and open triads indicate a faster gel migration for prism due to the compaction of the structure.
Figure 37B:
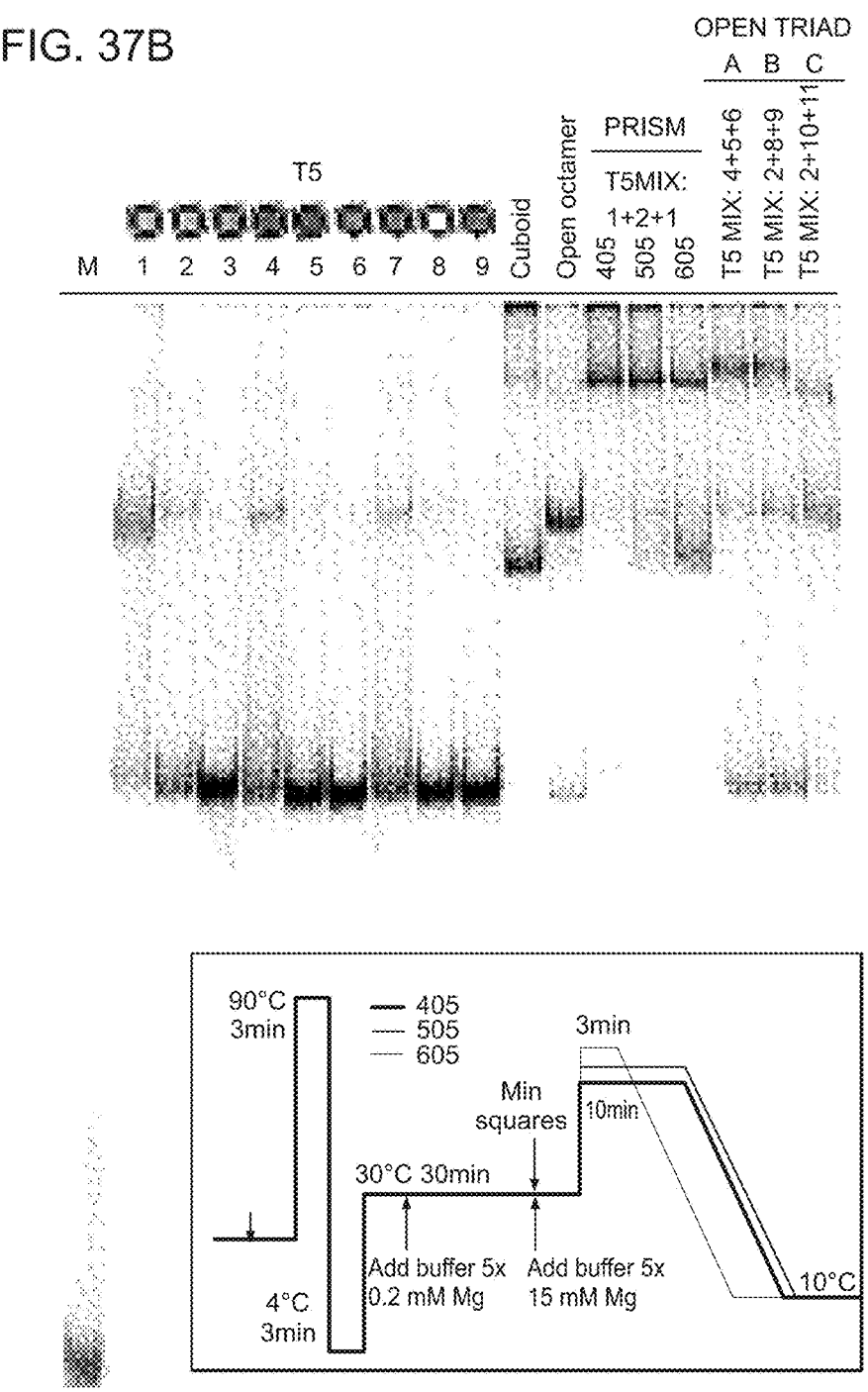

So far, supra-molecular assemblies based on variations of two tRNA-tectosquares were used to generate closed octamers (cuboids), open octamers (open cuboids) and tetramers of tectosquares. However, due to the flexibility of the tRNA variable stem it is possible to design more complex supra-molecular assemblies. In this section, the design and characterization of complex architectures based on variations of three tectosquares is presented (FIG. 37 A). These architectures are composed of twelve different tectoRNAs that use different, specific 3'-tail sequences and thus are fully programmable and addressable. There are 6 different 3'-tails that direct the supra-molecular assembly and by knocking out some of these interface points it is possible to rationally design closed and open triads. The first architecture is a closed triad in the shape of a triangular prism, which was obtained by programming the three tectosquares to have all six of the complementary 3'-tails. The second type of architecture is an open triad obtained by knocking out half of the 3'-tail interactions. Open triad A was designed by knocking out the 3'-tail interactions in locations numbered 1, 2 and 3. Similarly, open triad B was generated by knocking out 3'-tails numbered 4, 5 and 6. Alternatively, by knocking out only two of the 3'-tail interactions (1 and 6) an open triad in the shape of a ladder can be designed (open triad C). Eventually, triads A and B can be further designed to self-assemble through complementary 3'-tails to form more complex polyhedra in the shape of an octahedron.

Triangular prism, open triads and ladder were assembled in presence of 15 mM Mg2+ and characterized by native-PAGE (FIG. 37 B) using the same folding and assembly conditions as cuboids. The assembly and folding protocols for closed triads were also optimized by testing different incubation temperatures (FIG. 37 B inset). The results suggested that incubating the tectosquares at 40° C. followed by slow cooling gave the highest yield for prism. The migration of tectosquares, cuboids and open octamers were also compared by native gel. The results indicated that the supra-molecular assemblies composed of three tectosquares migrated well above the cuboid and open octamer bands. As triads are lower mobility products compared to cuboids, this result was in agreement with our estimations. Moreover, the migration rate of open triads (A and B) was slower compared to that of closed triads, which may indicate that the prism formed a compact architecture due to the closure of tectosquares. Using the association protocol at 40° C. the yield of correctly assembled closed triads is 44%, open triad A and B ~30%, and ladders (C) ~15%, as estimated from native-PAGE analysis. The low assembly yield of open triad C may be a result of destabilization of the supra-molecular assembly due to the knocked out 3'-tails (1 and 6), which may have forced the dissociation of the open triad into open octamers and tectosquares.

Figure 38D:
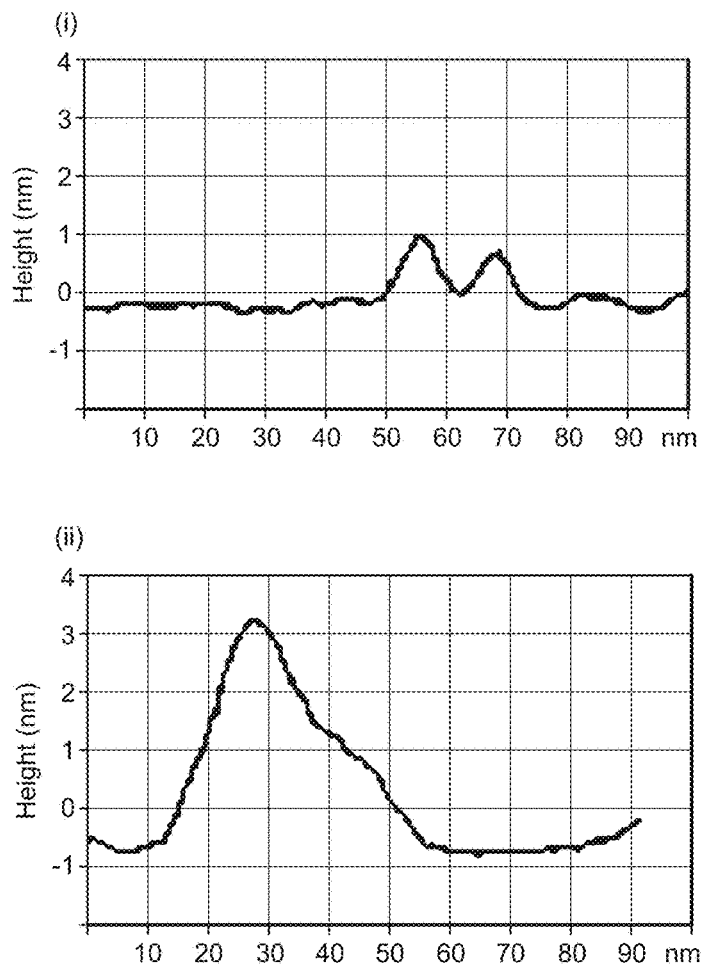
FIG. 38 (A-C) shows diagrams and AFM images of supra-molecular assemblies that are generated using three tectosquares. 200 nm and 50 nm scale AFM images were obtained in air for A) open triad-B) closed triad and C) open triad-(ladder). Tectosqures were assembled in solution in presence of 15 ml114 Mg(OAc)2 prior to imaging and the resultant assembly (130 nM) was deposited on a mica surface (see materials and methods in Appendix C). D Comparison of height profiles obtained from AFM analysis for (1) open triad and (ii) closed triad.
Figure 40:
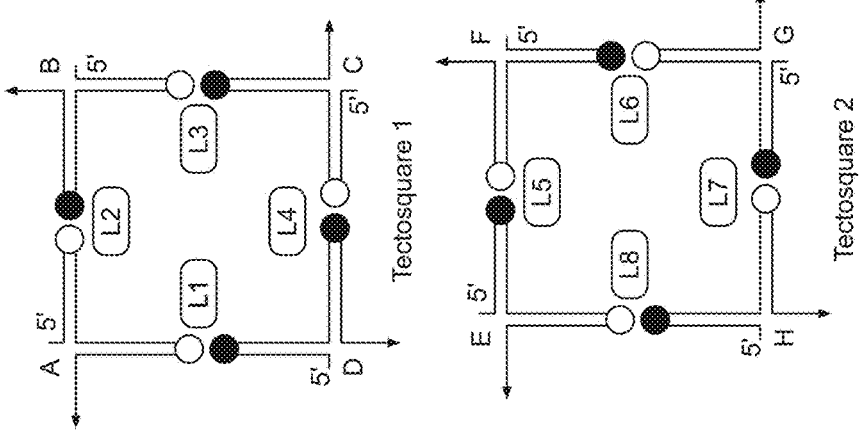
FIG. 40 shows a fully addressable cuboid was designed to self-assemble from eight different building blocks that contain eight different kissing loop complexes. This figure shows the programmations of loop-loop interactions used in tectosquare 1 and tectosquare 2.

The topologies of closed and open triads were further characterized using AFM. The constructs were assembled in solution in presence of 15 mM Mg2+ prior to loading on to the freshly cleaved mica surface as described previously (Appendix C Materials and methods). The images were acquired under tapping mode in air (FIG. 38). Open triads were observed to assemble into two dimensional finite-size triangular arrays, in agreement with the design (FIG. 38 A). On the other hand, closed triads were observed to assemble into compact architectures (FIG. 38 B). Open triads (triad C) that were programmed to form ladders were able to assemble into linear assemblies (FIG. 37 C); however, it was not possible to obtain a good yield of finite size nanoparticles, possibly due to the poor sequence design of 3'-tails that lead to unspecific assemblies. Open triad heights were all measured to be ~1.5 nm, consistent with the previously observed height for a tectosquare on a mica surface. The average height of a closed triad was measured to be ~4 nm, which is higher than that of an empty cuboid (FIG. 38 D ii). This result may be due to the fact that the prisms will most likely land on the mica surface laying on top of a tectosquare, while the edge of the prism will point upward. Due to the tensegrity principles of triangular objects, the prism may resist to deformation more than a cuboid does under the force applied by the AFM tip. The design of complex architectures may eventually be improved by using specific 3'-tails to avoid mispairings between the non-complementary 3'-tails. Thus it would be possible to generate supra-molecular architectures with high yield and homogeneous size population.

Example 19. Control of RNA Structure by the Use of Carbocyclic Sugars Constrained to North and South Conformations Carbocyclic sugars in modified nucleotides constrained to north/south conformations have A/B form (C2'/C3' exo) that can alter the helical properties of RNA duplexes and rigidify nucleotides due to their locked sugar puckers. In the experiments described herein, molecular dynamics (MD) simulations are used to study an RNA dodecamer and an HIV kissing loop complex, where several nucleotides are replaced with north and south constrained sugars. The overall dynamics of a modified RNA dodecamer where nucleotides are replaced by north constrained sugars show A form helix behavior, while a modified RNA dodecamer where nucleotides are replaced with south carbocyclic sugars show B-form DNA like behavior. The HIV kissing loop complex was modified by substituting north and south constrained sugars into flanking base and stem regions. The modified kissing loop complexes showed lower overall RMSD than the unmodified one. It was also found that the closed and open conformations of flanking bases in the kissing loop complex could be controlled by substituting north or south constrained sugars at specific positions. These results suggest that the proper use of north and south carbocyclic sugars can control helix conformations and stabilize RNA complexes thereby they can be used for RNA nanoparticle design to control shapes and chemical properties.

Most RNA structures (82%) in the protein data bank (PDB) which satisfy a minimum resolution of 3.0 Å have north (C3' endo) sugar pucker conformations, while a small number (10%) of the sugar puckers have south (C2' endo) conformations (Wadely, L. M. et al. (2007) J. Mol. Biol., 372, 942-957). RNA duplexes have A-form helix and backbone dihedral angles that are different from B-form DNA duplexes (Foloppe, N. et al. (2000) J. Comp. Chem., 21, 86-104). By using modified sugar puckers (Marquez, V. E. et al. (1996) J. Med. Chem., 39, 3739-3747; Wang, P. et al. (2000) J. Am. Chem. Soc., 122, 12422-12434) it is possible to induce deformations in the RNA structure. Modified nucleotides which have a north (or south) constrained sugar can lock the pseudo-rotational angle within the range of a north (south) conformation (Rodriguez, J. B. et al. (1993) Tetrahedron Lett., 34, 6233-6236; Altmann, K.-H. et al. (1994) Tetrahedron Lett., 35, 2331-2334; Rodriguez, J. B. et al. (1994) J. Med. Chem., 37, 3389-3399; Altmann, K.-H. et al. (1994) Tetrahedron Lett., 35, 7625-7628; Ezzitouni, A. et al. (1995) J. Chem. Soc., Chem. Commun., 13, 1345-1346; Siddiqui, M. A. et al. (1996) Nucleosides Nucleotides, 15, 235-250) in the pseudo-rotational cycle (Altona, C. et al. (1972) J. Am. Chem. Soc., 94, 8205-8212; Saenger, W. (1984) Springer-Verlag, New York, 51-104). One and two pairs of thymidine analogs containing north constrained sugars were substituted into the central region of the palindromic Dickerson dodecamer DNA, d(CGCGAAT-TCGCG)2 (SEQ ID NO: 75) (Wu, Z. R. et al. (2005) Proc Natl Acad Sci USA, 102, 24-28; Macias, A. T. et al. (2007) Biopol., 85, 438-449). The modified DNA structures showed more bending than the unmodified DNA. The structural bending depended on the number and the position of substituted modified thymidine pairs (Wu, et al. (2005); Macias et al. (2007); Wing, R. et al. (1980) Nature, 287, 755-258). The local structure near the modified thymidine pairs deformed into an A-form like helix.

A similar study was performed with Locked Nucleid Acid (LNA) (Pande, V. and Nilsson, L. (2008) Nucleic Acids Res., 36, 1508-1516), which has an RNA-like sugar conformation (C3' endo) induced by linking O2' and C4'. Due to the strongly locked sugar, LNA-RNA, LNA-DNA and LNA-LNA duplexes (Bondensgaard, K. et al, (2000) Chemistry, 6, 2687-2695; Nielsen, K. E. et al. (2000) Bioconjug. Chem., 11, 228-238; Petersen, M. et al. (2002) J. Am. Chem. Soc., 124, 5974-5982; Nielsen, K. E. et al. (2004) Bioconjug. Chem., 15, 449-457) adopt an A-form helix geometry and, for example, about 50% of the sugar puckers of the DNA strand in the LNA-DNA hybrid maintained north conformations. Therefore, it is possible to use LNA to lock the sugar pucker in a north conformation and rigidify or induce deformations in RNA. However, LNA has only the north sugar conformation and due to the O2'-C4' linkage, it does not have a 2'-hydroxyl. Therefore, the use of LNAs presents limitations on studying RNA structures where north and south constrained sugars and 2'-hydroxyls are necessary for specific geometries and chemistries.

Conformationally locked nucleotides (north and south) can be used for developing RNA based nano applications, for example tectosqares as described herein. One of these nanopatterns is a tectosquare ladder (Koyfman, A. Y. et al. (2005) J. Am. Chem., Soc., 127, 11886-11887), which was constructed by linear tectosquares assembly. Furthermore, the tectosquare can be used to form a ladder-like assembly with gold nano particles bound in the central openings of the tectosquare. Besides the square shapes of the nano particle design, circular multimer structures were also constructed by the assembly of a 56-mer RNA substrate, which contained two hairpin loops (Horiya, S. et al. (2003) Chem. & Bio., 10, 645-654). Another unique example of an RNA nano particle is the RNA hexagonal nanoring and RNA nanotube (Yingling, Y. G. et al. (2007) Nano Lett., 7, 2328-2334), as described herein, and in PCT/US2007/013027, incorporated by reference in its entirety herein. Compared to tectosquares and circular multimer assemblies, which can be expanded in the two-dimensional plane, the RNA hexagonal ring made by the assembly of RNAIi and RNAIIi kissing loops having a 120° corner angle may be used to build RNA nanotubes by stacking several RNA hexagonal rings along the tube axis. The RNA nanoring structure and RNA nanotubes can essentially be used as a delivery vehicle for siRNA therapeutics (Yingling et al. (2007)).

Figure 41F:
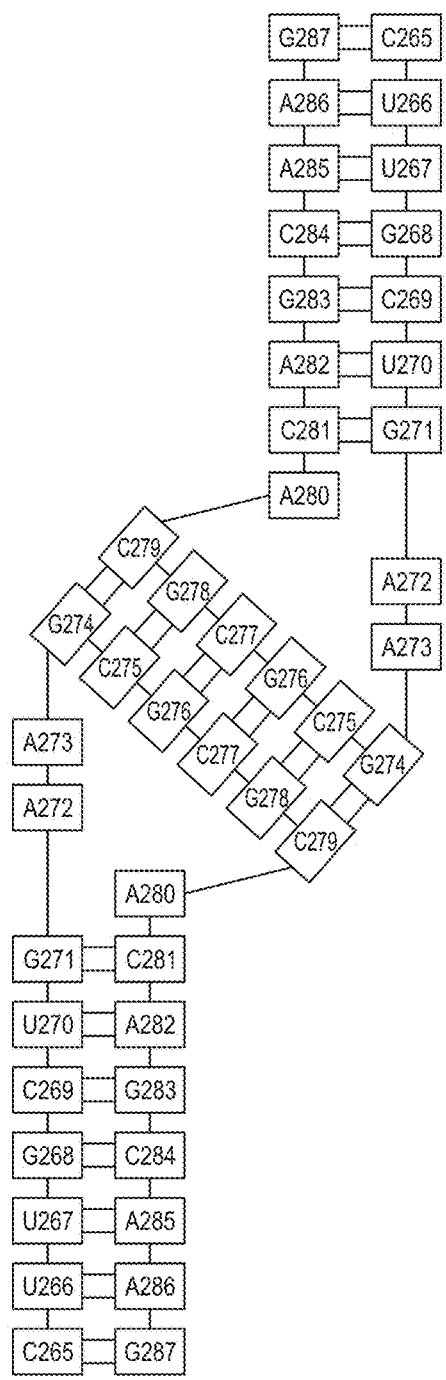
FIG. 41f discloses SEQ ID NOS 202 and 202.
Figure 42A:
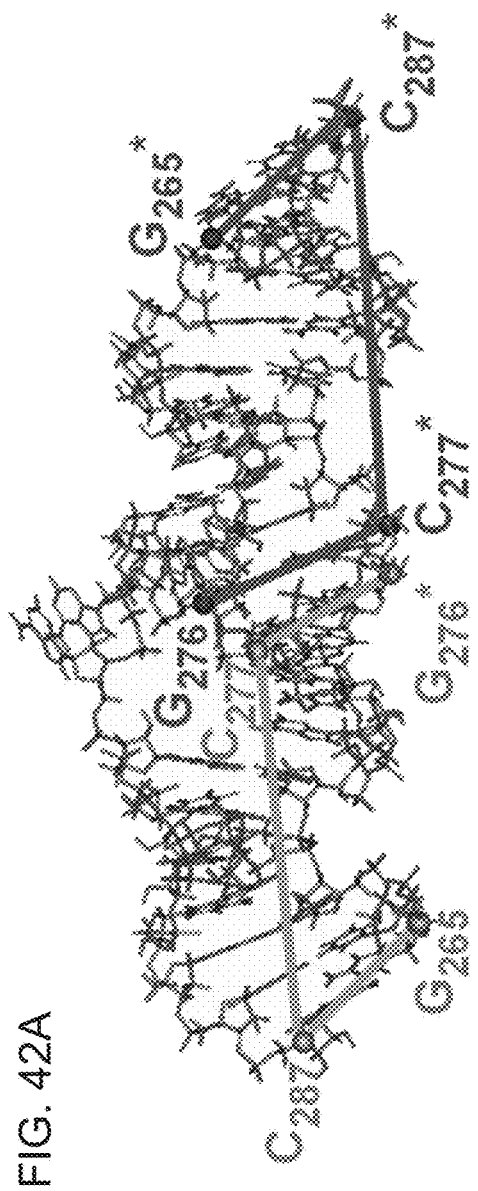
FIG. 42 shows (a) Twist motion is determined by measuring the torsion angle using the C4' atoms of C265, G287, C277, and G276* and the corresponding torsion angle on the other side (C4' at C265*, G287*, C277*, and G276). (b) structure bending is determined by measuring the average angle along the center of mass of C265 and G287, center of mass of G276, C277, G276*, and C277*, and the center of mass of C265* and G287*.

In the results presented here, the overall control of the structure and dynamics of RNAs imposed by the bicyclo [3.1.0]hexane structure of the modified nucleosides which contain an embedded cyclopentane ring constrained in either the north (FIG. 41(a)) or south (FIG. 41(b)) conformation depending on the location of the fused cyclopropane ring are examined. North or south modified nucleotides were substituted into an RNA 12mer dodecamer (5'-CGC-GAAUUCGCG-3' (SEQ ID NO: 76)) to investigate the role of north/south locked sugars on an RNA helix. The north modified nucleotide sugar pucker has a C2' exo (north) conformation on the pseudo-rotational cycle (Marquez (1996); Wang (2000)) and backbone dihedral angles that are the same as those of an RNA helix (Foloppe(2000)). However, the south modified nucleotide sugar pucker has a C3' exo (south) conformation with a backbone dihedral angle and sugar pucker belonging to the class of a B-form DNA. The Carbocyclic ring in both the modified sugars is locked to either a north or a south conformation and by appropriate substitution can rigidify and deform a structure.

One of the frequently used RNA structures in developing RNA nanoparticles is the kissing loop structure. RNA tectosquares (Chworos, A. et al. (2004) Sci., 306, 2068-2072 and circular multimers; Koyfman(2005); Horiya, S. et al. (2003) Chem. & Bio., 10, 645-654) are designed by using the dimerization initiation site (DIS) of the human immunodeficiency virus (HIV) and some selected mutant forms. In HIV-1, flanking purines A272 and G273(A273) in subtype A (MAL) and subtype B (Lai) in an x-ray structure (pdb code: 1XPF and 1XPE, respectively) are bulged out and stacked in pairs forming an open conformation (FIG. 41 (c)), while purines A272 and A273 in subtype F (pdb: 1ZCI) form a closed conformation (FIG. 41 (d)) (Ennifar, E. (2006) J. Mol. Biol, 356, 771-782). In the x-ray structure, the sugar puckers of all of the nucleotides in the subtype A and B kissing loop complex have a 3'-endo (north) conformation, except A271 and G(A)273 and their symmetrically placed nucleotides (A271* and G(A)273*) which have sugar puckers that are in a C2'-endo (south) conformation. Revlova et al. reported MD simulation results indicating that the sugar puckers of G271, A272, G(A)273, and the counterpart bases in subtype A and B oscillate between north and south conformations (Reblova, K. et al. (2007) Biophy. J., 93, 3932-3949; Reblova, K. et al. Nucleic Acid Res., 31, 6942-6952). During 30 ns of MD simulation with or without the presence of Mg2+ ions, the flanking bases in subtype A form non-closed conformations, locked stacked and 3R bulged out conformations where three bulged out flanking bases stack on each other, while one flanking base is bulged-in (see FIG. 41(e)). On the other hand, an open conformation of flanking bases in subtype B convert to a closed conformation in the presence of Mg2+ ions while without the presence of Mg2+ ions the flanking bases form a bulged-in and a bulged-out conformation. However, even in the presence of Mg2+ ions in subtype B, the time duration of a closed conformation is only 13 ns out of a total of 30 ns MD simulation time. In certain exemplary experiments, explicit solvent molecular dynamics simulations were used to study modified subtype B HIV kissing loop structures in which both north and south constrained sugars were substituted at various locations (see FIG. 41(f) for the secondary structure of subtype B). This replacement with constrained sugars locks the sugar pucker to either a north or a south conformation and therefore increases or prevents the possibility of forming a closed conformation. In addition, north constrained sugars were substituted into the HIV kissing loop stems in order to reduce the overall flexibility. Therefore, the proper use of specific north or south constrained sugars in RNA structures can induce certain deformations and stability and control the characteristics of potential building blocks in designing RNA nano particles.

Amber antechamber (Wang,B et al. J. Chem. Theory Comput., 2, 209-215) was used to assign atom and bond types to modified north and south nucleotides which contain north or south constrained carbocyclic sugars. Nucleic acid force fields were determined for the modified nucleic acids based on the atom and bond types. Dihedral force parameters for the north and south carbocyclic sugars were obtained from previous ab initio calculations (Wang (2000)). These parameters were applied to the constrained carbocyclic sugars in the modified nucleotides after scaling. ab initio calculations are performed using the GAUSSIAN suite of programs to compute the electrostatic potential (ESP). ESP was fit using restrained electrostatic potential (RESP) charge fitting with antechamber and the resultant partial charges were used for the modified north and south nucleotides. Once all of the force fields were prepared for the modified north and south nucleic acids, molecular dynamics (MD) simulations were applied to the modified nucleotide sugar pucker to see if they maintained the proper sugar puckers (north and south) in a vacuum and in explicit solvent.

A 12mer RNA palindromic dodecamer (5'-CGC-GAAUUCGCG-3' (SEQ ID NO: 76) was prepared with Accelrys DISCOVERY STUDIO. Modified north nucleotides were substituted into the RNA dodecamer except at the 5' and 3' ends to build a north modified RNA dodecamer. Similarly a south modified RNA dodecamer was prepared by substituting modified south nucleotides into the even nucleotide positions (2nd, $4^{th}$, $6^{th}$, 8th and 10th) in both strands. For the HIV kissing loop complex, the x-ray structure of subtype B was used. In the subtype B HIV kissing loop complex, both G271 and A273 have a C2' endo (south) conformation, while all the other nucleotides have a C3' (north) endo conformation (Ennifar, E. and Dumas, P. (2006) J. Mol. Biol, 356, 771-782). In addition, the flanking bases (A272, A273, A272* and A273*) in the subtype B x-ray structure form an open conformation. North and south modified nucleotides were substituted at G271 and A273 to determine the effect of the modified nucleotides on the overall dynamics and the closed/open conformation.

All simulations were performed using ff99 Cornell force field (Mathieu, F. et al. (2005) 5, 661-665; Wang, J. et al. (2000) J. Comput. Chem., 21, 1049-1074) with the Amber 10 molecular dynamics (MD) simulation package (D. A. Case et al. (2008), AMBER 10; D. A. Pearlman et al. (1995) Comp. Phys. Commun., 91, 1-41; D. A. Case et al. (2005) J. Computat. Chem., 26, 1668-1688). Once the modified nucleotides were substituted into the RNA dodecamer or HIV kissing loop complex, initial energy minimization was performed to remove bad atomic contacts. All minimized structures were neutralized by Na+ ions (22 Na+ ions for RNA dodecamer and 44 Na+ ions for HIV kissing loop complex) using the XLEAP module in Amber 10. A TIP3P water box was added with a 15 Å distance from each side of the solute. The minimum distance between solvent and solute atoms was set to 0.832 Å. Particle mesh ewald summation (PME) (Essmann, U et al. (1995) J. Chem. Phys., 103, 8577-8593) was used to calculate the electrostatic interactions and the non-bonded interactions were truncated at 9.0 Å. Overall minimization of the system was done while using harmonic constraints on the RNA. This was followed by heating the system to 300K while constraining the solute with a 200 kcal/(molÅ) harmonic constraint. Constraints were slowly released while the system was equilibrated. During the 30 ns MD production run, a parabolic restraint on distance (3.0 Å, 10 kcal/(molÅ)) was applied to the hydrogen bonds in the 5' and 3' CG base pairs. Since the restraint was applied only when the hydrogen bond distance was greater than 3.0 Å, the applied restrained energy on the system for the 30 ns was very small. SHAKE (Ryckaert, J.-P et al. (1977) J. Comput. Phys., 23, 327-341) was applied to all hydrogens to remove the fastest hydrogen vibrations and to allow longer simulation time steps. The pressure was maintained at 1.0 Pa and a constant temperature of 300K was maintained using a weak-coupling algorithm (Berendsen, H. J. C et al. (1984) J. Chem. Phys., 81, 3684-3690). A production simulation was performed for 30 ns with a 2 fs timestep.

Dynamics of Modified and Unmodified RNA Dodecamers

Two modified RNA dodecamers were prepared by substituting north or south constrained sugars into the 12mer RNA dodecamer (5'-CGCGAAUUCGCG-3'). A north dodecamer was obtained by substituting north constrained sugars into all nucleotides in both strands except the 5' and 3' terminals. A south dodecamer was prepared by substituting south constrained sugars at even nucleotides ($2^{nd}$, $4^{th}$, $6^{th}$, $8^{th}$ and $10^{th}$) in both strands. These unmodified and two modified RNA dodecamers (north and south modified dodecamers) were studied using 30 ns standard explicit solvent MD simulations.

The average overall RMSD of the unmodified dodecamer (FIG. 43(*a*)) was 2.13±0.5 Å from the starting structure. During a 30 ns simulation, all sugar puckers maintained a north conformation except the terminal nucleotides. The average length of the unmodified dodecamer, whose distance was measured between the center of mass of each of the terminal bases for the last 20 ns was 31.65±2.27 Å. As indicated by the low RMSD, the overall helix stayed in the A-form during the simulation, but the α and γ backbone torsion angles of a few nucleotides deviated from the canonical values for short periods of time (less than 5 ns). In order to obtain the RMSD after relaxation, the overall RMSD was recalculated relative to the average structure which was obtained from the last 20 ns of the MD trajectory and the resultant RMSD is plotted in FIG. 44(*a*). The average value of the recalculated RMSD for the unmodified dodecamer was 1.7±0.4 Å.

Figure 44:
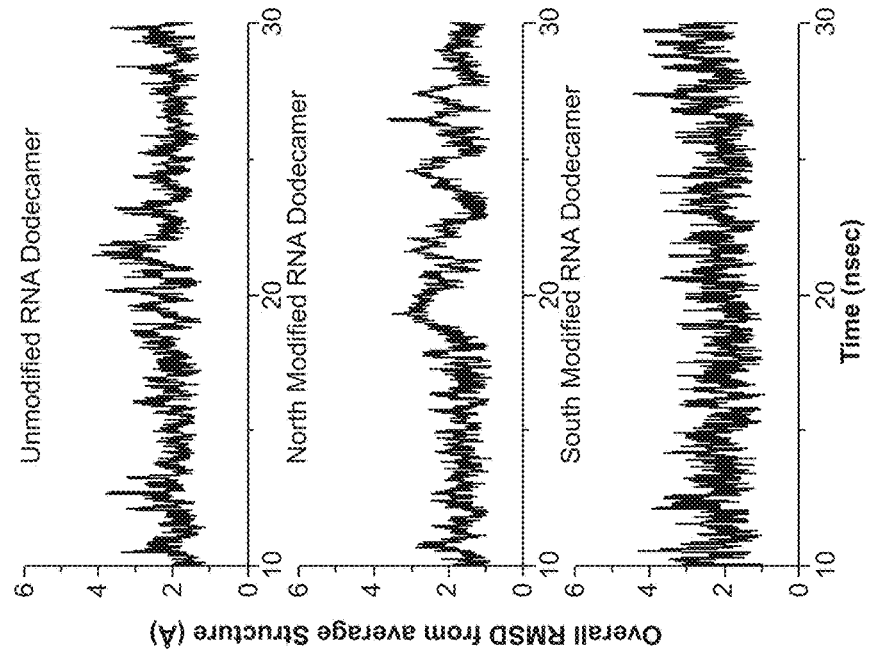
FIG. 44 shows overall RMSD of (a) unmodified dodecamer, (b) north dodecamer (all nucleotides are modified except 5' and 3' terminals) and (c) south dodecamer (2nd, 4$^{th}$, 6th, 8th and 10th nucleotides), relative to the average structure for 10-30 ns.
Figure 43:
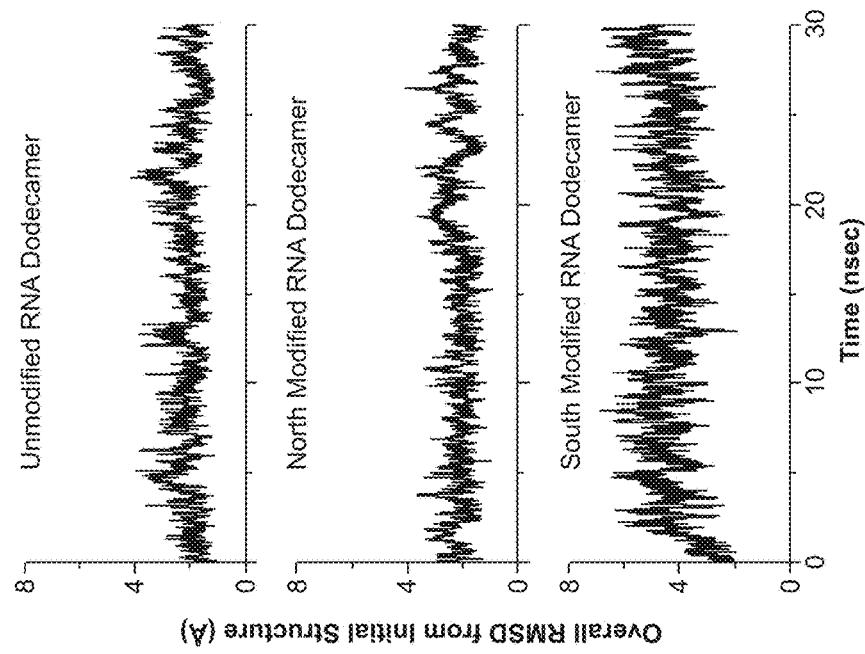
FIG. 43 shows overall RMSD of (a) unmodified dodecamer, (b) north dodecamer (all nucleotides are modified except 5' and 3' terminals) and (c) south dodecamer (2nd, 4$^{th}$, 6th, 8th and 10th nucleotides), relative to each initial structure.

The overall RMSD of the north modified dodecamer was 2.17±0.45 Å relative to the starting structure (see FIG. 43(*b*)) and the recalculated average RMSD for the 10-30 ns range (see FIG. 44(*b*)) was 1.5±0.37 Å, which is smaller than that of unmodified dodecamer. The average length of the north modified dodecamer for the last 20 ns was 28.77±2.27 Å, which is about 3 Å shorter than the unmodified dodecamer. The α and γ backbone torsion angles in the modified north dodeacmer, were more stable than those of the unmodified, due to the locked sugars. Therefore, the modified dodecamer maintained an A-form helix better than the unmodified one. The south dodecamer, however, showed the opposite behavior. As shown in FIG. 43, the overall RMSD behavior of the south dodecamer, which has a rapid increase before reaching a flat value after 5 ns, indicates that the dodecamer experiences large deformations due to the south constrained sugars relative to the beginning of the simulation. The average value of the overall RMSD of the south modified dodecamer relative to the starting structure was 4.38±0.78 Å, which is 2 Å greater than the previous two other cases, and the average RMSD for the last 20 ns in the south modified dodecamer was 1.58±0.37 Å, which indicated that the system was stabilized after rapid initial deformation. The north and south dodecamers show slightly smaller RMSDs and these results imply that both modified dodecamers reach better stability after 10 ns. RMSD results are listed in Table 6, below. Table 6 shows the average RMSDs, twist angles and bending angles. RMSD of 0-30 ns and 10-30 ns ranges are calculated relative to the corresponding time averaged structures. In HIV kissing loop complexes, torsion angles of stem1, stem2 and overall bending are also calculated.

TABLE 6

| | RMSD (Å) (0-30 ns) | RMSD (Å) (10-30 ns) | Twist (degree) | Bending (degree) |
|---|---|---|---|---|
| Unmodified dodecamer | 1.67 ± 0.4 | 1.69 ± 0.4 | N/A | N/A |
| North dodecamer | 1.54 ± 0.4 | 1.52 ± 0.4 | N/A | N/A |
| South dodecamer | 1.68 ± 0.6 | 1.58 ± 0.4 | N/A | N/A |
| Unmodified HIV kissing loop | 3.2 ± 0.8 | 3.0 ± 0.92 | −44.6 ± 17.6 −52.08 ± 12.3 | 150.7 ± 12 |
| $N_{271,273}$ | 2.47 ± 0.6 | 2.35 ± 0.7 | −49.1 ± 12.5 −49.27 ± 12.7 | 166.1 ± 7.33 |
| $N_{271}$ | 2.52 ± 0.6 | 2.57 ± 0.5 | −40.2 ± 13 −43.8 ± 12 | 160.3 ± 9.56 |
| $S_{271}$ | 3.26 ± 0.8 | 3.03 ± 0.7 | −51.3 ± 18.8 −42.0 ± 14 | 152.4 ± 12 |
| $S_{271,273}$ | 2.84 ± 0.7 | 2.68 ± 0.6 | −50.0 ± 13.4 −46.5 ± 13.4 | 159.6 ± 9.46 |

TABLE 6-continued

| | RMSD (Å) (0-30 ns) | RMSD (Å) (10-30 ns) | Twist (degree) | Bending (degree) |
|---|---|---|---|---|
| $N_{268,269,283,284}$ | 3.08 ± 0.9 | 2.67 ± 0.7 | −68.4 ± 21.7 −45.5 ± 17 | 150.5 ± 9.37 |
| $N_{storms}$ | 2.6 ± 0.6 | 2.37 ± 0.6 | −23.9 ± 14 −36.06 ± 15 | 156.04 ± 8.2 |

Additionally, the RMSD of the 0-30 ns range relative to average structure of the 0-30 ns range shows that the north modified dodecamer is the most stable. The average backbone torsion angles for the last 20 ns is calculated and summarized in Table 7, shown below. Table 7 shows the average backbone torsion angles between 10-30 ns. First column is average backbone torsion angles of the unmodified dodecamer and the second column is the average dihedral angles of the north constrained sugars in the dodecamer. The third and fourth columns are the average backbone dihedral angles of the unmodified and the south modified nucleotides in the south modified dodecamer. The last columns are the backbone angles of a B-form DNA.

TABLE 7

| | South Dodecamer | | | | |
|---|---|---|---|---|---|
| | Unmodified RNA (A-form) | North Dodecamer | Unmodified NT | South Sugar NT | DNA (B-Form) |
| α | 285 | 270 | 270...150 | 263 | 300 |
| β | 180 | 180 | 180 | 180 | 180 |
| γ | 60 | 74 | 50...180 | 81 | 55 |
| δ | 75 | 75 | 75 | 143 | 140 |
| τ | 210 | 205 | 210 | 185 | 190 |
| ζ | 290 | 295 | 285 | 267 | 260 |
| χ | 195 | 190 | 190 | 227.5 | 255 |

The backbone torsion angles for the north modified dodecamer are within the range of an A form helix. Unmodified nucleotides in the south modified dodecamer ($1^{st}$, $3^{rd}$, $5^{th}$, $7^{th}$ $9^{th}$, $11^{th}$ and $12^{th}$ nucleotides) also maintain A-form helix backbone dihedral angles, however, other nucleotides which have south constrained sugars ($2^{nd}$, $4^{th}$, $6^{th}$, $8^{th}$ and $10^{th}$ nucleotides) show different backbone dihedral angles which are observed in a B-form DNA. Therefore, the overall shape of the south dodecamer has a mixture of A and B-forms in its helix and this caused the elongation of the overall structure to 40 Å. The dihedral angle, δ in a south constrained sugar is 145° and this value is larger than that of an A form helix (75°). The average distance between two phosphates connected to the backbone of south constrained sugars was 7.2 Å, while the average corresponding phosphates distances of unmodified sugars was 6.2 Å. The difference in phosphate distances between the unmodified (and north) and south constrained sugars in the south dodecamer explains the elongation of the structure and the initial rapid increase in the RMSD in the south modified dodecamer. This overall length difference between the unmodified (and north) and south modified dodecamers is also found in A and B-form dodecamer structures in the protein data base (pdb). The average phosphate distance in the 12mer RNA dodecamer (pdb ID: 280D) and the B-form DNA (pdb ID: 1BNA) is 5.7 Å and 6.7 Å respectively and end to end distances (distance between C4' at both ends) of the both structures are 27.32 Å and 37 Å respectively.

Overall Structure and Dynamics of the HIV Kissing Loop

North and south constrained sugars were substituted into various positions of the HIV kissing loop structure (subtype B, Lai). In order to control the conformation of the flanking bases (open or closed), north and south constrained sugars were substituted at $G_{271}$ and at both $G_{271}$ and $A_{273}$. North constrained sugars were also substituted into the HIV kissing loop stems to induce structural stability. Unmodified and modified HIV kissing loop structures were studied using 30 ns standard explicit solvent simulations.

Unmodified HIV Kissing Loop

The overall RMSD of the unmodified HIV kissing loop complex relative to the initial structure is plotted in FIG. 45(*a*) and the average RMSD value is 4.78±1.11 Å, which is very close to the RMSD value (4.78±1.2 Å) reported by Reblova et al. As stated in the methods section, two dynamic motions were monitored during the 30 ns MD simulation. Twist motion along the HIV kissing loop structure was determined by measuring the average dihedral angle along the C4' atoms of $C_{265}$, $G_{287}$, $C_{277}$, and $G_{276}$* and the C4' atoms at the corresponding nucleotides on the other side (FIG. 42 (*a*)). The structure bending was determined by measuring the average angle along the center of mass of $C_{265}$ and $G_{287}$, center of mass of $G_{276}$, $C_{277}$, $G_{276}$*, and $C_{277}$*, and the center of mass of $C_{265}$* and $G_{287}$, as shown in FIG. 42(*b*). During 10-30 ns, the average twist angles of both sides were measured as −44.6±17.5° and −52.1±12.3°, respectively. These values imply that the twisting motion was non-symmetric since one side of the structure was less twisted but more unstable than the other side of the structure. The bending of the structure was measured as 150±12°.

The x-ray structure of subtype B shows that both $G_{271}$, $A_{273}$ have a C2' endo (south) conformation. During the MD simulation, the sugar puckers of $G_{271}$, $A_{272}$ and $A_{273}$ oscillated between north and south conformations. For the first 20 ns, the $G_{271}$ sugar pucker oscillated between a north and a south conformation, and then it stayed in a north conformation for last 10 ns. The $A_{272}$ sugar stayed in a north conformation, except for the first 6 ns and 16-18 ns. The sugar pucker of $A_{273}$ maintained a south conformation except in the ranges of 10-12 ns and 23-27 ns. The sugar of $G_{271}$* had a south conformation for the first 10 ns and then flipped to a north conformation for the rest of the simulation. The sugar pucker of $A_{272}$ and $A_{273}$ maintained the north and south conformation respectively, except for short flips over to the other conformation for a few nanoseconds. The 4 flanking bases ($A_{272}$, $A_{273}$, $A_{272}$*, and $A_{273}$*) formed open conformations from the beginning of the simulation to 7.2 ns. Between 7.2 ns and 7.5 ns, both flanking bases, $A_{272}$, and $A_{273}$ formed a bulged-in conformation and after 7.5 ns, $A_{273}$ rotated back to the bulged-out conformation while $A_{272}$ stayed in a bulged-in conformation making hydrogen bonds with other bases ($A_{280}$, $C_{281}$ and $G_{274}$*). Once the three the flanking bases, $A_{273}$, $A_{272}$*, and $A_{273}$* stacked in a bulged-out conformation and $A_{272}$ was in a bulged-in conformation at about 7.5 ns, these flanking bases maintained this formation (3R bulged-out) for the rest of the simulation (see FIG. 41(*e*)). In order to understand the structural changes of the flanking bases before and after 7.5 ns, the distance between the phosphates was calculated for $G_{271}$-$C_{275}$. The summation of the average phosphate distances along $G_{271}$, $A_{272}$, $A_{273}$, $G_{274}$ and $C_{275}$ for the 10 to 30 ns time period was 26 Å. Since the sugar puckers of $G_{271}$, $A_{272}$, $A_{273}$ had a south conformations during the 30 ns MD simulation, the P-P distance of $G_{271}$-$C_{275}$ was larger than the corresponding P-P distance in the RNA dodecamer (24.5 Å). The ratio between the summation and the direct P-P distance along $G_{271}$-$C_{275}$ was 1.68 for 10-30 ns range. However, the calculated ratio between 0-7 ns, during which time the flanking bases were opened and did not stack on each other, was 1.9. Therefore, the phosphate distance ratio before and after 7.5 ns was changed due to the conformation of the flanking bases.

North Constrained Sugars at $G_{271}$, $A_{273}$ ($N_{271.273}$)

The nucleotides of $G_{271}$, $A_{273}$ were replaced with north constrained sugars, where the x-ray structures (pdb: 1JJM, 1XPE) indicate south conformations. Nucleotide $A_{272}$, which is located between $G_{271}$ and $A_{273}$, was left unmodified. During the 30 ns MD simulation, the pseudo rotational angles of the replaced nucleotides sugar puckers remained in a north conformation due to the locked sugar. The sugar pucker of $A_{272}$ stayed in a north conformation except between 10 ns and 15 ns and the $A_{272}$* sugar had a south conformation for the 20-21 ns range. Therefore, $G_{271}$, $A_{272}$, $A_{273}$ and their symmetrical counterparts formed north conformations for most of the time during the 30 ns MD simulation. One of the remarkable results is the closed conformation of flanking bases $A_{272}$, $A_{273}$, and $A_{272}$* and $A_{273}$*. Revlova et al. reported that the closed conformation of the wild type HIV kissing loop complex in the presence of $Mg^{2+}$ ions survived 13 ns in a 30 ns MD simulation (Reblova (2003)). However, the modified kissing loop complex, $N_{271.273}$ induced a closed conformation near 0.5 ns and maintained it for the rest of the simulation (29.5 ns) even without $Mg^{2+}$ ions. Thus, it appears that the average P-P distance of $G_{271}$-$C_{275}$ of this modified HIV kissing loop structure for the 10-30 ns range is more stable and smaller (25.4 Å) than corresponding value of the unmodified kissing loop (26 Å). In addition, the value of 24.5 Å is consistent with the average P-P summation distance of the 5 nucleotides in the RNA dodecamer. Therefore, the shorter P-P distance in the modified HIV kissing loop complex made the backbone near the flanking bases tighten and this optimized the backbone geometry, thus forming the closed conformation. In addition, the P-P distance ratio of the modified HIV kissing loop ($N_{271.273}$) for the 10-30 ns range was 1.662, which is similar to that of the unmodified HIV kissing loop in the same time range (3R bulged out). Once the flanking bases formed a closed conformation, HO'2 of $A_{273}$* formed a hydrogen bond with H62-N6 of $A_{272}$, and O2P at $G_{274}$ formed a hydrogen bond with H62-N6 of $A_{272}$*. These flanking bases, $A_{272}$ and $A_{272}$* enclosed the inner flanking bases ($A_{273}$ and $A_{273}$*) firmly with these hydrogen bonds and contributed to the stability of the closed conformation for the rest of the MD simulation.

The overall RMSD relative to the initial structure is plotted in FIG. 5(*b*). Compared to the average overall RMSD of the unmodified HIV kissing loop complex (shown in FIG. 5(*a*)), the modified HIV kissing loop complex ($N_{271.273}$) has a slightly higher RMSD (5.11 Å vs. 4.77 Å). However, as shown in FIG. 45 (*b*), the RMSD variation of $N_{271.273}$ is more stable than that of the unmodified HIV kissing loop complex (FIG. 45(*a*)), after 5 ns. As was done in the south modified RNA dodecamer, the first 10 ns MD trajectory was ignored to remove the initial deformations due to the modified nucleotides and the RMSD was recalculated for the 10-30 ns range relative to a reference structure, which was the average structure of the 10-30 ns trajectory. For the 10-30 ns range, the recalculated RMSD of $N_{271.273}$ is plotted in FIG. 46(*b*) and the average value of the recalculated RMSD is 2.35±0.7 Å. This value is lower than that of the unmodified HIV kissing loop complex in FIG. 6(*a*) (3.0±0.93 Å). The RMSD that was obtained by the same method for the 0-30 ns range also showed a lower value compared to those of the unmodified HIV kissing loop (See Table 6). This result indicates that the north constrained sugars near the flanking bases reduces the RMSD after the initial 10 ns relaxation. The lowered RMSD in the modified HIV kissing loop complex ($N_{271.273}$) can be explained by monitoring the stabilities of the twist and the bending motions. During the 10-30 ns trajectory, the average twist dihedral angles of stem1 and stem2 in the modified kissing loop, $N_{271.273}$ were −49.1±12.5° and −49.3±12.7°, respectively. Compared to the asymmetrical twist motion in the unmodified HIV kissing loop complex, the modified HIV kissing loop complex showed a very symmetrical twist motion. Also, the average bending for the 10-30 ns range was 166±7.33°. Therefore, north constrained sugars at $G_{271}$, $A_{273}$ contributed to the reduction of the overall RMSD by stabilizing the twist and the bending motions.

In Table 8, below, the (P-P) column shows the average phosphate distances along G271-C275 (G271*-C275*) for the 10-30 ns range. The column (P-P)ratio is the average ratio between the P-P distance summation (P-P) and direct phosphate distance between G271 and C275. The last column is the type of flanking base conformation

TABLE 8

|  | P-P (Å) | (P-P)$_{ratio}$ | Flanking Base |
|---|---|---|---|
| Unmodified HIV kissing loop | 26 | 1.9 (before 7 ns) 1.68 (10-30 ns) | Open 3R bulged out |
| $N_{271, 273}$ | 24.5 | 1.862 | Closed |
| $N_{271}$ | 25.4 | 1.87 | Open |
| $S_{271}$ | 26 | 1.87 | Open |
| $S_{271, 273}$ | 27 | 2.04 | Open |
| $N_{268,269,283,284}$ | 24.8 | 1.75 | Stacking |

North Constrained Sugar at $G_{271}$ ($N_{271}$)

In order to study the role of the $G_{271}$ sugar pucker on the overall dynamics, a north constrained sugar was substituted into only the $G_{271}$ position, and the flanking bases were unmodified. This modification can provide more flexibility to the system than the previous modified HIV kissing loop complex ($N_{271.273}$). During the 30 ns of MD simulation, the pseudo rotational angle of $A_{272}$ and $A_{273}$ stayed in a north and south conformation respectively except that they reversed to south and north for a very short time (less than 1ns). On the other hand, the corresponding flanking base $A_{272}$* stayed south for the first 14 ns, changed to north for the next 12 ns, then changed to south again. $A_{273}$* oscillated between a north and a south conformation during the 30 ns trajectory. Since the flanking bases have more of a chance to be in a south conformation compared to the previous case, the average P-P distance near the flanking bases ($G_{271}$-$C_{275}$) for the 10-30 ns range was found to be 25.4 Å, which was 1 Å longer than the previous case and 0.6 Å shorter than that of the unmodified HIV kissing loop. However, the (P-P)$_{ratio}$ for $N_{271}$ for the 10-30 ns trajectory was 1.87 and this value was larger than that of $N_{271.273}$ (1.662) and close to the unmodified HIV kissing loop complex value (1.9) of the first 7 ns. Due to the greater flexibility in $A_{273}$, the flanking bases formed an open conformation for 28 ns from the beginning of the MD simulation. Near 28 ns, the flanking bases formed a closed conformation for the last 2 ns.

Figure 45:
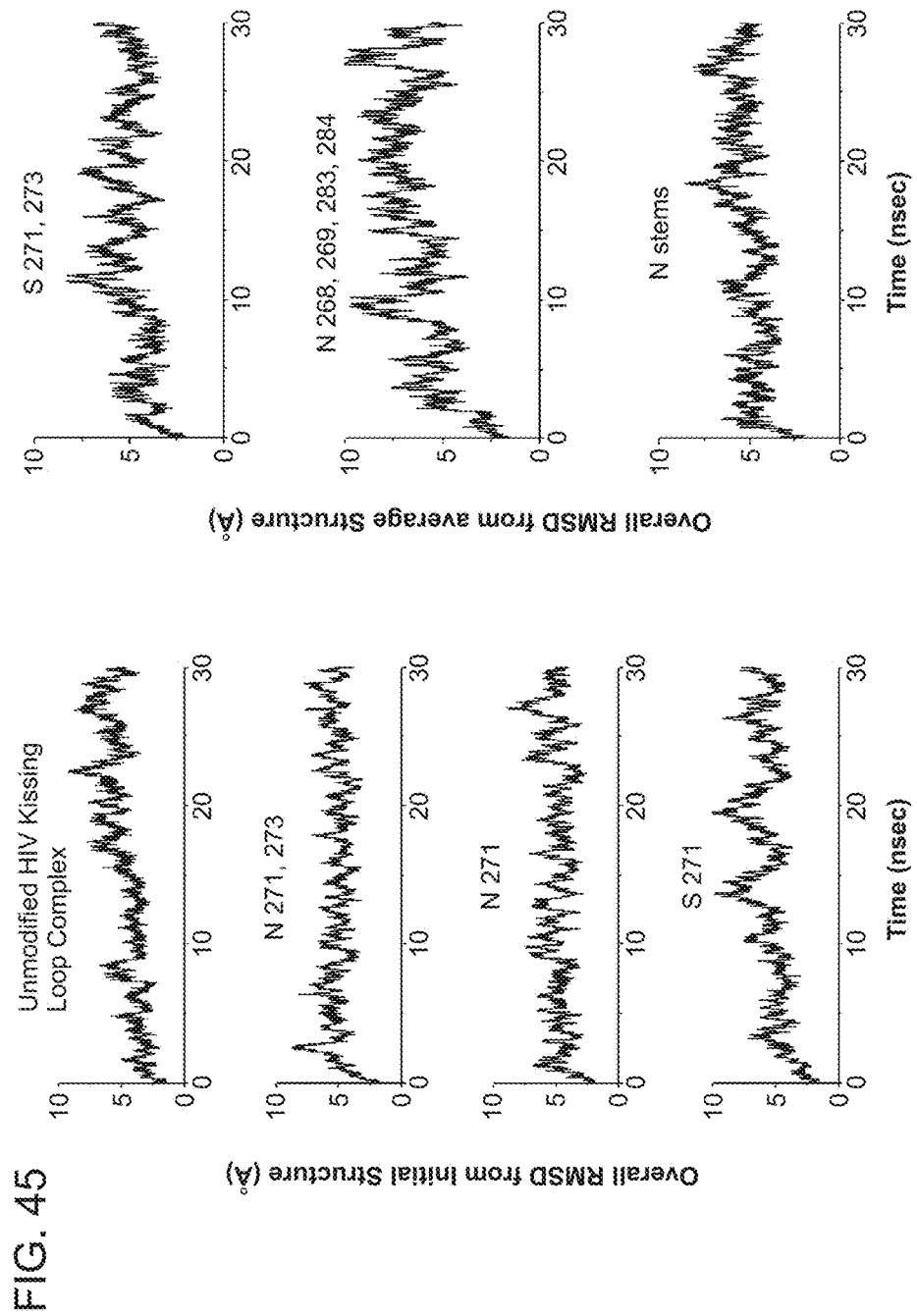
FIG. 45 shows overall RMSD of the HIV kissing loop structures relative to each initial structure: (a) unmodified HIV kissing loop complex, (b) N271, 273, (c) N271, (d) S271, (e) S271, 273, (f) N268, 269, 283, 284 and (g) Nstems.

Although only one north constrained sugar was substituted into each stem, it improved the overall RMSD significantly. The average overall RMSD relative to the initial structure was 4.89±0.94 Å (shown in FIG. 45(c)). The re-calculated value using the RMSD relative to the average structure for 10-30 ns was 2.57±0.55 Å, which was smaller than the unmodified HIV kissing loop complex, but slightly higher than previous case ($N_{271.273}$). The average twist motions of each side were measured as −40.2±13° and −43.8±12° and compared to the previous modified HIV kissing loop complex, ($N_{271.273}$). Symmetry and stability were slightly worse, but were still very stable compared to those of the unmodified HIV kissing loop complex. The bending of the system was measured as 163±9.66°, which indicated that $N_{271}$ experienced slightly more bending with increased flexibility than ($N_{271.273}$), but maintained better stability than the unmodified HIV kissing loop complex. Therefore, stabilization of twist and bending motions along the helical axis by substituting a north constrained sugar at $G_{271}$ can reduce the overall RMSD.

South Constrained Sugar at $G_{271}$ ($S_{271}$)

The local dynamics around the flanking bases was quite different when a south constrained sugar was substituted into $G_{271}$. The pseudo-rotational angle of the $A_{272}$ sugar became more varied in a south conformation for the 10-30 ns range, while the $A_{273}$ sugar retained a south conformation for most of the simulation time. The pseudo-rotation of $A_{272}$* stayed in a north conformation for most of the time, while the $A_{273}$* sugar oscillated between north and south conformations. Compared to the previous two cases, the increase in the south conformation distribution along $A_{272}$-$A_{273}$ produced a P-P distance in $S_{271}$ of 26 Å, which was 0.4 Å longer than $N_{271}$ and similar to that of the unmodified HIV kissing loop. The average (P-P)$_{ratio}$ in $S_{271}$ for 10-30 ns was 1.87 and this value was larger than the closed conformation in $N_{271.273}$ (1.62) and the same as the value of the open conformation in $N_{271}$ (1.87). During 30 ns MD simulation, $S_{271}$ did not induce a closed conformation.

Figure 46:
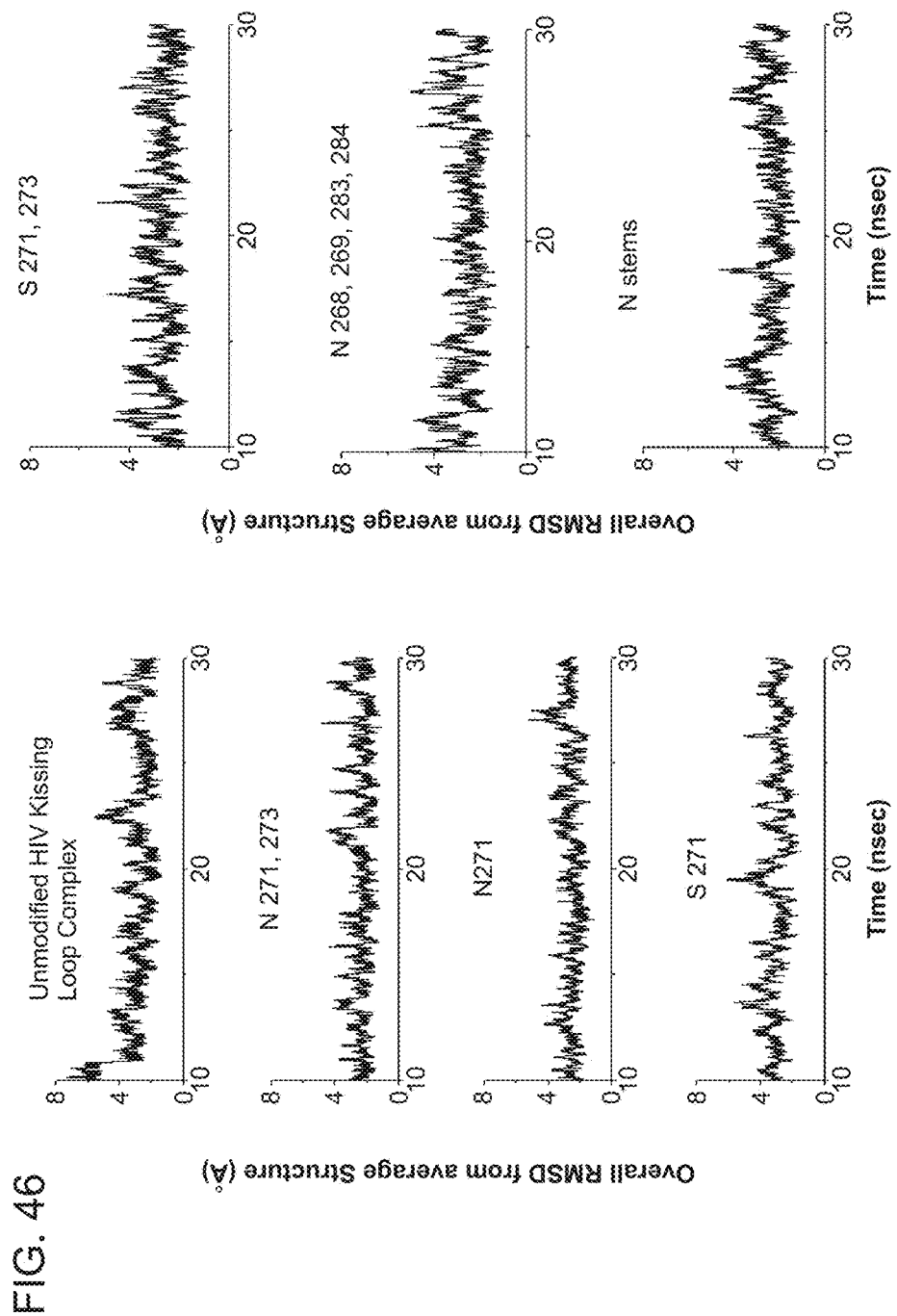
FIG. 46 shows overall RMSD of the HIV kissing loop structures relative to each average structure for 10-30 ns range: (a) unmodified HIV kissing loop complex, (b) N271, 273, (c) N271, (d) S271, (e) S271, 273, (f) N268, 269, 283, 284 and (g) Nstems.

The overall RMSD of $S_{271}$ was 5.39±1.56 Å relative to the start structure, and the recalculated RMSD using the average structure for 10-30 ns was 3.03±0.67 Å (see FIG. 46(d)). Therefore, even after relaxation, the overall structure was still as flexible as the unmodified HIV kissing loop complex (3.0±0.93 Å). The average twist torsion angle of stem1 was measured as 51.3±18.8° and that of stem2 was measured as −42.0±14.2°. As observed in the unmodified HIV kissing loop complex, both of the twist torsion angles and their stabilities were non-symmetric. The bending behavior for $S_{271}$ was measured as 152.4±12.1°, which was very close to the unmodified HIV kissing loop complex value (150±12°). Therefore the substitution of a south constrained sugar at $G_{271}$ did not affect the twist and bending motions and the overall RMSDs of the unmodified and modified ($S_{271}$) HIV kissing loop complex remained almost the same.

South Constrained Sugars at $G_{271}$ and $A_{273}$($S_{271.273}$)

Two south constrained sugars were substituted at $G_{271}$ and $A_{273}$. The pseudo rotation angle of $A_{272}$ retained a north conformation for the initial 15 ns and then began to oscillate between a north and a south conformation for the rest of the simulation. Meanwhile, the pseudo-rotation angle of $A_{272}$* stayed in a north conformation for the 30 ns simulation. The average P-P distance for the 10-30 ns trajectory along $G_{271}$-$C_{275}$ was 27 Å and the (P-P)$_{ratio}$ was 2.04. These values were larger than the corresponding values of $N_{271.273}$ (24.5 Å, 1.662) and the flanking bases of the modified HIV kissing loop complex ($S_{271.273}$) failed to form a closed conformation, during the 30 ns MD simulation. The overall RMSD of $S_{271.273}$ for the 30 ns simulation relative to the beginning structure was 4.85±1.0 Å and the recalculated RMSD for the 10-30 ns range relative to the average structure was 2.58±0.58 Å. The average twist angles of stem1 and stem2 showed a symmetrical twist behavior, −49.9±13.44° and −46.5±13.4°, respectively. The average bending for the 10-30 ns range was 159.6±9.46°. Therefore, the reduced RMSD of $S_{271.273}$ modified HIV kissing loop structure was due to the smaller variations in twist and bending motions compared to those of the unmodified and $S_{271}$ modified HIV kissing loop complex.

North Constrained Sugars in the Middle of Stems ($N_{268.269.283.284}$)

North constrained sugars were substituted into stem regions, $G_{268}$, $C_{269}$, $G_{283}$, $C_{284}$, and the corresponding positions in the other stem. These positions contain G-C base pairs in the middle of the stem regions. Since the constrained sugars were substituted into the middle of the stems, there was no affect on the flanking bases' sugar puckers due to the modified nucleotides. The sugar pucker of $G_{271}$ stayed north and the sugar puckers of $A_{272}$, and $A_{273}$ oscillated between a north and a south conformation. Similarly, $G_{271}*$ stayed in a north conformation while $A_{272}*$, and $A_{273}*$ oscillated between a north and a south conformation. The P-P distance ratio near the flanking bases was 1.75. The flanking bases did not obtain a closed conformation. Overall the RMSD relative to the initial structure was 6.3±1.6 Å, and the recalculated RMSD for the 10-30 ns range relative to the average structure was 2.67±0.65 Å, which indicated that the two pairs of north constrained sugars in the middle of stems, stabilized the overall structure. However, the average twist angles along stem1 and stem2 were −68.4±21.7° and −45.5±17° and these values imply that the modified sugars in the middle of the stems do not contribute to stabilizing the twist motions. Meanwhile, the structure bending was 150.4±9.4°, which is a smaller variation than that found in the unmodified HIV kissing loop complex (150.7±12.0°).

North Constrained Sugars in Stems ($N_{stems}$)

In this case, all of the nucleotides in both stem regions were replaced with north constrained sugars including the 5' and 3' terminals. During most of the MD simulation, sugar puckers in $A_{272}$ and $A_{273}$ became north and south conformations respectively and $A_{272}*$ and $A_{273}*$ obtained south conformations. The flanking bases, $A_{272}*$ and $A_{273}*$ rotated away from the HIV kissing loop cavity and $A_{272}*$ hydrogen bonded with $A_{280}*$ for less than 5 ns, while $A_{272}$ and $A_{273}$ did not make any hydrogen bonds. Since this conformation was maintained for the rest of the simulation, the flanking bases had no chance to form a closed conformation. Since all nucleotides in the stem regions were replaced with constrained north sugars, all backbone dihedral angles along the stem showed no deviation from canonical dihedral backbone angles. This caused extra stability in this modified HIV kissing loop complex. The overall RMSD for the 10-30 ns range relative to the average structure was 2.37±0.57 Å with a value as low as that of $N_{271.273}$. Variations in the twist motion in both stems were similar to each other (−24±14° and −36±15°) and these values were lower than $N_{268.269.283.284}$. The structure bending was 156±8.2°, which was lower that that of the unmodified HIV kissing loop complex. Therefore, these results imply that the reduced RMSD was produced by two stabilizing motions, twist motion due to the north constrained sugars at $G_{271}$, and structure bending due to the north constrained sugars in the stem regions.

In developing RNA based nanoparticles, it is expected that system stiffness and shape can be controlled by substituting north and south constrained sugars into selected positions. Our results show that there are various possibilities for the use of constrained sugars in RNA nanoparticle design.

The dynamic behaviors of the RNA dodecamer where north constrained sugars were substituted did not show any significant difference from an unmodified RNA dodecamer. However, the south modified dodecamer showed a rapid RMSD increase from the initial structure due to the substituted south constrained sugars, and the motion was stabilized during the 10-30 ns range. The overall structural properties of the south modified dodecamer showed a mixture of A and B form helixes and therefore elongation from the initial structure. Since the south modified RNA dodecamer had a B-form like helix, the major groove became wider and deeper and can possibly bind proteins more readily.

In using complex RNA structures, such as the HIV kissing loop, for developing nanoparticle design, it is possible to stabilize the overall twist and bending by substituting constrained sugars into proper positions. North constrained sugars at G271 and A273 (N271.273) showed the most stable twist motions and stable bending motions. A north constrained sugar at G271 and south constrained sugars at G271 and A273 also contributed to reduce overall RMSD by stabilizing twist and bending motions. However, a south constrained sugar at G271 was found to have no effect on RMSD reduction. On the other hand, the north constrained sugars in the stem regions decreased RMSD by stabilizing only bending motions. When all nucleotides in both stems were replaced with north constrained sugars, however, the lowered RMSD of the overall structure was caused by stabilizing both the twist and bending motions. It was also found that substituting north and south constrained sugars at proper positions could control flanking bases conformations. A closed conformation of the flanking bases was obtained with N271.273 for 1-30 ns, with the (P-P)ratio near the flanking bases being 1.68. On the other hand, flanking bases in S271 and S271.273 did not form a closed conformation during the 30 ns simulation, with a (P-P)ratio of 2.04. North constrained sugars at stem regions also showed no inducement of a closed conformation on the flanking bases.

The results presented herein show that the proper use of specific north or south carbocyclic sugars at specified locations in an RNA structure can stabilize and deform RNA structures to obtain defined RNA conformations with specific chemical properties and shapes for RNA nano-design.

Example 20. Computer Approach to Designing RNA-Based Structures

The computer-aided approach to designing RNA-based nanostructures has started with the development of the RNAJunction database. It is a large repository of RNA structural junctions (internal loops and loop-loop interactions), which can be used as building blocks for larger, biologically functionalized nanostructures. Our programs, NanoTiler and RNA2D3D, can utilize them, together with idealized fragments of A-form helices, to produce the desired 3D shapes. Up to this stage the building blocks are treated as rigid or near-rigid objects. However, experimental data shows that RNA structures are flexible and capable of accommodating their shape to the constraints of larger structural contexts.

FIGS. 47-59 present examples of RNA-based nanostructure designs, stressing the characterization of the structural flexibility of the building blocks and potential strategies for controlling these characteristics. The Figures show data that employs molecular dynamics simulations and analysis to characterize the stability and flexibility of the building blocks. Examples presented include various reprogrammed kissing loops (KL) based on the HIV-1 KL complex, as well as the use of modified nucleotides to change its characteristics. We contrast them with the dynamic behavior of other KLs. Larger characterized structures include tectosquare building blocks, in which the flexible KLs appear to be necessary for the assembly of the entire tectosquares, and a triangle and its individual large building block monomers.

Figure 47:
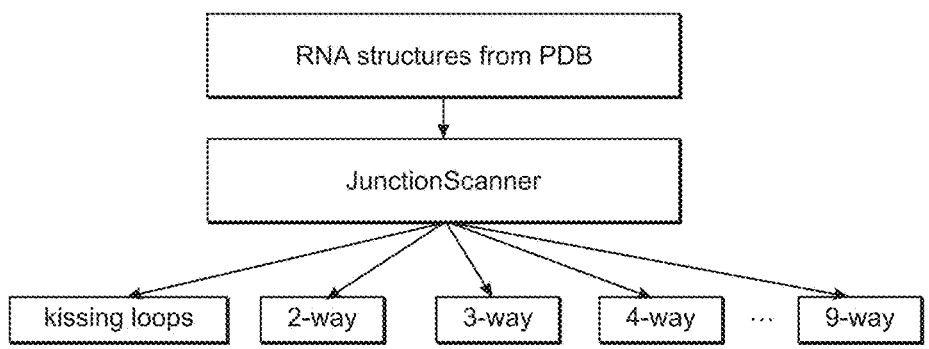
FIG. 47 shows a schematic.
Figure 48B:
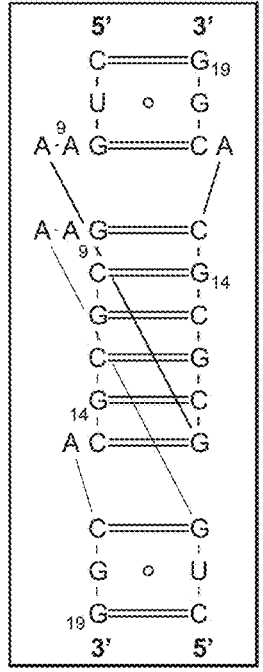
FIG. 48B discloses SEQ ID NOS 122 and 122, respectively, in order of appearance.
Figure 49:
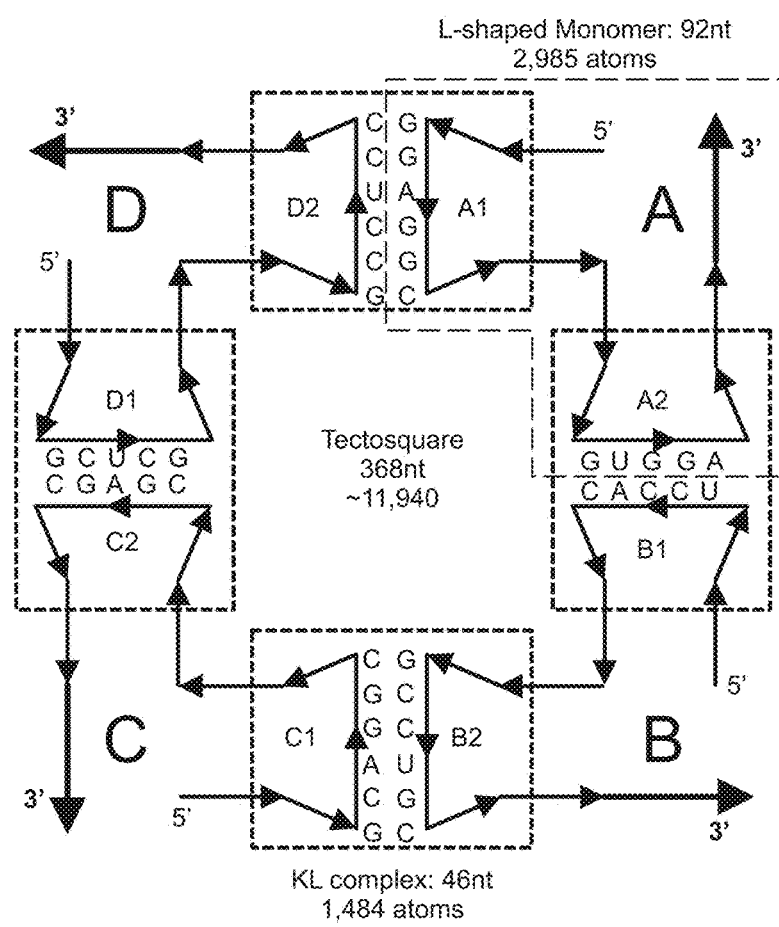
FIG. 49 shows the design of tectosquares. RNAs with engineered loop sequences self-assemble into tectosquares. L-shaped monomer building blocks with interacting tails and kissing loops can assemble into many different planar networks of predefined geometries.
Figure 51A:
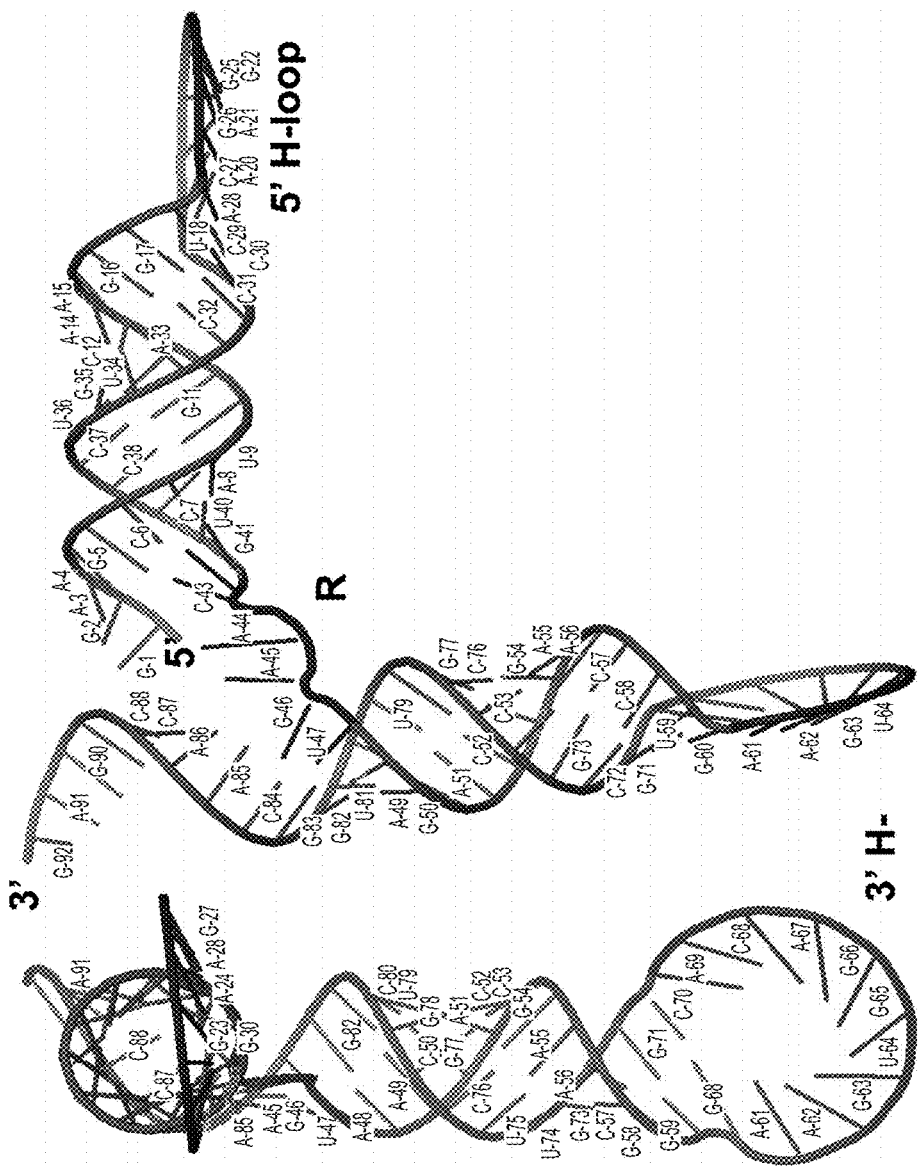
FIG. 51A discloses positions "A45" to "G59" and "A61" to "G71" as SEQ ID NOS 123-124, positions "G25" to "C38" and "A49 to "U64" as SEQ ID NOS 125-126, respectively, and FIG. 51B discloses positions "U79" to "G92" as SEQ ID NO: 127 and positions "C13" to "A28" and "G30" to "G39" as SEQ ID NOS 128-129, respectively.
Figure 51B:
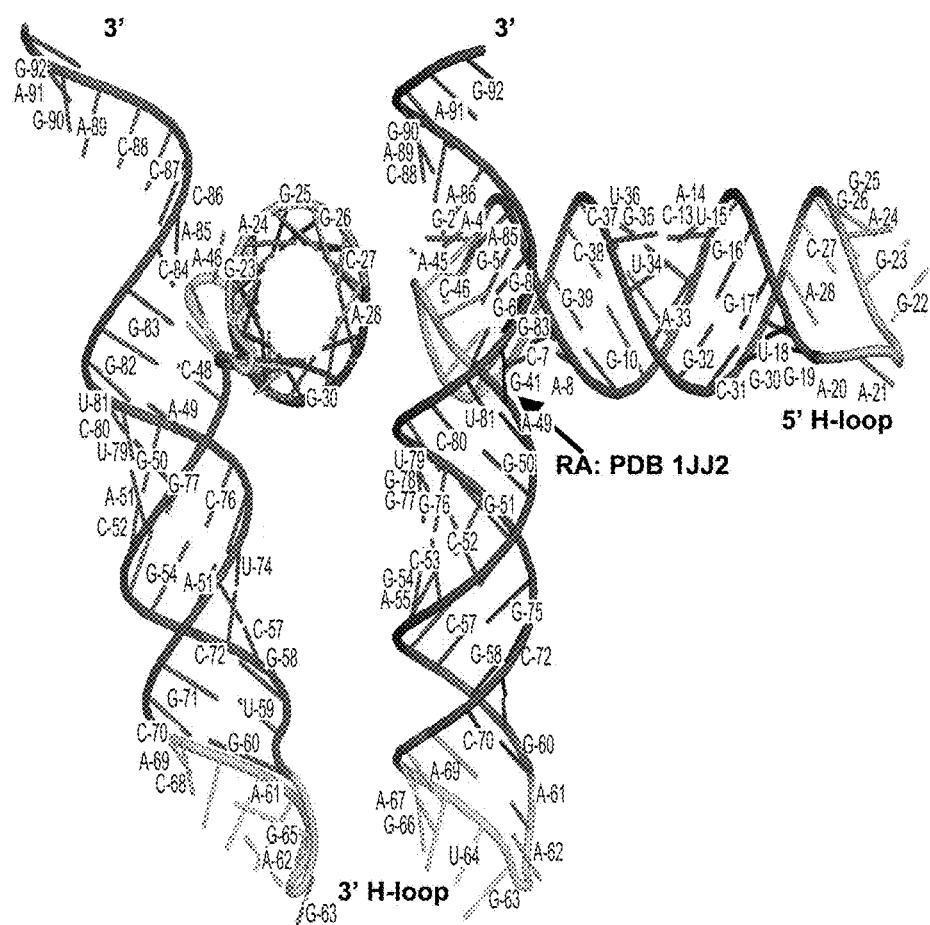
FIG. 51 shows Modeling with RNA2D3D. A) shows Raw 2D to 3D conversion Flat H-loops. Best-guess RA linker. Co-planar helices. B) 3'-end helix extension H-loops RA linker from PDB 1JJ2 (50S ribosomal unit of *Haloarcula marismortui*). Log cabin helix arrangement.
Figure 52:
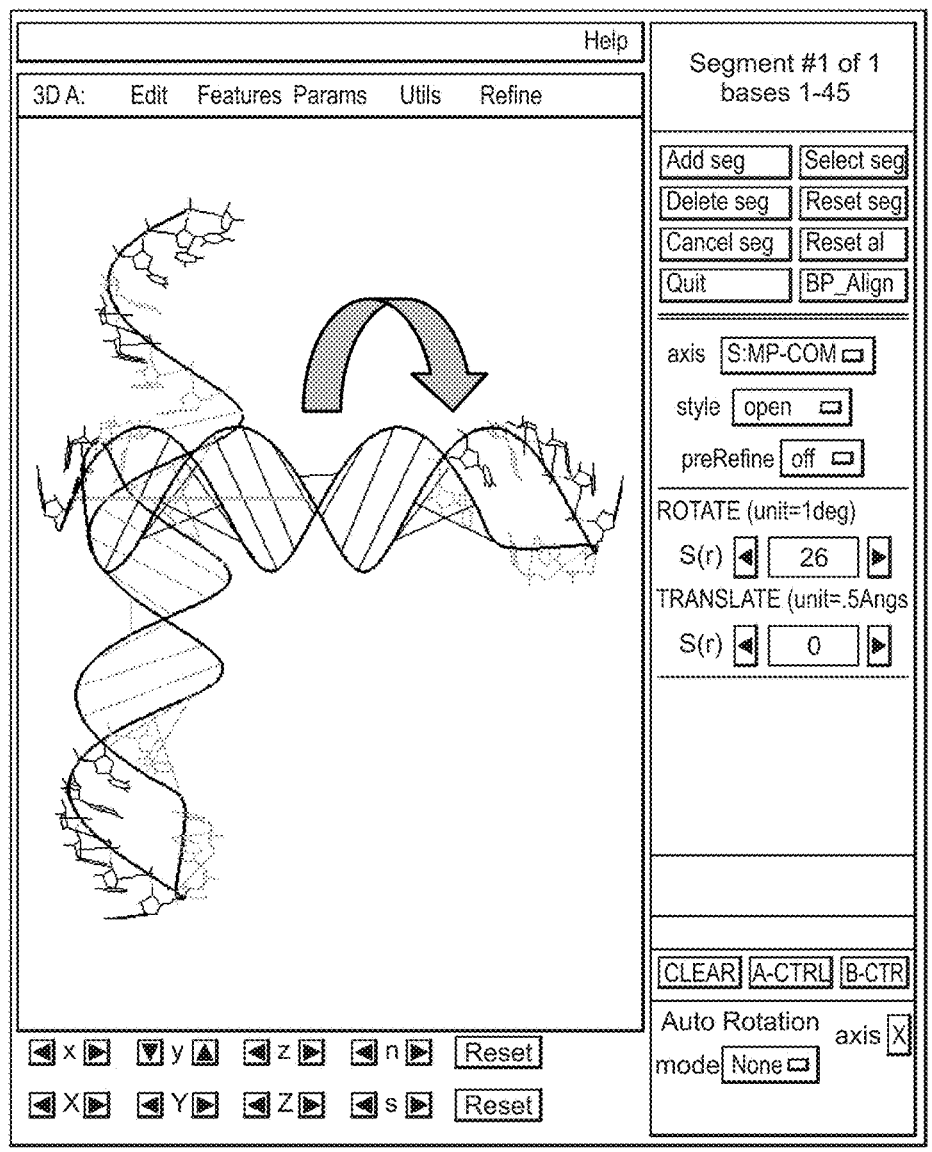
FIG. 52 shows characterizing an L-shaped Monomer. A tectosquare model based on idealized geometry L-shapes does not form a closed ring structure. By interactively adding 26° rotation to every 5' ideal A-type helix of every monomer (corner) in RNA2D3D we can bring the initially open H-loops into coaxial orientation.
Figure 52:
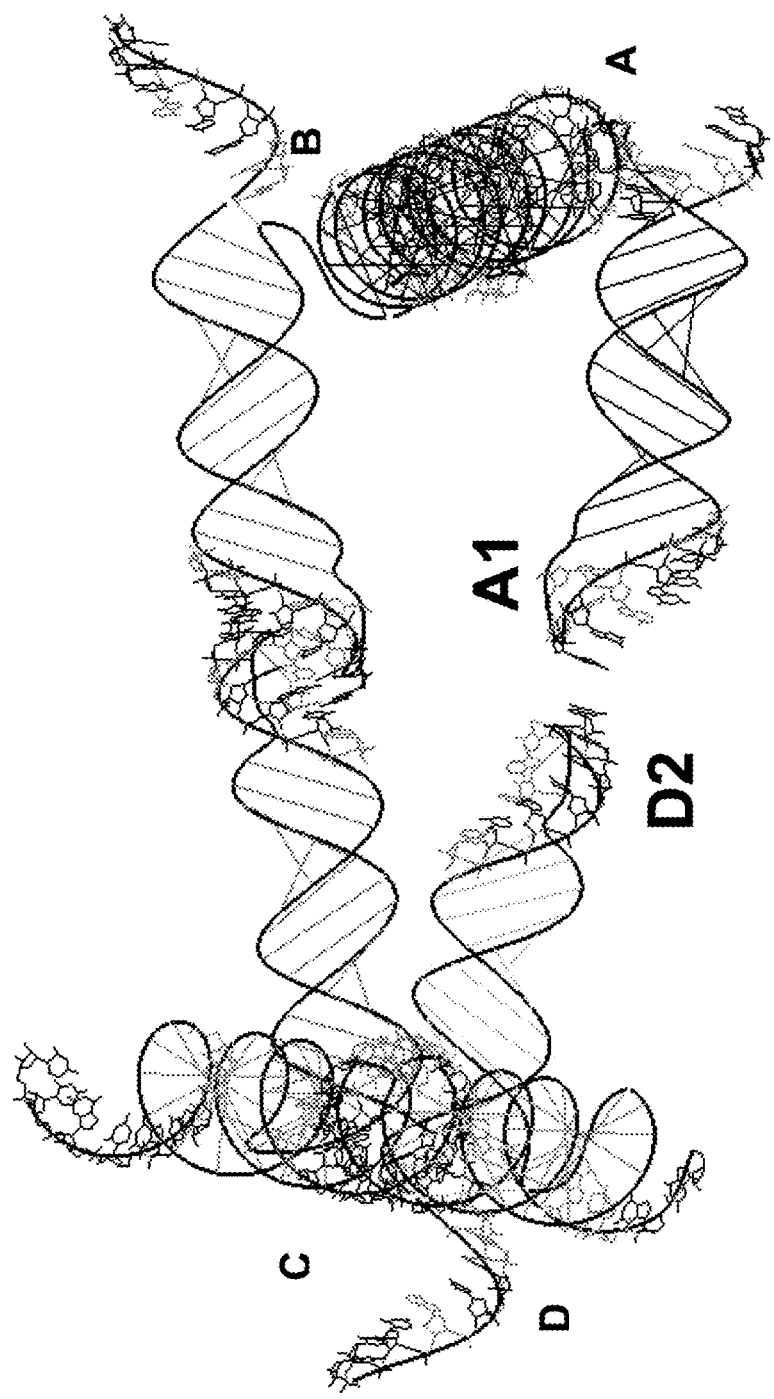
Figure 53:
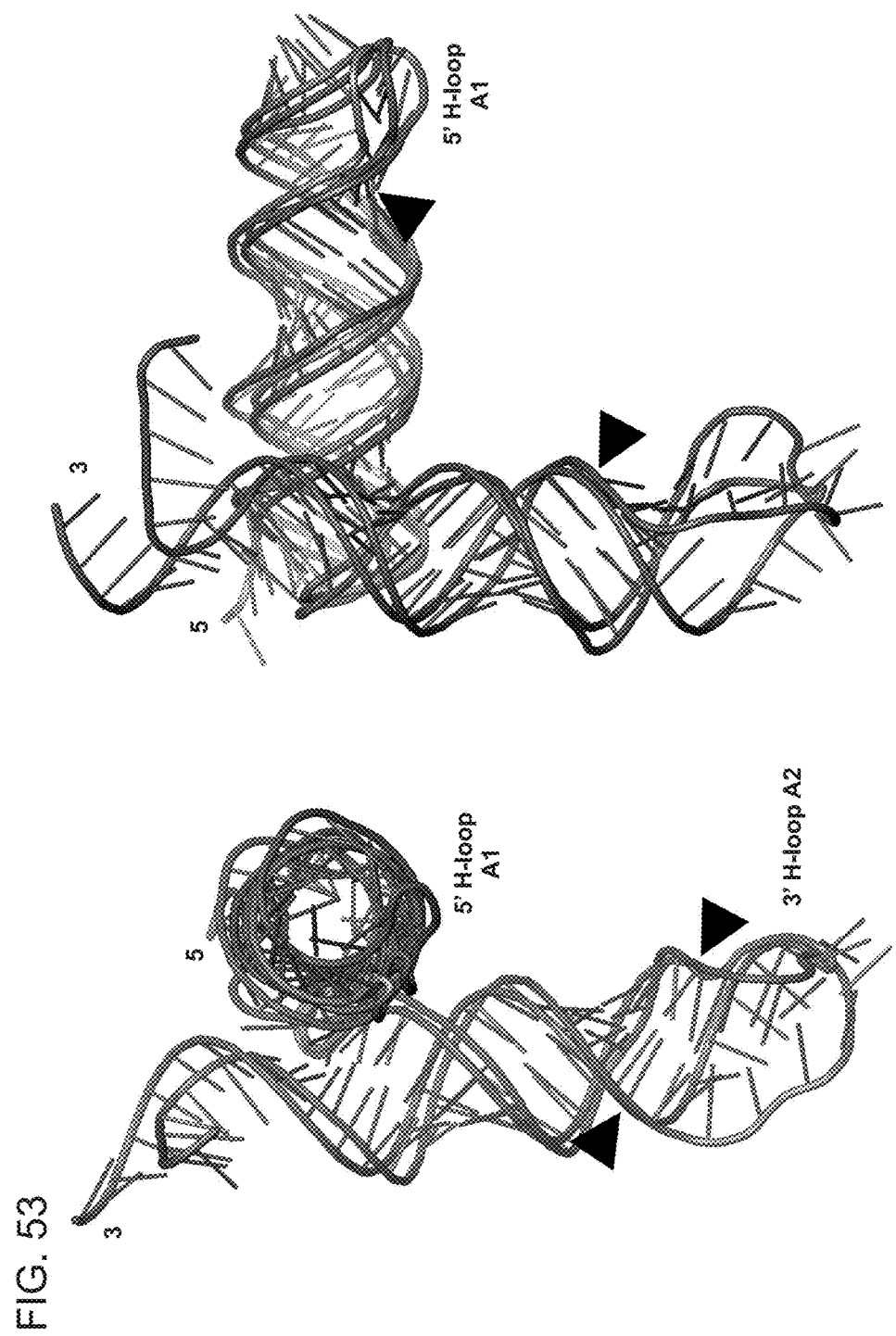
FIG. 53 shows further characterizing of an L-shaped Monomer. In the Figure Gray: an idealized monomer created with the help of RNA2D3D. Red: modified monomer (see above) used as a reference structure. Blue: MD trajectory structure selected based on its low RMSD value measured relative to the backbone P atoms of the two closing base pairs of both hairpin loops in the reference structure: U18-G30 and U59-G71, black arrows. (MD: Amber, PME, explicit solvent, 30 ns).

Our RNAJunction database contains more than 13,000 annotated 3D RNA multi-way junctions (2-way through 9-way), and loop-loop (kissing loop) interactions extracted from the PBD's RNA structures. The database is available on the world wide web at http://rnajunction.abcc.ncifcrf.gov. One can search for structural elements by PDB structural classification with optional Lilley topology notation, primary sequence, inter-helix angles, PDB code and more. The 3D junction structures have been subjected to energy minimization with the Amber package. The DB can be used in the analysis of structural and functional capabilities of RNA, as well as with designing of novel nano-scale RNA structures in mind, in which entries may be used as building blocks. FIG. 47 shows. FIG. 48 shows an example of the RNAJunction Web server query and results pages.

Figure 54:
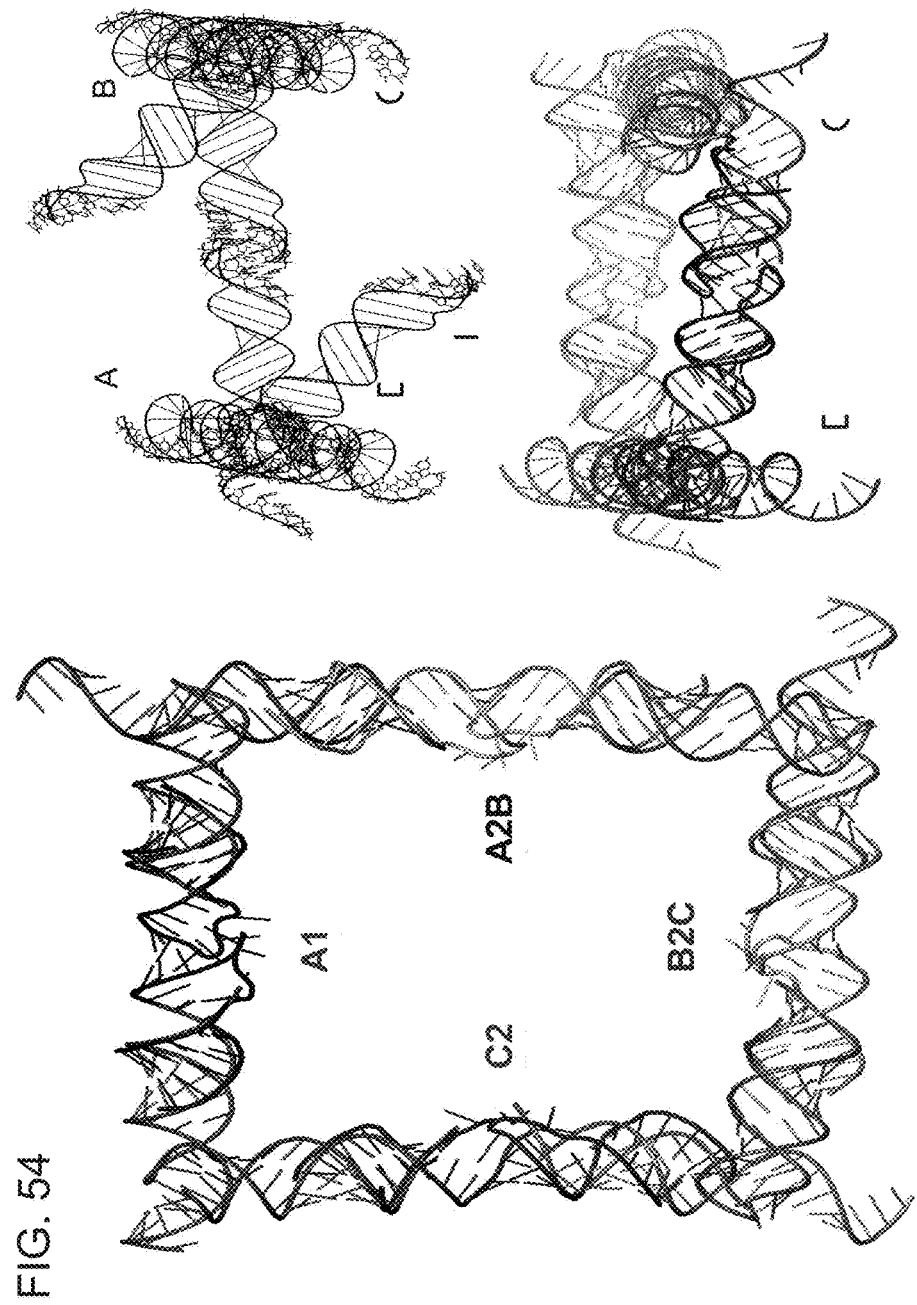
FIG. 54 shows characterizing HIV-1-based Kissing Loops. Here, four reprogrammed KLs, used in the tectosquare designs, were obtained by editing the HIV-1 structure (PDB: 2B8R). MD runs were performed for 20 ns or longer, in explicit solvent (water, Na+, Cl−), using the PME methodology in Amber. The MD results showed differences in dihedral and planar angles across the KLs relative to the WT KL.
Figure 55:
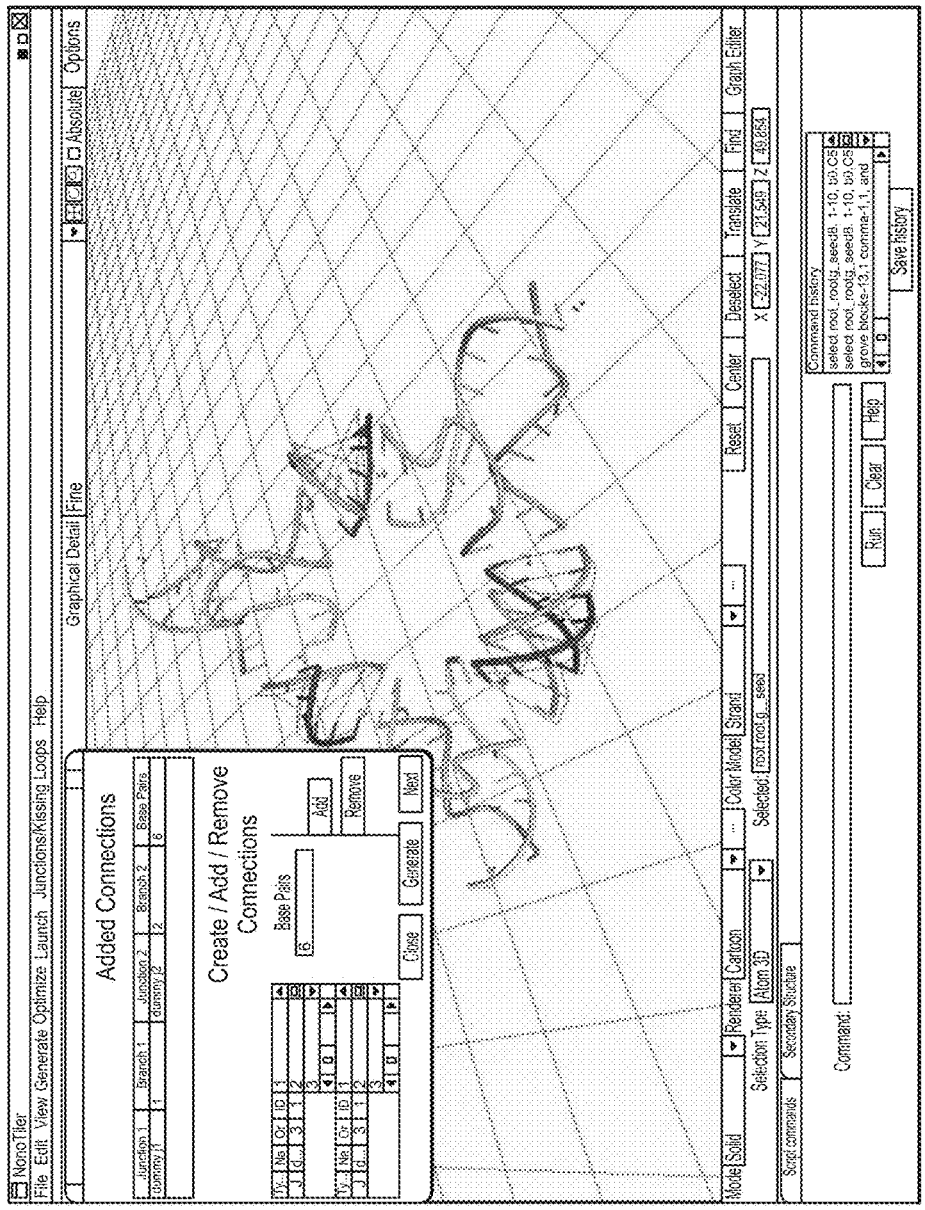
FIG. 55 shows NanoTiler: RNA Structure and Sequence Design. Nanotiler allows the following: detect junctions & kissing loops (RNAJunction DB); Generate artificial junctions; Generate structures using combinatorial search among junctions & connectivities; Connect junctions using constraints; Search for RNA "bridges" (single or double strands); 3D nucleotide mutations; Topology classification; Sequence optimization; Graphical user interface. Scripting language.

In FIG. 54, four reprogrammed KLs, used in the tectosquare designs, were obtained by editing the HIV-1 structure (PDB: 2B8R). MD runs were performed for 20 ns or longer, in explicit solvent (water, Na+, Cl−), using the PME methodology in Amber. The MD results showed differences in dihedral and planar angles across the KLs relative to the WT KL. FIG. 54 shows that s tectosquare based on idealized geometry does not close (top right). Using KLs with dihedral angles ranging from +16° to +24°, relative to the first MD trajectory frame, yields a good planar closure with very good square geometry. The dihedral angles across the KL interactions were measured for the atoms equivalent to those selected for characterization of the L-shapes (see previous panel). PyMOL RMSD-based pair fit of ideal monomer helices to the backbone Ps of the two base pairs closing the KL H-loops was used.

FIG. 56 shows design of a junction based triangle. In FIG. 56 we designed an RNA triangle starting from a 3-way junction. The algorithm found the optimal length of helical spacers such that ring-closure in the 3D model is feasible. The 3D model suggests the use of 3 RNA sequences of length 35 nt and 1 sequence of length 51 nt. After specifying the 3D geometry, a sequence optimization algorithm was applied.

The quality of the optimized sequences is evaluated by computing the free energy of binding of all sequence pairs. The goal is to maximize the energy difference between the free energy of binding of the designed strand pairs and those that should not pair.

FIG. 58 shows the design of a KL-based triangle. A triangle was designed with the help of NanoTiler. The design combines a KL complex (RNAJunction DB entry 12948), a two-way junction and fragments of A-form helices fitted to form a closed ring structure. A selection of several minimum and maximum RMSD structures from ~10 ns MD trajectories for the full triangle (219 nt, left) and the KL2 dimer (146 nt, right). RMSD was calculated relative to the first frame of the production MD run (Amber, PME, explicit solvent). Both structures remain planar. Higher mean RMSD of the KL2 dimer (8.18±2.16 Å vs triangle's 7.74±1.56 Å) reflects its scissors-like motions, deeper bending of the chains and the distortions of the larger of the two KL1, loops left unpaired in chain 1 (see above). In both cases the KL complexes hold strong, with the two base pairs C54-G187 and C55-G186 forming triple bonds with occupancy greater than 95% throughout the MD runs.

Taken together, the computer-aided RNA nanostructure design approach has been shown to produce experimentally verified self assembling structures (see the junction based triangle design, and others, not shown).

RNA structure variability information plays an important role in the design of nano-scale structures. It was found that characterizations of RNA building blocks and sub-assemblies with the help of molecular dynamics simulations can help in the design of nano structures from building blocks which otherwise may yield no static, geometric fit.

An RNA tectosquare design was examined and found that the assembly of the L-shaped building blocks depends mostly on the structural changes in the kissing loop motifs, but is also aided by the more limited flexibility of the rest of the L-shaped monomers. MD results show that the designed mutations within the HIV-1 kissing loops influence their stability, but not to the point of interfering with the tectosquare assembly.

Evaluation of theoretically weaker kissing loops used in the design of the triangular structure indicates their potential viability and awaits experimental verification of the results of MD simulations.

Example 21. In Vitro Assembly of Cubic RNA Based Scaffolds Designed in Silico

It is highly desirable to generate a library of nano-scaffolds that allow precise positioning of various therapeutic agents or sensors in 3D space to guarantee their simultaneous delivery to specific areas of the body. In the past 20 years, Seeman and co-workers have largely contributed to the fabrication of DNA-based nano-cages through molecular self-assembly (Seeman et al. 2007; Aldaye et al. 2008; Lin et al. 2009). Diverse 3D DNA nano-scaffolds with the connectivity of a cube (Chen et al. 1991), tetrahedral (Goodman et al. 2008); He et al. 2008), bipyramid (Erben et al. 2007), octahedral (Andersen et al. 2008) dodecahedra (He et al. 2008; Shih et al, 2004) and buckminster-fullerene (He et al. 2008) were constructed. The ability of DNA polyhedra to promote targeted delivery by functioning as nano-capsules for molecular cargo has been shown for rigid tetrahedral (Erben et al. 2006) and icosahedral (Bhatia et al. 2009) DNA cages. Recently, a powerful DNA "origami" technique (Rothemund et al. 2006) for the design of 2D addressable DNA shapes was applied towards the construction of nano-boxes (Andersen et al. 2009), pyramidal tetrahedrons (Ke et al. 2009), and other 3D objects (Dietz et al. 2009; Douglas et al. 2009).

To date, most of the nucleic acid based polyhedral nano-scaffolds designed in the laboratory have diameters greater than 15 nm and employ DNA molecules as building blocks (Lin et al. 2009; Dietz et al. 2009; Douglas et al. 2009). While these DNA structures have revealed the potential to develop programmable scaffolds for nanotechnological applications (Seeman et al. 2007; Aldaye et al. 2008; Lin et al. 2009), DNA biopolymers might not always be able to mimic all the biological functions of RNA. Despite being more chemically labile than DNA, natural RNA molecules are able to function as therapeutic agents such as small interfering and micro RNAs (siRNAs and miRNAs) which do not have DNA analogs Kim et al. 2007). Furthermore, natural RNA molecules comprise a wide range of working components of biologically essential molecular machines including ribozymes (Gesteland et al. 2005), regulatory aptamers (Gesteland et al. 2005) and nano-motors (Gesteland et al. 2005; Wendell et al. 2009).

As a result of greater natural versatility and biologically relevant functionality (Gesteland et al. 2005), RNA might offer building blocks and functional components that have no counterparts in the present day DNA world for building functional therapeutic nano-scaffolds. Previous work has demonstrated the design of modular RNA units forming small multimeric particles of various sizes (Jaeger et al. 2000; Chworos et al. 2004; Khaled et al. 2005; Guo et al. 2005; Jaeger et al. 2006; Afonin et al. 2008; Severcan et al. 2009), as well as programmable filaments (Jaeger et al. 2000; Koyfman et al. 2005; Nasalean et al. 2006) and 2D nano-arrays and nanogrids consisting of RNA squares (Chworos et al. 2004; Severcan et al. 2009). While previous work demonstrates that reliable prediction and design of the tertiary structure of RNA can be achieved to build supramolecular architectures (Jaeger et al. 2006; Severcan et al. 2009), the structural potential of RNA self-assembly for nano-construction of 3D nano-cages and 3D RNA networks has not yet been fully exploited.

Presented herein is a strategy to rationally design and construct 3D RNA nano-scaffolds, composed of six (A-F) or ten (A-J) strands assembled in the shape of a cube. Due to its geometrical simplicity and the relatively large number of participating modules, the cube is an attractive shape for a multifunctional nano-scaffold. The small size of the engineered nanoscaffold (one helical turn per side) allows for the use of relatively short RNA sequences (28-54 nts). This makes the sequences suitable for chemical synthesis, functionalization and/or selective point modifications. Furthermore, the number of possible functions within each scaffold is at least as large as the number of addressable nucleic acid units present in its composition.

Computational 3D models were generated using the NanoTiler software (Bendewald et al. 2008), as well as Accelrys Discovery Studio. The computational sequence optimization consists of sequence randomization and Monte Carlo optimization algorithms (FIG. 61). FIGS. 61 (A and B) shows a flow chart of sequence optimization steps. The initial sequence randomization is performed by choosing the nucleotides A, C, G, U with probabilities 0.2, 0.3, 0.3, 0.2 respectively (corresponding to a target G+C content of about 60%). Nucleotides that are designed to form a basepair (bp), are chosen to be complementary. Two stages of Monte-Carlo optimization are performed. The first optimization stage is based on the fast-to-compute rule-based scoring function. When a specified score threshold has been reached, the complete scoring function (consisting of the three components outlined in part B) is applied in a second stage of Monte Carlo optimization. B. All three components of the sequence design scoring function. (I) A scoring function that applies empirical rules that can be quickly determined based on the character string composition without folding predictions; (II) A thermodynamic scoring function that scores if both RNAcofold and RNAfold predictions are compatible with the desired folding characteristics of all designed sequences and sequence pairs; (III) A score comparing a multisequence structure prediction (based on placing predicted helices in order of a simple helix score) with the target secondary structure.

The objective function of the optimization is the weighted sum of three scores: (i) a rule-based score (Seiffert et al. 2008; Seeman et al. 1982) (ii) a score comparing the target secondary structure with RNAcofold (MAtthwes et al. 1999; Zuker et al. 2003; Berhart et al. 2006) predictions of all sequence pairs as well as with RNAfold (Mathews et al. 1999; Hofacker et al. 1994) predictions of all individual sequences, and (iii) a score evaluating a multi-sequence secondary structure prediction based on a trivial energy model (Beindewald et al. 2008). Three different cube types were engineered: two cubes with and without dangling ends, each containing six strands of equal length, and a ten stranded cube with dangling ends containing two different strand lengths (FIG. 1). These dangling ends can be modified into functional units as demonstrated below. The sizes of all cubes are 10 bps per side.

Several different techniques such as native poly-acrylamide gel electrophoresis (PAGE) experiments, dynamic light scattering (DLS), and cryogenic electron microscopy (cryo-EM) were employed to confirm the formation of closed RNA cubes of defined sizes. Hybrid RNA/DNA and DNA cubes were also analyzed. In contrast to the step-wise formation of covalently closed DNA cubes reported by Chen and Seeman (1991), ther approach to synthesizing RNA cubes described herein is a one pot self-assembly process. The self-assembly protocol is optimized to be used for all nano-cubes investigated in this project (see e.g., Materials and Methods).

Native-PAGE results presented in FIG. 72 demonstrate the reproducible self-assembly of six (AF) RNA, RNA/DNA, or DNA strands, into finite hexameric structures. Quantification of the bands (Materials and Methods) reveals that the average yields of the RNA or DNA hexamers are greater than 90%. To confirm the formation of the closed hexameric species, sequence A was mutated (Am) to prevent complementary base pairings with strands E, D, and F (SI, Table S1).

Thus, mixing strands Am, B, C, D, E, and F only leads to the formation of an "open" hexamer. PAGE experiments in FIG. 72a demonstrate different electrophoretic mobilities between "open" (lane #6) and "closed" (lane #7) hexamers. By adjusting the porosity of native gels, optimal separation between tetramers, pentamers and hexamers can be achieved. However, the retention factors (Rf) of tetrameric and pentameric assemblies can vary depending their strand composition, which might favor either circular or linear molecular species (data not shown).

Figure 72A:
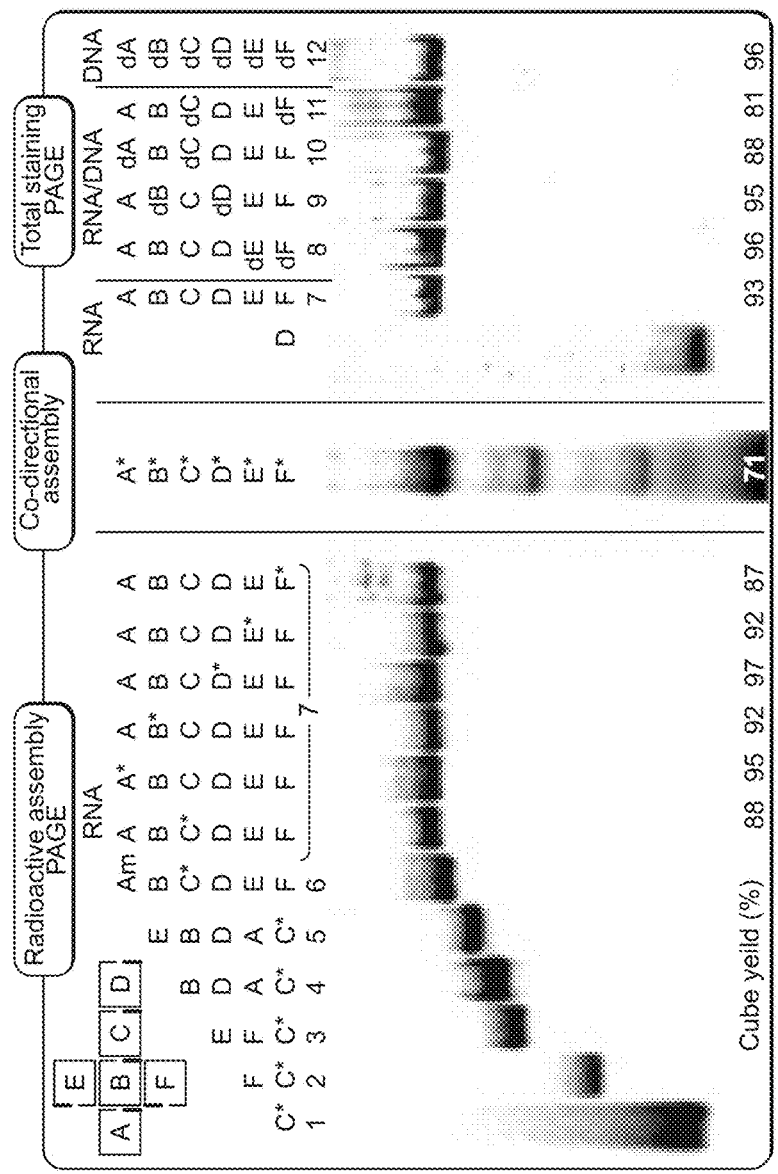
Figure 72B:
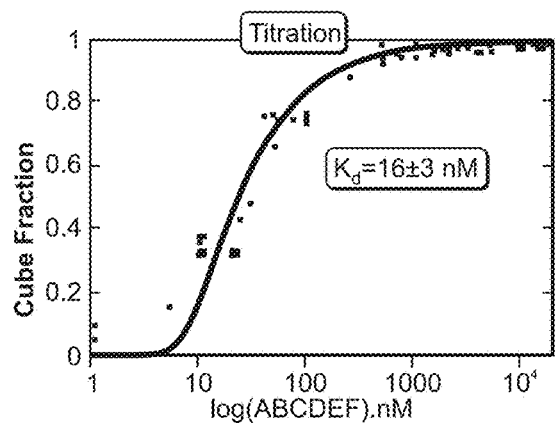

To verify that all 6 RNA strands participate in self-assembly of the hexamer, radio-assay PAGE experiments were carried out (FIG. 72a). In these experiments, each of the six radio-labeled molecules (marked with "*") was individually mixed with five other non-labeled molecules followed by the assembly protocol. The results show identical gel shifts for all 6 cubes with different labeled strands, suggesting the participation of all strands in the formation of a closed species (FIG. 72a, lanes #7). Likewise, the formation of DNA hexamers was confirmed by using three different labeled DNA strands (FIG. 62).

The assemblies of the 6 and 10 stranded cubes with 5' dangling ends were also confirmed by PAGE experiments and the yields for both nano-constructs were estimated to be greater than 90% (FIGS. 64 and 65, respectively). In the case of six stranded cubes, the sequence composition or the presence of the dangling ends can alter the relative gel shifts for tetramers, pentamers and hexamers.

All the assembly protocols used in this project involve stepwise incubation at several temperatures, while the production and folding of naturally transcribed RNAs is an isothermal process. To demonstrate the potential feasibility of cube assembly in conditions mimicking intracellular environment, its formation was monitored throughout an in vitro transcription reaction. Equimolar concentrations of DNA templates for all RNA strands were simultaneously added to the α[P32]-ATP body-labeling transcription mixture and the final products were characterized with PAGE. Co-transcriptional assembly results reveal the ability of all three nanoscaffolds to self-assemble isothermally (37° C.)

during in vitro transcription with yields greater than 70% (FIG. 72a; FIGS. 64 and 65).

Because the concentration of the RNA strands is a key factor in self-assembly processes, the apparent dissociation equilibrium constants (Kd) for the RNA and DNA hexamers was measured (see Materials and Methods). For the RNA hexamer, Kd was found to be ~16 nM (FIG. 72b), while the DNA hexamer Kd was measured to be at least 10 times higher (~170 nM, data not shown).

Nanostructures of hybrid (RNA/DNA) composition are of great interest due to their ability to maintain the diverse functionality of RNA, while incorporating the chemical stability of DNA. To test for hybrid cube viability, some of the RNA/DNA hybrids of the 6 stranded cube without dangling ends were characterized by total staining PAGE assembly experiments. The results (FIG. 72) demonstrated slight differences in the gel shifts for the major bands which can be attributed to the differences in shape and hydrodynamic radii of the cubes based on the number of A-form (RNA/RNA, RNA/DNA) and B-form (DNA/DNA) helices (see also Table 11). Table 11, shown below, shows the melting temperatures (Tm's) derived from melting curves in TGGE experiments for various RNA, RNA/DNA and DNA cubes. The thermal stabilities of the hybrid hexamers vary in function of RNA/DNA ratio and the location and orientation of the strands with respect of one another, leading to a somewhat erratic variation of Tm. Nevertheless, RNA nanocubes are always more stable than their DNA counterparts.

TABLE 11

| Cube Composition | # of RNA/RNA double helices | # of RNA/DNA double helices | # of DNA/DNA double helices | Measured Tm, ° C. |
|---|---|---|---|---|
| 6 stranded RNA, DNA and RNA/DNA cubes without dangling ends ||||
| ABCGEF | 0 | 0 | 12 | 31.2 |
| ABCDEF | 0 | 4 | 8 | 31.3 |
| ABCDEF | 0 | 8 | 4 | 34.4 |
| ABCDEF | 1 | 6 | 5 | 31.9 |
| ABCDEF | 2 | 8 | 2 | 35.8 |
| ABCDEF | 4 | 8 | 0 | 43.1 |
| ABCDEF | 5 | 6 | 1 | 45.8 |
| ABCDEF | 8 | 4 | 0 | 41.5 |
| ABCDEF | 12 | 0 | 0 | 54.4 |
| 6 stranded RNA and DNA cubes with dangling ends ||||
| ABCDEF | 0 | 0 | 12 | 30.5 |
| ABCDEF | 12 | 0 | 0 | 48.7 |
| 10 stranded RNA and DNA cubes with dangling ends ||||
| ABCDEFGHIJ | 0 | 0 | 12 | 29.2 |
| ABCDEFGHIJ | 12 | 0 | 0 | 43.1 |

Figure 72C:
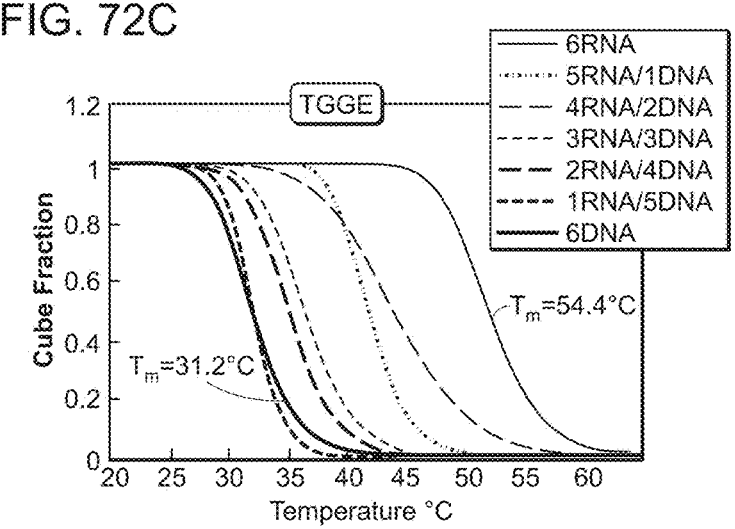
Figure 72D:
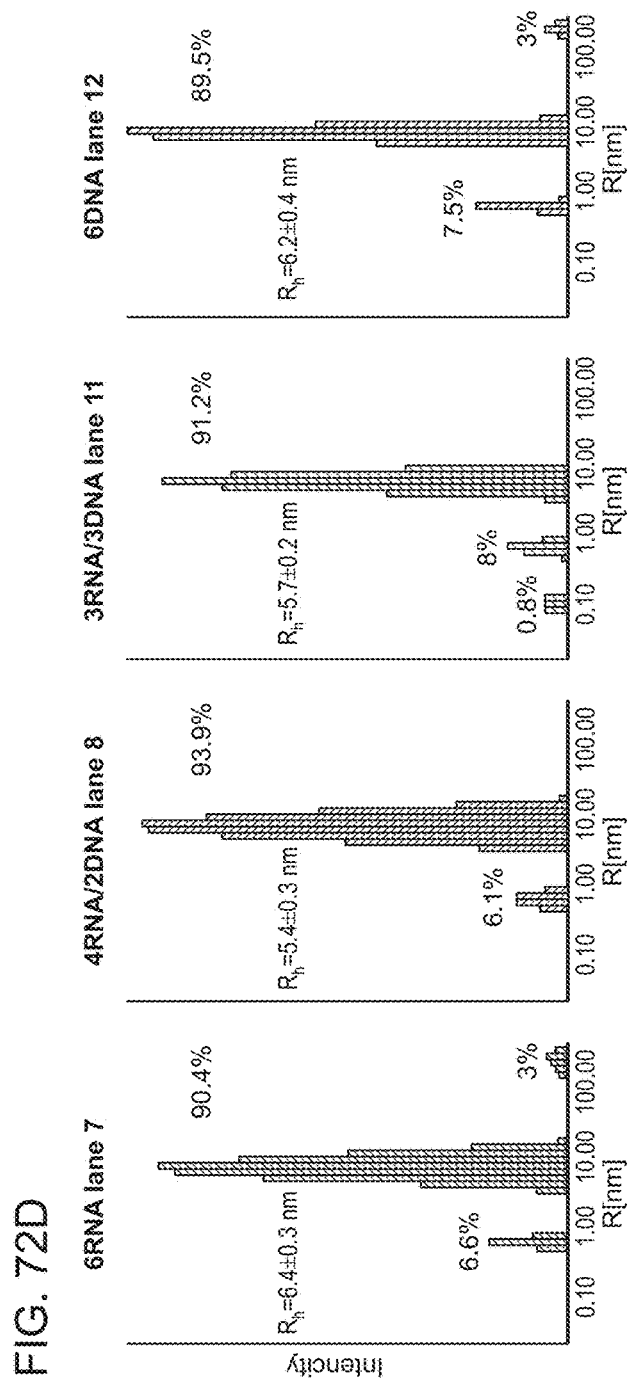

Melting temperatures (Tm's) were determined by TGGE experiments (Severcan et al. 2009) for the six stranded (FIG. 72c; SI, FIGS. 63 and 64) and ten stranded (FIG. 65) cubes by measuring the decrease in the yield of cubes versus temperature. Relative thermal stabilities of assembled RNA, DNA and RNA/DNA hybrid cubes were also compared by temperature gradient gel electrophoresis (TGGE) and are summarized in Table 11. The RNA cubes have Tm's about 15-20° C. higher than those of DNA cubes which can be explained by the higher thermal stability of A-form RNA duplexes versus B-form DNA duplexes (Freier et al. 1986; Santa Lucia et al. 1998; Sugimoto et al. 1996). However, the Tm values of RNA/DNA hybrids nanocubes can vary considerably in function of the number of strands of RNA and DNA entering into their composition as well as the location and orientation of the RNA strands with respect DNA strands (Table 11). These results suggest that the thermal stability of nano-scaffolds can be potentially tuned by altering the ratio of RNA to DNA strands and their location within the assembly.

Using dynamic light scattering (DLS), the hydrodynamic radii (Rh) for preassembled hexameric RNA and DNA particles were determined to be 6.4 and 6.2 nm, respectively (FIG. 72). These values are in good agreement with the predicted radii of circumscribed spheres around the RNA and DNA cube models of 6.5 and 6.3 nm, respectively (Materials and Methods, Eq. 2). The hydrodynamic radii of the 10 stranded and 6 stranded cubes with dangling ends are 6.9 and 7.1 nm, respectively (FIGS. 63 and 64). The larger radii can be attributed to the presence of 6 nt dangling ends and are consistent with estimated radii of 6.8 nm each and with PAGE results (FIG. 66).

Overall, PAGE results and DLS data strongly suggest the formation of closed, compact molecular complexes composed either of six or ten strands. However, some of the most convincing evidence for the formation of RNA cubes comes from cryogenic electron microscopy (cryo-EM) imaging and further single particle reconstruction (He et. al. 2008; Shih et al. 2004; Kato et al. 2009). The cryo-EM images show that most RNA particles have the expected size (FIG. 63) and are equally distributed in the entire imaging field (FIG. 67). Using the EMAN reconstruction packages (Ludtke et al. 1999), the 3D structures of the 6 stranded and 10 stranded cubes were obtained at resolution of 8.9 Å (from 2,038 particles) and 11.7 Å (from 1,677 particles), respectively (FIG. 67, and Materials and Methods). The computed projections from these 3D reconstructions match well with the class averages of observed particles with similar views (FIG. 73). The RNA cube reconstructions are in good agreement with the predicted 3D model displayed in FIG. 71.

To demonstrate the concept of functional activation through nano-scaffold assembly, Malachite Green (MG) aptamers (PDB ID: 1flt) (Baugh et al. 2000) were integrated into the dangling ends of the 10 stranded cube sequences. The triphenylmethane dye, MG was chosen as a signaling agent due to its fluorescent properties (Duxbury et al. 1993). In an unbound state, the MG molecule exhibits no fluorescence, however, upon binding to an RNA aptamer a large increase in fluorescence is observed (Afnin et al. 2008). The MG aptamer was separated into two strands, each of which was incorporated into the flanking sequence of two different strands of the cube (FIG. 74). The MG aptamer sequences were designed to have low mutual affinity, such that dimers would not form an active aptamer (FIG. 68). As seen in FIG. 74, emission remains relatively low for the monomer, dimer and all eight possible nonamers (FIG. 74, spectra 1-3; for all nonamers see FIG. 69). Analysis of the decamer (cube) spectrum (FIG. 74, spectrum 5) indicates a sharp increase in fluorescence due to full cube formation. Therefore, only when the cube is formed are the aptameric flanking sequences brought into close enough proximity to form the active MG binding aptamer. To reveal the potential multifunctionality of the nano-scaffold, a second aptamer was introduced into the same cube, resulting in a two fold increase in the MG emission signal (spectrum 6). The successful formation of functionalized nano-cubes was confirmed by native PAGE experiments (FIG. 74). As a control, a single molecule, with a MG aptamer embedded into the helical region was used (FIG. 74, sample S7, supporting Table 10, shown in FIG. 60). Table 10, shown in FIG. 60, shows the cube sequences and control MG aptamer sequence used in the experiments described herein. Letter sequences below the RNA strands indicate the desired interactions between different strands. Dots indicate the parts of the strands that are per design single-stranded. Sequence characters in lower letters were constrained to not change during the sequence optimization. RNA sequences were obtained by in vitro transcription of PCR generated DNA templates. DNA sequences entering into the composition of DNA nanocubes, were designed by replacing ribonucleotides with deoxynucleotides and uracils with thymines. They were chemically synthesized as shown.

Based on the emission signal of the control molecule, the yield of the functionally active cube S5 was estimated to be 77.3% at RNA concentration of 1 µM.

Figure 70A:
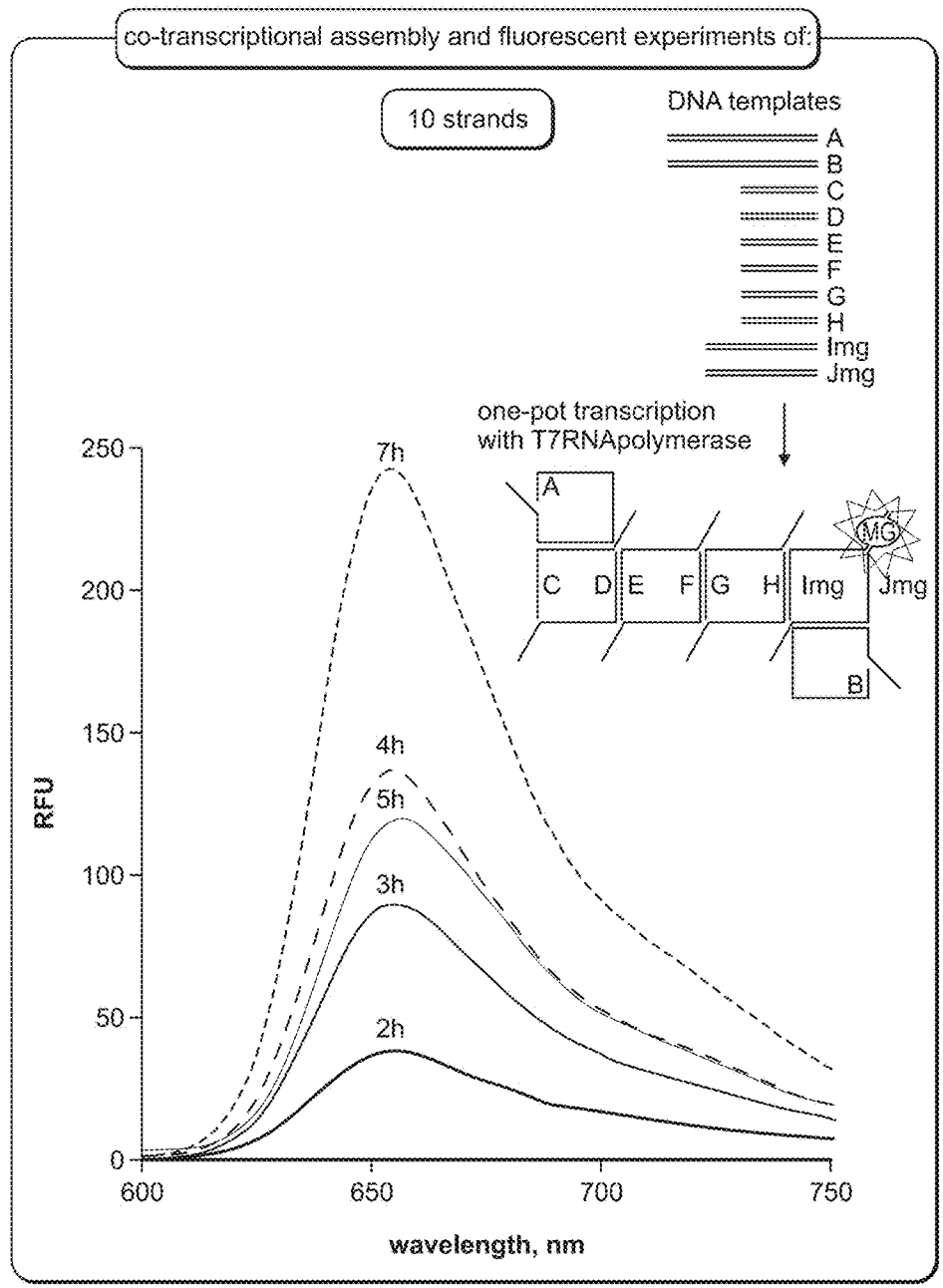
Figure 70B:
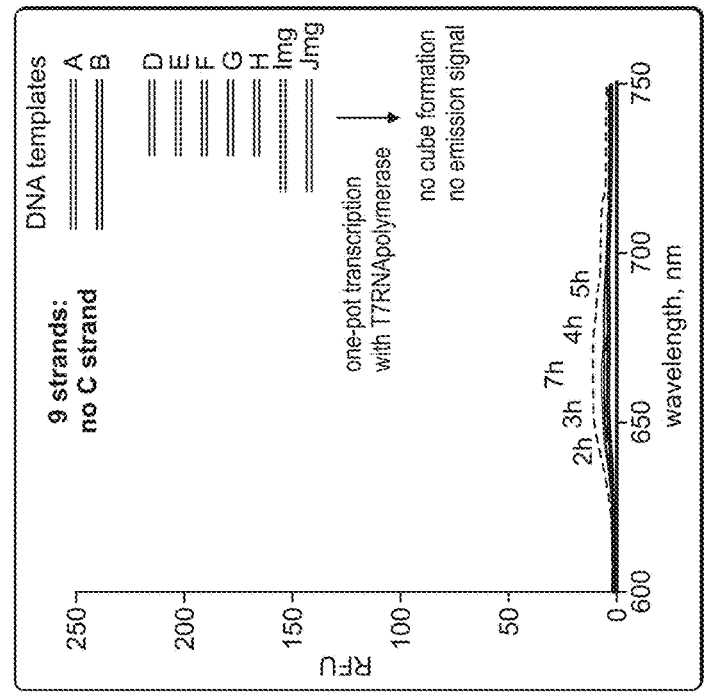
Figure 70C:
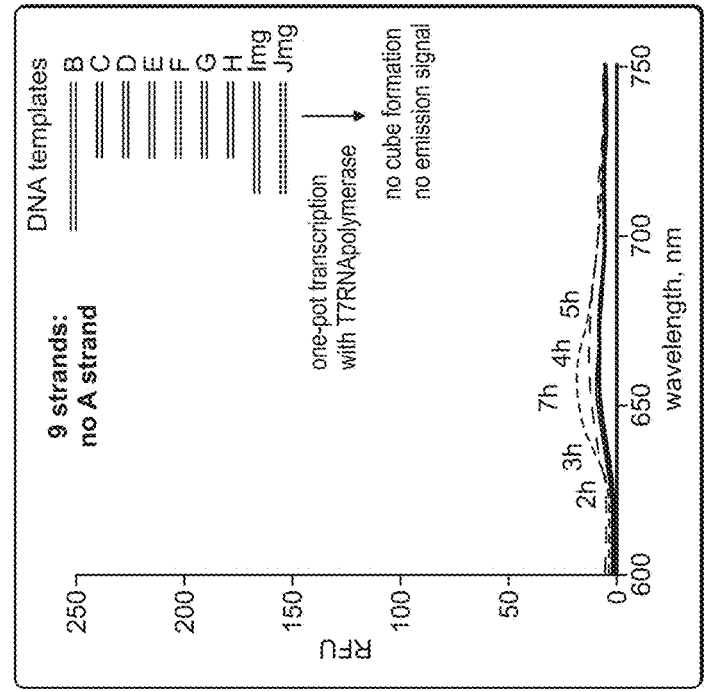
Figure 74C:
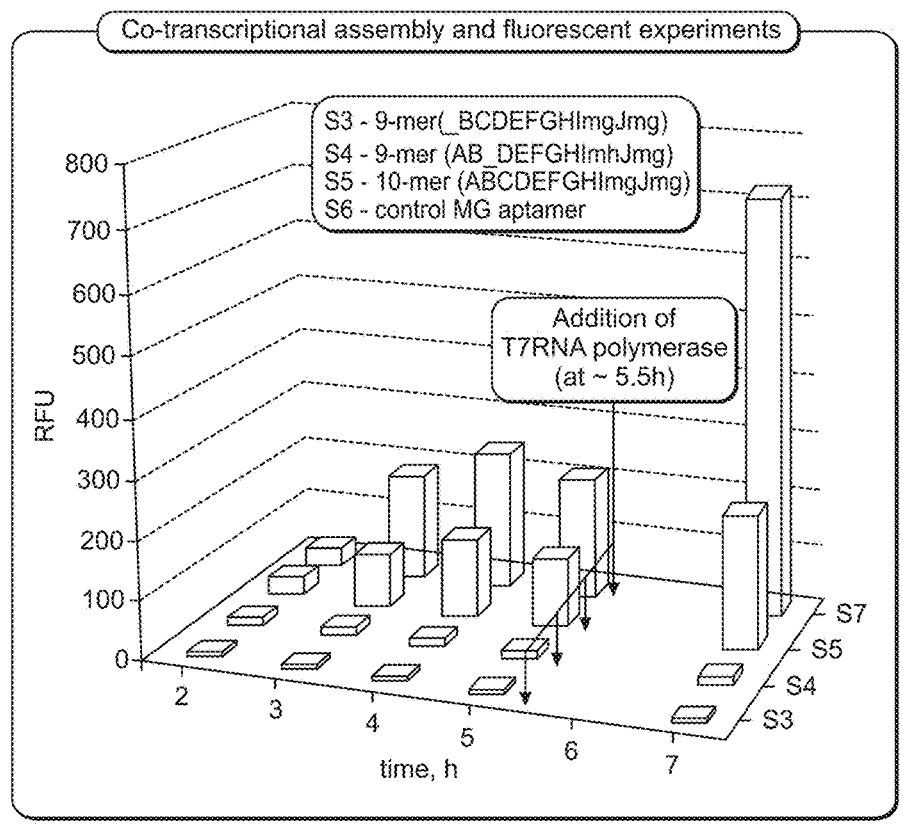

The assembly of the functionalized 10 stranded cube with MG aptamer was also monitored during in vitro transcription by following an increase in MG emission signal (FIG. 74c). Equimolar concentrations of 10 DNA templates for A-Jmg RNA strands (FIG. 74c, Sample S2) were simultaneously added to the transcription mixture as described above and aliquots of the transcription mixture were taken after 2, 3, 4, 5, and 7 hours for fluorescence measurements in presence of MG. Amplification of the emission signal over the course of the reaction confirms the proper folding of the MG aptamer into its active conformation upon cube assembly during transcription at 37° C. (FIG. 74c, sample S5; and FIG. 70a). After 5 hours, a slight decrease in emission signal occurs due to the partial or entire inactivation of the T7RNApolymerase and simultaneous RNA degradation. Additional T7RNA polymerase was therefore added to the transcription mixture at ~5.5 hours. By contrast to the transcription mixture containing the ten DNA templates coding for the 10 stranded cube, removal of one of the template essentially resulted in partial RNA assemblies unable to trigger the fluorescent signal emission in presence of MG (FIG. 74c, samples S3, S4 FIG. 70b-c). These results are consistent with the idea that the MG aptamer is optimally active only once the full RNA assembly is achieved. The 10 stranded cube has a lower emission signal than the control MG aptamer molecule (FIG. 74c, sample S7). This is expected as less MG aptamers are obtained in the 10 stranded RNA mix than in the MG aptamer control mix for an even amount of RNA produced during transcription.

As suggested previously, co-transcriptional assembly of functionalized nano-scaffolds confirm their ability to self-assemble isothermally (37° C.) during in vitro transcription, in conditions mimicking intracellular context.

In summary, the present inventors have demonstrated a strategy to design and engineer programmable, 3D RNA self-assembling nano-scaffolds with radii not exceeding 6.5 nm. The RNA component strands are short enough to be amenable to chemical synthesis. This allows (i) introduction of chemically stable RNA nucleotide analogs at specific sequence position to enhance their chemical stability, (ii) chemical functionalization important for therapeutic delivery and (iii) high yield of synthesis.

Thermal stabilities of these nano-scaffolds can be tuned by altering their strand compositions. Functionalization can be introduced through modification of the core strands and triggered by the full assembly of the nano-scaffold, thus providing vast potential for biomedical applications. In addition, the ability of these cubic RNA scaffolds to self-assemble isothermally at 37° C. during in vitro transcription opens a completely new route towards the in vivo construction of detection sensors, programmable packaging and cargo delivery systems.

Example 22. Molecular Dynamics Study of the RNA Ring Nanostructure: A Phenomenon of Self-Stabilization In recent years, significant progress in understanding RNA structure led to the emergence of 'RNA architectonics' a set of recipes for (self-)assembly of RNA nanostructures of arbitrary size and shape. Smallest RNA building blocks 'tectoRNAs' typically bearing welldefined structural features (e.g. angles) such as the 'right angle motif,' 'kink-turn motif' or 'RNAIi/RNAIIi complex' were manipulated (either experimentally or via computer simulation) into the desired 2D or 3D nanostructures (squares, hexagons, cubes, tetrahedrons, etc) that can be further assembled into periodic or quasi-periodic lattices. Compared to DNA nanostructures which have been extensively studied before, RNA as a nano-engineering material brings several additional challenging features. Firstly, due to the specificity of the interactions in RNA (such as a noticeable presence of non-Watson-Crick base pairing), it shows much larger structural modularity and diversity of tertiary structural building blocks, ~200 versus ~20 for DNA. Secondly, RNA nanostructures are often much more conformationally flexible than the DNA ones, which make them very promising in functional applications. The present study is direct to analysis, via all-atom classical molecular dynamics simulation, and the thermal dynamics as well as the response to an applied external force on a simple RNA nanostructure (13 nm in characteristic size), a hexagon-shaped RNA ring termed the 'nanoring'. It is composed of six 'RNAIi/RNAIIi complexes', joined by six 'kissing loop' motifs (see FIG. 75). While certain data about thermal stability of this and closely related RNA nanostructures are already available, both from experiments and simulations, a deeper and more detailed understanding of their stability and dynamics is needed. In particular, one of the main emphases of this work is on the effect of counterions, that may strongly affect the behavior of e.g. the kissing loop structural motifs. Another emphasis of the present study is on understanding the response of the above-mentioned nanostructure to an applied external force, an important factor in the context of a range of promising applications, including RNA nanostructures in man-made molecular machines.

Model

The NAMD package was used for all-atom molecular dynamics simulations of the RNA nanoring with the CHARMM27 force field. Visualization and processing of the simulation data are carried out with VMD and UCSF Chimera.

The RNA nanoring structure was solvated with 88 664 TIP3P water molecules (embedding the RNA ring into a water box of sufficient dimensions, ≈180° A×180° A×90° A to cover the ring completely with water), and then we add randomly 330 Na+ or 165 Mg2+ ions to the box in order to match the 330 negatively charged q=−1 phosphate groups of the nanoring, thus making sure that the system is electrically neutral ('no salt' system, see FIG. 75). Extra Na+, Mg2+, as well as Cl− ions were added to the simulation box in order to represent the following solutions: (i) 250 Na+ and 250 Cl− to represent a 0.16 M NaCl 'physiological solution', (ii) 664 Na+ and 664 Cl− to represent a 0.42 M 'sea water solution', (iii) 250 Mg2+ and 500 Cl− to represent a 0.16 M MgCl2 'physiological solution'.

The resulting system was simpulated at constant temperature and pressure (1 atm) via the means provided by the NAMD package. To control the temperature, the Langevin method with damping η=5 ps−1 is used. To maintain the constant pressure, the Nose-Hoover Langevin piston method (period of 100.0 fs and decay of 50.0 fs) is used, and periodic boundary conditions (PBC) are applied in all three dimensions. The time step is set to 2 fs and the cutoff for nonbonded interactions is 12 A°. Particle mesh Ewald summation (PME) was used to calculate the electrostatic interactions. Rigid TIP3P water molecules are handled via the SETTLE algorithm.

Structure and Dynamics of the RNA Nanoring in the Absence of External Forces

Starting from the initial structure shown in FIG. 75, a series of 2 ns runs were performed at different concentrations of ions and different temperatures ranging from 310 K to 510 K. For selected runs, the simulation was continued up to 6 ns, as described below in the text. During these runs, the behavior of the number of ions was monitored in the vicinity of RNA, the energy of interaction between the ions and the RNA, as well as the radius of gyration Rg and the root mean square deviation (RMSD) of the nanoring (for two latter analyses, we excluded the dangling unpaired tails of the nanoring visible in FIG. 75).

There are two reasons that led to the study of the ring at the highly elevated temperature of 510 K in comparison to the human body temperature 310 K. Firstly, the prospective use of the RNA nanoring as a construction block for more complex nanostructures may require knowledge of its properties in a wide temperature range. Secondly, since the equilibration of the ring at 310 K proceeds very slowly, a straightforward approach requires huge computational efforts (~40 h ns−1 in a typical parallel 32-processor run using a Sharcnet cluster). An insight into the behavior of the ring at this temperature is therefore obtained by doing 'quenched' runs. Namely, the configurations of the ring obtained after 2 and 6 ns equilibration runs at 510 K for Mg and Na, respectively, have been used as the starting points for the subsequent equilibration runs at 310 K.

Comparison of the Effects of Na and Mg

FIG. 76 shows the number of ions in the vicinity of the RNA in comparison with both Na and Mg at different concentrations at 310 K. Mg is found to be more efficient in solvating the RNA nanoring for the 'no salt' system, as well as at the equal concentrations of both ions. This is not surprising since this effect should be proportional to the ionic strength (i.e. concentration times charge squared). The efficiency of Mg in solvating the RNA nanoring shows up even if in our simulations we always find magnesium in the hydrated state, $Mg2+(H2O)6$, surrounded by six tightly bound water molecules, while Na is found to be much less solvated by water molecules, which can diffuse away from Na ions in the course of our simulations (FIG. 78).

While the difference in behavior of Na and Mg is clearly demonstrated in FIG. 76, at 310 K the equilibration process of the nanoring is probably not complete within the 2 ns time period since the number of ions adsorbed on the ring does not clearly show saturation. In a series of analogous runs made at 510 K the number of adsorbed ions does saturate by 2 ns; however, the interaction energy between RNA and ions as well as the RMSD of the nanoring continue to grow, suggesting that while the Manning condensation onto the ring has reached an equilibrium state, some slower processes, probably related to the migration/redistribution of the ions along the RNA ring, accompanied by a structural change in the ring, are taking place.

A sample configuration after a 2 ns equilibration with 165 Mg ions at 310 K is shown in FIG. 76 in comparison to another one (with 415 Mg) obtained after 2 ns at 510 K. Both Na and Mg ions seem to be distributed uniformly along the ring by the end of these runs. The structure of the ring is much better preserved at 310 K, though in-plane fluctuations and the out-of-plane bending of the ring are visible upon inspection of the trajectories. In fact, the number of hydrogen bonds between base pairs is reduced, compared to the initial structure, at both studied temperatures, as discussed herein. Nevertheless, during the times accessible in the simulations, a break of the nanoring (in a 'kissing loop' area) was observed only at 510 K for the 'no salt' Na system (after ~4 ns), while no clear-cut breaks were seen in all other runs, with Mg as well as in those with higher Na concentration.

The remarkable feature observed in the 510 K runs is a much higher concentration of ions near the RNA compared to that at 310 K. For example, at 510 K the number of Na ions in the vicinity of RNA increases up to a constant value of ≈0.8 Na per phosphate by t≈2 ns (FIG. 77), while it reaches only ≈0.5 Na per phosphate at 310 K (FIG. 2). This effect is clearly visible at other concentrations, and both with Mg and Na ions. For example in the snapshot with the 'physiological solution' (415 Mg) from FIG. 76, there is ≈1.15 Mg ions per two phosphates adsorbed at T=510 K compared to ≈0.8 Mg per two phosphates at 310 K (the first figure is more than unity due to the presence of some adsorbed Cl ions).

Quenched Runs

In order to better elucidate the behavior of the ions and the RNA nanoring during equilibration, some of the previously mentioned runs were extended up to 6 ns. In addition, 'quenched' 310 Kruns were carried out starting from configurations obtained at 510 K. FIGS. 77 and 79 compare the results of one such quenched run with the one obtained straightforwardly at 310 K starting from the 'standard' initial configuration depicted in FIG. 75. Data is shown from the following four runs: the runs for the 'no salt' (165 Mg) system, namely the one at 510 K (2 ns long, serving as a starting point for the 'quenched' run), and at 310 K, the quenched and regular runs (both 6 ns long); besides, 'no salt' (330 Na) system6 ns long run at 510 K is shown for comparison. Several points should be emphasized here. Firstly, an interesting consequence of the quenching process is the evaporation of the ions from the ring into solution upon a decrease in temperature (FIG. 77, top, green line). This phenomenon is present for both the systems with Mg and Na and has approximately the same magnitude. As can be seen from the snapshots in FIG. 78, the Mg ions evaporate together with the tightly bound first solvation spheres of water, while Na ions shed their water solvation spheres easily in the course of simulation. For both the quenched and nonquenched 310 K runs the number of ions near the RNA reaches a saturation value at about 3 ns. From the average of the endpoints of two ion evaporation/condensation curves (e.g. green and black lines in FIG. 77), it can be estimated that the equilibrium ion 'coverage' of the nanoring at 310 K as ≈0.7 Mg per two phosphates for the 'no salt' Mg system, compared to ≈0.9 at 510 K. The corresponding figures for the 'no salt' Na system (not shown in the figures) are ≈0.6 Na per phosphate at 310 K compared to ≈0.8 at 510 K. Secondly, as can be seen from FIG. 77 (bottom), soon after the number of ions near the nanoring stabilizes, the radius of gyration Rg of the nanoring reaches the same value for both quenched and non-quenched final configurations at 310 K. This occurs despite the persisting difference in microscopic detail between the two configurations. Indeed, the rather disordered 'quenched' state, depicted in FIG. 78 and further analyzed herein, shows no tendency to return to an ordered configuration, at least during 6 ns. This suggests that the 'quenched' ring is trapped in a long-lived intermediate metastable state, that it has been brought to at the higher temperature, but nevertheless it returns to the same overall shape. This observation supports the idea that the global shape measure, radius of gyration, is strongly influenced by the quantity and the valence of the adsorbed ions, no matter what the microscopic details are. The effect of the ion valence on the radius of gyration can also be seen in the 510 K runs in FIG. 3 where Mg, as compared to Na, not only adsorbs onto RNA better, but it also results in a more compact structure (a similar tendency is observed at 310 K in the runs that are not shown). The behavior of the RMSD for the nanoring is depicted in FIG. 79, where the overall RMSD values for the RNA nanoring, as well as those calculated for each 'native' base pair separately, are presented.

The overall RMSDs calculated from the initial structure in FIG. 75 do show saturation at 6 ns for both temperatures, but the values are quite large (6-7° A at 310 K and 13 A° at 510 K) which could possibly raise a question as to whether equilibration has been achieved in 6 ns (e.g. the RMSD for the quenched 310 K run replotted from different reference structure does not seem to show the clear-cut saturation in 6 ns, green symbols). A better representation of the RMSD for a trajectory would be a 2D map, which shows the RMSDs calculated starting from all time origins (FIG. 79, bottom).

From the grayscale patterns visible on these 2D RMSD maps, and from the corresponding section profiles, one can judge that at about 3 ns (this coincides with the time when the process of ion redistribution around the nanoring stabilizes, cf FIG. 77, top) the RMSD for both non-quenched and quenched 310 K runs changes its behavior toward slower growth, even though it still grows diffusively with time within the scale of the simulations. It is believed that such behavior of the RMSD can be explained by the large floppiness of the RNA nanoring. Indeed, according to the principal component analysis of the nanoring's trajectories, about ten of the largest principal components show a cosine-like time evolution, which evidences the purely diffusive randomized motion of the slowest modes. In spite of this floppy random motion of the slowest modes of the nanoring, the overall structure of the nanoring is well stabilized at 310 K, as evidenced both by the radius of gyration behavior, FIG. 77, bottom, and by the absence of any regular global dependence of the RMSDs calculated for separate base pairs on the base pair number along the ring, FIG. 79 (some of the peaks visible in this plot though can be associated with the groups of base pairs found in the 'kissing loops').

By contrast, for the 510 K runs, the radius of gyration does not show any convergence to a final stable value (see e.g. the curve in FIG. 77, bottom, for 330 Na system). Instead it is steadily decreasing, meaning that the ring collapses to a more compact, possibly globular, shape. It is noted here that the final equilibrium structure at 510 K should likely consist of unfolded single-stranded RNA fragments. Even though this unfolding cannot be observed in the simulation since it should happen on much longer time scales, than those accessible to us, one may wonder why on the way to this unfolded state the ring passes through a more compact, possibly globular one. One plausible explanation lies with the idea of 'self-stabilization' due to enhanced condensation of the ions with increasing temperature, as further discussed herein.

Ionic Distributions, Hydration and Structural Changes in the RNA Nanoring.

In order to better understand the behavior reported herein, it is instructive to look into the environments of ions and water molecules near the RNA and into the structure of the RNA nanoring itself, in their dependence on temperature.

Ion Binding.

FIG. 80 shows the radial distribution functions (RDFs) g(r) for Mg—P and Na—P pairs in the 'no salt' Mg and Na systems. One can see two main peaks associated with the hydrated Mg ions, surrounded by either one or two layers of water, respectively. No 'chelated' (in direct contact with O) Mg ions were found at 310 K, only a few (3 out of 165) in the 510 K run and the 310 K quenched run. As one can judge from the plots of the running coordination number N(r) (the volume integral of g(r)), the overall decrease of Mg ions around the RNA upon quench is due to the decrease of hydrated Mg. Qualitatively a similar picture is observed for the 'physiological solution' Mg system where, however, the chelated Mg ions are also found in the 310 K runs (in the same proportion, ≈7 out of 415). By contrast, in the 'no salt' Na system, most of Na ions are chelated (the strong g(r) peak in FIG. 80, right). The overall decrease of ions around the RNA in this case is due to the decrease of both chelated and hydrated (surrounded by one and two layers of water) Na.

One conclusion may be, therefore, that the evaporation process of ions appears to be independent of the hydration state of ions in the vicinity of RNA.

Hydration and Hydrogen Bonding.

FIG. 81 shows the RDFs for the P—OH2 pairs (where OH2 stands for water oxygen). One can observe reduced hydration of the nanoring at the higher temperature, T=510 K, while upon the quench to 310 K the number of water molecules in the vicinity of the ring is restored back to the number found in the 310 K run. Thus, the screening of the RNA phosphate groups proceeds differently at the two studied temperatures, and it represents what can be interpreted as a binding competition between the ions and the hydration water.

This picture is further corroborated by the hydrogen bonding patterns in the system. FIG. 82 demonstrates the behavior of those hydrogen bonds that form between the RNA and water, as well as of those found inside the RNA (i.e. between the base pairs). Instantaneous hydrogen bonds were measured via a facility provided in VMD, with slightly increased cutoffs for distance and angle (3.3° A and 30°, respectively, instead of the 'standard' values 3.0° A and 20°) in order to match the quantity of about 2.5 hydrogen bonds per base pair at 310 K. As attested to in FIG. 82, right, each base pair is thus hydrated on average by ≈15 water molecules at 10 K, both in the quenched and non-quenched runs, and this number settles down in the very beginning of the runs. At the same time, only ≈9 hydrogen bonds with surrounding water per base pair still survive at 510 K. No sequence-specific features of these hydration numbers were determined since their temporal fluctuations are larger than their apparent differences between the base pairs (FIG. 82, bottom).

Only about half of the hydrogen bonds between base pairs inside the RNA itself survives at 510 K (FIG. 82, left). Unlike those bonds between the RNA and water, these base pair hydrogen bonds do not recover quickly upon quench to 310 K (or they evolve much slower at the speeds not attainable in our simulations). Instead, the hydrogen atoms from these destroyed RNA-RNA hydrogen bonds serve as donors for creating additional hydrogen bonds with water, so that the quenched 310 K configurations are actually hydrated more than those obtained directly at 310 K (it becomes evident if one considers not only the phosphate hydration, as e.g. in FIG. 81, but the hydration of the whole RNA, data not shown).

Structural Transition in the Nanoring Backbone.

Apart from the obvious reduction of the hydrogen bonding between base pairs at the elevated temperature of 510 K, an interesting structural change in the RNA nanoring backbone takes place with the changing temperature, as evidenced by the radial distribution functions for the P-P pairs, and by the distributions of the P-P-P angles (FIG. 82, the case of Mg ions is shown). The g(r) plots reveal four peaks centered at 6.0 A°, 11.5 A°, 16.0° A and 17.5 A°, that correspond to the 1st, 2nd, 3rd P neighbours, and to the base pairs, respectively. Note also that at high T=510 K some peaks (notably, the second one) are shifted toward lower distances compared to the case of T=310 K, and the reverse process of shifting back to larger distances can be observed upon quench back to 310 K. Examination of the angular dependences reveals that this transition is associated with the population of P-P-P angles near $\theta \approx 110°$. Based on these plots one can conclude that, on average, the phosphates become closer to each other with increasing temperature. In other words, the one-dimensional RNA charge density along the ring effectively increases. According to the arguments presented in, further discussed herein, this should, in principle, result in a higher uptake of ions.

Forced Dynamics of the RNA Nanoring.

Having configurations that are essentially close to equilibrium in solutions of Na and Mg salts, external forcing is applied to the nanoring with the main purpose to determine its elastic response. Namely, a compressive (expansive) force, directed to (from) the center of mass of the ring, is applied to the 2310 atoms of the nucleic backbone using the steered molecular dynamics functionality of the NAMD package. This setup, dictated by the geometry of the ring, should give the average tensile or expansive elasticity of the ring. Note that the strength of the ring is mainly determined by the hydrogen bonding between base pairs, and therefore the magnitude of the applied force should be approximately comparable to the hydrogen bonding strength. Namely, since the ring contains 132 base pairs in total (excluding the unpaired tails), it may have some 132×2.5~300 hydrogen bonds, and since the force needed to break a single hydrogen bond is ~0.3 pN, the total force that can be sustained by the ring is less than ~100 pN (it is typically the forces of this order or less, that are required to unfold a chain-like RNA structure when applied to its two ends). This determines the order of magnitude of the force that needs to be applied to each of the atoms of the nucleic backbone in our simulations, as less than 0.05 pN. More specifically, in the simulation, a uniform acceleration was applied to each backbone atom (rather than a force). Given the average mass of the atoms in the backbone of $\approx 16$ amu, the acceleration applied should not exceed 0.02 A° ps-2 per atom. The caveat is that the forced dynamics of the ring under such weak forcing is expected to be extremely slow (e.g. up to ~µs in the unfolding experiments), and beyond the reach of our simulations. In attempts to circumvent this difficulty, the response of the ring to a wide range of forcing magnitudes starting from 0.01 A° ps$^{-2}$ and up to 1.0 A° ps$^{-2}$ was examined. However, only the smallest applied force assisted us in elucidating some of the elastic properties of the ring, while at higher forces we were able to obtain its transport properties only.

In the first two runs, the magnitude of forcing was increased in a quasi-linear (staircase-like) manner, from zero up to 1.0 A° ps$^{-2}$, by increments of 0.1 A° ps-2, with a time interval of 100 ps between the increments. In addition, two longer 1 ns runs at a constant forcing of 0.1 A° ps$^{-2}$ were made.

FIG. 83 shows the typical dependences of the radius of gyration Rg of the nanoring solvated in 165 Mg2+ ions versus time, both for compressive and expansive forcing. From the Rg(t) curves we observe that the response of the ring is smooth (apart from some fluctuations), namely parabolic or linear, for quasi-linearly increasing or constant forcing, respectively, and no equilibration or steady position is achieved. Thus, it can be problematic to determine the elastic properties of the ring in this regime of strong forcing. Such Rg(t) curves can be easily rationalized in the framework of the overdamped motion of a single noninteracting particle of a mass m, subjected to an external force. This is because the magnitude of the external force is too large to allow the interactions between the atoms in the RNA ring to show up in the forced dynamics. Namely, the equation of motion is $m\eta eff \cdot R = -ma$, where a is the acceleration, and $\eta eff$ is an effective damping of the motion of a particle. Integrating this equation, one obtains $R \propto -ct2/(2\eta eff)$ for the case of quasi-linear forcing a≈ct, and $R \propto -a0t/\eta eff$ for the case of constant forcing a=a0. Thus, one can determine the effective damping from these trajectories. It yields $\eta eff \approx 80$ ps-1 at T=310 K (for both quasi-linear compressive and expansive forcing of the ring) and $\eta eff \approx 45^{-1}$ at T=510 K. The value of $\eta eff$ obtained at 310 K is approximately three times larger than the one reported for the diffusion of a single nucleotide in water. Moreover, if the Arrhenius dependence $\eta = \eta 0 \exp(Ea/kBT)$ holds, one can estimate the activation energy as Ea≈460 K. For weaker constant forcing we obtain the values for the damping as follows: $\eta eff \approx 55$ ps$^{-1}$ for compression/expansion at T=310 K, and $\eta eff \approx 30$ ps$^{-1}$ for compression at T=510 K. These values are smaller than those obtained under the influence of stronger forcing; however, they still lie in a reasonable range (the activation energy remains approximately the same, Ea≈480 K).

Note that even though the applied forces were strong enough to yield the free drift of the RNA nanoring parts w.r.t. each other, and to preclude any elastic response, we obtained in this way a set of configurations spanning a whole range of Rg. The question we posed is whether this set of configurations can be used to estimate elastic properties via (possibly parabolic) energy-strain dependences? In order to answer this question, we determined the total potential energy of the RNA ring, E, for each of the configurations that correspond to the compression curves from FIG. 83.

As seen in FIG. 83, despite some dispersion of the data, obtained E(Rg) dependences are linear rather than parabolic. A possible explanation is that the configurations obtained are not representative of the equilibrium, which precludes a reliable determination of the elastic coefficient in this way too. It is worth to note that under such strong compression, the ring shows an interesting folding feature. Namely, under the compression regime described above, up to the forces of a≈1.0 A° ps-2 the ring compacts uniformly, without losing its hexagonal shape. However, at yet stronger compression (a $^1$1.5 A° ps-2, $Rg_1$ 50 A°) the ring starts to fold into a triangular shape (FIG. 10), where three of the six 'kissing loops' form angles and the three remaining ones belong to the sides of the triangle. Of course, at yet higher compressions the RNA acquires a completely spherical shape. Finally, two 2 ns runs that have been carried out at the smallest force we used, a=0.01 A° ps-2 (estimated to be about two times smaller than the one needed for breaking the hydrogen bonds in our system), are shown in FIG. 84. Even if the depicted Rg(t) dependences do not achieve a stable equilibrium yet, one can judge from the appearance of a steady plateaux at T=310 K, where the system spends a comparatively long time (>200 ps) before jumping to the next plateau, that in this series of runs the hypotheses of the free drift of the non-interacting RNA backbone particles under the effect of an external force is no longer valid, and equilibrium can be achieved, given longer annealing times. With the current simulation data of a maximum duration of 2 ns we can give only the lower bound for the compressive strain of the nanoring ($\delta Rg > 1.5$ A° at T=310 K). This enables us to give, respectively, an upper bound to the corresponding elastic coefficient (since the latter should be inversely proportional to the former). Namely, for the sake of simplicity, and because of the quasi-planar geometry, we write the following 2D formula for the linear elasticity in the plane of the ring:

$$\delta P = K_{2D} \frac{\delta S}{S}, \quad (1)$$

where $\delta P$ is the change of the '2D-pressure' (i.e. force per unit length of the nanoring perimeter), and $\delta S$ is the respective change of the surface in the plane of the ring. Note that this formula is analogous to the expression that defines the bulk modulus K in 3D ($\delta P = K \delta V V$, where V is the volume). Therefore, K2D, a quantity with the dimensions of Nm$^{-1}$, can be termed a '2D surface modulus'.

Furthermore, given the expressions for the '2D pressure' change $\delta P = aM/2\pi Rg$ (where M≈37951 amu is the total mass of the RNA backbone, to which the force is applied), we can estimate the upper bound for K2D as K2D<0.03 Nm$^{-1}$. In order to compare this value with some corresponding value in 3D, we divide K2D by the (approximately constant) thickness of the ring h≈30 A°, to obtain Keff<0.01 GPa at 310 K. This is a very low value, which is expected, as the RNA ring is a 'soft matter' material (water bulk modulus is ≈2.2 GPa, and typical values for DNA Young modulus are ~0.1 GPa).

The present study demonstrates some interesting features of the RNA nanoring, and opens some questions about the behavior observed.

The phenomenon of the evaporation of adsorbed ions from the RNA into water when the temperature is dropped merits further inquiry, as it can be of practical importance. Indeed, ions are known to be an important factor in the stabilization of the native folds of biopolymers because they efficiently screen the negatively charged phosphate groups. A higher uptake of ions by the RNA ring with an increase in temperature can be interpreted as a mechanism of 'self-stabilization' demonstrated by the RNA ring. This mechanism should be ubiquitous for other RNA structures as well.

This intriguing, at first glance, behavior can be readily rationalized even within the simple 'Manning condensation' theory if one takes into account the temperature dependence of the water dielectric constant $\epsilon$. The Manning theory describes the adsorption of counterions onto a rod-like charged polymer of infinite length. It shows that if the polymer (the RNA ring in our case) is charged too much, i.e. if its length per unit charge Le is small enough, Le<ZLB, where Z is the valence of counterions and LB is the so-called Bjerrum length $$L_B = e^2/4\pi\epsilon kT \quad (2),$$

then the counterions from the solution will condense onto the polymer, thus decreasing its effective charge and increasing Le, until the resulting density of charge falls to the critical value that corresponds to L˜e~LB. In equation (2), LB is the distance at which the electrostatic energy between two elementary charges e in a medium with the dielectric constant $\epsilon$ is ~kT. The remaining effective charge per nucleotide after the counterion condensation occurred is given by ˜q/e=Le/ZLB, i.e. it is inversely proportional to the Bjerrum length. As Le≈1.3° A for an A-form RNA double helix [13], and LB≈7 A° at T=310 K in water, the remaining charge per nucleotide would be, e.g. ˜q≈0.1e only for Mg ions (Z=2) condensation on a straight double helix.

It should be noted that Manning condensation theory has been derived for linear infinite length polymer geometries, and for low counterions strength I, i.e. for polymers whose diameter is much smaller than the Debye's length LD=1.0/√8πLBNAI, where NA is the Avogadro number. here, case LD~5 A° at T=310 K even for the 'no salt' Mg system (that contains barely the ions needed to neutralize RNA) i.e. it is comparable to the thickness of the ring. In the case of a polymer of a general shape, one can still obtain a similar insight into the thermodynamics of the counterion condensation by equating the chemical potentials of the free and condensed counterions in their equilibrium. The chemical potential of the free counterions in solution is μfree≈kT ln(c), where c is their concentration. The chemical potential of the condensed ions is given by an average interaction energy of an ion with the RNA polymer, μcond≈N˜qZe2/4πεRg=N˜qZkT IB/Rg, where N is the number of nucleotides and Rg is an average distance between the counterions and the charges in the RNA, i.e. it is a characteristic RNA size. This characteristic size can be approximately taken as Rg∝NLe for the linear geometries, and Rg∝N1/3Le for the globular geometries. Equating μcond=μfree, one can see that the remaining charge per nucleotide is again inversely proportional to LB:

$$\tilde{q} \propto \frac{R_g}{L_B NZ}. \quad (3)$$

If one neglects the variation of Rg with temperature, then the total temperature dependence of ˜q is determined by that of LB. For example if LB decreases while the temperature increases (as would be the case without taking into account the temperature dependence of $\epsilon$), the effective remaining charge ˜q would increase, and therefore, less ions would be adsorbed onto the polymer at a higher temperature. However, a sufficiently strong change of the dielectric constant E may actually reverse this picture. It is known that the experimental dielectric constant of water monotonically decreases with increasing temperature in the following fashion [20]: $\epsilon = \epsilon^*(T^*/T)1.4$ (by ≈2.0 times in the range 310-510 K), so that the Bjerrum length LB actually increases with temperature as LB∝T 0.4 according to equation (2). This leads to ˜q∝T−0.4, i.e. the remaining effective charge decreases with temperature due to stronger counterion condensation (by a factor of ≈1.2 times in the range 310-510 K). From FIG. 77 one can see that the remaining charge at 510 K is about 0.1e per phosphate at 510 K (16 Mg ions per 330 nucleotides), while it increases to ≈0.3e per phosphate upon evaporation of 30 Mg ions. Thus, the evaporation of ions from the ring upon quench that we observe in the present work may indeed be qualitatively explained via the behavior of the Bjerrum length (however, in our simulations the magnitude of the phenomenon seems to be stronger than that resulting from the crude estimation above). Even though the above-mentioned behavior of the water dielectric constant is known to lead to a decrease of ion solubility in water in some cases, simple salts are known to be unaffected (e.g. for NaCl the solubility slightly increases with increasing temperature, up to at least 600 K). On the other hand, the phase transitions or structural changes in some other salts (like the dehydration process in sodium sulphate) may lead to their solubility in water actually decreasing with increasing temperature, similar to the tendency we observe. Therefore, a further analysis of the structural changes/phase transitions in the RNA ring itself may lead to a complete explanation of the observed behavior of the ions.

One of the simplest structural changes in the ring is its thermal expansion (contraction). Indeed, we observe in our simulations that between 510 K and 310 K the ring contracts about 5% in size (this is roughly the same figure seen for pure water). A more subtle structural change in the RNA ring has been evident in section 3.3 from the analysis of the radial distribution functions g(r) for the P-P pairs and the P-P-P angular distributions. The shift of the second P-P neighbour peak with increasing temperature that corresponds to the change of the P-P-P angle from θ≈150° to a value θ≈110° (FIG. 82) may indicate that, on average, the RNA charge density effectively increases with the temperature. Given the 5% thermal expansion, this obviously cannot happen uniformly throughout the ring, but we may expect that the effective increase in charge density can occur at least locally. Indeed, visual inspection of the atomic configurations reveals that while such an angle change occurs throughout the ring, it is somewhat more enhanced in the regions of the kissing loops. It has been shown that such an increase in charge density leads on average to an increase of the number of the retained ions.

Methods

The experiments described herein were performed using, but not limited to, the following materials and methods:

TectoRNA Design and Synthesis.

Three-dimensional atomic models were manually constructed using Swiss-Pdb Viewer by connecting 90°-angle motifs and kissing loops with helical stems. 90°-angle motifs were extracted from the x-ray structures of *E. coli* 50S subunit (2AW4) for the 3WJ motif, yeast phenylalanine tRNAPhe (4TNA) and *Thermus thermophilus* tRNASer (1SER) for the tRNA motif. The kissing loop motif was extracted from the DIS HIV-1 kissing complex structure (IJJM). The computer generated models were used as scaffoldings to generate 2-D diagrams, and 1D sequences. Secondary structures were optimized using mFOLD software to obtain the most stable fold and eliminate alternative pairings.

Double stranded DNA templates containing 17 RNApol promoter at the 5' end were generated by PCR from synthetic DNA molecules. Forward and reverse primers were designed to hybridize to a template strand with a Tm 56° C. Primer sequences were optimized to eliminate energetic pairings within themselves. All synthetic oligonucleotides used in this study were purchased from. IDT Technologies (The full list of synthetic oligos is available in Table 1). The PCR reactions were performed using Taq DNA polymerase by hot-starting at 94° C. following a temperature programmed cycle (94° C., 56° C., 72° C.) in a total reaction volume of 125 IA.

The reaction mixture contained 0.3 pmol of template, 150 pmol each of both forward and reverse primers with 30 pl 5×PCR buffer (250 mM KCl, 50 mM Tris pH 8.9, 2.5% NP40, 5 mg/mL gelatin) in 2 mM MgCl2 plus 60 04 of each dNTP. Following DNA amplification, purification of PCR products was performed with a QiaQuick PCR purification kit (Qiagen).

RNA synthesis was performed enzymatically by in-vitro transcription of PCR generated double stranded DNA template using T7 RNA polymerase (10 U/u 1) during 4 hrs of incubation at 37° C. in a buffer containing 15 mM MgC12, 2 mIV1 spennidine, 50 ml\4 Tris 7.5, 2.5 mM of each NTP, 10 mM DTT, 0.01 mild inorganic pyrophosphatase and 0.8 U/111 RNasin to a total volume of 200 pl. The reaction was quenched by the addition of 5 ul DNase (10 U/u 1) in order to digest the DNA templates and incubated at 37° C. for 30 mins., followed by purification on 8% denaturing PAGE. RNA products were visualized by UV shadowing and cut from the gel, eluted overnight at 4° C. in crush and soak buffer (200 mM NaCl, 10 mM Tris pH 7.5, 0.5 M EDTA). The RNAs were precipitated in 2 volumes of pure ethanol and washed twice with 90% ethanol. Probe RNAs were 32P labeled at the 3' end by [3211 pCp ligation with T4 RNA ligase and purified on 8% denaturing PAGE.

Folding and Assembly of Tectosquares.

Tectosquare assembly was performed through one of two protocols. The assembly of RNA products was monitored by PAGE, using either $^{32}$P-alpha-ATP labeled RNA or 3'4321$^3$1pCp labeled RNA (GE Healthcare). Crude tectosquare mixture can be stored at 4° C. for several weeks without significant degradation. For visualization of the constructs by PAGE, one corner of the tectosquare (Unit A) constituted of a fixed amount of 3' end labeled RNA (1 nM) and unlabeled RNA.

Protocol 1:

Tectosquares are prepared by mixing equimolar concentrations of four tectoRNAs (200 nM) in water. The RNA was subjected to a denaturation-renaturating step by heating the samples to 90° C. for 3 mins, cooling on ice 3 mins followed by incubation at 30° C. for 3 mins. Next, a 5× concentrated buffer was added to the sample to reach 10 mM Tris-borate pH 8.2 (TB), 50 rnM KCl, and 0.2 mM Mg(OAc)2, and the sample was incubated at 30° C. for 30 mins.

Protocol 2:

This protocol adds one assembly step to Protocol 1 to further stabilize tectosquares for native PAGE and AFM studies. Following the incubation of tectosquares at 30° C. for 30 mins, the magnesium concentration is raised to 15 mM Mg(OAc)2 by the addition of a 2× concentrated buffer (RNA is diluted to 100 nM) and then further heated at 50° C. for 10 min and slow cooled to 10° C. over 30 min.

Native-PAGE and TGGE.

Native PAGE (using protocol 2) and TGGE (using protocol 1) experiments were performed essentially as previously described. For native-PAGE analysis, 10 μl of RNA sample (100 nM) was combined with 1 μl of gel loading buffer (0.01% bromophenol blue, 0.01% xylene cylanol, and 20% glycerol) and run on a 7% (29:1) non-denaturing PAGE at 50 W and 10° C. for various times. 2 mM Mg(OAc)2 was present in both gel and electrophoresis buffer. For TGGE analysis, the experimental setup was adjusted to have a linear temperature gradient perpendicular to the electric field. The temperature gradient was typically set up from 25° C. to 65° C. 20 ul of RNA sample (40 nM) was combined with 2 μl of gel loading buffer and run on 7% (29:1) non-denaturing PAGE at 20 W for 1 hr. 0.2 mM Mg(OAc)2 was present in both gel and electrophoresis buffer. The gels were dried and autoradiographed using a phosphorimager screen (Molecular Dynamics). Quantitation of gels was performed using the program. ImageQuant. The concentration of tectosquare (typically of 40 nM) was increased by a factor of five for the mutant tRNA-square in order to compensate for its lower yield of assembly. The thermal stability of the tRNA-square was however shown not to be concentration dependent in the range of RNA concentrations tested (40-200 nM) (data not shown).

$K_D$s Determination.

Apparent equilibrium constants of dissociation ($K_D$s) for KL interactions between two subunits of RNA-square (dimers AB, BC, CD or DA) were determined by titration over a range of concentrations from 1 nM to 512 nM as previously described. RNAs for this experiment were prepared by protocol 1, as described above. Fixed amounts of [32P] pCp 3' end labeled test RNA (0.5 nM final) were mixed with variable amounts of unlabeled test RNA and unlabeled probe RNA to make the indicated final concentration (1 nM to 512 nM) of each. Dimers (AB, BC, CD or DA) were then heated at 90° C. for 3 min, immediately cooled on ice for 3 min followed by incubation at 30° C. for 30 min in the presence of 0.2 mM Mg(OAc)2, 50 mM KCl and 10 mM Tris-borate pH 8.2 (TB). The resulting gel shifts were measured using Imagequant and interpreted with the program Kaleidagraph. $K_D$s values were determined as the concentration at which half of the RNA molecules are dimerized.

Lead-Induced Cleavage and RNase T1 Structural Probing.

Tectosquares were assembled (via protocol 1) and purified on 8% native-PAGE prior to the lead cleavage in order to equilibrate the concentration of regular and mutant tectosquares. Chemical and enzymatic probing were all performed on 400 nM of single tectoRNAs or 100 nM of purified tRNA-squares. Lead acetate (EMD) solution (80 mM) was prepared daily to avoid degradation. The reaction mixture constituted of tectoRNA (400 nM) or tectosquare (100 nM), association buffer (15 mM Mg(OAc)2, 25 mM K(OAc) and 25 mM HEPES pH 7.5), and 1 ul yeast tRNA (10 mg/mL). The cleavage reaction was initiated after adjusting the reaction mixture (10 µl) to a final concentration of 16 mM $Pb^{2+}$ and incubated for 5 min at 25° C. To quench the reaction, 5 ul of 0.1 M EDTA was added to the reaction mixture followed by ethanol precipitation. The RNAs were precipitated in EtOH at −20° C. for 1 hour and washed twice with 90% EtOH, dried, and then reconstituted in gel loading buffer. The RNA fragments were separated on denaturing polyacrylamide gels (15% acrylamide, 8 M urea). RNase T1 probing was performed according to the manufacturer recommendation and all the enzymes and buffers were purchased from AMBION°. Single tRNA-tectoRNAs (400 nM) or tectosquares (100 nM) were mixed with 10×RNA Structure Buffer (100 mM Tris pH 7, 1 M KCl, 100 mM MgCl2) and 1 ug of yeast tRNA. Constructs were then treated with RNaseT1 for 20 min at 25° C. in a final reaction volume of 10 µl. To stop the reaction 20 µl of inactivation/precipitation buffer was added to the reaction mixture. The RNA fragments were washed twice with 90% ethanol, reconstituted in gel loading buffer and separated on 15% denaturing gel. Alkaline hydrolysis ladders of tectoRNA or tectosquare were obtained by incubation at 95° C. for 10 min in presence of 50 mM sodium carbonate pH 9.2, 1 mM EDTA and 1 µg of yeast tRNA. Reaction volumes of 10 µl were directly loaded onto the gel after addition of blue/urea buffer.

Atomic Force Microscopy (AFM).

For AFM imaging, 20 µl tectosquare samples (100 nM RNA, TB buffer pH 8.2, 15 mM Mg(OAc)2, 50 mM KCl) were assembled in solution prior to depositing on freshly cleaved mica surface as described in the previous section: folding and assembly of tectosquares. After waiting for 60 sec, each sample was rinsed with a 2 mM Mg(OAc)2 solution and dried under nitrogen. Image acquisition, performed in air at room temperature, was in tapping mode using a Multimode microscope equipped with a Nanoscope IIIa controller (Veeco, Santa Barbara). Silicon probes (model NSC12 from MikroMesch) with resonance frequency ~150-250 kHz and spring constant ~4-8 N/m (Nanodevices, Santa Barbara, Calif.) were used. Images were processed by NANOSCOPE (DI) and leveled by a first order plane fit in order to correct the sample tilt.

TectoRNA Constructs.

Table 1 shows the list of tecto RNA constructs use in this study. TectoRNA nomenclature: A, B, C, and D indicate the type of the unit with respect of their KL motifs in a clock-wise fashion within the context of the tectosquare; sd stands for self-dimer; m stands for mutant; nucleotides underlined in yellow indicate the kissing loops; nucleotides underlined in blue indicates point mutations. Constructs tRNA-KL5a/b were used to measure the Kd of KL5.

Design.

Three dimensional atomic models of regular nanorings were constructed using Insight II by importing the kissing loop structure of the ColE1 plasmid ((PDB entryL 213J2) and connecting them by helical struts as described in detail (Yingling and Shapiro (2007). To model the stabilized nanorings, a 4WJ-A minor motif from the X-ray structure of the Haloarcula marismortui 50S ribosomal unit (PDB 1JJ2) was incorporated at the 5'-3' end junction using Swiss-Pdbviewer. The control building blocks were designed by switching the RNAIi/RNAIIi loop motif with the kissing loop motif extracted from the DIS HIV-1 kissing complex structure (IBM). The computer generated models were used as scaffoldings to generate 2-D diagrams, and ID sequences. Secondary structures were optimized using rnFOLD software to obtain the most stable fold and eliminate alternative pairings.

Synthesis.

All synthetic oligonucleotides were purchased from IDT Technologies. The full list of RNA sequences is available in the Table in FIG. 16. Double stranded DNA templates containing T7 RNApol promoter at the 5' end were generated by PCR from synthetic DNA molecules as described in detail I (Jaeger et al. (2001); Chworos et al. (2003); Yingling and Shapiro (2007); Severcan, I. et al. unpublished (2008)). The RNA synthesis was performed enzymatically by in-vitro transcription of PCR generated double stranded DNA template using T7 RNA polymerase (10 U/µl), following purification on 8% denaturing PAGE[2,17]. Probe RNAs were 32P labeled at the 3' end by [32P] pCp ligation with T4 RNA ligase and purified on 8% denaturing PAGE.

Nanoring Assembly.

In order to obtain the highest yield, the assembly protocol was optimized by testing several different folding and association conditions varying the $Mg^{2+}$ concentration, and association temperature (data not shown). Stepwise assembly approach has been found to increase the yield of product formation. Nanoring units were mixed and assembled in the first step at low $Mg^{2+}$ concentration. During the second step $Mg^{2+}$ concentration was increased to further stabilize the RNAIi/RNAIIi loop pairing. The assembly of RNA products was monitored by PAGE, using 3'[32P]pCp labeled RNA (GE Healthcare). For visualization of the constructs by native-PAGE, unit A of the nanoring constituted of a fixed amount of 3' end labeled RNA (1 nM) and unlabeled RNA.

Step 1:

Nanoring units (A and B) were mixed in equimolar concentrations in water to a specified final concentration. The nanoring was then subjected to a denaturation/renaturating step by heating first to 90° C. for 3 mins, cooling on ice 3 mins followed by incubation at 30° C. for 3 mins. Next, a 5× concentrated buffer (10 mM Trisborate pH 8.2 (TB), 50 mM KCl, 50 mM NaCl and 0.2 mM $Mg(OAc)_2$) was added to the sample and was incubated at 30° C. for 30 mins.

Step 2:

Following the incubation step magnesium concentration is raised to 2 mM Mg(OAc)2 by the addition of a 2× concentrated buffer (10 mM Tris-borate pH 8.2 (TB), 50 mM KCl, 50 mM NaCl and 2 mM Mg(OAc)2). Next, annealing was performed by incubating the sample at 50° C. for 10 min followed by cooling to 10° C. over approximately 30 min.

Step 3:

This step is used only for supra-molecular assembly of nanorings into arrays. Following step 2, arrays were generated by mixing in stoichiometric concentrations two nanorings that have complementary tails on ice. The sample was deposited on a freshly cleaved mica. Annealing was performed by incubating the sample at 50° C. for 10 min followed by cooling to 10° C. overnight in Styrofoam chamber.

Native Polyacrylamide Gel Electrophoresis.

Native-PAGE experiments were performed essentially as described (Jaeger et al. (2001); Chworos et al. (2004). Briefly, 10 ul of RNA sample at specified final concentration was combined with 1 gl of gel loading buffer (0.01% bromophenol blue, 0.01% xylene cylanol, and 20% glycerol) and run on a 5% (38.5:1) non-denaturing PAGE at 50 W and 10° C. for various times. 2 mM Mg(OAc)$_2$ was present in both gel and electrophoresis buffer.

Atomic Force Microscopy.

We have adopted a strategy reported previously (Chworos et a. (2004); Hansma, H. G. et al. J Microsc 212, 273-9 (2003)). Following step 2, 20 µl nanoring samples (1 µM A/B and 2 µM SD final concentrations) were directly deposited on mica surface. After waiting for 60 sec, mica surface was rinsed with a 2 mM Mg(OAc)2 solution and dried under nitrogen. All AFM images were acquired in air and the imaging was performed in tapping mode using a Multimode microscope equipped with a Nanoscope In a controller (Veeco, Santa Barbara). Silicon probes (model NSC12 from MikroMesch) with resonance frequency ~150-250 kHz and spring constant ~4-8 N/m (Nanodevices, Santa Barbara, Calif.) were used. Images were processed by NANOSCOPE (DI) and leveled by a first order plane fit in order to correct the sample tilt.

$K_D$ Determination.

Apparent equilibrium constants of dissociation (I(Ds) for RNAIi/RNAIIi interactions between two subunits of nanoring were determined by titration over a range of concentrations from 1 nM to 512 nM as previously described (Jaeger et al. (2001); Geary, C. et al. Nucleic Acids Res 36, 1138-52 (2008)) following step 1. Fixed amounts of [32P] pCp 3' end labeled test RNA. (0.5 nM final) were mixed with variable amounts of unlabeled test RNA and unlabeled probe. The resulting gel shifts were measured using Imagequant and interpreted with the program Kaleidagraph. Kds values were determined as the concentration at which half of the RNA molecules are dimerized.

TectoRNA Design and Synthesis.

Three dimensional atomic models were manually constructed using Swiss-Pdbviewer by connecting 90° motifs and kissing loops with helical stems. 90° motif was extracted from the x-ray structures of yeast phenylalanine tRNAPhe (4TNA) and *Thermus thermophilus* tRNAs' (1 SER) and the kissing loop motif was extracted from the DIS HIV-1 kissing complex structure (IJJM). The computer generated models were used as scaffoldings to generate 2-D diagrams, and 1D sequences. Secondary structures were optimized using mFOLD software to obtain the most stable fold and eliminate alternative pairings. The four specific tail-tail connectors of 6 bp were designed with a homemade program called ssRNA designer (available upon request). Double stranded DNA templates containing T7 RNApol promoter at the 5' end were generated by PCR from synthetic DNA molecules as described in detail in 23. All synthetic oligonucleotides used in this study were purchased from IDT Technologies (The full list of synthetic oligos is available in the Table in FIG. 39). The RNA synthesis was performed enzymatically by in-vitro transcription of PCR generated double stranded DNA template using T7 RNA polymerase (10 U/ul), following purification on 8% denaturing PAGE (Severcan (2008); Jaeger (2001)). Probe RNAs were 32P labeled at the 3' end by [32P] pCp ligation with 14 RNA ligase and purified on 8% denaturing PAGE.

Cuboid Assembly.

Cuboids were assembled using a stepwise assembly strategy. The assembly of RNA products was monitored by PAGE, using either 32P alpha-ATP labeled RNA or 3'432P1pCp labeled RNA (GE Healthcare). For visualization of the constructs by native-PAGE, one corner of the tectosquare (Unit A) or two corners of the cuboid (Unit A and unit A') constituted of a fixed amount of 3' end labeled RNA (1 nM) and unlabeled RNA.

Step 1: Two tectosquares that make up the cuboid are assembled separately by mixing equimolar concentrations of four tectoRNAs in water to a final concentration of 200 nM. The RNA was first subjected to a denaturation-renaturating step by heating the samples to 90° C. for 3 mins, cooling on ice 3 mins followed by incubation at 30° C. for 3 mins. Next, a 5× concentrated buffer was added to the sample to reach 10 mM Tris-borate pH 8.2 (TB), 50 mM KCl, and 0.2 mM Mg(OAc)2, and the sample was incubated at 30° C. for 30 mins.

Step 2: Following the incubation of tectosquares at 30° C. for 30 mins cuboids were generated by mixing two tectosquares that have complementary tail-tail interaction in stoichiometric concentrations on ice. Next, the magnesium concentration is raised to 15 mM Mg(OAc)2 by the addition of a 2× concentrated buffer diluting the final cuboid concentration to 50 nM. Annealing was performed by incubating the cuboid mixture at 60° C. for 3 min followed by cooling to 10° C. over approximately 30 min.

Crude tecto-square and cuboid mixture can be stored at 4° C. for several weeks without significant degradation. Folding protocol along with mono and divalent ions has been also a subject of our studies. In order to obtain the highest yield, the assembly protocol was optimized by testing several different folding and association protocols varying the Mg2+ concentration, association temperature and incubation times (data not shown). In physiological pH 0.2 mM Mg2+ concentration appears to be sufficient for proper loop-loop pairing which is the major interaction directing the assembly of the tectosquare with dissociation constants ranging 6-15 nM (Severcan et al. (2008). T-D loop-loop interaction in the 90° motif as well as the single stranded tail-tail interaction between the complementary tectosquares however requires much higher salt concentrations. The experiments also indicate that once the cuboid is stabilized at 15 mM Mg(OAc)2 the amount of Mg2+ in solution can be decreased without destabilizing the structure of the cuboid. Native-PAGE and TGGE. Native PAGE and TGGE experiments were performed essentially as described (Chworos et al. (2004); Jaeger et al. (2001); Szewczak et al. (1998)). For native-PAGE analysis, 10 µl of RNA sample (100 nM tectosquare or 50 nM cuboid) was combined with 1 µl of gel loading buffer (0.01% bromophenol blue, 0.01% xylene cylanol, and 20% glycerol) and run on a 5% (38.5:1) non-denaturing PAGE at 50 W and 10° C. for various times.

2 mM Mg(OAc)2 was present in both gel and electrophoresis buffer. For TGGE analysis, the experimental setup was adjusted to have a linear temperature gradient perpendicular to the electric field. The temperature gradient was typically set up from 25° C. to 65° C. 20 p.1 of RNA sample (40 nM or 20 nM cuboid) was combined with 2 p.1 of gel loading buffer and run on 5% (38.5:1) native PAGE at 20 W for 1 hr. Mg(OAc)2 was present in both gel and electrophoresis buffer in specified concentrations in both gel and electrophoresis buffer.

RNase T1 Structural Probing.

RNase T1 probing was performed according to the manufacturer recommendation and all the enzymes and buffers were purchased from AMBION°. Following the assembly protocol described above, tRNA monomers (800 nM), tectosquares (200 nM) and cuboids (100 nM) were mixed with 10×RNA Structure Buffer (100 mM Tris pH 7, 1 M KCl, 100 mM MgCl2) and 1 ug of yeast tRNA.

Constructs were then treated with specified amounts of RNaseT1 (1 U/μ) for 1 hr at 25° C. in a final reaction volume of 10 pl. To stop the reaction 20 pl of inactivation/precipitation buffer was added to the reaction mixture. The RNA fragments were washed twice with 90% ethanol, reconstituted in gel loading buffer and separated on 15% denaturing gel.

Functionalization of tectoRNAs with Biotin.

Streptavidin was conjugated to guanosine mono-phosphothioate (GMPS)-modified tectoRNAs by means of iodoacetyl-biotin linker, which was incorporated to a monophosphothioate at the 5' position of tectoRNAs. Synthesis of GMPS-modified RNAs were performed enzymatically by in-vitro transcription of PCR generated double stranded DNA template using T7 RNA polymerase (10 U/μl) during 4 hrs of incubation at 37° C. in a buffer containing 15 mM MgCl2, 2 mM spermidine, 50 mM Tris 7.5, 25 mM ATP/UTP/CTP, 10 mM GTP, 100 mM GMP(S), 10 mM DTT, 0.01 μg/μl inorganic pyrophosphatase and 0.8 U/μl RNasin to a total volume of 200 μl. 4 pi of GMPS/GTP (10 mM each) was continuously added every 30 min until the end of 4 hrs of incubation. The reaction was quenched by the addition of 5 pi DNase (10 U/μl) in order to digest the DNA templates and incubated at 37° C. for 30 min, followed by purification on 8% denaturing PAGE. RNA products were visualized by UV shadowing and cut from the gel, eluted overnight at 4° C. in crush and soak buffer (200 mM NaCi, 10 mM Tris pH 7.5, 0.5 M EDTA). The RNAs were precipitated in 2 volumes of pure ethanol, washed twice with 90% ethanol, pelleted and recuperated in water.

GMPS-modified RNA molecules were then functionalized by coupling with EZ-Link PEO-Iodoacetyl Biotin (PIAB) (Pierce Biotechnology) for 1 hr at 30° C. in buffer containing 2000 pmols of GMPS-modified RNA, 4 mM of PIAB and 0.05 rnM DTT, 50 mM Tris pH 8, 2.5 mM NaEDTA to a total volume of 100. The reaction was quenched by adding 4 μl of 100 mM DTT, 20 μl of 1M NaCl and 250 μl of Ethanol 100% followed by purification on 8% denaturing PAGE and elution protocol described above. Following gel purification, PIAB-modified RNAs were subjected to a second purification step using FPLC. Conjugation of streptavidin to addressable cuboids was performed by incorporating two biotinylated-monomers at opposite corners of cuboid during the cuboid assembly. In order to encapsulate streptavidin inside the cuboid the tectoRNAs Bc2 and Dc4 in tectosquare TS6 were functionalized with PIAB-linker. To attach the streptavidin outside the cuboid the tectoRNAs Bc4' and Dc2' in tectosquare TS7 were functionalized with PIAB-linker. Cuboid solution and streptavidin were mixed in varying molar ratios and incubated for 2 hrs at 25° C. The samples were directly loaded on 5% (38.5:1) non-denaturing PAGE containing 2 mM Mg(OAc)2.

Atomic Force Microscopy (AFM).

For AFM imaging tectosquares (100 nM) and cuboids (50 nM) were assembled in solution prior to directly depositing on freshly cleaved mica surface as described in the previous section: folding and assembly of cuboids. After waiting for 60 sec, mica surface was rinsed with a 2 mM Mg(OAc)2 solution and dried under nitrogen. For AFM imaging of 2D-grids, typically two tectosquares (20 nM) were mixed at 4° C. in TB buffer in the presence of 15 mM Mg(OAc)2 and 50 mM KCl, then placed on freshly cleaved mica disc, heated at 50° C. for 10 min and slowly cooled from 50° C. to 4° C. overnight in Styrofoam chamber. Image acquisition, performed in air at room temperature, was in tapping mode using a Multimode microscope equipped with a Nanoscope In a controller (Veeco, Santa Barbara). Silicon probes (model NSC12 from MikroMesch) with resonance frequency ~150-250 kHz and spring constant ~4-8 N/m (Nanodevices, Santa Barbara, Calif.) were used. Images were processed by NanoScope® (DI) and leveled by a first order plane fit in order to correct the sample tilt.

Supporting Tables.

Figure 39:
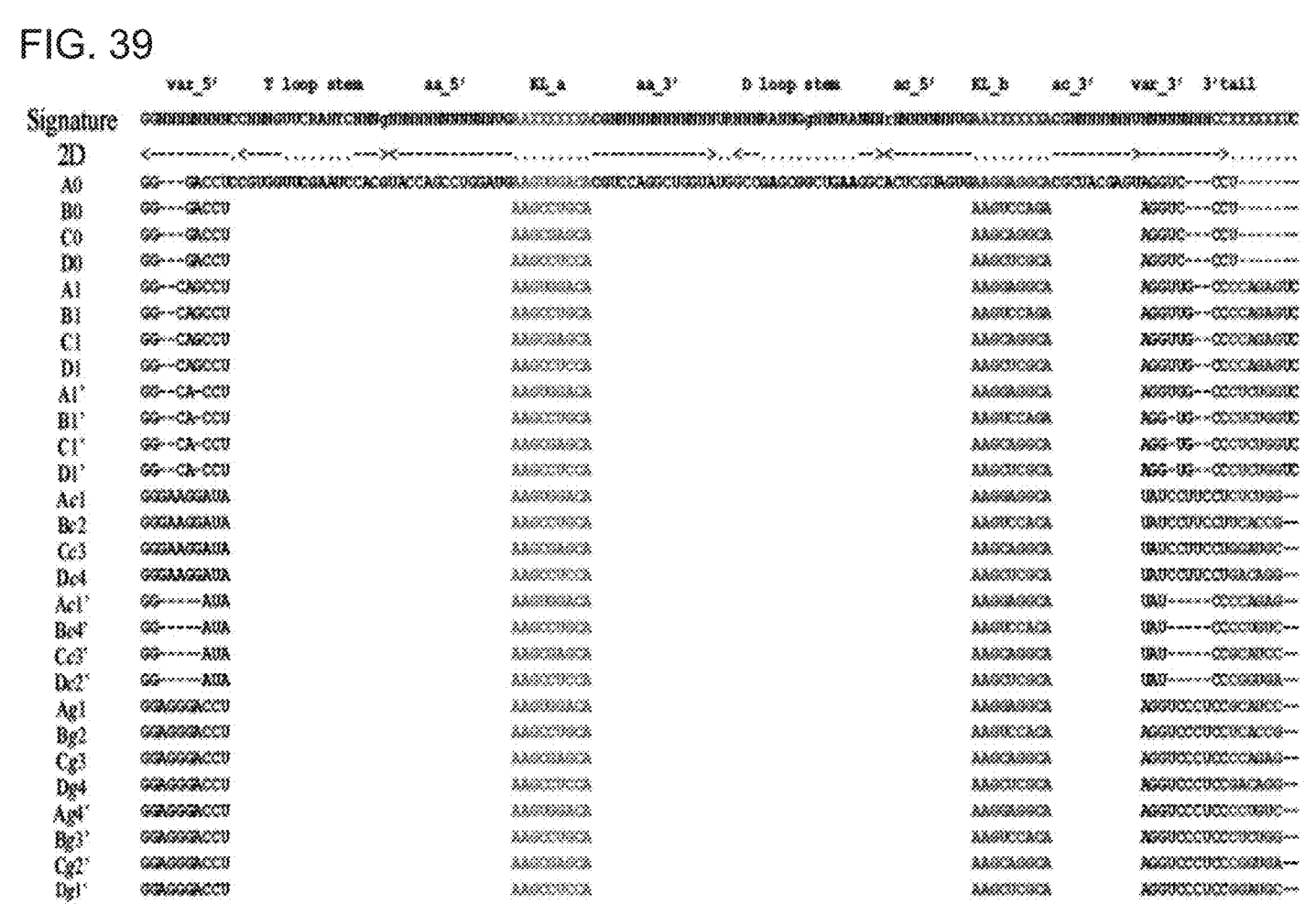

The Table in FIG. 39 shows a list of tectoRNAs used in the experiments described herein. TectoRNA nomenclature used is as follows: A, B, C, and D, and indicates the type of the unit with respect of their KL motifs in a clock-wise fashion within the context of the tectosquare. The unit letter is followed by e in the case of a fully addressable cube. The unit letter is followed by g (2D-grid) when the unit is designed to form 2D grid patterns. The units A0 to D0 have no tails in their variable stem. The symbol 0 followed by a number indicate that the unit has a complementary 3'-tail to the unit without the respective symbol (i.e. 1 is complementary to 1').

Table 5, below shows combinations of tectoRNAs that self-assemble to form various architectures designed in these studies.

TABLE 5

| | Mix A | | Mix B (Open Octamer) | | Mix C | | Mix D (Cuboid) | | Mix E (Addressable Cuboid) | | Mix F (Grid) | |
|---|---|---|---|---|---|---|---|---|---|---|---|---|
| | Ts1 | Ts2 | Ts1 | Ts3 | Ts1 | Ts4 | Ts1 | Ts5 | Ts6 | Ts7 | Ts8 | Ts9 |
| A0 | ■ | | ■ | | ■ | | | | | | | |
| B0 | ■ | | ■ | | | | | | | | | |
| C0 | ■ | | | | | | | | | | | |
| D0 | | | | | | | | | | | | |
| A1 | | ■ | | ■ | | ■ | | ■ | | | | |
| B1 | | ■ | | ■ | | ■ | | ■ | | | | |
| C1 | | ■ | | ■ | | ■ | | ■ | | | | |
| D1 | | ■ | | ■ | | ■ | | ■ | | | | |
| A1' | | | | | | | | | | ■ | | |
| B1' | | | | | | | | | ■ | ■ | | |
| C1' | | | | ■ | | ■ | | | ■ | | | |
| D1' | | ■ | | ■ | | ■ | | ■ | | | | |
| Ac1 | | | | | | | | | | ■ | | ■ |
| Bc2 | | | | | | | | | ■ | | | ■ |
| Cc3 | | | | | | | | | ■ | | | |
| Dc4 | | | | | | | | | ■ | | | |
| Ac1' | | | | | | | | | | ■ | | |
| Bc4' | | | | | | | | | | ■ | | ■ |
| Cc3' | | | | | | | | | | ■ | | |

TABLE 5-continued

| | Mix A | | Mix B (Open Octamer) | Mix C | Mix D (Cuboid) | | Mix E (Addressable Cuboid) | | Mix F (Grid) | |
|---|---|---|---|---|---|---|---|---|---|---|
| | Ts1 | Ts2 | Ts1 | Ts3 | Ts1 | Ts4 | Ts1 | Ts5 | Ts6 | Ts7 | Ts8 | Ts9 |
| Dc2' | | | | | | | | ■ | | |
| Ag1 | | | | | | | | | ■ | |
| Bg2 | | | | | | | | | ■ | |
| Cg3 | | | | | | | | | ■ | |
| Dg4 | | | | | | | | | ■ | |
| Ag4' | | | | | | | | | | ■ |
| Bg3' | | | | | | | | | | ■ |
| Cg2' | | | | | | | | | | ■ |
| Dg1' | | | | | | | | | | ■ |

The fully addressable cuboid was designed to self-assemble from eight different building blocks that contain eight different kissing loop complexes. Table 6, below shows the programmings of loop-loop interactions used in tectosquare the tectosquares described herein.

TABLE 6

Table discloses SEQ ID NOS: 63-70, respectively, in order of appearance. Thus, Unit A is SEQ ID NO: 63; Unit B is SEQ ID NO: 64; Unit C is SEQ ID NO: 65; Unit D is SEQ ID NO: 66; Unit E is SEQ ID NO: 67; Unit F is SEQ ID NO: 68; Unit G is SEQ ID NO: 69; and Unit H is SEQ ID NO: 70.

```
Unit Sequence

A   GGC AGC CUC CGU GGU UCG AAU CCA CGU ACC AGC CUG GAU GAA GUG GAC A CG UCC AGG CUG

GUA UGG CCG AGC GGC UGA AGG CAC UCG UAG UGA AGG AGG CAC GCU ACG AGU AGG UU G CCC

CAG AG UC

B   GGC ACC UCC GUG GUU CGA AUC CAC GUA CCA GCC UGG AUG AAG CCU GCA CGU CCA GGC UGG UAU

GGC CGA GCG GCU GAA GGC ACU CGU AGU GAA GUC CAC ACG CUA CGA GUA GGU GCC CGG UGA UC

C   GGC AGC CUC CGU GGU UCG AAU CCA CGU ACC AGC CUG GAU GAA GCG AGC A CG UCC AGG CUG

GUA UGG CCG AGC GGC UGA AGG CAC UCG UAG UGA AGC AGG CAC GCU ACG AGU AGG UU G CCG

CAU CC UC

D   GGC ACC UCC GUG GUU CGA AUC CAC GUA CCA GCC UGG AUG AAG CCU CCA CCU CCA GGC UGG UAU

GGC CGA GCG GCU GAA GGC ACU CGU AGU GAA GCU CGC ACG CUA CGA GUA GGU GCC CCU GUC UC

E   GGC ACC UCC GUG GUU CGA AUC CAC GUA CCA GCC UGG AUG AAG CGU UCA CGU CCA GGC UGG UAU

GGC CGA GCG GCU GAA GGC ACU CGU AGU GAA AGG CUC ACG CUA CGA GUA GGU GCC CUC UGG UC

F   GGC AGC CUC CGU GGU UCG AAU CCA CGU ACC AGC CUG GAU GAA GUC ACC A CG UCC AGG CUG

GUA UGG CCG AGC GGC UGA AGC ACU CGU ACU GAA AGA ACG CAC GCU ACG AGU AGG UU G CCG

ACA GG UC

G   GGC ACC UCC GUG GUU CGA AUC CAC GUA CCA GCC UGG AUG AAC GUG GUA CGU CCA GGC UGG UAU

GGC CGA GCG GCU GAA GGC ACU CGU AGU GAA GGU GAC ACG CUA CGA GUA GGU GCC GGA UGC UC

H   GGC AGC CUC CGU GGU UCG AAU CCA CGU ACC AGC CUG GAU GAA GAG CCU A CG UCC AGG CUG

GUA UGG CCG AGC GGC UGA AGG CAC UCG UAG UGA GAC CAC GAC GCU ACG AGU AGG UU G CCU

CAC CG UC
```

RMSD.

Several different RMSDs were calculated for every MD trajectory. The first RMSD was calculated over the whole simulation time range using the starting structure. The second RMSD was calculated for the 10-30 ns range to ignore the initial deformation stage due to the substituted modified nucleotides. The average structure for the 10-30 ns range was used as a reference structure for the second RMSD. An additional RMSD for the 0-30 ns range relative to the averaged structure for this time range was also calculated and compared with second RMSD.

Phosphates (P-P) Distance and Ratio.

The major difference in backbone dihedral angles between north and south constrained modified nucleotides is the δ angle. The δ angle of a north constrained sugar is 75°, while that of the south constrained modified nucleotide is 1450. The different δ angles between two constrained sugars causes the distance between the phosphate atoms to change. In order to measure the effect of north and south constrained sugar substitutions in RNA, the phosphate-phosphate (P-P) distance was measured. The distance between two consecutive 5' and 3' phosphates in south modified nucleotides was 7.2 Å, while that of north modified nucleotides was 6.2 Å. In the HIV kissing loop structure, summation of average (P-P) distance along G271, A272, A273, G 4 and C275 for 10 to 30 ns was measured. In addition, the direct phosphate distance between G271 and C275 Φ271-275) was measured to calculate a distance ratio. (P-P)ratio where Di is the distance between i'th and (i+1)th phosphates.

(P-P)ratio=

$$(P-P)_{ratio} = \frac{\sum_{i=271}^{274} D_i}{D_{271-275}}$$

This ratio is used to clarify the effect of constrained sugars on a closed and an open conformation in the HIV kissing loop complex. Meanwhile, the (P-P)ratio of the 5 nucleotides in the middle of the RNA dodecamers was also calculated to compare the backbone geometry change in the HIV kissing loop complexes and the RNA dodecamers due to the substituted modified nucleotides.

Measuring Dynamics.

The difference in dynamics due to the different constrained sugars in the HIV kissing loop complex were monitored by two motions; (1) twist motion and (2) bending along the helical axis. Twist motion was determined by measuring the dihedral angle along the C4' atoms of C265, G287, C277, and G276* and the corresponding dihedral angle on the other side (C4' at C265*, G287*, C277*, and G276). (see FIG. 2 (a)) Structure bending was determined by measuring the average angle between the center of mass of C265 and G287 (5' and 3' CG base pairs at the end), between the center of mass of G276, C277, G276*, and C277* (center of HIV kissing loop complex), and between the center of mass of C265* and G287*(the other end of 5' and 3' CG base pair). Detailed definitions are shown in FIG. 2 (b).

In order to specify each modified HIV kissing loop complex conveniently, we indicated the location(s) of the substituted modified nucleotides as subscripts of the type of modified nucleotide. For example, the kissing loop complex where north modified nucleotides were substituted at G271 and A273 (and the symmetrical ones, G271* and A273*) is specified by N271, 273. In addition, specifying a residue in this manner implies substitutions in the corresponding symmetrical residues.

RNA Preparation.

RNA molecules were prepared by transcription of PCR amplified DNA templates. Synthetic DNA molecules coding for the antisense sequence of the designed RNA were purchased from IDT DNA and amplified by PCR using primers containing the T7 RNA polymerase promoter. PCR products were purified using the QiaQuick PCR purification kit and RNA molecules were prepared by in vitro transcription using homemade T7 RNA polymerase and purified on denaturing urea gel (PAGE) (10% acrylamide, 8M urea). The RNA was eluted from gel slices overnight at 4° C. into buffer containing 300 mM NaCl, 10 mM Tris pH 7.5, 0.5 mM EDTA then ethanol precipitated, and rinsed twice with 90% ethanol, vacuum dried and dissolved in TE buffer.

pCp Labeling of RNA Molecules.

T4 RNA ligase was used to label the 3'-ends of RNA molecules by attaching [32P]Cp. Labeled material was purified on denaturing polyacylamide gels (10% acrylamide, 8M urea).

ATP Labeling of DNA.

T4 polynucleotide kinase was used to label the 5'-ends of DNA molecules by moving [32P] from the gamma position of ATP. Labeled material was purified on denaturing polyacrylamide gels (10% acrylamide, 8M urea).

Non-Denaturing PAGE, TGGE Experiments, and Kd Measurements.

All assembly experiments reported in this study were analyzed on 7% (37.5:1) non-denaturing polyacrylamide native gels containing 2 mM Mg(OAc)2 and 50 mM KCl and run at 4° C. with running buffer (89 mM Tris-borate, pH 8.3/15 or 2 mM Mg(OAc)2). Prior to the addition of the buffer and Mg(OAc)2, the RNA(DNA) samples containing cognate RNA(DNA) molecules at concentrations 1 μM were heated to 95° C. for two minutes and immediately snap cooled at 45° C. followed by assembly buffer addition (tris-borate buffer (89 mM, pH 8.3), 2 mM Mg(OAc)2, and 50 mM KCl) and incubation for 30 minutes. An equal volume of loading buffer (same buffer with 0.01% bromphenol blue, 0.01% xylene cyanol, 50% glycerol) was added to each sample before loading on native gel. Gels were run for 4 hours, at 25 W with temperature set to be below 10° C., dried under vacuum, exposed to a phosphoimager screen for 16 hours, and scanned using a Typhoon phosphoimager. For total gel staining, SYBR Green II RNA gel stain was used to visualize RNA or DNA bands using Typhoon phosphoimager with the emission of SYBR Green II centered at 520 nm. The stained RNA or DNA bands appear as black bands on the white background. For TGGE, analysis performed at 2 mM Mg(OAc)2, a linear temperature gradient, typically from 30 to 60° C., was applied perpendicular to the electric field. Cube concentration was typically 1 μM. Gels were run for 1 hour, at 30 W. Dissociation constants (Kd's) were calculated by plotting the fraction of a cube (f) versus the total concentration (CT) of the RNA strands corresponding to this particular fraction. The combined data collected from three independent measurements was subjected to nonlinear curve fitting with the equation:

$$Kd = ((C_T/6)^5(1-f)^6)/f \quad \text{(Eq. 1)}$$

which was solved for f and fit non-linearly to obtain Kd.

All gels were quantified using ImageQuant software. Equally sized boxes were drawn around the bands corresponding to the hexamers (cubes). The yield for each hexamer-forming complex was calculated by dividing the corresponding quantified value for hexamer by the total sum of the values for all complexes present in the corresponding lane. Dynamic Light Scattering. For DLS, 10 μL of sample solution containing preassembled RNA/DNA cubes were measured by DynaPro99 (Protein Solution/Wyatt) with the laser wavelength equal to 824 nm at 24° C. The theoretical hydrodynamic radii (Rh) were calculated using the equation:

$$Rh = (L\sqrt{3})/2 \quad \text{(Eq. 2)}$$

where L is the length (nm) of the cube side. Assuming a 0.23 nm rise per basepair and a 2.6 nm diameter of the RNA duplex, the side length of the RNA cube is calculated to be 7.5 nm. The DNA cube side length is calculated to be 7.3 nm using 0.33 and 2.0 nm for the rise per basepair and duplex diameter, respectively. For the cubes with dangling ends, the theoretical Rh's were calculated by measuring the distance between the center of mass and the furthest atom of the cube 3D CPK model.

Cryo-EM Imaging.

Samples containing the six-stranded RNA cube with dangling ends (S1) and the ten-stranded RNA cube (S2) for cryo-EM were prepared as described above. Micrographs were acquired using a Tecnai F20 Twin transmission electron microscope operating at 120 kV, a nominal magnification of 80,000×, and a dose of ~30 e−/Å2. 413 images for S1 and 335 images for S2 and were automatically collected by the Leginon system46 and recorded with a Tietz F415 4k×4k pixel CCD camera. Experimental data were processed using the Appion software package47. 2,038 particles for S1 and 1,677 particles for S2 were manually selected. The 3D reconstruction was carried out using the EMAN reconstruction package41. A resolution of 9.6 Å for S1 and 11.5 Å for S2 was determined by Fourier Shell Correlation (FSC) at a cutoff of 0.5.

Fluorescent Experiments.

The fluorescent experiments were carried out using a NanoDrop 3300 Fluorospectrometer with the following settings: excitation wavelength was set at blue in all experiments. Emission was scanned from 540 to 800 nm. Signal was registered in Relative Fluorescent Units (RFU) at 660 nm. All RNA complexes used in the fluorescent experiments were assembled as described above at 1 μM concentrations. The experiments with MG binding to the decamer (10 stranded cube) resulting in enhanced MG emission were repeated and reproduced (within 10% error) at least five times. The experiments with the nine nonamers and the 10 stranded cube with two embedded aptamers were repeated and reproduced twice (within 10% error).

Cryo-EM Imaging with Single Particle Reconstruction.

Samples were preserved in a thin layer of vitreous ice on 2.0×0.5 μm C-Flat holey carbon films (Protochips, Inc.) Grids were cleaned immediately prior to use in a Solarus plasma cleaner (8 seconds, 25% O2, 75% Ar). Samples were prepared by applying a drop (~3 μl) of the undiluted sample suspension to the plasma cleaned grid, blotting away with filter paper and immediately proceeding with vitrification in liquid ethane, using an FEI Vitrobot (4C, 95% RH). Data were acquired using a Tecnai F20 Twin transmission electron microscope operating at 120 kV, using a dose of ~30 e-/Å and a nominal underfocus ranging from 1.5 to 3.5 μm. All images were recorded with a Tietz F415 4k×4k pixel CCD camera (15 μm pixel) using the Leginon data collection software (Suloway et al., 2005). 413 images for sample 1 (S1) and 335 images for sample 2 (S2) were automatically collected at a nominal magnification of 80,000× at a pixel size of 0.105 nm at the specimen level. Experimental data were processed using the Appion software package (Lander et al., 2009), which interfaces with the Leginon database infrastructure. 2,038 particles for S1 and 1,677 particles for S2 were manually selected within Appion. The contrast transfer function (CTF) was estimated and corrected including astigmatism using ACE2, a variation of the software described in Mallick et al. (2005). Particles were extracted from the CTF corrected images with a box size of 160 pixels. The particle set was investigated for heterogeneity with the reference-free alignment and classification provided by the Xmipp MLalign2D program (Scheres et al., 2005a) using the fast algorithm (Scheres et al., 2005b). A 3D reconstruction was then carried out using EMAN (Ludtke et al., 1999) for 9 rounds of projection matching, 3 rounds at each angular increment of 5, 4, and then 3 degrees. 3D models were thresholded to have a volume of 94,000 Å$^3$, which is equivalent to a mass of 98 kDa based on the RNA density of 0.958 Å3/Da (Voss et al., 2005) and lowpass filtered to 20 Å. Resolution was assessed by calculating the Fourier Shell Correlation (FSC) at a cutoff of 0.5, which provided a value of 9.6 Å resolution for S1 and 11.5 Å resolution for S2.

INCORPORATION BY REFERENCE

The following specific references, also incorporated by reference, are indicated above by corresponding reference number.

Jaeger, L., Westhof, E. & Leontis, N. B. TectoRNA: modular assembly units for the construction of RNA nano-objects. Nucleic Acids Res 29, 455-63 (2001).

Chworos, A. et al. Building programmable jigsaw puzzles with RNA. Science 306, 2068-72 (2004).

Nasalean, L., Baudrey, S., Leontis, N. B. & Jaeger, L. Controlling RNA self-assembly to form filaments. Nucleic Acids Res 34, 1381-92 (2006).

Famulok, M., Hartig, 3. S. & Mayer, G. Functional aptamers and aptazymes in biotechnology, diagnostics, and therapy. Chemical Reviews 107, 3715-3743 (2007).

Lee, J. F., Stovall, G. M. & Ellington, A. D. Aptamer therapeutics advance. Curr Opin Chem Biol 10, 282-9 (2006).

Hoeprich, S. et al. Bacterial virus phi29 pRNA as a hammerhead ribozyme escort to destroy hepatitis B virus. Gene Ther 10, 1258-67 (2003).

Yingling, Y. G. & Shapiro, B. A. Computational design of an RNA hexagonal nanoring and an RNA nanotube. Nano Lett 7, 2328-34 (2007).

Jaeger, L. & Leontis, N. B. Tecto-RNA: One-Dimensional Self-Assembly through Tertiary Interactions This work was carried out in Strasbourg with the support of grants to N.B.L. from the NIH (1R15 GM55898) and the NIH Fogarty Institute (1-F06-TW02251-01) and the support of the CNRS to L.J. The authors wish to thank Eric Westhof for his support and encouragement of this work. Angew Chem Int Ed Engl 39, 2521-2524 (2000).

Shu, D., Moll, W. D., Deng, Z., Mao, C. & Guo, P. Bottom-up Assembly of RNA Arrays and Superstructures as Potential Parts in Nanotechnology. Nano Lett 4, 1717-1723 (2004).

Guo, P. RNA nanotechnology: engineering, assembly and applications in detection, gene delivery and therapy. J Nanosci Nanotechnol 5, 1964-82 (2005).

Lescoute, A. & Westhof, E. The A-minor motifs in the decoding recognition process. Biochimie 88, 993-9 (2006).

Lee, A. 3. Crothers, D. M. The solution structure of an RNA loop-loop complex: the ColE1 inverted loop sequence. Structure 6, 993-1005 (1998).

Eguchi, Y. & Tomizawa, J. Complexes formed by complementary RNA stem-loops. Their formations, structures and interaction with ColE1 Rom protein. J Mol Biol 220, 831-42 (1991).

Horiya, S. et al. RNA LEGO: magnesium-dependent formation of specific RNA assemblies through kissing interactions. Chem Biol 10, 645-54 (2003).

Ennifar, E., Walter, P., Ehresmann, B., Ehresmann, C. & Dumas, P. Crystal structures of coaxially stacked kissing complexes of the HIV-1 RNA dimerization initiation site. Nature Structural Biology 8, 1064-1068 (2001).

Severcan, I., Geary, C., Verzemniek, E., Chworos, A. & Jaeger, L. Square-Shaped RNA Nanoparticles from Different RNA Folds. unpublished (2008).

Hansma, H. G., Oroudjev, E., Baudrey, S. & Jaeger, L. TectoRNA and 'kissing-loop' RNA: atomic force microscopy of self-assembling RNA structures. J Microsc 212, 273-9 (2003).

Zandi, R., Reguera, D., Bruinsma, R. F., Gelbart, W. M. & Rudnick, J. Origin of icosahedral symmetry in viruses. Proc Natl Acad Sci USA 101, 15556-60 (2004).

Michel, 3. P. et al. Nanoindentation studies of full and empty viral capsids and the effects of capsid protein mutations on elasticity and strength. Proc Nall Acad Sci USA 103, 6184-9 (2006).

Edeling, M. A., Smith, C. & Owen, D. Life of a clathrin coat: insights from clathrin and AP structures. Nat Rev Mal Cell Biol 7, 32-44 (2006).

Theil, E. C., Matzapetakis, M. & Liu, X. Ferritins: iron/oxygen biominerals in protein nanocages. J Biol Inorg Chem 11, 803-10 (2006).

Chen, C. et al. Nanoparticle-templated assembly of viral protein cages. Nano Lett 6, 611-5 (2006).

Chen, J. H. & Seeman, N. C. Synthesis from DNA of a Molecule with the Connectivity of a Cube. Nature 350, 631-633 (1991).

Zhang, Y. & Seeman, N. C. Construction of a DNA-Truncated Octahedron. Journal of American Chemical Society 116, 1661-1669 (1994).

Shih, W. M., Quispe, 3. D. & Joyce, G. F. A 1.7-kilobase single-stranded DNA that folds into a nanoscale octahedron. Nature 427, 618-21 (2004).

Goodman, R. P., Berry, R. M. & Turberfield, A. J. The single-step synthesis of a DNA tetrahedron. Chem Commun (Camb), 1372-3 (2004).

Erben, C. M., Goodman, R. P. & Turberfield, A. J. A self-assembled DNA bipyramid. J Am Chem Sac 129, 6992-3 (2007).

Erben, C. M., Goodman, R. P. & Turberfield, A. 3. Single-molecule protein encapsulation in a rigid DNA cage. Angew Chem Int Ed Engl 45, 7414-7 (2006).

He, Y. et al. Hierarchical self-assembly of DNA into symmetric supramolecular polyhedra. Nature 452, 198-201 (2008).

Padilla, J. E., Colovos, C. & Yeates, T. O. Nanohedra: using symmetry to design self assembling protein cages, layers, crystals, and filaments. Proc Natl Acad Sci USA 98, 2217-21 (2001).

Matsuura, K., Murasato, K. & Kimizuka, N. Artificial peptide-nanospheres self-assembled from three-way junctions of beta-sheet-forming peptides. J Am Chem Soc 127, 10148-9 (2005).

Khaled, A., Guo, S., Li, F. & Guo, P. Controllable self-assembly of nanoparticles for specific delivery of multiple therapeutic molecules to cancer cells using RNA nanotechnology. Nano Lett 5, 1797-808 (2005).

Tang, L. et al. The structure of pariacoto virus reveals a dodecahedral cage of duplex RNA. Nat Struct Biol 8, 77-83 (2001).

Geary, C., Baudrey, S. & Jaeger, L. Comprehensive features of natural and in vitro selected GNRA tetraloop-binding receptors. Nucleic Acids Res 36, 1138-52 (2008).

Jaeger, L. & Leontis, N. B. Tecto-RNA: One-Dimensional Self-Assembly through Tertiary Interactions This work was carried out in Strasbourg with the support of grants to N.B.L. from the NIH (1R15 GM55898) and the NIH Fogarty Institute (1-F06-TW02251-01) and the support of the CNRS to L.J. The authors wish to thank Eric Westhof for his support and encouragement of this work. Angew Chem Int Ed Engl 39, 2521-2524 (2000).

Bates, A. D. et al. Construction and characterization of a gold nanoparticle wire assembled using Mg2+-dependent RNA-RNA interactions. Nano Lett 6, 445-8 (2006).

Jaeger, L. & Chworos, A. The architectonics of programmable RNA and DNA nanostructures. Curr Opin Struct Biol 16, 531-43 (2006).

Severcan, I., Geary, C., Verzemniek, E., Chworos, A. & Jaeger, L. Square-Shaped RNA Nanoparticles from Different RNA Folds. unpublished (2008).

Pan, T., Gutell, R. R. & Uhlenbeck, 0. C. Folding of circularly permuted transfer RNAs. Science 254, 1361-4 (1991).

Pan, T. & Uhlenbeck, 0. C. Circularly permuted DNA, RNA and proteins—a review. Gene 125, 111-4 (1993).

Horiya, S. et al. RNA LEGO: magnesium-dependent formation of specific RNA assemblies through kissing interactions. Chem Biol 10, 645-54 (2003).

Nakano, M., Moody, E. M., Liang, J. & Bevilacqua, P. C. Selection for thermodynamically stable DNA tetraloops using temperature gradient gel electrophoresis reveals four motifs: d(cGNNAg), d(cGNABg),d(cCNNGg), and d(gCNNGc). Biochemistry 41, 14281-92 (2002).

Hansma, H. G., Oroudjev, E., Baudrey, S. & Jaeger, L. TectoRNA and 'kissing-loop' RNA: atomic force microscopy of self-assembling RNA structures. J Microsc 212, 273-9 (2003).

Jaeger, L., Westhof, E. & Leontis, N. B. TectoRNA: modular assembly units for the construction of RNA nano-objects. Nucleic Acids Res 29, 455-63 (2001).

Szewczak, A. A., Podell, E. R., Bevilacqua, P. C. & Cech, T. R. Thermodynamic stability of the P4-P6 domain RNA tertiary structure measured by temperature gradient gel electrophoresis. Biochemistry 37, 11162-70 (1998).

Wadely, L. M., Keating, K. S., Durate, C. M., Pyle, A. M. (2007) Evaluating and learning from RNA pseudotorsional space: quantitative validation of a reduced representation for RNA structure. J. Mol. Biol., 372, 942-957.

Foloppe, N., Mackerell, A. D. Jr. (2000) All-atom empirical force field for nucleic acids: I. Parameter optimization bsed on slamm molecule and condensed phase macromolecular target data. J. Comp. Chem., 21, 86-104.

Marquez, V. E., Siddiqui, M. A., Ezzitouni, A., Russ, P., Wang, J. (1996) Nucleosides with a twist. Can fixed forms of sugar ring pucker influence biological activity in nucleosides and oligonucleotides? J. Med. Chem., 39, 3739-3747.

Wang, P., Brank, A. S., Banavali, N. K., Nicklaus, M. C., Marquez, V. E., Christman, J. K., MacKerell, A. D. Jr. (2000) Use of oligodeoxyribonucleotides with conformationally constrained abasic sugar targets to probe the mechanism of base flipping by HhaI DNA (cytosine C5)-methyltransferase. J. Am. Chem. Soc., 122, 12422-12434.

Rodriguez, J. B., Marquez, V. E., Nicklaus, M. C., Barchi, J. J., Jr. (1993) Synthesis of cyclopropane-fused dideoxycarbocyclic nucleosides structurally related to neplanocin C. Tetrahedron Lett., 34, 6233-6236.

Altmann, K.-H., Kesselring, R., Francotte, E., Rihs, G. (1994) 4',6'-Methano carbocyclic thymidine: A conformationally constrained building block for oligonucleotides. Tetrahedron Lett., 35, 2331-2334.

Rodriguez, J. B., Marquez, V. E., Nicklaus, M. C., Mitsuya, H., Barchi, J. J., Jr. (1994) Conformationally locked nucleoside analogues. Synthesis of dideoxycarbocyclic nucleoside analogues structurally related to neplanocin C. J. Med. Chem., 37, 3389-3399.

Altmann, K.-H., Imwinkelried, R., Kesselring, R., Rihs, G. 1',6'-(1994) Methano carbocyclic thymidine: Synthesis and X-ray crystal structure, and effect on nucleic acid duplex stability. Tetrahedron Lett., 35, 7625-7628.

Ezzitouni, A., Barchi, J. J., Jr., Marquez, V. E. (1995) A simple approach to 1,1'-methano carbocyclic thymidine. J. Chem. Soc., Chem. Commun., 13, 1345-1346.

Siddiqui, M. A., Ford, H., Jr., George, C., Marquez, V. E. (1996) Synthesis, conformational analysis, and biological activity of a rigid carbocyclic analogue of 2'-deoxyaristeromycin built on a bicyclo [3.1.0] hexane template. Nucleosides Nucleotides, 15, 235-250.

Altona, C., Sundaralingam, M. (1972) Conformational analysis of the sugar ring in nucleosides and bucleotides. A new description using the concept of pseudorotation. J. Am. Chem. Soc., 94, 8205-8212.

Saenger, W. (1984) Principles of nucleic acid structure, Springer-Verlag, New York, 51-104.

Wu, Z. R., Maderia, M., Barchi, J. J., Jr., Marquez, V. E., Bax, A. (2005) Changes in DNA bending induced by restricting nucleotide ring pucker studied by weak alignment NMR spectroscopy. Proc Natl Acad Sci USA, 102, 24-28.

Macias, A. T., Banavali, N. K, MacKerell, A. D. Jr. (2007) DNA bending induced by carbocyclic sugar analogas constrained to the north conformation. Biopol., 85, 438-449.

Wing, R., Drew, H., Takano, T., Broka, C., Tanaka, S., Ikeda, H., Dickerson, R. E. (1980) Crystal structure analysis of a complete turn of B-DNA. Nature, 287, 755-258.

Pande, V., Nilsson, L. (2008) Insights into structure, dynamics and hydration of Locked Nucleic Acid (LAN) strand-based duplexes from molecular dynamics simulations. Nucleic Acids Res., 36, 1508-1516.

Bondensgaard, K., Petersen, M., Singh, S. K., Rajwanshi, V. K., Kumar, R., Wengel, J. and Jacobsen, J. P. (2000) Structural studies of LNA: RNA duplexes by NMR: conformations and implications for RNase H activity. Chemistry, 6, 2687-2695.

Nielsen, K. E., Singh, S. K., Wengel, J. and Jacobsen, J. P. (2000) Solution structure of an LNA hybridized to DNA: NMR study of the d(CT(L)GCT(L)T(L)CT(L)GC): (GCAGAAGCAG) (SEQ ID NO: 77) duplex containing four locked nucleotides. Bioconjug. Chem., 11, 228-238.

Petersen, M., Bondensgaard, K., Wengel, J. and Jacobsen, J. P. (2002) Locked Nucleic Acid (LNA) recognition of RNA: NMR solution structures of LNA: RNA hybrids. J. Am. Chem. Soc., 124, 5974-5982.

Nielsen, K. E., Rasmussen, J., Kumar, R., Wengel, J., Jacobsen, J. P. and Petersen, M. (2004) NMR studies of fully modified Locked Nucleic Acids (LNA) hybrids: solution structure of an LNA: RNA hybrid and characterization of an LNA: DNA hybrid. Bioconjug. Chem., 15, 449-457.

Chworos, A., Severcan, I., Koyfman, A. Y., Weinkam, P., Oroudjev, E., Hansma, H., G., Jaeger, L. (2004) Building programmable jigsaw puzzles with RNA. Sci., 306, 2068-2072.

Koyfman, A. Y., Braun, G., Magonov, S., Chworos, A., Reich, N. O., Jaeger, L. (2005) Controlled spacing of cationic gold nanoparticles by nanocrown RNA. J. Am. Chem., Soc., 127, 11886-11887.

Horiya, S., Li, X., Kawai, G., Saito, R., Katoh, A., Koh, K., Harada, K. (2003) RNA LEGO: Magnesium-dependent formation of specific RNA assemblies through kissing interactions. Chem. & Bio., 10, 645-654.

Yingling, Y. G., Shapiro, B. A. (2007) Computational design of an RNA hexagonal nanoring and an RNA nanotube. Nano Lett., 7, 2328-2334.

Bindewald, E., Grunewald, C., Boyle, B., O'Connor, M., Shapiro, B. A. (2008) Computational strategies for the automated design of RNA nanoscale structure from building blocks using NanoTiler. J. Mol. Graph. Model. 27, 299-308.

Bindewald, E., Hayes, R., Yingling, Y. G., Shapiro, B. A. (2008) RNAJunction: a database of junctions and kissing loops for three-dimensional structural analysis and nanodesign. Nucleic Acids Res. 36, 392-397.

Ennifar, E., Dumas, P. (2006) Polymorphism of bulged-out residues in HIV-1 RNA DIS kissing complex and structure comparison with solution studies. J. Mol. Biol, 356, 771-782.

Reblova, K., Fadrna, E., Sarzynska, J., Kulinski, T., Kulhannek, P., Ennifar, E., Koca, J., Sponer, J. (2007) Conformations of flanking bases in HIV-1 RNA DIS kissing complexes studies by molecular dynamics. Biophy. J., 93, 3932-3949.

Reblova, K., Spackova, N, Sponer, J. E., Koca, J., Sponer, J. (2003) Molecular dynamics simulations of RNA kissing-loop motifs revel structure dynamics and formation of cation-binding pockets. Nucleic Acid Res., 31, 6942-6952.

Wang, B., Merz, K. M.Jr. (2006) A fast QM/MM (quantum mechanical/molecular nechanical) approach to calculate nuclear magnetic resonance chemical shifts for macromolecules. J. Chem. Theory Comput., 2, 209-215.

Mathieu, F., Liao, S., Kopatsch, J., Wang, T., Mao, C., Seeman, N. C. (2005) Six-helix bundles designed from DNA. Nano Lett., 5, 661-665.

Wang, J., Cieplak, P., Kollman, P. A. (2000) How well does a restrained electrostatic potential (RESP) model perform in calculating conformational energies of organic and biological molecules? J. Comput. Chem., 21, 1049-1074.

D. A. Case, T. A. Darden, T. E. Cheatham, III, C. L. Simmerling, J. Wang, R. E. Duke, R. Luo, M. Crowley, R. C. Walker, W. Zhang, K. M. Merz, B. Wang, S. Hayik, A. Roitberg, G. Seabra, I. Kolossvary, K. F. Wong, F. Paesani, J. Vanicek, X. Wu, S. R. Brozell, T. Steinbrecher, H. Gohlke, L. Yang, C. Tan, J. Mongan, V. Hornak, G. Cui, D. H. Mathews, M. G. Seetin, C. Sagui, V. Babin, and P. A. Kollman (2008), AMBER 10, University of California, San Francisco.

D. A. Pearlman, D. A. Case, J. W. Caldwell, W. S. Ross, T. E. Cheatham, III, S. DeBolt, D. Ferguson, G. Seibel, and P. Kollman. (1995) AMBER, a package of computer programs for applying molecular mechanics, normal mode analysis, molecular dynamics and free energy calculations to simulate the structural and energetic properties of molecules. Comp. Phys. Commun., 91, 1-41.

D. A. Case, T. Cheatham, T. Darden, H. Gohlke, R. Luo, K. M. Merz, Jr., A. Onufriev, C. Simmerling, B. Wang and R. Woods. (2005) The Amber biomolecular simulation programs. J. Computat. Chem., 26, 1668-1688.

Essmann, U, Perera, L, Berkowitz, M. L., Darden, T. A., Lee, H., Pedersen, L. G. (1995) A smooth particle mesh ewald method. J. Chem. Phys., 103, 8577-8593.

Ryckaert, J.-P., Ciccotti, G., Berendsen, H. J. C. (1977) Numerical integration of the Cartesian equations of motion of a system with constraints: Molecular dynamics of n-alkanes. J. Comput. Phys., 23, 327-341.

Berendsen, H. J. C, Postma, J. P. M, van Gunsteren, W. F., DiNola, A, Haak, J. R. (1984) Molecular dynamics with coupling to an external bath. J. Chem. Phys., 81, 3684-3690

Koyfman, A. Y., Braun, G., Magonov, S., Chworos, A., Reich, N. O., Jaeger, L.: Controlled spacing of cationic gold nanoparticles by nanocrown RNA. J. Am. Chem. Soc., 2005, Vol. 127, 11886-11887.

S. Horiya, X. Li, G. Kawai, R. Saito, A. Katoh, K. Kobayashi and K. Harada: RNA LEGO: magnesium-dependent formation of specific RNA assemblies through kissing interactions. Chem Biol 2003, JO, 645-654.

Lee, A. J., Crothers, D. M.: The solution structure of an RNA loop-loop complex: the ColE1 inverted loop sequence. Structure, 1998, Vol. 6, 993-1005.

Dieckmann et al, JMB, 1997 (Solution structure of the RNA-based ATP aptamer).

Seeman, N. C. An overview of structural DNA nanotechnology. Mol Biotechnol 37, 246-257 (2007).

Aldaye, F. A., Palmer, A. L. & Sleiman, H. F. Assembling materials with DNA as the guide. Science 321, 1795-1799 (2008).

Lin, C., Liu, Y. & Yan, H. Designer DNA Nanoarchitectures (dagger). Biochemistry (2009).

Chen, J. H. & Seeman, N. C. The electrophoretic properties of a DNA cube and itsnsubstructure catenanes. Electrophoresis 12, 607-611 (1991).

Goodman, R. P. et al. Reconfigurable, braced, three-dimensional DNA nanostructures. Nat Nanotechnol 3, 93-96 (2008).

He, Y. et al. Hierarchical self-assembly of DNA into symmetric supramolecular polyhedra. Nature 452, 198-201 (2008).

Erben, C. M., Goodman, R. P. & Turberfield, A. J. A self-assembled DNA bipyramid. J Am Chem Soc 129, 6992-6993 (2007).

Andersen, F. F. et al. Assembly and structural analysis of a covalently closed nano-scale DNA cage. Nucleic Acids Res 36, 1113-1119 (2008).

Shih, W. M., Quispe, J. D. & Joyce, G. F. A 1.7-kilobase single-stranded DNA that folds into a nanoscale octahedron. Nature 427, 618-621 (2004).

Zimmermann, J., Cebulla, M. P., Monninghoff, S. & von Kiedrowski, G. Self-assembly of a DNA dodecahedron from 20 trisoligonucleotides with C(3h) linkers. Angew Chem Int Ed Engl 47, 3626-3630 (2008).

Erben, C. M., Goodman, R. P. & Turberfield, A. J. Single-molecule protein encapsulation in a rigid DNA cage. Angew Chem Int Ed Engl 45, 7414-7417 (2006).

Bhatia, D. et al. Icosahedral DNA Nanocapsules by Modular Assembly. Angew Chem Int Ed Engl (2009).

Rothemund, P. W. Folding DNA to create nanoscale shapes and patterns. Nature 440, 297-302 (2006).

Andersen, E. S. et al. Self-assembly of a nanoscale DNA box with a controllable lid. Nature 459, 73-76 (2009).

Ke, Y. et al. Scaffolded DNA Origami of a DNA Tetrahedron Molecular Container. Nano Lett (2009).

Dietz, H., Douglas, S. M. & Shih, W. M. Folding DNA into twisted and curved nanoscale shapes. Science 325, 725-730 (2009).

Douglas, S. M. et al. Self-assembly of DNA into nanoscale three-dimensional shapes. Nature 459, 414-418 (2009).

Kim, D. H. & Rossi, J. J. Strategies for silencing human disease using RNA interference. Nat Rev Genet 8, 173-184 (2007).

Gesteland, R. F., Cech, T. R. & Atkins, J. F. The RNA world, Third Edition. (Cold Spring Harbor Laboratory Press, Cold Spring Harbor, N. Y.; 2005).

Wendell, D. et al. Translocation of double-stranded DNA through membrane-adapted phi29 motor protein nanopores. Nat Nanotechnol 4, 765-772 (2009).

Jaeger, L. & Leontis, N. B. Tecto-RNA: One-Dimensional Self-Assembly through Tertiary Interactions. Angew Chem Int Ed Engl 39, 2521-2524 (2000).

Chworos, A. et al. Building programmable jigsaw puzzles with RNA. Science 306, 2068-2072 (2004).

Khaled, A., Guo, S., Li, F. & Guo, P. Controllable self-assembly of nanoparticles for specific delivery of multiple therapeutic molecules to cancer cells using RNA nanotechnology. Nano Lett 5, 1797-1808 (2005).

Guo, P. RNA nanotechnology: engineering, assembly and applications in detection, gene delivery and therapy. J Nanosci Nanotechnol 5, 1964-1982 (2005).

Jaeger, L. & Chworos, A. The architectonics of programmable RNA and DNA nanostructures. Curr Opin Struct Biol 16, 531-543 (2006).

Afonin, K. A., Cieply, D. J. & Leontis, N. B. Specific RNA self-assembly with minimal paranemic motifs. J Am Chem Soc 130, 93-102 (2008).

Severcan, I., Geary, C., Verzemnieks, E., Chworos, A. & Jaeger, L. Square-shaped RNA particles from different RNA folds. Nano Lett 9, 1270-1277 (2009).

Koyfman, A. Y. et al. Controlled spacing of cationic gold nanoparticles by nanocrown RNA. J Am Chem Soc 127, 11886-11887 (2005).

Nasalean, L., Baudrey, S., Leontis, N. B. & Jaeger, L. Controlling RNA self-assembly to form filaments. Nucleic Acids Res 34, 1381-1392 (2006).

Bindewald, E., Grunewald, C., Boyle, B., O'Connor, M. & Shapiro, B. A. Computational strategies for the automated design of RNA nanoscale structures from building blocks using NanoTiler. J Mol Graph Model 27, 299-308 (2008).

Seiffert, J. & Huhle, A. A full-automatic sequence design algorithm for branched DNA structures. J Biomol Struct Dyn 25, 453-466 (2008).

Seeman, N. C. Nucleic acid junctions and lattices. J Theor Biol 99, 237-247 (1982).

Mathews, D. H., Sabina, J., Zuker, M. & Turner, D. H. Expanded sequence dependence of thermodynamic parameters improves prediction of RNA secondary structure. J Mol Biol 288, 911-940 (1999).

Zuker, M. Mfold web server for nucleic acid folding and hybridization prediction. Nucleic Acids Res 31, 3406-3415 (2003).

Bernhart, S. H. et al. Partition function and base pairing probabilities of RNA heterodimers. Algorithms Mol Biol 1, 3 (2006).

Hofacker, I. L. Fast Folding and Comparison of RNA Secondary Structures. Monatshefte f Chemie 125, 167-188 (1994).

Freier, S. M. et al. Improved free-energy parameters for predictions of RNA duplex stability. Proc Natl Acad Sci USA 83, 9373-9377 (1986).

SantaLucia, J., Jr. A unified view of polymer, dumbbell, and oligonucleotide DNA nearest-neighbor thermodynamics. Proc Natl Acad Sci USA 95, 1460-1465 (1998).

Sugimoto, N., Nakano, S., Yoneyama, M. & Honda, K. Improved thermodynamic parameters and helix initiation factor to predict stability of DNA duplexes. Nucleic Acids Res 24, 4501-4505 (1996).

Kato, T., Goodman, R. P., Erben, C. M., Turberfield, A. J. & Namba, K. High-resolution structuralanalysis of a DNA nanostructure by cryoEM. Nano Lett 9, 2747-2750 (2009).

Ludtke, S. J., Baldwin, P. R. & Chiu, W. EMAN: semiautomated software for highresolution single-particle reconstructions. J Struct Biol 128, 82-97 (1999).

Baugh, C., Grate, D. & Wilson, C. 2.8 Å crystal structure of the malachite green aptamer. J Mol Biol 301, 117-128 (2000).

Duxbury, D. F. The photochemistry and photophysics of triphenylmethane dyes in solid and liquid media. Chem. Rev. 93, 381-433 (1993).

Afonin, K. A., Danilov, E. O., Novikova, I. V. & Leontis, N. B. TokenRNA: a new type of sequence-specific, label-free fluorescent biosensor for folded RNA molecules. Chembiochem 9, 1902-1905 (2008).

Marky, L. A. & Breslauer, K. J. Calculating thermodynamic data for transitions of any molecularity from equilibrium melting curves. Biopolymers 26, 1601-1620 (1987).
Suloway, C. et al. Automated molecular microscopy: the new Leginon system. J Struct Biol 151, 41-60 (2005).
Lander, G. C. et al. Appion: an integrated, database-driven pipeline to facilitate EM image processing. J Struct Biol 166, 95-102 (2009).
G. C. Landera, S. M. Staggb, N. R. Vossa, A. Chenga, D. Fellmanna, J. Pulokasa, C. Yoshiokaa, C. Irvinga, A. Muldera, P. Laua, D. Lyumkisa, C. S. Pottera and B. Carragher (2009). "Appion: an integrated, database-driven pipeline to facilitate EM image processing." J Struct Biol v166(1): pp. 95-102.
N. B. Leontis and E. Westhof. (2001) "Geometric Nomenclature and Classification of RNA base pairs", RNA, 7, pp. 499-512.
S. J. Ludtke, P. R. Baldwin, and W. Chiu. (1999). "EMAN: semiautomated software for highresolution single-particle reconstructions." J Struct Biol v128(1): pp. 82-97.
Mallick, Carragher, Potter, and Kriegman (2005). "ACE: automated CTF estimation." Ultramicroscopy vi 104(1): pp. 8-29.
L. A. Marky and K. J. Breslauer. (1987) "Calculating thermodynamic data for transitions of any molecularity from equilibrium melting curves", Biopolymers, 1987, 26, 1601-1620.
S. H. Scheres, M. Valle, R. Nuñez, C. O. Sorzano, R. Marabini, G. T. Herman, J. M. Carazo. (2005a). "Maximum-likelihood multi-reference refinement for electron microscopy images." J. Mol. Biol v348(1), pp. 139-149.
S. H. W. Scheres, M. Valle and J.-M. Carazo. (2005b). "Fast maximum-likelihood refinement of electron microscopy images." Bioinformatics v21(Suppl 2), pp. ii243-244.
C. Suloway, J. Pulokas, D. Fellmann, A. Cheng, F. Guerra, J. Quispe, S. Stagg, C. S. Potter, B. Carragher. (2005). "Automated molecular microscopy: the new Leginon system." J Struct Biol v151(1): pp. 41-60.
N. R. Vossa and M. Gerstein. (2005). 'Calculation of standard atomic volumes for RNA and comparison with proteins: RNA is packed more tightly.' J Mol Biol. v346 (2): pp. 477-92. PubMed: 15670598
Holbrook S R 2005 Curr. Opin. Struct. Biol. 15 302.
Yingling Y G and Shapiro B A 2007 Nano Lett. 7 2328.
Sponer J and Lankas F (ed) 2006 Computational Studies of RNA and DNA (Challenges and Advances in Computational Chemistry and Physics vol 2) (Berlin: Springer).
Woodson S A 2005 Curr. Opin. Chem. Biol. 9 104.
Vieregg J, Cheng W, Bustamante C and Tinoco Jr I 2007. J. Am. Chem. Soc. 129 14966.
Phillips J C, Braun R, Wang W, Gumbart J, Tajkhorshid E, Villa E, Chipot C, Skeel R D, Kal'e L and Schulten K 2005. J. Comput. Chem. 26 1781.
Mackerell A D, Bashford D, Bellott M, Dunbrack R L, Evanseck J D, Field M J, Fischer S, Gao J, Guo H and Ha S 1998 J. Phys. Chem. B 102 3586.
Humphrey W, Dalke A and Schulten K 1996 J. Mol. Graph. 14 33.
Pettersen E F, Goddard T D, Huang C C, Couch G S, Greenblatt D M, Meng E C and Ferrin T E 2004 J. Comput. Chem. 25 1605.
Manning G S 1978 Q. Rev. Biophys. 11 179.
Heilman-Miller S L, Thirumalai D and Woodson S A 2001. J. Mol. Biol. 306 1157.
Paliy M, Melnik R and Shapiro B 2009 in preparation.
Hess B 2000 Phys. Rev. E 62 8438.
Hess B 2002 Phys. Rev. E 65 031910.
Draper D E 2004 RNA 10 335.
Hyeon C and Thirumalai D 2007 Biophys. J. 92 731
Hyeon C, Dima R I and Thirumalai D 2006 J. Chem. Phys. 125 194905.
Rouzina I and Bloomfield V A 1999 Biophys. J. 77 3242.
Gu B, Zhang F S, Wang Z P and Zhou H Y 2008 Phys. Rev. Lett. 100 088104.
Kusalik P G and Svishchev I M 1994 Science 265 1219.
Zhou J Li Z and Sadus R J 2007 J. Chem. Phys. 127 154509.
Halgren T A and Damm W 2001 Curr. Opin. Struct. Biol. 11 236.
S Patel Jr A D M and III C L B 2004 J. Comput. Chem. 25 1504.
Gresh N, Sponer J E, Spackova N, Leszczynski J and Sponer J 2003 J. Phys. Chem. B 107 8669.
Case D A et al 2008 AMBER 10 (San Francisco, Calif.: University of California) http://amber.scripps.edu.
Tepper Y, Wu H L and Voth G A 2006 J. Chem. Phys. 124 024503.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A synthetic polyvalent RNA nanocube comprising approximately 90 degree angle bend RNA motifs as building blocks, wherein the 90 degree angle bend motif is selected from the group consisting of: right angle (RA) motifs, three way junction (3WJ) motifs, four way junction motifs and class II tRNA motifs, and wherein said RA motifs are selected from the group consisting of SEQ ID NO: 1, SEQ ID NO: 2, SEQ ID NO: 3 and SEQ ID NO: 4.

2. The polyvalent RNA nanocube of claim 1, wherein the 3WJ motif is selected from the group consisting of: SEQ ID NO: 5, SEQ ID NO: 6, SEQ ID NO: 7 and SEQ ID NO: 8.

3. The polyvalent RNA nanocube of claim 1, wherein the class II tRNA motif is selected from the group consisting of: SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16.

4. The polyvalent RNA nanocube of claim 1, wherein the polyvalent RNA nanocube comprises SEQ ID NO: 9, 10, 11 and 12.

5. The polyvalent RNA nanoparticle of claim 1, wherein the polyvalent RNA nanocube comprises SEQ ID NO: 13, 14, 15 and 16.

6. The polyvalent nanocube of claim 1, wherein the nanoparticle comprises one or more agents.

7. The polyvalent nanocube of claim 6, wherein the agent is selected from the group consisting of: a therapeutic agent, an imaging agent and a diagnostic agent.

8. A drug delivery composition comprising the polyvalent RNA nanocube of claim 1, wherein the drug delivery composition can gain entry into a cell or tissue.

9. The drug delivery composition of claim 8, further comprising an agent selected from the group consisting of a therapeutic agent, an imaging agent and a diagnostic agent.

10. The drug delivery composition of claim 8, further comprising biotin.

11. A method for making the polyvalent nanocube of claim 1, the method comprising:
   overexpressing an RNA sequence comprising an approximately 90 degree angle bend RNA motif in a cell, wherein the 90 degree angle bend motif is selected from the group consisting of: right angle (RA) motifs, three way junction (3WJ) motifs, four way junction motifs and class II tRNA motifs, and wherein said RA motifs are selected from the group consisting of SEQ ID NO: 1, SEQ ID NO: 2, SEQ ID NO: 3 and SEQ ID NO:4; and
   allowing the RNA sequences to assemble into a polyvalent nanocube;
   thereby making a polyvalent nanocube.

12. A method for making the polyvalent nanocube of claim 1, comprising:
   mixing a sample comprising RNA sequences comprising an approximately 90 degree angle bend RNA motif, wherein the 90 degree angle bend motif is selected from the group consisting of: right angle (RA) motifs, three way junction (3WJ) motifs, four way junction motifs and class II tRNA motifs, and wherein said RA motifs are selected from the group consisting of SEQ ID NO: 1, SEQ ID NO: 2, SEQ ID NO: 3 and SEQ ID NO:4;

heating the sample;

cooling the sample; and allowing the RNA sequences to assemble into a polyvalent nanocube;

thereby making a polyvalent nanocube.

13. A kit comprising the polyvalent nanocube according to claim 1 and instructions for use.

14. The polyvalent RNA nanocube of claim 1, wherein said nanocube structure consists of six or ten strands.

15. The polyvalent RNA nanocube of claim 1, wherein the RNA nanocube comprises at least one 5' dangling end.

16. The polyvalent RNA nanocube of claim 1, wherein the approximately 90 degree angle bend RNA motifs comprise seven to ten base pair connector sizes.

17. A synthetic polyvalent RNA nanocube comprising approximately 90 degree angle bend RNA motifs as building blocks, wherein the 90 degree angle bend motif comprises at least two different structural elements, wherein a first element is a right angle (RA) motif selected from the group consisting of: SEQ ID NO: 1, SEQ ID NO: 2, SEQ ID NO: 3 and SEQ ID NO: 4 and a second element is selected from the group consisting of: three way junction (3WJ) motifs, four way junction motifs and class II tRNA motifs.

18. The synthetic polyvalent RNA nanocube of claim 17, wherein said 3WJ motif is selected from the group consisting of: SEQ ID NO: 5, SEQ ID NO: 6, SEQ ID NO: 7 and SEQ ID NO: 8.

19. The synthetic polyvalent RNA nanocube of claim 17, wherein said class II tRNA motif is selected from the group consisting of: SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16.

* * * * *